US009718847B2

(12) United States Patent
Zhang et al.

(10) Patent No.: US 9,718,847 B2
(45) Date of Patent: *Aug. 1, 2017

(54) HETEROCYCLIC COMPOUNDS AND USES THEREOF

(71) Applicant: Plexxikon Inc., Berkeley, CA (US)

(72) Inventors: Jiazhong Zhang, Foster City, CA (US); John Buell, San Francisco, CA (US); Katrina Chan, Fremont, CA (US); Prabha N. Ibrahim, Mountain View, CA (US); Jack Lin, Hercules, CA (US); Phuongly Pham, San Francisco, CA (US); Songyuan Shi, Fremont, CA (US); Wayne Spevak, Berkeley, CA (US); Guoxian Wu, Foster City, CA (US); Jeffrey Wu, Berkeley, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,986

(22) Filed: Sep. 15, 2014

(65) Prior Publication Data

US 2015/0133400 A1 May 14, 2015

Related U.S. Application Data

(63) Continuation of application No. PCT/US2014/029701, filed on Mar. 14, 2014.

(60) Provisional application No. 61/872,347, filed on Aug. 30, 2013, provisional application No. 61/798,856, filed on Mar. 15, 2013.

(51) Int. Cl.

| | |
|---|---|
| *C07D 471/04* | (2006.01) |
| *C07F 9/6561* | (2006.01) |
| *A61K 31/422* | (2006.01) |
| *A61K 31/437* | (2006.01) |
| *A61K 31/444* | (2006.01) |
| *A61K 31/4545* | (2006.01) |
| *A61K 31/497* | (2006.01) |
| *A61K 31/506* | (2006.01) |
| *A61K 31/675* | (2006.01) |
| *A61K 31/695* | (2006.01) |
| *C07D 413/04* | (2006.01) |
| *C07D 413/14* | (2006.01) |
| *C07F 7/10* | (2006.01) |

(52) U.S. Cl.

CPC .......... *C07F 9/6561* (2013.01); *A61K 31/422* (2013.01); *A61K 31/437* (2013.01); *A61K 31/444* (2013.01); *A61K 31/4545* (2013.01); *A61K 31/497* (2013.01); *A61K 31/506* (2013.01); *A61K 31/675* (2013.01); *A61K 31/695* (2013.01); *C07D 413/04* (2013.01); *C07D 413/14* (2013.01); *C07D 471/04* (2013.01); *C07F 7/10* (2013.01)

(58) Field of Classification Search

CPC .................................................... C07D 471/04

See application file for complete search history.

(56) References Cited

U.S. PATENT DOCUMENTS

| | | | | |
|---|---|---|---|---|
| 5,317,103 | A | 5/1994 | Baker et al. | |
| 5,998,438 | A | 12/1999 | Slassi et al. | |
| 6,358,992 | B1 | 3/2002 | Pamukcu et al. | |
| 6,479,507 | B2 | 11/2002 | Cheng et al. | |
| 6,906,084 | B2 | 6/2005 | Nazaré et al. | |
| 7,202,266 | B2 | 4/2007 | Arnold et al. | |
| 7,348,338 | B2 | 3/2008 | Arnold et al. | |
| 7,354,924 | B2 * | 4/2008 | Wang .................. | A61K 31/496 514/241 |
| 7,432,375 | B2 | 10/2008 | Graczyk et al. | |
| 7,476,746 | B2 | 1/2009 | Artis et al. | |
| 7,491,831 | B2 | 2/2009 | Artis et al. | |
| 7,498,342 | B2 | 3/2009 | Ibrahim et al. | |
| 7,504,509 | B2 | 3/2009 | Ibrahim et al. | |
| 7,517,970 | B2 | 4/2009 | West et al. | |
| 7,531,568 | B2 | 5/2009 | Lin et al. | |
| 7,572,806 | B2 | 8/2009 | Arnold et al. | |
| 7,585,859 | B2 | 9/2009 | Ibrahim et al. | |
| 7,605,168 | B2 | 10/2009 | Ibrahim et al. | |
| 7,696,229 | B2 | 4/2010 | Dunn et al. | |
| 7,723,374 | B2 | 5/2010 | Artis et al. | |
| 7,846,941 | B2 | 12/2010 | Ibrahim et al. | |
| 7,863,288 | B2 | 1/2011 | Ibrahim et al. | |
| 7,863,289 | B2 | 1/2011 | Spevak et al. | |
| 7,872,018 | B2 | 1/2011 | Ibrahim et al. | |
| 7,893,075 | B2 | 2/2011 | Zhang et al. | |
| 7,947,708 | B2 | 5/2011 | Ibrahim et al. | |
| 7,956,082 | B2 | 6/2011 | Kugimiya et al. | |

(Continued)

FOREIGN PATENT DOCUMENTS

| | | |
|---|---|---|
| EP | 2119703 A1 | 11/2009 |
| WO | WO-01/46178 | 6/2001 |

(Continued)

OTHER PUBLICATIONS

Henry R. Henze and Charles M. Blair "The Number of Structurally Isomeric Alcohols of the Methanol Series" Journal of the American Chemical Society 1931, 3042.*

Kottenhahn, Alfred P "The ferric chloride oxidation of 5-substituted o-semidines and the polarographic properties of the products." Journal of Organic Chemistry 1963 28(11), 3114-20.*

Rautio et. al. "Prodrugs: design and clinical Applications" Nature Reviews Drug Discovery 2008, 7, 255-270.*

Beaumont "Design of Ester Prodrugs to Enhance Oral Absorption of Poorly Permeable Compounds: Challenges to the Discovery Scientist" Current Drug Metabolism, 2003, 4, 461-485.*

Pozharskii et. al. Heterocycles in Life and Society Wiley, 1997, pp. 1-6.*

(Continued)

*Primary Examiner* — David K O'Dell

(74) *Attorney, Agent, or Firm* — Sheppard Mullin Richter & Hampton LLP

(57) ABSTRACT

Heterocyclic compounds of formula (I), methods for their preparation, pharmaceutical compositions containing such a compound and their therapeutic uses.

21 Claims, No Drawings

(56) References Cited

U.S. PATENT DOCUMENTS

| | | | |
|---|---|---|---|
| 8,053,463 B2 | 11/2011 | Lin et al. | |
| 8,067,434 B2 | 11/2011 | Ibrahim et al. | |
| 8,071,581 B2 * | 12/2011 | Smith | C07D 519/00 435/184 |
| 8,110,576 B2 | 2/2012 | Ibrahim et al. | |
| 8,119,637 B2 | 2/2012 | Ibrahim et al. | |
| 8,129,404 B2 | 3/2012 | Ibrahim et al. | |
| 8,143,271 B2 | 3/2012 | Ibrahim et al. | |
| 8,153,641 B2 | 4/2012 | Ibrahim et al. | |
| 8,158,636 B2 | 4/2012 | Ibrahim et al. | |
| 8,198,273 B2 | 6/2012 | Ibrahim et al. | |
| 8,268,858 B2 | 9/2012 | Wu et al. | |
| 8,367,828 B2 | 2/2013 | Arnold et al. | |
| 8,404,700 B2 | 3/2013 | Zhang et al. | |
| 8,415,469 B2 | 4/2013 | Ibrahim et al. | |
| 8,461,169 B2 | 6/2013 | Zhang et al. | |
| 8,470,818 B2 | 6/2013 | Ibrahim et al. | |
| 8,642,606 B2 | 2/2014 | Ibrahim et al. | |
| 8,673,928 B2 | 3/2014 | Ibrahim et al. | |
| 8,722,702 B2 | 5/2014 | Zhang et al. | |
| 8,865,735 B2 | 10/2014 | Ibrahim et al. | |
| 8,901,118 B2 | 12/2014 | Zhang et al. | |
| 8,901,301 B2 | 12/2014 | Ibrahim et al. | |
| 8,912,204 B2 | 12/2014 | Ibrahim et al. | |
| 2004/0009983 A1 | 1/2004 | Cox et al. | |
| 2004/0092569 A1 | 5/2004 | Demain et al. | |
| 2004/0142864 A1 | 7/2004 | Bremer et al. | |
| 2004/0167188 A1 | 8/2004 | Xin et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0030583 A1 | 2/2006 | Arnold et al. | |
| 2006/0058339 A1 | 3/2006 | Ibrahim et al. | |
| 2006/0135540 A1 | 6/2006 | Lin et al. | |
| 2006/0160135 A1 | 7/2006 | Wang et al. | |
| 2006/0183758 A1 * | 8/2006 | Beard et al. | 514/260.1 |
| 2007/0066641 A1 | 3/2007 | Ibrahim et al. | |
| 2007/0072904 A1 | 3/2007 | Lin et al. | |
| 2008/0171772 A1 | 7/2008 | Beard et al. | |
| 2008/0221127 A1 | 9/2008 | Lin et al. | |
| 2008/0234349 A1 | 9/2008 | Lin et al. | |
| 2008/0249110 A1 | 10/2008 | Bonnert et al. | |
| 2008/0249137 A1 | 10/2008 | Lin et al. | |
| 2009/0047246 A1 | 2/2009 | Beigelman et al. | |
| 2009/0069565 A1 | 3/2009 | Nazaré et al. | |
| 2009/0221608 A1 | 9/2009 | Cui et al. | |
| 2009/0325970 A1 * | 12/2009 | Yuan | C07D 487/04 514/249 |
| 2010/0190777 A1 | 7/2010 | Wu et al. | |
| 2010/0310659 A1 | 12/2010 | Desai et al. | |
| 2011/0046370 A1 | 2/2011 | Sim et al. | |
| 2011/0092538 A1 | 4/2011 | Spevak et al. | |
| 2011/0112127 A1 | 5/2011 | Zhang et al. | |
| 2011/0166174 A1 | 7/2011 | Ibrahim et al. | |
| 2011/0183988 A1 | 7/2011 | Ibrahim et al. | |
| 2011/0218198 A1 | 9/2011 | Wucherer-Plietker et al. | |
| 2011/0281888 A1 | 11/2011 | Mulvihill et al. | |
| 2012/0015966 A1 | 1/2012 | Lin et al. | |
| 2012/0053177 A1 | 3/2012 | Ibrahim et al. | |
| 2012/0122860 A1 | 5/2012 | Visor et al. | |
| 2012/0165366 A1 | 6/2012 | Ibrahim et al. | |
| 2012/0245174 A1 | 9/2012 | Ibrahim et al. | |
| 2013/0237531 A1 | 9/2013 | Wu et al. | |
| 2013/0261117 A1 | 10/2013 | Ibrahim et al. | |
| 2013/0274259 A1 | 10/2013 | Zhang et al. | |
| 2013/0303534 A1 | 11/2013 | Ibrahim et al. | |
| 2014/0037617 A1 | 2/2014 | Bollag et al. | |
| 2014/0038948 A1 | 2/2014 | Wu et al. | |
| 2014/0045840 A1 | 2/2014 | Zhang et al. | |
| 2014/0094611 A1 | 4/2014 | Ibrahim et al. | |
| 2014/0128373 A1 | 5/2014 | Ibrahim et al. | |
| 2014/0128390 A1 | 5/2014 | Lin et al. | |
| 2014/0213554 A1 | 7/2014 | Wu et al. | |
| 2014/0243365 A1 | 8/2014 | Zhang et al. | |
| 2014/0288070 A1 | 9/2014 | Ibrahim et al. | |
| 2014/0303121 A1 | 10/2014 | Zhang et al. | |
| 2014/0303187 A1 | 10/2014 | Wu et al. | |
| 2014/0357612 A1 | 12/2014 | Zhang et al. | |
| 2015/0080372 A1 | 3/2015 | Ibrahim et al. | |
| 2015/0133400 A1 | 5/2015 | Zhang et al. | |
| 2015/0166547 A1 | 6/2015 | Ibrahim et al. | |
| 2015/0183793 A1 | 7/2015 | Zhang et al. | |
| 2016/0075712 A1 | 3/2016 | Shi et al. | |
| 2016/0168146 A1 | 6/2016 | Wu et al. | |
| 2016/0243092 A1 | 8/2016 | Bollag et al. | |

FOREIGN PATENT DOCUMENTS

| | | |
|---|---|---|
| WO | WO 03/082869 A1 | 10/2003 |
| WO | WO 2004/014851 A1 | 2/2004 |
| WO | WO 2004/078756 A1 | 9/2004 |
| WO | WO-2006/015123 | 2/2006 |
| WO | WO 2007/013896 | 5/2007 |
| WO | WO 2008/110508 A1 | 9/2008 |
| WO | WO 2008/155000 A1 | 12/2008 |
| WO | WO-2009/152072 | 12/2009 |
| WO | WO-2009/155052 | 12/2009 |
| WO | WO 2010/068292 | 6/2010 |
| WO | WO 2010/111527 | 9/2010 |
| WO | WO 2010/129467 | 11/2010 |
| WO | WO-2012/069917 | 5/2012 |
| WO | WO 2012/104007 A1 | 8/2012 |
| WO | WO-2013/061977 | 5/2013 |
| WO | WO-2013/078254 | 5/2013 |
| WO | WO-2013/087744 | 6/2013 |
| WO | WO-2013/092463 | 6/2013 |
| WO | WO-2015/002754 | 1/2015 |
| WO | WO-2015/004533 | 1/2015 |
| WO | WO-2015/004534 | 1/2015 |

OTHER PUBLICATIONS

Pitt "Heteroaromatic Rings of the Future" J. Med. Chem. 2009, 52, 2952-2963.*

Bobko, et al., "Synthesis of 2,5-disubstituted-3-cyanoindoles," Tetrahedron Lett., 53(2): 200-202 (2011).

Database Reaxys [Online] Elsevier Information Systems GmbH, Frankfurt/Main (DE); XP002725967, Database accession No. 7647302, 7665443 (XRNs) abstract & Chem. Pharm. Bull., 44(10): 1831-1839 (1996).

Database Reaxys [Online] Elsevier Information Systems GmbH, Frankfurt/Main (DE); XP002725968, Database accession No. 8234793, 8235134 (XRNs) abstract & Zeitschrift Für Naturforschun—Section B Journal of Chemical Sciences, 53(10): 1216-1222 (1998).

Furdas, et al., "Inhibition of bromodomain-mediated protein-protein interactions as a novel therapeutic strategy," Medchemcomm, 3(2): 123-134 (2012).

Hay, et al., "The design and synthesis of 5- and 6-isoxazolylbenzimidazoles as selective inhibitors of the BET bromodomains," Medchemcomm, 4(1): 140-144 (2012).

Hewings, et al., "3,5-Dimethylisoxazoles Act as Acetyl-lysine-mimetic Bromodomain Ligands," J. Med. Chem., 54(19): 6761-6770 (2011).

International Search Report and Written Opinion for PCT/US2014/029701, dated Jul. 8, 2014.

Mirguet, et al., "From ApoA1 upregulation to BET family bromodomain inhibition: Discovery of I-BET151," Bioorg.Med. Chem. Lett., 22(8): 2963-2967 (2012).

Scribner, et al., "Synthesis and biological activity of anticoccidial agents: 2,3-diarylindoles," Biorg. Med. Chem. Lett., 19(5): 1517-1521 (2009).

Hay, "Discovery and Optimization of Small-Molecule Ligands for the CBP/p300 Bromodomains," J. Am. Chem. Soc., (2014), 136:9308-9319.

Wolff, "Burger's Medicinal Chemistry, 5ed Part I," John Wiley & Sons, (1995), pp. 975-977.

Banker, et al., "Modern Pharmacuetics, 3ed.," Marcel Dekker, New York, (1996), pp. 451 and 596.

(56) References Cited

OTHER PUBLICATIONS

U.S. Appl. No. 14/798,167, filed Jul. 13, 2015, Ibrahim et al.
U.S. Appl. No. 14/602,119, filed Jan. 21, 2015, Ibrahim et al.
U.S. Appl. No. 14/637,303, filed Mar. 3, 2015, Lin et al.
U.S. Appl. No. 14/733,830, filed Jun. 8, 2015, Zhang et al.
U.S. Appl. No. 14/839,668, filed Aug. 28, 2015, Ibrahim.
U.S. Appl. No. 14/846,545, filed Sep. 4, 2015, Zhang et al.
U.S. Appl. No. 15/093,660, filed Apr. 7, 2016, Lin et al.
U.S. Appl. No. 15/147,709, filed May 5, 2016, Ibrahim et al.
U.S. Appl. No. 15/147,692, filed May 5, 2016, Ibrahim et al.
U.S. Appl. No. 15/161,103, filed May 20, 2016, Ibrahim.
U.S. Appl. No. 15/160,551, filed May 20, 2016, Ibrahim et al.
U.S. Appl. No. 15/160,729, filed May 20, 2016, Ibrahim et al.
U.S. Appl. No. 15/221,474, filed Jul. 27, 2016, Holladay et al.

* cited by examiner

HETEROCYCLIC COMPOUNDS AND USES THEREOF

CROSS-REFERENCE TO RELATED APPLICATIONS

This application is a continuation application of International Application No. PCT/US2014/029701, which claims the benefit under of 35 U.S.C. §119(e) of U.S. Provisional Applications 61/798,856, filed on Mar. 15, 2013, and 61/872,347, filed on Aug. 30, 2013, both of which are incorporated by reference.

FIELD

The present disclosure relates to bromodomain proteins and compounds which modulate bromodomains, and uses therefor. Particular embodiments contemplate disease indications which are amenable to treatment by modulation of bromodomains by the compounds of the present disclosure. The information provided is intended solely to assist the understanding of the reader. None of the information provided nor references cited is admitted to be prior art to the present disclosure. Each of the references cited is incorporated herein in its entirety and for any purpose.

SUMMARY

In one aspect, the present disclosure provides a compound of formula (I):

(I)

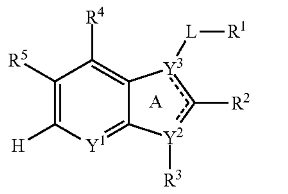

or a pharmaceutically acceptable salt, a solvate, a tautomer, an isomer, or a deuterated analog thereof, wherein:

(i) $Y^2$ is N and $Y^3$ is C; or (ii) $Y^2$ is C and $Y^3$ is N;

$Y^1$ is CH or N;

L is a bond, optionally substituted $C_{1-6}$alkylene, optionally substituted deuterated $C_{1-6}$alkylene, —$C(R^6R^7)$—, —$C(O)NR^9$—, —$CH_2N(R^9)$—, —$SO_2N(R^9)$—, —$N(R^9)C(O)N(R^9)$—, —$N(R^9)SO_2$—, —$N(R^9)CH_2$—, —$OC_{1-4}$alkylene-, —$C_{1-4}$alkylene-O—, —$NR^9C(O)$—, —$N(R^9)SO_2$—, —C(O)—, —S(O)—, —$SO_2$—, —O—, —S—, —P(O)($R^a$)—, optionally substituted $C_{2-6}$alkenylene, optionally substituted —CH═C($R^b$)— or optionally substituted —Si($R^c$)($R^c$)—; or $R^6$ and $R^7$ taken together with the carbon atom to which they attach form an optionally substituted 3- to 6-membered ring having from 0-2 heteroatoms selected from O, N or S or an oxo; $R^a$ is optionally substituted $C_{1-6}$alkyl, optionally substituted aryl or optionally substituted heteroaryl; $R^b$ is H or $C_{1-6}$alkyl; or $R^b$ and $R^1$ taken together with the carbon atom to which they attach form an optionally substituted 3- to 6-membered carbocyclic ring or an optionally substituted 4- to 8-membered heterocyclic ring having from 1-2 heteroatoms as ring members selected from O, N or S, wherein the nitrogen or sulfur ring atoms can be optionally oxidized; each $R^c$ is independently $C_{1-6}$alkyl or $C_{1-6}$alkoxy; $R^9$ is H, $C_{1-4}$alkyl or $C_{1-4}$haloalkyl;

$R^1$, $R^2$, $R^4$, $R^6$ and $R^7$ are each independently H, optionally substituted $C_{1-6}$alkyl, optionally substituted $C_{1-6}$ alkenyl, optionally substituted $C_{1-6}$ alkynyl, optionally substituted aryl, optionally substituted heteroaryl, optionally substituted cycloalkyl, optionally substituted cycloalkenyl, optionally substituted heterocycloalkyl, optionally substituted heterocycloalkylalkyl, optionally substituted cycloalkylalkyl, optionally substituted arylalkyl, optionally substituted heteroarylalkyl, optionally substituted heterocycloalkylalkyl, optionally substituted —Si($R^c$)($R^c$) or $R^{13}$ selected from halogen, —CN, —OH, —$NH_2$, —$NO_2$, —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —CH═C($R^g$)($R^g$), —$OR^g$, —$SR^g$, —OC(O)$R^g$, —OC(S)$R^g$, —P(═O)H$R^g$, —P(═O)$R^gR^g$, —PH(═O)$OR^g$, —P(═O)$(OR^g)_2$, —OP(═O)$(OR^g)_2$, —C(O)H, —O(CO)$OR^g$, —C(O)$R^g$, —C(S)$R^g$, —C(O)$OR^g$, —C(S)$OR^g$, —S(O)$R^g$, —$S(O)_2R^g$, —C(O)NH$R^g$, —C(S)NH$R^g$, —C(O)$NR^gR^g$, —C(S)$NR^gR^g$, —$S(O)_2NHR^g$, —$S(O)_2NR^gR^g$, —C(NH)NH$R^g$, —C(NH)$NR^gR^g$, —NHC(O)$R^g$, —NHC(S)$R^g$, —$NR^gC(O)R^g$, —$NR^gC(S)R^g$, —$NHS(O)_2R^g$, —$NR^gS(O)_2R^g$, —NHC(O)NH$R^g$, —NHC(S)NH$R^g$, —$NR^gC(O)NH_2$, —$NR^gC(S)NH_2$, —$NR^gC(O)NHR^g$, —$NR^gC(S)NHR^g$, —NHC(O)$NR^gR^g$, —NHC(S)$NR^gR^g$, —$NR^gC(O)NR^gR^g$, —$NR^gC(S)NR^gR^g$, —$NHS(O)_2NHR^g$, —$NR^gS(O)_2NH_2$, —$NR^gS(O)_2NHR^g$, —$NHS(O)_2NR^gR^g$, —$NR^gS(O)_2NR^gR^g$, —NH$R^g$ or —$NR^gR^g$, wherein each $R^g$ is independently H, optionally substituted $C_{1-6}$alkyl, optionally substituted $C_{1-6}$ alkenyl, optionally substituted $C_{1-6}$ alkynyl, optionally substituted aryl, optionally substituted heteroaryl, optionally substituted cycloalkyl, optionally substituted heterocycloalkyl, optionally substituted heterocycloalkylalkyl, optionally substituted cycloalkylalkyl, optionally substituted arylalkyl, optionally substituted heteroarylalkyl or optionally substituted heterocycloalkylalkyl; or two $R^g$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein the aliphatic or aromatic portion of $R^g$ is optionally substituted with from 1-3 $R^h$ substituents independently selected from halogen, —CN, —OH, —$NH_2$, —$NO_2$, —CH═C($R^i$)($R^i$), —C(O)OH, —C(S)OH, —C(O)$NH_2$, —C(S)$NH_2$, —$B(OH)_2$, —$Si(R^i)_3$, —$S(O)_2NH_2$, —NHC(O)$NH_2$, —NHC(S)$NH_2$, —$NHS(O)_2NH_2$, —C(NH)$NH_2$, —$OR^i$, —$SR^i$, —OC(O)$R^i$, —OC(S)$R^i$, —P(═O)H$R^i$, —P(═O)$R^iR^i$, —PH(═O)$OR^i$, —P(═O)$(OR^i)_2$, —OP(═O)$(OR^i)_2$, —C(O)H, —O(CO)$OR^i$, —C(O)$R^i$, —C(S)$R^i$, —C(O)$OR^i$, —C(S)$OR^i$, —S(O)$R^i$, —$S(O)_2R^i$, —C(O)NH$R^i$, —C(S)NH$R^i$, —C(O)$NR^iR^i$, —C(S)$NR^iR^i$, —$S(O)_2NHR^i$, —$S(O)_2NR^iR^i$, —C(NH)NH$R^i$, —C(NH)$NR^iR^i$, —NHC(O)$R^i$, —NHC(S)$R^i$, —$NR^iC(O)R^i$, —$NR^iC(S)R^i$, —$NHS(O)_2R^i$, —$NR^iS(O)_2R^i$, —NHC(O)NH$R^i$, —NHC(S)NH$R^i$, —$NR^iC(O)NH_2$, —$NR^iC(S)NH_2$, —$NR^iC(O)NHR^i$, —$NR^iC(S)NHR^i$, —NHC(O)$NR^iR^i$, —NHC(S)$NR^iR^i$, —$NR^iC(O)NR^iR^i$, —$NR^iC(S)NR^iR^i$, —$NHS(O)_2NHR^i$, —$NR^iS(O)_2NH_2$, —$NR^iS(O)_2NHR^i$, —$NHS(O)_2NR^iR^i$, —$NR^iS(O)_2NR^iR^i$, $R^i$, —NH$R^i$ or —$NR^iR^i$, wherein each $R^i$ is independently $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl or heterocycloalkyl-$C_{1-4}$alkyl, wherein each $R^i$ is further optionally substituted with from 1-3 $R^p$ groups independently selected from halogen, CN, —OH, —$NH_2$, —$N(R^q)(R^q)$, —$NO_2$, —C(O)OH, —$C(O)NH_2$, —$S(O)_2NH_2$, —$NHC(O)NH_2$, —$C(NH)NH_2$, —$P(=O)HR^q$, —$P(=O)R^qR^q$, —$PH(=O)OR^q$, —$P(=O)(OR^q)_2$, —$OP(=O)(OR^q)_2$, —$OC(O)R^q$, —$OC(S)R^q$, —$C(O)R^q$, —$C(S)R^q$, —$C(O)OR^q$, —$S(O)_2R^q$, —$C(O)NHR^q$, $C_{1-6}$alkyl, $C_{1-6}$alkoxy, halogen, $C_{1-6}$ haloalkyl or $C_{1-6}$ haloalkoxy, wherein $R^q$ is $C_{1-6}$alkyl;

$R^3$ is H, halogen, —CN, optionally substituted $C_{1-6}$alkyl, optionally substituted deuterated $C_{1-6}$alkyl optionally substituted aryl, optionally substituted aryl-$C_{1-4}$alkyl, optionally substituted heteroaryl, optionally substituted heteroaryl-$C_{1-4}$alkyl, optionally substituted $C_{3-8}$ cycloalkyl, optionally substituted $C_{3-8}$ cycloalkenyl, optionally substituted $C_{3-8}$ cycloalkyl-$C_{1-4}$alkyl, optionally substituted $C_{2-6}$ alkynyl, optionally substituted heterocycloalkyl, optionally substituted heterocycloalkyl-$C_{1-4}$alkyl or R' selected from halogen, —CN, —OH, —$NH_2$, —$NO_2$, —C(O)OH, —C(S)OH, —$C(O)NH_2$, —$C(S)NH_2$, —$S(O)_2NH_2$, —$NHC(O)NH_2$, —$NHC(S)NH_2$, —$NHS(O)_2NH_2$, —$C(NH)NH_2$, —$CH=C(R^k)(R^k)$, —$OR^k$, —$SR^k$, —$OC(O)R^k$, —$OC(S)R^k$, —$P(=O)HR^k$, —$P(=O)R^kR^k$, —$PH(=O)OR^k$, —$P(=O)(OR^k)_2$, —$OP(=O)(OR^k)_2$, —C(O)H, —$O(CO)OR^k$, —$C(O)R^k$, —$C(S)R^k$, —$C(O)OR^k$, —$C(S)OR^k$, —$S(O)R^k$, —$S(O)_2R^k$, —$C(O)NHR^k$, —$C(S)NHR^k$, —$C(O)NR^kR^k$, —$C(S)NR^kR^k$, —$S(O)_2NHR^k$, —$S(O)_2NR^kR^k$, —$C(NH)NHR^k$, —$C(NH)NR^kR^k$, —$NHC(O)R^k$, —$NHC(S)R^k$, —$NR^kC(O)R^k$, —$NR^kC(S)R^k$, —$NHS(O)_2R^k$, —$NR^kS(O)_2R^k$, —$NHC(O)NHR^k$, —$NHC(S)NHR^k$, —$NR^kC(O)NH_2$, —$NR^kC(S)NH_2$, —$NR^kC(O)NHR^k$, —$NR^kC(S)NHR^k$, —$NHC(O)NR^kR^k$, —$NHC(S)NR^kR^k$, —$NR^kC(O)NR^kR^k$, —$NR^kC(S)NR^kR^k$, —$NHS(O)_2NHR^k$, —$NR^kS(O)_2NH_2$, —$NR^kS(O)_2NHR^k$, —$NHS(O)_2NR^kR^k$, —$NR^kS(O)_2NR^kR^k$, —$NHR^k$ or —$NR^kR^k$; or two $R^k$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein each $R^k$ is independently H, $C_{1-6}$alkyl or aryl, arylalkyl, heteroaryl, heteroarylalkyl, heterocycloalkyl, heterocycloalkylalkyl, cycloalkyl or cycloalkylalkyl, wherein $R^k$ is optionally substituted with from 1-3 $R^h$;

$R^5$ is an optionally substituted 5- or 6-membered heteroaryl having from 1 to 4 heteroatoms as ring members selected from O, N or S or an optionally substituted heterocycloalkyl; and ------ is a single bond or a double bond, optionally, ring A is aromatic, with the proviso that the compound is other than 3,5-dimethyl-4-(1H-pyrrolo[2,3-b]pyridin-5-yl)isoxazole; or $R^3$ and -L-R' are not simultaneously hydrogen.

In another aspect, the present disclosure provides a compound having formula (I'):

(I')

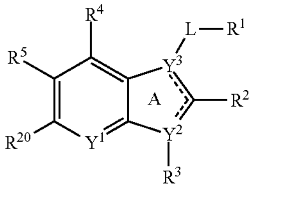

or a pharmaceutically acceptable salt, a solvate, a tautomer, an isomer, or a deuterated analog thereof, wherein: $R^{20}$ is halogen, $C_{1-4}$alkyl, $C_{1-4}$alkoxy, $C_{1-4}$haloalkyl, $C_{1-4}$haloalkoxy, —OH or CN. Variables $R^1$, $R^2$, $R^3$, $R^4$, $R^5$, $Y^1$, $Y^2$, $Y^3$ and L are as defined in any embodiments of formula (I).

In another aspect, the present disclosure provides a composition. The composition includes a compound of any of formulas (I), (I'), (II), (III), (IV), (V), (Va) or (Vb) or any of the formulas and subformulas as described herein, or a compound as recited in any of the claims and described herein, or a pharmaceutically acceptable salt, solvate, tautomer or isomer thereof, and a pharmaceutically acceptable excipient or carrier. The present disclosure also provides a composition, which includes a compound as recited in the claims and described herein, a pharmaceutically acceptable excipient or carrier, and another therapeutic agent.

In another aspect, the present disclosure provides a method for modulating a bromodomain protein. The method includes administering to a subject in need thereof a compound of any of formulas (I), (I') (II), (III), (IV), (V), (Va) or (Vb), or any of the formulas and subformulas as described herein, or a compound as recited in any of the claims and described herein, or a pharmaceutically acceptable salt, solvate, tautomer or isomer thereof, or a pharmaceutical composition as described herein.

In still another aspect, the present disclosure provides a method for treating a subject suffering from or at risk of diseases or conditions mediated or modulated by a bromodomain protein. The method includes administering to the subject an effective amount of a compound of any of formulas (I), (I'), (II), (III), (IV), (V), (Va) or (Vb), or any of the subformulas, or a compound as recited in any of the claims and described herein, or a pharmaceutically acceptable salt, solvate, tautomer or isomer thereof, or a composition comprising or including a compound of any of formulas (I), (I'), (II), (III), (IV), (V), (Va) or (Vb) or any of the subformulas described herein, or a compound as recited in any of the claims or described herein, or a pharmaceutically acceptable salt, solvate, tautomer or isomer thereof.

DETAILED DESCRIPTION

I. Definitions

As used herein the following definitions apply unless clearly indicated otherwise:

It is noted here that as used in this specification and the appended claims, the singular forms "a," "an," and "the" include plural reference unless the context clearly dictates otherwise.

"Halogen" or "halo" means all halogens, that is, chloro (Cl), fluoro (F), bromo (Br), or iodo (I).

"Hydroxyl" or "hydroxy" means the group —OH.

"Thiol" means the group —SH.

"Heteroatom" is meant to include oxygen (O), nitrogen (N), and sulfur (S). The term "oxo" refers to an oxygen connected via a double bond to another atom, i.e. carbon.

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl means a straight or branched hydrocarbon having 1, 2, 3, 4, 5 or 6 carbon atoms and includes, but is not limited to, $C_{1-2}$ alkyl, $C_1$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes an alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. As used herein, "deuterated $C_{1-6}$alkyl" is meant to include partially deuterated or perdeuterated $C_{1-6}$alkyl groups. Non-limiting examples include $—CD_3$, $CD_3CH_2—$, $CD_3CD_2$-, $—CD(CD_3)_2$, $—CD(CH_3)_2$, and the like.

The term "alkylene" by itself or as part of another substituent means a linear or branched saturated divalent hydrocarbon moiety derived from an alkane having the number of carbon atoms indicated in the prefix. For example, $C_{1-6}$ means one to six carbons; $C_{1-6}$alkylene is meant to include methylene, ethylene, propylene, 2-methylpropylene, pentylene, hexylene and the like. $C_{1-4}$alkylene includes methylene $—CH_2—$, ethylene $—CH_2CH_2—$, propylene $—CH_2CH_2CH_2—$, and isopropylene $—CH(CH_3)CH_2—$, $—CH_2CH(CH_3)—$, $—CH_2—(CH_2)_2CH_2—$, $—CH_2—CH(CH_3)CH_2—$, $—CH_2—C(CH_3)_2—$, $—CH_2—CH_2CH(CH_3)—$. Typically, an alkyl (or alkylene) group will have from 1 to 24 carbon atoms, with those groups having 10 or fewer, 8 or fewer, or 6 or fewer carbon atoms being preferred in the present disclosure. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

The term "alkenyl" means a linear monovalent hydrocarbon radical or a branched monovalent hydrocarbon radical having the number of carbon atoms indicated in the prefix and containing at least one double bond. For example, $C_2$-$C_6$)alkenyl is meant to include ethenyl, propenyl, and the like. Similarly, the term "alkynyl" means a linear monovalent hydrocarbon radical or a branched monovalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkenylene" means a linear bivalent hydrocarbon radical moiety or a branched divalent hydrocarbon radical moiety having the number of carbon atoms indicated in the prefix and containing at least one double bond. For example, i.e., $C_{2-6}$ means two to six carbons; $C_{2-6}$ alkenylene is meant to include, but is not limited to, $—CH{=}CH—$, $—CH_2—CH{=}CH—$, $—CH_2—CH{=}C(CH_3)—$, $—CH{=}CH—CH{=}CH—$, and the like). Similarly, the term "alkynylene" means a linear bivalent hydrocarbon radical moiety or a branched divalent hydrocarbon radical moiety containing at least one triple bond and having the number of carbon atoms indicated in the prefix. For example, ($C_{2-6}$ means two to six carbons; $C_{2-6}$ alkynylene is meant to include, but is not limited to, $—C{\equiv}C—$, $—C{\equiv}CCH_2—$, $—CH_2—C{\equiv}CCH_2—$, $—C{\equiv}CCH(CH_3)—$, and the like. When a prefix is not included to indicate the number of carbon atoms in an alkenylene or alkynylene portion, the alkenylene moiety or portion thereof or the alkynylene moiety or portion thereof will have 12 or fewer main chain carbon atoms or 8 or fewer main chain carbon atoms or 6 or fewer main chain carbon atoms, or 4 or fewer main chain carbon atoms.

"Cycloalkyl", "Carbocyclic" or "Carbocycle" by itself or as part of another substituent, means saturated or unsaturated, non-aromatic monocyclic, bicyclic or tricyclic carbon ring systems having the number of carbon atoms indicated in the prefix or if unspecified having 3-10, also preferably 3-8, more preferably 3-6, ring members per ring, such as cyclopropyl, cyclobutyl, cyclopentyl, cyclohexyl, 1-cyclohexenyl, cycloheptyl, cyclooctyl, adamantyl, bicyclo[3.1.0]hexan-3-yl, spiro[3,3]heptan-2-yl, and the like, where one or two ring carbon atoms may optionally be replaced by a carbonyl. Cycloalkyl means hydrocarbon rings having the indicated number of ring atoms (e.g., $C_{3-8}$ cycloalkyl means three to eight ring carbon atoms). "Cycloalkyl" or "carbocycle" means a mono-, bicyclic or polycyclic group such as, for example, bicyclo[2.2.1]heptane, bicyclo[2.2.2]octane, spiro[3,3]heptane, bicyclo[3.1.0]hexane, etc. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s).

"Cycloalkylene" by itself or as part of another substituent, means a divalent saturated or unsaturated, non-aromatic monocyclic, bicyclic or tricyclic carbon ring systems having the number of carbon atoms indicated in the prefix or if unspecified having 3-10, also 3-8, more preferably 3-6, ring members per ring. "Cycloalkylene" also means a divalent cycloalkyl moiety, where the cycloalkyl as defined above having 3-10, also 3-8, more preferably 3-6, ring members per ring. Exemplary cycloalkylene includes, e.g., 1,2-, 1,3-, or 1,4-cis or trans-cyclohexylene, 2-methyl-1,4-cyclohexylene, 2,2-dimethyl-1,4-cyclohexylene, and the like.

"Cycloalkylalkyl" means an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

"Cycloalkylalkenyl" means an -(alkenylene)-cycloalkyl group where alkenylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{2-4}$ alkenyl is meant to have 3 to 8 ring carbon atoms and 2 to 4 alkenylene chain carbon atoms. Exemplary cycloalkylalkenyl includes, e.g., 2-cyclopropylvinyl, 2-cyclopentylvinyl, and the like.

"Cycloalkylalkynyl" means an -(alkynylene)-cycloalkyl group where alkynylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{2-4}$alkynyl is meant to have 3 to 8 ring carbon atoms and 2 to 4 alkynylene chain carbon atoms. Exemplary cycloalkylalkynyl includes, e.g., 2-cyclopropylethynyl, 2-cyclobutylethynyl, 2-cyclopentylethynyl and the like.

"Cycloalkenyl" by itself or as part of another substituent, means a non-aromatic monocyclic, bicyclic or tricyclic carbon ring system having the number of carbon atoms indicated in the prefix or if unspecified having 3-10, also 3-8, more preferably 3-6, ring members per ring, which contains at least one carbon-carbon double bond. Exemplary cycloalkenyl includes, e.g., 1-cyclohexenyl, 4-cyclohexenyl, 1-cyclopentenyl, 2-cyclopentenyl and the like.

"Cycloalkenylene" by itself or as part of another substituent, means a divalent unsaturated, non-aromatic monocyclic, bicyclic or tricyclic carbon ring system having the number of carbon atoms indicated in the prefix or if unspecified having 3-10, also 3-8, more preferably 3-6, ring members per ring. "Cycloalkenylene" also means a divalent cycloalkenyl moiety, where the cycloalkenyl as defined herein having 3-10, also 3-8, more preferably 3-6, ring members per ring. Exemplary cycloalkenylene includes, e.g., cyclohexene-1,4-diyl, 2-methyl-cyclohexene-1,4-diyl, 3-methyl-cyclohexene-1,4-diyl, 3,3-dimethyl-cyclohexene-1,4-diyl, cyclohexene-1,2-diyl, cyclohexene-1,3-diyl, and the like.

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, fluoromethyl, 2,2,2-trifluoroethyl, 4-chlorobutyl, 3-bromopropyl, and the like.

"Haloalkoxy" means a —O-haloalkyl group, where haloalkyl is as defined herein, e.g., trifluoromethoxy, 2,2,2-trifluoroethoxy, difluoromethoxy, fluoromethoxy, and the like.

"Alkoxy" means a —O-alkyl group, where alkyl is as defined herein. "Cycloalkoxy" means —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —$NH_2$.

"Alkylamino" means a —NH-alkyl group, where alkyl is as defined herein. Exemplary alkylamino groups include $CH_3NH$—, ethylamino, and the like.

"Dialkylamino" means a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —$NR^{dd}R^{ee}$, where $R^{dd}$ and $R^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Alkylthio" means —S-alkyl, where alkyl is as defined herein. Exemplary alkylthio groups include $CH_3S$—, ethylthio, and the like. The term "thioalkoxy" refers to a —O-alkylthio group, where the alkylthio group is as defined herein, e.g., thiomethoxy, thioethoxy, and the like.

"Aryl" by itself or as part of another substituent means a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl, 2-naphthyl and 4-biphenyl. Exemplary aryl groups, such as phenyl or naphthyl, may be optionally fused with a cycloalkyl of preferably 5-7, more preferably 5-6, ring members.

"Arylene" by itself or as part of another substituent, means a divalent monocyclic, bicyclic or polycyclic polyunsaturated aromatic hydrocarbon radical containing 6 to 14 ring carbon atoms, which can be a single ring or multiple rings (up to three rings) which are fused together or linked covalently. Arylene can be a divalent radical of the aryl group, where the aryl is as defined herein. Exemplary arylene includes, e.g., phenylene, biphenylene, and the like.

"Arylalkyl" means -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

"Arylalkoxy" means —O-(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkoxy include benzyloxy, phenethyloxy, and the like.

"Aryloxy" means —O-aryl, where the aryl group is as defined herein. Exemplary aryloxy includes, e.g., phenoxy.

"Arylthio" means —S-aryl, where the aryl group is as defined herein. Exemplary arylthio includes, e.g., phenylthio.

"Heteroaryl" by itself or as part of another substituent means a monocyclic aromatic ring radical containing 5 or 6 ring atoms, or a bicyclic aromatic radical having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridinyl, benzothiazolyl, benzothienyl, quinolyl, isoquinolyl, indazolyl, pteridinyl and thiadiazolyl. "Nitrogen containing heteroaryl" means heteroaryl wherein any of the heteroatoms is N. As used herein, "heterocyclic aromatic ring" is meant to be a heteroaryl ring.

"Heteroarylene" by itself or as part of another substituent, means a divalent monocyclic aromatic ring radical containing 5 or 6 ring atoms, or a divalent bicyclic aromatic radical having 8 to 10 atoms, containing one or more, preferably 1-4, more preferably 1-3, even more preferably 1-2, heteroatoms independently selected from the group consisting of O, S, and N. Heteroarylene can be a divalent radical of heteroaryl group, where the heteroaryl is as defined herein. Exemplary heteroarylene includes, e.g., pyridine-2,5-diyl, pyrimidine-2,5-diyl, pyridazine-3,5-diyl, pyrazine-2,5-diyl, and the like.

"Heteroarylalkyl" means -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. Non-limiting examples of heteroarylalkyl include 2-pyridylmethyl, 4-pyridylmethyl, 2-thiazolylethyl, and the like.

"Heterocycloalkyl" by itself or as part of another substituent, means a saturated or unsaturated non-aromatic cycloalkyl group that contains from one to five ring heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, preferably 4 to 10 ring atoms, more preferably 5 to 8 ring atoms in which one to five ring atoms are heteroatoms selected from —N═, —N—, —O—, —S—, —S(O)—, or —$S(O)_2$— and further wherein one or two ring atoms are optionally replaced by a —C(O)— group. The heterocycloalkyl can also be a heterocyclic alkyl ring fused with a cycloalkyl, an aryl or a heteroaryl ring. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non limiting examples of heterocycloalkyl groups include oxetanyl, azetidinyl, pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, 1-methylpyridin-2-one moiety, 1-methyl-2-oxo-3-pyridyl, 1-methyl-2-oxo-4-pyridyl, 1-methyl-2-oxo-5-pyridyl, 1-methyl-2-oxo-6-pyridyl, 1,3-dimethylpyridin-2-one-4-yl, 1,3-dimethylpyridin-2-one-5-yl, 1-methylpyridin-2-one-4-yl, 1-methylpyridin-2-one-5-yl, 1-isopropyllpyridin-2-one-5-yl, 3-methyl-1H-pyridin-2-one-5-yl, 2-pyridone-5-yl, and the like. A heterocycloalkyl group can be attached to the remainder of the molecule through a ring carbon or a heteroatom. As used herein, the term "heterocycloalkylene" by itself or as part of another substituent, refers to a divalent heterocycloalkyl, where the heterocycloalkyl is as defined herein. Non-limiting examples of heterocycloalkylene include piperazine-1,4-diyl, piperidine-1,4-diyl, 1,2,3,6-tetrahydropyridine-1,4-diyl, 1,2,3,6-tetrahydropyridine-1,5-diyl, 2,3,6,7-tetrahydro-1H-azepine-1,4-diyl, 2,3,6,7-tetrahydro-1H-azepine-1,5-diyl, 2,5-dihydro-1H-pyrrole-1,3-diyl, azabicyclo[3.2.1]octane-3,8-diyl, 3,8-diazabicyclo[3.2.1]octane-3,8-diyl, 8-azabicyclo[3.2.1]octane-3,8-diyl, 2-azabicyclo[2.2.2]octane-2,5-diyl, 2,5-diazabicyclo[2.2.2]octane-2,5-diyl, 3-oxomorpholin-2-yl, 3-oxomorpholin-4-yl, 3-oxomorpholin-5-yl, 3-oxomorpholin-6-yl, 2-oxopiperazin-3-yl, 2-oxopiperazin-4-yl, 2-oxopiperazin-5-yl, 2-oxopiperazin-6-yl, 2-oxopiperazin-7-yl, piperazin-1-oxide-2-yl, piperazin-1-oxide-3-yl, piperazin-1-oxide-4-yl, pyridine-2-one-3-yl, pyridine-2-one-4-yl, pyridine-2-one-5-yl, pyridine-2-one-6-yl, pyridine-2-one-7-yl, piperidinyl, morpholinyl, piperazinyl, isoxazolinyl, pyrazolinyl, imidazolinyl, pyrazol-5-one-3-yl, pyrazol-5-one-4-yl, pyrrolidine-2,5-dione-1-yl, pyrrolidine-2,5-dione-3-yl, pyrrolidine-2,5-dione-4-yl, imidazolidine-2,4-dione-1-yl, imidazolidine-2,4-dione-3-yl, imidazolidine-2,4-dione-5-yl, pyrrolidinyl, tetrahydroquinolinyl, decahydroquinolinyl, tetrahydrobenzooxazepinyl, dihydrodibenzooxepinyl, and the like.

"Heterocycle" or "Heterocyclic" by itself or as part of another substituent, means a heteroaryl or heterocycloalkyl ring or moiety, where heteroaryl and heterocycloalkyl are as defined herein.

"Heterocycloalkylene" by itself or as part of another substituent, means a divalent heterocycloalkyl, where the heterocycloalkyl is as defined herein. Exemplary heterocycloalkyl includes, e.g., piperazine-1,4-diyl, piperidine-1,4-diyl, 1,2,3,6-tetrahydropyridine-1,4-diyl, 3-azabicyclo[3.2.1]octane-3,8-diyl, 3,8-diazabicyclo[3.2.1]octane-3,8-diyl, 8-azabicyclo[3.2.1]octane-3,8-diyl, 2-azabicyclo[2.2.2]octane-2,5-diyl, 2,5-diazabicyclo[2.2.2]octane-2,5-diyl, 2,3,6,7-tetrahydro-1H-azepine-1,4-diyl, 2,3,6,7-tetrahydro-1H-azepine-1,5-diyl, 2,5-dihydro-1H-pyrrole-1,3-diyl and the like.

"Heterocycloalkylalkyl" means -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Non-limiting examples of heterocycloalkylalkyl include 2-pyridylmethyl, 2-thiazolylethyl, pyrrolidin-1-ylmethyl, 2-piperidinylmethyl and the like.

The substituents for alkyl, alkenyl, alkynyl, alkoxy, haloalkyl, haloalkoxy, cycloalkyl, cycloalkylalkyl, heterocycloalkyl, heterocycloalkylalkyl, heterocycloalkenyl, alkylene, alkenylene, or alkynlene include, but are not limited to, R', halogen, —OH, —$NH_2$, —$NO_2$, —CN, —C(O)OH, —C(S)OH, —$B(OH)_2$, —$Si(Me)_3$, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —OR', —$Si(R')_3$, —SR', —OC(O)R', —OC(S)R', —C(O)R', —C(S)R', —C(O)OR', —C(S)OR', —S(O)R', —$S(O)_2$R', —C(O)NHR', —C(S)NHR', —C(O)NR'R", —C(S)NR'R, —$S(O)_2$NHR', —$S(O)_2$NR'R", —C(NH)NHR', —C(NH)NR'R", —NHC(O)R', —NHC(S)R', —NR"C(O)R', —NR'C(S)R", —$NHS(O)_2$R', —NR'$S(O)_2$R", —NHC(O)NHR', —NHC(S)NHR', —NR'C (O)$NH_2$, —NR'C(S)$NH_2$, —NR'C(O)NHR", —NR'C(S)NHR", —NHC(O)NR'R", —NHC(S)NR'R", —NR'C(O)NR"R'", —NR'"C(S)NR'R", —NHS$(O)_2$NHR', —NR'S$(O)_2$$NH_2$, —NR'S$(O)_2$NHR", —NHS$(O)_2$NR'R", —NR'S$(O)_2$NR"R'", —NHR', and —NR'R" in a number ranging from zero to (2m'+1), where m' is the total number of carbon atoms in such group. R', R" and R'" each independently refer to hydrogen, $C_{1-8}$ alkyl, heterocycloalkyl, aryl, heteroaryl, arylalkyl, heteroarylalkyl, aryl substituted with 1-3 halogens, $C_{1-8}$ alkoxy, haloalkyl, haloalkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R'" can be further substituted with $R^{a1}$, halogen, —OH, —$NH_2$, —$NO_2$, —CN, —C(O)OH, —C(S)OH, —C(O)$NH_2$, —C(S)$NH_2$, —S$(O)_2$$NH_2$, —NHC(O)$NH_2$, —NHC(S)$NH_2$, —NHS$(O)_2$$NH_2$, —C(NH)$NH_2$, —O$R^{a1}$, —S$R^{a1}$, —OC(O)$R^{a1}$, —OC(S)$R^{a1}$, —C(O)$R^{a1}$, —C(S)$R^{a1}$, —C(O)O$R^{a1}$, —C(S)O$R^{a1}$, —S(O)$R^{a1}$, —S$(O)_2$$R^{a1}$, —C(O)NH$R^{a1}$, —C(S)NH$R^{a1}$, —C(O)N$R^{a1}R^{a2}$, —C(S)N$R^{a1}R^{a2}$, —S$(O)_2$NH$R^{a1}$, —S$(O)_2$N$R^{a1}R^{a2}$, —C(NH)NH$R^{a1}$, —C(NH)N$R^{a1}R^{a2}$, —NHC(O)$R^{a1}$, —NHC(S)$R^{a1}$, —N$R^{a2}$C(O)$R^{a1}$, —N$R^{a1}$C(S)$R^{a2}$, —NHS$(O)_2$$R^{a1}$, —N$R^{a1}$S$(O)_2$$R^{a2}$, —NHC(O)NH$R^{a1}$, —NHC(S)NH$R^{a1}$, —N$R^{a1}$C(O)$NH_2$, —N$R^{a1}$C(S)$NH_2$, —N$R^{a1}$C(O)NH$R^{a2}$, —N$R^{a1}$C(S)NH$R^{a2}$, —NHC(O)N$R^{a1}R^{a2}$, —NHC(S)N$R^{a1}R^{a2}$, —N$R^{a1}$C(O)N$R^{a2}R^{a3}$, —N$R^{a3}$C(S)N$R^{a1}R^{a2}$, —NHS$(O)_2$NH$R^{a1}$, —N$R^{a1}$S$(O)_2$$NH_2$, —N$R^{a1}$S$(O)_2$NH$R^{a2}$, —NHS$(O)_2$N$R^{a1}R^{a2}$, —N$R^{a1}$S$(O)_2$N$R^{a2}R^{a3}$, —NH$R^{a1}$, and —N$R^{a1}R^{a2}$ in a number ranging from zero to (2n'+1), where n' is the total number of carbon atoms in such group. $R^{a1}$, $R^{a2}$ and $R^{a3}$ each independently refer to hydrogen, $C_{1-8}$ alkyl, heterocycloalkyl, aryl, heteroaryl, arylalkyl, heteroarylalkyl, aryl substituted with 1-3 halogens, $C_{1-8}$ alkoxy, haloalkyl, haloalkoxy or $C_{1-8}$ thioalkoxy groups, or unsubstituted aryl-$C_{1-4}$ alkyl groups. $R^{a1}$, $R^{a2}$ and $R^{a3}$ can be further substituted with $R^{b1}$, halogen, —OH, —$NH_2$, —$NO_2$, —CN, —C(O)OH, —C(S)OH, —C(O)$NH_2$, —C(S)$NH_2$, —S$(O)_2$$NH_2$, —NHC(O)$NH_2$, —NHC(S)$NH_2$, —NHS$(O)_2$$NH_2$, —C(NH)$NH_2$, —O$R^{b1}$, —S$R^{b1}$, —OC(O)$R^{b1}$, —OC(S)$R^{b1}$, —C(O)$R^{b1}$, —C(S)$R^{b1}$, —C(O)O$R^{b1}$, —C(S)O$R^{b1}$, —S(O)$R^{b1}$, —S$(O)_2$$R^{b1}$, —C(O)NH$R^{b1}$, —C(S)NH$R^{b1}$, —C(O)N$R^{b1}R^{b2}$, —C(S)N$R^{b1}R^{b2}$, —S$(O)_2$NH$R^{b1}$, —S$(O)_2$N$R^{b1}R^{b2}$, —C(NH)NH$R^{b1}$, —C(NH)N$R^{b1}R^{b2}$, —NHC(O)$R^{b1}$, —NHC(S)$R^{b1}$, —N$R^{b2}$C(O)$R^{b1}$, —N$R^{b1}$C(S)$R^{b2}$, —NHS$(O)_2$$R^{b1}$, —N$R^{b1}$ S$(O)_2$$R^{b2}$, —NHC(O)NH$R^{b1}$, —NHC(S)NH$R^{b1}$, —N$R^{b1}$C(O)$NH_2$, —N$R^{b1}$C(S)$NH_2$, —N$R^{b1}$C(O)NH$R^{b2}$, —N$R^{b1}$C(S)NH$R^{b2}$, —NHC(O)N$R^{b1}R^{b2}$, —NHC(S)N$R^{b1}R^{b2}$, —N$R^{b1}$C(O)N$R^{b2}R^{b3}$, —N$R^{b3}$C(S)N$R^{b1}R^{b2}$, —NHS$(O)_2$NH$R^{b1}$, —N$R^{b1}$S$(O)_2$$NH_2$, —N$R^{b1}$S$(O)_2$NH$R^{b2}$, —NHS$(O)_2$N$R^{b1}R^{b2}$, —N$R^{b1}$S$(O)_2$N$R^{b2}R^{b3}$, —NH$R^{b1}$, and —N$R^{b1}R^{b2}$ in a number ranging from zero to (2p'+1), where p' is the total number of carbon atoms in such group. $R^{b1}$, $R^{b2}$ and $R^{b3}$ each independently refer to hydrogen, $C_{1-8}$ alkyl, heterocycloalkyl, aryl, heteroaryl, arylalkyl, heteroarylalkyl, aryl substituted with 1-3 halogens, $C_{1-8}$ alkoxy, haloalkyl, haloalkoxy or $C_{1-8}$ thioalkoxy groups, or unsubstituted aryl-$C_{1-4}$ alkyl groups.

Substituents for the aryl and heteroaryl groups are varied and include, but are not limited to: R', halogen, —OH, —$NH_2$, —$NO_2$, —CN, —C(O)OH, —C(S)OH, —C(O)$NH_2$, —C(S)$NH_2$, —S$(O)_2$$NH_2$, —NHC(O)$NH_2$, —NHC(S)$NH_2$, —NHS$(O)_2$$NH_2$, —C(NH)$NH_2$, —OR', —SR', —OC(O)R', —OC(S)R', —C(O)R', —C(S)R', —C(O)OR', —C(S)OR', —S(O)R', —S$(O)_2$R', —C(O)NHR', —C(S)NHR', —C(O)NR'R", —C(S)NR'R'", —S$(O)_2$NHR', —S$(O)_2$NR'R', —C(NH)NHR', —C(NH)NR'R", —NHC(O)R', —NHC(S)R', —NR"C(O)R', —NR'C(S)R", —NHS$(O)_2$R', —NR'S$(O)_2$R", —NHC(O)NHR', —NHC(S)NHR', —NR'C(O)$NH_2$, —NR'C(S)$NH_2$, —NR'C(O)NHR", —NR'C(S)NHR", —NHC(O)NR'R", —NHC(S)NR'R", —NR'C(O)NR"R'", —NR'"C(S)NR'R", —NHS$(O)_2$NHR', —NR'S$(O)_2$$NH_2$, —NR'S$(O)_2$NHR", —NHS$(O)_2$NR'R", —NR'S$(O)_2$NR"R'", —NHR', —NR'R", —$N_3$, perfluoro$(C_1$-$C_4)$alkoxy, and perfluoro$(C_1$-$C_4)$alkyl, in a number ranging from zero to the total number of open valences on the aromatic ring system; and where R', R" and R'" are independently selected from hydrogen, haloalkyl, haloalkoxy, $C_{1-8}$ alkyl, $C_{3-6}$ cycloalkyl, cycloalkylalkyl, $C_{2-8}$ alkenyl, $C_2$ alkynyl, aryl, arylalkyl, heteroaryl, heteroarylalkyl, aryl-$C_{1-4}$ alkyl, and aryloxy-$C_{1-4}$ alkyl. Other suitable substituents include each of the above aryl substituents attached to a ring atom by an alkylene tether of from 1-4 carbon atoms. R', R" and R'" can be further substituted with $R^{a1}$, halogen, —OH, —$NH_2$, —$NO_2$, —CN, —C(O)OH, —C(S)OH, —C(O)$NH_2$, —C(S)$NH_2$, —S$(O)_2$$NH_2$, —NHC(O)$NH_2$, —NHC(S)$NH_2$, —NHS$(O)_2$$NH_2$, —C(NH)$NH_2$, —O$R^{a1}$, —S$R^{a1}$, —OC(O)$R^{a1}$, —OC(S)$R^{a1}$, —C(O)$R^{a1}$, —C(S)$R^{a1}$, —C(O)O$R^{a1}$, —C(S)O$R^{a1}$, —S(O)$R^{a1}$, —S$(O)_2$$R^{a1}$, —C(O)NH$R^{a1}$, —C(S)NH$R^{a1}$, —C(O)N$R^{a1}R^{a2}$, —C(S)N$R^{a1}R^{a2}$, —S$(O)_2$NH$R^{a1}$, S$(O)_2$N$R^{a1}R^{a2}$, —C(NH)NH$R^{a1}$, —C(NH)N$R^{a1}R^{a2}$, —NHC(O)$R^{a1}$, —NHC(S)$R^{a1}$, —N$R^{a2}$C(O)$R^{a1}$, —N$R^{a1}$C(S)$R^{a2}$, —NHS$(O)_2$$R^{a1}$, —N$R^{a1}$S$(O)_2$$R^{a2}$, —NHC(O)NH$R^{a1}$, —NHC(S)NH$R^{a1}$, —N$R^{a1}$C(O)$NH_2$, —N$R^{a1}$C(S)$NH_2$, —N$R^{a1}$C(O)NH$R^{a2}$, —N$R^{a1}$C(S)NH$R^{a2}$, —NHC(O)N$R^{a1}R^{a2}$, —NHC(S)N$R^{a1}R^{a2}$, —N$R^{a1}$C(O)N$R^{a2}R^{a3}$, —N$R^{a3}$C(S)N$R^{a1}R^{a2}$, —NHS$(O)_2$NH$R^{a1}$, —N$R^{a1}$S$(O)_2$$NH_2$, —N$R^{a1}$S$(O)_2$NH$R^{a2}$, —NHS$(O)_2$N$R^{a1}R^{a2}$, —N$R^{a1}$S$(O)_2$N$R^{a2}R^{a3}$, —NH$R^{a1}$, —N$R^{a1}R^{a2}$, —$N_3$, perfluoro$(C_1$-$C_4)$alkoxy, and perfluoro$(C_1$-$C_4)$alkyl, in a number ranging from zero to the total number of open valences on the aromatic ring system; and where $R^{a1}$, $R^{a2}$ and $R^{a1}$ are each independently selected from hydrogen, haloalkyl, haloalkoxy, $C_{1-8}$ alkyl, $C_{3-6}$ cycloalkyl, cycloalkylalkyl, $C_{2-8}$ alkenyl, $C_{2-8}$ alkynyl, aryl, arylalkyl, heteroaryl, heteroarylalkyl, aryl-$C_{1-4}$ alkyl, or aryloxy-$C_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-$(CH_2)_r$—B—, wherein A and B are independently —$CH_2$—, —O—, —NH—, —S—, —S(O)—, —S$(O)_2$—, —S$(O)_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —$(CH_2)_s$—X—$(CH_2)_t$—, where s and t are independently integers of from 0 to 3, and X is —O—, —NR'—, —S—, —S(O)—, —S$(O)_2$—, or —S$(O)_2$NR'—.

The substituent R' in —NR'— and —$S(O)_2NR'$— is selected from hydrogen or unsubstituted $C_{1-6}$ alkyl.

"Protecting group" refers to a grouping of atoms that when attached to a reactive group in a molecule masks, reduces or prevents that reactivity. Examples of protecting groups can be found in T. W. Greene and P. G. Wuts, Protective Groups in Organic Chemistry, (Wiley, 4th ed. 2006), Beaucage and Iyer, *Tetrahedron* 48:2223-2311 (1992), and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2$═$CHCH_2$—, and the like, groups of the formula —C(O)R', wherein R' is, for example, methyl, phenyl, trifluoromethyl, and the like, groups of the formula —$SO_2R''$, wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, Current Protocols in Nucleic Acid Chemistry, John Wiley and Sons, New York, Volume 1, 2000).

"Optional" or "Optionally" as used throughout the specification means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In the present context, the term "therapeutically effective" or "effective amount" indicates that a compound or amount of the compound when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

Bromodomains are a family of (~110 amino acid) structurally and evolutionary conserved protein interaction modules that specifically recognize acetylated lysines present in substrate proteins, notably histones. Bromodomains exist as components of large multidomain nuclear proteins that are associated with chromatin remodeling, cell signaling and transcriptional control. There are a total of 61 human bromodomains found within 46 human proteins. Examples of bromodomain-containing proteins with known functions include: (i) histone acetyltransferases (HATs), including CREBBP, GCN5, PCAF and TAFII250; (ii) methyltransferases such as ASH1L and MLL; (iii) components of chromatin-remodeling complexes such as Swi2/Snf2; and (iv) a number of transcriptional regulators (Florence et al. *Front. Biosci.* 2001, 6, D1008-1018).

As used herein, the terms "bromodomain mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present disclosure relates to treating or lessening the severity of one or more diseases in which one or more of the bromodomain-containing proteins, such as BET proteins, such as BRD2, BRD3, BRD4, and/or BRDT, or a mutant thereof, are known to play a role. For example, a disease or condition in which the biological function of bromodomain affects the development and/or course of the disease or condition, and/or in which modulation of bromodomain alters the development, course, and/or symptoms. Bromodomain mediated disease or condition includes a disease or condition for which bromodomain inhibition provides a therapeutic benefit, e.g. wherein treatment with bromodomain inhibitors, including compounds described herein, provides a therapeutic benefit to the subject suffering from or at risk of the disease or condition. The term "inhibiting bromodomain" or "bromodomain inhibitor" means a compound which inhibits the binding of a bromodomain with its cognate acetylated proteins, for example, the bromodomain inhibitor is a compound which inhibits the binding of a bromodomain to acetylated lysine residues.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an protein such as a bromodomain. Generally a ligand or modulator will be a small molecule, where "small molecule refers to a compound with a molecular weight of 1500 Daltons or less, or preferably 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 μM or less, 100 nM or less, 10 nM or less, or 1 nM or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the present disclosure, the term "synthesizing" and like terms means chemical synthesis from one or more precursor materials.

As used herein, the term "lone pair" or "lone pair of electrons" refers to a pair of electrons in the outermost shell of an atom, in particular a nitrogen atom, that are not used in bonding.

As used herein, the term "modulating" or "modulate" refers to an effect of altering a biological activity, especially a biological activity associated with a particular biomolecule such as a bromodomain protein. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

"Prodrug" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N═C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular formulae but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007).

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

The terms "prevent", "preventing", "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or reacquiring a disorder or condition or one or more of its attendant symptoms.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury); disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal cord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The compounds of the present disclosure may also contain unnatural proportions of atomic isotopes at one or more of the atoms that constitute such compounds. For example, the compounds may be radiolabelled with radioactive isotopes, such as for example tritium ($^3H$), iodine-125 ($^{125}I$), carbon-14 ($^{14}C$) carbon-11 ($^{11}C$) or fluorine-18 ($^{18}F$). All isotopic variations of the compounds of the present disclosure, whether radioactive or not, are intended to be encompassed within the scope of the present disclosure.

The term "deuterated" as used herein alone or as part of a group, means substituted deuterium atoms. When a particular position is designated as holding deuterium (stated as "D" or "deuterium"), it is understood that the abundance of deuterium at that position is substantially greater than the natural abundance of deuterium, which is 0.015% (i.e., at least 50.1% incorporation of deuterium).

The term "deuterated analog" as used herein alone or as part of a group, means substituted deuterium atoms in place of hydrogen. The deuterated analog of the present disclosure may be a fully or partially deuterium substituted derivative. Preferably the deuterium substituted compound of the present disclosure holds a fully or partially deuterium substituted alkyl, aryl or heteroaryl group. In one embodiment, the deuterium substituted compound of the present disclosure holds a fully or partially deuterium substituted alkyl group, e.g., $—CD_3$, $CD_2CD_3$, $—CD_2CD_2CD_3$ (n-propyl-D7), $—CD(CD_3)_2$ (iso-propyl-D7), $—CD_2CD_2CD_2CD_3$ (n-butyl-D9), $—CD_2$-$CD(CD_3)_2$ (iso-butyl-D9) and the like. In another embodiment, the deuterium substituted compound of the present disclosure holds a fully or partially deuterium substituted aryl, such as phenyl, e.g., $C_6D_5$ or a fully or partially deuterium substituted heteroaryl, e.g., pyrazoly-$d_2$, thiazolyl-$d_2$, pyridyl-$d_3$, and the like.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Unless otherwise stated, when a position is designated specifically as "H" or "hydrogen", the position is understood to have hydrogen at its natural abundance isotopic composition or its isotopes, such as deuterium (D) or tritium ($^3H$). Certain isotopically-labeled compounds of the present disclosure (e.g., those labeled with $^3H$ and $^{14}C$) are useful in compound and/or substrate tissue distribution assays. Tritiated (i.e., $^3H$) and carbon-14 (i.e., $^4C$) and fluorine-18 ($^{18}F$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the Schemes and in the Examples herein below, by substituting an isotopically labeled reagent for a non-isotopically labeled reagent.

II. General

The present disclosure concerns compounds of Formulas (I), (I'), (II), (III), (IV), (V), (Va) or (Vb), and all sub-generic formulae, compounds as recited in the claims, and compounds described herein that are modulators of bromodomains and the use of such compounds in the treatment of diseases or conditions.

III. Compounds

In one aspect, the present disclosure provides compounds of formula (I):

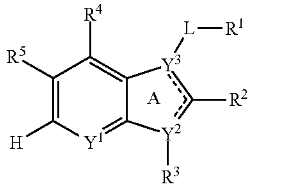

(I)

or a pharmaceutically acceptable salt, a prodrug, solvate, a tautomer, an isomer or a deuterated analog thereof; wherein the variables R', $R^2$, $R^3$, $R^4$, $R^5$, L, Y', $Y^2$, $Y^3$ and symbol ------ are as defined in the Summary. In some embodiments of compounds of formula (I), the symbol ------ is a single bond or a double bond to maintain the 5-member ring A being aromatic. In one embodiment of the compounds of formula (I), the symbol ------ represents a single bond.

In some embodiments of compounds of formula (I), (i) $Y^2$ is N and $Y^3$ is C; or (ii) $Y^2$ is C and $Y^3$ is N;

$Y^1$ is CH or N;

L is a bond, optionally substituted $C_{1-6}$alkylene, optionally substituted deuterated $C_{1-6}$alkylene optionally substituted —C($R^6R^7$)—, —C(O)N$R^9$—, —$CH_2$N($R^9$)—, —$SO_2$N($R^9$)—, —N($R^9$)C(O)N($R^9$)—, —N($R^9$)$SO_2$—, —N($R^9$)$CH_2$—, —O$C_{1-4}$alkylene-, —$C_{1-4}$alkylene-O—, —N$R^9$C(O)—, —N($R^5$)$SO_2$—, —C(O)—, —S(O)—, —$SO_2$—, —O—, —S—, —P(O)($R^a$)—, optionally substituted $C_{2-6}$alkenylene, optionally substituted —CH═C($R^b$)— or —Si($R^c$)($R^c$)—, wherein $R^6$ and $R^7$ are each independently H, D, halogen, —OH, $C_{1-6}$alkyl, deuterated $C_{1-6}$alkyl, $C_{2-6}$-alkenyl, $C_{2-6}$alkynyl, aryl, aryl-$C_{1-4}$ alkyl, $C_{1-6}$alkoxy, $C_{3-6}$cycloalkyl, $C_{3-6}$cycloalkyl-$C_{1-4}$alkyl, heterocycloalkyl, heterocycloalkyl-$C_{1-4}$alkyl, heteroaryl, heteroarylalkyl, $C_{1-6}$haloalkyl, $C_{1-6}$haloalkoxy, $R^j$, —O$R^d$, —N$R^d R^d$, —C(O)O$R^d$, —OC(O)$R^d$, —OC(O)O$R^d$, —C(O)$R^d$, —NHC(O)$R^d$, —C(O)N$R^d R^d$, —$SO_2R^d$, —NH$SO_2R^d$ or —$SO_2$N$R^d R^d$; or $R^6$ and $R^7$ taken together with the carbon atom to which they attach form an optionally substituted 3- to 6-membered ring having from 0-2 heteroatoms selected from O, N or S or an oxo; wherein at each occurrence, $R^6$ or $R^7$ is further optionally substituted with from 1-3 independently selected $R^h$ members; wherein the aliphatic or aromatic portion of L is optionally substituted with from 1-3 $R^e$ substituents independently selected from $C_{1-6}$alkyl, $C_{1-6}$alkoxy, halogen, —OH, —CN, —$NH_2$, vinyl, ethynyl, $C_{3-6}$cycloalkyl, aryl, $C_{1-6}$haloalkyl, $C_{1-6}$haloalkoxy, —C(O)O$R^f$, —OC(O)$R^f$, —OC(O)O$R^f$, —C(O)$R^f$, —NHC(O)$R^f$, —C(O)N$R^f R^f$, —$SO_2R^f$, —NH$SO_2R^f$ or —$SO_2$N$R^f R^f$; $R^9$ is H, $C_{1-4}$alkyl or $C_{1-4}$haloalkyl; $R^a$ is optionally substituted $C_{1-6}$alkyl, optionally substituted aryl or optionally substituted heteroaryl; each $R^d$ is independently selected from H, $C_{1-6}$alkyl, $C_{3-6}$cycloalkyl, $C_{3-6}$cycloalkyl-$C_{1-4}$alkyl or aryl, each of which is optionally substituted; each $R^f$ is independently H or $C_{1-6}$alkyl; $R^b$ is H or $C_{1-6}$alkyl; or $R^b$ and $R^1$ taken together with the carbon atom to which they attach form an optionally substituted 3- to 6-membered carbocyclic ring or an optionally substituted 4- to 8-membered heterocyclic ring having from 1-2 heteroatoms as ring members selected from O, N or S, wherein the nitrogen or sulfur ring atoms can be optionally oxidized; each $R^c$ is independently $C_{1-6}$alkyl or $C_{1-6}$alkoxy;

$R^1$, $R^2$ and $R^4$ are each independently H, optionally substituted $C_{1-6}$alkyl, optionally substituted $C_{1-6}$ alkenyl, optionally substituted $C_{1-6}$ alkynyl, optionally substituted aryl, optionally substituted heteroaryl, optionally substituted cycloalkyl, optionally substituted cycloalkenyl, optionally substituted heterocycloalkyl, optionally substituted heterocycloalkylalkyl, optionally substituted cycloalkylalkyl, optionally substituted arylalkyl, optionally substituted heteroarylalkyl, optionally substituted heterocycloalkylalkyl or $R^{13}$, wherein $R^{13}$ is selected from halogen, —CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —CH═C($R^g$)($R^g$), —O$R^g$, —S$R^g$, —OC(O)$R^g$, —OC(S)$R^g$, —P(═O)H$R^g$, —P(═O)$R^g R^g$, —PH(═O)O$R^g$, —P(═O)(O$R^g$)$_2$, —OP(═O)(O$R^g$)$_2$, —C(O)H, —O(CO)O$R^g$, —C(O)$R^g$, —C(S)$R^g$, —C(O)O$R^g$, —C(S)O$R^g$, —S(O)$R^g$, —S(O)$_2R^g$, —C(O)NH$R^g$, —C(S)NH$R^g$, —C(O)N$R^g R^g$, —C(S)N$R^g R^g$, —S(O)$_2$NH$R^g$, —S(O)$_2$N$R^g R^g$, —C(NH)NH$R^g$, —C(NH)N$R^g R^g$, —NHC(O)$R^g$, —NHC(S)$R^g$, —N$R^g$C(O)$R^g$, —N$R^g$C(S)$R^g$, —NHS(O)$_2R^g$, —N$R^g$S(O)$_2R^g$, —NHC(O)NH$R^g$, —NHC(S)NH$R^g$, —N$R^g$C(O)$NH_2$, —N$R^g$C(S)$NH_2$, —N$R^g$C(O)NH$R^g$, —N$R^g$C(S)NH$R^g$, —NHC(O)N$R^g R^g$, —NHC(S)N$R^g R^g$, —N$R^g$C(O)N$R^g R^g$, —N$R^g$C(S)N$R^g R^g$, —NHS(O)$_2$NH$R^g$, —N$R^g$S(O)$_2NH_2$, —N$R^g$S(O)$_2$NH$R^g$, —NHS(O)$_2$N$R^g R^g$, —N$R^g$S(O)$_2$N$R^g R^g$, —NH$R^g$ or —N$R^g R^g$, wherein each $R^g$ is independently H, optionally substituted $C_{1-6}$alkyl, optionally substituted $C_{1-6}$ alkenyl, optionally substituted $C_{1-6}$ alkynyl, optionally substituted aryl, optionally substituted heteroaryl, optionally substituted cycloalkyl, optionally substituted heterocycloalkyl, optionally substituted heterocycloalkylalkyl, optionally substituted cycloalkylalkyl, optionally substituted arylalkyl, optionally substituted heteroarylalkyl or optionally substituted heterocycloalkylalkyl; or two $R^g$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein the aliphatic or aromatic portion of $R^g$ is optionally substituted with from 1-3 $R^h$ substituents independently selected from halogen, —CN, —OH, —$NH_2$, —$NO_2$, —CH═C($R^i$)($R^i$), —C(O)OH, —C(S)OH, —C(O)$NH_2$, —C(S)$NH_2$, —B(OH)$_2$, —Si($R^i$)$_3$, —S(O)$_2NH_2$, —NHC(O)$NH_2$, —NHC(S)$NH_2$, —NHS(O)$_2NH_2$, —C(NH)$NH_2$, —O$R^i$, —S$R^i$, —OC(O)$R^i$, —OC(S)$R^i$, —P(═O)H$R^i$, —P(═O)$R^i R^i$, —PH(═O)O$R^i$, —P(═O)(O$R^i$)$_2$, —OP(═O)(O$R^i$)$_2$, —C(O)H, —O(CO)O$R^i$, —C(O)$R^i$, —C(S)$R^i$, —C(O)O$R^i$, —C(S)O$R^i$, —S(O)$R^i$, —S(O)$_2R^i$, —C(O)NH$R^i$, —C(S)NH$R^i$, —C(O)N$R^i R^i$, —C(S)N$R^i R^i$, —S(O)$_2$NH$R^i$, —S(O)$_2$N$R^i R^i$, —C(NH)NH$R^i$, —C(NH)N$R^i R^i$, —NHC(O)$R^i$, —NHC(S)$R^i$, —N$R^i$C(O)$R^i$, —N$R^i$C(S)$R^i$, —NHS(O)$_2R^i$, —N$R^i$S(O)$_2R^i$, —NHC(O)NH$R^i$, —NHC(S)NH$R^i$, —N$R^i$C(O)$NH_2$, —N$R^i$C(S)$NH_2$, —N$R^i$C(O)NH$R^i$, —N$R^i$C(S)NH$R^i$, —NHC(O)N$R^i R^i$, —NHC(S)N$R^i R^i$, —N$R^i$C(O)N$R^i R^i$, —N$R^i$C(S)N$R^i R^i$, —NHS(O)$_2$NH$R^i$, —N$R^i$S(O)$_2NH_2$, —N$R^i$S(O)$_2$NH$R^i$, —NHS(O)$_2$N$R^i R^i$, —N$R^i$S(O)$_2$N$R^i R^i$, $R^i$, —NH$R^i$ or —N$R^i R^i$, wherein each $R^i$ is independently $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl or heterocycloalkyl-$C_{1-4}$alkyl, wherein each $R^i$ is further optionally substituted with from 1-3 $R^p$ groups independently selected from halogen, CN, —OH, —$NH_2$, —N($R^q$)($R^q$), —$NO_2$, —C(O)OH, —C(O)$NH_2$, —S(O)$_2NH_2$, —NHC(O)$NH_2$, —C(NH)$NH_2$, —P(═O)H$R^q$, —P(═O)$R^q R^q$, —PH(═O)O$R^q$, —P(═O)(O$R^q$)$_2$, —OP(═O)(O$R^q$)$_2$, —OC(O)$R^q$, —OC(S)$R^q$, —C(O)$R^q$, —C(S)

$R^q$, —C(O)OR$^q$, —S(O)$_2$R$^q$, —C(O)NHR$^q$, $C_{1-6}$alkyl, $C_{1-6}$alkoxy, halogen, $C_{1-6}$ haloalkyl or $C_{1-6}$ haloalkoxy, wherein $R^q$ is $C_{1-6}$alkyl;

$R^3$ is H, halogen, —CN, optionally substituted $C_{1-6}$alkyl, optionally substituted deuterated $C_{1-6}$alkyl, optionally substituted aryl, optionally substituted aryl-$C_{1-4}$alkyl, optionally substituted heteroaryl, optionally substituted heteroaryl-$C_{1-4}$alkyl, optionally substituted $C_{3-8}$ cycloalkyl, optionally substituted $C_{3-8}$ cycloalkenyl, optionally substituted $C_{3-8}$ cycloalkyl-$C_{1-4}$alkyl, optionally substituted $C_{2-6}$ alkynyl, optionally substituted heterocycloalkyl, optionally substituted heterocycloalkyl-$C_{1-4}$alkyl or $R^j$ selected from halogen, —CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —CH═C($R^k$)($R^k$), —O$R^k$, —S$R^k$, —OC(O)$R^k$, —OC(S)$R^k$, —P(═O)H$R^k$, —P(═O)$R^kR^k$, —PH(═O)O$R^k$, —P(═O)(O$R^k$)$_2$, —OP(═O)(O$R^k$)$_2$, —C(O)H, —O(CO)O$R^k$, —C(O)$R^k$, —C(S)$R^k$, —C(O)O$R^k$, —C(S)O$R^k$, —S(O)$R^k$, —S(O)$_2R^k$, —C(O)NH$R^k$, —C(S)NH$R^k$, —C(O)N$R^kR^k$, —C(S)N$R^kR^k$, —S(O)$_2$NH$R^k$, —S(O)$_2$N$R^kR^k$, —C(NH)NH$R^k$, —C(NH)N$R^kR^k$, —NHC(O)$R^k$, —NHC(S)$R^k$, —N$R^k$C(O)$R^k$, —N$R^k$C(S)$R^k$, —NHS(O)$_2R^k$, —N$R^k$S(O)$_2R^k$, —NHC(O)NH$R^k$, —NHC(S)NH$R^k$, —N$R^k$C(O)$NH_2$, —N$R^k$C(S)$NH_2$, —N$R^k$C(O)NH$R^k$, —N$R^k$C(S)NH$R^k$, —NHC(O)N$R^kR^k$, —NHC(S)N$R^kR^k$, —N$R^k$C(O)N$R^kR^k$, —N$R^k$C(S)N$R^kR^k$, —NHS(O)$_2$NH$R^k$, —N$R^k$S(O)$_2NH_2$, —N$R^k$S(O)$_2$NH$R^k$, —NHS(O)$_2$N$R^kR^k$, —N$R^k$S(O)$_2$N$R^kR^k$, —NH$R^k$ or —N$R^kR^k$; or two $R^k$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein each $R^k$ is independently H, $C_{1-6}$alkyl or aryl, arylalkyl, heteroaryl, heteroarylalkyl, heterocycloalkyl, heterocycloalkylalkyl, cycloalkyl or cycloalkylalkyl, wherein the aliphatic or aromatic portion of $R^k$ is optionally substituted with from 1-3 $R^h$;

$R^5$ is an optionally substituted 5- or 6-membered heteroaryl having from 1 to 4 heteroatoms as ring members selected from O, N or S; or optionally substituted heterocycloalkyl; and ═══ is a single bond or a double bond to maintain the 5-member ring A being aromatic, with the proviso that the compound is other than 3,5-dimethyl-4-(1H-pyrrolo[2,3-b]pyridin-5-yl)isoxazole. In certain embodiments, when $Y^3$ is N, $Y^3$ and L do not form a nitrogen-nitrogen bond, for example, the bond between $Y^3$ and L is other than a nitrogen-nitrogen bond. In some embodiments, $R^5$ is an optionally substituted 5- or 6-membered heteroaryl having from 1 to 4 heteroatoms as ring members selected from O, N or S. In another embodiment, $R^5$ is an optionally substituted heterocycloalkyl.

In some embodiments of compounds of formula (I), or any subformulas of formula (I) or any embodiments as described herein, $R^2$ and/or $R^3$ are other than hydrogen. In some embodiments, when L is —C(O)— or —$CH_2$—, $R^2$ and/or $R^3$ are other than hydrogen. In one embodiment, $R^2$ is other than hydrogen. In another embodiment, $R^3$ is other than hydrogen. In yet another embodiment, $R^2$ and $R^3$ are other than hydrogen. In another embodiment, $R^2$ is hydrogen and $R^3$ is other than hydrogen. In some embodiments, $R^2$, $R^3$ and -L-$R^1$ are not simultaneously hydrogen. In some embodiments, $R^3$ and -L-$R^1$ are not simultaneously hydrogen. In some preferred embodiments, $R^3$ is other than hydrogen and -L-$R^1$ is other than hydrogen. In other preferred embodiments, -L-$R^1$ is other than hydrogen. In some embodiments, when $Y^1$ and $Y^2$ are N and $Y^3$ is C, $R^3$ and -L-$R^1$ are not simultaneously hydrogen. In some embodiments, when $Y^1$ and $Y^2$ are N and $Y^3$ is C, $R^3$ and -L-$R^1$ are not hydrogen. In another embodiment, $R^2$ is hydrogen, -L-$R^1$ is other than hydrogen and $R^3$ is other than hydrogen. In some embodiments, when L is a bond, $R^3$ and $R^1$ are not simultaneously hydrogen. In some embodiments, when L is a bond, $R^3$ and $R^1$ are not hydrogen. In some embodiments, when $R^2$ and $R^4$ are hydrogen, -L-$R^1$ substituent is not hydrogen. In other embodiments, when $R^2$ and $R^4$ are hydrogen, $R^3$ is not hydrogen. In other embodiments, when the -L-$R^1$ substituent is hydrogen, $R^3$ is a substituent other than hydrogen. In other embodiments, when $R^3$ is hydrogen, the -L-$R^1$ group is other than hydrogen. In some embodiments, when $Y^1$ and $Y^2$ are N and $R^3$ is H, then, $R^1$ is other than H or optionally substituted aryl or heteroaryl. In some embodiments, when $Y^1$ is N, $Y^2$ is N, L is —C(O)—, —S—, —CH(OH)— or —$CH_2$— and $R^3$ is H, then, $R^1$ is other than optionally substituted aryl or heteroaryl. In some embodiments, when $Y^1$ and $Y^2$ are N, $R^5$ is optionally substituted pyrazolyl, optionally substituted pyrdyl, optionally substituted thiophenyl, optionally substituted furanyl, optionally substituted pyrrolyl, optionally substituted imidazolyl or optionally substituted 4-morpholino and $R^3$ is H, then, $R^1$ is not optionally substituted aryl or heteroaryl. In some embodiments, when $Y^1$ is CH, $Y^2$ is N and $Y^3$ is C, then, $R^3$ is other than H or W. In some embodiments, when $Y^1$ is CH, $Y^2$ is N and $Y^3$ is C, then, $R^3$ is other than H or —S(O)$_2R^k$ or —C(O)$R^k$.

In some embodiments of compounds of formula (I), (i) $Y^1$ is N; $Y^2$ is N and $Y^3$ is C; or (ii) $Y^1$ is N; $Y^2$ is C and $Y^3$ is N;

L is optionally substituted $C_{1-6}$alkylene, optionally substituted deuterated $C_{1-6}$alkylene optionally substituted —C($R^6R^7$)—, —C(O)N$R^9$—, —$CH_2$N($R^9$)—, —$SO_2$N($R^9$)—, —N($R^9$)C(O)N($R^9$)—, —N($R^9$)$SO_2$—, —N($R^9$)$CH_2$—, —O$C_{1-4}$alkylene-, —$C_{1-4}$alkylene-O—, —N$R^9$C(O)—, —N($R^5$)$SO_2$—, —C(O)—, —S(O)—, —$SO_2$—, —O—, —S—, —P(O)($R^a$)—, optionally substituted $C_{2-6}$alkenylene, optionally substituted —CH═C($R^b$)— or —Si($R^c$)($R^c$)—, wherein $R^6$ and $R^7$ are each independently H, D, halogen, —OH, $C_{1-6}$alkyl, deuterated $C_{1-6}$alkyl, $C_{2-6}$-alkenyl, $C_{2-6}$alkynyl, aryl, aryl-$C_{1-4}$ alkyl, $C_{1-6}$alkoxy, $C_{3-6}$cycloalkyl, $C_{3-6}$cycloalkyl-$C_{1-4}$alkyl, heterocycloalkyl, heterocycloalkyl-$C_{1-4}$alkyl, heteroaryl, heteroarylalkyl, $C_{1-6}$haloalkyl, $C_{1-6}$haloalkoxy, $R^j$, —O$R^d$, —N$R^dR^d$, —C(O)O$R^d$, —OC(O)$R^d$, —OC(O)O$R^d$, —C(O)$R^d$, —NHC(O)$R^d$, —C(O)N$R^dR^d$, —$SO_2R^d$, —NH$SO_2R^d$ or —$SO_2$N$R^dR^d$; or $R^6$ and $R^7$ taken together with the carbon atom to which they attach form an optionally substituted 3- to 6-membered ring having from 0-2 heteroatoms selected from O, N or S or an oxo; wherein at each occurrence, $R^6$ or $R^7$ is further optionally substituted with from 1-3 independently selected $R^h$ members; wherein the aliphatic or aromatic portion of L is optionally substituted with from 1-3 $R^e$ substituents independently selected from $C_{1-6}$alkyl, $C_{1-6}$alkoxy, halogen, —OH, —CN, —$NH_2$, vinyl, ethynyl, $C_{3-6}$cycloalkyl, aryl, $C_{1-6}$haloalkyl, $C_{1-6}$haloalkoxy, —C(O)O$R^f$, —OC(O)$R^f$, —OC(O)O$R^f$, —C(O)$R^f$, —NHC(O)$R^f$, —C(O)N$R^fR^f$, —$SO_2R^f$, —NH$SO_2R^f$ or —$SO_2$N$R^fR^f$; $R^9$ is H, $C_{1-4}$alkyl or $C_{1-4}$haloalkyl; $R^a$ is optionally substituted $C_{1-6}$alkyl, optionally substituted aryl or optionally substituted heteroaryl; each $R^d$ is independently selected from H, $C_{1-6}$alkyl, $C_{3-6}$cycloalkyl, $C_{3-6}$cycloalkyl-$C_{1-4}$alkyl or aryl, each of which is optionally substituted; each $R^f$ is independently H or $C_{1-6}$alkyl; $R^b$ is H or $C_{1-6}$alkyl; or $R^b$ and $R^1$ taken together with the carbon atom to which they attach form an optionally substituted 3- to 6-membered carbocyclic ring or an optionally substituted 4- to 8-membered heterocyclic ring having from 1-2 heteroatoms as ring members selected from O, N or S, wherein the nitrogen or sulfur ring atoms can be optionally oxidized; each $R^c$ is independently $C_{1-6}$alkyl or $C_{1-6}$alkoxy;

$R^2$ and $R^4$ are H;

$R^3$ is halogen, —CN, optionally substituted $C_{1-6}$alkyl, optionally substituted deuterated $C_{1-6}$alkyl, optionally substituted aryl, optionally substituted aryl-$C_{1-4}$alkyl, optionally substituted heteroaryl, optionally substituted heteroaryl-$C_{1-4}$alkyl, optionally substituted $C_{3-8}$ cycloalkyl, optionally substituted $C_{3-8}$ cycloalkenyl, optionally substituted $C_{3-8}$ cycloalkyl-$C_{1-4}$alkyl, optionally substituted $C_{2-6}$ alkynyl, optionally substituted heterocycloalkyl, optionally substituted heterocycloalkyl-$C_{1-4}$alkyl or $R^j$ selected from halogen, —CN, —OH, —$NH_2$, —$NO_2$, —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —CH═C$(R^k)(R^k)$, —$OR^k$, —$SR^k$, —OC(O)$R^k$, —OC(S)$R^k$, —P(═O)$HR^k$, —P(═O)$R^kR^k$, —PH(═O)$OR^k$, —P(═O)$(OR^k)_2$, —OP(═O)$(OR^k)_2$, —C(O)H, —O(CO)$OR^k$, —C(O)$R^k$, —C(S)$R^k$, —C(O)$OR^k$, —C(S)$OR^k$, —S(O)$R^k$, —$S(O)_2R^k$, —C(O)$NHR^k$, —C(S)$NHR^k$, —C(O)$NR^kR^k$, —C(S)$NR^kR^k$, —$S(O)_2NHR^k$, —$S(O)_2NR^kR^k$, —C(NH)$NHR^k$, —C(NH)$NR^kR^k$, —NHC(O)$R^k$, —$NR^k$C(S)$R^k$, —$NR^k$C(O)$R^k$, —$NR^k$C(S)$R^k$, —$NHS(O)_2R^k$, —$NR^kS(O)_2R^k$, —NHC(O)$NHR^k$, —NHC(S)$NHR^k$, —$NR^k$C(O)$NH_2$, —$NR^k$C(S)$NH_2$, —$NR^k$C(O)$NHR^k$, —$NR^k$C(S)$NHR^k$, —NHC(O)$NR^kR^k$, —NHC(S)$NR^kR^k$, —$NR^k$C(O)$NR^kR^k$, —$NR^k$C(S)$NR^kR^k$, —$NHS(O)_2NHR^k$, —$NR^kS(O)_2NH_2$, —$NR^kS(O)_2NHR^k$, —$NHS(O)_2NR^kR^k$, —$NR^kS(O)_2NR^kR^k$, —$NHR^k$ or —$NR^kR^k$; or two $R^k$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein each $R^k$ is independently H, $C_{1-6}$alkyl or aryl, arylalkyl, heteroaryl, heteroarylalkyl, heterocycloalkyl, heterocycloalkylalkyl, cycloalkyl or cycloalkylalkyl, wherein the aliphatic or aromatic portion of $R^k$ is optionally substituted with from 1-3 $R^h$;

$R^5$ is an optionally substituted 5- or 6-membered heteroaryl having from 1 to 4 heteroatoms as ring members selected from O, N or S; or optionally substituted heterocycloalkyl; and ------ is a single bond or a double bond to maintain the 5-member ring A being aromatic, with the proviso that the compound is other than 3,5-dimethyl-4-(1H-pyrrolo[2,3-b]pyridin-5-yl)isoxazole; or $R^3$ and -L-R' are not simultaneously hydrogen. In some preferred embodiments, $R^5$ is an optionally substituted 5-membered heteroaryl. In other embodiments, $R^5$ is a heterocycloalkyl having from 1-2 ring heteroatoms selected from O, N or S, wherein one or two of the ring carbon atoms are optionally replaced by —C(O)—, wherein the heterocycloalkyl is optionally substituted with 1-2 members selected from $C_{1-4}$alkyl, OH or $NH_2$.

In some embodiments of compounds of formula (I), the compounds have molecular weights less than 600. In some preferred embodiments, the compounds have molecular weights less than 550. In other preferred embodiments, the compounds have molecular weights less than 500. In yet other preferred embodiments, the compounds have molecular weights less than 450. In still other preferred embodiments, the compounds have molecular weights less than 400. In other preferred embodiments, the compounds have molecular weights less than 300.

In some embodiments of compounds of formula (I), $Y^1$ is N. In other embodiments of compounds of formula (I), $Y^1$ is CH. In other embodiments of compounds of formula (I), $Y^2$ is C and $Y^3$ is N. In other embodiments of compounds of formula (I), $Y^2$ is N and $Y^3$ is C. In some preferred embodiments, $Y^1$ is N. In other preferred embodiments, $Y^1$ is N, $Y^2$ is N and $Y^3$ is C. In other preferred embodiments, $Y^1$ is N, $Y^2$ is C and $Y^3$ is N. All the other variables are as defined in Formula (I) or any of the subgeneric formulas of formula (I) (e.g., formulas (II), (III), (IV) or (V)) or in any of the embodiments of compounds of formula (I) as described herein.

In some embodiments of compounds of formula (I), L is a bond, $C_{1-6}$alkylene, deuterated $C_{1-6}$alkylene, —C$(R^6R^7)$—, —C(O)—, —S(O)—, —$SO_2$—, —O—, —S—, —P(O)$(R^a)$—, $C_{2-6}$alkenylene, —CH═C$(R^b)$— or —Si$(R^c)(R^c)$—. The substituents $R^6$, $R^7$, $R^a$ and $R^b$ are as defined in Formula (I) or any of the subgeneric formulas of formula (I) (e.g., formulas (II), (III), (IV) or (V)) or in any of the embodiments of compounds of formula (I) as described herein. In some instances, $R^6$ and $R^7$ are each independently H, halogen, —OH, $C_{1-6}$alkyl, deuterated $C_{1-6}$alkyl, aryl, aryl-$C_{1-4}$ alkyl, $C_{1-6}$alkoxy, $C_{3-6}$cycloalkyl, $C_{3-6}$cycloalkyl-$C_{1-4}$alkyl, heterocycloalkyl, heterocycloalkyl-$C_{1-4}$alkyl, heteroaryl, heteroarylalkyl, $C_{1-6}$haloalkyl, $C_{1-6}$haloalkoxy, —$OR^d$, —$NR^dR^d$, —C(O)$OR^d$, —OC(O)$R^d$, —OC(O)$OR^d$, —C(O)$R^d$, —NHC(O)$R^d$, —C(O)$NR^dR^d$, —$SO_2R^d$, —$NHSO_2R^d$ or —$SO_2NR^dR^d$; or $R^6$ and $R^7$ taken together with the carbon atom to which they attach form a 3- to 6-membered ring having from 0-2 heteroatoms selected from O, N or S. $R^d$ is as defined in Formula (I) or any of the subgeneric formulas of formula (I) (e.g., formulas (II), (III), (IV) or (V)) or in any of the embodiments of compounds of formula (I)) as described herein. In other instances, $R^b$ and $R^1$ taken together with the carbon atom to which they attach form an optionally substituted 3- to 6-membered carbocyclic ring or an optionally substituted 3- to 8-membered heterocyclic ring having from 1-2 heteroatoms as ring members selected from O, N or S, wherein the nitrogen or sulfur ring atoms can be optionally oxidized. In one instance, L is a bond. In another instance, L is —C$(R^6R^7)$—. All the other variables are as defined in Formula (I) or any of the subgeneric formulas of formula (I) (e.g., formulas (II), (III), (IV) or (V)) or in any of the embodiments of compounds of formula (I) as described herein.

In some embodiments of compounds of formula (I), L is —C(O)$NR^9$—, —$CH_2N(R^9)$—, —$SO_2N(R^9)$—, —$N(R^9)$C(O)$N(R^9)$—, —$N(R^9)SO_2$—, —$N(R^9)CH_2$—, —O$C_{1-4}$alkylene-, —$C_{1-4}$alkylene-O—, —$NR^9$C(O)— or —$N(R^9)SO_2$—, where $R^9$ is H, $C_{1-4}$alkyl or $C_{1-4}$haloalkyl. All the other variables are as defined in Formula (I) or any of the subgeneric formulas of formula (I) (e.g., formulas (II), (III), (IV) or (V)) or in any of the embodiments of compounds of formula (I) as described herein.

In some embodiments of compounds of formula (I), L is a bond, —$CD_2$-, $C_{1-6}$alkylene, —C$(R^6R^7)$—, —C(O)—, —S(O)—, —$SO_2$—, —O—, —S—, —P(O)$(R^a)$—, $C_{2-6}$alkenylene, —CH═C$(R^b)$— or —Si$(R^c)(R^c)$—, wherein $R^6$, $R^7$, $R^a$, $R^b$ and $R^c$ are as defined in any of the embodiments of Formula (I) or any of the subgeneric formulas of formula (I) or in any of the embodiments of compounds of formula (I) as described herein.

In some embodiments of compounds of formula (I), L is a bond, —$CD_2$-, $C_{1-6}$alkylene, —C(O)—, —S(O)—, —$SO_2$—, —O—, —S—, —P(O)($C_{1-6}$alkyl)-, —P(O)(aryl)-, —CH(OH)—, —CHF—, —$CF_2$—, —CH($C_{1-6}$ alkyl)-, —C($OC_{1-6}$alkyl)-, —C($C_{1-6}$alkyl)$_2$-, —CH($C_{3-6}$cycloalkyl)-, —CH(haloalkyl)-, —C($C_{3-6}$cycloalkyl)$_2$-, $C_{2-6}$alkenylene, —CH($R^8$)—, —C($C_{1-6}$alkyl)($R^8$)—, —CHCH═C($R^b$)— or —Si($R^c$)($R^c$)—, each $R^8$ is independently selected from $C_{1-6}$alkyl, haloalkyl, haloalkoxy, $R^d$, —$OR^d$, —$NR^dR^d$, —C(O)$OR^d$, —OC(O)$R^d$, —OC(O)$OR^d$, —C(O)$R^d$, —NHC(O)$R^d$, —C(O)$NR^dR^d$, —$SO_2R^d$, —$NHSO_2R^d$ or —$SO_2NR^dR^d$; wherein the aliphatic or aromatic portion of L is optionally further substituted with from 1-3 $R^e$ substituents. In some instances, $R^8$ is further substituted with 1-3 $R^{10}$ independently selected from $C_{1-6}$alkyl, $C_{1-6}$alkoxy, halogen, —OH, —CN, —$NH_2$, $C_{3-6}$cycloalkyl, aryl, $C_{1-6}$haloalkyl or $C_{1-6}$haloalkoxy. In certain embodiments, L is a bond, —$CH_2$—, —$CD_2$-, —C(O)—, —C($OC_{1-6}$ alkyl)-, —CH($C_{1-6}$alkyl)-, —C($C_{1-6}$alkyl)$_2$-, —CH(OH)—, —CHF—, —S(O)—, —$SO_2$—, —O—, —S—, —P(O)($C_{1-6}$alkyl)-, —P(O)($C_6H_5$)—, —CH($C_{3-6}$ cycloalkyl)-, —C($C_{3-6}$cycloalkyl)$_2$-, —C(OH)($C_{1-6}$alkyl)-, —CH(COOH)—, —CH(CON$R^b$)—, —Si($C_{1-6}$alkyl)$_2$- or —CH($CD_2$OH)—, each of which is optionally substituted with from 1-3 $R^e$ groups. All the other variables are as defined in any of the embodiments of Formula (I) or any of the subgeneric formulas of formula (I) or in any of the embodiments of compounds of formula (I) as described herein.

In some embodiments of compounds of formula (I), L is —CH═C($R^b$)—, wherein $R^b$ and $R^1$ taken together with the carbon atom to which they attach form 3- to 6-membered carbocyclic ring selected from cyclopropane, cyclobutane, cyclopentane, cyclohexane, cyclopentene or cyclohexene, each of which is optionally substituted with from 1-3 $R^j$; or 1-3 $R^h$; or 1-3 $R^e$ groups. In some embodiments, —CH═C($R^b$)($R^1$) is cyclopropylidenemethyl, cyclobutylidenemethyl, cyclopentylidenemethyl, cyclohexylidenemethyl, (E)-cyclopent-2-en-1-ylidenemethyl, cyclopent-3-en-1-ylidenemethyl, cyclohex-2-en-1-ylidenemethyl, cyclohex-3-en-1-ylidenemethyl, each of which is optionally substituted with from 1-3 $R^j$; or 1-3 $R^h$; or 1-3 $R^e$ groups.

In some embodiments of compounds of formula (I), L is —CH═C($R^b$)—, wherein $R^b$ and $R^1$ taken together with the carbon atom to which they attach form 4- to 8-membered heterocycloalkyl ring selected from oxetane, azetidine, pyrrolidine, tetrahydrofuran, tetrahydropyran, piperidine, piperazine, tetrahydrothiopyran, tetrahydrothiopyran-S-oxide or tetrahydrothiopyran-S,S-oxide, each of which is optionally substituted with from 1-3 $R^j$; or 1-3 $R^h$; or 1-3 $R^e$ groups. In some embodiments, —CH═C($R^b$)($R^1$) is oxetan-3-ylidenemethyl, tetrahydropyran-4-ylidenemethyl, tetrahydropyran-3-ylidenemethyl, azetidin-3-ylidenemethyl, pyrrolidin-3-ylidenemethyl, tetrahydrofuran-3-ylidenemethyl, tetrahydrothiopyran-4-ylidenemethyl, tetrahydrothiopyran-3-ylidenemethyl, tetrahydrothiopyran-S-oxide-4-ylidenemethyl or tetrahydrothiopyran-S,S-oxide-4-ylidenemethyl, each of which is optionally substituted with from 1-3 $R^j$; or 1-3 $R^h$ groups.

In some embodiments of compounds of formula (I), L is a bond, —$CH_2$—, —$CD_2$-, —C(O)—, —CH(OH)—, —CH($OCH_3$)—, —C($CH_3$)$_2$—, —CH(cyclopropyl)-, —C(cyclopropyl)$_2$-, —CH(cyclobutyl)-, —CH(cyclopentyl)-, —CH(cyclohexyl)-, —CH(—CH═$CH_2$)—, —CH(—C≡CH)—, —C($C_{1-6}$alkyl)(OH)—, —CH(butyl)-, —CH(butyl)(OH)—, —CH(propyl)-, —CH($CH_3$)—, —CHF—, —S(O)—, —$SO_2$—, —O—, —S—, —P(O)($CH_3$)—, —P(O)($C_6H_5$)—, —CH($C_{3-6}$cycloalkyl)-, —C($C_{3-6}$cycloalkyl)$_2$-, —C(OH)($C_{1-6}$alkyl)-, —CH(COOH)—, —CH(CON$R^b$)—, —Si($C_{1-6}$alkyl)$_2$- or —CH($CD_2$OH)—, —CH(C(O)OEt)-, —CH($CH_2$F)—, —CH($CH_2$OH)—, —CH($CH_2$CN)—, —CH(COOH)—, —CH(CONH-cyclopropyl)-, —Si(i-propyl)$_2$-, —CH($CH_2CH_3$)—, —CH(Ph)-, —CH($CD_3$)-, —CH(pyridyl)-, —CH(pyridyl)(OH)—, —CH(2-pyridyl)-, —CH(2-pyridyl)(OH)—, or —CH($CD_2$OH)—, each of which is optionally substituted with from 1-3 $R^j$; or 1-3 $R^h$; or 1-3 $R^c$; or 1-3 $R^{10}$; or 1-3 $R^g$ substituents. All the other variables $R^1$ to $R^5$ and $Y^1$ to $Y^3$ are as defined in any of the embodiments of Formula (I) or any of the subgeneric formulas of formula (I) or in any of the embodiments of compounds of formula (I) as described herein.

In some embodiments of compounds of formula (I), L is —$CH_2$—, —$CD_2$-, —C(O)—, —CH(OH)—, —CH($OCH_3$)—, —C($CH_3$)$_2$—, —CH(cyclopropyl)-, —C(cyclopropyl)$_2$-, —CH(cyclobutyl)-, —CH(cyclopentyl)-, —CH(cyclohexyl)-, —CH(—CH═$CH_2$)—, —CH(—C≡CH)—, —C($C_{1-6}$alkyl)(OH)—, —CH(butyl)-, —CH(butyl)(OH)—, —CH(propyl)-, —CH($CH_3$)—, —CHF—, —S(O)—, —$SO_2$—, —O—, —S—, —P(O)($CH_3$)—, —P(O)($C_6H_5$)—, —CH($C_{3-6}$cycloalkyl)-, —C($C_{3-6}$cycloalkyl)$_2$-, —C(OH)($C_{1-6}$alkyl)-, —CH(COOH)—, —CH(CON$R^b$)—, —Si($C_{1-6}$alkyl)$_2$- or —CH($CD_2$OH)—, —CH(C(O)OEt)-, —CH($CH_2$F)—, —CH($CH_2$OH)—, —CH($CH_2$CN)—, —CH(COOH)—, —CH(CONH-cyclopropyl)-, —Si(i-propyl)$_2$-, —CH($CH_2CH_3$)—, —CH(Ph)-, —CH($CD_3$)-, —CH(pyridyl)-, —CH(pyridyl)(OH)—, —CH(2-pyridyl)-, —CH(2-pyridyl)(OH)—, or —CH($CD_2$OH)—, each of which is optionally substituted with from 1-3 $R^j$; or 1-3 $R^h$; or 1-3 $R^e$; or 1-3 $R^{10}$; or 1-3 $R^g$ substituents. All the other variables $R^1$ to $R^5$ and $Y^1$ to $Y^3$ are as defined in any of the embodiments of Formula (I) or any of the subgeneric formulas of formula (I) or in any of the embodiments of compounds of formula (I) as described herein.

In some embodiments of compounds of formula (I), L is —$CH_2$—, —$CD_2$-, —C(O)—, —C($CH_3$)$_2$—, —CH(cyclopropyl)-, —$SO_2$—, —CH($CH_2CH_3$)—, —CH(Ph)-, —CH($CD_3$)-, —CH(pyridyl)-, —CH(pyridyl)(OH)—, —CH(2-pyridyl)-, —CH(2-pyridyl)(OH)—, or —CH($CD_2$OH)—, each of which is optionally substituted with from 1-3 $R^j$; or 1-3 $R^h$; or 1-3 $R^e$; or 1-3 $R^{10}$; or 1-3 $R^g$ substituents. In some preferred embodiments, L is $CH_2$, —CH($CH_3$)—, —CH($CH_2CH_3$)— or —CH(Ph)-. All the other variables $R^1$ to $R^5$ and $Y^1$ to $Y^3$ are as defined in any of the embodiments of Formula (I) or any of the subgeneric formulas of formula (I) or in any of the embodiments of compounds of formula (I) as described herein.

In some embodiments of compounds of formula (I), sub-generic formulas and any embodiments as described herein, L is —C($R^6$)($R^7$)—. In certain instances, $R^6$ is $C_{1-6}$alkyl or $C_{3-6}$cycloalkyl, each of which is optionally substituted with from 1-2 independently selected $R^p$ groups. In some preferred embodiments, L is —C($R^6$)($R^7$)—, wherein $R^6$ is H or D and $R^7$ is H, D, $C_{1-4}$alkyl, deuterated $C_{1-4}$alkyl, aryl or heteroaryl, wherein the alkyl, aryl or heteroaryl is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In other preferred embodiments, L is —$CH_2$—, —$CD_2$-, —CH($R^7$)— or —CD($R^7$)—, wherein $R^7$ is defined herein. All the other variables $R^1$ to $R^5$ and $Y^1$ to $Y^3$ are as defined in any of the embodiments of Formula (I) or any of the subgeneric formulas of formula (I) or in any of the embodiments of compounds of formula (I) as described herein.

In any of the embodiments of compounds of formulas (I), or any of the subgeneric formulas of formula (I) (e.g., formulas (II), (III), (IV) or (V)) or in any of the embodiments of compounds of formula (I) as described herein, the hydrogen atoms in L are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in L is optionally replaced by a deuterium atom with at least 52.5%, 60%, 70%, 75%, 80%, 90%, 95%, 99%, 99.5% or 99.9% deuterium incorporation for each deuterium.

In any of the embodiments of compounds of formulas (I), $R^5$ is an optionally substituted 5-membered heteroaryl having from 2 to 4 heteroatoms as ring members selected from O, N or S. In some instances, $R^5$ is optionally substituted with from 1-2 $R^{11}$ groups independently selected from D, halogen, $C_{1-6}$alkyl, $C_{1-4}$haloalkyl, OH, $NH_2$, $C_{1-4}$haloalkoxy, CN or $R^p$, wherein the hydrogen is optionally replaced with from 1 to 6 deuterium atoms. In some instances, $R^{11}$ is D, halogen, $C_{1-6}$alkyl, $C_{1-4}$haloalkyl, $C_{1-4}$haloalkoxy or CN, wherein the hydrogen is optionally replaced with from 1 to 6 deuterium atoms. In certain instances, $R^{11}$ is $C_{1-6}$alkyl or deuterated $C_{1-6}$alkyl. In some instances, $R^5$ is optionally substituted with from 1-2 $R^{12}$ members independently selected from D, halogen, $CH_3$, $CD_3$, —$CF_3$, —$CHF_2$, $CH_2F$, $CH_2Cl$ or CN. In some preferred embodiments, $R^5$ is 5-membered heteroaryl substituted with from 1-2 methyl or $CD_3$ groups. In other preferred embodiments, $R^5$ is 5-membered heteroaryl substituted with from two methyl or $CD_3$ groups. All the other variables $R^1$ to $R^4$, $Y^1$ to $Y^3$ and L are as defined in any of the embodiments of Formula (I) or any of the subgeneric formulas of formula (I) or in any of the embodiments of compounds of formula (I) as described herein.

In any of the embodiments of compounds of formulas (I), $R^5$ is a 5-membered heteroaryl selected from:

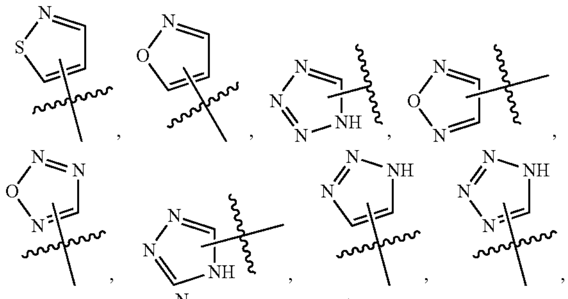

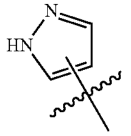

or

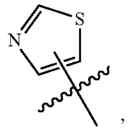

, each of which is optionally substituted, e.g., with from 1-2 $R^{11}$; or 1-2 $R^{12}$ groups, wherein the wavy line indicates the point of attachment to the rest of molecule.

In some embodiments, $R^5$ is a 5-membered heteroaryl selected from:

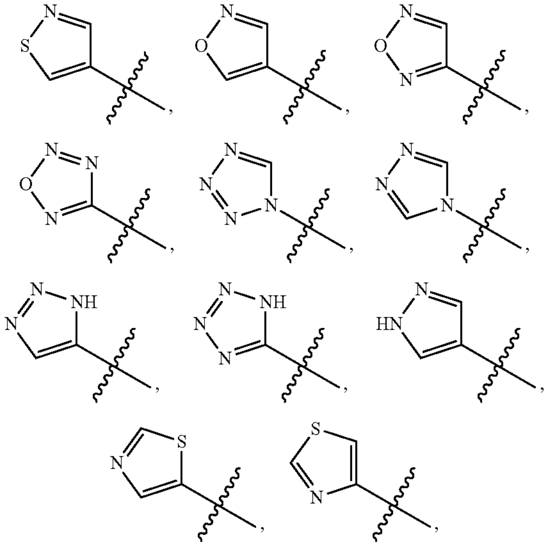

, each of which is optionally substituted, e.g., with from 1-2 $R^{11}$; or 1-2 $R^{12}$ groups, wherein the wavy line indicates the point of attachment to the rest of molecule. In some embodiments, $R^5$ is an optionally substituted 4-isoxazolyl, 2-isoxazolyl or 3-isoxazolyl, each of which is optionally substituted with from 1-2 $C_{1-6}$alkyl. In certain instances, $R^5$ is selected from:

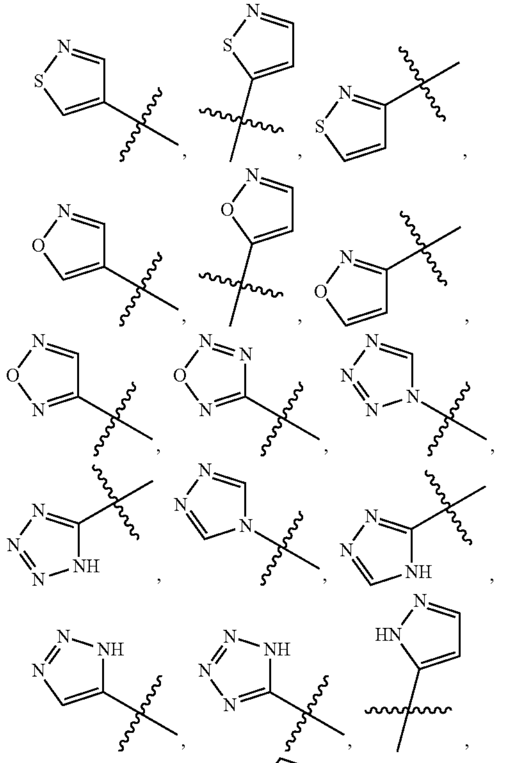

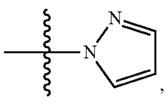

,

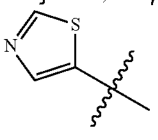

or

-continued

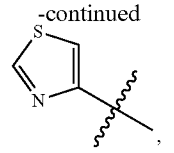

each of which is optionally substituted with from 1-2 $R^{11}$; or 1-2 $R^{12}$ groups, wherein the wavy line indicates the point of attachment to the rest of molecule. In some embodiments, $R^5$ is selected from:

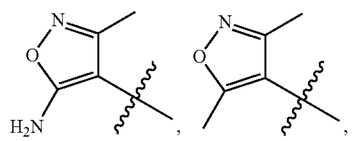

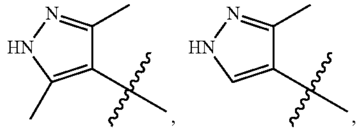

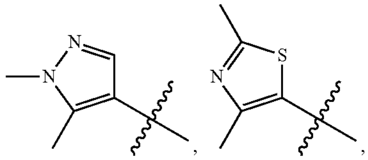

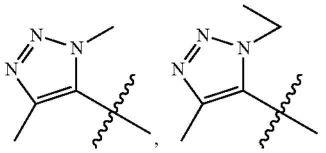

or

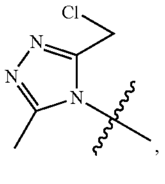

wherein the wavy line indicates the point of attachment to the rest of molecule. In some embodiments, $R^5$ is selected from:

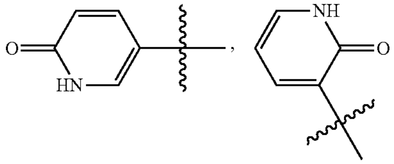

or

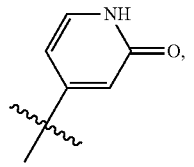

each of which is optionally substituted with from 1-2 independently selected $R^{11}$; or 1-2 independently selected $R^{12}$ groups; or 1-2 members independently selected from $C_{1-4}$alkyl; or 1-2 members independently selected from D, $CH_3$ or $CD_3$; or 2 members independently selected from $CH_3$ or $CD_3$, wherein the wavy line indicates the point of attachment to the rest of molecule. In some embodiments, $R^5$ is selected from:

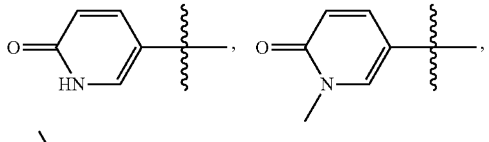

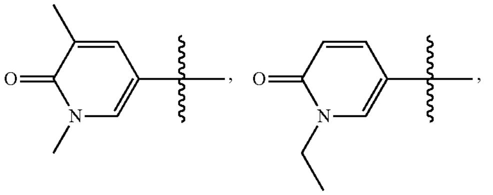

or

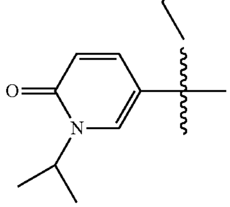

each of which is optionally substituted with from 1-2 members independently selected from $C_{1-4}$alkyl; or 1-2 members independently selected from D, $CH_3$ or $CD_3$; or 2 members independently selected from $CH_3$ or $CD_3$, wherein the wavy line indicates the point of attachment to the rest of molecule. In one embodiment, $R^5$ is 4-isoxazolyl, optionally substituted with from 1-2 $R^{11}$; or 1-2 $R^{12}$ groups. In one instance, $R^5$ is 4-isoxazolyl optionally substituted with 1-2 members independently selected from D, $CH_3$ or $CD_3$. In another instance, $R^5$ is 4-isoxazolyl substituted with 1-2 members independently selected from D, $CH_3$ or $CD_3$. In another instance, $R^5$ is 4-isoxazolyl substituted with 2 members independently selected from $CH_3$ or $CD_3$. In another instance, $R^5$ is 3,5-dimethyl-4-isoxazolyl. In one embodiment, $R^5$ is 1H-1,2,3-triazol-4-yl substituted with 1-2 members independently selected from $CH_3$ or $CD_3$. In another embodiment, $R^5$ is 1H-1,2,3-triazol-4-yl substituted with 2 members independently selected from $CH_3$ or $CD_3$. In another embodiment, $R^5$ is 3,5-dimethyl-1,2,3-triazol-4-yl. In some embodiments, $R^5$ is 1H-pyrazol-5-yl or 1H-pyrazol-4-yl, each is of which is substituted with 1-2 members independently selected from $CH_3$ or $CD_3$. In other embodiments, $R^5$ is 1H-pyrazol-5-yl or 1H-pyrazol-4-yl, each is of which is substituted with 2 members independently selected from $CH_3$ or $CD_3$. In one embodiment, $R^5$ is 2,4-dimethyl-pyrazol-3-yl. All the other variables $R^1$ to $R^4$, $Y^1$ to $Y^3$ and L are as defined in any of the embodiments of Formula (I) or any of the subgeneric formulas of formula (I) or in any of the embodiments of compounds of formula (I) as described herein.

In any of the embodiments of compounds of formulas (I), $R^5$ is an optionally substituted 6-membered heteroaryl having from 1 to 2 nitrogen atoms as ring members. In some embodiments, $R^5$ is optionally substituted with from 1-3 $R^{11}$; or 1-3 $R^{12}$ groups. In some embodiments, $R^5$ is optionally substituted with from 1-2 $R^{11}$; or 1-2 $R^{12}$ groups. All the other variables $R^1$ to $R^4$, $Y^1$ to $Y^3$ and L are as defined in any of the embodiments of Formula (I) or any of the subgeneric formulas of formula (I) or in any of the embodiments of compounds of formula (I) as described herein.

In any of the embodiments of compounds of formulas (I), $R^5$ is an optionally substituted 6-membered heteroaryl selected from 2-pyridyl, 3-pyridyl, 4-pyridyl, 2-pyrimidinyl, 4-pyrimidinyl, 5-pyrimidinyl, 2-pyrazinyl, 2-pyridazinyl or 3-pyridazinyl, each of which is optionally substituted with from 1-2 $R^{11}$; or 1-2 $R^{12}$ groups. In some embodiments, $R^5$ is 2-pyridyl, 3-pyridyl, 4-pyridyl, 2-pyrimidinyl, 4-pyrimidinyl or 5-pyrimidinyl, each of which is optionally substituted with from 1-2 $R^{11}$; or 1-2 $R^{12}$ groups. All the other variables $R^1$ to $R^4$, $Y^1$ to $Y^3$ and L are as defined in any of the embodiments of Formula (I) or any of the subgeneric formulas of formula (I) or in any of the embodiments of compounds of formula (I) as described herein.

In any of the embodiments of compounds of formulas (I), $R^5$ is an optionally substituted heterocycloalkyl. In some embodiments, $R^5$ is 1H-pyridin-2-one-5-yl, 1H-pyridin-2-one-4-yl or 1H-pyridin-2-one-6-yl, each of which is optionally substituted with from 1-2 $R^{11}$; or 1-2 $R^{12}$ groups. In certain instances, $R^5$ is 1H-pyridin-2-one-5-yl, 1H-pyridin-2-one-4-yl or 1H-pyridin-2-one-6-yl, each of which is optionally substituted with from 1-2 $C_{1-4}$alkyl. In some instances, $R^5$ is 1H-pyridin-2-one-5-yl, 1H-pyridin-2-one-4-yl or 1H-pyridin-2-one-6-yl, each of which is substituted with from 1-2 substituents independently selected from methyl, $CD_3$, ethyl or isopropyl. In some instances, $R^5$ is 1H-pyridin-2-one-5-yl, 1H-pyridin-2-one-4-yl or 1H-pyridin-2-one-6-yl, each of which is substituted with from 2 substituents independently selected from $CD_3$ or $CH_3$. In certain instances, $R^5$ is 1,3-dimethyl-pyridin-2-one-5-yl, 1,3-dimethyl-pyridin-2-one-4-yl or 1,3-dimethyl-pyridin-2-one-6-yl.

In some embodiments of compounds of formula (I), $R^1$, $R^6$, $R^7$, $R^2$ and $R^3$ are each independently selected from $C_{1-6}$alkyl, deuterated $C_{1-6}$alkyl, $C_{1-6}$alkoxy, $C_{2-6}$alkenyl-$X^1$—, $C_{2-6}$alkynyl-$X^1$—, —$X^1$-aryl, aryl-$C_{1-4}$alkyl-$X^1$—, heteroaryl-$X^1$—, heteroaryl-$C_{1-4}$ alkyl-$X^1$—, $C_{3-8}$cycloalkyl-$X^1$—, $C_{3-6}$cycloalkyl-$X^1$—, $C_{3-6}$cycloalkenyl-$X^1$—, $C_{3-6}$cycloalkyl-$C_{1-4}$alkyl-$X^1$—, heterocyclyl-$X^1$—, heterocyclyl-$C_{1-4}$alkyl-$X^1$—, $CH_2$=CH—$X^1$, $C_{3-6}$cycloalkyl-$C_{2-4}$alkenyl-$X^1$, $C_{3-6}$cycloalkyl-$C_{2-4}$alkynyl-$X^1$, halogen, —CN, —OH, —$NH_2$, —$NO_2$, —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —CH=C($R^g$)($R^g$), —$OR^g$, —$SR^g$, —OC(O)$R^g$, —OC(S)$R^g$, —P(=O)H$R^g$, —P(=O)$R^gR^g$, —PH(=O)$OR^g$, —P(=O)$(OR^g)_2$, —OP(=O)$(OR^g)_2$, —C(O)H, —O(CO)$OR^g$, —C(O)$R^g$, —C(S)$R^g$, —C(O)$OR^g$, —C(S)$OR^g$, —S(O)$R^g$, —$S(O)_2R^g$, —C(O)NH$R^g$, —C(S)NH$R^g$, —C(O)N$R^gR^g$, —C(S)N$R^gR^g$, —$S(O)_2$NH$R^g$, —$S(O)_2$N$R^gR^g$, —C(NH)NH$R^g$, —C(NH)N$R^gR^g$, —NHC(O)$R^g$, —NHC(S)$R^g$, —N$R^g$C(O)$R^g$, —N$R^g$C(S)$R^g$, —$NHS(O)_2R^g$, —N$R^g$$S(O)_2R^g$, —NHC(O)NH$R^g$, —NHC(S)NH$R^g$, —N$R^g$C(O)$NH_2$, —N$R^g$C(S)$NH_2$, —N$R^g$C(O)NH$R^g$, —N$R^g$C(S)NH$R^g$, —NHC(O)N$R^gR^g$, —NHC(S)N$R^gR^g$, —N$R^g$C(O)N$R^gR^g$, —N$R^g$C(S)N$R^gR^g$, —$NHS(O)_2$NH$R^g$, —N$R^g$$S(O)_2NH_2$, —N$R^g$$S(O)_2$NH$R^g$, —$NHS(O)_2$N$R^gR^g$, —N$R^g$$S(O)_2$N$R^gR^g$, —NH$R^g$ or —N$R^gR^g$, wherein each $R^g$ is independently H, $C_{1-6}$alkyl, $C_{1-6}$ alkenyl, $C_{1-6}$ alkynyl, aryl, heteroaryl, cycloalkyl, heterocycloalkyl, heterocycloalkylalkyl, cycloalkylalkyl, arylalkyl, heteroarylalkyl or heterocycloalkylalkyl; or two $R^g$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized; wherein each $R^g$ is further optionally substituted with 1-3 $R^r$ substituents independently selected from $C_{1-6}$alkyl, —$OCH_3$, —$OCH_2CH_3$, —O—$CH(CH_3)_2$, —Cl, —F, —$CH_2F$, —$CHF_2$, $CF_3$, —$OCF_3$, —$OCHF_2$ or —$OCH_2F$; wherein $X^1$ is a bond or —C(O)— and wherein the aliphatic or aromatic portion of $R^1$, $R^6$, $R^7$, $R^2$ or $R^3$ is optionally substituted with from 1-5 $R^h$ substituents independently selected from halogen, —CN, —OH, —$NH_2$, —$NO_2$, —CH=C($R^i$)($R^i$), —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —$OR^i$, —$SR^i$, —OC(O)$R^i$, —OC(S)$R^i$, —P(=O)H$R^i$, —P(=O)$R^iR^i$, —PH(=O)$OR^i$, —P(=O)$(OR^i)_2$, —OP(=O)$(OR^i)_2$, —C(O)H, —O(CO)$OR^i$, —C(O)$R^i$, —C(S)$R^i$, —C(O)$OR^i$, —C(S)$OR^i$, —S(O)$R^i$, —$S(O)_2R^i$, —C(O)NH$R^i$, —C(S)NH$R^i$, —C(O)N$R^iR^i$, —C(S)N$R^iR^i$, —$S(O)_2$NH$R^i$, —$S(O)_2$N$R^iR^i$, —C(NH)NH$R^i$, —C(NH)N$R^iR^i$, —NHC(O)$R^i$, —NHC(S)$R^i$, —N$R^i$C(O)$R^i$, —N$R^i$C(S)$R^i$, —$NHS(O)_2R^i$, —N$R^i$$S(O)_2R^i$, —NHC(O)NH$R^i$, —NHC(S)NH$R^i$, —N$R^i$C(O)$NH_2$, —N$R^i$C(S)$NH_2$, —N$R^i$C(O)NH$R^i$, —N$R^i$C(S)NH$R^i$, —NHC(O)N$R^iR^i$, —NHC(S)N$R^iR^i$, —N$R^i$C(O)N$R^iR^i$, —N$R^i$C(S)N$R^iR^i$, —$NHS(O)_2$NH$R^i$, —N$R^i$$S(O)_2NH_2$, —N$R^i$$S(O)_2$NH$R^i$, —$NHS(O)_2$N$R^iR^i$, —N$R^i$$S(O)_2$N$R^iR^i$, $R^i$, —NH$R^i$ or —N$R^iR^i$, wherein each $R^i$ is independently $C_{1-6}$alkyl, aryl, aryl-$C_{1-2}$alkyl, $C_{3-6}$cycloalkyl, $C_{3-6}$cycloalkyl-$C_{1-4}$ alkyl, heteroaryl, heteroaryl-$C_{1-4}$alkyl, heterocycloalkyl or heterocycloalkyl-$C_{1-4}$alkyl, wherein each R' is further optionally substituted with from 1-3 $R^p$ groups independently selected from halogen, CN, —OH, —$NH_2$, —N($R^q$)($R^q$), —$NO_2$, —C(O)OH, —C(O)$NH_2$, —$S(O)_2NH_2$, —NHC(O)$NH_2$, —C(NH)$NH_2$, —P(=O)H$R^q$, —P(=O)$R^qR^q$, —PH(=O)$OR^q$, —P(=O)$(OR^q)_2$, —OP(=O)$(OR^q)_2$, —OC(O)$R^q$, —OC(S)$R^q$, —C(O)$R^q$, —C(S)$R^q$, —C(O)$OR^q$, —$S(O)_2R^q$, —C(O)NH$R^q$, $C_{1-6}$alkyl, $C_{1-6}$alkoxy, halogen, $C_{1-6}$haloalkyl or $C_{1-6}$haloalkoxy, wherein $R^q$ is $C_{1-6}$alkyl; In some instances, $X^1$ is a bond. In other instances, $X^1$ is —C(O)—. In some instances, $R^h$ is CN, —$CH_3$, —$OCH_3$, —$OCH_2CH_3$, —O—$CH(CH_3)_2$, —Cl, —F, —$CH_2F$, —$CHF_2$, $CF_3$, —$OCF_3$, —$OCHF_2$ or —$OCH_2F$, —P(=O)$CH_3$, —P(=O)$(CH_3)_2$, —PH(=O)O($C_{1-4}$alkyl), —P(=O)$(OC_{1-4}alkyl)_2$, —OP(=O)$(OC_{1-4}alkyl)_2$, $C_{1-6}$alkyl, phenyl, perdeuterated phenyl, benzyl, cyclopropyl, cyclobutyl, cyclopentyl, cyclohexyl, cyclopropylmethyl, cyclobutylmethyl, cyclopentylmethyl, cyclohexylmethyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl, 4-morpholinylcarbonyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, dimethylcarbamoyl, acetamido, propanoyl, thiomorpholino, 1, pyrrolidinyl, methylsofonylamino, methylsulfonyl, propanoylamino, 1-cyclopentenyl, 1-cyclohexenyl, 1,2,3,6-tetrahydropyridin-4-yl, 1,2,3,6-tetrahydropyridin-5-yl, 2,5-dihydro-1H-pyrrol-3-yl, 2,5-dihydro-pyrrol-1-yl, each of which is optionally substituted with 1-3 $R^s$ groups independently selected from OH, $NH_2$, CN, —$CH_3$, —$OCH_3$, —$OCH_2CH_3$, —O—$CH(CH_3)_2$, —Cl, —F, —$CH_2F$, —$CHF_2$, $CF_3$, —$OCF_3$, —$OCHF_2$, —$OCH_2F$, $C_{1-6}$alkyl, 4-morpholinyl, 4-morpholinylcarbonyl, cyclopropyl, cyclopropylmethyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, acetamido, propanoyl, methylsofonylamino, methylsulfonyl, propanoylamino, dimethylcarbamoyl or ethoxycarbonylamino. In other instances, $R^g$ is halogen, $C_{1-6}$alkyl, phenyl, perdeuterated phenyl, benzyl, cyclopropyl, cyclobutyl, cyclopentyl, cyclohexyl, cyclopropylmethyl, cyclobutylmethyl, cyclopentylmethyl, cyclohexylmethyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl, 4-morpholinylcarbonyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, dimethylcarbamoyl, acetamido, propanoyl, 4-thiomorpholino, 4-thiomorpholino-S,S-oxide, 1-pyrrolidinyl, methylsulfonylamino, methylsulfonyl, propanoylamino, 1-cyclopentenyl, 1-cyclohexenyl, 1,2,3,6-tetrahydropyridin-4-yl, 1,2,3,6-tetrahydropyridin-5-yl, 2,5-dihydro-1H-pyrrol-3-yl, 2,5-dihydro-pyrrol-1-yl, 2-norbornyl, each of which is optionally substituted with 1-3 $R^s$ groups; or two adjacent $R^h$ groups on an aromatic ring are taken together to form a 5- or 6-membered ring having from 0-2 heteroatoms as ring members selected from O, N or S wherein the 5- or 6-membered ring is optionally substituted with from 1-2 $R^s$ groups. In other instances, $R^g$, $R^i$ or $R^h$ is each independently $C_{1-6}$alkyl or $C_{1-4}$alkoxy, each of which is optionally substituted with a member selected from $C_{1-6}$alkyl, methoxy, phenyl, cyclopropyl, cyclobutyl, cyclopentyl, cyclohexyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl. In yet other instances, $R^p$ is selected from $C_{1-6}$alkyl, —CN, —$OCH_3$, —$OCH_2CH_3$, —O—$CH(CH_3)_2$, —Cl, —F, —$CHF_2$, $CF_3$, —$OCF_3$, —$OCHF_2$, —$OCH_2F$, —NH—$C_{1-6}$alkyl, —N($C_{1-6}$alkyl)($C_{1-6}$alkyl). In some preferred embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of formula (I) described herein.

In some embodiments of compounds of formula (I), $R^1$, $R^6$, $R^7$, $R^2$ and $R^3$ are each independently selected from halogen, —CN, vinyl-$X^1$, $C_{1-6}$alkyl-$X^1$, $C_{1-6}$alkoxy-$X^1$, $C_{2-6}$ alkynyl-$X^1$, $C_{3-6}$ cycloalkyl-$X^1$, $C_{3-6}$cycloalkenyl-$X^1$—, $C_{3-6}$ cycloalkyl-$C_{1-4}$alkyl-$X^1$, $C_{3-6}$ cycloalkyl-$C_{2-4}$ alkynyl-$X^1$, aryl-$X^1$, aryl-$C_{1-4}$alkyl-$X^1$, heteroaryl-$X^1$, heteroaryl-$C_{1-4}$ heterocyclyl-$X^1$, heterocyclyl-$C_{1-4}$alkyl, —C(O)—$R^g$, —C(O)$NHR^g$, —C(O)$NR^gR^g$, —NHC(O)$R^g$, —NHC(O)$OR^g$, —NHC(O)$NHR^g$, —NHC(O)$NR^gR^g$, —$NR^gR^g$, —$NHR^g$, —C(O)$OR^g$, —OC(O)$R^g$, —$SO_2R^g$, —$NHSO_2R^g$, —$NHSO_2NHR^g$, —$NHSO_2NR^gR^g$, —$SO_2NHR^g$ or —$SO_2NR^gR^g$, wherein at each occurrence $R^1$, $R^6$, $R^7$, $R^2$ or $R^3$ is optionally substituted with from 1-4 $R^h$ members. In some instances, each $R^h$ is independently selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$ cycloalkyl-$C_{1-4}$alkyl, aryl, aryl-$C_{1-4}$alkyl, heteroaryl, heteroaryl-$C_{1-4}$ alkyl, heterocyclyl or heterocyclyl-$C_{1-4}$alkyl or $R^{13}$. In one instance, $R^1$, $R^6$, $R^7$, $R^2$ or $R^3$ is H. In other instances, two adjacent $R^h$ substituents on an aromatic ring are taken together to form a 5 or 6-membered ring having from 0-2 heteroatoms selected from O, N or S. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^{11}$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of formula (I) described herein.

In some embodiments of compounds of formula (I), $R^1$, $R^6$, $R^7$, $R^2$ and $R^3$ are each independently selected from halogen, CN, vinyl, $C_{1-6}$alkyl, $C_{1-6}$alkoxy, $C_{2-6}$ alkynyl, $C_{3-8}$ cycloalkyl, $C_{3-6}$ cycloalkyl, $C_{3-6}$cycloalkenyl, $C_{3-6}$ cycloalkyl-$C_{1-4}$alkyl, $C_{3-6}$ cycloalkyl-$C_{2-4}$alkynyl, aryl, aryl-$C_{1-4}$alkyl, heteroaryl, heteroaryl-$C_{1-4}$ alkyl, heterocycloalkyl, heterocycloalkyl-$C_{1-4}$alkyl, —C(O)—$R^g$, —C(O)$NHR^g$, —C(O)$NR^gR^g$, —NHC(O)$R^g$, —NHC(O)$OR^g$, —NHC(O)$NHR^g$, —NHC(O)$NR^gR^g$, —$NR^gR^g$, —$NHR^g$, —C(O)$OR^g$, —OC(O)$R^g$, —$SO_2R^g$, —$NHSO_2R^g$, —$NHSO_2NHR^g$, —$NHSO_2NR^gR^g$, —$SO_2NHR^g$ or —$SO_2NR^gR^g$, each of which is optionally independently substituted with from 1-4 $R^h$ substituents; or optionally independently substituted with from 1-4 $R^i$ substituents; or optionally independently substituted with from 1-4 $R^p$ substituents; or optionally substituted with from 1-4 $R^{14}$ substituents selected from halogen, —CN, $C_{1-6}$alkyl, $C_{1-6}$alkoxy, $C_{1-6}$haloalkyl, $C_{1-6}$ haloalkoxy, $C_{3-6}$cycloalkyl, $C_{3-6}$cycloalkyl-$C_{1-4}$alkyl, heterocycloalkyl-$C_{1-4}$alkyl, —C(O)—$R^c$, —C(O)$NHR^c$, —C(O)$NR^iR^i$, —NHC(O)$R^i$, —P(=O)$HR^i$, —P(=O)$R^iR^i$, —PH(=O)$OR^i$, —P(=O)$(OR^i)_2$, —OP(=O)$(OR^i)_2$, —NHC(O)$OR^i$, —NHC(O)$NHR^i$, —$NR^iR^i$, —C(O)$OR^i$, —OC(O)$R^i$, —OC(O)$NHR^i$, —$SO_2R^i$, —$NHSO_2R^i$, —$SO_2NHR^i$ or —$SO_2NR^iR^i$; or optionally independently substituted with from 1-4 $R^{15}$ substituents selected from $C_{1-6}$alkyl, —OH, —CN, —$NO_2$, —$NH_2$, —$NHCH_3$, —$N(CH_3)_2$, —$OCH_3$, —$OCH_2CH_3$, —O—$CH(CH_3)_2$, —Cl, —F, —$CH_2F$, —$CHF_2$, $CF_3$, —$OCF_3$, —$OCHF_2$, —$OCH_2F$, 4-morpholinyl, cyclopropyl, cyclopropoxy, cyclopropylmethyl, 1-pyrrolidinyl, 1-pyrrolidinylcarbonyl, 1-piperidinylcarbonyl, acetyl, methoxycarbonyl, acetamido, dimethylcarbamoyl, methylcarbamoyl, methylsulfonyl or methylsulfonylamino. In some instances, $R^i$ is $C_{3-6}$cycloalkyl, $C_{3-6}$cycloalkyl-$C_{1-4}$alkyl, heterocycloalkyl or heterocycloalkyl-$C_{1-4}$alkyl. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of formula (I) described herein.

In some embodiments of compounds of formula (I), $R^1$, $R^6$, $R^7$, $R^2$ and $R^3$ are each independently selected from aryl, heteroaryl, $C_{2-6}$ alkynyl, $C_{3-6}$cycloalkenyl, heterocycloalkyl, —C(O)—$R^g$, —C(O)$NHR^g$, —C(O)$NR^gR^g$, —C(O)$OR^g$, —$SO_2NHR^g$ or —$SO_2NR^gR^g$, each of which is optionally substituted with from (i) 1-4 $R^h$ substituents; or (ii) 1-4 $R^i$ substituents; or (iii) 1-4 $R^p$ substituents; or (iv) 1-4 $R^{14}$ substituents selected from halogen, —CN, $C_{1-6}$alkyl, $C_{1-6}$alkoxy, $C_{1-6}$haloalkyl, $C_{1-6}$haloalkoxy, $C_{3-6}$cycloalkyl, $C_{3-6}$cycloalkyl-$C_{1-4}$alkyl, heterocycloalkyl-$C_{1-4}$alkyl, —C(O)NHR', —C(O)$NR^cR^i$, —NHC(O)$R^i$, —NHC(O)$OR^i$, —NHC(O)$NHR^i$, —$NR^iR^i$, —$NHR^i$, —C(O)$OR^i$, —P(=O)$HR^i$, —P(=O)$R^iR^i$, —PH(=O)$OR^i$, —P(=O)$(OR^i)_2$, —OP(=O)$(OR^i)_2$, —OC(O)$R^i$, —OC(O)$NHR^i$, —$SO_2R^i$, —$NHSO_2R^i$, —$SO_2NHR^i$ or —$SO_2NR^iR^i$; or (v) 1-4 $R^{15}$ groups; or (vi) 1-4 $R^{16}$ substituents independently selected from $C_{1-6}$alkyl, —OH, —CN, —$NO_2$, —$NH_2$, —$NHCH_3$, —$N(CH_3)_2$, —$OCH_3$, —$OCH_2CH_3$, —O—$CH(CH_3)_2$, —Cl, —F, —$CH_2F$, —$CHF_2$, $CF_3$, —$OCF_3$, —$OCHF_2$, —$OCH_2F$, 4-morpholinyl, thiomorpholino, 1-piperidinyl, cyclopropyl, 1-cyanocyclopropyl, cyclopropoxy, cyclopropylmethyl, 1-pyrrolidinyl, 1-piperazinyl, 1-piperazinylcarbonyl, 1-pyrrolidinylcarbonyl, 1-piperidinylcarbonyl, acetyl, methoxycarbonyl, acetamido, dimethylcarbamoyl, methylcarbamoyl, methylsulfonyl, methylsulfonylamino, —C(O)—$R^t$, —C(O)NH$R^t$, —C(O)N$R^tR^t$, —NHC(O)$R^t$, —P(=O)H$R^t$, —P(=O)$R^tR^t$, —PH(=O)O$R^t$, —P(=O)(O$R^t$)$_2$, —OP(=O)(O$R^t$)$_2$, —C(O)O$R^t$, —OC(O)$R^t$, —$SO_2R^t$, —NH$SO_2R^t$, —$SO_2$NH$R^t$, —$SO_2$N$R^tR^t$, wherein each $R^t$ is independently $C_{1-6}$alkyl, $C_{3-6}$cycloalkyl, phenyl or heterocycloalkyl, wherein $R^t$ is further optionally substituted with from 1-3 $R^p$, $R^q$ or $R^s$ group; or (vii) 1-4 $R^{17}$ substituents selected from F, Cl, I, —$CH_3$, —$OCH_3$, $OCH_2CH_3$, —O—CH$(CH_3)_2$, —OH, —CN, —$NO_2$, —$NH_2$, —NH$CH_3$, —N$(CH_3)_2$, —$CH_2$F, —$CHF_2$, $CF_3$, —$OCF_3$, —$OCHF_2$, —$OCH_2$F, cyclopropyl, cyclopropylmethyl, 1-cyanocyclopropyl, 1-carboxycyclopropyl, cyclobutyl, cyclopentyl, cyclohexyl, —P(O)$(OH)_2$, —PH(=O)—$C_{1-6}$alkyl, —P(=O)($C_{1-6}$alkyl)$_2$, —PH(=O)O($C_{1-6}$alkyl), —P(=O)(O$C_{1-6}$alkyl)$_2$, —OP(=O)(O$C_{1-6}$ alkyl)$_2$, —NHC(O)—$C_{1-6}$alkyl, —C(O)NH—$C_{1-6}$alkyl, —NH—C(O)—$NH_2$, —NHC(O)NH—$C_{1-6}$alkyl, NHC(O)O—$C_{1-6}$alkyl, —C(O)—$C_{1-6}$alkyl, —C(O)O—$C_{1-6}$alkyl, —COOH, —$CH_2$COOH, —$CF_2$COOH, —OC(O)—$C_{1-6}$ alkyl, —NH$SO_2CH_3$, $NH_2$C(O)—, $CH_3$NHC(O)—, $NH_2SO_2$—, $CH_3SO_2$—, $(CH_3)_2$NC(O)—, $CH_3$C(O)NH—, $CH_3SO_2$NH—, benzyl, benzyl-C(O), ($C_{1-4}$alkyl)OC(O)—, cyclopropyl-C(O)—, cyclopropylethyl-C(O)—, cyclobutyl-C(O)—, cyclobutylmethyl-C(O)—, Ph-NH—C(O)—, 4-morpholinyl, 4-morpholinylmethyl, 4-morpholinylethyl, thiomorpholino, 4-thiomorpholinyl-C(O)—, 4-morpholinyl-C(O)—, 1-piperidinyl, 1-piperidinyl-C(O)—, p-$CH_3$-Ph-$SO_2$NH—, Ph-$SO_2$NH—, propyl-$SO_2$NH—, cyclopropyl-$SO_2$NH—, cyclobutyl-$SO_2$NH—, butyl$SO_2$NH—, ethoxycarbonyl-NH—, methoxycarbonyl-NH—, cyclopropoxy, cyclopropylmethyl, 1-pyrrolidinyl, 1-piperazinyl, 1-piperazinylcarbonyl, 4-methyl-1-piperazinylcarbonyl, 1-pyrrolidinylcarbonyl, 1-piperidinylcarbonyl, acetyl, methoxycarbonyl, acetamido, dimethylcarbamoyl, methylcarbamoyl, ethoxycarbonylamino, 4-pyrazolyl, 1,2,3,4-tetrazol-5-yl, 1-azetidinyl, 2-azetidinyl, 3-azetidinyl, 2-oxetanyl, 3-oxetanyl, 1-morpholinylethyl, 3-methoxypropoxy, 2-(4-morpholinyl)ethoxy, 4-morpholinylmethylcarbonyl or 4-morpholinylethylcarbonyl, wherein at each occurrence, $R^{17}$ is further optionally substituted with from 1-3 substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —NH$CH_3$, —N$(CH_3)_2$, —$CH_2$F, —$CHF_2$, $CF_3$, —$OCF_3$, —$OCHF_2$, —$OCH_2$F, $CH_3$C(O)—, —COOH, $CH_3$C(O)O—, $CH_3$OC(O)—, $CH_3$NHC(O)—, $CH_3$C(O)NH—, $(CH_3)_2$NC(O)—, $(CH_3)_2$NS(O)$_2$—, $(CH_3)_2$S(O)$_2$NH— or $CH_3SO_2$. In some embodiments, $R^2$ is H; $R^6$ and $R^7$ are each independently H, D, 4 alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from aryl, heteroaryl, $C_{2-6}$ alkynyl, $C_{3-6}$cycloalkenyl or heterocycloalkyl, each of which is optionally substituted with (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ groups; or (vi) 1-4 $R^{16}$ substituents; or (vii) substituents. In some preferred embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from halogen, —CN, $C_{1-6}$alkyl, $C_{1-6}$alkoxy, 2-pyridyl, 3-pyridyl, 4-pyridyl, perdeuterated pyridyl, phenyl, perdeuterated phenyl, 1-pyrazolyl, 3-1H-pyrazolyl, 4-1H-pyrazolyl, vinyl, ethynyl, propynyl, 3-fluoropropynyl, cyclopropyl-ethynyl, cyclobutyl-ethynyl, cyclopentyl-ethynyl, cyclohexyl-ethynyl, 1-cyclopentenyl-ethynyl, 2-thiazolyl, 4-thiazolyl, 5-thiazolyl, cyclopropyl, cyclobutyl, cyclopentyl, cyclohexyl, cyclopropylmethyl, cyclobutylmethyl, cyclopentylmethyl, cyclohexylmethyl, 1-piperazinyl, 1-piperidinyl, morpholinyl, 1,2,5,6-tetrahydropyridin-4-yl, 1,2,5,6-tetrahydropyridin-3-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, 1-cyclohexenyl, 1-cyclopentenyl, 1-cyclooctenyl, 2-pyrimidinyl, 4-pyrimidinyl, 5-pyrimidinyl, 2-pyrazinyl, 3-pyridazinyl, 4-pyridazinyl, 5,6-dihydro-2H-pyran-4-yl, 5,6-dihydro-2H-pyran-3-yl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl or 3-thiophenyl, each of which is optionally substituted with from (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ groups; or (vi) 1-4 $R^{16}$ substituents; or (vii) $R^{17}$ substituents. In certain embodiments, the hydrogen atoms in $R^1$, $R^6$, $R^7$, $R^2$ or $R^3$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^1$, $R^6$, $R^7$, $R^2$ or $R^3$ is optionally replaced by a deuterium atom with at least 52.5%, 60%, 70%, 75%, 80%, 90%, 95%, 99%, 99.5% or 99.9% deuterium incorporation for each deuterium. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from halogen, —CN, $C_{1-6}$alkyl, $C_{1-6}$alkoxy, 2-pyridyl, 3-pyridyl, 4-pyridyl, 2-methoxy-4-pyridyl, phenyl, 1-pyrazolyl, 3-1H-pyrazolyl, 4-1H-pyrazolyl, 1-methyl-4-pyrazolyl, 1,3-dimethyl-5-pyrazolyl, vinyl, ethynyl, propynyl, 3-fluoropropynyl, cyclopropyl-ethynyl, cyclobutyl-ethynyl, cyclopentyl-ethynyl, cyclohexyl-ethynyl, 1-cyclopentenyl-ethynyl, 2-thiazolyl, 4-thiazolyl, 5-thiazolyl, cyclopropyl, cyclobutyl, cyclopentyl, cyclohexyl, cyclopropylmethyl, cyclobutylmethyl, cyclopentylmethyl, cyclohexylmethyl, 2-cyclopropylethyl, 2-cyclobutylethyl, 1-methyl-1-cyclopropyl, 1-cyclopropylethyl, 1-methyl-1-cyclobutyl, 1-cyclobutylethyl, methoxymethoxy, 4-morpholinylmethoxy, 1-piperidinylmethoxy, 4,4-difluoropiperidinyl, 4-ethoxycarbonyl-1-piperazinyl, 1-piperazinyl, 1-piperidinyl, 4-morpholinyl, 1,2,3,6-tetrahydropyridin-4-yl, 1,2,3,6-tetrahydropyridin-5-yl, 1-cyclopropylcarbonyl-2,3,6-trihydropyridin-4-yl, 2,2,6,6-tetramethyl-1,5-dihydropyridin-4-yl, 2,2,6,6-tetramethyl-1,5-dihydropyridin-3-yl, 1-cyclopropylcarbonyl-2,3,6-trihydropyridin-5-yl, 1-methylsulfonyl-2,3,6-trihydropyridin-4-yl, 1-methylsulfonyl-2,3,6-trihydropyridin-5-yl, 1-(4-morpholinylcarbonyl)-2,3,6-trihydropyridin-4-yl, 1-(4-morpholinylcarbonyl)-2,3,6-trihydropyridin-5-yl, 1-t-butoxycarbonyl-2,3,6-trihydropyridin-4-yl, 1-t-butoxycarbonyl-2,3,6-trihydropyridin-5-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, 1-cyclohexenyl, 1-cyclopentenyl, 1-cyclooctenyl, 2-pyrimidinyl, 4-pyrimidinyl, 5-pyrimidinyl, 2-cyclopropyl-5-pyrimidinyl, 2-cyclopropyl-pyrimidin-5-yl, 2-pyrazinyl, 3-pyridazinyl, 4-pyridazinyl, 5,6-dihydro-2H-pyran-4-yl, 5,6-dihydro-2H-pyran-3-yl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl, 3-thiophenyl, 3-chloro-5-thiophenyl or 1-cyclopropylcarbonyl-piperidin-4-yl, each of which is optionally substituted with from 1-4 $R^{15}$ or $R^{16}$ substituents; or 1-4 $R^{17}$ substituents, wherein at each occurrence, $R^{17}$ is further optionally substituted with from 1-3 $R^{18}$ substituents selected from CN, F, Cl, I, —$OCH_3$, $C_{1-6}$alkyl, cyclopropyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$—. In some instances, $R^t$ is $C_{1-6}$alkyl, $C_{3-6}$cycloalkyl, $C_{3-6}$cycloalkyl-$C_{1-2}$alkyl, 4-morpholinyl, 1-pyrrolidinyl, 2-pyrrolidinyl, 3-pyrrolidinyl, 1-azetidinyl, 2-azetidinyl, 3-azetidinyl, 2-oxatanyl, 3-oxatanyl, 2-oxo-1-pyrrolidinyl, 1-piperidinyl, 2-piperidinyl, 3-piperidinyl, 4-piperidinyl, piperazinyl, phenyl or benzyl, each of which is optionally substituted with 1-3 substituents selected from —$CH_3$, —$OCH_3$, F, Cl, CN, $CF_3$, $CHF_2$, $CH_2F$, —$OCF_3$, —$N(CH_3)_2$, —$NHCH_3$. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from 3-fluoropropynyl, 2-pyridyl, 3-pyridyl, 4-pyridyl, 2-methoxy-4-pyridyl, phenyl, 1-pyrazolyl, 3-1H-pyrazolyl, 4-1H-pyrazolyl, 1-methyl-4-pyrazolyl, 1,3-dimethyl-5-pyrazolyl, 4-morpholinyl, 3-isoxazolyl, 4-isoxazolyl, 5-isoxazolyl, 2,5-dimethyl-4-isoxazolyl, 2-thiazolyl, 4-thiazolyl, 5-thiazolyl, 2-methyl-5-thiazolyl, 1-isopropyl-pyrazol-4-yl, 1-cyclohexenyl, 1-cyclopentenyl, 1-cyclooctenyl, 1,2,3,6-tetrahydropyridin-4-yl, 1,2,3,6-tetrahydropyridin-5-yl, cyclopropyl, 2,5-dihydro-1H-pyrrol-3-yl, 2,5-dihydro-1H-pyrrol-2-yl or 2,5-dihydropyrrol-1-yl, each of which is optionally substituted with from 1-4 $R^{15}$ or $R^{16}$ substituents; or 1-4 substituents, wherein at each occurrence, $R^{17}$ is further optionally substituted with from 1-3$R^{18}$ substituents selected from CN, F, Cl, I, —$OCH_3$, $C_{1-6}$alkyl, cyclopropyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$—. In some instances, $R^t$ is $C_{1-6}$alkyl, $C_{3-6}$cycloalkyl, $C_{3-6}$cycloalkyl-$C_{1-2}$alkyl, 4-morpholinyl, 1-pyrrolidinyl, 2-pyrrolidinyl, 3-pyrrolidinyl, 1-azetidinyl, 2-azetidinyl, 3-azetidinyl, 2-oxatanyl, 3-oxatanyl, 2-oxo-1-pyrrolidinyl, 1-piperidinyl, 2-piperidinyl, 3-piperidinyl, 4-piperidinyl, piperazinyl, phenyl or benzyl, each of which is optionally substituted with 1-3 substituents selected from —$CH_3$, —$OCH_3$, F, Cl, CN, $CF_3$, $CHF_2$, $CH_2F$, —$OCF_3$, —$N(CH_3)_2$, —$NHCH_3$. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently H, CN, vinyl, $C_{1-6}$alkyl, deuterated $C_{1-6}$alkyl, perdeuterated $C_{1-6}$alkyl, halogen, $C_{1-6}$alkoxy, 2-cyclopropylethynyl, pyridyl, phenyl, benzyl, pyrazolyl, oxazolyl, thiozolyl, pyrimidinyl, pyrazinyl, pyridazinyl, cyclopropyl, cyclopropylmethyl, cyclopropylcarbonyl, cyclobutyl, cyclobutylmethyl, cyclopentyl, cyclopentylmethyl, cyclohexyl, cyclohexylmethyl, benzoyl, phenylcarbamoyl, piperidinyl, piperazinyl, morpholinyl, cyclopentenyl, cyclohexenyl, 1,2,3,6-tetrahydropyridin-4-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, each of which is optionally substituted with from 1-4 members independently selected from halogen, —$CH_3$, $CD_3$, —$OCH_3$, CN, $CF_3$, $CF_3O$—, —$CF_2H$, $CHF_2O$—, —$N(CH_3)_2$, —$NHCH_3$, $CH_3CONH$—, $NH_2C(O)$—, $CH_3NHC(O)$—, $(CH_3)_2NC(O)$—, cyclopropyl, 1-cyanocyclopropyl, $CH_3SO_2NH$—, cyclopropyl-$SO_2NH$—, butyl-$SO_2NH$—, p-$CH_3C_6H_4SO_2NH$—, $NH_2SO_2$—, $CH_3NHSO_2$—, $(CH_3)_2NSO_2$—, 4-morpholinyl, piperidinyl, 4-methyl-1-piperazinyl, cyclopropylcarbonyl, cyclobutylcarbonyl, cyclopentylcarbonyl, cyclohexylcarbonyl, 4-morpholinylcarbonyl, piperdinylcarbonyl, piperazinylcarbonyl, t-butoxycarbonyl or 2-(4-morpholinyl)-ethyl. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from Cl, Br, phenyl, 4-fluorophenyl, 2-fluorophenyl, 3-fluorophenyl, 2-pyridyl, 3-pyridyl, 4-pyridyl, 1-cyclopropylcarbonyl-1,2,3,6-tetrahydropyridin-4-yl, 1-morpholinocarbonyl, 1,2,3,6- tetrahydropyridin-4-yl, 1,2,3,6-tetrahydropyridin-5-yl, 1,3-dimethyl-pyrazol-4-yl or 1-(4-piperidinyl)pyrazol-4-yl, 3,4-dimethyl-1H-pyrazol-5-yl, 1-(cyclopropylcarbonyl)-2,5-dihydro-pyrrol-3-yl, 3-fluoro-propynyl, 3,5-dimethyl-isoxazol-4-yl, 5-thiazolyl, each of which is optionally substituted with from 1-3 $R^{19}$ substituents independently selected from F, Cl, —$CH_3$,-Et, propyl, isopropyl, 2-methylpropyl, $CD_3$, —$OCH_3$, CN, $CH_2F$, —$CF_2H$, $CF_3$, $CF_3O$—, $CHF_2O$—, $CH_2FO$—, $NH_2$, —$N(CH_3)_2$, —$NHCH_3$, $CH_3CONH$—, $NH_2C(O)$—, $CH_3NHC(O)$—, $(CH_3)_2NC(O)$—, —PH(═O)($C_{1-4}$alkyl), —P(═O)($C_{1-4}$alkyl)$_2$, —PH═O)$CH_3$, —P(═O)$(CH_3)_2$, cyclopropyl, 1-cyanocyclopropyl, 4-morpholinyl, 4-morpholinylmethyl, 4-thiomorpholinyl, 4-morpholinylcarbonyl, 4-thiomorpholinylcarbonyl, 4-morpholinylmethylcarbonyl, 4-thiomorpholinylmethylcarbonyl, cyclopropylcarbonyl, cyclobuylcarbonyl, cyclopentylcarbonyl, cyclohexylcarbonyl, 4-piperidinyl, 4-piperidinylcarbonyl, 1-piperidinylcarbonyl, 1-piperazinylcarbonyl, t-butoxycarbonyl, 2-(4-morpholinyl)-ethyl, 2-(4-morpholinyl)-ethoxy, 1,2-dihydroxyethylcarbonyl, 3-methoxypropoxy, 1-pyrrolidinyl, $PhSO_2NH$—, $C_{1-4}$alkyl-$SO_2NH$—, cyclopropyl-$SO_2NH$—, p-$CH_3C_6H_4SO_2NH$—, $NH_2SO_2$—, $C_{1-4}$alkyl-$NHSO_2$—, ($C_{1-4}$alkyl)$_2NSO_2$—, $C_{1-4}$alkyl-NHC(O)—, $C_{1-4}$alkyl-C(O)—, $C_{1-4}$alkyl-$SO_2$—, 4-morpholinyl-$C_{1-4}$alkoxy, or 1-pyrrolidinylcarbonyl, each of which is optionally substituted with from 1-2 $C_{1-4}$alkyl groups. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently aryl optionally substituted with from: (i) 1-3 $R^h$ substituents; or two adjacent $R^h$ substituents on the aryl ring together with the atoms to which they are attached, form a 5- or 6-membered ring having from 0-2 additional heteroatoms selected from O, N or S and optionally substituted with from 1-3 $R^p$ substituents; or (ii) 1-3 $R^i$ substituents; or (iii) 1-3 $R^p$ substituents; or (iv) 1-3 $R^{15}$ substituents; or (v) 1-3 $R^{15}$ or $R^{16}$ substituents; or (vi) 1-3 $R^{17}$ substituents, wherein each of $R^1$, $R^6$, $R^7$, $R^2$, $R^3$, $R^h$, $R^i$, $R^p$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$. In some instances, $R^1$, $R^6$, $R^7$, $R^2$ or $R^3$ is phenyl or perdeuterated phenyl ($C_6D_5$), each of which is optionally substituted with from 1-3 $R^{15}$ or $R^{16}$ substituents; or 1-3 $R^{17}$ substituents, wherein $R^{15}$, $R^{16}$ and $R^{17}$ are each further optionally substituted with 1-3 $R^{18}$ groups. In other instances, $R^1$, $R^6$, $R^7$, $R^2$ or $R^3$ is phenyl optionally substituted with from 1-3 substituents independently selected from F, Cl, $CH_3$, —$OCH_3$, $CF_3$, $CF_3O$—, —$CFH_2$, —$CF_2H$, $CHF_2O$—, $CH_2FO$—, —$NHCH_3$, —$N(CH_3)_2$, —CN, 4-morpholinyl, 4-morpholinylmethyl, 1-piperidinyl, 4-methyl-1-piperazinyl, 1-pyrrolidinyl, 1-pyrrolidinylcarbonyl, 4-morpholinylcarbonyl, 1-piperidinylcarbonyl, 4-methyl-1-piperazinylcarbonyl, 1-pyrrolidinylcarbonyl, cyclopropyl, cyclopropylcarbonyl, 4-morpholinylethyl, $CH_3SO_2$, $CH_3SO_2NH$—, $CH_3C(O)$—, 4-morpholinylmethylcarbonyl, 1,2-dihydroxypropanoyl, $(CH_3)_2NC(O)$— or methoxycarbonylamino, each of which is optionally substituted with 1-2 groups independently selected from $C_{1-6}$alkyl, $C_{1-4}$alkoxy, 4-morpholinyl or 4-morpholinylmethyl. In other instances, $R^1$, $R^6$, $R^7$, $R^2$ or $R^3$ is 1-naphthyl, or 2-naphthyl, each of which is optionally substituted with from 1-3 $R^{15}$ or $R^{16}$ substituents; or 1-3 $R^{17}$ substituents, wherein $R^{15}$, $R^{16}$ and $R^{17}$ are each further optionally substituted with 1-3 $R^{18}$ groups. In certain embodiments, the hydrogen atoms in $R^6$, $R^7$, $R^2$ or $R^3$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^1$, $R^6$, $R^7$, $R^2$ or $R^3$ is optionally replaced by a deuterium atom with at least 52.5%, 60%, 70%, 75%, 80%, 90%, 95%, 99%, 99.5% or 99.9% deuterium incorporation for each deuterium. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently 1H-4-benzotriazolyl, 1H-5-benzotriazolyl, 1H-4-benzimidazolyl, 1H-5-benzimidazolyl, 1H-4-indazolyl, 1H-5-indazolyl, 1H-6-indazolyl, 1H-7-indazolyl, 1H-4-indolyl, 1H-5-indolyl, 1H-6-indolyl, 1H-7-indolyl, 2-oxo-6-indolinyl, 2-oxo-4-indolinyl, 2-oxo-5-indolinyl, 2-oxo-7-indolinyl, 1,2-benzoxazol-4-yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl, 1,3-benzoxazol-7-yl, 1,2-benzothiazol-4-yl, 1,2-benzothiazol-5-yl, 1,2-benzothiazol-6-yl, 1,2-benzothiazol-7-yl, 5-quinolinyl, 6-quinolinyl, 7-quinolinyl, 8-quinolinyl, 5-isoquinolinyl, 6-isoquinolinyl, 7-isoquinolinyl, 8-isoquinolinyl, 5-cinnolinyl, 6-cinnolinyl, 7-cinnolinyl, 8-cinnolinyl, 5-quinazolinyl, 6-quinazolinyl, 7-quinazolinyl, 8-quinazolinyl, 5-quinoxalinyl, 6-quinoxalinyl, 7-quinoxalinyl, 8-quinoxalinyl, 4-indanyl, 5-indanyl, 5-tetralinyl, 6-tetralinyl, 1,3-dihydroisobenzofuran-4-yl, 1,3-dihydroisobenzofuran-5-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-dihydroisobenzothiophen-4-yl, 1,3-dihydroisobenzothiophen-5-yl, 2,3-dihydrobenzothiophen-4-yl, 2,3-dihydrobenzothiophen-5-yl, 2,3-dihydrobenzothiophen-6-yl, 2,3-dihydrobenzothiophen-7-yl, 4-indolinyl, 5-indolinyl, 6-indolinyl, 7-indolinyl, 5-isochromanyl, 6-isochromanyl, 7-isochromanyl, 8-isochromanyl, 5-chromanyl, 6-chromanyl, 7-chromanyl, 8-chromanyl, 2,3-dihydro-1,3-benzothiazo-4-yl, 2,3-dihydro-1,3-benzothiazo-5-yl, 2,3-dihydro-1,3-benzothiazo-6-yl, 2,3-dihydro-1,3-benzothiazo-7-yl, 2,3-dihydro-1,2-benzothiazo-4-yl, 2,3-dihydro-1,2-benzothiazo-5-yl, 2,3-dihydro-1,2-benzothiazo-6-yl, 2,3-dihydro-1,2-benzothiazo-7-yl, 2,3-dihydro-1,3-benzoxazol-4-yl, 2,3-dihydro-1,3-benzoxazol-5-yl, 2,3-dihydro-1,3-benzoxazol-6-yl, 2,3-dihydro-1,3-benzoxazol-7-yl, 2,3-dihydro-1,2-benzoxazol-4-yl, 2,3-dihydro-1,2-benzoxazol-5-yl, 2,3-dihydro-1,2-benzoxazol-6-yl, 2,3-dihydro-1,2-benzoxazol-7-yl, 4-benzofuranyl, 5-benzofuranyl, 6-benzofuranyl, 7-benzofuranyl, 4-benzo[b]thiophenyl, 5-benzo[b]thiophenyl, 6-benzo[b]thiophenyl, 7-benzo[b]thiophenyl, 4-benzo[c]thiophenyl, 5-benzo[c]thiophenyl 2,3-dihydro-1,4-benzodioxin-5-yl, 1,3-benzodioxol-4-yl, 1,3-benzodioxol-5-yl, indanyl, 1,2-benzoxazol-4- yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl or 1,3-benzoxazol-7-yl, each of which is optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —PH(═O)$CH_3$, —P(═O)$(CH_3)_2$, —PH(═O)$OCH_3$, —P(═O)$(OCH_3)_2$, —OP(═O)$(OCH_3)_2$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently a heteroaryl optionally substituted with from: (i) 1-3 $R^h$ substituents; or two adjacent $R^h$ substituents on the heteroaryl together with the atoms to which they are attached, form a 5- or 6-membered ring having from 0-2 additional heteroatoms selected from O, N or S and optionally substituted with from 1-3 $R^p$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —PH(═O)$CH_3$, —P(═O)$(CH_3)_2$, —PH(═O)$OCH_3$, —P(═O)$(OCH_3)_2$, —OP(═O)$(OCH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$. In some instances, $R^1$, $R^6$, $R^7$, $R^2$ or $R^3$ is an optionally substituted 5- or 6-membered heteroaryl. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently 5-pyrimidinyl, 2-pyrimidinyl, 4-pyrimidinyl, 2-pyridyl, 3-pyridyl, 4-pyridyl, 2-pyrazinyl, 2-pyridazinyl, 3-pyridazinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl or 3-thiophenyl, each of which is optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 substituents; or (vii) 1-3 $R^{17}$ substituents, wherein each of $R^h$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —PH(═O)$CH_3$, —P(═O)$(CH_3)_2$, —PH(═O)$OCH_3$, —P(═O)$(OCH_3)_2$, —OP(═O)$(OCH_3)_2$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$. In some embodiments, $R^2$ is H; $R^6$ and $R^7$ are each independently H, D, $C_1$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from 1-benzotriazolyl, 1-benzimidazolyl, 1H-2-benzimidazolyl, 1-indazolyl, 1H-3-indazolyl, 1-indolyl, 1H-2-indolyl, 1H-3-indolyl, 1,2-benzoxazol-3-yl, 1,3-benzoxazol-2-yl, 1,2-benzothiazol-3-yl, 1,3-benzothiazol-2-yl, 2-quinolinyl, 3-quinolinyl, 4-quinolinyl, 1-isoquinolinyl, 3-isoquinolinyl, 4-isoquinolinyl, 3-cinnolinyl, 4-cinnolinyl, 2-quinazolinyl, 4-quinazolinyl, 2-quinoxalinyl, 2-benzofuranyl, 3-benzofuranyl, 2-benzo[b]thiophenyl, 3-benzo[b]thiophenyl or 1-benzo[c]thiophenyl each of which is optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from:

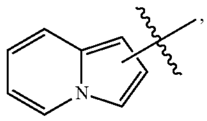 , 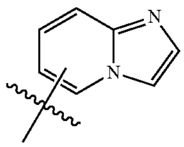 ,

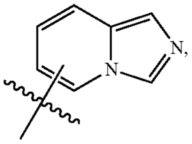 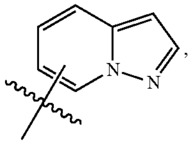 ,

-continued

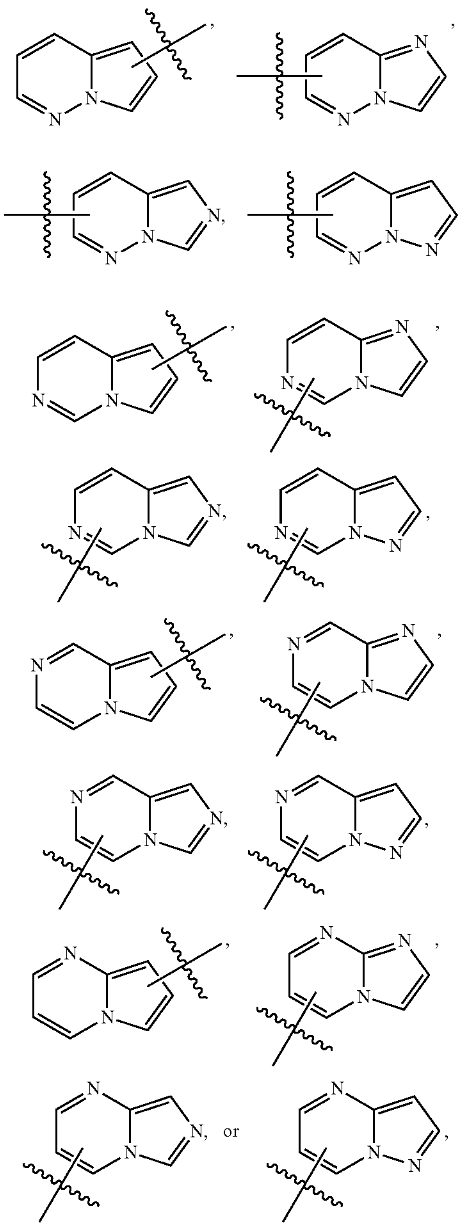

each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —PH(═O)$CH_3$, —P(═O)$(CH_3)_2$, —PH(═O)($OC_{1-6}$alkyl), —P(═O)($OC_{1-6}$ alkyl$)_2$, —OP(═O)($OC_{1-6}$alkyl$)_2$, —$CHF_2$, $CF_3$, —$OCF_3$, —$OCHF_2$, —$OCH_2F$, $CH_3C(O)$—, $CH_3C(O)O$—, $CH_3$ OC(O)—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, where the wavy line indicates the point of attachment to the rest of the molecule. The notation

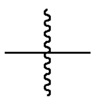

means $R^1$, $R^6$, $R^7$, $R^2$ or $R^3$ can be attached to the rest of the molecule at any of the available positions of the $R^1$, $R^6$, $R^7$, $R^2$ and $R^3$ group set forth above. For example,

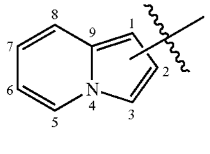

is meant to include 1-indolizinyl, 2-indolizinyl, 3-indolizinyl, 4-indolizinyl, 5-indolizinyl, 6-indolizinyl, 7-indolizinyl, and 8-indolizinyl (i.e., substitutions can be at 1, 2, 3, 5, 6, 7 or 8 positions of the indolizine ring). In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from:

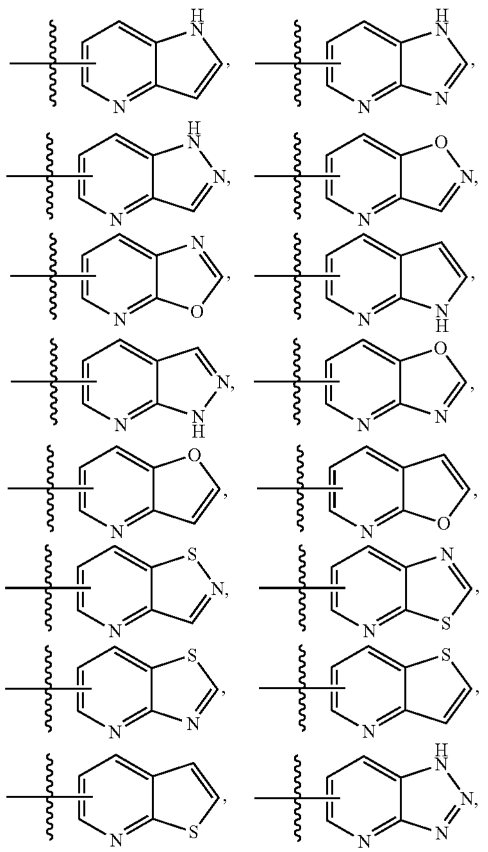

-continued

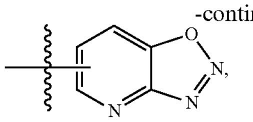, 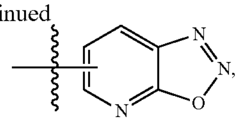

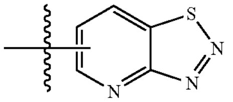 or 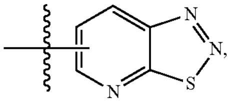

each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 substituents; or (vii) 1-3 substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, —PH(═O)$CH_3$, —P(═O)$(CH_3)_2$, —PH(═O)($OC_{1-6}$alkyl), —P(═O)($OC_{1-6}$ alkyl$)_2$, —OP(═O)($OC_{1-6}$alkyl$)_2$, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, where the wavy line indicates the point of attachment to the rest of the molecule. The notation

means $R^1$, $R^6$, $R^7$, $R^2$ or $R^3$ can be attached to the rest of the molecule at any of the available positions of the R', $R^6$, $R^7$, $R^2$ or $R^3$ group set forth above. For example,

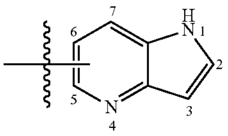

is meant to include 1H-pyrrolo[3,2-b]pyridin-1-yl, 1H-pyrrolo[3,2-b]pyridin-2-yl, 1H-pyrrolo[3,2-b]pyridin-3-yl, 1H-pyrrolo[3,2-b]pyridin-5-yl, 1H-pyrrolo[3,2-b]pyridin-6-yl and 1H-pyrrolo[3,2-b]pyridin-7-yl (i.e., substitutions can be at 1, 2, 3, 5, 6, or 7 positions of the pyrrolo[3,2-b]pyridine ring). In some embodiments, $R^2$ is H; $R^6$ and $R^7$ are each independently H, D, $C_{1-4}$ alkyl, aryl or heteroaryl, each of which is optionally substituted with 1-2 $R^g$, or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from:

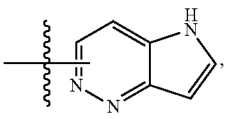, 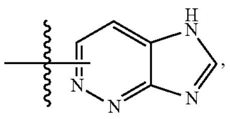,

-continued

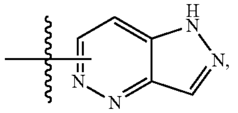, 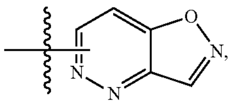,

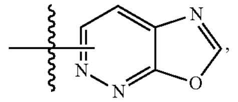, 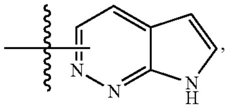,

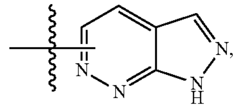, 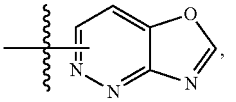,

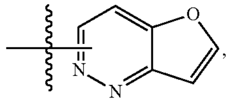, 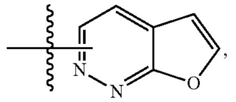,

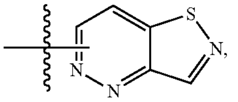, 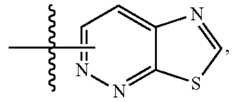,

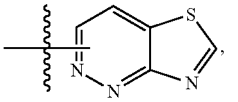, 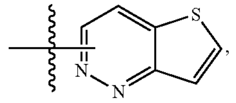,

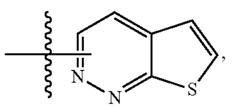, 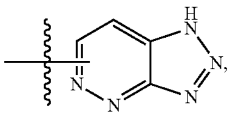,

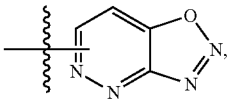, 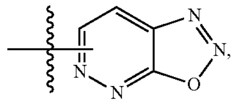,

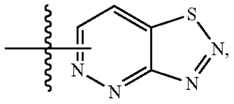 or 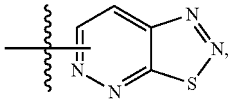

each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, cyclopropyl, 1-azetidinyl, 2-azetidinyl, 3-azetidinyl, 2-oxetanyl, 3-oxetanyl, —PH(═O)$CH_3$, —P(═O)$(CH_3)_2$, —PH(═O)($OC_{1-6}$alkyl), —P(═O)($OC_{1-6}$alkyl$)_2$, —OP(═O)($OC_{1-6}$alkyl$)_2$, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, where the wavy line indicates the point of attachment to the rest of the molecule. The notation

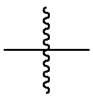

means $R^1$, $R^6$, $R^7$, $R^2$ or $R^3$ can be attached to the rest of the molecule at any of the available positions of the $R^1$, $R^6$, $R^7$, $R^2$ or $R^3$ group set forth above. For example,

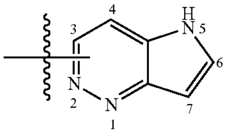

is meant to include 5H-pyrrolo[3,2-c]pyridazin-3-yl, 5H-pyrrolo[3,2-c]pyridazin-4-yl, 5H-pyrrolo[3,2-c]pyridazin-5-yl, 5H-pyrrolo[3,2-c]pyridazin-6-yl, 5H-pyrrolo[3,2-c]pyridazin-7-yl (i.e., substitutions can be at 3, 4, 5, 6, or 7 positions of the 5H-pyrrolo[3,2-c]pyridazine ring). In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ or $R^3$ is each independently selected from:

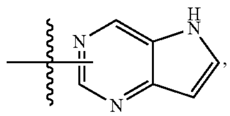, 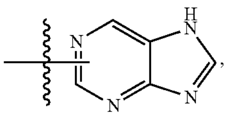,

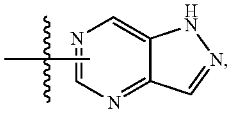, 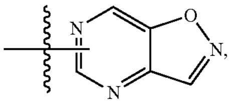,

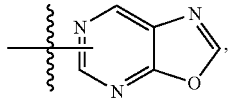, 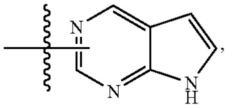,

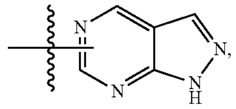, 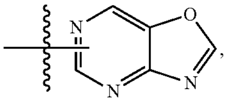,

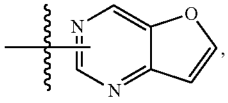, 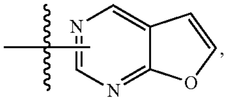,

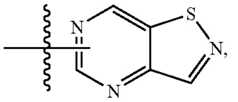, 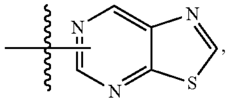,

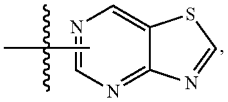, 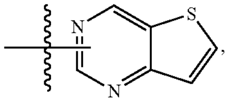,

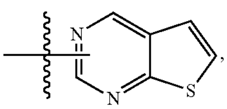, 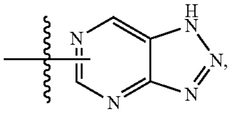,

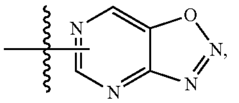, 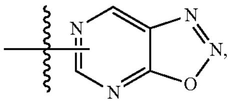,

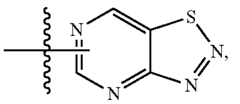, 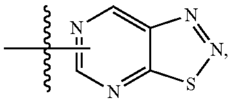, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, —PH(═O)$CH_3$, —P(═O)$(CH_3)_2$, —PH(═O)($OC_{1-6}$alkyl), —P(═O)$(OC_{1-6}alkyl)_2$, —OP(═O)$(OC_{1-6}alkyl)_2$, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, where the wavy line indicates the point of attachment to the rest of the molecule. The notation

means $R^1$, $R^6$, $R^7$, $R^2$ or $R^3$ can be attached to the rest of the molecule at any of the available positions of the R', $R^6$, $R^7$, $R^2$ or $R^3$ group set forth above. For example,

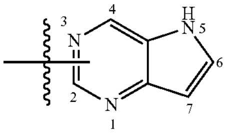

is meant to include 5H-pyrrolo[3,2-c]pyrimidin-2-yl, 5H-pyrrolo[3,2-c]pyrimidin-4-yl, 5H-pyrrolo[3,2-c]pyrimidin-5-yl, 5H-pyrrolo[3,2-c]pyrimidin-6-yl and 5H-pyrrolo[3,2-c]pyrimidin-7-yl (i.e., substitutions can be at 2, 4, 5, 6, or 7 positions of the 5H-pyrrolo[3,2-c]pyrimidine ring). In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently selected from:

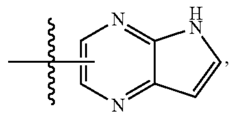, 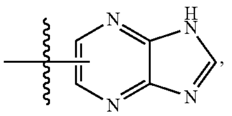,

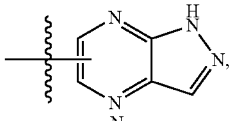, 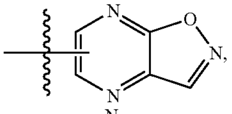,

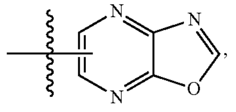, 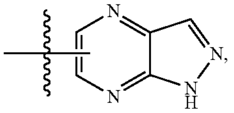,

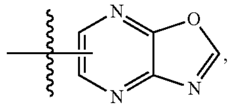, 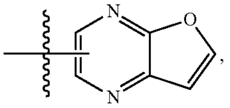,

-continued

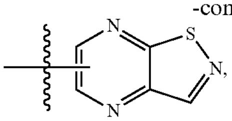, 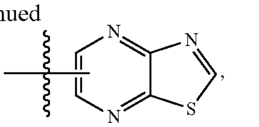,

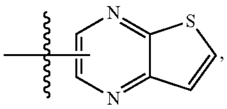, 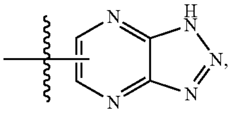,

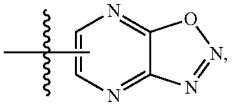, or 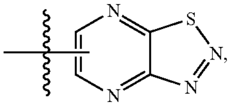, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, —PH(=O)$CH_3$, —P(=O)$(CH_3)_2$, —PH(=O)(O$C_{1-6}$alkyl), —P(=O)(O$C_{1-6}$ alkyl$)_2$, —OP(=O)(O$C_{1-6}$alkyl$)_2$, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, where the wavy line indicates the point of attachment to the rest of the molecule. The notation

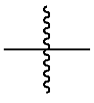

means $R^1$, $R^6$, $R^7$, $R^2$ or $R^3$ can be attached to the rest of the molecule at any of the available positions of the $R^1$, $R^6$, $R^7$, $R^2$ or $R^3$ group set forth above. For example,

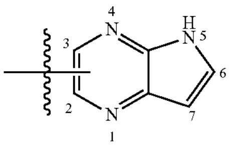

is meant to include 5H-pyrrolo[2,3-b]pyrazin-2-yl, 5H-pyrrolo[2,3-b]pyrazin-3-yl, 5H-pyrrolo[2,3-b]pyrazin-5-yl, 5H-pyrrolo[2,3-b]pyrazin-6-yl, 5H-pyrrolo[2,3-b]pyrazin-7-yl, (i.e., substitutions can be at 2, 3, 5, 6, or 7 positions of the 5H-pyrrolo[2,3-b]pyrazine ring). In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ or $R^3$ is each independently cycloalkyl or cycloalkenyl, each of which is optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently cyclopropyl, cyclobutyl, cyclopentyl, cyclohexyl, cycloheptyl, cyclooctyl, 1-cyclopentenyl, 3-cyclopentenyl, 4-cyclopentenyl, 1-cyclohexenyl, 3-cyclohexenyl, 4-cyclohexenyl, 1-cyclohexenyl, 1-octenyl, 1,4-cyclohexadienyl, 1,4-cyclohexadien-3-yl or cyclooctatetraene, each of which is optionally substituted with from: (i) 1-3 $R^h$ substituents; or (ii) 1-3 substituents; or (iii) 1-3 $R^{13}$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some instances, $R^6$, $R^7$, $R^2$ and $R^3$ are each independently cyclopentenyl, cyclohexenyl or cyclopropyl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently heterocycloalkyl, optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently 1-aziridinyl, 2-aziridinyl, 1-1-azetidinyl, 2-azetidinyl, 3-azetidinyl, 1-pyrrolidinyl, 2-pyrrolidinyl, 3-pyrrolidinyl, 2,3-dihydro-1H-pyrrol-1-yl, 2,3-dihydro-1H-pyrrol-2-yl, 2,3-dihydro-1H-pyrrol-3-yl, 2,3-dihydro-1H-pyrrol-4-yl, 2,3-dihydro-1H-pyrrol-5-yl, 2,5-dihydro-1H-pyrrol-1-yl, 2,5-dihydro-1H-pyrrol-2-yl, 2,5-dihydro-1H-pyrrol-3-yl, 2,3-dihydro-1H-imidazol-1-yl, 2,3-dihydro-1H-imidazol-2-yl, 2,3-dihydro-1H-imidazol-4-yl, 2,3-dihydrothiazol-2-yl, 2,3-dihydrothiazol-4-yl, 2,3-dihydrothiazol-5-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5- dihydrofuran-3-yl, 2,3-dihydropyran-2-yl, 2,3-dihydropyran-3-yl, 2,3-dihydropyran-4-yl, 2,3-dihydropyran-5-yl, 2,3-dihydropyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 1-piperidinyl, 2-piperidinyl, 3-piperidinyl, 4-piperidinyl, 1-piperazinyl, 2-piperazinyl, 2-morpholinyl, 3-morpholinyl, 4-morpholinyl, 1,2,3,6-tetrahydropyridin-1-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, or 1,2,3,6-tetrahydropyridin-6-yl, each of which is optionally substituted with from: (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^p$, $R^{14}$, $R^{15}$, $R^{16}$ or $R^{17}$ substituent is further optionally substituted with from 1-3 $R^{18}$ substituents. In some instances, $R^1$, $R^6$, $R^7$, $R^2$ or $R^3$ is each independently 1-aziridinyl, 2-aziridinyl, 2,3-dihydro-1H-pyrrol-5-yl, 2,5-dihydro-1H-pyrrol-3-yl, 2,3-dihydro-1H-imidazol-4-yl, 2,3-dihydrofuran-4-yl, 2,3-dihydrofuran-5-yl, 2,3-dihydrofuran-4-yl, 2,3-dihydrofuran-5-yl, 2,5-dihydrofuran-3-yl, 2,3-dihydropyran-5-yl, 2,3-dihydropyran-6-yl, 3,6-dihydro-2H-pyran-4-yl, 3,6-dihydro-2H-pyran-5-yl, 1,2,3,6-tetrahydropyridin-4-yl or 1,2,3,6-tetrahydropyridin-5-yl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In other instances, $R^1$, $R^6$, $R^7$, $R^2$ and $R^3$ are each independently 1,2,3,6-tetrahydropyridin-4-yl or 1,2,3,6-tetrahydropyridin-5-yl, 2,5-dihydro-1H-pyrrol-1-yl, 2,5-dihydro-1H-pyrrol-2-yl or 2,5-dihydro-1H-pyrrol-3-yl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In one embodiment, $R^1$ is heterocycloalkyl optionally substituted with from: (i) 1-3 independently selected $R^h$ substituents; or (ii) 1-3 independently selected $R^i$ substituents; or (iii) 1-3 independently selected $R^p$ substituents; or (iv) 1-3 independently selected $R^{14}$ substituents; or (v) 1-3 independently selected $R^{15}$ substituents; or (vi) 1-3 independently selected $R^{16}$ substituents; or (vii) 1-3 independently selected $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In another embodiment, $R^3$ is heterocycloalkyl optionally substituted with from: (i) 1-3 independently selected $R^h$ substituents; or (ii) 1-3 independently selected $R^i$ substituents; or (iii) 1-3 independently selected $R^p$ substituents; or (iv) 1-3 independently selected $R^{14}$ substituents; or (v) 1-3 independently selected $R^{15}$ substituents; or (vi) 1-3 independently selected $R^{16}$ substituents; or (vii) 1-3 independently selected $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently $C_{2-4}$alkenyl or $C_{2-4}$alkynyl, each of which is optionally substituted with from: each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$, substituent is further optionally substituted with from 1-3 $R^{18}$ substituents. In some embodiments, $R^2$ is H; $R^6$ and $R^7$ are each independently H, D, $C_1$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^s$ and L are as defined in any of the embodiments of compounds of formula (I) as described herein.

In some embodiments of compounds of formula (I), $R^1$, $R^6$, $R^7$, $R^2$ and $R^3$ are each independently vinyl, ethynyl, 1-propynyl, 3-fluoro-propynyl or cyclopropylethynyl, each of which is optionally substituted with from: from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some instances, $R^1$, $R^6$, $R^7$, $R^2$ or $R^3$ is each independently ethynyl, 1-propynyl, 3-fluoro-propynyl or cyclopropylethynyl, each of which is optionally substituted with from: from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, $R^5$ and L are as defined in any of the embodiments of compounds of formula (I) as described herein.

In some embodiments of compounds of formula (I), $R^1$, $R^6$, $R^7$, $R^2$ and $R^3$ are each independently halogen, $C_{1-6}$alkyl, CN, —C(O)—$R^t$, —C(O)NH$R^t$, —C(O)N$R^tR^t$, —NHC(O)$R^t$, —C(O)O$R^t$, —OC(O)$R^t$, —SO$_2R^t$, —NHSO$_2R^t$, —SO$_2$NH$R^t$, —SO$_2$N$R^tR^t$, wherein each $R^t$ is independently $C_{1-6}$alkyl, $C_{3-6}$cycloalkyl, phenyl or heterocycloalkyl, wherein $R^k$ is further optionally substituted with from 1-3 $R^p$ groups. In some instances, $R^t$ is $C_{1-6}$alkyl, $C_{3-6}$cycloalkyl, phenyl, 4-morpholinyl, 1-piperidinyl, 3-piperidinyl, 4-piperidinyl, 1-piperazinyl or 2-piperazinyl, wherein $R^t$ is further optionally substituted with from 1-3 $R^p$ group. In some embodiments, $R^2$ is H; $R^6$ and $R^7$ are each independently H, D, $C_{1-4}$ alkyl, aryl or heteroaryl, each of which is optionally substituted with 1-2 $R^g$; or 1-2 $R^h$; or 1-2 $R^i$; or 1-2 $R^{11}$ or 1-2 $R^{12}$ groups; and $R^1$ and $R^3$ are as defined herein. All the other variables $Y^1$, $Y^2$, $Y^3$, $R^4$, and L are as defined in any of the embodiments of compounds of formula (I) as described herein.

In some embodiments of compounds of formula (I), $R^6$ and $R^7$ substituents together with the atoms to which they are attached form a 5- or 6-membered ring having from 0-2 heteroatoms selected from N, O or S, wherein the ring is optionally substituted with from (i) 1-3 $R^h$ substituents; or (ii) 1-3 $R^i$ substituents; or (iii) 1-3 $R^p$ substituents; or (iv) 1-3

$R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In certain embodiments, the 5- or 6-membered ring is selected from cyclopentane, cyclohexane, pyrrolidine, pyrrole, pyrazole, imidazole, oxazole, isoxazole, thiazole, isothiazole, tetrahydrofuran, tetrahydropyran, 1,4-dioxane, pyridine, pyrazine, piperidine, piperazine, pyrimidine or pyridazine ring system, each of which is optionally substituted with from 1-3 $R^{15}$; or 1-3 $R^{16}$; or 1-3 $R^{17}$ substituents wherein $R^{15}$, $R^{16}$ or $R^{17}$ substituent is further optionally substituted with from 1-3 $R^{18}$ substituents. All the other variables $Y^1$, $Y^2$, $Y^3$, $R^4$, $R^5$ and L are as defined in any of the embodiments of compounds of formula (I) as described herein.

In any of the embodiments of compounds of formulas (I), $R^1$ is cycloalkyl or heterocycloalkyl, each of which is optionally substituted with from (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ substituents; or (vi) 1-4 $R^{16}$ substituents; or (vii) 1-4 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents.

In any of the embodiments of compounds of formulas (I), $R^1$ is aryl or heteroaryl, each of which is optionally substituted with from (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ substituents; or (vi) 1-4 $R^{16}$ substituents; or (vii) 1-4 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents.

In any of the embodiments of compounds of formulas (I), $R^1$ is H, halogen, phenyl, $C_{1-6}$alkyl, 4-pyrazolyl, cyclopropyl, cyclobutyl, cyclopentyl, cyclohexyl, 1,1-difluoro-4-cyclohexyl, 4,4-difluorocyclohexyl, 1-fluorocyclohexyl, 1,4,4-trifluorocyclohexyl, 3,3-difluorocyclobutyl, cycloheptyl, cyclooctyl, 1-piperidinyl, 4-piperidinyl, 1-piperazinyl, 2-pyridyl, 3-pyridyl, 4-pyridyl, 3-pyridazinyl, 4-pyridazinyl 1-cyclohexenyl, 1-pentenyl, 4-thiomorpholinyl, 1,1-dioxothian-4-yl, 1,1-dioxothiomorpholin-4-yl, morpholinyl, 2-norbornyl, bicyclo[4.1.0]heptan-3-yl, spiro[5,2]octan-3-yl, spiro[3,3]heptan-2-yl, tetrahydropyran-4-yl, tetrahydropyran-2-yl, tetrahydropyran-3-yl, 4-methyltetrahydropyran-4-yl, tetrahydrofuran-3-yl, oxetan-2-yl, each of which is optionally substituted with from (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ substituents; or (vi) 1-4 $R^{16}$ substituents; or (vii) 1-4 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents; or two adjacent $R^h$ substituents on aryl or heteroaryl ring taken together with the atoms to which they are attached, form a 5- or 6-membered ring having from 0-2 additional heteroatoms selected from O, N or S and optionally substituted with from 1-3 $R^p$; or 1-3 $R^s$ substituents. In some embodiments, $R^1$ is a substituent other than hydrogen. All the other variables $Y^1$, $Y^2$, $Y^3$, $R^2$, $R^3$, $R^4$, $R^5$, $R^6$, $R^7$ and L are as defined in any of the embodiments of compounds of formula (I) as described herein. In some embodiments, when L is a bond, $R^1$ is other than hydrogen.

In any of the embodiments of compounds of formulas (I), $R^1$ is —CH═C($R^g$)($R^g$), wherein the two $R^g$ groups taken together with the carbon atom to which they attach form a 4- to 6-membered ring having from 0-2 heteroatoms as ring members selected from N, O or S, wherein the N or S atoms are optionally oxidized; a ring carbon atom is optionally replaced with a —C(O)— group and the 4- to 6-membered ring is optionally substituted with from (i) 1-4 $R^h$ substituents; or (ii) 1-4 $R^i$ substituents; or (iii) 1-4 $R^p$ substituents; or (iv) 1-4 $R^{14}$ substituents; or (v) 1-4 $R^{15}$ substituents; or (vi) 1-4 $R^{16}$ substituents; or (vii) 1-4 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^1$ is cyclopropylidenemethyl, cyclobutylidenemethyl, cyclopentylidenemethyl, cyclohexylidenemethyl, (E)-cyclopent-2-en-1-ylidenemethyl, cyclopent-3-en-1-ylidenemethyl, cyclohex-2-en-1-ylidenemethyl, cyclohex-3-en-1-ylidenemethyl, each of which is optionally substituted with from (i) 1-2 $R^h$ substituents; or (ii) 1-4 $R^i$ substituents; or (iii) 1-2 $R^p$ substituents; or (iv) 1-2 $R^{14}$ substituents; or (v) 1-2 $R^{15}$ substituents; or (vi) 1-2 substituents; or (vii) 1-2 $R^{17}$ substituents, wherein each of $R^h$, $R^p$, $R^{14}$, $R^{15}$, $R^{16}$ or $R^{17}$ substituent is further optionally substituted with from 1-3 $R^{18}$ substituents. In other embodiments, $R^1$ is oxetan-3-ylidenemethyl, tetrahydropyran-4-ylidenemethyl, tetrahydropyran-3-ylidenemethyl, azetidin-3-ylidenemethyl, pyrrolidin-3-ylidenemethyl, tetrahydrofuran-3-ylidenemethyl, tetrahydrothiopyran-4-ylidenemethyl, tetrahydrothiopyran-3-ylidenemethyl, tetrahydrothiopyran-S-oxide-4-ylidenemethyl or tetrahydrothiopyran-S,S-oxide-4-ylidenemethyl, each of which is optionally substituted with from (i) 1-2 $R^h$ substituents; or (ii) 1-4 $R^i$ substituents; or (iii) 1-2 $R^p$ substituents; or (iv) 1-2 $R^{14}$ substituents; or (v) 1-2 $R^{15}$ substituents; or (vi) 1-2 $R^{16}$ substituents; or (vii) 1-2 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. All the other variables $Y^1$, $Y^2$, $Y^3$, $R^2$, $R^3$, $R^4$, $R^5$, $R^6$, $R^7$ and L are as defined in any of the embodiments of compounds of formula (I) as described herein In any of the embodiments of compounds of formulas (I), $R^1$ is H, halogen, deuterated $C_{1-6}$alkyl, $C_{1-6}$alkyl, aryl, aryl-$C_{1-4}$alkyl, $C_{3-6}$-cycloalkyl, $C_{3-6}$-cycloalkylalkyl, heteroaryl, heteroarylalkyl, heterocycloalkyl, heterocycloalkylalkyl, $C_{2-6}$alkenyl or $C_{2-6}$alkynyl, each of which is optionally substituted with from 1-3 $R^j$ groups; or 1-3 $R^h$ groups, wherein two $R^j$ substituents when attached to adjacent atoms of aryl, heteroaryl, cycloalkyl or heterocycloalkyl ring are optionally taken together to form a 5- or 6-membered ring having from 0-2 heteroatoms selected from O, N or S, wherein the 5- or 6-membered ring is optionally substituted with from 1-3 $R^h$ groups; or two $R^j$ groups when attached to the same carbon or nitrogen atom are optionally taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized. In some embodiments, two $R^h$ substituents when attached to adjacent atoms of aryl, heteroaryl, cycloalkyl or heterocycloalkyl ring are optionally taken together to form a 5- or 6-membered ring having from 0-2 heteroatoms selected from O, N or S, wherein the 5- or 6-membered ring is optionally substituted with from 1-3 members independently selected from halogen, $C_{1-6}$alkyl, —OH, $C_{1-6}$alkoxy, $C_{1-6}$haloalkyl, $C_{1-6}$haloalkoxy, —CN, —$NH_2$, —NH($C_{1-6}$ alkyl) or —N($C_{1-6}$alkyl)$_2$; or two $R^h$ groups when attached to the same carbon or nitrogen atom are optionally taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized. In some preferred embodiments, R' is cyclcoalkyl, heterocycloalkyl, aryl or heteroaryl, each of which is optionally substituted with from 1-3 $R^h$ substituents; or 1-3 $R^i$ substituents; or 1-3 $R^p$ substituents; or 1-3 $R^{14}$ substituents; or 1-3 $R^{15}$ substituents; or 1-3$R^{16}$ substituents; or 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents.

In any of the embodiments of compounds of formulas (I), $R^2$ is H, $C_{1-6}$alkyl, aryl, $C_{3-6}$cycloalkyl, heteroaryl, heterocycloalkyl, each of which is optionally substituted with from 1-3 $R^j$ groups. In some embodiments, $R^2$ is H, phenyl, $C_{1-6}$alkyl or $C_{3-6}$alkyl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In one instance, $R^2$ is H. In some instances, $R^2$ is H, halogen, $C_{1-4}$alkyl, $C_{1-4}$alkoxy, $C_{1-4}$haloalkyl, $C_{1-4}$haloalkoxy, —OH or CN. In other instances, $R^2$ is halogen, $C_{1-4}$alkyl, $C_{1-4}$alkoxy, $C_{1-4}$haloalkyl, $C_{1-4}$haloalkoxy, —OH or CN. In yet other instances, $R^2$ is H, halogen, $CH_3$, $CD_3$, $CH_3O$, $CF_3$, $CHF_2$, $CH_2F$, $CF_3O$, $CHF_2O$ $CH_2FO$, OH or CN. In one preferred embodiment, $R^2$ is H. All the other variables $Y^1$, $Y^2$, $Y^3$, $R^1$, $R^3$, $R^4$, $R^5$, $R^6$, $R^7$ and L are as defined in any of the embodiments of compounds of formula (I) as described herein.

In any of the embodiments of compounds of formulas (I), $R^4$ is H, halogen, $C_{1-6}$alkyl, $C_{1-6}$ alkoxy, CN, $C_{1-4}$haloalkyl, $C_{1-4}$haloalkoxy, OH, CN, vinyl or ethynyl, each of which is optionally substituted with from 1-3 members independently selected from halogen, $C_{1-4}$alkyl, $CH_3O$, CN, $CF_3$, $CHF_2$—, $CH_2F$—, $CF_3O$ $CHF_2O$— or $CH_2FO$—. In one embodiment, $R^4$ is H. In some instances, $R^4$ is H, halogen, $C_{1-4}$alkyl, $C_{1-4}$alkoxy, $C_{1-4}$haloalkyl, $C_{1-4}$haloalkoxy, —OH or CN. In other instances, $R^4$ is halogen, $C_{1-4}$alkyl, $C_{1-4}$alkoxy, $C_{1-4}$haloalkyl, $C_{1-4}$haloalkoxy, —OH or CN. In yet other instances, $R^4$ is H, halogen, $CH_3$, $CD_3$, $CH_3O$, $CF_3$, $CHF_2$, $CH_2F$, $CF_3O$, $CHF_2O$ $CH_2FO$, OH or CN. All the other variables $Y^1$, $Y^2$, $Y^3$, $R^1$, $R^3$, $R^2$, $R^5$, $R^6$, $R^7$ and L are as defined in any of the embodiments of compounds of formula (I) as described herein.

In any of the embodiments of compounds of formulas (I), $R^3$ is H, halogen, CN, $C_{1-6}$alkyl, deuterated $C_{1-6}$alkyl, aryl-$X^2$—, heteroaryl-$X^2$—, heterocycloalkyl-$X^2$, $C_{3-6}$cycloalkyl-$X^2$—, alkynyl-$X^2$—, $C_{1-6}$haloalkyl or $X^2$ is a bond, $C_{1-4}$alkylene or —C(O)—, wherein $R^3$ is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^3$ is aryl, heteroaryl, heterocycloakyl or $C_{3-6}$alkynyl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents; or two adjacent substituents on an aromatic ring are taken together with the atoms to which they attach form a 5- or 6-membered ring having from 0-2 heteroatoms selected from O, N or S. In some instances, $X^2$ is a bond, —C(O) or —$CH_2$—. In certain embodiments, $R^3$ is H, CN, $CH_3$, $CD_3$, phenyl, benzyl, 2-hydroxyethynyl, 2-hydroxymethylethynyl, 2-pyridyl, 3-pyridyl, 4-pyridyl, 2-pyridylmethyl, 3-pyridylmethyl, 4-pyridylmethyl, 2-pyridylcarbonyl, 3-pyridylcarbonyl, 4-pyridylcarbonyl, 5-pyrimidinyl, 4-pyrimidinyl, 3-thiophenyl, 2-thiophenyl, 5-oxazolyl, 2-oxazolyl, 4-oxazolyl, phenylsulfonyl, $C_{1-6}$sulfonyl, 1-pyrazolyl, 3-pyrazolyl, 4-pyrazolyl, 1-propynyl, carboxyl, 3-tetrafuranyl, cyclopropyl, cyclopropylmethyl, cyclobutyl, cyclobutylmethyl, cyclopentyl, cyclopentylmethyl, cyclohexylmethyl, cyclohexyl, 4-tetrafuranyl, 2-oxetanyl, 2-azetidinyl, 3-azetidinyl, 3-oxetanyl, —$CF_3$, —$CF_2H$, —$CHF_2$ or $CH_2CF_3$, (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. In some embodiments, $R^3$ is a substituent other than hydrogen. In some preferred embodiments, $R^3$ is halogen, aryl, heteroaryl or $C_{2-6}$alkynyl, wherein aryl, heteroaryl or $C_{2-6}$alkynyl is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents. All the other variables $Y^1$, $Y^2$, $Y^3$, $R^1$, $R^4$, $R^2$, $R^5$, $R^6$, $R^7$ and L are as defined in any of the embodiments of compounds of formula (I) as described herein.

In any of the embodiments of compounds of formulas (I), $R^3$ is H, halogen, —CN, —$CD_3$, deuterated, $C_{1-6}$alkyl, $C_{1-6}$alkyl, aryl, aryl-$C_{1-4}$alkyl, heteroaryl, heteroaryl-$C_{1-4}$ alkyl, $C_{3-8}$ cycloalkyl, $C_{3-8}$ cycloalkenyl, $C_{3-8}$ cycloalkyl-$C_{1-4}$alkyl, $C_{2-6}$ alkynyl, heterocycloalkyl, heterocycloalkyl-$C_{1-4}$alkyl or R, wherein each $R^3$ is optionally substituted with from 1-3 $R^m$ groups independently selected from CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —CH=C(R″)(R″), —OR″, —SR″, —OC(O)R″, —OC(S)R″, —P(=O)HR″, —P(=O)R″R″, —PH(=O)OR″, —P(=O)(OR″)$_2$, —OP(=O)(OR″)$_2$, —C(O)H, —O(CO)OR″, —C(O)R″, —C(S)R″, —C(O)OR″, —C(S)OR″, —S(O)R″, —S(O)$_2$R″, —C(O)NHR″, —C(S)NHR″, —C(O)NR″R″, —C(S)NR″R″, —S(O)$_2$NHR″, —S(O)$_2$NR″R″, —C(NH)NHR″, —C(NH)NR″R″, —NHC(O)R″, —NHC(S)R″, —NR″C(O)R″, —NR″C(S)R″, —NHS(O)$_2$R″, —NR″S(O)$_2$R″, —NHC(O)NHR″, —NHC(S)NHR″, —NR″C(O)$NH_2$, —NR″C(S)$NH_2$, —NR″(O)NHR″, —NR″C(S)NHR″, —NHC(O)NR″R″, —NHC(S)NR″R″, —NR″C(O)NR″R″, —NR″C(S)NR″R″, —NHS(O)$_2$NHR″, —NR″S(O)$_2NH_2$, —NR″S(O)$_2$NHR″, —NHS(O)$_2$NR″R″, —NR″S(O)$_2$NR″R″, —NHR″, R″ or —NR″R″, wherein each R″ is independently selected from H, $C_{1-6}$alkyl or aryl, arylalkyl, heteroaryl, heteroarylalkyl, heterocycloalkyl, heterocycloalkylalkyl, cycloalkyl or cycloalkylalkyl; or two R″ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized, wherein the aliphatic or aromatic portion of R″ is further optionally substituted with from 1-3 $R^h$. In any of the embodiments of compounds of formulas (I), $R^3$ is halogen, —CN, —$CD_3$, deuterated $C_{1-6}$alkyl, aryl, aryl-$C_{1-4}$alkyl, heteroaryl, heteroaryl-$C_{1-4}$ alkyl, $C_{3-8}$ cycloalkyl, $C_{3-8}$ cycloalkenyl, $C_{3-8}$ cycloalkyl-$C_{1-4}$alkyl, $C_{2-6}$ alkynyl, heterocycloalkyl, heterocycloalkyl-$C_{1-4}$alkyl or wherein each $R^3$ is optionally substituted with from 1-3 $R^o$ members independently selected from halogen, vinyl, $C_{1-6}$alkyl, —OH, $C_{1-6}$alkoxy, $C_{1-6}$haloalkyl $C_{1-6}$haloalkoxy, —CN, —$NH_2$, —NH($C_{1-6}$alkyl), —N($C_{1-6}$alkyl)$_2$, $C_{3-6}$cycloalkyl, heterocycloalkyl, aryl, heteroaryl, wherein each $R^o$ is further independently optionally substituted with from 1-3 $R^h$. In any of the embodiments of compounds of formulas (I), $R^3$ is aryl, heteroaryl or $C_{2-6}$ alkynyl, each of which is optionally substituted with from 1-3 independently selected $R^m$; or 1-3 independently selected $R^o$. All the other variables $Y^1$, $Y^2$, $Y^3$, $R^1$, $R^4$, $R^2$, $R^5$, $R^6$, $R^7$ and L are as defined in any of the embodiments of compounds of formula (I) as described herein.

In any of the embodiments of compounds of formulas (I), $R^3$ is halogen, phenyl, 4-pyridyl, 3-pyridyl, 5-pyrimidinyl, ethynyl, 2-hydroxymethylethynyl, 2-trimethylsilylethynyl, 5-oxazolyl, 2-oxazolyl, 4-oxazolyl, 2-pyrazinyl, 4-pyrazolyl, 1H-4-pyrazolyl, 1-methyl-2-oxo-3-pyridyl, 1-methyl-2-oxo-4-pyridyl, 1-methyl-2-oxo-5-pyridyl or 1-methyl-2-oxo-6-pyridyl each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents.

In any of the embodiments of compounds of formulas (I), $R^3$ is

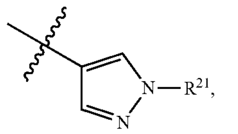

wherein $R^{21}$ is $R^h$; or $R^i$; or $R^p$; or $R^{14}$; or $R^{15}$; or $R^{16}$; or $R^{17}$; or $R^{18}$ and wherein the wavy line indicates the point of attachment to the rest of the molecule, wherein each of $R^h$, $R^i$, $R^p$, $R^{14}$, $R^{15}$, $R^{16}$ or $R^{17}$ substituent is further optionally substituted with from 1-3 $R^{18}$ substituents. In one embodiment, $R^{21}$ is H. In some embodiments, $R^{21}$ is $—CH_3$, $CD_3$, $—CH_2CH_3$, $—CHF_2$, $—CH_2CF_3$, $—CH_2CH_2F$, isobutyl, 2-morpholinoethyl, 3-oxetanyl, $—CH_2CN$, 2-cyanoethyl, benzyl, phenethyl, $—CH_2COOH$, $—CH_2CH_2COOH$ or t-butoxycarbonyl.

In any of the embodiments of compounds of formulas (I), $R^3$ is

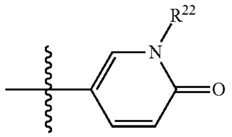

,

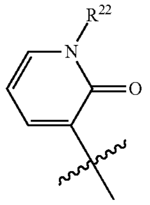

, or

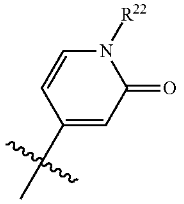

, wherein $R^{22}$ is $C_{1-4}$alkyl optionally substituted with from 1-2 substituents independently selected from halogen, $C_{1-4}$alkyl, $C_{1-4}$alkoxy, $C_{1-4}$haloalkyl, $C_{1-4}$haloalkoxy, —OH or CN or a deuterated analog thereof. In some embodiments, $R^{22}$ is $CH_3$ or $CD_3$. In some embodiments of compound of formula (I) or (I'), $R^3$ is

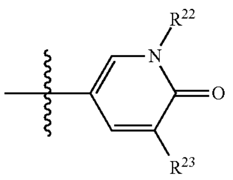

or

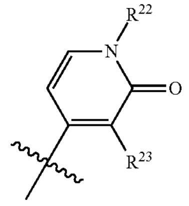

wherein $R^{22}$ and $R^{23}$ are each independently $C_{1-4}$alkyl optionally substituted with from 1-2 substituents independently selected from halogen, $C_{1-4}$alkyl, $C_{1-4}$alkoxy, $C_{1-4}$haloalkyl, $C_{1-4}$haloalkoxy, —OH or CN or a deuterated analog thereof. In some embodiments, $R^{22}$ and $R^{23}$ are $CH_3$. In other embodiments, $R^{22}$ and $R^{23}$ are $CD_3$.

In some embodiments, the present disclosure provides a compound having formula (I'):

(I)

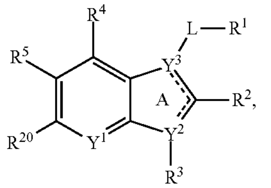

or a pharmaceutically acceptable salt, a solvate, a tautomer, an isomer, or a deuterated analog thereof, wherein $R^{20}$ is halogen, $C_{1-4}$alkyl, $C_{1-4}$alkoxy, $C_{1-4}$haloalkyl, $C_{1-4}$haloalkoxy, —OH or CN, or a deuterated analog thereof. Other variables $R^1$, $R^2$, $R^3$, $R^4$, $R^5$, $Y^1$, $Y^2$, $Y^3$ and L are as defined in any embodiments of formula (I). In some instances, $R^{20}$ is halogen, $C_{1-2}$alkyl, $C_{1-2}$alkoxy, $C_{1-2}$haloalkyl, $C_{1-2}$haloalkoxy, —OH or CN. In other instances, $R^{20}$ is halogen, $CH_3$, $CD_3$, $CH_3O$, $CF_3$, $CHF_2$, $CH_2F$, $OCF_3$, $OCHF_2$, $OCH_2F$, OH or CN. In some instances, $R^{20}$, $R^4$ and $R^2$ are each independently halogen, $C_{1-4}$alkyl, $C_{1-4}$alkoxy, $C_{1-4}$haloalkyl, $C_{1-4}$haloalkoxy, —OH or CN, or a deuterated analog thereof.

In any of the embodiments of compounds of formulas (I) or (I'), the hydrogen atoms in $R^1$, $R^6$, $R^7$, $R^2$ or $R^3$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^1$, $R^6$, $R^7$, $R^2$ or $R^3$ is optionally replaced by a deuterium atom with at least 52.5%, 60%, 70%, 75%, 80%, 90%, 95%, 99%, 99.5% or 99.9% deuterium incorporation for each deuterium.

Subformulae of Formulas (I) or (I')

In some embodiments, compounds of formula (I) or (I') have subformula (II):

(II)

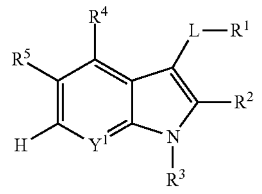

In one embodiment, $Y^1$ is N. In another embodiment, $R^4$ is H. In another embodiment, $R^2$ is H. In some embodiments, $R^5$ is optionally substituted heteroaryl or optionally substituted heterocycloalkyl. The variables and substituents $R^1$, $R^2$, $R^3$, $R^4$, $R^5$, L and $Y^1$ are as defined in any of embodiments of compounds of formula (I) or any embodiment as described herein.

In some embodiments, compounds of formula (I) or (I') have subformula (III):

(III)

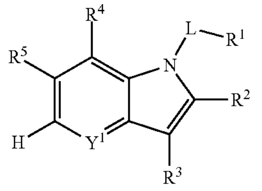

In one embodiment, $Y^1$ is N. In another embodiment, $R^4$ is H. In another embodiment, $R^2$ is H. The variables and substituents $R^1$, $R^2$, $R^3$, $R^4$, $R^5$, L and $Y^1$ are as defined in any of embodiments of compounds of formula (I) or any embodiment as described herein.

In some embodiments, compounds of formula (I) or (I') have subformula (IV):

(IV)

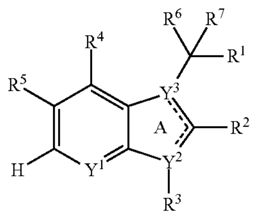

In one embodiment, $Y^1$ is N. In another embodiment, $Y^2$ is N and $Y^3$ is C. In yet another embodiment, $Y^2$ is C and $Y^3$ is N. In another embodiment, $R^4$ is H. In another embodiment, $R^2$ is H. The variables and substituents $R^1$, $R^2$, $R^3$, $R^4$, $R^5$, $R^6$, $R^7$, $Y^1$, $Y^2$ and $Y^3$ are as defined in any of embodiments of compounds of formula (I) or any embodiment as described herein.

In some embodiments, compounds of formula (I) or (I') have subformula (V):

(V)

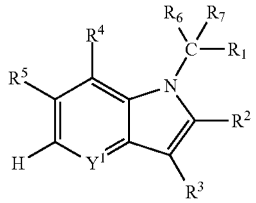

In one embodiment, $Y^1$ is N. In another embodiment, $R^4$ is H. In another embodiment, $R^2$ is H. The variables and substituents $R^1$, $R^2$, $R^3$, $R^4$, $R^5$, $R^6$, $R^7$, and $Y^1$ are as defined in any of embodiments of compounds of formula (I) or any embodiment as described herein. In some embodiments, $R^5$ is 5- or 6-membered heteroaryl or heterocycloalkyl, each of which is substituted with from 1-2 members independently selected from $C_{1-4}$alkyl, $C_{1-4}$alkoxy, $C_{1-4}$haloalkyl or $C_{1-4}$ haloalkoxy or deuterated analogs. In some embodiments, $R^5$ is 5- or 6-membered heteroaryl or heterocycloalkyl, each of which is substituted with 2 members selected from $C_{1-4}$alkyl or its deuterated analogs. In certain embodiments, $R^5$ is 5- or 6-membered heteroaryl or heterocycloalkyl, each of which is substituted with 2 members independently selected from $CH_3$, $CD_3$, $CH_2CH_3$ or isopropyl. In certain embodiments, $R^5$ is 5- or 6-membered heteroaryl or heterocycloalkyl, each of which is substituted with 2 members independently selected from $CH_3$ or $CD_3$. In certain embodiments, $R^5$ is 5- or 6-membered heteroaryl or heterocycloalkyl, each of which is substituted with 2 members selected from $CH_3$ or $CD_3$.

In some embodiments, compounds of formulas (I), (I') or (V) have subformulas (Va) or (Vb):

(Va)

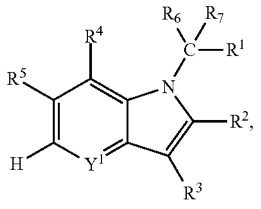

(Vb)

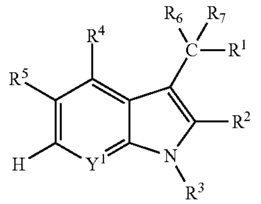

In one embodiment, $R^4$ is H. In another embodiment, $R^2$ is H. The variables and substituents $R^1$, $R^2$, $R^3$, $R^4$, $R^5$, $R^6$, $R^7$, $Y^1$, $Y^2$ and $Y^3$ are as defined in any of embodiments of compounds of formula (I) or any embodiment as described herein.

In some embodiments, compounds of formulas (I), (I'), (V) or (Va) have subformula (Va-1):

(Va-1)

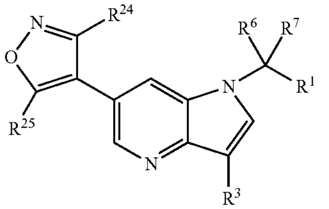

$R^{24}$ and $R^{25}$ are each independently $C_{1-2}$alkyl or deuterated $C_{1-2}$alkyl, each of which is optionally substituted with from 1-2 halogens. The variables and substituents $R^1$, $R^3$, $R^6$ and $R^7$ are as defined in any of embodiments of compounds of formula (I) or any embodiment as described herein. In some instances, $R^{24}$ and $R^{25}$ are each independently methyl, ethyl, $CD_3$ or $CD_2CD_3$. In certain instances, $R^{24}$ and $R^{25}$ are methyl, ethyl, $CD_3$ or $CD_2CD_3$. In other instances, $R^{24}$ and $R^{25}$ are $CH_3$. In one instance, $R^{24}$ and $R^{25}$ are $CD_3$. In some embodiments, $R^6$ and $R^7$ are each independently selected from H, D, $C_{1-4}$alkyl, phenyl or 2-pyridyl, each of which is optionally substituted with from 1-2 independently selected $R^{12}$; or 1-2 independently selected $R^{12}$; or 1-2 independently selected $R^{18}$ groups; or 1-2 members independently selected from $C_{1-4}$alkyl, CN or OH; or $R^6$ and $R^7$ are taken together with the carbon atom to which they attach form a 3- to 6-membered carbocyclic ring, which is optionally substituted with from 1-2 independently selected $R^{12}$; 1-2 independently selected $R^{13}$ or 1-2 independently selected $R^{18}$ groups. The variables and substituents $R^1$, $R^3$, $R^6$ and $R^7$ are as defined in any of embodiments of compounds of formula (I) or any embodiment as described herein.

In some embodiments, compounds of formulas (I), (I'), (V) or (Va) have subformula (Va-2):

(Va-2)

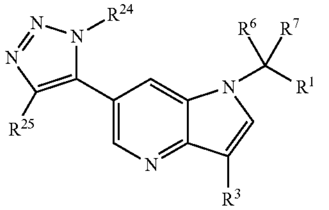

$R^{24}$ and $R^{25}$ are as defined in formula (Va-1). The variables and substituents $R^1$, $R^3$, $R^6$ and $R^7$ are as defined in any of embodiments of compounds of formula (I) or any embodiment as described herein.

In some embodiments, compounds of formulas (I), (I'), (V) or (Va) have subformula (Va-3):

(Va-3)

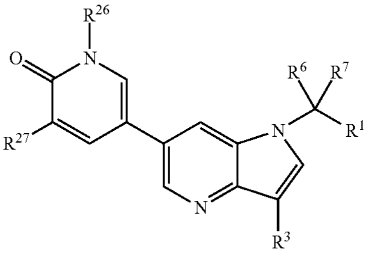

$R^{26}$ and $R^{27}$ are each independently H, D, $C_{1-4}$alkyl or deuterated $C_{1-4}$alkyl. In one embodiment, $R^{26}$ is $C_{1-4}$alkyl and $R^{27}$ is H or $C_{1-4}$alkyl. In another embodiment, $R^{26}$ and $R^{27}$ are H. In another embodiment, $R^{26}$ and $R^{27}$ are methyl or $CD_3$. The variables and substituents $R^1$, $R^3$, $R^6$ and $R^7$ are as defined in any of embodiments of compounds of formula (I) or any embodiment as described herein.

In some embodiments, the present disclosure provides any of the compounds set forth in Tables 1-31, or a pharmaceutically acceptable salt, hydrate, solvate, tautomer or isomer thereof. In certain embodiments, the present disclosure provides the above selected compounds and pharmaceutically acceptable salts thereof. In certain embodiments, the present disclosure provides any of compounds P-0001 to P-0106, P-0108 to P-0245, P-0250-0372, P-0373 to P-0420, P-0424, P-0427 to P-0438, P-0440 to P-0443, P-0448, and P-0451 to P-0622, and P-700 to P-814 as described herein or a pharmaceutically acceptable salt, hydrate, solvate, tautomer or isomer thereof. In certain embodiments, the present disclosure provides any of the compounds described in formulas (I), (I'), (II), (III), (IV), (V), (Va), (Va-1), (Va-2) or (Va-3), or any of the subformulas as described herein, any of the compounds described in the examples and any of the compounds described herein, or a pharmaceutically acceptable salt, hydrate, solvate, tautomer or isomer thereof.

In some embodiments, the present disclosure provides a compound selected from those set forth in Tables 27, 28, 29 30, and 31 or a pharmaceutically acceptable salt, hydrate, solvate, tautomer or isomer thereof.

In some embodiments, the present disclosure provides any of the compounds selected from those set forth in Tables 1-27, 28 and 29, for example, compounds P-0001 to P-0106, P-0108 to P-0245, P-0250-0372, and P-0373 to P-0420, P-0424, P-0427 to P-0438, P-0440 to P-0443, P-0448, and P-0451 to P-0622, e.g., compounds P-0001, P-0002, P-0003, P-0004, P-0005, P-0006, P-0007, P-0008, P-0009, P-0010, P-0011, P-0012, P-0013, P-0014, P-0015, P-0016, P-0017, P-0018, P-0019, P-0020, P-0021, P-0022, P-0023, P-0024, P-0025, P-0026, P-0027, P-0028, P-0029, P-0030, P-0031, P-0032, P-0033, P-0034, P-0035, P-0036, P-0037, P-0038, P-0039, P-0040, P-0041, P-0042, P-0043, P-0044, P-0045, P-0046, P-0047, P-0048, P-0049, P-0050, P-0051, P-0052, P-0053, P-0054, P-0055, P-0056, P-0057, P-0058, P-0059, P-0060, P-0061, P-0062, P-0063, P-0064, P-0065, P-0066, P-0067, P-0068, P-0069, P-0070, P-0071, P-0072, P-0073, P-0074, P-0075, P-0076, P-0077, P-0078, P-0079, P-0080, P-0081, P-0082, P-0083, P-0084, P-0085, P-0086, P-0087, P-0088, P-0089, P-0090, P-0091, P-0092, P-0093, P-0094, P-0095, P-0096, P-0097, P-0098, P-0099, P-0100, P-0101, P-0102, P-0103, P-0104, P-0105, P-0106, P-0108, P-0109, P-0110, P-0111, P-0112, P-0113, P-0114, P-0115, P-0116, P-0117, P-0118, P-0119, P-0120, P-0121, P-0122, P-0123, P-0125, P-0126, P-0127, P-0128, P-0129, P-0130, P-0131, P-0132, P-0134, P-0135, P-0136, P-0137, P-0138, P-0139, P-0140, P-0141, P-0142, P-0143, P-0144, P-0145, P-0146, P-0147, P-0148, P-0149, P-0150, P-0151, P-0152, P-0153, P-0154, P-0156, P-0157, P-0158, P-0159, P-0160, P-0161, P-0163, P-0164, P-0165, P-0167, P-0168, P-0169, P-0170, P-0171, P-0172, P-0173, P-0174, P-0175, P-0176, P-0179, P-0180, P-0181, P-0182, P-0183, P-0185, P-0186, P-0187, P-0188, P-0189, P-0190, P-0191, P-0192, P-0193, P-0194, P-0195, P-0196, P-0197, P-0198, P-0199, P-0200, P-0201, P-0202, P-0203, P-0204, P-0205, P-0206, P-0207, P-0208, P-0209, P-0210, P-0211, P-0212, P-0213, P-0214, P-0215, P-0216, P-0217, P-0218, P-0219, P-0220, P-0221, P-0222, P-0223, P-0224, P-0225, P-0226, P-0227, P-0228, P-0229, P-0230, P-0231, P-0232, P-0233, P-0234, P-0235, P-0236, P-0237, P-0238, P-0239, P-0240, P-0241, P-0242, P-0243, P-0244, P-0245, P-0250, P-0251, P-0252, P-0253, P-0254, P-0255, P-0256, P-0257, P-0258, P-0259, P-0260, P-0261, P-0262, P-0263, P-0264, P-0265, P-0266, P-0267, P-0268, P-0269, P-0270, P-0271, P-0272, P-0273, P-0274, P-0275, P-0276, P-0277, P-0278, P-0279, P-0280, P-0281, P-0282, P-0283, P-0284, P-0285, P-0286, P-0287, P-0288, P-0289, P-0290, P-0291, P-0292, P-0293, P-0294, P-0295, P-0296, P-0297, P-0298, P-0299, P-0300, P-0301, P-0302, P-0303, P-0304, P-0305, P-0306, P-0307, P-0308, P-0309, P-0310, P-0311, P-0312, P-0313, P-0314, P-0315, P-0316, P-0317, P-0318, P-0319, P-0320, P-0321, P-0322, P-0323, P-0324, P-0325, P-0326, P-0327, P-0328, P-0329, P-0330, P-0331, P-0332, P-0333, P-0334, P-0335, P-0336, P-0337, P-0338, P-0339, P-0340, P-0341, P-0342, P-0343, P-0344, P-0345, P-0346, P-0347, P-0348, P-0349, P-0350, P-0351, P-0352, P-0353, P-0354, P-0355, P-0356, P-0357, P-0358, P-0359, P-0360, P-0361, P-0362, P-0363, P-0364, P-0365, P-0366, P-0367, P-0368, P-0369, P-0370, P-0371, P-0372, P-0373, P-0374, P-0375, P-0376, P-0377, P-0378, P-0378, P-0379, P-0381, P-0382, P-0383, P-0384, P-0385, P-0386, P-0387, P-0388, P-0389, P-0390, P-0391, P-0392, P-0393, P-0394, P-0395, P-0396, P-0397, P-0399, P-0400, P-0401, P-0402, P-0403, P-0404, P-0405, P-0406, P-0407, P-0408, P-0409, P-0410, P-0411, P-0412, P-0413, P-0414, P-0415, P-0416, P-0417, P-0418, P-0419, P-0420, P-0424, P-0427, P-0428, P-0429, P-0430, P-0431, P-0432, P-0433, P-0434, P-0435, P-0436, P-0437, P-0438, P-0440, P-0441, P-0442, P-0443, P-0448, P-0451, P-0452, P-0453, P-0454, P-0455, P-0456, P-0457, P-0458, P-0459, P-0460, P-0461, P-0462, P-0463, P-0464, P-0465, P-0466, P-0467, P-0468, P-0469, P-0470, P-0471, P-0472, P-0473, P-0474, P-0475, P-0476, P-0477, P-0478, P-0479, P-0480, P-0481, P-0482, P-0483, P-0484, P-0485, P-0486, P-0487, P-0488, P-0489, P-0490, P-0491, P-0492, P-0493, P-0494, P-0495, P-0496, P-0497, P-0498, P-0499, P-0500, P-0501, P-0502, P-0503, P-0504, P-0505, P-0506, P-0507, P-0508, P-0509, P-0510, P-0511, P-0512, P-0513, P-0514, P-0515, P-0516, P-0517, P-0518, P-0519, P-0520, P-0521, P-0522, P-0523, P-0524, P-0525, P-0526, P-0527, P-0528, P-0529, P-0530, P-0531, P-0532, P-0533, P-0534, P-0535, P-0536, P-0537, P-0538, P-0539, P-0540, P-0541, P-0542, P-0543, P-0544, P-0545, P-0546, P-0547, P-0548, P-0549, P-0550, P-0551, P-0552, P-0553, P-0554, P-0555, P-0556, P-0557, P-0558, P-0559, P-0560, P-0561, P-0562, P-0563, P-0564, P-0565, P-0566, P-0567, P-0568, P-0569, P-0570, P-0571, P-0572, P-0573, P-0574, P-0575, P-0576, P-0577, P-0578, P-0579, P-0580, P-0581, P-0582, P-0583, P-0584, P-0585, P-0586, P-0587, P-0588, P-0589, P-0590, P-0591, P-0592, P-0593, P-0594, P-0595, P-0596, P-0597, P-0598, P-0599, P-0600, P-0601, P-0602, P-0603, P-0604, P-0605, P-0606, P-0607, P-0608, P-0609, P-0610, P-0611, P-0612, P-0613, P-0614, P-0615, P-0616, P-0617, P-0618, P-0619, P-0620, P-0621 or P-0622, or a pharmaceutically acceptable salt, hydrate, solvate, tautomer or isomer thereof.

In some embodiments, the present disclosure provides any of the compounds selected from those set forth in Table 30, for example, compounds P-0700 to P-0822, e.g., compounds P-0700, P-0701, P-0702, P-0703, P-0704, P-0705, P-0706, P-0707, P-0708, P-0709, P-0710, P-0711, P-0712, P-0713, P-0714, P-0715, P-0716, P-0717, P-0718, P-0719, P-0720, P-0721, P-0722, P-0723, P-0724, P-0725, P-0726, P-0727, P-0728, P-0729, P-0730, P-0731, P-0732, P-0733, P-0734, P-0735, P-0736, P-0737, P-0738, P-0739, P-0740, P-0741, P-0742, P-0743, P-0744, P-0745, P-0746, P-0747, P-0748, P-0749, P-0750, P-0751, P-0752, P-0753, P-0754, P-0755, P-0756, P-0757, P-0758, P-0759, P-0760, P-0761, P-0762, P-0763, P-0764, P-0765, P-0766, P-0767, P-0768, P-0769, P-0770, P-0771, P-0772, P-0773, P-0774, P-0775, P-0776, P-0777, P-0778, P-0779, P-0780, P-0781, P-0782, P-0783, P-0784, P-0785, P-0786, P-0787, P-0788, P-0789, P-0790, P-0791, P-0792, P-0793, P-0794, P-0795, P-0796, P-0797, P-0798, P-0799, P-0800, P-0801, P-0802, P-0803, P-0804, P-0805, P-0806, P-807, P-0808, P-0809, P-0810, P-0811, P-0812, P-0813, P-0814, P-0815, P-0816, P-0817, P-0818, P-0819, P-0820, P-0821 or P-0822, or a pharmaceutically acceptable salt, hydrate, solvate, tautomer or isomer thereof.

In some embodiments, the present disclosure provides any of the compounds selected from those set forth in Table 31, for example, compounds P-0900 to P-1053, e.g., compounds P-0900, P-0901, P-0902, P-0903, P-0904, P-0905, P-0906, P-0907, P-0908, P-0909, P-0910, P-0911, P-0912, P-0913, P-0914, P-0915, P-0916, P-0917, P-0918, P-0919, P-0920, P-0921, P-0922, P-0923, P-0924, P-0925, P-0926, P-0927, P-0928, P-0929, P-0930, P-0931, P-0932, P-0933, P-0934, P-0935, P-0936, P-0937, P-0938, P-0939, P-0940, P-0941, P-0942, P-0943, P-0944, P-0945, P-0946, P-0947, P-0948, P-0949, P-0950, P-0951, P-0952, P-0953, P-0954, P-0955, P-0956, P-0957, P-0958, P-0959, P-0960, P-0961, P-0962, P-0963, P-0964, P-0965, P-0966, P-0967, P-0968, P-0969, P-0970, P-0971, P-0972, P-0973, P-0974, P-0975, P-0976, P-0977, P-0978, P-0979, P-0980, P-0981, P-0982, P-0983, P-0984, P-0985, P-0986, P-0987, P-0988, P-0989, P-0990, P-0991, P-0992, P-0993, P-0994, P-0995, P-0996, P-0997, P-0998, P-0999, P-1000, P-1001, P-1002, P-1003, P-1004, P-1005, P-1006, P-1007, P-1008, P-1009, P-1010, P-1011, P-1012, P-1013, P-1014, P-1015, P-1016, P-1017, P-1018, P-1019, P-1020, P-1021, P-1022, P-1023, P-1024, P-1025, P-1026, P-1027, P-1028, P-1029, P-1030, P-1031, P-1032, P-1033, P-1034, P-1035, P-1036, P-1037, P-1038, P-1039, P-1040, P-1041, P-1042, P-1043, P-1044, P-1045, P-1046, P-1047, P-1048, P-1049, P-1050, P-1051, P-1052, P-1053, or a pharmaceutically acceptable salt, hydrate, solvate, tautomer or isomer thereof.

Intermediates

In another aspect, the present disclosure provides intermediates that are useful for the preparation of the compounds described in formulas (I), (I'), (II), (III), (IV), (V), (Va), (Va-1), (Va-2) or (Va-3), or any of the subformulas as described herein, any of the compounds described in the examples and any of the compounds described herein. In some embodiments, the present disclosure provides an intermediate compound of formula (VI):

(VI)

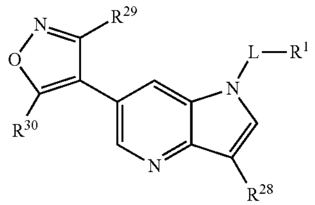

$R^{28}$ is halogen, tosyl, $CH_3SO_3$— or $CF_3SO_3$. In some embodiments, $R^{28}$ is halogen. In one embodiment, $R^{28}$ is Br or I. In one embodiment, $R^{28}$ is I. $R^{29}$ and $R^{30}$ are each independently selected from $C_{1-4}$alkyl, $C_{1-4}$alkoxy, $C_{1-4}$haloalkyl or $C_{1-4}$ haloalkoxy. In some embodiments, $R^{29}$ and $R^{30}$ are each independently $C_{1-2}$alkyl or deuterated $C_{1-2}$alkyl, each of which is optionally substituted with from 1-2 halogens. In certain embodiments, $R^{29}$ and $R^{30}$ are each independently methyl, ethyl, $CD_3$ or $CD_2CD_3$. In some embodiments, $R^{29}$ and $R^{30}$ are methyl, ethyl, $CD_3$ or $CD_2CD_3$. In some embodiments, $R^{29}$ and $R^{30}$ are methyl or $CD_3$. In one embodiment, $R^{29}$ and $R^{30}$ are methyl. In another embodiment, $R^{29}$ and $R^{30}$ are $CD_3$. L and $R^1$ are as defined in any embodiments of compounds of formula (I), or the subgeneric formulas of formula (I), or any embodiments as described herein. In some embodiments of compounds of formula (VI), L is a bond and $R^1$ is H. In other embodiments of compounds of formula (VI), L is —$C(R^6)(R^7)$—, where $R^6$, $R^7$ and $R^1$ are as defined in any embodiments of compounds of formula (I), or the subgeneric formulas of formula (I), or any embodiments as described herein. In certain instances, $R^6$ and $R^7$ are H, $C_{1-4}$alkyl, cycloalkyl, aryl or heteroaryl, wherein the aliphatic or aromatic porton of $R^6$ and $R^7$ is optionally substituted with from 1-3 independently selected $R^h$ groups; or 1-3 independently selected $R^{11}$ groups or 1-3 independently selected $R^{12}$ groups; or 1-3 independently selected $R^{13}$ groups. In certain instances, $R^6$ is H and $R^7$ is $C_{1-4}$alkyl, $C_{3-6}$cycloalkyl, aryl or heteroaryl. In some instances, $R^1$ is $C_{4-8}$ cycloalkyl, heterocycloalkyl, aryl or heteroaryl, each of which is optionally substituted. In certain instances, $R^1$ is $C_{4-8}$ cycloalkyl, heterocycloalkyl, aryl or heteroaryl, each of which is optionally substituted with from (i) 1-3 $R^h$ substituents; or (ii) 1-3 $R^i$ substituents; or (iii) 1-3 $R^p$ substituents; or (iv) 1-3 $R^{14}$ substituents; or (v) 1-3 $R^{15}$ substituents; or (vi) 1-3 $R^{16}$ substituents; or (vii) 1-3 $R^{17}$ substituents, wherein each of $R^h$, $R^i$, $R^p$, $R^{14}$, $R^{15}$, $R^{16}$ or $R^{17}$ substituent is further optionally substituted with from 1-3 $R^{18}$ substituents.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of bromodomain function are readily available to those skilled in the art of organic chemical synthesis.

Alternative Compound Forms or Derivatives

Compounds contemplated herein are described with reference to both generic formulae and specific compounds. In addition, compounds disclosed herein may exist in a number of different forms or derivatives, all within the scope of the present disclosure. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the present disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.,* 40:2011-2016; Shan et al., 1997, *J Pharm Sci* 86(7):756-757; Bagshawe, 1995, *Drug Dev. Res.,* 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically acceptable salts

Unless specified to the contrary, specification of a compound herein includes pharmaceutically acceptable salts of such compound. Thus, compounds described herein and recited in any of the claims can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the present disclosure may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences,* 19th ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other compound forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the present disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the present disclosure with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

IV. Formulations and Administration

In another aspect, the present disclosure provides pharmaceutical compositions comprising/including a pharmaceutically acceptable carrier, excipient and/or diluent and a compound of the present disclosure described herein or a pharmaceutically acceptable salt or solvate thereof. In an exemplary embodiment, the present disclosure provides a pharmaceutical formulation comprising/including a compound as described herein. In some embodiments, the present disclosure provides pharmaceutical composition comprising/including a compound having any of formulas (I), (I'), (II), (III), (IV), (V), (Va) or (Vb), and any of the subgeneric formulas as described herein, a compound as described herein and a pharmaceutically acceptable carrier, excipient and/or diluents.

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy,* 21st edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the present disclosure (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the present disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present disclosure provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. The compounds as disclosed herein may be used in adjuvant or neoadjuvant therapy in combination with other therapy or therapeutic agents as described herein.

V. Disease Indications and Modulations of Bromodomains
Exemplary Diseases Associated with Bromodomains Members of the BET (Bromodomain and Extra Terminal) family of bromodomain proteins (BRD2, BRD3, BRD4 and BRDT) have been associated with a variety of disorders including neurological diseases, autoimmune and inflammatory diseases, metabolic diseases (Muller et al. *Expert Rev. Mol. Med.* 2011, September 13; 13:e29; Prinjha et al. *Trends Pharmacol. Sci.* 2012, 33, 146-153; Belkina et al. *J. Immunol.* 2013, 190, 3670-3678; and Belkina et al. *Nature Rev. Cancer* 2012, 12, 465-477) and cancers (Alsarraj et al. *International Journal of Breast Cancer* 2012, 1-7; Barbieri et al. *Briefings in Functional Genomics* 2013, 1-12; Blobel et al. *Cancer Cell* 2011, 20, 287-288; Dang *Cell* 2012, 149, 22-35). In addition, some viruses make use of these proteins to tether their genomes to the host cells chromatin, as part of the process of viral replication (You et al *Cell,* 2004 117, 349-60).

The compounds of formulas (I), (I'), (II), (III), (IV), (V), (Va) or (Vb), or any of the subformulas or compounds as described herein are useful for treating disorders related to one or more proteins involved in epigenetic regulation, such as proteins containing acetyl-lysine recognition motifs, i.e., bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others.

The presence of bromodomains has been associated with a number of different types of cancers, and other diseases and conditions, as described below. Bromodomain inhibitors are useful in the treatment of systemic or tissue inflammation, inflammatory responses to infection or hypoxia, cellular activation and proliferation, lipid metabolism, fibrosis and in the prevention and treatment of viral infections.

Bromodomain inhibitors such as compounds of formulas (I), (I'), (II), (III), (IV), (V), (Va) or (Vb), or any of the subformulas or compounds as described herein are useful in the prevention and treatment of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors such as compounds of formulas (I), (I'), (II), (III), (IV), (V), (Va) or (Vb), or any of the subformulas or compounds as described herein are useful in the prevention and treatment of acute inflammatory conditions, including, but not limiting to, such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors such as compounds of formulas (I), (I'), (II), (III), (IV), (V), (Va) or (Vb), or any of the subformulas or compounds as described herein are useful in the prevention and treatment of autoimmune and inflammatory diseases or conditions which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors such as compounds of formulas (I), (I'), (II), (III), (IV), (V), (Va) or (Vb), or any of the subformulas or compounds as described herein are useful in the prevention and treatment of diseases or conditions associated with ischemia-reperfusion injury, including, but not limiting to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors such as compounds of formulas (I), (I'), (II), (III), (IV), (V), (Va) or (Vb), or any of the subformulas or compounds as described herein are useful in the prevention and treatment of hypercholesterolemia, atherosclerosis and Alzheimer's disease.

Bromodomain inhibitors such as compounds of formulas (I), (I'), (II), (III), (IV), (V), (Va) or (Vb), or any of the subformulas or compounds as described herein are useful in the prevention and treatment of cancers including, but not limiting to, hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

Bromodomain Activity Assays

A number of different assays for bromodomain activity can be utilized for assaying for active modulators and/or determining specificity of a modulator for a particular bromodomain or group. In addition to the assay mentioned in the Examples below, one of ordinary skill in the art will know of other assays that can be utilized and can modify an assay for a particular application.

In certain embodiments, compounds of formulas (I), (I'), (II), (III), (IV), (V), (Va) or (Vb), or any of the subformulas, or a compound set forth in Tables 1-31 or compounds as disclosed herein are active in an assay measuring bromodomain protein activity. In some embodiments, a compound of formulas (I), (I'), (II), (III), (IV), (V), (Va) or (Vb), or any of the subformulas or a compound as described herein has an $IC_{50}$ of less than 10,000 nM, 1,000 nM, less than 500 nM, less than 100 nM, less than 50 nM, less than 20 nM, less than 10 nM, less than 5 nM, or less than 1 nM as determined in a generally accepted bromodomain activity assay or a bromodomain activity assay as described herein. In some embodiments, the assay for measuring bromodomain activity includes an assay (e.g., biochemical or cell-bases assays) such as described in Example 57 or an assay known in the art.

In some embodiments, compounds of formulas (I), (I'), (II), (III), (IV), (V), (Va) or (Vb), or any of the subformulas as described herein or a compound sets forth in Tables 1-31, or a compound as described herein are active in an assay measuring bromodomain activity. In some embodiments a compound as described herein has an $IC_{50}$ of less than 10,000 nM, 1,000 nM, less than 500 nM, less than 100 nM, less than 50 nM, less than 20 nM, less than 10 nM, less than 5 nM, or less than 1 nM as determined in a generally accepted bromodomain activity assay. In some embodiments, a compound as described herein has an $IC_{50}$ of less than 100 nM, less than 10 nM, or less than 1 nM in a bromodomain activity assay.

Modulation of Bromodomain

In another aspect, the present disclosure provides a method for modulating or inhibiting a bromodomain protein The method includes administering to a subject an effective amount of a compound of any of formulas (I), (I'), (II), (III), (IV), (V), (Va) or (Vb), and any of the subgeneric formulas as described herein, or a compound set forth in Tables 1-31, or a compound as described herein, or a pharmaceutically acceptable salt, hydrate, solvate, tautomer or isomer thereof, or a composition comprising a compound of any of the formulas as described herein, thereby, modulating or inhibiting the bromodomain. In some embodiments, the method includes contacting a cell in vivo or in vitro with a compound of formulas (I), (I'), (II), (III), (IV), (V), (Va) or (Vb), or any of the subformulas as described herein, or a compound set forth in Tables 1-31, or a compound as disclosed herein, or a pharmaceutically acceptable salt, hydrate, solvate, tautomer or isomer thereof, or a composition comprising a compound of any of the formulas as described herein.

VI. Methods for Treating Conditions Mediated by Bromodomain

In another aspect, the present disclosure provides a method for treating a subject suffering from or at risk of a bromodomain mediated diseases or conditions, wherein inhibition of bromodomain plays a role or provides a benefit. The method includes administering to the subject an effective amount of a compound of any of formulas (I), (I'), (II), (III), (IV), (V), (Va) or (Vb), or a compound disclosed in the Examples, a compound set forth in Tables 1-31, or a compound as described herein, or a pharmaceutically acceptable salt, hydrate, solvate, tautomer or isomer thereof, or a composition comprising a compound of any of the formulas as described herein. In certain embodiments, the method involves administering to the subject an effective amount of any one or more compound(s) as described herein in combination with one or more other therapies or therapeutic agents for the disease or condition. In some embodiments, the method involves administering to the subject an effective amount of any one or more compound(s) as described herein in combination with one or more other therapeutic agents for the disease or condition.

In some embodiments, the present disclosure provides a method of suppressing undesired proliferation of tumor cells mediated by bromodomain. The method includes contacting tumor cells with an effective amount of a compound of any of formulas (I), (I'), (II), (III), (IV), (V), (Va) or (Vb), or any of the subformulas as described herein, or any compound as described herein, or a pharmaceutically acceptable salt, hydrate, solvate, tautomer or isomer thereof, or a composition comprising a compound as described herein. In some instances, the tumor cells are mediated by BET protein, BRD4 protein or a mutant thereof.

In certain embodiments, the present disclosure provides a method of treating a patient, where inhibition of bromodomain (e.g., BET protein or BRD4 protein) provides a benefit. The method includes administering to the patient in need thereof an effective amount of a compound of any of formulas (I), (I'), (II), (III), (IV), (V), (Va) or (Vb), or any of the subformulas as described herein, or any compound as described herein, or a pharmaceutically acceptable salt, hydrate, solvate, tautomer or isomer thereof, or a composition comprising a compound as described herein.

In some embodiments, the diseases or conditions treatable with the compounds of the present disclosure include, but are not limited to, a cancer, e.g., hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In certain embodiments, the cancer treatable with the compounds of the present disclosure is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In other embodiments, the cancers or tumors treatable with the compounds of the present disclosure include benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In some embodiments, the present disclosure provides methods for treating an autoimmune and inflammatory disease or condition in a subject by administration of an effective amount of a compound of formulas (I), (I'), (II), (III), (IV), (V), (Va) or (Vb), or a compound as described herein. The diseases or conditions treatable with the compounds of the present disclosure include, but are not limited to, inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Bane syndrome, Behcet's disease, scleracierma, mycosis fungoides, acute inflammatory responses (such as acute respiratory distress syndrome and ischemia/reperfusion injury), and Graves' disease. In certain embodiments, the diseases and conditions treatable with the compounds of the present disclosure include systemic or tissue inflammation, inflammatory responses to infection or hypoxia, cellular activation and proliferation, lipid metabolism, fibrosis and viral infections.

In some embodiments, the present disclosure provides methods for treating a subject suffering or at risk of chronic autoimmune and inflammatory conditions by administering to the subject in need thereof an effective amount of a compound of formulas (I), (I'), (II), (III), (IV), (V), (Va) or (Vb), or a compound as described herein. The chronic autoimmune and inflammatory conditions treatable with the compounds of the present disclosure include, but are not limited to, rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs. In one embodiment, the disease or condition is sepsis, burns, pancreatitis, major trauma, hemorrhage or ischemia. In another embodiment, the disease or condition treatable with the compounds of the present disclosure includes sepsis, sepsis syndrome, septic shock or endotoxaemia. In another embodiment, the disease or condition treatable with the compounds of the present disclosure includes acute or chronic pancreatitis. In another embodiment, the disease or condition treatable with the compounds of the present disclosure includes burns.

In some embodiments, the present disclosure provides methods for treating a subject suffering or at risk of acute inflammatory conditions by administering to the subject in need thereof an effective amount of a compound of formulas (I), (I'), (II), (III), (IV), (V), (Va) or (Vb), or a compound as described herein. The acute inflammatory conditions, include, but are not limited to, acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

In some embodiments, the present disclosure provides methods for treating a subject suffering or at risk of autoimmune and inflammatory diseases or conditions by administering to the subject in need thereof an effective amount of a compound of formulas (I), (I'), (II), (III), (IV), (V), (Va) or (Vb), or a compound as described herein. The autoimmune and inflammatory diseases or conditions treatable with the compounds of the present disclosure which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

In some embodiments, the present disclosure provides methods for treating a subject suffering or at risk of ischemia-reperfusion injury by administering to the subject in need thereof an effective amount of a compound of formulas (I), (I'), (II), (III), (IV), (V), (Va) or (Vb), or a compound as described herein. The ischemia-reperfusion injury, includes, but is not limited to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal and peripheral limb embolism.

In some embodiments, the present disclosure provides methods for treating a subject suffering or at risk of hypercholesterolemia, atherosclerosis or Alzheimer's disease by administering to the subject in need thereof an effective amount of a compound of formulas (I), (I'), (II), (III), (IV), (V), (Va) or (Vb), or a compound as described herein.

In some embodiments, the present disclosure provides methods for treating any bromodomain mediated disease or condition, including any bromodomain mutant mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In some embodiments, a compound of any of formulas (I), (I'), (II), (III), (IV), (V), (Va) or (Vb), or any of the subformulas as described herein, or a compound as described herein, or pharmaceutically acceptable salts, hydrates, solvates, tautomers or isomers thereof, or a composition comprising a compound as described herein is a bromodomain inhibitor and has an $IC_{50}$ of less than 500 nM, less than 100 nM, less than 50 nM, less than 20 nM, less than 10 nM, less than 5 nM, or less than 1 nM as determined in a generally accepted bromodomain activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to bromodomain, e.g., BET protein, BRD2, BRD3 or BRD4 protein. In some embodiments, a compound as described herein will selectively inhibit one or more bromodomain relative to one or more other proteins.

In some embodiments, the present disclosure provides a method for inhibiting a bromodomain or mutant bromodomain. The method includes contacting a compound of any of formulas (I), (I'), (II), or any of the subformulas as described herein, or a compound as described herein, or a composition comprising a compound as described herein, or a pharmaceutically acceptable salt, hydrate, solvate, tautomer or isomer thereof with a cell or a bromodomain protein in vitro or in vivo.

In certain embodiments, the present disclosure provides use of a compound of any of formulas (I), (I'), (II), (III), (IV), (V), (Va) or (Vb), or any of the subformulas as described herein, or a compound as described herein, or a composition comprising a compound as described herein, or a pharmaceutically acceptable salt, hydrate, solvate, tautomer or isomer thereof in the manufacture of a medicament for the treatment of a disease or condition as described herein. In other embodiments, the present disclosure provides a compound of any of formulas (I), (I'), (II), (III), (IV), (V), (Va) or (Vb), or any of the subformulas as described herein, or a compound as described herein, or a composition comprising a compound as described herein, or a pharmaceutically acceptable salt, hydrate, solvate, tautomer or isomer thereof for use in treating a disease or condition as described herein.

Combination Therapy

Bromodomain modulators may be usefully combined with another pharmacologically active compound, or with two or more other pharmacologically active compounds, particularly in the treatment of cancer and other diseases and indications described herein. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides methods for treating a bromodomain or mutant bromodomain mediated disease or condition in an animal subject in need thereof, wherein the method involves administering to the subject an effective amount of any one or more compound(s) as described herein, or one or more compounds of any of formulas (I), (I'), (II), (III), (IV), (V), (Va) or (Vb), or any of the subformulas as described herein, or pharmaceutically acceptable salts, solvates, tautomers or isomers thereof, or a composition comprising a compound as described herein in combination with one or more other therapeutic agent as described herein. In certain embodiments, the present disclosure provides methods for treating bromodomain or mutant bromodomain mediated disease or condition in an animal subject in need thereof, wherein the method involves administering to the subject an effective amount of any one or more compound(s) as described herein, or one or more compounds of any of formulas (I), (I'), (II), (III), (IV), (V), (Va) or (Vb), or any of the subformulas as described herein, or pharmaceutically acceptable salts, solvates, tautomers or isomers thereof, or a composition comprising a compound as described herein in combination with one or more other therapies for the disease or condition.

In some embodiments, the present disclosure provides a composition, e.g., a pharmaceutical composition comprising a compound of any of formulas (I), (I'), (II), (III), (IV), (V), (Va) or (Vb), or a compound disclosed in the Examples, a compound set forth in Tables 1-31, or a compound as described herein, or a pharmaceutically acceptable salt, hydrate, solvate, tautomer or isomer thereof and one or more other therapeutic agents. In some embodiments, the one or more other therapeutic agents are selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, LGX818, BGB-283, PLX3397 and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In one embodiment, the method of treating a cancer involves administering to the subject an effective amount of a composition including any one or more compound(s) of Formulae (I), (I'), (II), (III), (IV), (V), (Va) or (Vb), or any of the subformulas as described herein or a compound as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, PD98059, RDEA119 (BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate(BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib(TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, XL-184 free base (Cabozantinib), XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441. Tarceva (Erlotinib, OSI-774), CUDC-101 and WZ4002. In another embodiment, the therapeutic agent for combination is a c-Fms and/or c-Kit inhibitor as described in US Patent Application Publication Nos. 2009/0076046 and 2011/0112127, which are incorporated herein by reference in their entirety and for all purposes. In one embodiment, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In some embodiments, bromodomain modulator, particularly a compound of any of (I), (I'), (II), (III), (IV), (V), (Va) or (Vb), or any of the subformulas as described herein, or a compound described herein, or a pharmaceutically acceptable salt, solvate, tautomer or isomer thereof, may be administered simultaneously, sequentially or separately in combination with one or more agents as described above.

In some embodiments, the present disclosure provides methods for treating a disease or condition mediated by bromodomain, including any mutations thereof, by administering to a subject an effective amount of a composition as described herein, which includes any one or more compound (s) as described herein in combination with one or more other therapeutic agents as described herein. In other embodiments, the present disclosure provides methods for treating a disease or condition mediated by bromodomain protein or mutant bromodomain protein, including any mutations thereof, by administering to a subject an effective amount of a composition as described herein, which includes any one or more compound(s) as described herein in combination with one or more other suitable therapies for treating the disease or condition.

In some embodiments, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one aspect, the composition includes any one or more compound (s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In one embodiment, the present disclosure provides methods for treating a disease or condition mediated by bromodomain or mutant bromodomain protein, by administering to the subject an effective amount of a composition including any one or more compound(s) as described herein in combination with one or more other suitable therapies as described herein for treating the disease. In one embodiment, the present disclosure provides methods for treating a cancer mediated by bromodomain or mutant bromodomain by administering to the subject an effective amount of a composition including any one or more compound(s) as described herein. In one embodiment, the present disclosure provides methods for treating a cancer mediated by bromodomain by administering to the subject an effective amount of a composition including any one or more compound(s) as described herein in combination with one or more suitable anticancer therapies, such as one or more chemotherapeutic drugs or agents as described herein.

In some embodiments, the present disclosure provides a method of treating a cancer as described herein in a subject in need thereof by administering to the subject an effective amount of a compound or a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the present disclosure provides a method of treating a cancer in a subject in need thereof by administering to the subject an effective amount of a compound as described herein and applying a radiation treatment as described herein either separately or simultaneously. In one embodiment, the present disclosure provides a method for treating a cancer in a subject in need thereof by administering an effective amount of a compound as described herein to the subject followed by a radiation treatment (e.g. x-ray, γ-ray, or electron, proton, neutron, or α particle beam). In another embodiment, the present disclosure provides a method for treating a cancer in a subject in need thereof by applying a radiation treatment (e.g. x-ray, γ-ray, or electron, proton, neutron, or α particle beam) to the subject followed by administering an effective amount of a compound as described herein to the subject. In yet another embodiment, the present disclosure provides a method for treating a cancer in a subject in need thereof by administering a compound as described herein and a radiation therapy (e.g. x-ray, γ-ray, or electron, proton, neutron, or α particle beam) to the subject simultaneously.

In another aspect, the present disclosure provides kits or containers that include a compound of any of formulas (I), (I'), (II), (III), (IV), (V), (Va) or (Vb), or any of the subformulas as described herein, or a pharmaceutically acceptable salt thereof, a compound as described herein or a composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a bromodomain protein mediated disease or condition; the kit or container disclosed herein may include written instructions for use and/or other indication that the compound or composition is suitable or approved for administration to a mammal, e.g., a human, for a bromodomain-mediated disease or condition; and the compound or composition may be packaged in unit dose or single dose form, e.g., single dose pills, capsules, or the like.

VII. Examples

The following examples are offered to illustrate, but not to limit the present disclosure.

Compounds within the scope of this disclosure can be synthesized as described below, using a variety of reactions known to the skilled artisan. One skilled in the art will also recognize that alternative methods may be employed to synthesize the target compounds of the present disclosure, and that the approaches described within the body of this document are not exhaustive, but do provide broadly applicable and practical routes to compounds of interest. In some examples, the mass spectrometry result indicated for a compound may have more than one value due to the isotope distribution of an atom in the molecule, such as a compound having a bromo or chloro substituent.

Certain molecules claimed in this patent can exist in different enantiomeric and diastereomeric forms or one or more hydrogen atoms of the molecules can be replaced by one or more deuterium atoms including perdeuterated analogs, all such variants of these compounds are claimed. Further, it should be noted that the term "deuterated analog" refers to compounds where at least one hydrogen atom has been replaced by a deuterium atom.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

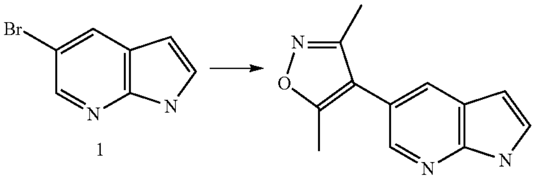

1

P-0246

Step 1—Preparation of 3,5-dimethyl-4-(1H-pyrrolo[3,2-b]pyridin-6-yl)isoxazole (P-0246)

To 6-bromo-2-methyl-1H-pyrrolo[3,2-b]pyridine (1, 2.12 g, 10.76 mmol) in tetrahydrofuran (120 ml), under nitrogen, were added 1,1'-bis(diphenylphosphino)ferrocene-palladium(II)dichloride dichloromethane (0.1 g, 0.12 mmol), 3,5-Dimethyl-isoxazol-4-yl boronic acid (1.9 g, 13.48 mmol), and 1M potassium carbonate in water (60 ml). The reaction was heated at 85° C. for 3 days. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride to give product (P-0246, 1.2 g, 52.3%). MS (ESI) $[M+H^+]^+$=214.2.

TABLE 1

| The following compounds were prepared as depicted in example 1, using the appropriate starting materials. | | | |
|---|---|---|---|
| No. | Name | Compound | MH (+) |
| P-0017 | 3,5-dimethyl-4-(2-methyl-1H-pyrrolo[2,3-b]pyridin-5-yl)isoxazole | 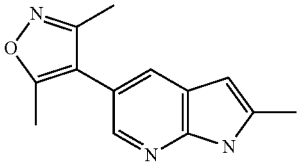 [SMILES: Cc1cc2cc(-c3c(C)noc3C)cnc2[nH]1] | 214.2 |
| P-0010 | 3,5-dimethyl-4-[3-(2-pyrrolidin-1-ylethyl)-1H-indol-5-yl]isoxazole | 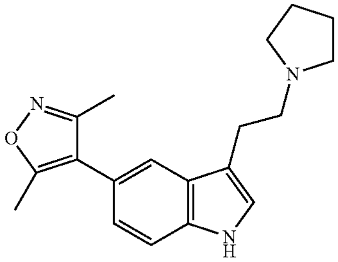 [SMILES: Cc1noc(C)c1-c1ccc2[nH]cc(CCN3CCCC3)c2c1] | 310.3 |
| P-0001 | 3,5-dimethyl-4-(2-phenyl-1H-pyrrolo[2,3-b]pyridin-5-yl)isoxazole | 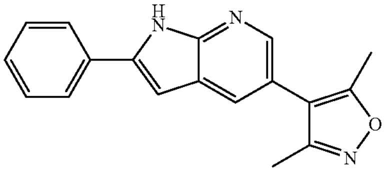 [SMILES: Cc1noc(C)c1-c1cnc2[nH]c(-c3ccccc3)cc2c1] | 290.2 |
| P-0002 | 4-(1H-indol-5-yl)-3,5-dimethyl-isoxazole | 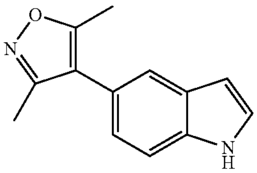 [SMILES: Cc1noc(C)c1-c1ccc2[nH]ccc2c1] | 212.9 |
| P-0018 | 3,5-dimethyl-4-(1H-pyrrolo[3,2-b]pyridin-6-yl)isoxazole | 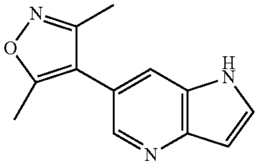 [SMILES: Cc1noc(C)c1-c1cnc2cc[nH]c2c1] | 214.0 |
| P-0035 | 4-(2-ethyl-1H-pyrrolo[2,3-b]pyridin-5-yl)-3,5-dimethyl-isoxazole | 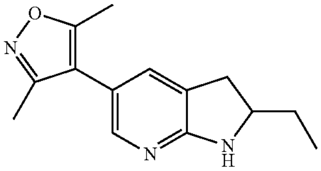 [SMILES: CCC1Cc2cc(-c3c(C)noc3C)cnc2N1] | 242.0 |

Example 2

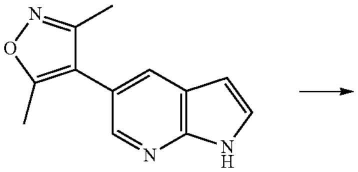

P-0246

-continued

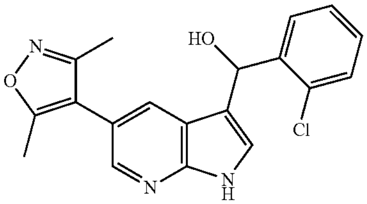

P-0019

+

-continued

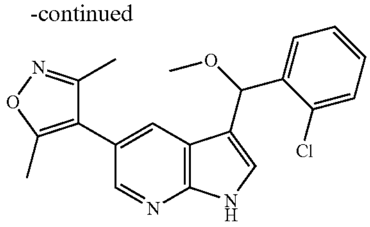

P-0020

Step 1—Preparation of (2-chlorophenyl)-[5-(3,5-dimethylisoxazol-4-yl)-1H-pyrrolo[2,3-b]pyridin-3-yl]methanol P-0019 and 4-[3-[(2-chlorophenyl)-methoxy-methyl]-1H-pyrrolo[2,3-b]pyridin-5-yl]-3,5-dimethyl-isoxazole P-0020: To 3,5-dimethyl-4-(1H-pyrrolo[2,3-b]pyridin-5-yl)isoxazole (P-0246, 0.08 g, 0.35 mmol) in methanol (10 mL) were added 2-chlorobenzaldehyde (0.07 g, 0.5 mmol) and potassium hydroxide (0.3 g, 0.01 mol). The reaction was stirred at room temperature overnight. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give product (P-0019, 0.090 g, 72.3%), MS (ESI) $[M+H^+]^+$=354.1; and product (P-0020, 4.4 mg, 4.4%), MS (ESI) $[M+H^+]^+$=367.8.

TABLE 2

The following compounds were prepared as depicted in example 2, using the appropriate starting materials.

| Cmpd # | Name | Compound | MH (+) |
|---|---|---|---|
| P-0009 | [5-(3,5-dimethylisoxazol-4-yl)-2-methyl-1H-pyrrolo[2,3-b]pyridin-3-yl]-(3-pyridyl)methanol | 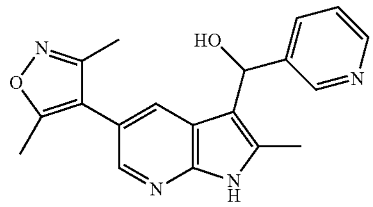 [SMILES: Cc1noc(C)c1-c1cnc2[nH]c(C)c(C(O)c3cccnc3)c2c1] | 334.9 |
| P-0011 | 4-[3-[(5-fluoro-2-methoxy-3-pyridyl)-methoxy-methyl]-1H-pyrrolo[2,3-b]pyridin-5-yl]-3,5-dimethyl-isoxazole | 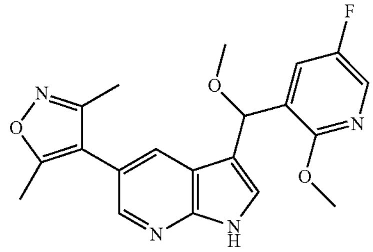 [SMILES: COc1ncc(F)cc1C(OC)c1c[nH]c2ncc(-c3c(C)noc3C)cc12] | 383.4 |
| P-0012 | [5-(3,5-dimethylisoxazol-4-yl)-1H-pyrrolo[2,3-b]pyridin-3-yl]-[6-(2,2,2-trifluoroethoxy)-3-pyridyl]methanol | 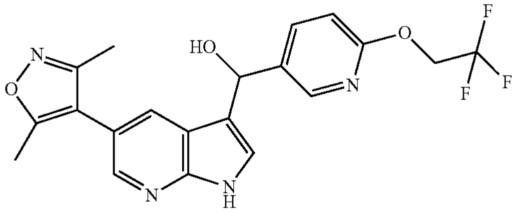 [SMILES: Cc1noc(C)c1-c1cnc2[nH]cc(C(O)c3ccc(OCC(F)(F)F)nc3)c2c1] | 419.3 |
| P-0013 | 4-[3-[methoxy-[6-(trifluoromethyl)-3-pyridyl]methyl]-1H-pyrrolo[2,3-b]pyridin-5-yl]-3,5-dimethyl-isoxazole | 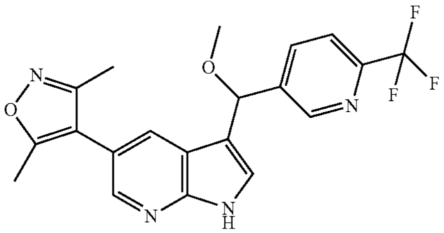 [SMILES: COC(c1ccc(C(F)(F)F)nc1)c1c[nH]c2ncc(-c3c(C)noc3C)cc12] | 403.3 |
| P-0014 | 4-[3-[(2-chloro-6-fluoro-phenyl)-methoxy-methyl]-1H-pyrrolo[2,3-b]pyridin-5-yl]-3,5-dimethyl-isoxazole | 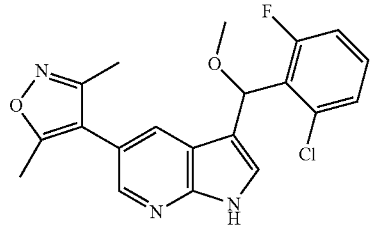 [SMILES: COC(c1c(F)cccc1Cl)c1c[nH]c2ncc(-c3c(C)noc3C)cc12] | 386.0 |

TABLE 2-continued

The following compounds were prepared as depicted in example 2, using the appropriate starting materials.

| Cmpd # | Name | Compound | MH (+) |
|---|---|---|---|
| P-0021 | (2-chloro-6-fluoro-phenyl)-[5-(3,5-dimethylisoxazol-4-yl)-1H-pyrrolo[2,3-b]pyridin-3-yl]methanol | 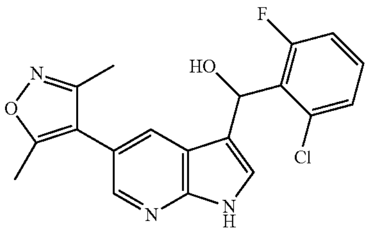 [SMILES: Cc1noc(C)c1-c1cnc2[nH]cc(C(O)c3c(F)cccc3Cl)c2c1] | 371.8 |
| P-0022 | [5-(3,5-dimethylisoxazol-4-yl)-1H-pyrrolo[2,3-b]pyridin-3-yl]-(5-fluoro-2-methoxy-3-pyridyl)methanol | 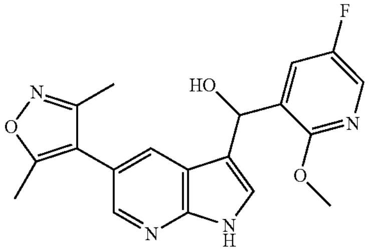 [SMILES: COc1ncc(F)cc1C(O)c1c[nH]c2ncc(-c3c(C)noc3C)cc12] | 369.3 |
| P-0023 | [5-(3,5-dimethylisoxazol-4-yl)-1H-pyrrolo[2,3-b]pyridin-3-yl]-[6-(trifluoromethyl)-3-pyridyl]methanol | 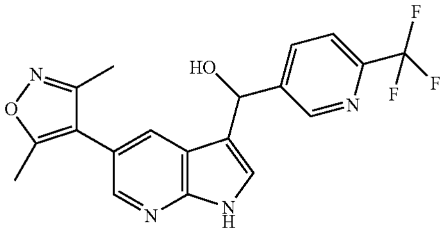 [SMILES: Cc1noc(C)c1-c1cnc2[nH]cc(C(O)c3ccc(C(F)(F)F)nc3)c2c1] | 389.1 |
| P-0024 | l-[5-(3,5-dimethylisoxazol-4-yl)-1H-pyrrolo[2,3-b]pyridin-3-yl]-4,4-difluoro-cyclohexanol | 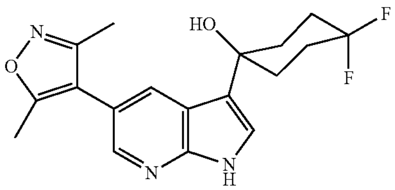 [SMILES: Cc1noc(C)c1-c1cnc2[nH]cc(C3(O)CCC(F)(F)CC3)c2c1] | 348.2 |
| P-0025 | [5-(3,5-dimethylisoxazol-4-yl)-1H-pyrrolo[2,3-b]pyridin-3-yl]-(5-fluoro-6-methoxy-3-pyridyl)methanol | 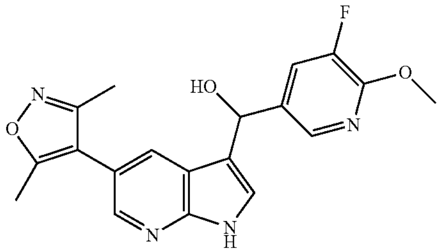 [SMILES: COc1ncc(C(O)c2c[nH]c3ncc(-c4c(C)noc4C)cc23)cc1F] | 368.9 |
| P-0030 | (4,4-difluorocyclohexyl)-[5-(3,5-dimethylisoxazol-4-yl)-1H-pyrrolo[2,3-b]pyridin-3-yl]methanol | 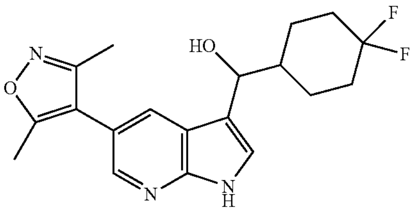 [SMILES: Cc1noc(C)c1-c1cnc2[nH]cc(C(O)C3CCC(F)(F)CC3)c2c1] | 362.2 |

TABLE 2-continued

| The following compounds were prepared as depicted in example 2, using the appropriate starting materials. | | | |
|---|---|---|---|
| Cmpd # | Name | Compound | MH (+) |
| P-0039 | [5-(3,5-dimethylisoxazol-4-yl)-1H-pyrrolo[2,3-b]pyridin-3-yl]-[3-(trifluoromethoxy)phenyl]methanol | 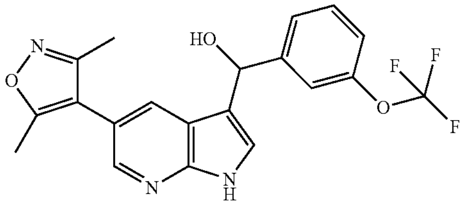 [SMILES: Cc1noc(C)c1-c1cnc2[nH]cc(C(O)c3cccc(OC(F)(F)F)c3)c2c1] | 404.3 |
| P-0040 | [2-(difluoromethoxy)phenyl]-[5-(3,5-dimethylisoxazol-4-yl)-1H-pyrrolo[2,3-b]pyridin-3-yl]methanol | 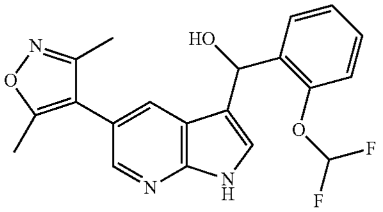 [SMILES: Cc1noc(C)c1-c1cnc2[nH]cc(C(O)c3ccccc3OC(F)F)c2c1] | 386.1 |
| P-0041 | (2,2-difluoro-1,3-benzodioxol-4-yl)-[5-(3,5-dimethylisoxazol-4-yl)-1H-pyrrolo[2,3-b]pyridin-3-yl]methanol | 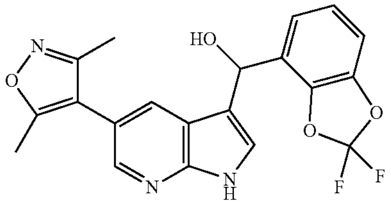 [SMILES: Cc1noc(C)c1-c1cnc2[nH]cc(C(O)c3cccc4c3OC(F)(F)O4)c2c1] | 400.3 |
| P-0042 | (2-chlorophenyl)-[5-(3,5-dimethylisoxazol-4-yl)-2-ethyl-1H-pyrrolo[2,3-b]pyridin-3-yl]methanol | 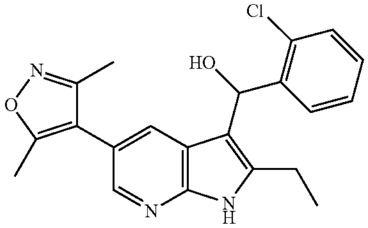 [SMILES: CCc1[nH]c2ncc(-c3c(C)noc3C)cc2c1C(O)c1ccccc1Cl] | 382.1 |
| P-0043 | [5-(3,5-dimethylisoxazol-4-yl)-2-ethyl-1H-pyrrolo[2,3-b]pyridin-3-yl]-[3-(trifluoromethoxy)phenyl]methanol | 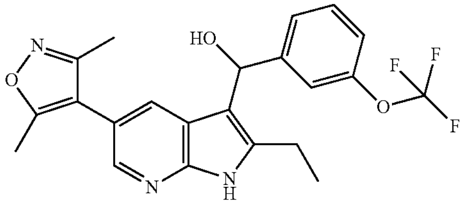 [SMILES: CCc1[nH]c2ncc(-c3c(C)noc3C)cc2c1C(O)c1cccc(OC(F)(F)F)c1] | 432.3 |
| P-0044 | (4,4-difluorocyclohexyl)-[5-(3,5-dimethylisoxazol-4-yl)-2-ethyl-1H-pyrrolo[2,3-b]pyridin-3-yl]methanol | 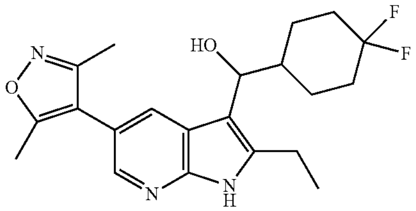 [SMILES: CCc1[nH]c2ncc(-c3c(C)noc3C)cc2c1C(O)C1CCC(F)(F)CC1] | 390.4 |
| P-0045 | 4-[3-[(4,4-difluorocyclohexyl)-methoxy-methyl]-2-ethyl-1H-pyrrolo[2,3-b]pyridin-5-yl]-3,5-dimethyl-isoxazole | 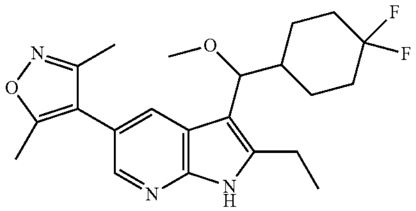 [SMILES: CCc1[nH]c2ncc(-c3c(C)noc3C)cc2c1C(OC)C1CCC(F)(F)CC1] | 403.9 |

TABLE 2-continued

The following compounds were prepared as depicted in example 2, using the appropriate starting materials.

| Cmpd # | Name | Compound | MH (+) |
|---|---|---|---|
| P-0069 | 4-[3-[cyclopropyl(methoxy)methyl]-1H-pyrrolo[3,2-b]pyridin-6-yl]-3,5-dimethyl-isoxazole | 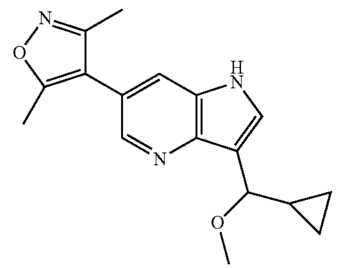 [SMILES: COC(c1c[nH]c2cc(-c3c(C)noc3C)cnc12)C1CC1] | 298.0 |
| P-0073 | 4-[3-[(4,4-difluorocyclohexyl)-methoxy-methyl]-1H-pyrrolo[2,3-b]pyridin-5-yl]-3,5-dimethyl-isoxazole | 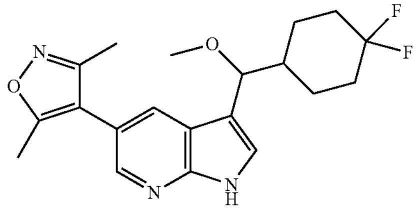 [SMILES: COC(c1c[nH]c2ncc(-c3c(C)noc3C)cc12)C1CCC(F)(F)CC1] | 376.4 |

Example 3

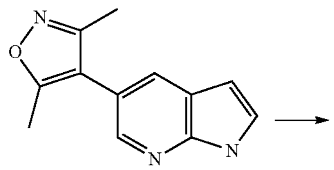

P-0246

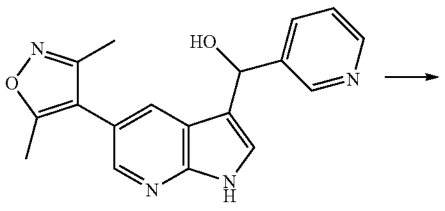

2

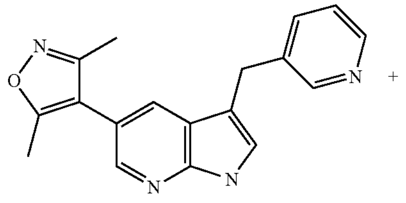

P-0003

-continued

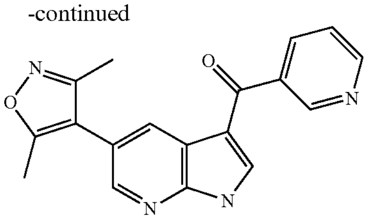

P-0004

Step 1—Preparation of [5-(3,5-dimethylisoxazol-4-yl)-1H-pyrrolo[2,3-b]pyridin-3-yl]-(3-pyridyl)methanol 2: To 3,5-dimethyl-4-(1H-pyrrolo[2,3-b]pyridin-5-yl)isoxazole (P-0246), 0.6 g, 2.81 mmol) in methanol (20 mL) were added pyridine-3-carbaldehyde (0.31 g, 2.87 mmol) and potassium hydroxide (0.3 g, 0.01 mol). The reaction was stirred at room temperature overnight. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give product (2, 0.35 g, 38.8%).

Step 2—Preparation of 3,5-dimethyl-4-[3-(3-pyridylmethyl)-1H-pyrrolo[2,3-b]pyridin-5-yl]isoxazole P-0003 and [5-(3,5-dimethylisoxazol-4-yl)-1H-pyrrolo[2,3-b]pyridin-3-yl]-(3-pyridyl)methanone (P-0004): To [5-(3,5-dimethylisoxazol-4-yl)-1H-pyrrolo[2,3-b]pyridin-3-yl]-(3-pyridyl) methanol (2, 180 mg, 0.56 mmol) in dichloroethane (20 mL) were added triethylsilane (1.5 ml, 9.39 mmol) and trifluoroacetic acid (0.8 ml, 8.07 mmol). The reaction was stirred at 80° C. for 4 hours under air. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 2% to 20% methanol in methylene chloride to give product as a mixture, which was then further purified with prep-HPLC to give product (P-0003, 1.5 mg, 0.76%), MS (ESI) $[M+H^+]^+=305.3$; and product (P-0004, 64 mg, 36%), MS (ESI) $[M+H^+]^+=318.8$.

TABLE 3

The following compounds were prepared as depicted in example 3, using the appropriate starting materials.

| No. | name | Compound | MH(+) |
|---|---|---|---|
| P-0005 | 3,5-dimethyl-4-[2-methyl-3-(3-pyridylmethyl)-1H-pyrrolo[2,3-b]pyridin-5-yl]isoxazole | 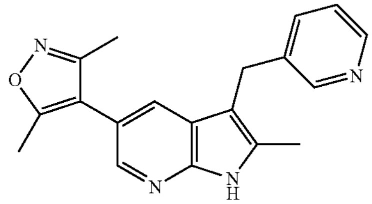 [SMILES: Cc1noc(C)c1-c1cnc2[nH]c(C)c(Cc3cccnc3)c2c1] | 319.0 |
| P-0007 | 4-[2-(4-fluorophenyl)-3-(3-pyridylmethyl)-1H-pyrrolo[2,3-b]pyridin-5-yl]-3,5-dimethyl-isoxazole | 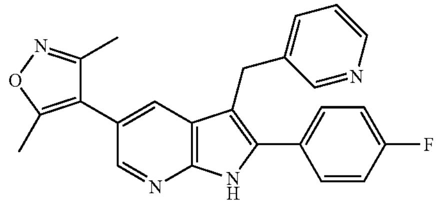 [SMILES: Cc1noc(C)c1-c1cnc2[nH]c(-c3ccc(F)cc3)c(Cc3cccnc3)c2c1] | 399.3 |
| P-0015 | 3,5-dimethyl-4-[3-[[4-(trifluoromethyl)phenyl]methyl]-1H-pyrrolo[2,3-b]pyridin-5-yl]isoxazole | 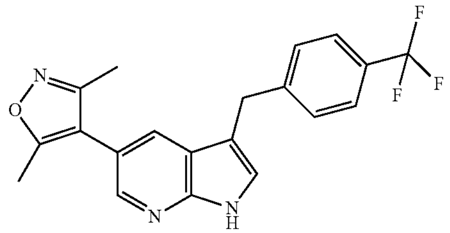 [SMILES: Cc1noc(C)c1-c1cnc2[nH]cc(Cc3ccc(C(F)(F)F)cc3)c2c1] | 371.9 |
| P-0016 | [5-(3,5-dimethylisoxazol-4-yl)-1H-pyrrolo[2,3-b]pyridin-3-yl]-[4-(trifluoromethyl)phenyl]methanone | 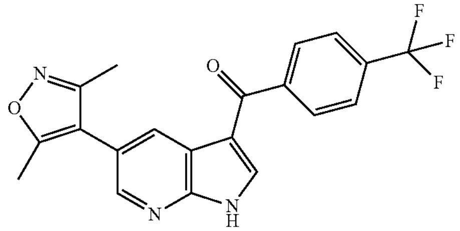 [SMILES: Cc1noc(C)c1-c1cnc2[nH]cc(C(=O)c3ccc(C(F)(F)F)cc3)c2c1] | 385.8 |
| P-0026 | 4-[3-[(2-chlorophenyl)methyl]-1H-pyrrolo[2,3-b]pyridin-5-yl]-3,5-dimethyl-isoxazole | 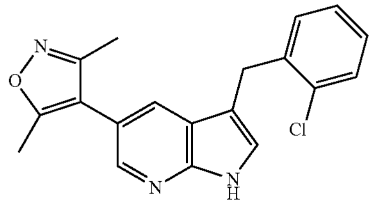 [SMILES: Cc1noc(C)c1-c1cnc2[nH]cc(Cc3ccccc3Cl)c2c1] | 338.1 |
| P-0027 | 4-[3-[(2-chloro-6-fluoro-phenyl)methyl]-1H-pyrrolo[2,3-b]pyridin-5-yl]-3,5-dimethyl-isoxazole | 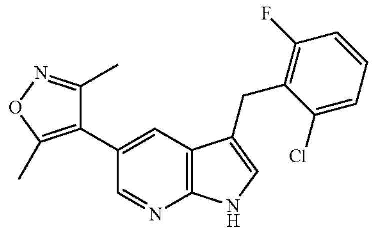 [SMILES: Cc1noc(C)c1-c1cnc2[nH]cc(Cc3c(F)cccc3Cl)c2c1] | 356.1 |

TABLE 3-continued

The following compounds were prepared as depicted in example 3, using the appropriate starting materials.

| No. | name | Compound | MH(+) |
|---|---|---|---|
| P-0028 | 4-[3-[(5-fluoro-2-methoxy-3-pyridyl)methyl]-1H-pyrrolo[2,3 b]pyridin-5-yl]-3,5-dimethyl-isoxazole | 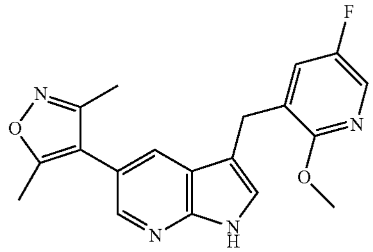 [SMILES: COc1ncc(F)cc1Cc1c[nH]c2ncc(-c3c(C)noc3C)cc12] | 353.3 |
| P-0029 | 4-[3-(4,4-difluorocyclohexen-l-yl)-1H-pyrrolo[2,3-b]pyridin-5-yl]-3,5-dimethyl-isoxazole | 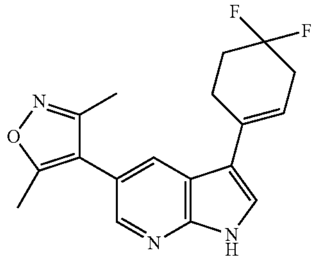 [SMILES: Cc1noc(C)c1-c1cnc2[nH]cc(C3=CCC(F)(F)CC3)c2c1] | 329.8 |
| P-0034 | 4-[3-[(4,4-difluorocyclohexyl)methyl]-1H-pyrrolo[2,3-b]pyridin-5-yl]-3,5-dimethyl-isoxazole | 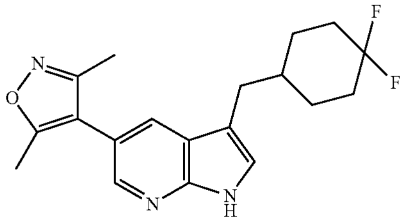 [SMILES: Cc1noc(C)c1-c1cnc2[nH]cc(CC3CCC(F)(F)CC3)c2c1] | 346.3 |
| P-0047 | 4-[3-[[2-(difluoromethoxy)phenyl]methyl]-1H-pyrrolo[2,3-b]pyridin-5-yl]-3,5-dimethyl-isoxazole | 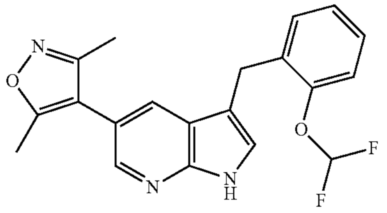 [SMILES: Cc1noc(C)c1-c1cnc2[nH]cc(Cc3ccccc3OC(F)F)c2c1] | 370.2 |
| P-0046 | 3,5-dimethyl-4-[3-[[3-(trifluoromethoxy)phenyl]methyl]-1H-pyrrolo[2,3-b]pyridin-5-yl]isoxazole | 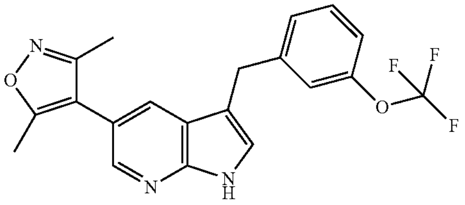 [SMILES: Cc1noc(C)c1-c1cnc2[nH]cc(Cc3cccc(OC(F)(F)F)c3)c2c1] | 388.3 |
| P-0048 | 4-[3-[(2,2-difluoro-1,3-benzodioxol-4-yl)methyl]-1H-pyrrolo[2,3-b]pyridin-5-yl]-3,5-dimethyl-isoxazole | 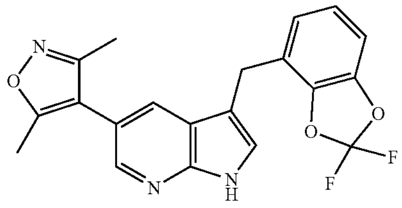 [SMILES: Cc1noc(C)c1-c1cnc2[nH]cc(Cc3cccc4c3OC(F)(F)O4)c2c1] | 384.3 |

TABLE 3-continued

The following compounds were prepared as depicted in example 3, using the appropriate starting materials.

| No. | name | Compound | MH(+) |
|---|---|---|---|
| P-0049 | 4-[3-[(2-chlorophenyl)methyl]-2-ethyl-1H-pyrrolo[2,3-b]pyridin-5-yl]-3,5-dimethyl-isoxazole | 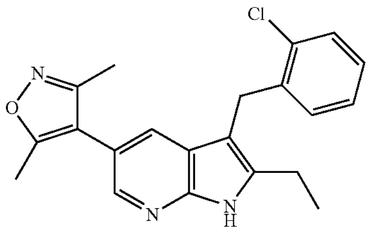 [SMILES: CCc1[nH]c2ncc(-c3c(C)noc3C)cc2c1Cc1ccccc1Cl] | 366.2 |
| P-0050 | 4-[2-ethyl-3-[[3-(trifluoromethoxy)phenyl]methyl]-1H-pyrrolo[2,3-b]pyridin-5-yl]-3,5-dimethyl-isoxazole | 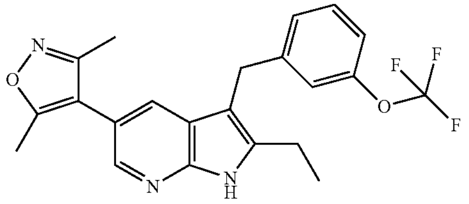 [SMILES: CCc1[nH]c2ncc(-c3c(C)noc3C)cc2c1Cc1cccc(OC(F)(F)F)c1] | 416.3 |
| P-0051 | 4-[3-[(4,4-difluorocyclohexyl)methyl]-2-ethyl-1H-pyrrolo[2,3-b]pyridin-5-yl]-3,5-dimethyl-isoxazole | 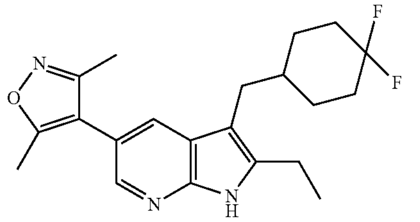 [SMILES: CCc1[nH]c2ncc(-c3c(C)noc3C)cc2c1CC1CCC(F)(F)CC1] | 374.3 |
| P-0070 | 4-[3-(cyclopropylmethyl)-1H-pyrrolo[3,2-b]pyridin-6-yl]-3,5-dimethyl-isoxazole | 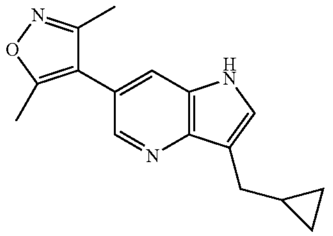 [SMILES: Cc1noc(C)c1-c1cnc2c(CC3CC3)c[nH]c2c1] | 268.2 |

Example 4

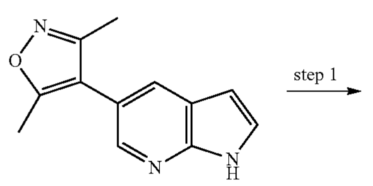

P-0246

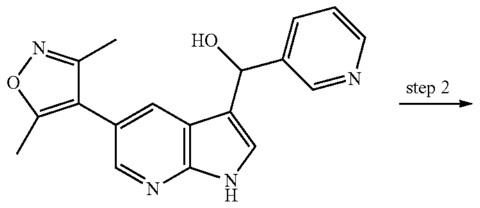

3

-continued

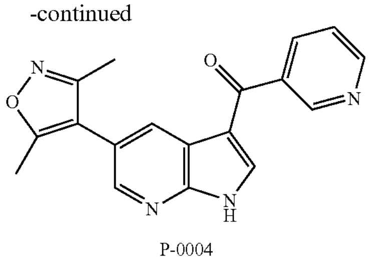

P-0004

Step 1—Preparation of [5-(3,5-dimethylisoxazol-4-yl)-1H-pyrrolo[2,3-b]pyridin-3-yl]-(3-pyridyl)methanol 3: To 3,5-dimethyl-4-(1H-pyrrolo[2,3-b]pyridin-5-yl)isoxazole (P-0246, 0.6 g, 2.81 mmol) in methanol (20 mL) were added pyridine-3-carbaldehyde (0.31 g, 2.87 mmol) and potassium hydroxide (0.3 g, 0.01 mol). The reaction was stirred at room temperature overnight. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give product around (3, 0.35 g, 38.8%)

Step 2—Preparation of [5-(3,5-dimethylisoxazol-4-yl)-1H-pyrrolo[2,3-b]pyridin-3-yl]-(3-pyridyl)methanone P-0004.

To [5-(3,5-dimethylisoxazol-4-yl)-1H-pyrrolo[2,3-b]pyridin-3-yl]-(3-pyridyl)methanol (3, 0.15 g, 0.47 mmol) in dichloromethane (10 mL) was added Dess-Martin periodinane (0.24 g, 0.56 mmol). The reaction was stirred at room temperature for 20 minutes. The reaction was concentrated, and purified with silica gel column chromatography eluting with 2% to 25% methanol in methylene chloride to give crude product, which was then further purified with prep-HPLC to give (P-0004, 2.2 mg, 1.5%). MS(ESI) $[M+H^+]^+=318.8$.

-continued

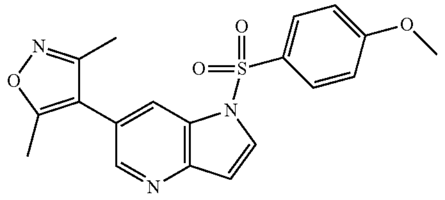

P-0032

TABLE 4

The following compounds were prepared as depicted in example 4, using the appropriate starting materials.

| Cmpd # | name | Compound | MH(+) |
| --- | --- | --- | --- |
| P-0006 | [5-(3,5-dimethylisoxazol-4-yl)-2-methyl-1H-pyrrolo[2,3-b]pyridin-3-yl]-(3-pyridyl)methanone | 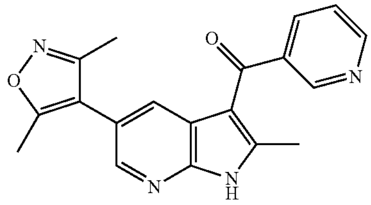 [SMILES: Cc1noc(C)c1-c1cnc2[nH]c(C)c(C(=O)c3cccnc3)c2c1] | 333.2 |
| P-0008 | [5-(3,5-dimethylisoxazol-4-yl)-2-(4-fluorophenyl)-1H-pyrrolo[2,3-b]pyridin-3-yl]-(3-pyridyl)methanone | 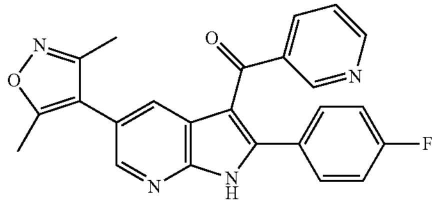 [SMILES: Cc1noc(C)c1-c1cnc2[nH]c(-c3ccc(F)cc3)c(C(=O)c3cccnc3)c2c1] | 412.9 |
| P-0031 | (4,4-difluorocyclohexyl)-[5-(3,5-dimethylisoxazol-4-yl)-1H-pyrrolo[2,3-b]pyridin-3-yl]methanone | 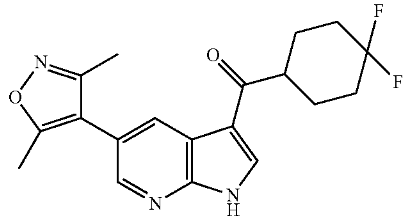 [SMILES: Cc1noc(C)c1-c1cnc2[nH]cc(C(=O)C3CCC(F)(F)CC3)c2c1] | 359.9 |

Example 5

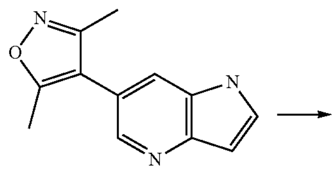

P-0018

Preparation of 4-[1-(4-methoxyphenyl)sulfonylpyrrolo[3,2-b]pyridin-6-yl]-3,5-dimethyl-isoxazole P-0032: To 3,5-dimethyl-4-(1H-pyrrolo[3,2-b]pyridin-6-yl)isoxazole (P-0018, 0.06 g, 0.28 mmol) in tetrahydrofuran ("THF") (10 mL) were added sodium hydride (60% in mineral oil, 0.02 g, 0.5 mmol). 10 minutes later, 4-methoxybenzenesulfonyl chloride (0.1 g, 0.48 mmol) was added to the reaction. The reaction was stirred at room temperature for 1 hour. The reaction was poured into water, extracted with ethyl acetate. The organic layer was washed with brine, and the organic layer was dried over sodium sulfate, concentrated, and purified with silica gel column chromatography eluting with 20% to 100% ethyl acetate in hexane to give product (P-0032, 0.09 g, 83.4%). MS (ESI) $[M+H^+]^+=383.9$.

TABLE 5

The following compounds were prepared as depicted in example 5, using the appropriate starting materials.

| Cmpd # | name | Structure | MH(+) |
|---|---|---|---|
| P-0033 | 4-[1-(4-isopropoxyphenyl)sulfonylpyrrolo[3,2-b]pyridin-6-yl]-3,5-dimethyl-isoxazole | 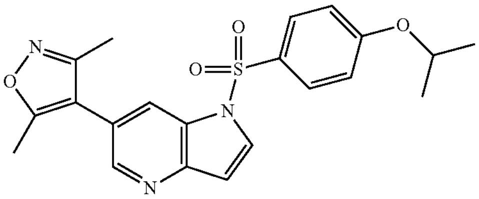 [SMILES: Cc1noc(C)c1-c1cnc2ccn(S(=O)(=O)c3ccc(OC(C)C)cc3)c2c1] | 412.7 |
| P-0036 | 4-(1-butylsulfonylpyrrolo[3,2-b]pyridin-6-yl)-3,5-dimethyl-isoxazole | 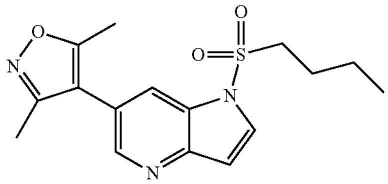 [SMILES: CCCCS(=O)(=O)n1ccc2ncc(-c3c(C)noc3C)cc21] | 334.2 |
| P-0037 | 4-(1-cyclopentylsulfonylpyrrolo[3,2-b]pyridin-6-yl)-3,5-dimethyl-isoxazole | 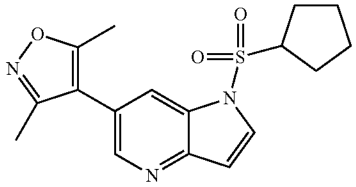 [SMILES: Cc1noc(C)c1-c1cnc2ccn(S(=O)(=O)C3CCCC3)c2c1] | 346.1 |
| P-0038 | 4-[1-(benzenesulfonyl)pyrrolo[3,2-b]pyridin-6-yl]-3,5-dimethyl-isoxazole | 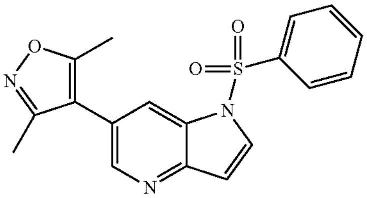 [SMILES: Cc1noc(C)c1-c1cnc2ccn(S(=O)(=O)c3ccccc3)c2c1] | 354.0 |
| P-0052 | 4-[1-(4-fluorophenyl)sulfonylpyrrolo[3,2-b]pyridin-6-yl]-3,5-dimethyl-isoxazole | 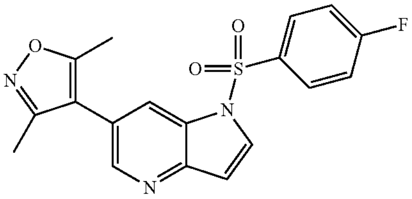 [SMILES: Cc1noc(C)c1-c1cnc2ccn(S(=O)(=O)c3ccc(F)cc3)c2c1] | 372.1 |
| P-0053 | 4-[1-(4-chlorophenyl)sulfonylpyrrolo[3,2-b]pyridin-6-yl]-3,5-dimethyl-isoxazole | 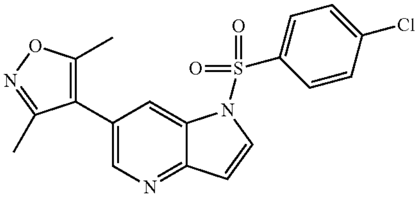 [SMILES: Cc1noc(C)c1-c1cnc2ccn(S(=O)(=O)c3ccc(Cl)cc3)c2c1] | 388.0 |
| P-0054 | 4-[1-[1-(difluoromethyl)pyrazol-4-yl]sulfonylpyrrolo[3,2-b]pyridin-6-yl]-3,5-dimethyl-isoxazole | 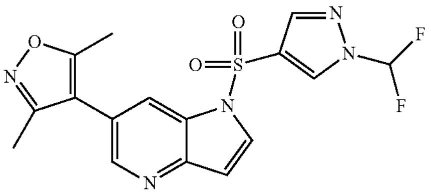 [SMILES: Cc1noc(C)c1-c1cnc2ccn(S(=O)(=O)c3cnn(C(F)F)c3)c2c1] | 394.1 |

TABLE 5-continued

The following compounds were prepared as depicted in example 5, using the appropriate starting materials.

| Cmpd # | name | Structure | MH(+) |
|---|---|---|---|
| P-0055 | 3,5-dimethyl-4-[1-(2-thienylsulfonyl)pyrrolo[3,2-b]pyridin-6-yl]isoxazole | 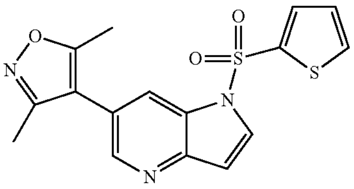 [SMILES: Cc1noc(C)c1-c1cnc2ccn(S(=O)(=O)c3cccs3)c2c1] | 359.9 |
| P-0056 | 4-[1-(3-fluorophenyl)sulfonylpyrrolo[3,2-b]pyridin-6-yl]-3,5-dimethyl-isoxazole | 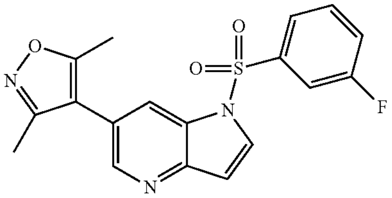 [SMILES: Cc1noc(C)c1-c1cnc2ccn(S(=O)(=O)c3cccc(F)c3)c2c1] | 371.9 |
| P-0057 | 4-[1-(3-chlorophenyl)sulfonylpyrrolo[3,2-b]pyridin-6-yl]-3,5-dimethyl-isoxazole | 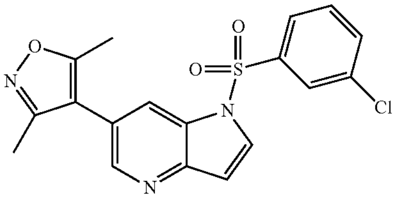 [SMILES: Cc1noc(C)c1-c1cnc2ccn(S(=O)(=O)c3cccc(Cl)c3)c2c1] | 387.7 |
| P-0058 | 4-[1-[1-(difluoromethyl)-3-methyl-pyrazol-4-yl]sulfonylpyrrolo[3,2-b]pyridin-6-yl]-3,5-dimethyl-isoxazole | 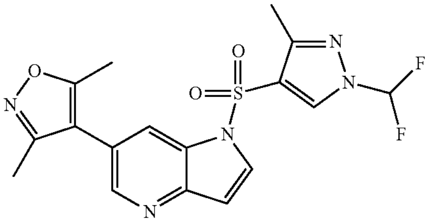 [SMILES: Cc1nn(C(F)F)cc1S(=O)(=O)n1ccc2ncc(-c3c(C)noc3C)cc21] | 408.1 |
| P-0059 | 3,5-dimethyl-4-[1-[(4-methyl-2-thienyl)sulfonyl]pyrrolo[3,2-b]pyridin-6-yl]isoxazole | 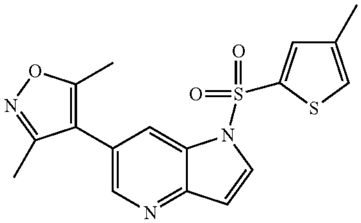 [SMILES: Cc1csc(S(=O)(=O)n2ccc3ncc(-c4c(C)noc4C)cc32)c1] | 374.0 |
| P-0060 | 4-[1-(2-fluorophenyl)sulfonylpyrrolo[3,2-b]pyridin-6-yl]-3,5-dimethyl-isoxazole | 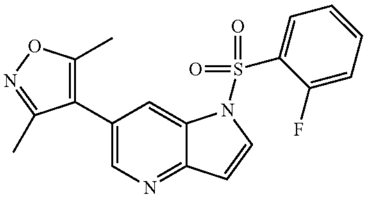 [SMILES: Cc1noc(C)c1-c1cnc2ccn(S(=O)(=O)c3ccccc3F)c2c1] | 372.0 |
| P-0061 | 4-[1-[3-(difluoromethoxy)phenyl]sulfonylpyrrolo[3,2-b]pyridin-6-yl]-3,5-dimethyl-isoxazole | 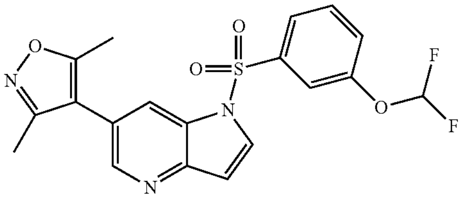 [SMILES: Cc1noc(C)c1-c1cnc2ccn(S(=O)(=O)c3cccc(OC(F)F)c3)c2c1] | 419.8 |

TABLE 5-continued

The following compounds were prepared as depicted in example 5, using the appropriate starting materials.

| Cmpd # | name | Structure | MH(+) |
| --- | --- | --- | --- |
| P-0062 | 3,5-dimethyl-4-[1-[(5-methyl-2-thienyl)sulfonyl]pyrrolo[3,2-b]pyridin-6-yl]isoxazole | 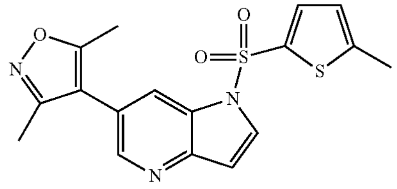 [SMILES: Cc1ccc(S(=O)(=O)n2ccc3ncc(-c4c(C)noc4C)cc32)s1] | 374.1 |
| P-0065 | 4-[1-(2-methoxyphenyl)sulfonylpyrrolo[3,2-b]pyridin-6-yl]-3,5-dimethyl-isoxazole | 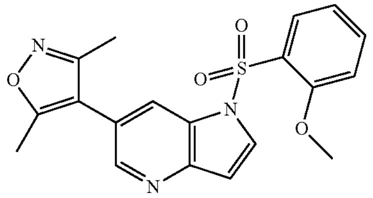 [SMILES: COc1ccccc1S(=O)(=O)n1ccc2ncc(-c3c(C)noc3C)cc21] | 384.0 |
| P-0066 | 4-(1-cyclohexylsulfonylpyrrolo[3,2-b]pyridin-6-yl)-3,5-dimethyl-isoxazole | 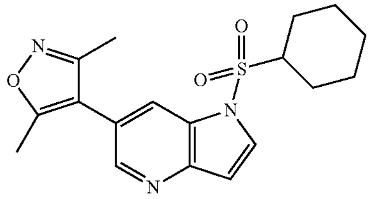 [SMILES: Cc1noc(C)c1-c1cnc2ccn(S(=O)(=O)C3CCCCC3)c2c1] | 360.1 |
| P-0067 | 3,5-dimethyl-4-[1-(1-piperidylsulfonyl)pyrrolo[3,2-b]pyridin-6-yl]isoxazole | 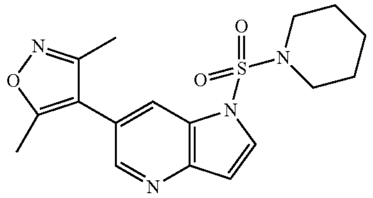 [SMILES: Cc1noc(C)c1-c1cnc2ccn(S(=O)(=O)N3CCCCC3)c2c1] | 360.9 |
| P-0068 | 3,5-dimethyl-4-(1-pyrrolidin-1-ylsulfonylpyrrolo[3,2-b]pyridin-6-yl)isoxazole | 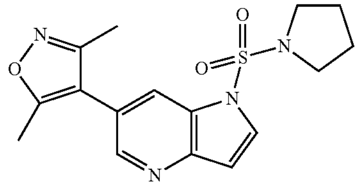 [SMILES: Cc1noc(C)c1-c1cnc2ccn(S(=O)(=O)N3CCCC3)c2c1] | 347.2 |
| P-0071 | 4-[1-cyclohexylsulfonyl-3-[cyclopropyl(methoxy)methyl]pyrrolo[3,2-b]pyridin-6-yl]-3,5-dimethyl-isoxazole | 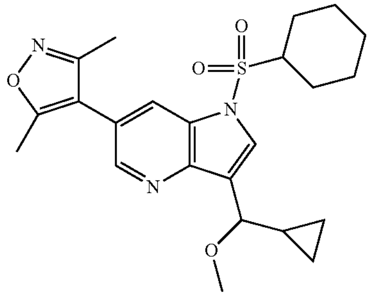 [SMILES: COC(c1cn(S(=O)(=O)C2CCCCC2)c2cc(-c3c(C)noc3C)cnc12)C1CC1] | 444.0 |

TABLE 5-continued

The following compounds were prepared as depicted in example 5, using the appropriate starting materials.

| Cmpd # | name | Structure | MH(+) |
|---|---|---|---|
| P-0074 | 4-[3-(cyclopropylmethyl)-1-(3,3,3-trifluoropropylsulfonyl)pyrrolo[3,2-b]pyridin-6-yl]-3,5-dimethyl-isoxazole | 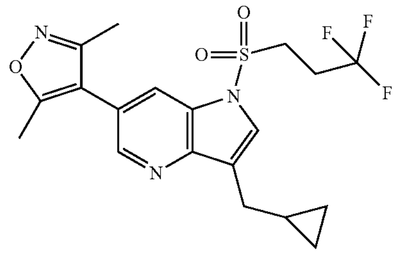 [SMILES: Cc1noc(C)c1-c1cnc2c(CC3CC3)cn(S(=O)(=O)CCC(F)(F)F)c2c1] | 428.2 |
| P-0075 | 4-[1-cyclohexylsulfonyl-3-(cyclopropylmethyl)pyrrolo[3,2-b]pyridin-6-yl]-3,5-dimethyl-isoxazole | 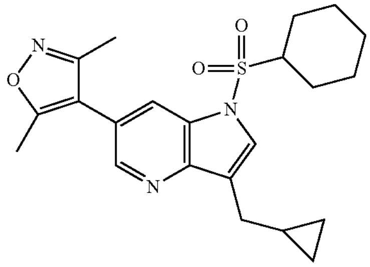 [SMILES: Cc1noc(C)c1-c1cnc2c(CC3CC3)cn(S(=O)(=O)C3CCCCC3)c2c1] | 414.0 |
| P-0076 | 4-[1-(benzenesulfonyl)-3-iodo-pyrrolo[3,2-b]pyridin-6-yl]-3,5-dimethyl-isoxazole | 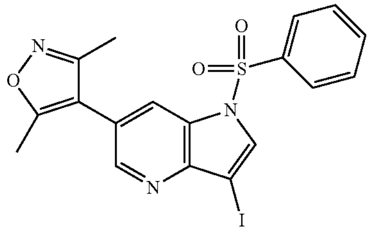 [SMILES: Cc1noc(C)c1-c1cnc2c(I)cn(S(=O)(=O)c3ccccc3)c2c1] | 480.0 |
| P-0078 | 4-[3-[(4,4-difluorocyclohexyl)-methoxy-methyl]-1-ethylsulfonyl-pyrrolo[2,3-b]pyridin-5-yl]-3,5-dimethyl-isoxazole | 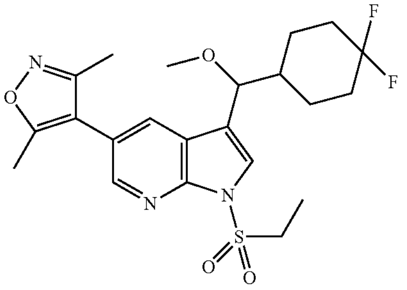 [SMILES: CCS(=O)(=O)n1cc(C(OC)C2CCC(F)(F)CC2)c2cc(-c3c(C)noc3C)cnc21] | 467.9 |
| P-0087 | 4-[1-(benzenesulfonyl)-3-iodo-pyrrolo[2,3-b]pyridin-5-yl]-3,5-dimethyl-isoxazole | 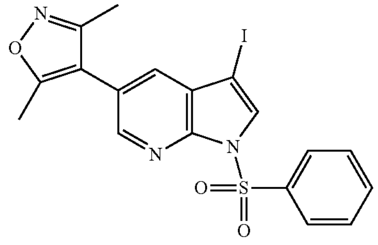 [SMILES: Cc1noc(C)c1-c1cnc2c(c1)c(I)cn2S(=O)(=O)c1ccccc1] | 480.0 |

TABLE 5-continued

The following compounds were prepared as depicted in example 5, using the appropriate starting materials.

| Cmpd # | name | Structure | MH(+) |
| --- | --- | --- | --- |
| P-0102 | 4-[1-(benzenesulfonyl)-3-(2-cyclopropylpyrimidin-5-yl)pyrrolo[3,2-b]pyridin-6-yl]-3,5-dimethyl-isoxazole | 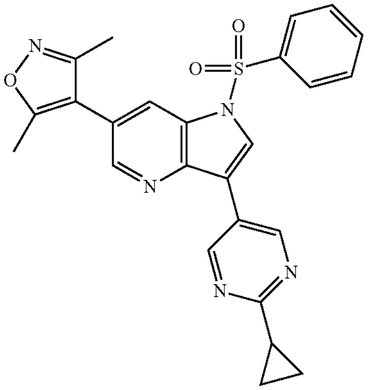 [SMILES: Cc1noc(C)c1-c1cnc2c(-c3cnc(C4CC4)nc3)cn(S(=O)(=O)c3ccccc3)c2c1] | 471.9 |
| P-0103 | 4-[1-cyclopentylsulfonyl-3-(2-cyclopropylpyrimidin-5-yl)pyrrolo[3,2-b]pyridin-6-yl]-3,5-dimethyl-isoxazole | 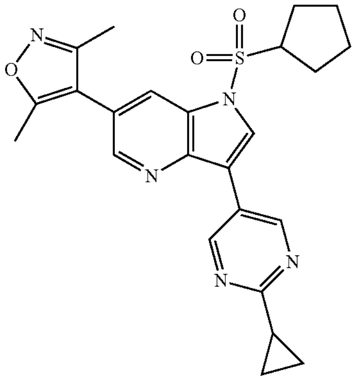 [SMILES: Cc1noc(C)c1-c1cnc2c(-c3cnc(C4CC4)nc3)cn(S(=O)(=O)C3CCCC3)c2c1] | 464.3 |
| P-0104 | 4-[1-(benzenesulfonyl)-3-(2-methoxypyrimidin-5-yl)pyrrolo[3,2-b]pyridin-6-yl]-3,5-dimethyl-isoxazole | 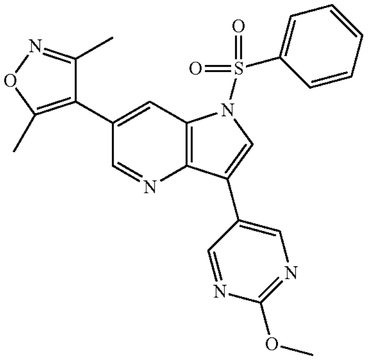 [SMILES: COc1ncc(-c2cn(S(=O)(=O)c3ccccc3)c3cc(-c4c(C)noc4C)cnc23)cn1] | 461.9 |
| P-0105 | 4-[1-cyclopentylsulfonyl-3-(2-methoxypyrimidin-5-yl)pyrrolo[3,2-b]pyridin-6-yl]-3,5-dimethyl-isoxazole | 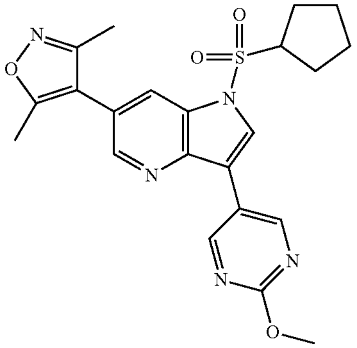 [SMILES: COc1ncc(-c2cn(S(=O)(=O)C3CCCC3)c3cc(-c4c(C)noc4C)cnc23)cn1] | 454.0 |

TABLE 5-continued

| Cmpd # | name | Structure | MH(+) |
|---|---|---|---|
| The following compounds were prepared as depicted in example 5, using the appropriate starting materials. | | | |
| P-0111 | 3,5-dimethyl-4-[3-(1-methylpyrazol-4-yl)-1-propylsulfonyl-pyrrolo[3,2-b]pyridin-6-yl]isoxazole | 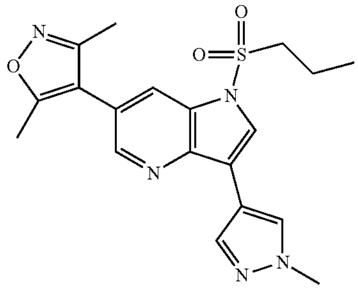 [SMILES: CCCS(=O)(=O)n1cc(-c2cnn(C)c2)c2ncc(-c3c(C)noc3C)cc21] | 399.8 |
| P-0112 | 4-[1-cyclopentylsulfonyl-3-(1-methylpyrazol-4-yl)pyrrolo[3,2-b]pyridin-6-yl]-3,5-dimethyl-isoxazole | 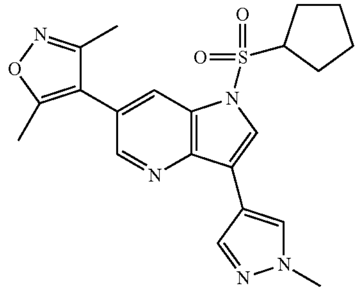 [SMILES: Cc1noc(C)c1-c1cnc2c(-c3cnn(C)c3)cn(S(=O)(=O)C3CCCC3)c2c1] | 425.9 |
| P-0121 | 4-[1-(2-fluorophenyl)sulfonyl-3-(1-methylpyrazol-4-yl)pyrrolo[3,2-b]pyridin-6-yl]-3,5-dimethyl-isoxazole | 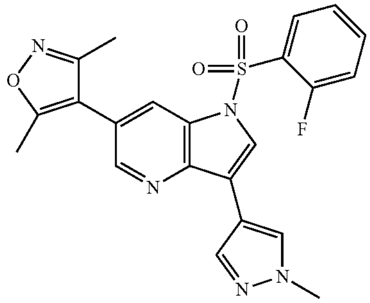 [SMILES: Cc1noc(C)c1-c1cnc2c(-c3cnn(C)c3)cn(S(=O)(=O)c3ccccc3F)c2c1] | 452.2 |
| P-0122 | 4-[1-(3-fluorophenyl)sulfonyl-3-(1-methylpyrazol-4-yl)pyrrolo[3,2-b]pyridin-6-yl]-3,5-dimethyl-isoxazole | 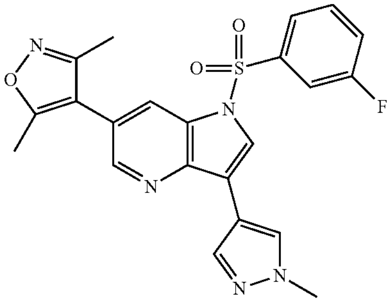 [SMILES: Cc1noc(C)c1-c1cnc2c(-c3cnn(C)c3)cn(S(=O)(=O)c3cccc(F)c3)c2c1] | 452.2 |
| P-0123 | 4-[1-(4-fluorophenyl)sulfonyl-3-(1-methylpyrazol-4-yl)pyrrolo[3,2-b]pyridin-6-yl]-3,5-dimethyl-isoxazole | 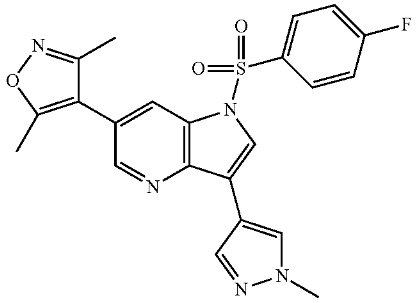 [SMILES: Cc1noc(C)c1-c1cnc2c(-c3cnn(C)c3)cn(S(=O)(=O)c3ccc(F)cc3)c2c1] | 452.2 |

TABLE 5-continued

| The following compounds were prepared as depicted in example 5, using the appropriate starting materials. | | | |
|---|---|---|---|
| Cmpd # | name | Structure | MH(+) |
| P-0124 | 4-[1-(benzenesulfonyl)-3-(1-ethylpyrazol-4-yl)pyrrolo[3,2-b]pyridin-6-yl]-3,5-dimethyl-isoxazole | 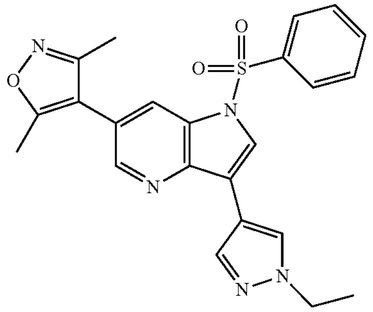 [SMILES: CCn1cc(-c2cn(S(=O)(=O)c3ccccc3)c3cc(-c4c(C)noc4C)cnc23)cn1] | 448.0 |
| P-0125 | 4-[3-(1-ethylpyrazol-4-yl)-1-(2-fluorophenyl)sulfonyl-pyrrolo[3,2-b]pyridin-6-yl]-3,5-dimethyl-isoxazole | 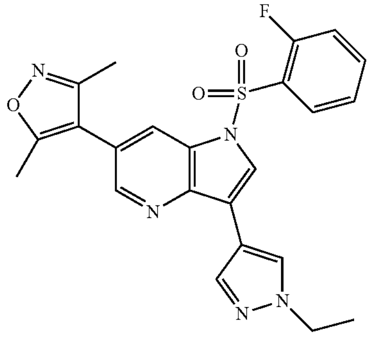 [SMILES: CCn1cc(-c2cn(S(=O)(=O)c3ccccc3F)c3cc(-c4c(C)noc4C)cnc23)cn1] | 466.0 |
| P-0126 | 4-[3-(1-allylpyrazol-4-yl)-1-benzenesulfonyl)pyrrolo[3,2-b]pyridin-6-yl]-3,5-dimethyl-isoxazole | 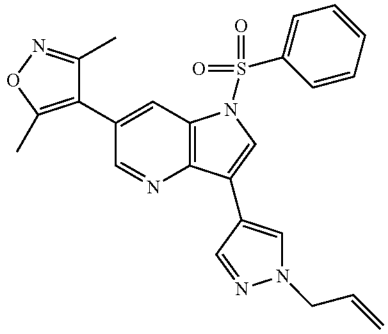 [SMILES: C=CCn1cc(-c2cn(S(=O)(=O)c3ccccc3)c3cc(-c4c(C)noc4C)cnc23)cn1] | 460.4 |
| P-0127 | 4-[3-(1-allylpyrazol-4-yl)-1-(2-fluorophenyl)sulfonyl-pyrrolo[3,2-b]pyridin-6-yl]-3,5-dimethyl-isoxazole | 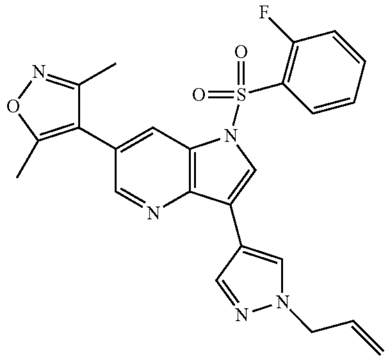 [SMILES: C=CCn1cc(-c2cn(S(=O)(=O)c3ccccc3F)c3cc(-c4c(C)noc4C)cnc23)cn1] | 478.3 |

TABLE 5-continued

| The following compounds were prepared as depicted in example 5, using the appropriate starting materials. | | | |
|---|---|---|---|
| Cmpd # | name | Structure | MH(+) |
| P-0128 | 4-[3-(1-allylpyrazol-4-yl)-1-cyclopentylsulfonyl-pyrrolo[3,2-b]pyridin-6-yl]-3,5-dimethyl-isoxazole | 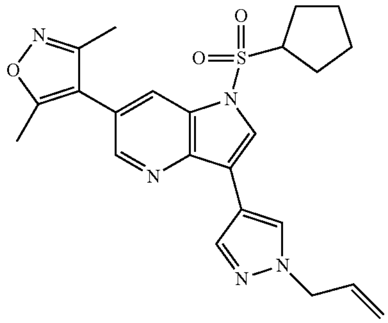 [SMILES: C=CCn1cc(-c2cn(S(=O)(=O)C3CCCC3)c3cc(-c4c(C)noc4C)cnc23)cn1] | 452.4 |
| P-0129 | 4-[3-(1-allylpyrazol-4-yl)-1-(3,3,3-trifluoropropylsulfonyl)pyrrolo[3,2-b]pyridin-6-yl]-3,5-dimethyl-isoxazole | 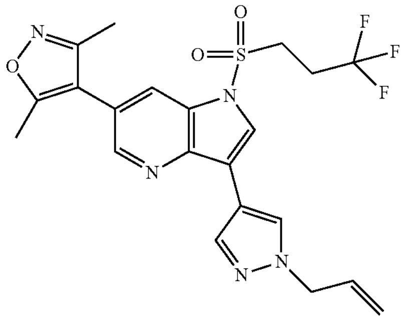 [SMILES: C=CCn1cc(-c2cn(S(=O)(=O)CCC(F)(F)F)c3cc(-c4c(C)noc4C)cnc23)cn1] | 480.3 |
| P-0132 | 4-[3-[1-(difluoromethyl)pyrazol-4-yl]-1-(2-fluorophenyl)sulfonyl-pyrrolo[3,2-b]pyridin-6-yl]-3,5-dimethyl-isoxazole | 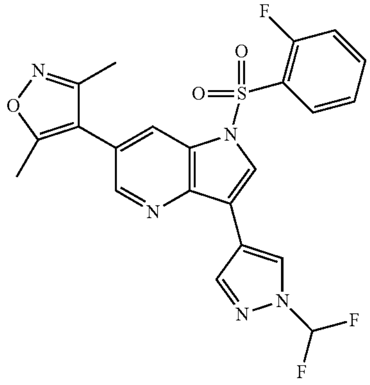 [SMILES: Cc1noc(C)c1-c1cnc2c(-c3cnn(C(F)F)c3)cn(S(=O)(=O)c3ccccc3F)c2c1] | 487.9 |
| P-0133 | 4-[1-cyclopentylsulfonyl-3-[1-(difluoromethyl)pyrazol-4-yl]pyrrolo[3,2-b]pyridin-6-yl]-3,5-dimethyl-isoxazole | 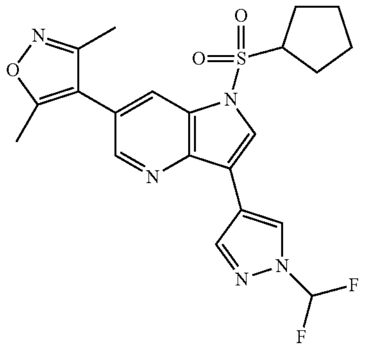 [SMILES: Cc1noc(C)c1-c1cnc2c(-c3cnn(C(F)F)c3)cn(S(=O)(=O)C3CCCC3)c2c1] | 462.1 |

TABLE 5-continued

| The following compounds were prepared as depicted in example 5, using the appropriate starting materials. | | | |
|---|---|---|---|
| Cmpd # | name | Structure | MH(+) |
| P-0134 | 4-[1-cyclobutylsulfonyl-3-[1-(difluoromethyl)pyrazol-4-yl]pyrrolo[3,2-b]pyridin-6-yl]-3,5-dimethyl-isoxazole | 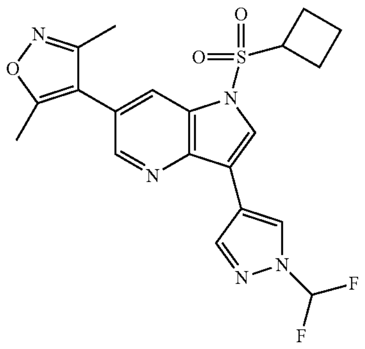 [SMILES: Cc1noc(C)c1-c1cnc2c(-c3cnn(C(F)F)c3)cn(S(=O)(=O)C3CCC3)c2c1] | 448.0 |
| P-0135 | 4-[3-[1-(difluoromethyl)pyrazol-4-yl]-1-propylsulfonyl-pyrrolo[3,2-b]pyridin-6-yl]-3,5-dimethyl-isoxazole | 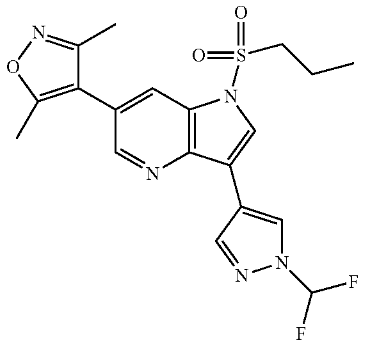 [SMILES: CCCS(=O)(=O)n1cc(-c2cnn(C(F)F)c2)c2ncc(-c3c(C)noc3C)cc21] | 436.2 |
| P-0136 | 4-[3-[1-(difluoromethyl)pyrazol-4-yl]-1-(3,3,3-trifluoropropylsulfonyl)pyrrolo[3,2-b]pyridin-6-yl]-3,5-dimethyl-isoxazole | 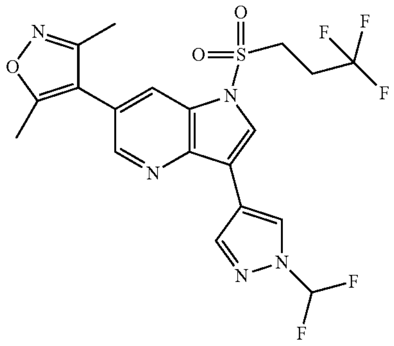 [SMILES: Cc1noc(C)c1-c1cnc2c(-c3cnn(C(F)F)c3)cn(S(=O)(=O)CCC(F)(F)F)c2c1] | 490.1 |
| P-0137 | 4-[3-(1-allylpyrazol-4-yl)-1-propylsulfonyl-pyrrolo[3,2-b]pyridin-6-yl]-3,5-dimethyl-isoxazole | 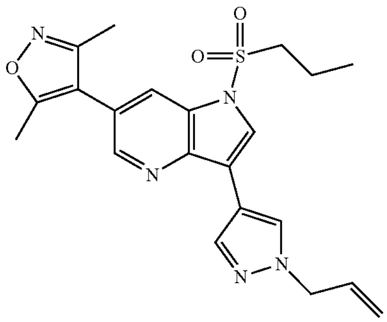 [SMILES: C=CCn1cc(-c2cn(S(=O)(=O)CCC)c3cc(-c4c(C)noc4C)cnc23)cn1] | 426.3 |

TABLE 5-continued

| The following compounds were prepared as depicted in example 5, using the appropriate starting materials. | | | |
|---|---|---|---|
| Cmpd # | name | Structure | MH(+) |
| P-0138 | 4-[3-(1-allylpyrazol-4-yl)-1-sec-butylsulfonyl-pyrrolo[3,2-b]pyridin-6-yl]-3,5-dimethyl-isoxazole | 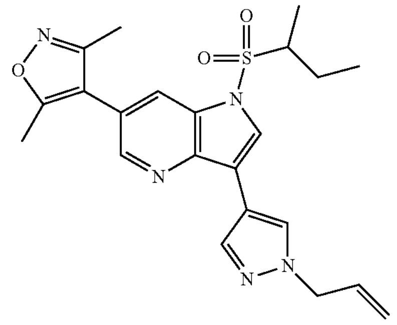 [SMILES: C=CCn1cc(-c2cn(S(=O)(=O)C(C)CC)c3cc(-c4c(C)noc4C)cnc23)cn1] | 440.4 |
| P-0139 | 4-[3-(1-allylpyrazol-4-yl)-1-cyclopropylsulfonyl-pyrrolo[3,2-b]pyridin-6-yl]-3,5-dimethyl-isoxazole | 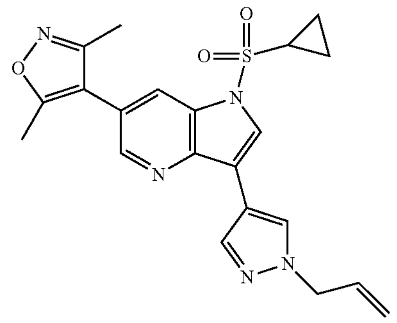 [SMILES: C=CCn1cc(-c2cn(S(=O)(=O)C3CC3)c3cc(-c4c(C)noc4C)cnc23)cn1] | 423.9 |
| P-0140 | 4-[3-(1-allylpyrazol-4-yl)-1-(cyclopropylmethylsulfonyl)pyrrolo[3,2-b]pyridin-6-yl]-3,5-dimethyl-isoxazole | 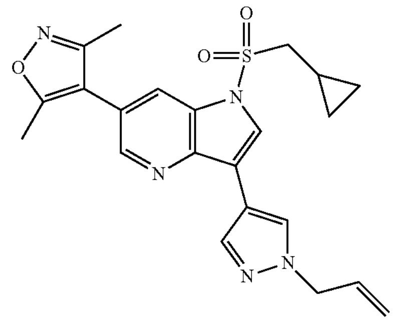 [SMILES: C=CCn1cc(-c2cn(S(=O)(=O)CC3CC3)c3cc(-c4c(C)noc4C)cnc23)cn1] | 438.2 |
| P-0149 | 4-[1-cyclopentylsulfonyl-3-[1-(2,2,2-trifluoroethyl)pyrazol-4-yl]pyrrolo[3,2-b]pyridin-6-yl]-3,5-dimethyl-isoxazole | 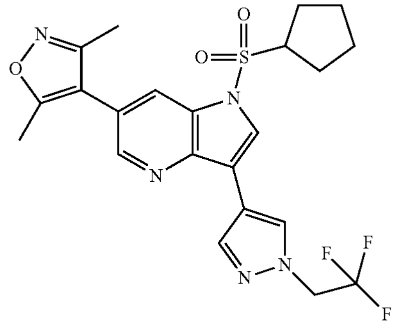 [SMILES: Cc1noc(C)c1-c1cnc2c(-c3cnn(CC(F)(F)F)c3)cn(S(=O)(=O)C3CCCC3)c2c1] | 494.0 |

TABLE 5-continued

| The following compounds were prepared as depicted in example 5, using the appropriate starting materials. | | | |
|---|---|---|---|
| Cmpd # | name | Structure | MH(+) |
| P-0150 | 3,5-dimethyl-4-[1-propylsulfonyl-3-[1-(2,2,2-trifluoroethyl)pyrazol-4-yl]pyrrolo[3,2-b]pyridin-6-yl]isoxazole | 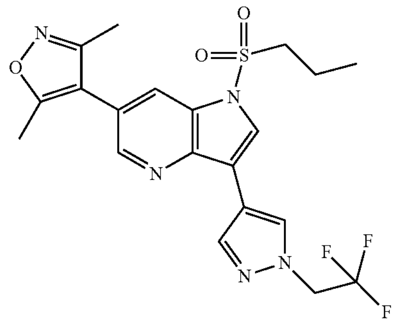 [SMILES: CCCS(=O)(=O)n1cc(-c2cnn(CC(F)(F)F)c2)c2ncc(-c3c(C)noc3C)cc21] | 468.2 |
| P-0151 | 4-[1-cyclopentylsulfonyl-3-[1-(2-methoxyethyl)pyrazol-4-yl]pyrrolo[3,2-b]pyridin-6-yl]-3,5-dimethyl-isoxazole | 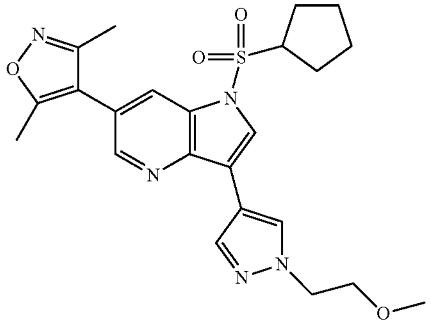 [SMILES: COCCn1cc(-c2cn(S(=O)(=O)C3CCCC3)c3cc(-c4c(C)noc4C)cnc23)cn1] | 469.9 |
| P-0152 | 4-[3-[1-(2-methoxyethyl)pyrazol-4-yl]-1-propylsulfonyl-pyrrolo[3,2-b]pyridin-6-yl]-3,5-dimethyl-isoxazole | 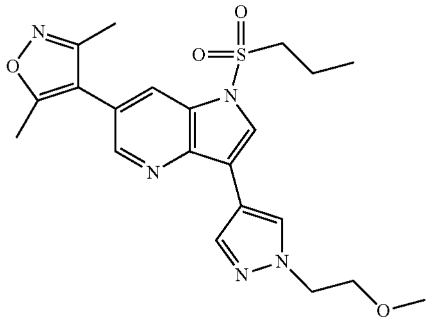 [SMILES: CCCS(=O)(=O)n1cc(-c2cnn(CCOC)c2)c2ncc(-c3c(C)noc3C)cc21] | 444.0 |
| P-0153 | 4-[1-cyclopentylsulfonyl-3-(1-tetrahydrofuran-3-ylpyrazol-4-yl)pyrrolo[3,2-b]pyridin-6-yl]-3,5-dimethyl-isoxazole | 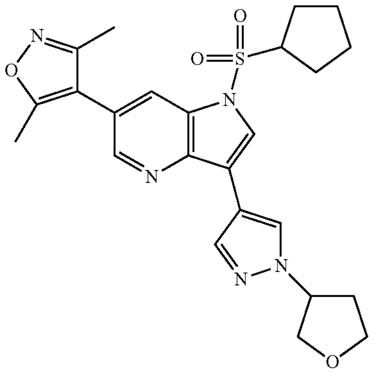 [SMILES: Cc1noc(C)c1-c1cnc2c(-c3cnn(C4CCOC4)c3)cn(S(=O)(=O)C3CCCC3)c2c1] | 482.0 |

TABLE 5-continued

| The following compounds were prepared as depicted in example 5, using the appropriate starting materials. | | | |
|---|---|---|---|
| Cmpd # | name | Structure | MH(+) |
| P-0154 | 3,5-dimethyl-4-[1-propylsulfonyl-3-(1-tetrahydrofuran-3-ylpyrazol-4-yl)pyrrolo[3,2-b]pyridin-6-yl]isoxazole | 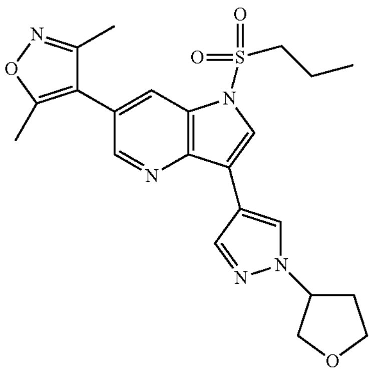 [SMILES: CCCS(=O)(=O)n1cc(-c2cnn(C3CCOC3)c2)c2ncc(-c3c(C)noc3C)cc21] | 456.3 |
| P-0230 | 4-[1-(benzenesulfonyl)-3-(1-methylpyrazol-4-yl)indol-6-yl]-3,5-dimethyl-isoxazole | 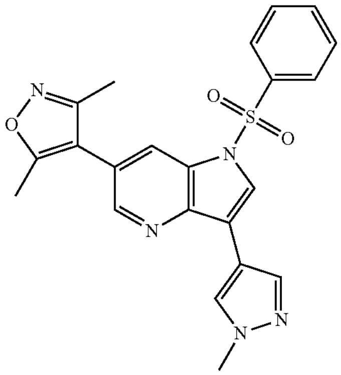 [SMILES: Cc1noc(C)c1-c1cnc2c(-c3cnn(C)c3)cn(S(=O)(=O)c3ccccc3)c2c1] | 433.3 |
| P-0231 | 4-[1-cyclopentylsulfonyl-3-(1-methylpyrazol-4-yl)indol-6-yl]-3,5-dimethyl-isoxazole | 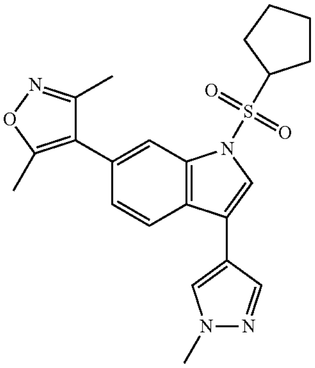 [SMILES: Cc1noc(C)c1-c1ccc2c(-c3cnn(C)c3)cn(S(=O)(=O)C3CCCC3)c2c1] | 425.2 |

Example 6

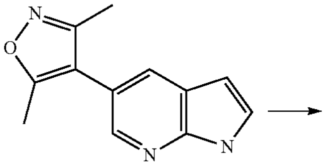

P-0246

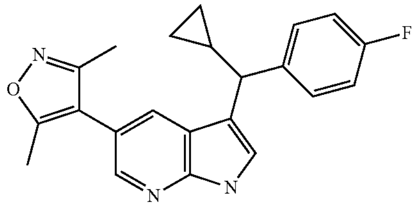

P-0064

Preparation of 4-[3-[cyclopropyl-(4-fluorophenyl)methyl]-1H-pyrrolo[2,3-b]pyridin-5-yl]-3,5-dimethyl-isoxazole P-0064

To cyclopropyl-(4-fluorophenyl)methanol (0.33 g, 1.99 mmol) in methylene chloride (10.0 mL) were added 3,5-dimethyl-4-(1H-pyrrolo[2,3-b]pyridin-5-yl)isoxazole (P-0246, 0.3 g, 1.41 mmol) and trifluoroacetic acid (2 g, 17.54 mmol). The reaction was stirred at room temperature overnight. The reaction was poured into aqueous potassium carbonate, extracted by ethyl acetate. The organic layer was washed with brine, dried over anhydrous sodium sulfate, and filtered. The filtrate was concentrated, and purified with silica gel column chromatography eluting with 20% to 100% ethyl acetate in hexane to crude product, which was then further purified by prep-HPLC to give product (P-0064, 5.3 mg, 1.0%) as a white solid. MS (ESI) $[M+H^+]^+=362.4$.

TABLE 6

The following compounds were prepared as depicted in example 6, using the appropriate starting materials.

| No. | name | Structure | MH(+) |
|---|---|---|---|
| P-0063 | 4-[3-[1-(4-fluorophenyl)-1-methyl-ethyl]-1H-pyrrolo[2,3-b]pyridin-5-yl]-3,5-dimethyl-isoxazole | 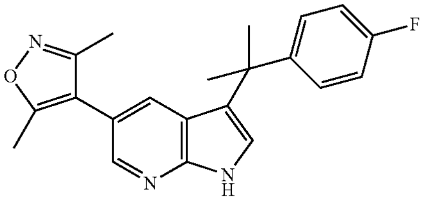 [SMILES: Cc1noc(C)c1-c1cnc2[nH]cc(C(C)(C)c3ccc(F)cc3)c2c1] | 350.3 |
| P-0085 | 4-[3-[dicyclopropyl-(4-fluorophenyl)methyl]-1H-pyrrolo[2,3-b]pyridin-5-yl]-3,5-dimethyl-isoxazole | 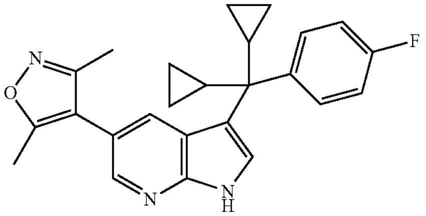 [SMILES: Cc1noc(C)c1-c1cnc2[nH]cc(C(c3ccc(F)cc3)(C3CC3)C3CC3)c2c1] | 402.4 |

Example 7

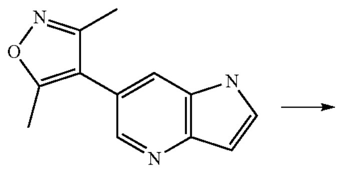

P-0018

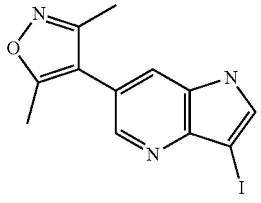

P-0072

Preparation of 4-(3-iodo-1H-pyrrolo[3,2-b]pyridin-6-yl)-3,5-dimethyl-isoxazole P-0072

To 3,5-dimethyl-4-(1H-pyrrolo[3,2-b]pyridin-6-yl)isoxazole (P-0018, 1 g, 4.69 mmol) in dichloromethane (50 mL) was N-iodosuccinimide (1.11 g, 4.92 mmol) at room temperature. The reaction was stirred at room temperature for 4 hours. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0072, 0.9 g, 56.6%). MS (ESI) $[M+H^+]^+=339.6$.

TABLE 7

| The following compounds were prepared as depicted in example 7, using the appropriate starting materials. | | | |
|---|---|---|---|
| Cmpd # | name | Structure | MH(+) |
| P-0086 | 4-(3-iodo-1H-pyrrolo[2,3-b]pyridin-5-yl)-3,5-dimethyl-isoxazole | 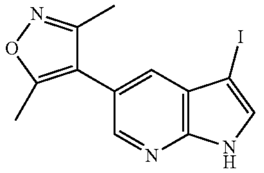 [SMILES: Cc1noc(C)c1-c1cnc2[nH]cc(I)c2c1] | 340.0 |

Example 8

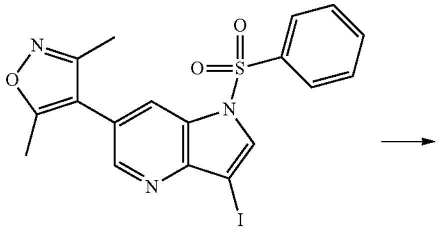

P-0076

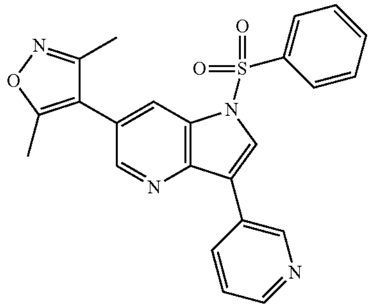

P-0084

+

-continued

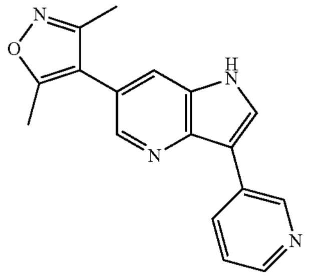

P-0083

Preparation of 4-[1-(benzenesulfonyl)-3-(3-pyridyl)pyrrolo[3,2-b]pyridin-6-yl]-3,5-dimethyl-isoxazole P-0084 and 3,5-dimethyl-4-[3-(3-pyridyl)-1H-pyrrolo[3,2-b]pyridin-6-yl]isoxazole P-0083

To 4-[1-(benzenesulfonyl)-3-iodo-pyrrolo[3,2-b]pyridin-6-yl]-3,5-dimethyl-isoxazole (P-0076, 0.05 g, 0.09 mmol) in acetonitrile (4 ml), under nitrogen, were added 3-pyridylboronic acid (0.03 g, 0.24 mmol), [1,1'-bis(diphenylphosphino)ferrocene]dichloropalladium(II) (0.02 g, 0.03 mmol), and 1M potassium carbonate in water (1.3 ml). The reaction was heated under microwave at 160° C. for 10 minutes. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride to give crude product, which was then further purified by prep-HPLC to give product (P-0084, 2.0 mg, 4.9%), MS(ESI) $[M+H^+]^+=431.1$; and product (P-0083, 3.8 mg, 12.1%), MS (ESI) $[M+H^+]^+=290.8$.

TABLE 8

| The following compounds were prepared as depicted in example 8, using the appropriate starting materials. | | | |
|---|---|---|---|
| Cmpd # | name | Structure | MH(+) |
| P-0110 | 4-[1-(benzenesulfonyl)-3-(1-methylpyrazol-4-yl)pyrrolo[3,2-b]pyridin-6-yl]-3,5-dimethyl-isoxazole | 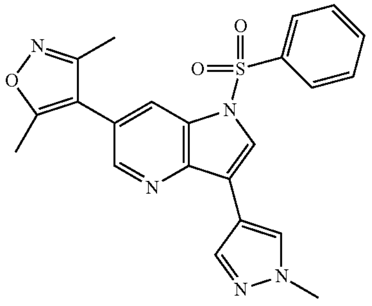 [SMILES: Cc1noc(C)c1-c1cnc2c(-c3cnn(C)c3)cn(S(=O)(=O)c3ccccc3)c2c1] | 433.9 |

TABLE 8-continued

| The following compounds were prepared as depicted in example 8, using the appropriate starting materials. | | | |
|---|---|---|---|
| Cmpd # | name | Structure | MH(+) |
| P-0131 | 4-[1-(benzenesulfonyl)-3-[1-(difluoromethyl)pyrazol-4-yl]pyrrolo[3,2-b]pyridin-6-yl]-3,5-dimethyl-isoxazole | 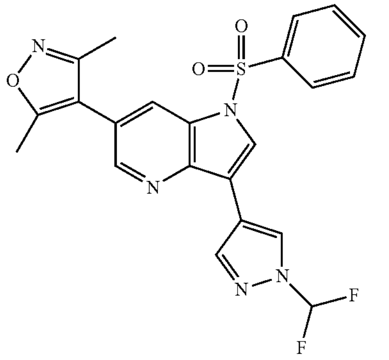 [SMILES: Cc1noc(C)c1-c1cnc2c(-c3cnn(C(F)F)c3)cn(S(=O)(=O)c3ccccc3)c2c1] | 470.0 |
| P-0146 | 4-[1-(benzenesulfonyl)-3-[1-(2,2,2-trifluoroethyl)pyrazol-4-yl]pyrrolo[3,2-b]pyridin-6-yl]-3,5-dimethyl-isoxazole | 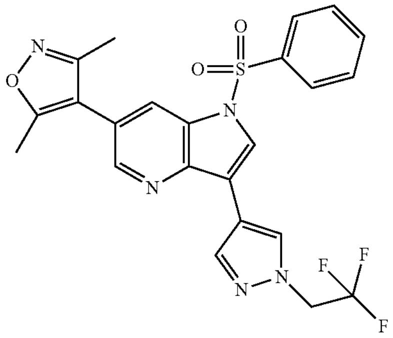 [SMILES: Cc1noc(C)c1-c1cnc2c(-c3cnn(CC(F)(F)F)c3)cn(S(=O)(=O)c3ccccc3)c2c1] | 502.0 |
| P-0147 | 4-[1-(benzenesulfonyl)-3-[1-(2-methoxyethyl)pyrazol-4-yl]pyrrolo[3,2-b]pyridin-6-yl]-3,5-dimethyl-isoxazole | 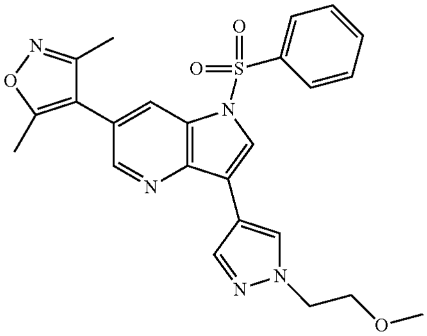 [SMILES: COCCn1cc(-c2cn(S(=O)(=O)c3ccccc3)c3cc(-c4c(C)noc4C)cnc23)cn1] | 478.0 |
| p-0148 | 4-[1-(benzenesulfonyl)-3-(1-tetrahydrofuran-3-ylpyrazol-4-yl)pyrrolo[3,2-b]pyridin-6-yl]-3,5-dimethyl-isoxazole | 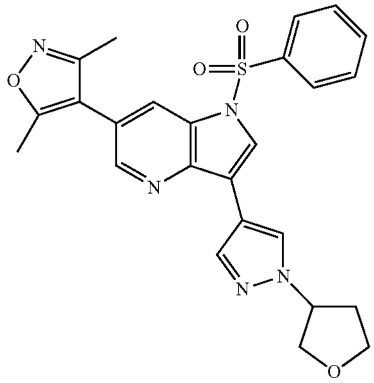 [SMILES: Cc1noc(C)c1-c1cnc2c(-c3cnn(C4CCOC4)c3)cn(S(=O)(=O)c3ccccc3)c2c1] | 490.0 |

TABLE 8-continued

| The following compounds were prepared as depicted in example 8, using the appropriate starting materials. | | | |
|---|---|---|---|
| Cmpd # | name | Structure | MH(+) |
| P-0077 | 4-[1-(benzenesulfonyl)-3-phenyl-pyrrolo[3,2-b]pyridin-6-yl]-3,5-dimethyl-isoxazole | 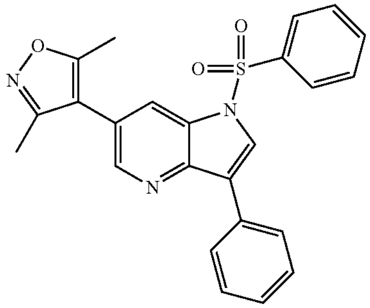 [SMILES: Cc1noc(C)c1-c1cnc2c(-c3ccccc3)cn(S(=O)(=O)c3ccccc3)c2c1] | 429.8 |
| P-0163 | 4-[1-(benzenesulfonyl)-3-(1H-pyrazol-4-yl)pyrrolo[3,2-b]pyridin-6-yl]-3,5-dimethyl-isoxazole | 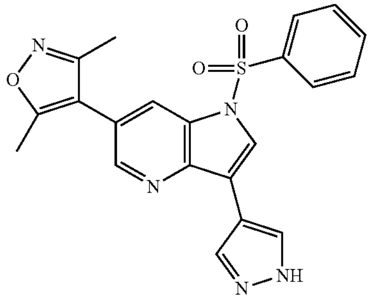 [SMILES: Cc1noc(C)c1-c1cnc2c(-c3cn[nH]c3)cn(S(=O)(=O)c3ccccc3)c2c1] | 419.9 |
| P-0164 | 4-[1-(benzenesulfonyl)-3-(3-methyl-1H-pyrazol-5-yl)pyrrolo[3,2-b]pyridin-6-yl]-3,5-dimethyl-isoxazole | 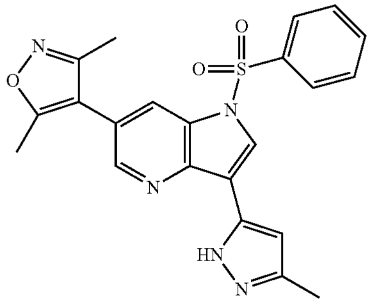 [SMILES: Cc1cc(-c2cn(S(=O)(=O)c3ccccc3)c3cc(-c4c(C)noc4C)cnc23)[nH]n1] | 434.3 |
| P-0167 | 4-[1-cyclopentylsulfonyl-3-(1H-pyrazol-4-yl)pyrrolo[3,2-b]pyridin-6-yl]-3,5-dimethyl-isoxazole | 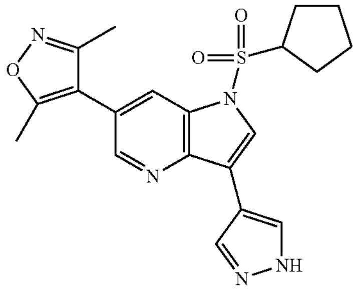 [SMILES: Cc1noc(C)c1-c1cnc2c(-c3cn[nH]c3)cn(S(=O)(=O)C3CCCC3)c2c1] | 412.2 |

TABLE 8-continued

| Cmpd # | name | Structure | MH(+) |
|---|---|---|---|
| P-0168 | 4-[1-(benzenesulfonyl)-3-(1-tetrahydropyran-2-ylpyrazol-4-yl)pyrrolo[3,2-b]pyridin-6-yl]-3,5-dimethyl-isoxazole | 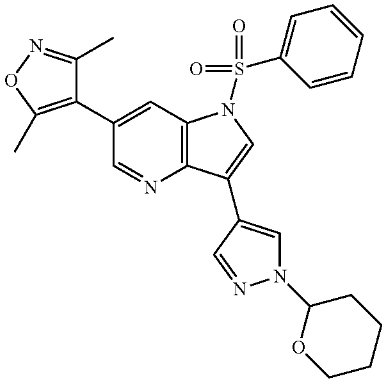 [SMILES: Cc1noc(C)c1-c1cnc2c(-c3cnn(C4CCCCO4)c3)cn(S(=O)(=O)c3ccccc3)c2c1] | 504.3 |
| P-0191 | 4-[1-(benzenesulfonyl)-3-(2-methylthiazol-4-yl)pyrrolo[3,2-b]pyridin-6-yl]-3,5-dimethyl-isoxazole | 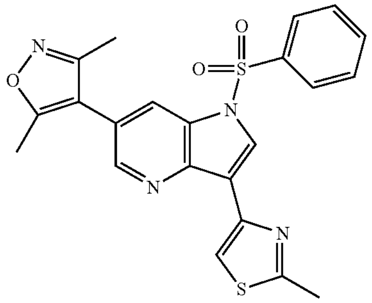 [SMILES: Cc1nc(-c2cn(S(=O)(=O)c3ccccc3)c3cc(-c4c(C)noc4C)cnc23)cs1] | 450.9 |
| P-0199 | 3,5-dimethyl-4-[1-(1-phenylethyl)-3-(1H-pyrazol-4-yl)pyrrolo[3,2-b]pyridin-6-yl]isoxazole | 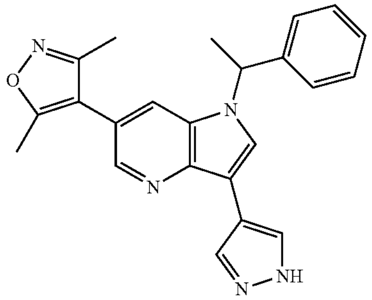 [SMILES: Cc1noc(C)c1-c1cnc2c(-c3cn[nH]c3)cn(C(C)c3ccccc3)c2c1] | 383.9 |
| P-0200 | 4-[3-(1-ethylpyrazol-4-yl)-1-(1-phenylethyl)pyrrolo[3,2-b]pyridin-6-yl]-3,5-dimethyl-isoxazole | 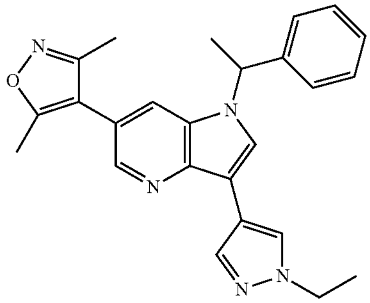 [SMILES: CCn1cc(-c2cn(C(C)c3ccccc3)c3cc(-c4c(C)noc4C)cnc23)cn1] | 412.3 |

The following compounds were prepared as depicted in example 8, using the appropriate starting materials.

TABLE 8-continued

| The following compounds were prepared as depicted in example 8, using the appropriate starting materials. | | | |
|---|---|---|---|
| Cmpd # | name | Structure | MH(+) |
| P-0201 | 4-[3-(1-allylpyrazol-4-yl)-1-(1-phenylethyl)pyrrolo[3,2-b]pyridin-6-yl]-3,5-dimethyl-isoxazole | 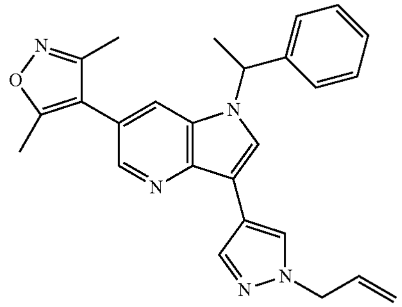 [SMILES: C=CCn1cc(-c2cn(C(C)c3ccccc3)c3cc(-c4c(C)noc4C)cnc23)cn1] | 424.0 |
| P-0202 | 3,5-dimethyl-4-[1-(1-phenylethyl)-3-[1-(2,2,2-trifluoroethyl)pyrazol-4-yl]pyrrolo[3,2-b]pyridin-6-yl]isoxazole | 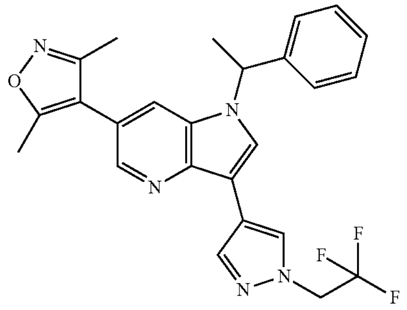 [SMILES: Cc1noc(C)c1-c1cnc2c(-c3cnn(CC(F)(F)F)c3)cn(C(C)c3ccccc3)c2c1] | 465.9 |
| P-0203 | 4-[3-[1-(2-methoxyethyl)pyrazol-4-yl]-1-(1-phenylethyl)pyrrolo[3,2-b]pyridin-6-yl]-3,5-dimethyl-isoxazole | 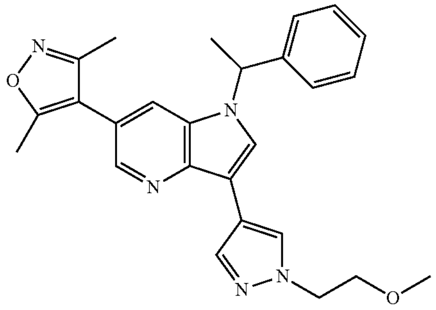 [SMILES: COCCn1cc(-c2cn(C(C)c3ccccc3)c3cc(-c4c(C)noc4C)cnc23)cn1] | 442.1 |
| P-0204 | 3,5-dimethyl-4-[1-(1-phenylethyl)-3-(1-tetrahydrofuran-3-ylpyrazol-4-yl)pyrrolo[3,2-b]pyridin-6-yl]isoxazole | 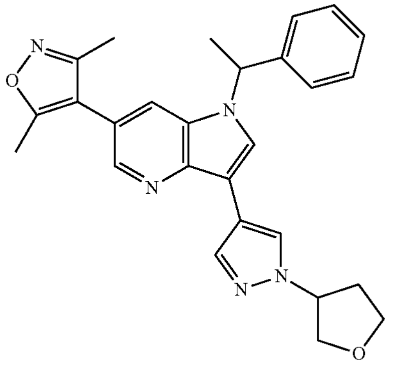 [SMILES: Cc1noc(C)c1-c1cnc2c(-c3cnn(C4CCOC4)c3)cn(C(C)c3ccccc3)c2c1] | 454.0 |

TABLE 8-continued

| The following compounds were prepared as depicted in example 8, using the appropriate starting materials. | | | |
|---|---|---|---|
| Cmpd # | name | Structure | MH(+) |
| P-0205 | 4-[3-(1,3-dimethylpyrazol-4-yl)-1-(1-phenylethyl)pyrrolo[3,2-b]pyridin-6-yl]-3,5-dimethyl-isoxazole | 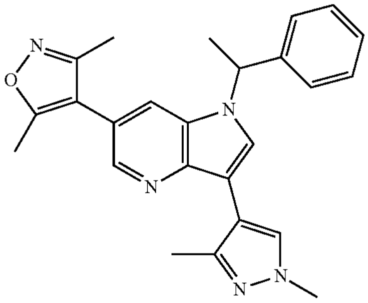 [SMILES: Cc1nn(C)cc1-c1cn(C(C)c2ccccc2)c2cc(-c3c(C)noc3C)cnc12] | 412.0 |
| P-0216 | 4-[3-(1-cyclopropylpyrazol-4-yl)-1-(1-phenylethyl)pyrrolo[3,2-b]pyridin-6-yl]-3,5-dimethyl-isoxazole | 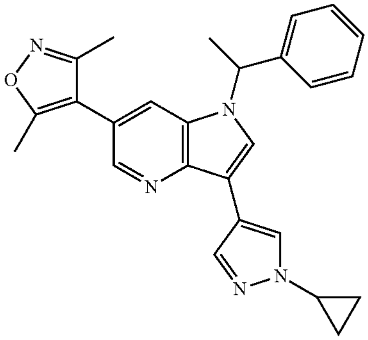 [SMILES: Cc1noc(C)c1-c1cnc2c(-c3cnn(C4CC4)c3)cn(C(C)c3ccccc3)c2c1] | 424.0 |
| P-0219 | 4-[1-[dideuterio-(4,4-difluorocyclohexyl)methyl]-3-[1-(difluoromethyl)pyrazol-4-yl]pyrrolo[3,2-b]pyridin-6-yl]-3,5-dimethyl-isoxazole | 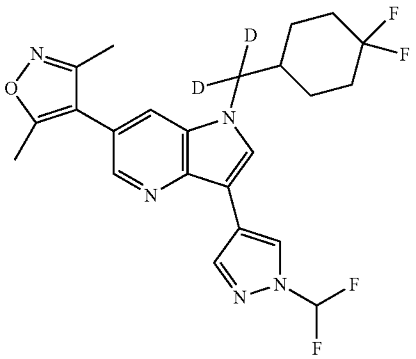 [SMILES: [2H]C([2H])(C1CCC(F)(F)CC1)n1cc(-c2cnn(C(F)F)c2)c2ncc(-c3c(C)noc3C)cc21] | 464.0 |
| P-0220 | 4-[3-(1-cyclopropylpyrazol-4-yl)-1-[dideuterio-(4,4-difluorocyclohexyl)methyl]pyrrolo[3,2-b]pyridin-6-yl]-3,5-dimethyl-isoxazole | 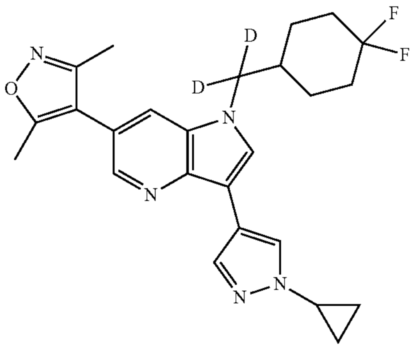 [SMILES: [2H]C([2H])(C1CCC(F)(F)CC1)n1cc(-c2cnn(C3CC3)c2)c2ncc(-c3c(C)noc3C)cc21] | 454.0 |

TABLE 8-continued

The following compounds were prepared as depicted in example 8, using the appropriate starting materials.

| Cmpd # | name | Structure | MH(+) |
|---|---|---|---|
| P-0221 | 4-[1-[dideuterio-(4,4-difluorocyclohexyl)methyl]-3-[1-(2,2,2-trifluoroethyl)pyrazol-4-yl]pyrrolo[3,2-b]pyridin-6-yl]-3,5-dimethyl-isoxazole | 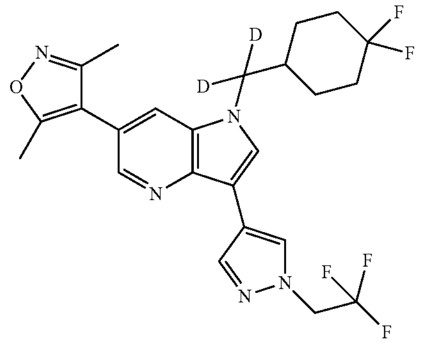 [SMILES: [2H]C([2H])(C1CCC(F)(F)CC1)n1cc(-c2cnn(CC(F)(F)F)c2)c2ncc(-c3c(C)noc3C)cc21] | 496.0 |
| P-0235 | 4-[3-[1-(difluoromethyl)pyrazol-4-yl]-1-[(1-fluorocyclohexyl)methyl]pyrrolo[3,2-b]pyridin-6-yl]-3,5-dimethyl-isoxazole | 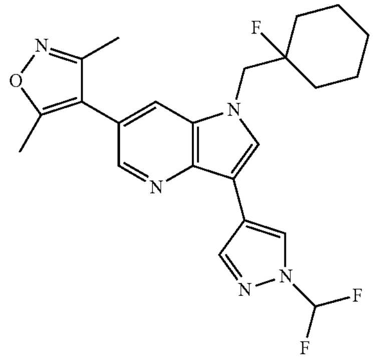 [SMILES: Cc1noc(C)c1-c1cnc2c(-c3cnn(C(F)F)c3)cn(CC3(F)CCCCC3)c2c1] | 444.2 |
| P-0236 | 4-[3-(1-cyclopropylpyrazol-4-yl)-1-[(1-fluorocyclohexyl)methyl]pyrrolo[3,2-b]pyridin-6-yl]-3,5-dimethyl-isoxazole | 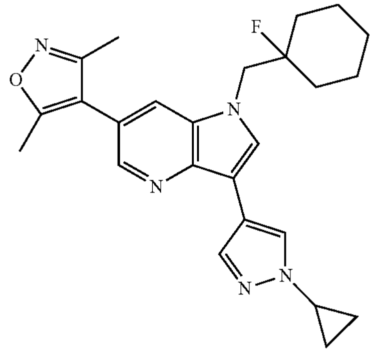 [SMILES: Cc1noc(C)c1-c1cnc2c(-c3cnn(C4CC4)c3)cn(CC3(F)CCCCC3)c2c1] | 434.0 |
| P-0237 | 4-[1-[(1-fluorocyclohexyl)methyl]-3-[1-(2,2,2-trifluoroethyl)pyrazol-4-yl]pyrrolo[3,2-b]pyridin-6-yl]-3,5-dimethyl-isoxazole | 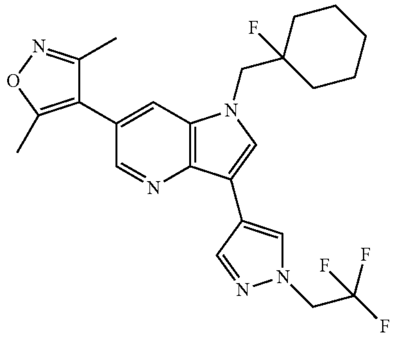 [SMILES: Cc1noc(C)c1-c1cnc2c(-c3cnn(CC(F)(F)F)c3)cn(CC3(F)CCCCC3)c2c1] | 476.0 |

TABLE 8-continued

The following compounds were prepared as depicted in example 8, using the appropriate starting materials.

| Cmpd # | name | Structure | MH(+) |
|---|---|---|---|
| P-0238 | 4-[1-[(1-fluorocyclohexyl)methyl]-3-[1-(2-methoxyethyl)pyrazol-4-yl]pyrrolo[3,2-b]pyridin-6-yl]-3,5-dimethyl-isoxazole | 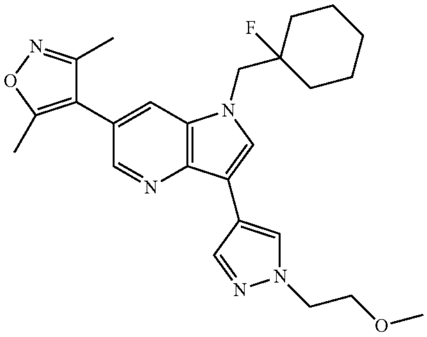 [SMILES: COCCn1cc(-c2cn(CC3(F)CCCCC3)c3cc(-c4c(C)noc4C)cnc23)cn1] | 452.3 |
| P-0239 | 4-[1-[(1-fluorocyclohexyl)methyl]-3-(1H-pyrazol-4-yl)pyrrolo[3,2-b]pyridin-6-yl]-3,5-dimethyl-isoxazole | 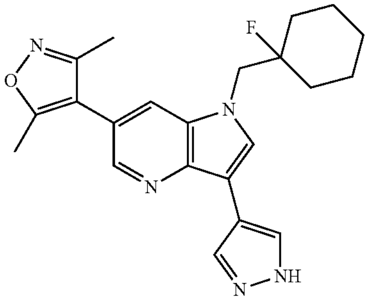 [SMILES: Cc1noc(C)c1-c1cnc2c(-c3cn[nH]c3)cn(CC3(F)CCCCC3)c2c1] | 393.9 |
| P-0241 | 4-[3-[1-(difluoromethyl)pyrazol-4-yl]-1-[(8-fluoro-1,4-dioxaspiro[4.5]decan-8-yl)methyl]pyrrolo[3,2-b]pyridin-6-yl]-3,5-dimethyl-isoxazole | 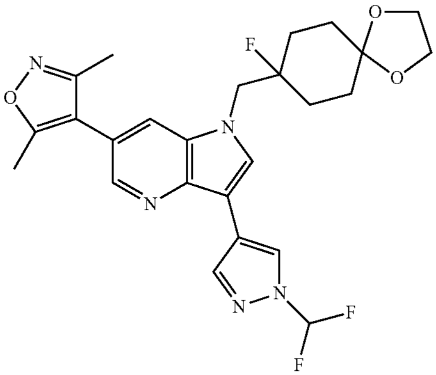 [SMILES: Cc1noc(C)c1-c1cnc2c(-c3cnn(C(F)F)c3)cn(CC3(F)CCC4(CC3)OCCO4)c2c1] | 502.3 |

Example 9

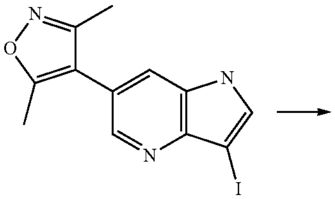

P-0072

-continued

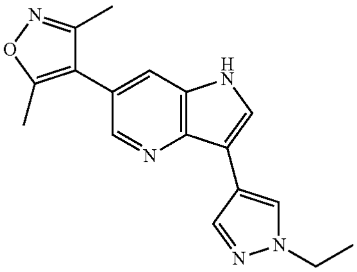

4

Preparation of 4-[3-(1-ethylpyrazol-4-yl)-1H-pyrrolo[3,2-b]pyridin-6-yl]-3,5-dimethyl-isoxazole 4

To 4-(3-iodo-1H-pyrrolo[3,2-b]pyridin-6-yl)-3,5-dimethyl-isoxazole (P-0072, 0.8 g, 2.36 mmol) in acetonitrile (12 ml), under nitrogen, were added 1-ethyl-4-(4,4,5,5-tetramethyl-1,3,2-dioxaborolan-2-yl)pyrazole (0.6 g, 2.7 mmol), [1,1'-bis(diphenylphosphino)ferrocene]dichloropalladium(II) (0.1 g, 0.131 mmol), and 1M potassium carbonate in water (5 ml). The reaction was heated under microwave at 170° C. for 10 minutes. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride to give product (4, 0.066 g, 9.1%).

Example 10

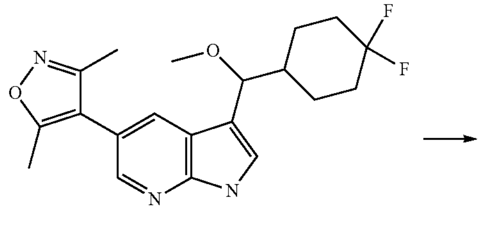

P-0073

-continued

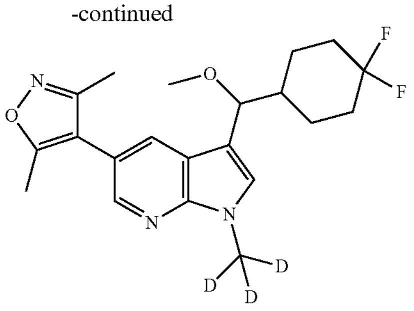

P-0080

Preparation of 4-[3-[(4,4-difluorocyclohexyl)-methoxy-methyl]-1-(trideuteriomethyl)pyrrolo[2,3-b]pyridin-5-yl]-3,5-dimethyl-isoxazole P-0080

To 4-[3-[(4,4-difluorocyclohexyl)-methoxy-methyl]-1H-pyrrolo[2,3-b]pyridin-5-yl]-3,5-dimethyl-isoxazole (P-0073, 0.03 g, 0.08 mmol) in THF (8 mL) were added sodium hydride (60% in mineral oil, 4 mg, 0.1 mmol). 10 minutes later, trideuterio(iodo)methane (0.01 g, 0.08 mmol) was added to the reaction. The reaction was stirred at room temperature overnight. The reaction was poured into water, extracted with ethyl acetate. The organic layer was washed with brine, and the organic layer was dried over sodium sulfate, concentrated, and purified with silica gel column chromatography eluting with 20% to 100% ethyl acetate in hexane to give product, which was further purified by prep-HPLC to obtain product (P-0080, 15 mg, 8.9%). MS (ESI) $[M+H^+]^+$=393.4.

TABLE 9

The following compounds were prepared as depicted in example 10, using the appropriate starting materials.

| Cmpd # | name | Structure | MH(+) |
|---|---|---|---|
| P-0088 | 4-[3-iodo-1-(trideuteriomethyl)pyrrolo[2,3-b]pyridin-5-yl]-3,5-dimethyl-isoxazole | 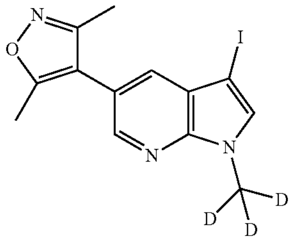 [SMILES: [2H]C([2H])([2H])n1cc(I)c2cc(-c3c(C)noc3C)cnc21] | 357.1 |
| P-0178 | 3,5-dimethyl-4-[1-(oxetan-3-yl)-3-phenylsulfanyl-pyrrolo[2,3-b]pyridin-5-yl]isoxazole | 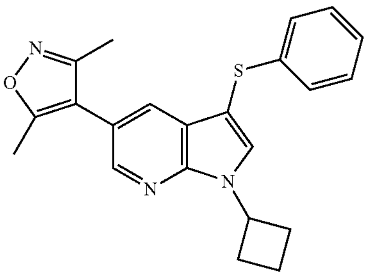 [SMILES: Cc1noc(C)c1-c1cnc2c(c1)c(Sc1ccccc1)cn2C1CCC1] | 377.9 |

TABLE 9-continued

The following compounds were prepared as depicted in example 10, using the appropriate starting materials.

| Cmpd # | name | Structure | MH(+) |
|---|---|---|---|
| P-0180 | 3,5-dimethyl-4-(3-phenylsulfanyl-1-tetrahydrofuran-3-yl-pyrrolo[2,3-b]pyridin-5-yl)isoxazole | 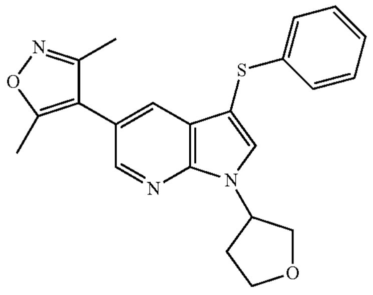 [SMILES: Cc1noc(C)c1-c1cnc2c(c1)c(Sc1ccccc1)cn2C1CCOC1] | 391.9 |
| P-0182 | 3,5-dimethyl-4-(3-phenylsulfanyl-1-tetrahydropyran-4-yl-pyrrolo[2,3-b]pyridin-5-yl)isoxazole | 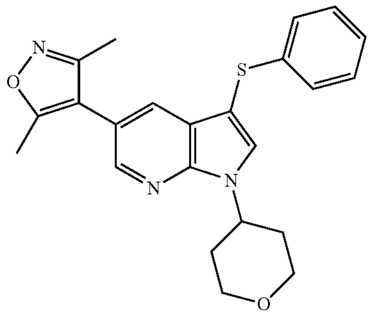 [SMILES: Cc1noc(C)c1-c1cnc2c(c1)c(Sc1ccccc1)cn2C1CCOCC1] | 405.9 |

Example 11

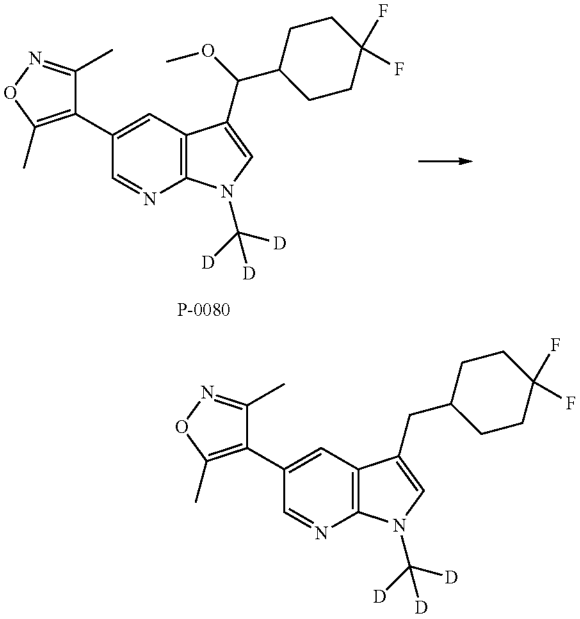

P-0080

P-0079

Preparation of 4-[3-[(4,4-difluorocyclohexyl)methyl]-1-(trideuteriomethyl)pyrrolo[2,3-b]pyridin-5-yl]-3,5-dimethyl-isoxazole P-0079

To 4-[3-[(4,4-difluorocyclohexyl)-methoxy-methyl]-1-(trideuteriomethyl)pyrrolo[2,3-b]pyridin-5-yl]-3,5-dimethyl-isoxazole (P-0080, 15 mg, 0.04 mmol in dichloroethane (10 mL), under nitrogen, were added triethylsilane (1 ml, 6.26 mmol) and trifluoroacetic acid (0.5 ml, 5.04 mmol). The reaction was stirred at 80° C. for 4 hours. The reaction was poured into aqueous potassium carbonate, extracted with ethyl acetate. The organic layer was washed with brine, and the organic layer was dried over sodium sulfate, concentrated, to give crude product, which was then further purified with prep-HPLC to give product (P-0079, 5 mg, 36.1%). MS (ESI) $[M+H^+]^+=363.4$.

TABLE 10

The following compounds were prepared as depicted in example 11, using the appropriate starting materials.

| Cmpd # | Name | Structure | MH(+) |
|---|---|---|---|
| P-0093 | 4-[[5-(3,5-dimethylisoxazol-4-yl)-1H-pyrrolo[2,3-b]pyridin-3-yl]methylene]thiane 1-oxide | 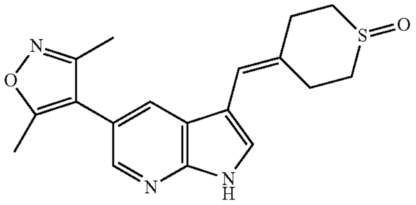 [SMILES: Cc1noc(C)c1-c1cnc2[nH]cc(C=C3CCS(=O)CC3)c2c1] | 342.1 |
| P-0096 | 4-[[1-(benzenesulfonyl)-5-(3,5-dimethylisoxazol-4-yl)pyrrolo[2,3-b]pyridin-3-yl]methyl]thiane 1,1-dioxide | 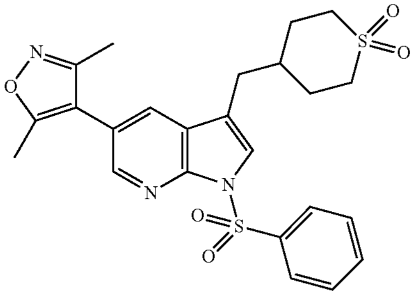 [SMILES: Cc1noc(C)c1-c1cnc2c(c1)c(CC1CCS(=O)(=O)CC1)cn2S(=O)(=O)c1ccccc1] | 499.9 |
| P-0097 | 4-[[1-(benzenesulfonyl)-5-(3,5-dimethylisoxazol-4-yl)pyrrolo[2,3-b]pyridin-3-yl]methylene]thiane 1,1-dioxide | 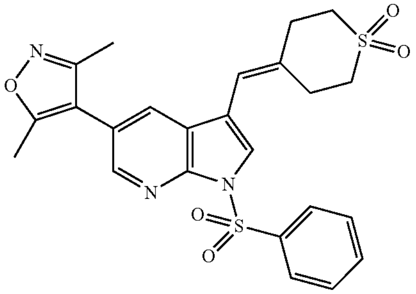 [SMILES: Cc1noc(C)c1-c1cnc2c(c1)c(C=C1CCS(=O)(=O)CC1)cn2S(=O)(=O)c1ccccc1] | 497.9 |
| P-0092 | benzyl 4-[[5-(3,5-dimethylisoxazol-4-yl)-1-(trideuteriomethyl)pyrrolo[2,3-b]pyridin-3-yl]methyl]piperidine-1-carboxylate | 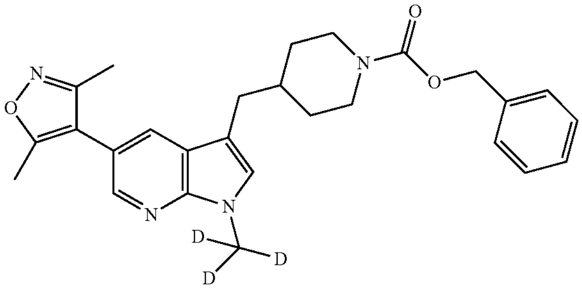 [SMILES: [2H]C([2H])([2H])n1cc(CC2CCN(C(=O)OCc3ccccc3)CC2)c2cc(-c3c(C)noc3C)cnc21] | 462.5 |

Example 12

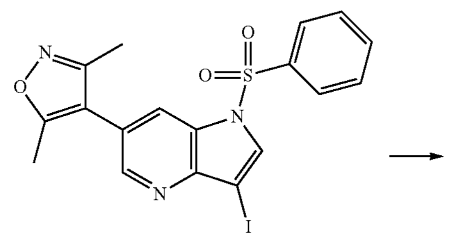

P-0076

-continued

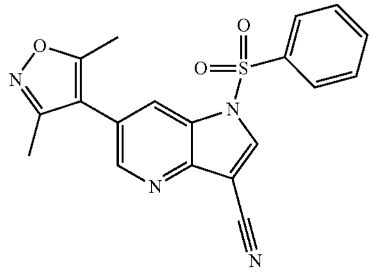

P-0081

+

-continued

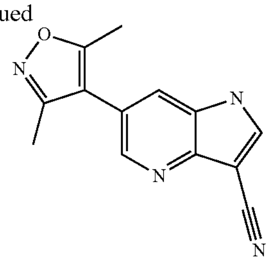

P-0082

-continued

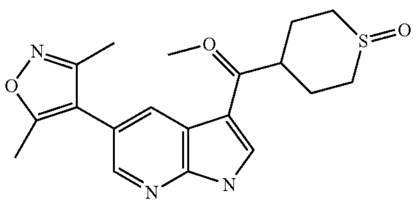

6

Preparation of 1-(benzenesulfonyl)-6-(3,5-dimethylisoxazol-4-yl)pyrrolo[3,2-b]pyridine-3-carbonitrile P-0081 and 6-(3,5-dimethylisoxazol-4-yl)-1H-pyrrolo[3,2-b]pyridine-3-carbonitrile P-0082

To 4-[1-(benzenesulfonyl)-3-iodo-pyrrolo[3,2-b]pyridin-6-yl]-3,5-dimethyl-isoxazole (P-0076, 105 mg, 0.22 mmol) were added Tris(dibenzylideneacetone)dipalladium (0) (5 mg, 0.005 mmol), 1,1'-Bis(diphenylphosphino)ferrocene (5 mg, 0.01 mmol), Zinc (5 mg, 0.076 mmol), Zinc cyanide (30 mg, 0.255 mmol), and N,N-Dimethylacetamide (10 ml). The reaction mixture filled with nitrogen. The reaction was heated to 120° C. overnight. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0081, 0.0199 g, 24.0%), MS (ESI) $[M+H^+]^+=379.0$; and product (P-0082, 17.5 mg, 33.5%), MS (ESI) $[M+H^+]^+=239.0$.

Example 13

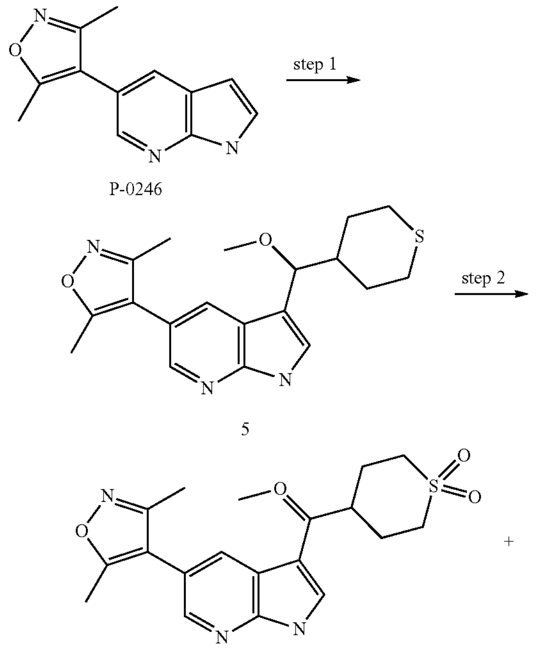

P-0246

5

P-0089

Step 1—Preparation of 4-[3-[methoxy(tetrahydrothiopyran-4-yl)methyl]-1H-pyrrolo[2,3-b]pyridin-5-yl]-3,5-dimethyl-isoxazole 5: To 3,5-dimethyl-4-(1H-pyrrolo[2,3-b]pyridin-5-yl)isoxazole (P-0246, 0.2 g, 0.94 mmol) in methanol (10 mL) were added tetrahydrothiopyran-4-carbaldehyde (0.15 g, 1.13 mmol) and potassium hydroxide (0.3 g, 0.01 mol). The reaction was stirred at room temperature overnight. The reaction was worked up by pouring into water, and extracted with ethyl acetate and in brine. The organic layer was dried over anhydrous sodium sulfate, and filtered. The filtrate was concentrated and purified with silica gel column chromatography eluting with 5% to 100% ethyl acetate in hexane to give product (5, 0.1 g, 30%).

Step 2—Preparation of 4-[[5-(3,5-dimethylisoxazol-4-yl)-1H-pyrrolo[2,3-b]pyridin-3-yl]-methoxy-methyl]thiane 1,1-dioxide P-0089 and 4-[[5-(3,5-dimethylisoxazol-4-yl)-1H-pyrrolo[2,3-b]pyridin-3-yl]-methoxy-methyl]thiane 1-oxide (6): To 4-[3-[methoxy(tetrahydrothiopyran-4-yl)methyl]-1H-pyrrolo[2,3-b]pyridin-5-yl]-3,5-dimethyl-isoxazole (5, 0.1 g, 0.28 mmol) in methylene chloride (10 ml) was added 3-chlorobenzenecarboperoxoic acid (77%, 0.1 g, 0.45 mmol) at room temperature. The reaction was stirred at room temperature for 4 hours. The reaction was concentrated, poured into aqueous potassium carbonate, and extracted with ethyl acetate and in brine. The organic layer was dried over anhydrous sodium sulfate, and filtered. The filtrate was concentrated and purified with silica gel column chromatography eluting with 5% to 100% ethyl acetate in hexane to give product (P-0089, 16 mg, 14.7%), MS (ESI) $[M+H^+]^+=390.2$; and product (6, 20 mg, 19.1%).

Example 14

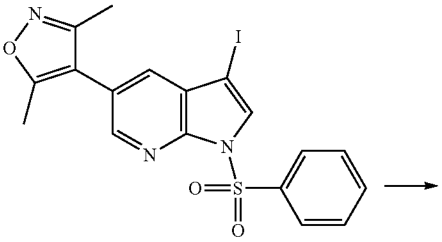

P-0087

-continued

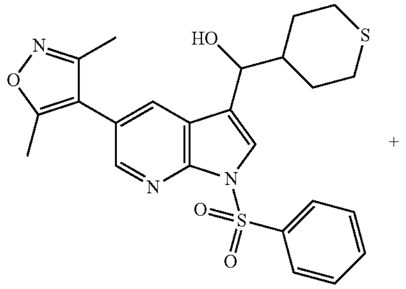

P-0090

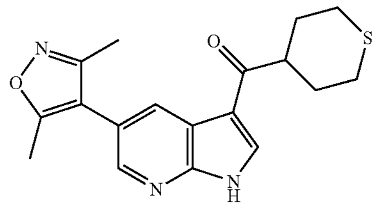

P-0091

Preparation of [1-(benzenesulfonyl)-5-(3,5-dimethylisoxazol-4-yl)pyrrolo[2,3-b]pyridin-3-yl]-tetrahydrothiopyran-4-yl-methanol P-0090 and [6-(3,5-dimethylisoxazol-4-yl)-1H-pyrrolo[3,2-b]pyridin-3-yl]-tetrahydrothiopyran-4-yl-methanone P-0091

To a solution of 4-[1-(benzenesulfonyl)-3-iodo-pyrrolo[2,3-b]pyridin-5-yl]-3,5-dimethyl-isoxazole (P-0087, 0.7 g, 1.46 mmol) in tetrahydrofuran (8.0 mL) at −50° C. under nitrogen was added 2M isopropylmagnesium chloride (0.8 ml) slowly. The reaction was allowed to warm to 5° C. in 70 minutes. Then, the reaction was cooled to −45° C., followed by adding tetrahydrothiopyran-4-carbaldehyde (0.21 g, 1.61 mmol). The reaction was allowed to warm to room temperature overnight. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0090, 0.33 g, 46.7%), MS (ESI) $[M+H^+]^+$=483.9; and product (P-0091, 3.5 mg, 0.5%), MS (ESI) $[M+H^+]^+$=341.8.

TABLE 11

The following compounds were prepared as depicted in example 14, using the appropriate starting materials.

| Cmpd # | Name | Structure | MH(+) |
|---|---|---|---|
| P-0101 | (4,4-difluorocyclohexyl)-[5-(3,5-dimethylisoxazol-4-yl)-1-methyl-pyrrolo[2,3-b]pyridin-3-yl]methanol | 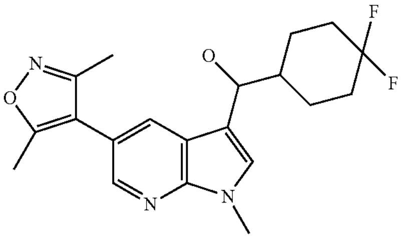 [SMILES: Cc1noc(C)c1-c1cnc2c(c1)c(C(O)C1CCC(F)(F)CC1)cn2C] | 376.1 |

Example 15

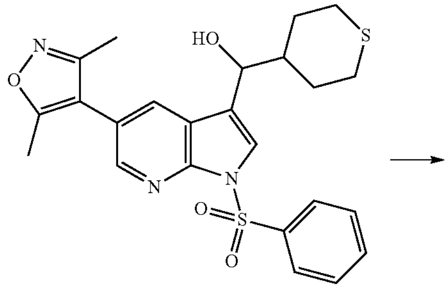

P-0090

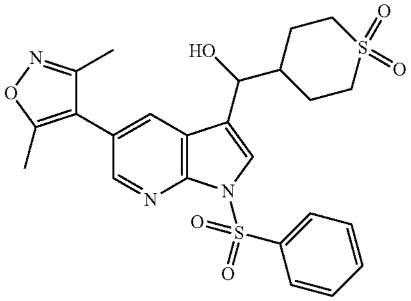

P-0094

Preparation of—[1-(benzenesulfonyl)-5-(3,5-dimethylisoxazol-4-yl)pyrrolo[2,3-b]pyridin-3-yl]-(1,1-dioxothian-4-yl)methanol P-0094

To [1-(benzenesulfonyl)-5-(3,5-dimethylisoxazol-4-yl)pyrrolo[2,3-b]pyridin-3-yl]-tetrahydrothiopyran-4-yl-methanol (P-0090, 0.32 g, 0.66 mmol) in methylene chloride (20 ml) was added 3-chlorobenzenecarboperoxoic acid (77%, 0.3 g, 1.32 mmol) at −40° C. The reaction was allowed to warm to room temperature for overnight. The reaction was concentrated, poured into aqueous potassium carbonate, and extracted with ethyl acetate and in brine. The organic layer was dried over anhydrous sodium sulfate, and filtered. The filtrate was concentrated and purified with silica gel column chromatography eluting with 5% to 100% ethyl acetate in hexane to give product (P-0094, 0.270 g, 79.4%). MS (ESI) $[M+H^+]^+$=515.9.

TABLE 12

The following compounds were prepared as depicted in example 15, using the appropriate starting materials.

| Cmpd # | name | Structure | MH(+) |
|---|---|---|---|
| P-0179 | 4-[3-(benzenesulfonyl)-1-(oxetan-3-yl)pyrrolo[2,3-b]pyridin-5-yl]-3,5-dimethyl-isoxazole | 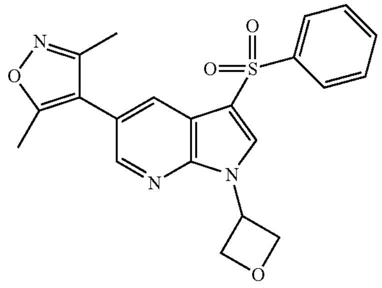 [SMILES: Cc1noc(C)c1-c1cnc2c(c1)c(S(=O)(=O)c1ccccc1)cn2C1COC1] | 410.0 |
| P-0181 | 4-[3-(benzenesulfonyl)-1-tetrahydrofuran-3-yl-pyrrolo[2,3-b]pyridin-5-yl]-3,5-dimethyl-isoxazole | 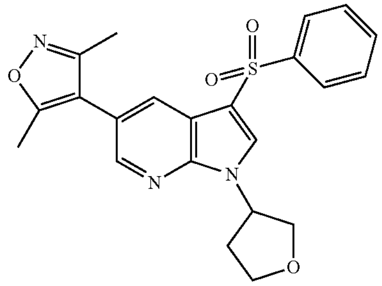 [SMILES: Cc1noc(C)c1-c1cnc2c(c1)c(S(=O)(=O)c1ccccc1)cn2C1CCOC1] | 423.9 |
| P-0183 | 4-[3-(benzenesulfonyl)-1-tetrahydropyran-4-yl-pyrrolo[2,3-b]pyridin-5-yl]-3,5-dimethyl-isoxazole | 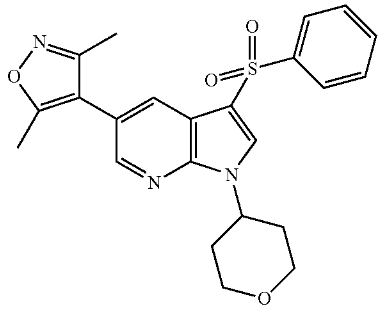 [SMILES: Cc1noc(C)c1-c1cnc2c(c1)c(S(=O)(=O)c1ccccc1)cn2C1CCOCC1] | 438.0 |
| P-0185 | 4-[3-(benzenesulfonyl)-1-(1-methylpyrazol-4-yl)pyrrolo[2,3-b]pyridin-5-yl]-3,5-dimethyl-isoxazole | 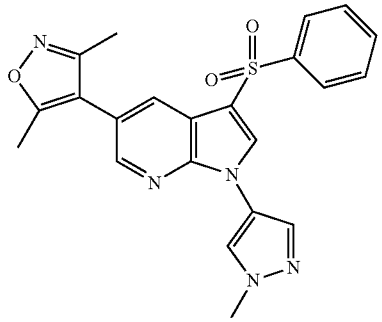 [SMILES: Cc1noc(C)c1-c1cnc2c(c1)c(S(=O)(=O)c1ccccc1)cn2-c1cnn(C)c1] | 434.2 |

Example 16

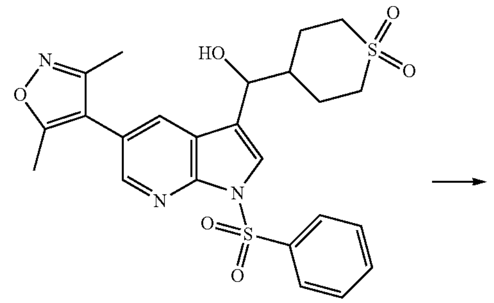

P-0094

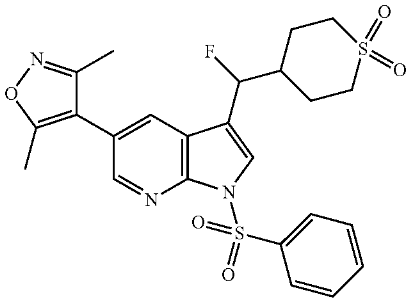

P-0095

Preparation of—4-[[1-(benzenesulfonyl)-5-(3,5-dimethylisoxazol-4-yl)pyrrolo[2,3-b]pyridin-3-yl]-fluoro-methyl]thiane 1,1-dioxide P-0095

To a solution of [1-(benzenesulfonyl)-5-(3,5-dimethylisoxazol-4-yl)pyrrolo[2,3-b]pyridin-3-yl]-(1,1-dioxothian-4-yl)methanol (P-0094, 0.07 g, 0.14 mmol) in dichloromethane (10 mL) was added 2-methoxy-N-(2-methoxyethyl)-N-(trifluoro-1{4}-sulfanyl)ethanamine (0.08 ml, 0.45 mmol) at −50° C. The reaction was allowed to room temperature for 1 hour. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 2% to 20% methanol in methylene chloride to give product (P-0095, 0.05 g, 71.2%). MS (ESI) $[M+H^+]^+$=517.9.

TABLE 13

The following compounds were prepared as depicted in example 16, using the appropriate starting materials.

| Cmpd | name | Structure | MH(+) |
|---|---|---|---|
| P-0187 | 4-[1-(2-fluoro-1-phenyl-ethyl)-3-(1-methylpyrazol-4-yl)pyrrolo[3,2-b]pyridin-6-yl]-3,5-dimethyl-isoxazole | 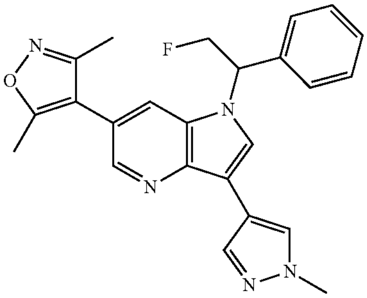 [SMILES: Cc1noc(C)c1-c1cnc2c(-c3cnn(C)c3)cn(C(CF)c3ccccc3)c2c1] | 416.5 |
| P-0233 | 4-[1-(2,2-dideuterio-2-fluoro-1-phenyl-ethyl)-3-(1-methylpyrazol-4-yl)pyrrolo[3,2-b]pyridin-6-yl]-3,5-dimethyl-isoxazole | 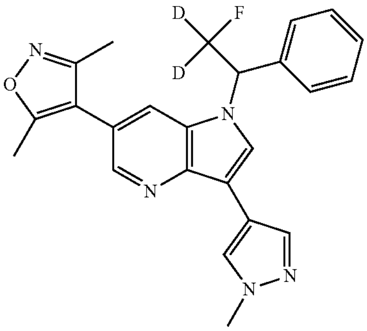 [SMILES: [2H]C([2H])(F)C(c1ccccc1)n1cc(-c2cnn(C)c2)c2ncc(-c3c(C)noc3C)cc21] | 417.9 |

Example 17

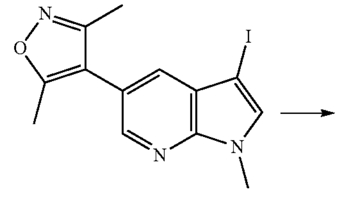

7

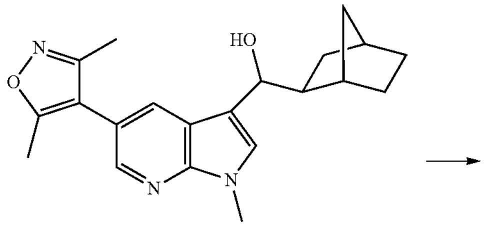

8

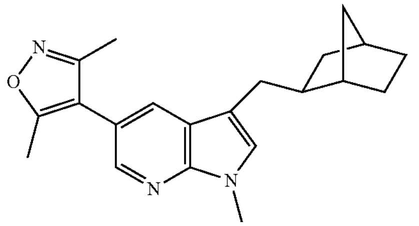

P-0100

Step 1—Preparation of [5-(3,5-dimethylisoxazol-4-yl)-1-methyl-pyrrolo[2,3-b]pyridin-3-yl]-norbornan-2-yl-methanol 8: To a solution of 4-(3-iodo-1-methyl-pyrrolo[2,3-b]pyridin-5-yl)-3,5-dimethyl-isoxazole (7, 0.4 g, 1.13 mmol) in tetrahydrofuran (5 ml) at −50° C. under nitrogen was added 2M isopropylmagnesium chloride (0.64 ml) slowly. The reaction was allowed to warm to 5° C. in 70 minutes. Then, the reaction was cooled to −45° C., followed by adding norbornane-2-carbaldehyde (0.11 g, 0.91 mmol). The reaction was allowed to warm to room temperature for 1 hour. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (8, 0.172 g, 43.4%)

Step 2—Preparation of 3,5-dimethyl-4-[1-methyl-3-(norbornan-2-ylmethyl)pyrrolo[2,3-b]pyridin-5-yl]isoxazole P-0100: To [5-(3,5-dimethylisoxazol-4-yl)-1-methyl-pyrrolo[2,3-b]pyridin-3-yl]-norbornan-2-yl-methanol (8, 172.8 mg, 0.49 mmol) in dichloroethane (20 mL), under nitrogen, were added triethylsilane (1 ml, 6.26 mmol) and trifluoroacetic acid (0.5 ml, 5.04 mmol). The reaction was stirred at room temperature overnight. The reaction was poured into aqueous potassium carbonate, extracted with ethyl acetate. The organic layer was washed with brine, and the organic layer was dried over sodium sulfate, concentrated, to give crude product, which was then further purified with prep-HPLC to give pure product (P-0100, 2.4 mg, 1.4%) as a white solid. MS (ESI) $[M+H^+]^+$=336.4.

Example 18

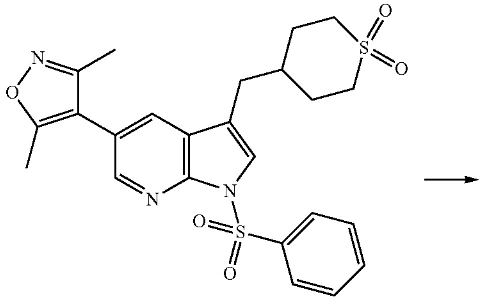

P-0096

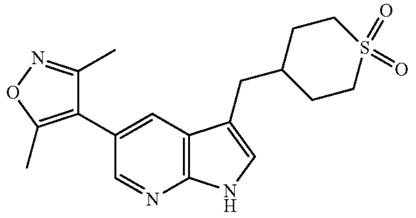

P-0098

Preparation of 4-[[5-(3,5-dimethylisoxazol-4-yl)-1H-pyrrolo[2,3-b]pyridin-3-yl]methyl]thiane 1,1-dioxide P-0098

To 4-[[1-(benzenesulfonyl)-5-(3,5-dimethylisoxazol-4-yl)pyrrolo[2,3-b]pyridin-3-yl]methyl]thiane 1,1-dioxide (P-0096, 0.05 g, 0.1 mmol) in methanol (10 ml) was added potassium hydroxide (0.33 g, 5.94 mmol) at room temperature. The reaction was stirred at temperature overnight. The reaction was poured into water, and extracted with ethyl acetate. The organic layer was washed with brine, dried over sodium sulfate, and filtered. The filtrate was concentrated and purified with silica gel column chromatography eluting with 20% to 100% ethyl acetate in hexane to give product (P-0098, 6.9 mg, 19.2%). MS (ESI) $[M+H^+]^+$=360.4.

TABLE 14

The following compounds were prepared as depicted in example 18, using the appropriate starting materials.

| Cmpd | name | Structure | MH(+) |
|---|---|---|---|
| P-0099 | 4-[[5-(3,5-dimethylisoxazol-4-yl)-1H-pyrrolo[2,3-b]pyridin-3-yl]methylene]thiane 1,1-dioxide | 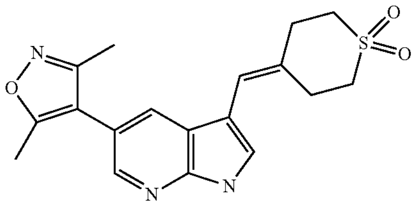 [SMILES: Cc1noc(C)c1-c1cnc2[nH]cc(C=C3CCS(=O)(=O)CC3)c2c1] | 357.8 |

Example 19

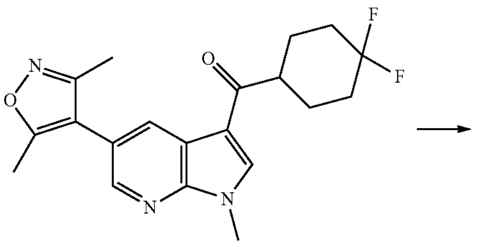

9

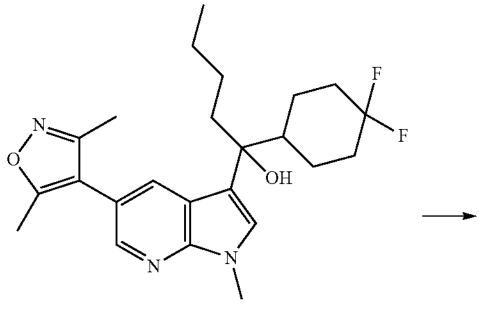

P-0108

-continued

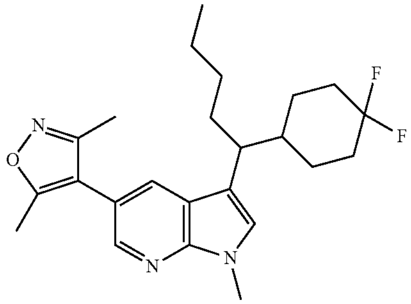

P-0109

Step 1—Preparation of 1-(4,4-difluorocyclohexyl)-1-[5-(3,5-dimethylisoxazol-4-yl)-1-methyl-pyrrolo[2,3-b]pyridin-3-yl]pentan-1-ol P-0108: To (4,4-difluorocyclohexyl)-

[5-(3,5-dimethylisoxazol-4-yl)-1-methyl-pyrrolo[2,3-b]pyridin-3-yl]methanone (9, 0.2 g, 0.54 mmol) in THF (10 mL) under an atmosphere of nitrogen at −78° C., was added 1.6M butyllithium in THF (0.37 ml). The reaction was stirred at −78° C. for 1 hour. The reaction was poured into water, extracted with ethyl acetate. The organic layer was washed with brine, and the organic layer was dried over sodium sulfate, concentrated, and purified with silica gel column chromatography eluting with 20% to 100% ethyl acetate in hexane to give product (P-0108, 0.15 g, 64.9%). MS (ESI) $[M+H^+]^+=432.0$.

Step 2—Preparation of 4-[3-[1-(4,4-difluorocyclohexyl)pentyl]-1-methyl-pyrrolo[2,3-b]pyridin-5-yl]-3,5-dimethyl-isoxazole P-0109: To 1-(4,4-difluorocyclohexyl)-1-[5-(3,5-dimethylisoxazol-4-yl)-1-methyl-pyrrolo[2,3-b]pyridin-3-yl]pentan-1-ol (P-0108, 80 mg, 0.19 mmol) in dichloroethane (15 mL), under air, were added triethylsilane (1 ml, 6.26 mmol) and trifluoroacetic acid (0.7 ml, 7.06 mmol). The reaction was stirred at 80° C. for 4 hours. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0109, 0.0323 g, 41.9%).

TABLE 15

The following compounds were prepared as depicted in exmaple 19, using the appropriate starting materials.

| Cmpd | name | Structure | MH(+) |
|---|---|---|---|
| P-0118 | 4-[3-[1-(4,4-difluorocyclohexyl)propyl]-1-methyl-pyrrolo[2,3-b]pyridin-5-yl]-3,5-dimethyl-isoxazole | 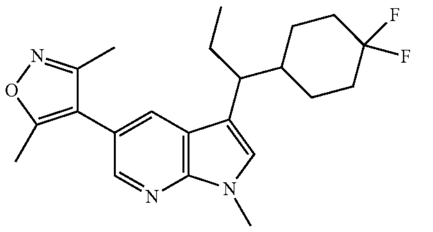 [SMILES: CCC(c1cn(C)c2ncc(-c3c(C)noc3C)cc12)C1CCC(F)(F)CC1] | 388.3 |

Example 20

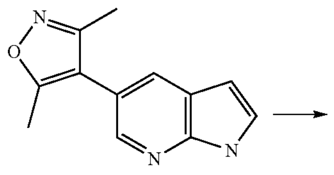

P-0246

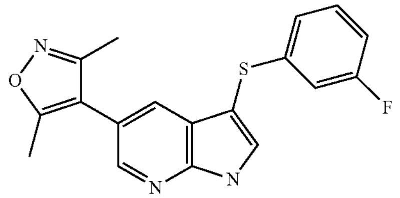

P-0141

Preparation of 4-[3-(3-fluorophenyl)sulfanyl-1H-pyrrolo[2,3-b]pyridin-5-yl]-3,5-dimethyl-isoxazole P-0141

To 3,5-dimethyl-4-(1H-pyrrolo[2,3-b]pyridin-5-yl)isoxazole (P-0246, 0.3 g, 1.41 mmol) in dimethylformamide ("DMF") (5 ml), under nitrogen, was added sodium hydride (60% in mineral oil, 0.2 g, 5 mmol) at room temperature. After 10 minutes, 1-fluoro-3-[(3-fluorophenyl)disulfanyl]benzene (0.4 ml, 1.43 mmol) was added. The reaction was stirred overnight. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0141, 0.21 g, 44.0%). MS (ESI) $[M+H^+]^+=339.8$.

TABLE 16

The following compounds were prepared as depicted in example 20, using the appropriate starting materials.

| Cmpd | name | Structure | MH(+) |
|---|---|---|---|
| P-0144 | 3,5-dimethyl-4-(3-phenylsulfanyl-1H-pyrrolo[2,3-b]pyridin-5-yl)isoxazole | 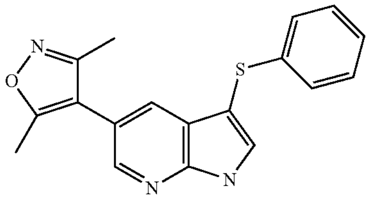 [SMILES: Cc1noc(C)c1-c1cnc2[nH]cc(Sc3ccccc3)c2c1] | 322.1 |

Example 21

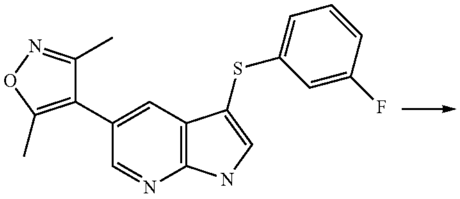

P-0141

-continued

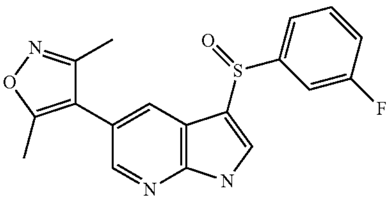

P-0142

+

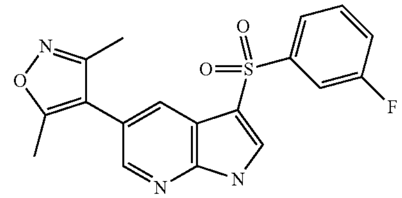

P-0143

Preparation of 4-[3-(3-fluorophenyl)sulfinyl-1H-pyrrolo[2,3-b]pyridin-5-yl]-3,5-dimethyl-isoxazole P-0142 and 4-[3-(3-fluorophenyl)sulfonyl-1H-pyrrolo[2,3-b]pyridin-5-yl]-3,5-dimethyl-isoxazole P-0143

To 4-[3-(3-fluorophenyl)sulfanyl-1H-pyrrolo[2,3-b]pyridin-5-yl]-3,5-dimethyl-isoxazole (P-0141, 0.11 g, 0.32 mmol) in methylene chloride (5 ml), at −30° C., was added 3-chlorobenzenecarboperoxoic acid (77%, 0.12 ml, 0.49 mmol). The reaction was allowed to warm to room temperature in 1 hour. The reaction mixture was purified directly with silica gel column chromatography eluting with 20% to 100% ethyl acetate in hexane to give product (P-0142, 10.3 mg, 8.9%), MS (ESI) $[M+H^+]^+=356.1$; and product (P-0143, 31.4 mg, 26.1%), MS (ESI) $[M+H^+]^+=371.9$.

TABLE 17

| The following compounds were prepared as depicted in example 21, using the appropriate starting materials. | | | |
|---|---|---|---|
| Cmpd | name | Structure | MH(+) |
| P-0145 | 4-[3-(benzenesulfonyl)-1H-pyrrolo[2,3-b]pyridin-5-yl]-3,5-dimethyl-isoxazole | 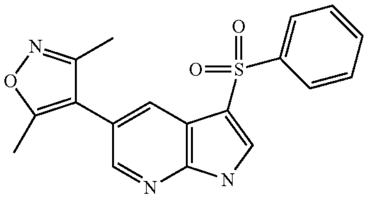 [SMILES: Cc1noc(C)c1-c1cnc2[nH]cc(S(=O)(=O)c3ccccc3)c2c1] | 354 |

Example 22

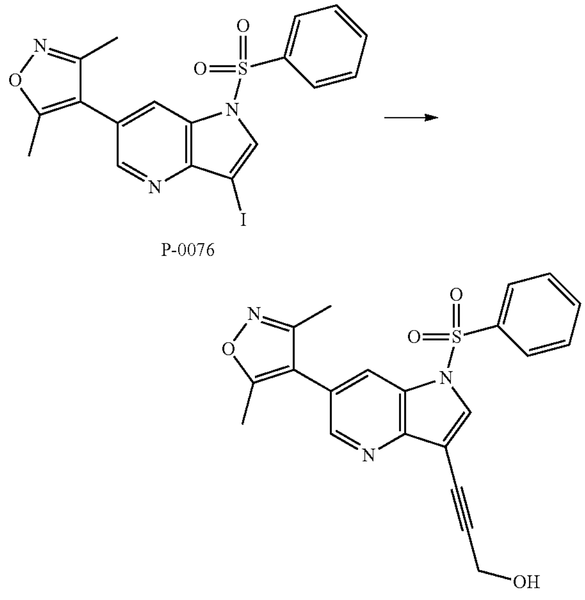

P-0076

P-0155

Preparation of—3-[1-(benzenesulfonyl)-6-(3,5-dimethylisoxazol-4-yl)pyrrolo[3,2-b]pyridin-3-yl]prop-2-yn-1-ol P-0155

To 4-[1-(benzenesulfonyl)-3-iodo-pyrrolo[3,2-b]pyridin-6-yl]-3,5-dimethyl-isoxazole (P-0076, 200 mg, 0.42 mmol) in diethylamine (8 ml) were added propargyl alcohol (0.21 ml, 3.57 mmol), copper(I) iodide (10 mg, 0.05 mmol), palladium(II) acetate (10 mg, 0.04 mmol), and triphenylphosphine (25 mg, 0.1 mmol). The reaction mixture was filled with nitrogen, and heated to 60° C. for 3 hours. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0155, 80 mg, 47.1%). MS (ESI) $[M+H^+]^+$=408.4.

TABLE 18

| The following compounds were prepared as depicted in example 22, using the appropriate starting materials. | | | |
|---|---|---|---|
| Cmpd | name | Structure | MH(+) |
| P-0156 | 3-[1-cyclopentylsulfonyl-6-(3,5-dimethylisoxazol-4-yl)pyrrolo[3,2-b]pyridin-3-yl]prop-2-yn-1-ol | 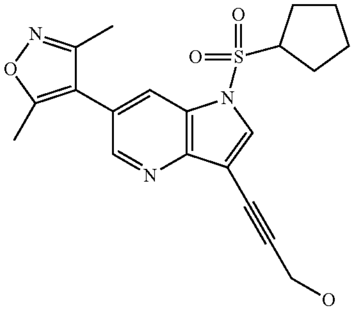 | 400.3 |

Example 23

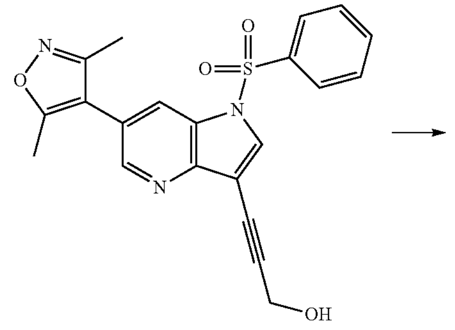

P-0155

-continued

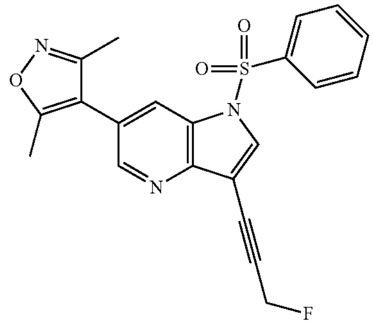

P-0157

Preparation of 3-[1-(benzenesulfonyl)-6-(3,5-dimethylisoxazol-4-yl)pyrrolo[3,2-b]pyridin-3-yl]prop-2-yn-1-ol P-0157

To a solution of 3-[1-(benzenesulfonyl)-6-(3,5-dimethylisoxazol-4-yl)pyrrolo[3,2-b]pyridin-3-yl]prop-2-yn-1-ol (P-0155, 0.06 g, 0.15 mmol) in dichloromethane (10 mL) was added 2-methoxy-N-(2-methoxyethyl)-N-(trifluoro-1{4}-sulfanyl)ethanamine (0.06 ml, 0.31 mmol) at −50° C. The reaction was allowed to warm to room temperature for 1 hour. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 10% to 100% ethyl acetate in hexane, and then further purified with prep-HPLC to give product (P-0157, 1.3 mg, 2.2%). MS (ESI) $[M+H^+]^+$=410.2.

TABLE 19

The following compounds were prepared as depicted in example 23, using the appropriate starting materials.

| Cmpd | name | Structure | MH(+) |
|---|---|---|---|
| P-0158 | 4-[1-cyclopentylsulfonyl-3-(3-fluoroprop-1-ynyl)pyrrolo[3,2-b]pyridin-6-yl]-3,5-dimethyl-isoxazole | 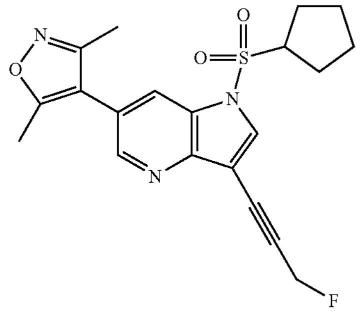 [SMILES: Cc1noc(C)c1-c1cnc2c(C#CCF)cn(S(=O)(=O)C3CCCC3)c2c1] | 402.3 |

Example 24

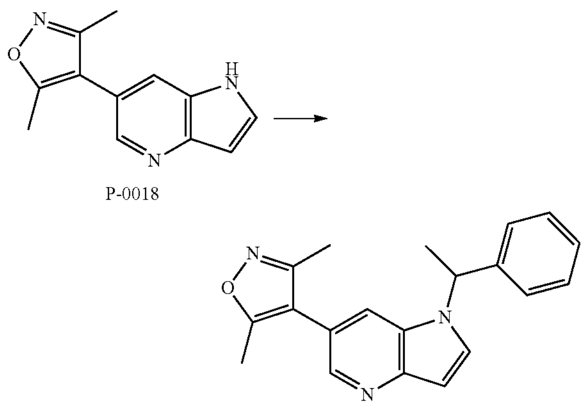

P-0018

P-0159

Preparation of 3,5-dimethyl-4-[1-(1-phenylethyl)pyrrolo[3,2-b]pyridin-6-yl]isoxazole P-0159

To 3,5-dimethyl-4-(1H-pyrrolo[3,2-b]pyridin-6-yl)isoxazole (P-0018, 0.05 g, 0.23 mmol) in DMF (5 ml), was added sodium hydride (60%, 0.01 g, 0.27 mmol) at room temperature. After 10 minutes, 1-chloroethylbenzene (0.11 ml, 0.71 mmol) was added. The reaction was stirred at room temperature for 2 hours. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0159, 16.2 mg, 21.8%). MS (ESI) $[M+H^+]^+$=318.3.

TABLE 20

The following compounds were prepared as depicted in example 24, using the appropriate starting materials.

| Cmpd | Name | Structure | MH(+) |
|---|---|---|---|
| P-0160 | 4-[3-(1-allylpyrazol-4-yl)-1-benzyl-pyrrolo[3,2-b]pyridin-6-yl]-3,5-dimethyl-isoxazole | 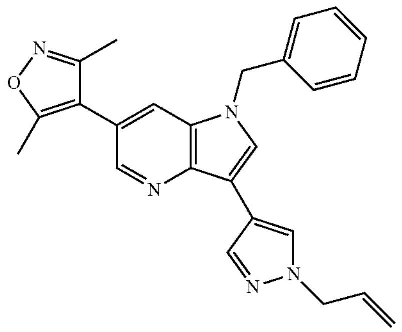 [SMILES: C=CCn1cc(-c2cn(Cc3ccccc3)c3cc(-c4c(C)noc4C)cnc23)cn1] | 411.0 |
| P-0161 | 3,5-dimethyl-4-[3-(1-methylpyrazol-4-yl)-1-(1-phenylethyl)pyrrolo[3,2-b]pyridin-6-yl]isoxazole | 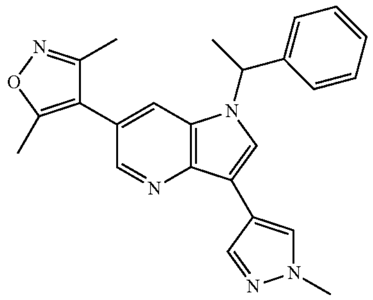 [SMILES: Cc1noc(C)c1-c1cnc2c(-c3cnn(C)c3)cn(C(C)c3ccccc3)c2c1] | 398.1 |
| P-0162 | 4-(1-benzylpyrrolo[3,2-b]pyridin-6-yl)-3,5-dimethyl-isoxazole | 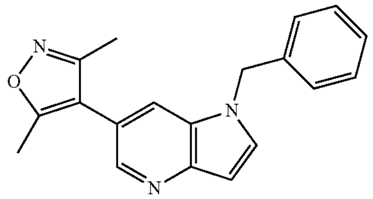 [SMILES: Cc1noc(C)c1-c1cnc2ccn(Cc3ccccc3)c2c1] | 304.4 |
| P-0171 | 3,5-dimethyl-4-[3-(1-methylpyrazol-4-yl)-1-(thiazol-4-ylmethyl)pyrrolo[3,2-b]pyridin-6-yl]isoxazole | 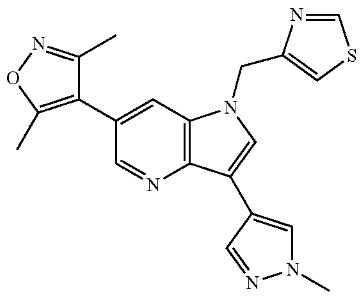 [SMILES: Cc1noc(C)c1-c1cnc2c(-c3cnn(C)c3)cn(Cc3cscn3)c2c1] | 391.2 |

TABLE 20-continued

The following compounds were prepared as depicted in example 24, using the appropriate starting materials.

| Cmpd | Name | Structure | MH(+) |
|---|---|---|---|
| P-0172 | 4-[1-[(2-fluorophenyl)methyl]-3-(1-methylpyrazol-4-yl)pyrrolo[3,2-b]pyridin-6-yl]-3,5-dimethyl-isoxazole | 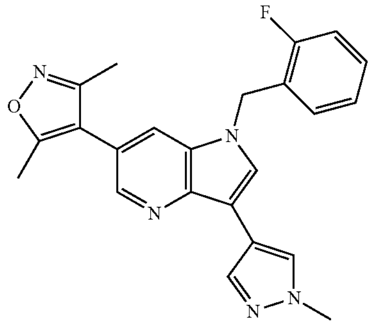 [SMILES: Cc1noc(C)c1-c1cnc2c(-c3cnn(C)c3)cn(Cc3ccccc3F)c2c1] | 402.6 |
| P-0173 | 4-[1-[(2,6-difluorophenyl)methyl]-3-(1-methylpyrazol-4-yl)pyrrolo[3,2-b]pyridin-6-yl]-3,5-dimethyl-isoxazole | 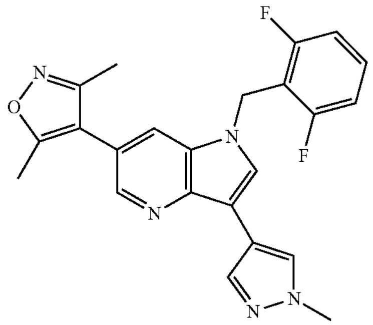 [SMILES: Cc1noc(C)c1-c1cnc2c(-c3cnn(C)c3)cn(Cc3c(F)cccc3F)c2c1] | 420.6 |
| P-0176 | 4-[3-[1-(difluoromethyl)pyrazol-4-yl]-1-[(2-fluorophenyl)methyl]pyrrolo[3,2-b]pyridin-6-yl]-3,5-dimethyl-isoxazole | 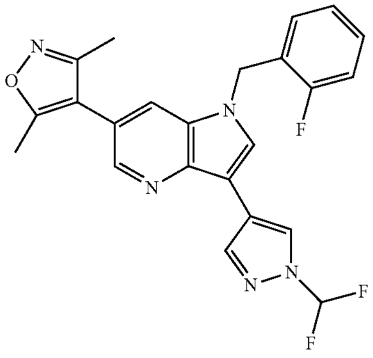 [SMILES: Cc1noc(C)c1-c1cnc2c(-c3cnn(C(F)F)c3)cn(Cc3ccccc3F)c2c1] | 438.0 |
| P-0177 | 4-[3-[1-(difluoromethyl)pyrazol-4-yl]-1-(1-phenylethyl)pyrrolo[3,2-b]pyridin-6-yl]-3,5-dimethyl-isoxazole | 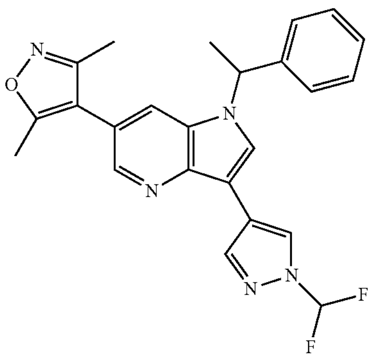 [SMILES: Cc1noc(C)c1-c1cnc2c(-c3cnn(C(F)F)c3)cn(C(C)c3ccccc3)c2c1] | 434.7 |

TABLE 20-continued

The following compounds were prepared as depicted in example 24, using the appropriate starting materials.

| Cmpd | Name | Structure | MH(+) |
| --- | --- | --- | --- |
| P-0186 | ethyl 2-[6-(3,5-dimethylisoxazol-4-yl)-3-(1-methylpyrazol-4-yl)pyrrolo[3,2-b]pyridin-1-yl]-2-phenyl-acetate | 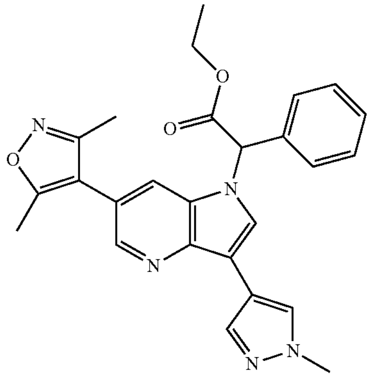 [SMILES: CCOC(=O)C(c1ccccc1)n1cc(-c2cnn(C)c2)c2ncc(-c3c(C)noc3C)cc21] | 456.8 |
| P-0188 | 3,5-dimethyl-4-[3-(1-methylpyrazol-4-yl)-1-[[2-(trifluoromethyl)phenyl]methyl]pyrrolo[3,2-b]pyridin-6-yl]isoxazole | 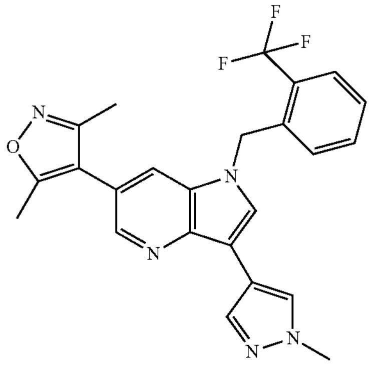 [SMILES: Cc1noc(C)c1-c1cnc2c(-c3cnn(C)c3)cn(Cc3ccccc3C(F)(F)F)c2c1] | 452.4 |
| P-0189 | 4-[1-[(2,6-dichlorophenyl)methyl]-3-(1-methylpyrazol-4-yl)pyrrolo[3,2-b]pyridin-6-yl]-3,5-dimethyl-isoxazole | 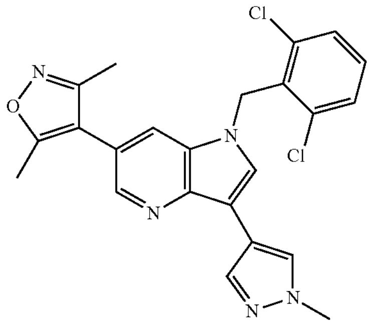 [SMILES: Cc1noc(C)c1-c1cnc2c(-c3cnn(C)c3)cn(Cc3c(Cl)cccc3Cl)c2c1] | 453.3 |
| P-0190 | 4-[1-[(2-chloro-5-fluoro-phenyl)methyl]-3-(1-methylpyrazol-4-yl)pyrrolo[3,2-b]pyridin-6-yl]-3,5-dimethyl-isoxazole | 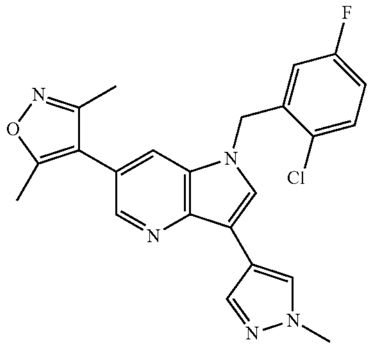 [SMILES: Cc1noc(C)c1-c1cnc2c(-c3cnn(C)c3)cn(Cc3cc(F)ccc3Cl)c2c1] | 436.8 |

TABLE 20-continued

The following compounds were prepared as depicted in example 24, using the appropriate starting materials.

| Cmpd | Name | Structure | MH(+) |
|---|---|---|---|
| P-0193 | 4-[1-[(2-chlorophenyl)methyl]-3-(1-methylpyrazol-4-yl)pyrrolo[3,2-b]pyridin-6-yl]-3,5-dimethyl-isoxazole | 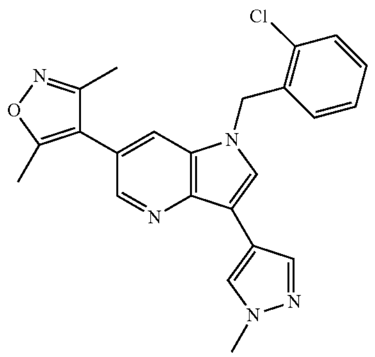 [SMILES: Cc1noc(C)c1-c1cnc2c(-c3cnn(C)c3)cn(Cc3ccccc3Cl)c2c1] | 418.2 |
| P-0194 | 3,5-dimethyl-4-[3-(1-methylpyrazol-4-yl)-1-[[2-(trifluoromethoxy)phenyl]methyl]pyrrolo[3,2-b]pyridin-6-yl]isoxazole | 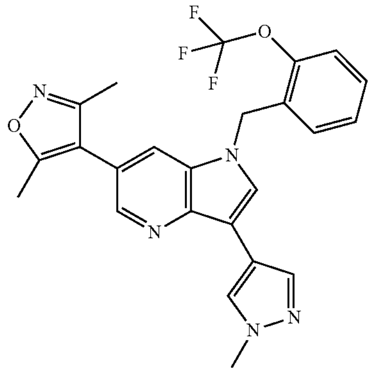 [SMILES: Cc1noc(C)c1-c1cnc2c(-c3cnn(C)c3)cn(Cc3ccccc3OC(F)(F)F)c2c1] | 468.3 |
| P-0198 | 3,5-dimethyl-4-[3-(1-methylpyrazol-4-yl)-1-(2-pyridylmethyl)pyrrolo[3,2-b]pyridin-6-yl]isoxazole | 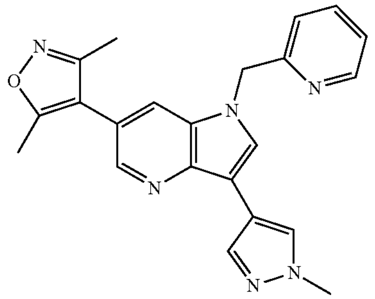 [SMILES: Cc1noc(C)c1-c1cnc2c(-c3cnn(C)c3)cn(Cc3ccccn3)c2c1] | 385.0 |
| P-0217 | 3,5-dimethyl-4-[3-(1-methylpyrazol-4-yl)-1-[1-(2-pyridyl)ethyl]pyrrolo[3,2-b]pyridin-6-yl]isoxazole | 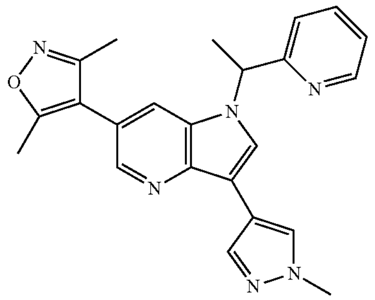 [SMILES: Cc1noc(C)c1-c1cnc2c(-c3cnn(C)c3)cn(C(C)c3ccccn3)c2c1] | 399.3 |

TABLE 20-continued

| The following compounds were prepared as depicted in example 24, using the appropriate starting materials. | | | |
|---|---|---|---|
| Cmpd | Name | Structure | MH(+) |
| P-0224 | 4-[3-iodo-1-(1-phenylethyl)pyrrolo[3,2-b]pyridin-6-yl]-3,5-dimethyl-isoxazole | 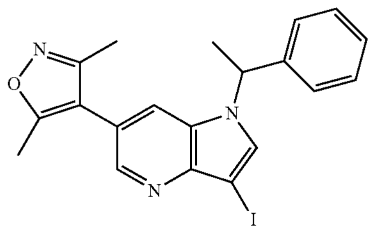 [SMILES: Cc1noc(C)c1-c1cnc2c(I)cn(C(C)c3ccccc3)c2c1] | 444.0 |
| P-0130 | [6-(3,5-dimethylisoxazol-4-yl)-3-iodo-pyrrolo[3,2-b]pyridin-1-yl]-triisopropyl-silane | 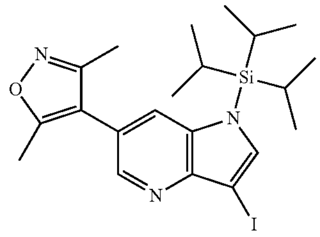 [SMILES: Cc1noc(C)c1-c1cnc2c(I)cn([Si](C(C)C)(C(C)C)C(C)C)c2c1] | 496.0 |
| P-0170 | 3,5-dimethyl-4-[3-(1-methylpyrazol-4-yl)-1-[(2-methylthiazol-4-yl)methyl]pyrrolo[3,2-b]pyridin-6-yl]isoxazole | 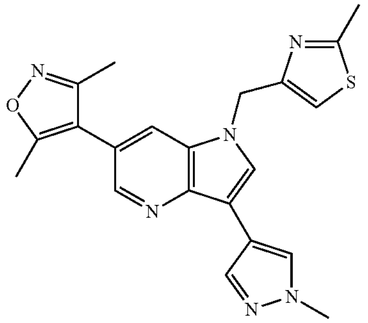 [SMILES: Cc1nc(Cn2cc(-c3cnn(C)c3)c3ncc(-c4c(C)noc4C)cc32)cs1] | 405.2 |
| P-0195 | 3,5-dimethyl-4-[3-(1-methylpyrazol-4-yl)-1-(3-pyridylmethyl)pyrrolo[3,2-b]pyridin-6-yl]isoxazole | 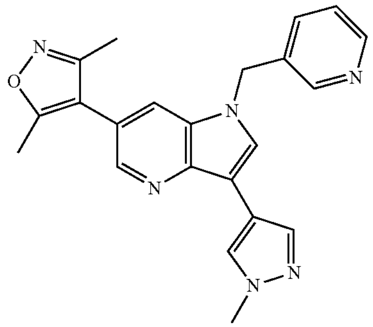 [SMILES: Cc1noc(C)c1-c1cnc2c(-c3cnn(C)c3)cn(Cc3cccnc3)c2c1] | 385.2 |
| P-0222 | 3,5-dimethyl-4-[3-(1-methylpyrazol-4-yl)-1-[(1S)-1-phenylethyl]pyrrolo[3,2-b]pyridin-6-yl]isoxazole | 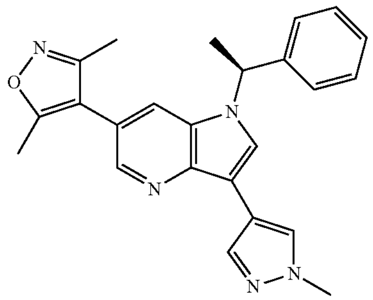 [SMILES: Cc1noc(C)c1-c1cnc2c(-c3cnn(C)c3)cn([C@@H](C)c3ccccc3)c2c1] | 398.1 |

TABLE 20-continued

The following compounds were prepared as depicted in example 24, using the appropriate starting materials.

| Cmpd | Name | Structure | MH(+) |
| --- | --- | --- | --- |
| P-0223 | 3,5-dimethyl-4-[3-(1-methylpyrazol-4-yl)-1-[(1R)-1-phenylethyl]pyrrolo[3,2-b]pyridin-6-yl]isoxazole | 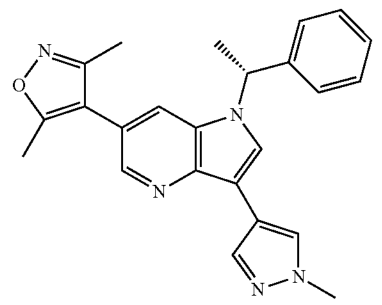 [SMILES: Cc1noc(C)c1-c1cnc2c(-c3cnn(C)c3)cn([C@H](C)c3ccccc3)c2c1] | 398.1 |
| P-0226 | 4-[1-[(2-fluorophenyl)methyl]-3-(1-methylpyrazol-4-yl)indol-6-yl]-3,5-dimethyl-isoxazole | 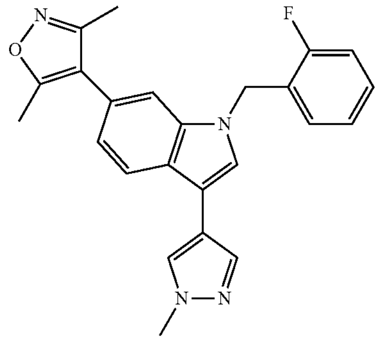 [SMILES: Cc1noc(C)c1-c1ccc2c(-c3cnn(C)c3)cn(Cc3ccccc3F)c2c1] | 401.2 |
| P-0227 | 4-[1-[(2-chlorophenyl)methyl]-3-(1-methylpyrazol-4-yl)indol-6-yl]-3,5-dimethyl-isoxazole | 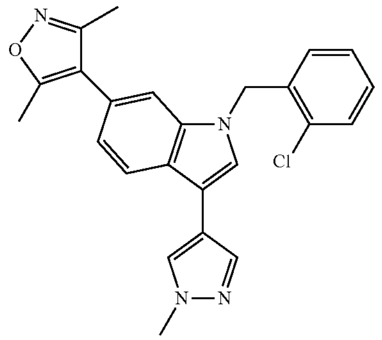 [SMILES: Cc1noc(C)c1-c1ccc2c(-c3cnn(C)c3)cn(Cc3ccccc3Cl)c2c1] | 417.1 |
| P-0228 | 3,5-dimethyl-4-[3-(1-methylpyrazol-4-yl)-1-[[2-(trifluoromethyl)phenyl]methyl]indol-6-yl]isoxazole | 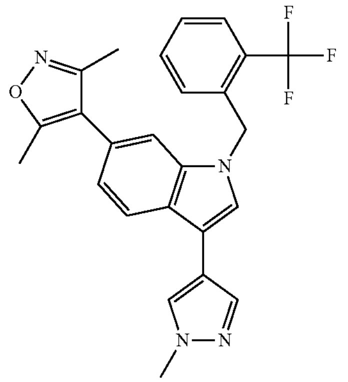 [SMILES: Cc1noc(C)c1-c1ccc2c(-c3cnn(C)c3)cn(Cc3ccccc3C(F)(F)F)c2c1] | 451.3 |

TABLE 20-continued

| The following compounds were prepared as depicted in example 24, using the appropriate starting materials. | | | |
|---|---|---|---|
| Cmpd | Name | Structure | MH(+) |
| P-0229 | 4-[1-[(2,6-difluorophenyl)methyl]-3-(1-methylpyrazol-4-yl)indol-6-yl]-3,5-dimethyl-isoxazole | 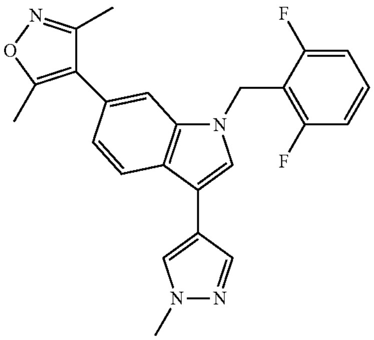 [SMILES: Cc1noc(C)c1-c1ccc2c(-c3cnn(C)c3)cn(Cc3c(F)cccc3F)c2c1] | 419.2 |
| P-0232 | 3,5-dimethyl-4-[3-(1-methylpyrazol-4-yl)-1-(1-phenylethyl)indol-6-yl]isoxazole | 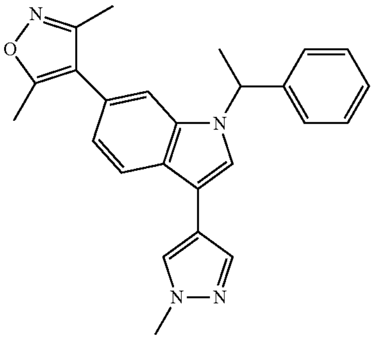 [SMILES: Cc1noc(C)c1-c1ccc2c(-c3cnn(C)c3)cn(C(C)c3ccccc3)c2c1] | 397.0 |

Example 25

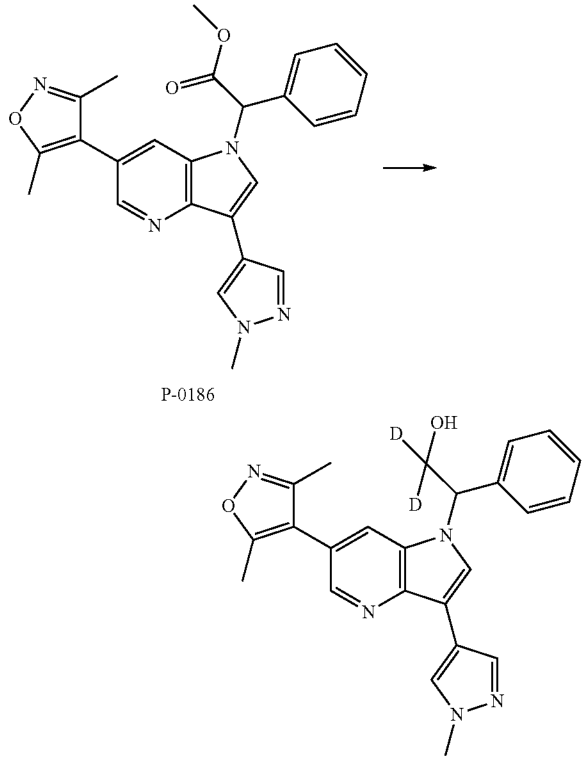

P-0186

P-0218

Preparation of 1,1-dideuterio-2-[6-(3,5-dimethyl-isoxazol-4-yl)-3-(1-methylpyrazol-4-yl)pyrrolo[3,2-b]pyridin-1-yl]-2-phenyl-ethanol P-0218

To ethyl 2-[6-(3,5-dimethylisoxazol-4-yl)-3-(1-methyl-pyrazol-4-yl)pyrrolo[3,2-b]pyridin-1-yl]-2-phenyl-acetate (P-0186, 0.2 g, 0.44 mmol), at room temperature, was added lithium tetradeuterioalumanuide (0.07 g, 1.67 mmol). The reaction was stirred for 2 hours and then sodium sulfate decahydrate was added. After stirring at room temperature for 40 minutes, the reaction was filtered, concentrated, and purified by silica gel column chromatography eluting with 20% to 100% ethyl acetate in hexane to give product. (P-0218, 0.17 g, 93%) MS (ESI) $[M+H^+]^+=415.9$.

Example 26

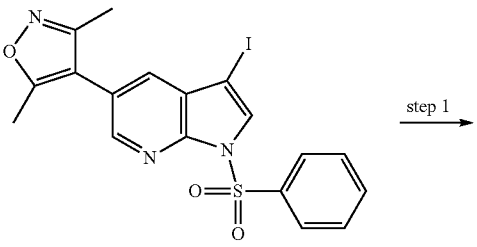

P-0087

-continued

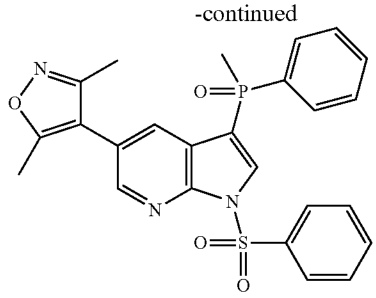

10

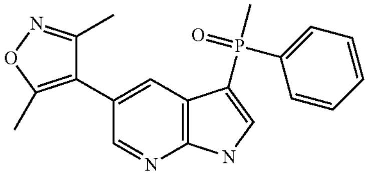

P-0165

Step 1—Preparation of 4-[1-(benzenesulfonyl)-3-[methyl(phenyl)phosphoryl]pyrrolo[2,3-b]pyridin-5-yl]-3,5-dimethyl-isoxazole 10: To 4-[1-(benzenesulfonyl)-3-iodo-pyrrolo[2,3-b]pyridin-5-yl]-3,5-dimethyl-isoxazole (P-0087, 0.16 g, 0.33 mmol) in tetrahydrofuran (5 mL) at −40° C. under nitrogen was added 2M isopropylmagnesium chloride (0.2 ml) slowly. The reaction was allowed to warm to 5° C. in 50 minutes. Then, the reaction was cooled to at −40° C., followed by adding [chloro(methyl)phosphoryl]benzene (0.1 g, 0.57 mmol). The reaction was allowed to warm to room temperature overnight. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (10, 0.040 g, 24.4%).

Step 2—3,5-dimethyl-4-[3-[methyl(phenyl)phosphoryl]-1H-pyrrolo[2,3-b]pyridin-5-yl]isoxazole P-0165: To 4-[1-(benzenesulfonyl)-3-[methyl(phenyl)phosphoryl]pyrrolo[2,3-b]pyridin-5-yl]-3,5-dimethyl-isoxazole (10, 0.03 g, 0.06 mmol) in methanol (5 mL) were added potassium hydroxide (100 mg, 1.78 mmol). The reaction was stirred at room temperature overnight. The reaction was concentrated, and purified with silica gel column chromatography eluting with 1% to 15% methanol in methylene chloride to give product (P-0165, 8.0 mg, 37.3%). MS (ESI) $[M+H^+]^+$=351.8.

TABLE 21

The following compounds were prepared as depicted in example 26, using the appropriate starting materials.

| Cmpd | name | Structure | MH(+) |
|---|---|---|---|
| P-0166 | 4-(3-diphenylphosphoryl-1H-pyrrolo[2,3-b]pyridin-5-yl)-3,5-dimethyl-isoxazole | 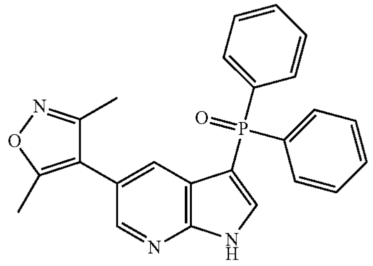 [SMILES: Cc1noc(C)c1-c1cnc2[nH]cc(P(=O)(c3ccccc3)c3ccccc3)c2c1] | 413.9 |

Example 27

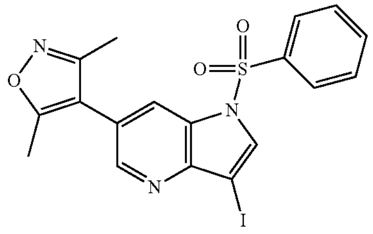

P-0076

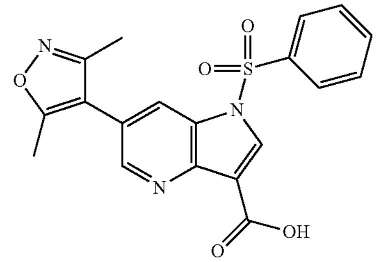

P-0169

Preparation of 1-(benzenesulfonyl)-5-(3,5-dimethyl-isoxazol-4-yl)pyrrolo[2,3-b]pyridine-3-carboxylic acid P-0169

To 4-[1-(benzenesulfonyl)-3-iodo-pyrrolo[2,3-b]pyridin-5-yl]-3,5-dimethyl-isoxazole (P-0076, 0.24 g, 0.5 mmol) in THF (5 ml), under nitrogen at −40° C., was added 2M chloro(isopropyl)magnesium in THF (0.28 ml). The reaction was allowed to warm to 5° C. in 50 minutes. The reaction was cooled to -40° C., followed by adding a big piece of dry ice. The reaction was allowed to warm to room temperature for 1 hour. The reaction was poured into water, acidified with 1N HCl to pH around 7, and extracted with ethyl acetate. The organic layer was washed with brine, dried over sodium sulfate, and filtered. The filtrate was concentrated, and washed with ethyl acetate and hexane to give product (P-0169, 0.070 g, 35.2%). MS (ESI) $[M+H^+]^+$=397.8.

Example 28

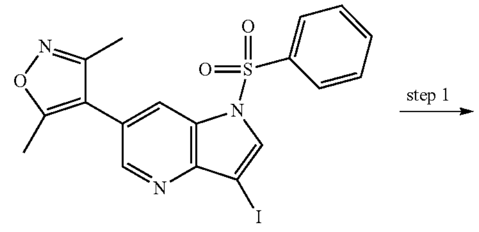

P-0076

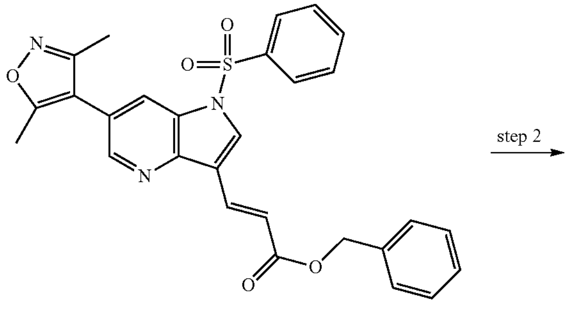

11

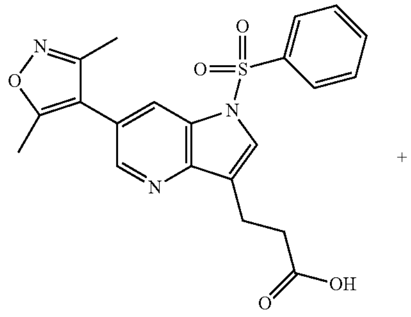

P-0174

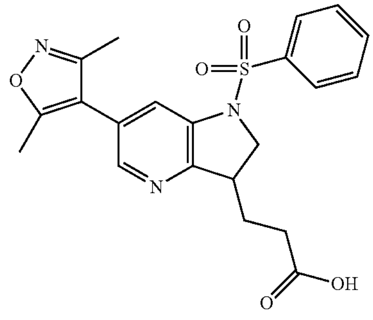

P-0175

Step 1—Preparation of benzyl (E)-3-[1-(benzenesulfonyl)-6-(3,5-dimethylisoxazol-4-yl)pyrrolo[3,2-b]pyridin-3-yl]prop-2-enoate 11: To 4-[1-(benzenesulfonyl)-3-iodo-pyrrolo[3,2-b]pyridin-6-yl]-3,5-dimethyl-isoxazole (P-0076, 0.4 g, 0.83 mmol) in toluene (15 ml), under nitrogen, were added silver carbonate (0.14 g, 0.51 mmol), palladium (II) acetate (0.02 g, 0.09 mmol), and benzyl prop-2-enoate (0.3 g, 1.85 mmol). The reaction was allowed to warm to 85° C. overnight. The reaction was poured into water, acidified with 1N HCl to pH around 7, and extracted with ethyl acetate. The organic layer was washed with brine, dried over sodium sulfate, and filtered. The filtrate was concentrated, and washed with ethyl acetate and hexane to give product (11, 0.30 g, 70.0%). MS (ESI) $[M+H^+]^+$=514.0.

Step 2—Preparation of 3-[1-(benzenesulfonyl)-6-(3,5-dimethylisoxazol-4-yl)pyrrolo[3,2-b]pyridin-3-yl]propanoic acid P-0174 and 3-[1-(benzenesulfonyl)-6-(3,5-dimethylisoxazol-4-yl)-2,3-dihydropyrrolo[3,2-b]pyridin-3-yl]propanoic acid P-0175: To benzyl (E)-3-[1-(benzenesulfonyl)-6-(3,5-dimethylisoxazol-4-yl)pyrrolo[3,2-b]pyridin-3-yl]prop-2-enoate (11, 0.15 g, 0.29 mmol) in THF (25 mL) was added 20% $Pd(OH)_2$ on carbon around 100 mg. The reaction was stirred under hydrogen at room temperature for 15 minutes. The reaction was filtered, concentrated, and purified with silica gel column chromatography eluting with 2% to 20% methanol in methylene chloride to give a mixture of products, which were then further purified with prep-HPLC to give pure product (P-0174, 12.5 mg, 10.1%), MS (ESI) [M+H+]+=425.9; and product (P-0175, 2.5 mg, 2.0%). MS (ESI) $[M+H^+]^+$=428.3.

Example 29

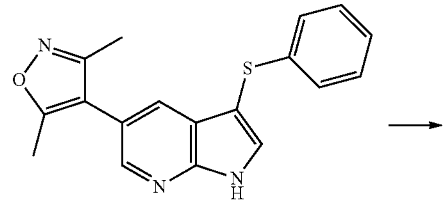

P-0144

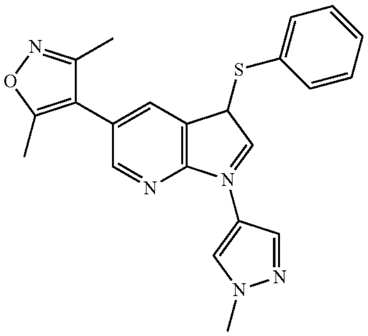

P-0184

Preparation of 3,5-dimethyl-4-[1-(1-methylpyrazol-4-yl)-3-phenylsulfanyl-pyrrolo[2,3-b]pyridin-5-yl]isoxazole P-0184

To 3,5-dimethyl-4-(3-phenylsulfanyl-1H-pyrrolo[2,3-b]pyridin-5-yl)isoxazole (P-0144, 0.5 g, 1.56 mmol) in toluene (10 ml), were added 4-bromo-1-methyl-pyrazole (0.33 g, 2.05 mmol), copper(I) iodide (0.1 g, 0.53 mmol), N,N'-dimethylethylenediamine (0.05 ml, 0.45 mmol), and potassium phosphate tribasic (0.31 ml, 3.77 mmol). The reaction was stirred at 120° C. under nitrogen overnight. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 2% to 20% methanol in methylene chloride to give crude product, which was then further purified with prep-HPLC to give pure product (P-0184, 20 mg, 3.2%). MS (ESI) $[M+H^{\pm}]^{+}$=401.9.

Example 30

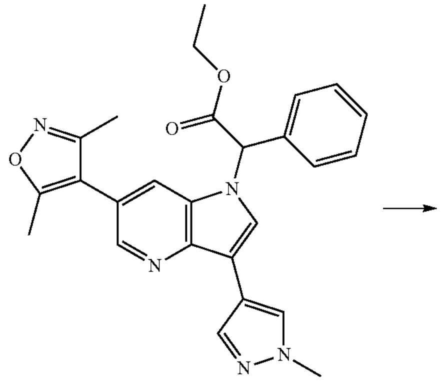

P-0186

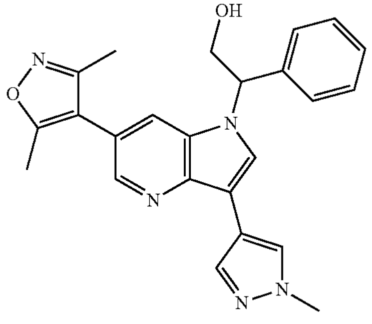

P-0192

Preparation of 2-[6-(3,5-dimethylisoxazol-4-yl)-3-(1-methylpyrazol-4-yl)pyrrolo[3,2-b]pyridin-1-yl]-2-phenyl-ethanol P-0192

To ethyl 2-[6-(3,5-dimethylisoxazol-4-yl)-3-(1-methylpyrazol-4-yl)pyrrolo[3,2-b]pyridin-1-yl]-2-phenyl-acetate (P-0186, 0.36 g, 0.079 mmol) in THF (50.0 mL), at -30° C., was added 1M solution of lithium aluminum hydride in THF (0.79 ml). The reaction was allowed to warm to 10° C. in 2 hours. To the reaction, was added sodium sulfate decahydrate. After stirring at room temperature for 40 minutes, the reaction was filtered, concentrated, and purified with silica gel column chromatography eluting with 20% to 100% ethyl acetate in hexane to give product (P-0192, 0.20 g, 61.2%). MS (ESI) $[M+H^{+}]^{+}$=414.3.

Example 31

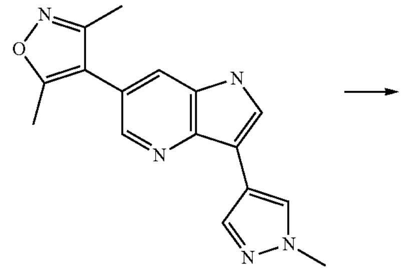

12

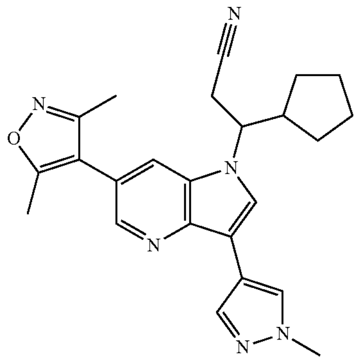

P-0197

Preparation of 3-cyclopentyl-3-[6-(3,5-dimethylisoxazol-4-yl)-3-(1-methylpyrazol-4-yl)pyrrolo[3,2-b]pyridin-1-yl]propanenitrile P-0197

To 3,5-dimethyl-4-[3-(1-methylpyrazol-4-yl)-1H-pyrrolo[3,2-b]pyridin-6-yl]isoxazole (12, 0.08 g, 0.27 mmol) in dimethylsulfoxide ("DMSO") (2 ml), were added (E)-3-cyclopentylprop-2-enenitrile (0.1 g, 0.83 mmol) and potassium carbonate (0.1 g, 0.72 mmol). The reaction was stirred at room temperature over 10 days. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride give crude product, which was then further purified with prep-HPLC to give product (P-0197, 20.4 mg, 18.1%). MS (ESI) $[M+H^{+}]^{+}$=415.4.

TABLE 22

The following compound was prepared as depicted in example 31, using the appropriate starting materials.

| Cmpd | name | Structure | MH(+) |
|---|---|---|---|
| P-0196 | 3-cyclopentyl-3-[6-(3,5-dimethylisoxazol-4-yl)pyrrolo[3,2-b]pyridin-1-yl]propanenitrile | 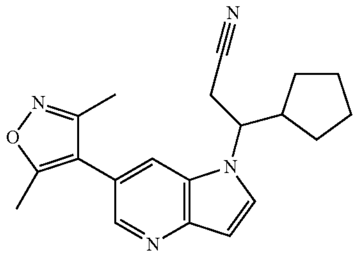 [SMILES: Cc1noc(C)c1-c1cnc2ccn(C(CC#N)C3CCCC3)c2c1] | 334.9 |

Example 32

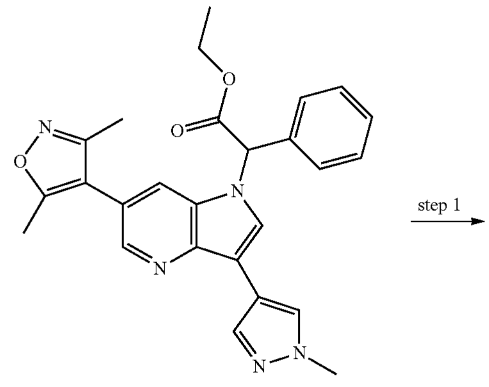

P-0186

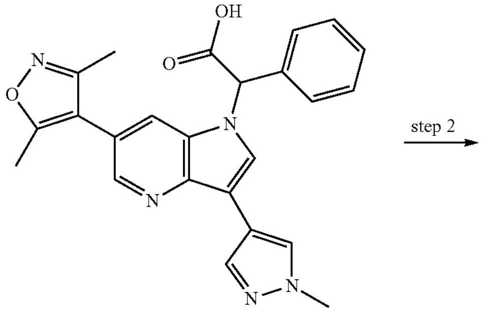

P-0206

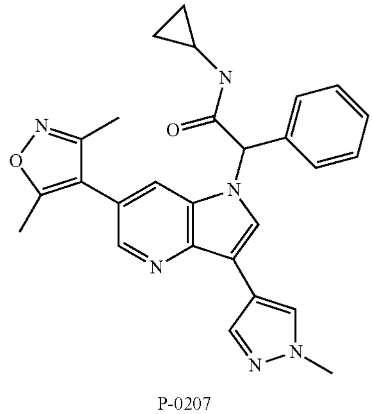

P-0207

Step 1—Preparation of 2-[6-(3,5-dimethylisoxazol-4-yl)-3-(1-methylpyrazol-4-yl)pyrrolo[3,2-b]pyridin-1-yl]-2-phenyl-acetic acid P-0206: To ethyl 2-[6-(3,5-dimethylisoxazol-4-yl)-3-(1-methylpyrazol-4-yl)pyrrolo[3,2-b]pyridin-1-yl]-2-phenyl-acetate (P-0186, 0.2 g, 0.44 mmol) in THF (4.0 ml) was added 1 M potassium carbonate in water (2 ml). The reaction was stirred at 70° C. overnight. The reaction was then heated in a microwave at 140° C. for 25 minutes. The reaction was poured into water, adjusting pH to 4 with 1 M HCl, extracted with ethyl acetate. The organic layer was washed with brine, and the organic layer was dried over sodium sulfate, concentrated, and purified with silica gel column chromatography eluting with 2% to 20% methanol in methylene chloride to give product (P-0206, 120 mg, 63.9%). MS (ESI) {$M+H^+$}$^+$=427.9.

Step 2—Preparation of N-cyclopropyl-2-[6-(3,5-dimethylisoxazol-4-yl)-3-(1-methylpyrazol-4-yl)pyrrolo[3,2-b]pyridin-1-yl]-2-phenyl-acetamide P-0207: To 2-[6-(3,5-dimethylisoxazol-4-yl)-3-(1-methylpyrazol-4-yl)pyrrolo[3,2-b]pyridin-1-yl]-2-phenyl-acetic acid (P-0206, 0.05 g, 0.4 mmol) in dimethylacetamide (5 ml) was added PYBOP (Bromo-tris-pyrrolidino phosphoniumhexafluorophosphate) (0.12 g, 0.23 mmol). The reaction was stirred at room temperature for 40 minutes, followed by adding cyclopropanamine (0.03 g, 0.052 mmol) and N,N-diisopropylethylamine (0.13 ml, 0.77 mmol). The reaction was stirred at room temperature for 2 hours. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give product (P-0207, 0.040 g, 73.3%). MS (ESI) [$M+H^+$]$^+$=467.0.

Example 33

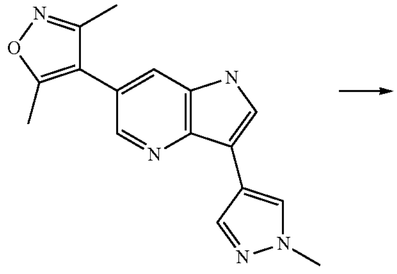

12

-continued

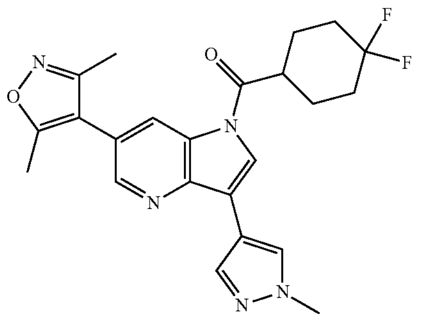

P-0208

-continued

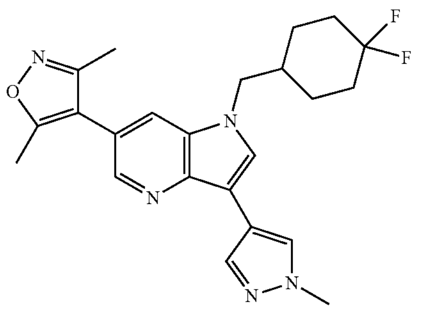

P-0209

Preparation of 4,4-difluorocyclohexyl)-[6-(3,5-dimethylisoxazol-4-yl)-3-(1-methylpyrazol-4-yl)pyrrolo[3,2-b]pyridin-1-yl]methanone P-0208

To 3,5-dimethyl-4-[3-(1-methylpyrazol-4-yl)-1H-pyrrolo[3,2-b]pyridin-6-yl]isoxazole (12, 0.4 g, 1.36 mmol) in THF (15 ml), was added sodium hydride (60% in mineral oil, 0.12 g, 3 mmol) at room temperature. After 10 minutes, 4,4-difluorocyclohexanecarbonyl chloride (0.33 g, 1.81 mmol) was added. The reaction was stirred at room temperature overnight. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride give product (P-0208, 560 mg, 93.5%). MS (ESI) $[M+H^+]^+$=440.3.

Example 34

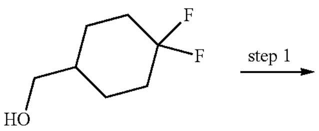

13

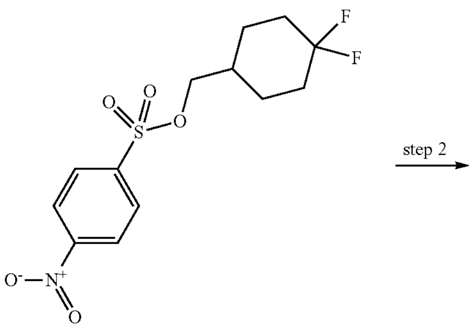

14

Step 1—Preparation of (4,4-difluorocyclohexyl)methyl 4-nitrobenzenesulfonate 14: To (1-fluorocyclohexyl)methanol (13, 0.3 g, 2.27 mmol) in methylene chloride (15 mL) were added triethylamine (0.42 ml, 3 mmol), and 4-nitrobenzenesulfonyl chloride (0.49 g, 2.2 mmol). The reaction was stirred at room temperature overnight. The reaction was poured into water, and extracted with ethyl acetate. The organic layer was washed with brine, dried over sodium sulfate, and filtered. The filtrate was concentrated, and purified with silica gel column chromatography eluting with 10% to 100% ethyl acetate in hexane to give product (14, 0.45 g, 67.2%).

Step 2—Preparation of 4-[1-[(4,4-difluorocyclohexyl)methyl]-3-(1-methylpyrazol-4-yl)pyrrolo[3,2-b]pyridin-6-yl]-3,5-dimethyl-isoxazole P-0209: To 3,5-dimethyl-4-[3-(1-methylpyrazol-4-yl)-1H-pyrrolo[3,2-b]pyridin-6-yl]isoxazole (14, 0.04 g, 0.14 mmol) in DMF (3 ml), was added sodium hydride (60% in mineral oil, 0.01 g, 0.25 mmol) at room temperature. After 10 minutes, (4,4-difluorocyclohexyl)methyl 4-nitrobenzenesulfonate (0.05 g, 0.16 mmol) was added. The reaction was stirred at room temperature for 4 hours. The reaction was poured into water, and extracted with ethyl acetate. The organic layer was washed with brine, dried over sodium sulfate, and filtered. The filtrate was concentrated, and purified with silica gel column chromatography eluting with 2% to 15% methanol in methylene chloride give crude product, which was then further purified with prep-HPLC to give pure product (P-0209, 19.1 mg, 32.9%). MS (ESI) $[M+H^+]^+$=426.4.

TABLE 23

The following compounds were prepared as depicted in example 34, using the appropriate starting materials.

| No. | name | Structure | MH(+) |
| --- | --- | --- | --- |
| P-0211 | 4-[1-[dideuterio-(4,4-difluorocyclohexyl)methyl]-3-(1-methylpyrazol-4-yl)pyrrolo[3,2-b]pyridin-6-yl]-3,5-dimethyl-isoxazole | 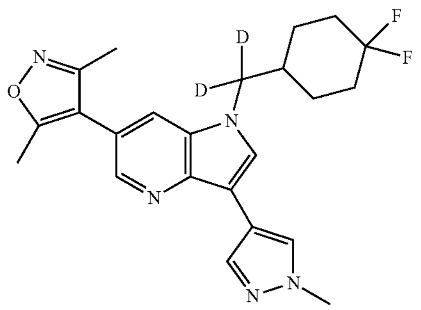 [SMILES: [2H]C([2H])(C1CCC(F)(F)CC1)n1cc(-c2cnn(C)c2)c2ncc(-c3c(C)noc3C)cc21] | 428.0 |
| P-0213 | 4-[1-[(3,3-difluorocyclobutyl)methyl]-3-(1-methylpyrazol-4-yl)pyrrolo[3,2-b]pyridin-6-yl]-3,5-dimethyl-isoxazole | 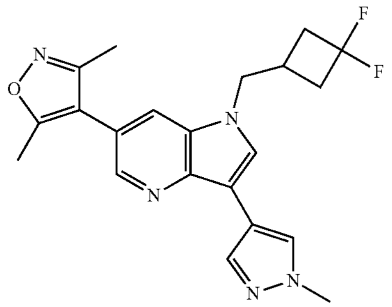 [SMILES: Cc1noc(C)c1-c1cnc2c(-c3cnn(C)c3)cn(CC3CC(F)(F)C3)c2c1] | 398.0 |
| P-0214 | 4-[1-[dideuterio-(3,3-difluorocyclobutyl)methyl]-3-(1-methylpyrazol-4-yl)pyrrolo[3,2-b]pyridin-6-yl]-3,5-dimethyl-isoxazole | 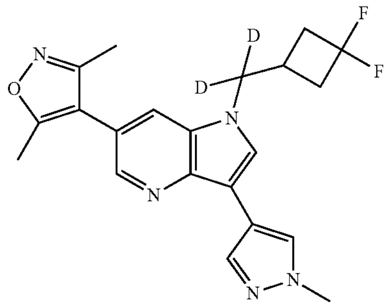 [SMILES: [2H]C([2H])(C1CC(F)(F)C1)n1cc(-c2cnn(C)c2)c2ncc(-c3c(C)noc3C)cc21] | 400.2 |
| P-0210 | 4-[1-[(4,4-difluorocyclohexyl)methyl]-3-[1-(difluoromethyl)pyrazol-4-yl]pyrrolo[3,2-b]pyridin-6-yl]-3,5-dimethyl-isoxazole | 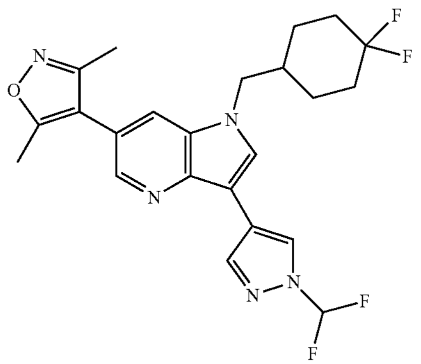 [SMILES: Cc1noc(C)c1-c1cnc2c(-c3cnn(C(F)F)c3)cn(CC3CCC(F)(F)CC3)c2c1] | 462.4 |

Example 35A

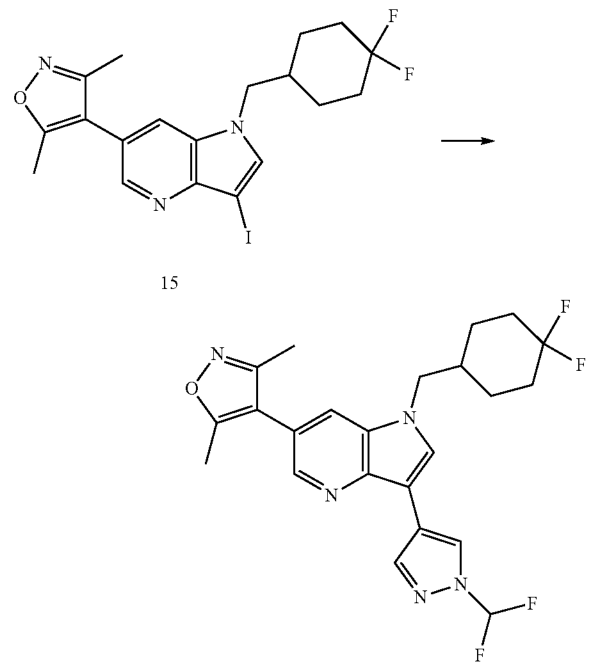

15

P-0210

Preparation of 4-[1-[(4,4-difluorocyclohexyl)methyl]-3-[1-(difluoromethyl)pyrazol-4-yl]pyrrolo[3,2-b]pyridin-6-yl]-3,5-dimethyl-isoxazole P-0210

In three 10 mL of microwave tubes, 4-[1-[(4,4-difluorocyclohexyl)methyl]-3-iodo-pyrrolo[3,2-b]pyridin-6-yl]-3,5-dimethyl-isoxazole (15, 0.47 g, 1 mmol) in acetonitrile (15 ml) was added by 4-[1-[(4,4-difluorocyclohexyl)methyl]-3-iodo-pyrrolo[3,2-b]pyridin-6-yl]-3,5-dimethyl-isoxazole (0.47 g, 1 mmol), 1M potassium carbonate in water (7.2 ml), and [1,1'-bis(diphenylphosphino)ferrocene]dichloropalladium(II) (0.08 g, 0.1 mmol). The reaction mixture was heated by microwave to 120° C. for 30 minutes. The reaction mixture was diluted with water and extracted with ethyl acetate. The organic layer was washed with water and brine. The organic layer was separated and then dried over MgSO4. After filtration, the volatiles were removed under vacuum. The crude material was purified by silica gel chromatography ethyl acetate/hexane (0-50% gradient) to give product (P-0210, 260 mg, 57%) MS (ESI) $[M+H^+]^+=462.1$.

Example 35B

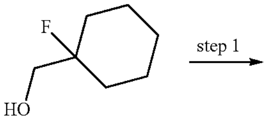

16

-continued

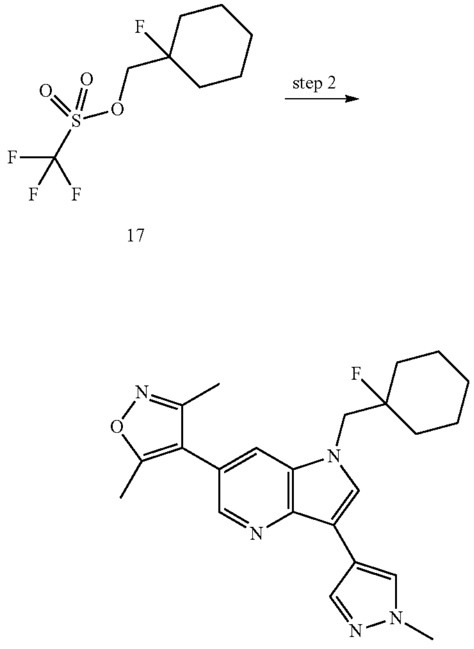

17

P-212

Step 1—Preparation of (1-fluorocyclohexyl)methyl trifluoromethanesulfonate 17: To (1-fluorocyclohexyl)methanol (16, 0.34 g, 2.57 mmol) in methylene chloride (15 mL) was added triethylamine (0.47 ml, 3.4 mmol). The reaction was cooled to −30° C., followed by adding trifluoromethylsulfonyl trifluoromethanesulfonate (0.8 g, 2.84 mmol) slowly. The reaction was allowed to warm to room temperature in 1 hour. The reaction was poured into water, and extracted with ethyl acetate. The organic layer was washed with brine, dried over sodium sulfate, and filtered. The filtrate was concentrated to give crude product (17, 0.66 g, 97.1%), that was used directly in the next Step without further purification.

Step 2—Preparation of 4-[1-[(1-fluorocyclohexyl)methyl]-3-(1-methylpyrazol-4-yl)pyrrolo[3,2-b]pyridin-6-yl]-3,5-dimethyl-isoxazole P-0212: To 3,5-dimethyl-4-[3-(1-methylpyrazol-4-yl)-1H-pyrrolo[3,2-b]pyridin-6-yl]isoxazole (0.1 g, 0.34mmol) in DMF (5 ml), was added cesium carbonate (0.05 ml, 0.61 mmol) at room temperature. After 10 minutes, (1-fluorocyclohexyl)methyl trifluoromethanesulfonate (17, 0.14 g, 0.53 mmol) was added. The reaction was stirred at 90° C. overnight. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give product (P-0212, 60 mg, 43.2%). MS (ESI) $[M+H^+]^+=408.0$.

TABLE 24

The following compounds were prepared as depicted in example 35, using the appropriate starting materials.

| No. | name | Structure | MH(+) |
|---|---|---|---|
| P-0240 | 4-[1-[(8-fluoro-1,4-dioxaspiro[4.5]decan-8-yl)methyl]-3-iodo-pyrrolo[3,2-b]pyridin-6-yl]-3,5-dimethyl-isoxazole | 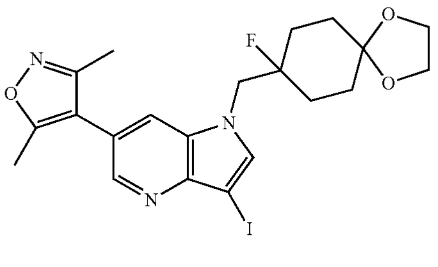 [SMILES: Cc1noc(C)c1-c1cnc2c(I)cn(CC3(F)CCC4(CC3)OCCO4)c2c1] | 511.8 |
| P-0234 | 4-[1-[(1-fluorocyclohexyl)methyl]-3-iodo-pyrrolo[3,2-b] pyridin-6-yl]-3,5-dimethyl-isoxazole | 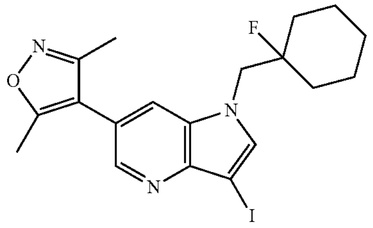 [SMILES: Cc1noc(C)c1-c1cnc2c(I)cn(CC3(F)CCCCC3)c2c1] | 454.0 |

Example 36

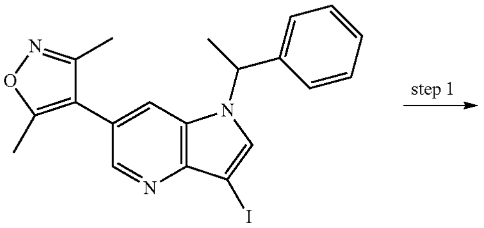

P-0224

-continued

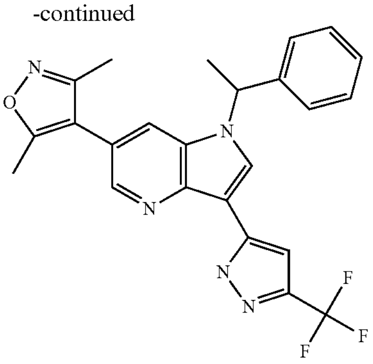

P-0215

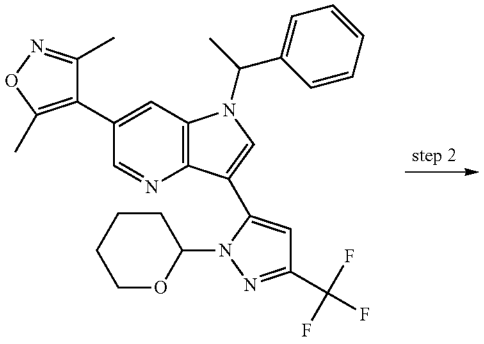

18

Step 1—Preparation of 3,5-dimethyl-4-[1-(1-phenylethyl)-3-[2-tetrahydropyran-2-yl-5-(trifluoromethyl)pyrazol-3-yl]pyrrolo[3,2-b]pyridin-6-yl]isoxazole 18: To 4-[3-iodo-1-(1-phenylethyl)pyrrolo[3,2-b]pyridin-6-yl]-3,5-dimethyl-isoxazole (P-0224, 0.06 g, 0.13 mmol) in acetonitrile (3.0 ml), were added [2-tetrahydropyran-2-yl-5-(trifluoromethyl)pyrazol-3-yl]boronic acid (0.05 g, 0.2 mmol), [1,1'-bis(diphenylphosphino)ferrocene]dichloropalladium(II) (0.02 g, 0.03 mmol), and 1M potassium carbonate in water (1.2 ml). The reaction was micro-waved at 160° C. for 30 minutes. The reaction was poured into water, extracted with ethyl acetate. The organic layer was washed with brine, and the organic layer was dried over sodium sulfate, concentrated, and purified with silica gel column chromatography eluting with 2% to 20% methanol in methylene chloride to give crude product (18, 60 mg, 85.6%).

Step 2—Preparation of 3,5-dimethyl-4-[1-(1-phenylethyl)-3-[3-(trifluoromethyl)-1H-pyrazol-5-yl]pyrrolo[3,2-b]pyridin-6-yl]isoxazole P-0215: To 3,5-dimethyl-4-[1-(1- phenylethyl)-3-[2-tetrahydropyran-2-yl-5-(trifluoromethyl) pyrazol-3-yl]pyrrolo[3,2-b]pyridin-6-yl]isoxazole (18, 0.05 g, 0.09 mmol) in dioxane (6.0 ml), was added 3 mL of concentrated HCl. The reaction was stirred at room temperature for 40 minutes. The reaction was poured into aqueous potassium carbonate, pH around 9, extracted with ethyl acetate. The organic layer was washed with brine, and the organic layer was dried over sodium sulfate, concentrated, and purified with silica gel column chromatography eluting with 2% to 20% methanol in methylene chloride to give product (P-0215, 4.8 mg, 17.6%). MS (ESI) {M+H$^+$}$^+$=452.2.

Example 37

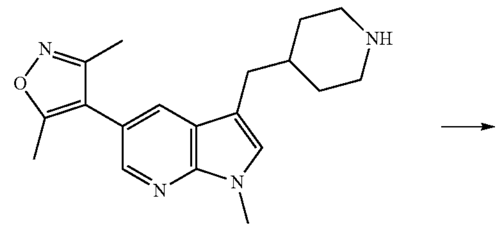

19

-continued

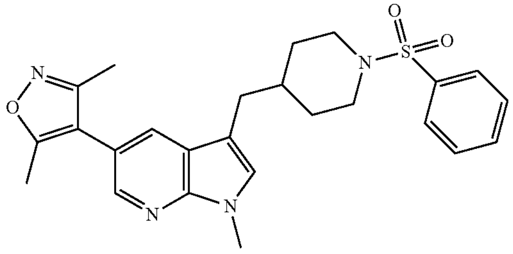

P-0113

Preparation of 4-[3-[[1-(benzenesulfonyl)-4-piperidyl]methyl]-1-methyl-pyrrolo[2,3-b]pyridin-5-yl]-3,5-dimethyl-isoxazole P-0113

To a solution of 3,5-dimethyl-4-[1-methyl-3-(4-piperidylmethyl)pyrrolo[2,3-b]pyridin-5-yl]isoxazole (19, 100 mg, 0.31 mmol) in pyridine (2 ml) was added benzenesulfonyl chloride (54.44 mg, 0.31 mmol) slowly. The reaction was allowed to run at room temperature overnight. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0113, 11.4 mg, 8.0%). MS (ESI) [M+H$^+$]$^+$=464.4.

TABLE 25

The following compounds were prepared as depicted in example 37, using the appropriate starting materials.

| Cmpd | name | Structure | MH(+) |
|---|---|---|---|
| P-0114 | 4-[[5-(3,5-dimethylisoxazol-4-yl)-1-methyl-pyrrolo[2,3-b]pyridin-3-yl]methyl]-N-phenyl-piperidine-1-carboxamide | 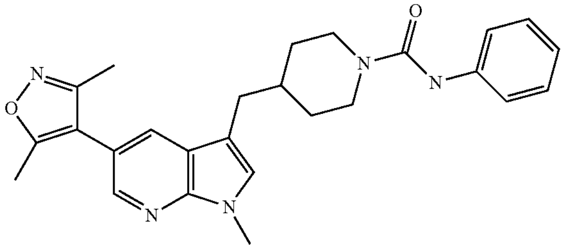 [SMILES: Cc1noc(C)c1-c1cnc2c(c1)c(CC1CCN(C(=O)Nc3ccccc3)CC1)cn2C] | 444.2 |
| P-0115 | [4-[[5-(3,5-dimethylisoxazol-4-yl)-1-methyl-pyrrolo[2,3-b]pyridin-3-yl]methyl]-1-piperidyl]-phenyl-methanone | 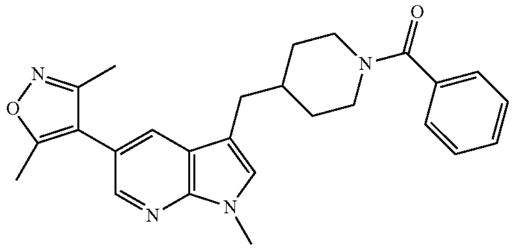 [SMILES: Cc1noc(C)c1-c1cnc2c(c1)c(CC1CCN(C(=O)c3ccccc3)CC1)cn2C] | 429.2 |
| P-0116 | 4-[3-[(1-ethylsulfonyl-4-piperidyl)methyl]-1-methyl-pyrrolo[2,3-b]pyridin-5-yl]-3,5-dimethyl-isoxazole | 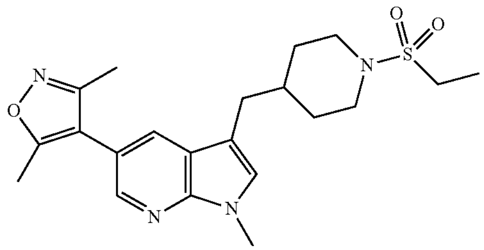 [SMILES: CCS(=O)(=O)N1CCC(Cc2cn(C)c3ncc(-c4c(C)noc4C)cc23)CC1] | 416.9 |

TABLE 25-continued

The following compounds were prepared as depicted in example 37, using the appropriate starting materials.

| Cmpd | name | Structure | MH(+) |
|---|---|---|---|
| P-0117 | 4-[[5-(3,5-dimethylisoxazol-4-yl)-1-methyl-pyrrolo[2,3-b]pyridin-3-yl]methyl]-N-ethyl-piperidine-1-carboxamide | 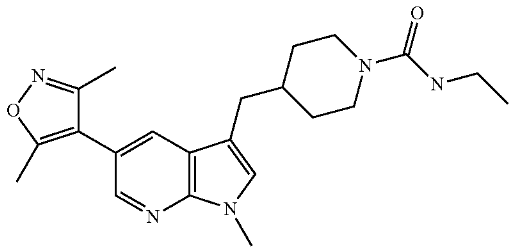 [SMILES: CCNC(=O)N1CCC(Cc2cn(C)c3ncc(-c4c(C)noc4C)cc23)CC1] | 395.9 |
| P-0119 | 4-[3-[(1-cyclopentylsulfonyl-4-piperidyl)methyl]-1-methyl-pyrrolo[2,3-b]pyridin-5-yl]-3,5-dimethyl-isoxazole | 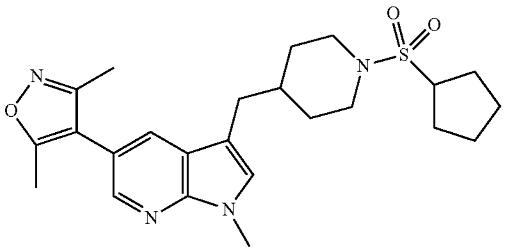 [SMILES: Cc1noc(C)c1-c1cnc2c(c1)c(CC1CCN(S(=O)(=O)C3CCCC3)CC1)cn2C] | 456.9 |
| P-0120 | 1-[4-[[5-(3,5-dimethylisoxazol-4-yl)-1-methyl-pyrrolo[2,3-b]pyridin-3-yl]methyl]-1-piperidyl]ethanone | 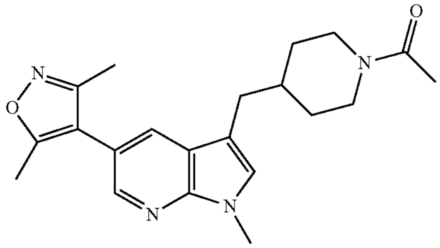 [SMILES: CC(=O)N1CCC(Cc2cn(C)c3ncc(-c4c(C)noc4C)cc23)CC1] | 367.1 |
| P-0106 | 1-[4-[[5-(3,5-dimethylisoxazol-4-yl)-1-methyl-pyrrolo[2,3-b]pyridin-3-yl]methyl]-1-piperidyl]-2,2,2-trifluoro-ethanone | 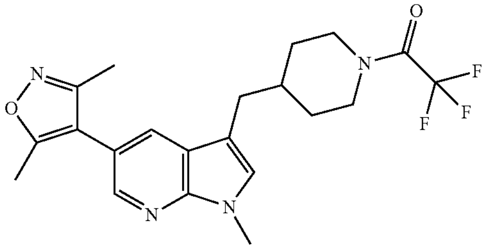 [SMILES: Cc1noc(C)c1-c1cnc2c(c1)c(CC1CCN(C(=O)C(F)(F)F)CC1)cn2C] | 420.9 |

Example 38

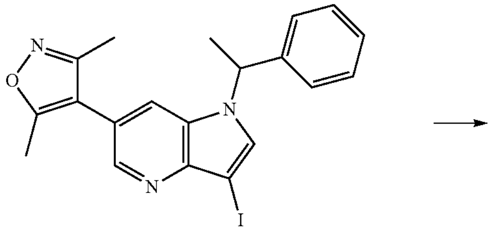

P-0224

-continued

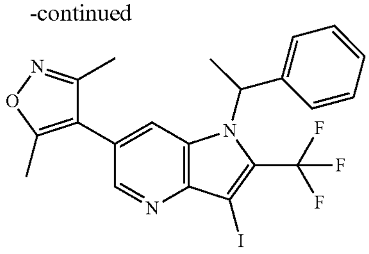

P-0245

Preparation of 4-[3-iodo-1-(1-phenylethyl)-2-(trifluoromethyl)pyrrolo[3,2-b]pyridin-6-yl]-3,5-dimethyl-isoxazole P-0245

To 4-[3-iodo-1-(1-phenylethyl)pyrrolo[3,2-b]pyridin-6-yl]-3,5-dimethyl-isoxazole (P-0224, 100 mg, 0.23 mmol) and zinc trifluoromethanesulfinate (149.58 mg, 0.45 mmol)

was added DMSO (1 ml) followed by water (0.4 ml). The reaction was cooled in an ice bath and tert-butyl hydroperoxide (0.095 ml, 0.75 mmol) was added dropwise (1 min addition time). The reaction was removed from the ice bath and allowed to warm to room temperature and then placed in an oil bath at 50° C. and allowed to stir overnight. After overnight, a second addition of zinc trifluoromethanesulfinate (140 mg, 0.42 mmol) followed by the addition of tert-butyl hydroperoxide (0.095 ml, 0.75 mmol) was performed at room temperature. The reaction was placed in an oil bath at 50° C. for an additional 12 hours. The reaction was extracted with saturated sodium bicarbonate and ethyl acetate. The organic layer was separated and the aqueous layer was extracted 3 more times with 10 mL portions of ethyl acetate. The organic layers were combined and the volatiles were removed by rotary evaporation to provide the crude product that was purified by flash chromatography (5-60% ethyl acetate in hexanes). Fractions containing desired product were all impure, so they were combined and the desired product was purified by reverse phase HPLC. This provided 6 mg of desired product P-0245 as an off-white solid after lyophilization. MS (ESI) $[M+H^+]^+=512.1$ -continued

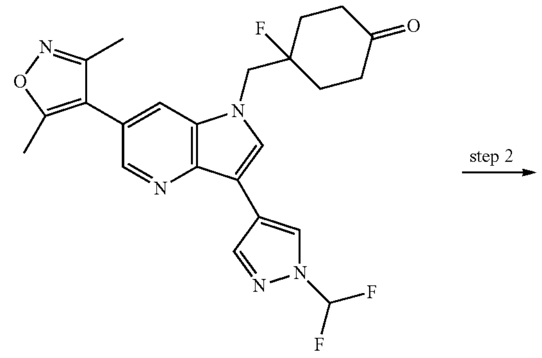

P-0242

TABLE 26

| The following compounds were prepared as depicted in example 38, using the appropriate starting materials. | | | |
|---|---|---|---|
| Cmpd | name | Structure | MH(+) |
| P-0225 | 4-[3-iodo-2-(trifluoromethyl)-1H-pyrrolo[3,2-b]pyridin-6-yl]-3,5-dimethyl-isoxazole | 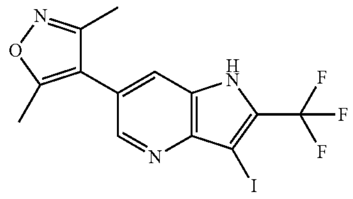 [SMILES: Cc1noc(C)c1-c1cnc2c(I)c(C(F)(F)F)[nH]c2c1] | 407.9 |

Example 39

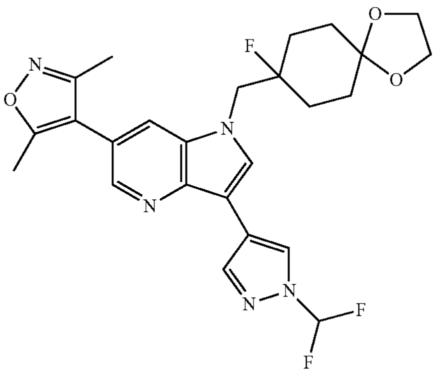

P-0241

-continued

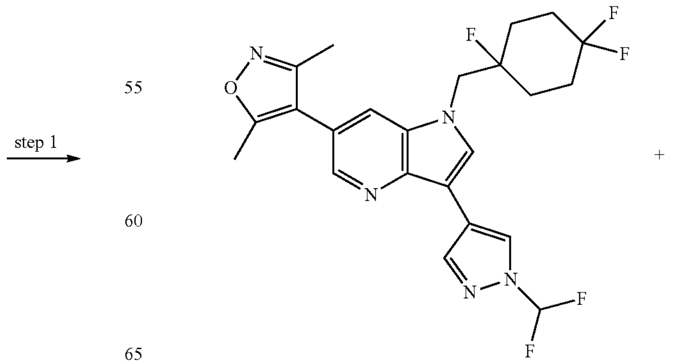

P-0243

-continued

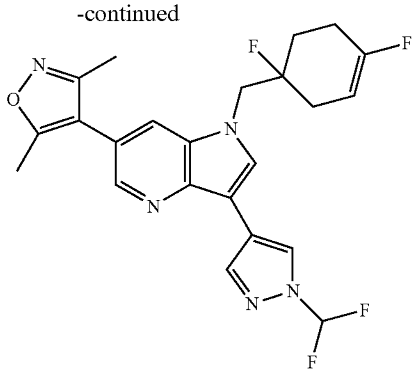

P-0244

Step 1—Preparation of 4-[[3-[1-(difluoromethyl)pyrazol-4-yl]-6-(3,5-dimethylisoxazol-4-yl)pyrrolo[3,2-b]pyridin-1-yl]methyl]-4-fluoro-cyclohexanone P-0242: To 4-[3-[1-(difluoromethyl)pyrazol-4-yl]-1-[(8-fluoro-1,4-dioxaspiro[4.5]decan-8-yl)methyl]pyrrolo[3,2-b]pyridin-6-yl]-3,5-dimethyl-isoxazole (P-0241, 0.38 g, 0.76 mmol) in THF (15 ml) was added 5 mL of 4N HCl. The reaction was stirred at 40° C. for 5 hours. The reaction was poured into aqueous potassium carbonate, and extracted with ethyl acetate. The organic layer was washed with brine, dried over sodium sulfate, and filtered. The filtrate was concentrated, and purified by silica gel column chromatography eluting with 2% to 15% methanol in methylene chloride to give product (P-0242, 300 mg, 86.5%). MS (ESI) $[M+H^+]^+$=458.2.

Step 2—Preparation of 4-[3-[1-(difluoromethyl)pyrazol-4-yl]-1-[(1,4,4-trifluorocyclohexyl)methyl]pyrrolo[3,2-b]pyridin-6-yl]-3,5-dimethyl-isoxazole P-0243 and 4-[1-[(1,4-difluorocyclohex-3-en-1-yl)methyl]-3-(1-methylpyrazol-4-yl)pyrrolo[3,2-b]pyridin-6-yl]-3,5-dimethyl-isoxazole P-0244: To 4-[[3-[1-(difluoromethyl)pyrazol-4-yl]-6-(3,5-dimethylisoxazol-4-yl)pyrrolo[3,2-b]pyridin-1-yl]methyl]-4-fluoro-cyclohexanone (P-0242, 0.13 g, 0.28 mmol) in dichloromethane (10 ml), cooled to −78° C., was added N-ethyl-N-(trifluoro-1{4}-sulfanyl)ethanamine (0.3 g, 1.86 mmol). The reaction was allowed to warm to room temperature overnight. The reaction was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (P-0243, 10 mg, 7.3%), MS (ESI) $[M+H^+]^+$=480.0; and product (P-0244, 5.1 mg, 3.9%), $[M+H^+]^+$=460.2.

Compounds listed in Table 27 below, e.g., compounds P-0001 to P-0106 and P-0108 to P-0245 were prepared according to the protocols set forth in Examples 1 to 39. The $^1H$ NMR and mass spectroscopy data were consistent with the structures of the compounds.

TABLE 27

| | Compound |
|---|---|
| P-0001 | 3,5-dimethyl-4-(2-phenyl-1H-pyrrolo[2,3-b]pyridin-5-yl)isoxazole |
| P-0002 | 4-(1H-indol-5-yl)-3,5-dimethyl-isoxazole |
| P-0003 | 3,5-dimethyl-4-[3-(3-pyridylmethyl)-1H-pyrrolo[2,3-b]pyridin-5-yl]isoxazole |
| P-0004 | [5-(3,5-dimethylisoxazol-4-yl)-1H-pyrrolo[2,3-b]pyridin-3-yl]-(3-pyridyl)methanone |
| P-0005 | 3,5-dimethyl-4-[2-methyl-3-(3-pyridylmethyl)-1H-pyrrolo[2,3-b]pyridin-5-yl]isoxazole |
| P-0006 | [5-(3,5-dimethylisoxazol-4-yl)-2-methyl-1H-pyrrolo[2,3-b]pyridin-3-yl]-(3-pyridyl)methanone |
| P-0007 | 4-[2-(4-fluorophenyl)-3-(3-pyridylmethyl)-1H-pyrrolo[2,3-b]pyridin-5-yl]-3,5-dimethyl-isoxazole |
| P-0008 | [5-(3,5-dimethylisoxazol-4-yl)-2-(4-fluorophenyl)-1H-pyrrolo[2,3-b]pyridin-3-yl]-(3-pyridyl)methanone |
| P-0009 | [5-(3,5-dimethylisoxazol-4-yl)-2-methyl-1H-pyrrolo[2,3-b]pyridin-3-yl]-(3-pyridyl)methanol |
| P-0010 | 3,5-dimethyl-4-[3-(2-pyrrolidin-1-ylethyl)-1H-indol-5-yl]isoxazole |
| P-0011 | 4-[3-[(5-fluoro-2-methoxy-3-pyridyl)-methoxy-methyl]-1H-pyrrolo[2,3-b]pyridin-5-yl]-3,5-dimethyl-isoxazole |
| P-0012 | [5-(3,5-dimethylisoxazol-4-yl)-1H-pyrrolo[2,3-b]pyridin-3-yl]-[6-(2,2,2-trifluoroethoxy)-3-pyridyl]methanol |
| P-0013 | 4-[3-[methoxy-[6-(trifluoromethyl)-3-pyridyl]methyl]-1H-pyrrolo[2,3-b]pyridin-5-yl]-3,5-dimethyl-isoxazole |
| P-0014 | 4-[3-[(2-chloro-6-fluoro-phenyl)-methoxy-methyl]-1H-pyrrolo[2,3-b]pyridin-5-yl]-3,5-dimethyl-isoxazole |
| P-0015 | 3,5-dimethyl-4-[3-[[4-(trifluoromethyl)phenyl]methyl]-1H-pyrrolo[2,3-b]pyridin-5-yl]isoxazole |
| P-0016 | [5-(3,5-dimethylisoxazol-4-yl)-1H-pyrrolo[2,3-b]pyridin-3-yl]-[4-(trifluoromethyl)phenyl]methanone |
| P-0017 | 3,5-dimethyl-4-(2-methyl-1H-pyrrolo[2,3-b]pyridin-5-yl)isoxazole |
| P-0018 | 3,5-dimethyl-4-(1H-pyrrolo[3,2-b]pyridin-6-yl)isoxazole |
| P-0019 | (2-chlorophenyl)-[5-(3,5-dimethylisoxazol-4-yl)-1H-pyrrolo[2,3-b]pyridin-3-yl]methanol |
| P-0020 | 4-[3-[(2-chlorophenyl)-methoxy-methyl]-1H-pyrrolo[2,3-b]pyridin-5-yl]-3,5-dimethyl-isoxazole |
| P-0021 | (2-chloro-6-fluoro-phenyl)-[5-(3,5-dimethylisoxazol-4-yl)-1H-pyrrolo[2,3-b]pyridin-3-yl]methanol |
| P-0022 | [5-(3,5-dimethylisoxazol-4-yl)-1H-pyrrolo[2,3-b]pyridin-3-yl]-(5-fluoro-2-methoxy-3-pyridyl)methanol |
| P-0023 | [5-(3,5-dimethylisoxazol-4-yl)-1H-pyrrolo[2,3-b]pyridin-3-yl]-[6-(tnfluoromethyl)-3-pyridyl]methanol |

TABLE 27-continued

| | Compound |
|---|---|
| P-0024 | 1-[5-(3,5-dimethylisoxazol-4-yl)-1H-pyrrolo[2,3-b]pyridin-3-yl]-4,4-difluoro-cyclohexanol |
| P-0025 | [5-(3,5-dimethylisoxazol-4-yl)-1H-pyrrolo[2,3-b]pyridin-3-yl]-(5-fluoro-6-methoxy-3-pyridyl)methanol |
| P-0026 | 4-[3-[(2-chlorophenyl)methyl]-1H-pyrrolo[2,3-b]pyridin-5-yl]-3,5-dimethyl-isoxazole |
| P-0027 | 4-[3-[(2-chloro-6-fluoro-phenyl)methyl]-1H-pyrrolo[2,3-b]pyridin-5-yl]-3,5-dimethyl-isoxazole |
| P-0028 | 4-[3-[(5-fluoro-2-methoxy-3-pyridyl)methyl]-1H-pyrrolo[2,3-b]pyridin-5-yl]-3,5-dimethyl-isoxazole |
| P-0029 | 4-[3-(4,4-difluorocyclohexen-1-yl)-1H-pyrrolo[2,3-b]pyridin-5-yl]-3,5-dimethyl-isoxazole |
| P-0030 | (4,4-difluorocyclohexyl)-[5-(3,5-dimethylisoxazol-4-yl)-1H-pyrrolo[2,3-b]pyridin-3-yl]methanol |
| P-0031 | (4,4-difluorocyclohexyl)-[5-(3,5-dimethylisoxazol-4-yl)-1H-pyrrolo[2,3-b]pyridin-3-yl]methanone |
| P-0032 | 4-[1-(4-methoxyphenyl)sulfonylpyrrolo[3,2-b]pyridin-6-yl]-3,5-dimethyl-isoxazole |
| P-0033 | 4-[1-(4-isopropoxyphenyl)sulfonylpyrrolo[3,2-b]pyridin-6-yl]-3,5-dimethyl-isoxazole |
| P-0034 | 4-[3-[(4,4-difluorocyclohexyl)methyl]-1H-pyrrolo[2,3-b]pyridin-5-yl]-3,5-dimethyl-isoxazole |
| P-0035 | 4-(2-ethyl-1H-pyrrolo[2,3-b]pyridin-5-yl)-3,5-dimethyl-isoxazole |
| P-0036 | 4-(1-butylsulfonylpyrrolo[3,2-b]pyridin-6-yl)-3,5-dimethyl-isoxazole |
| P-0037 | 4-(1-cyclopentylsulfonylpyrrolo[3,2-b]pyridin-6-yl)-3,5-dimethyl-isoxazole |
| P-0038 | 4-[1-(benzenesulfonyl)pyrrolo[3,2-b]pyridin-6-yl]-3,5-dimethyl-isoxazole |
| P-0039 | [5-(3,5-dimethylisoxazol-4-yl)-1H-pyrrolo[2,3-b]pyridin-3-yl]-[3-(trifluoromethoxy)phenyl]methanol |
| P-0040 | [2-(difluoromethoxy)phenyl]-[5-(3,5-dimethylisoxazol-4-yl)-1H-pyrrolo[2,3-b]pyridin-3-yl]methanol |
| P-0041 | (2,2-difluoro-1,3-benzodioxo1-4-yl)-[5-(3,5-dimethylisoxazol-4-yl)-1H-pyrrolo[2,3-b]pyridin-3-yl]methanol |
| P-0042 | (2-chlorophenyl)-[5-(3,5-dimethylisoxazol-4-yl)-2-ethyl-1H-pyrrolo[2,3-b]pyridin-3-yl]methanol |
| P-0043 | [5-(3,5-dimethylisoxazol-4-yl)-2-ethyl-1H-pyrrolo[2,3-b]pyridin-3-yl]-[3-(trifluoromethoxy)phenyl]methanol |
| P-0044 | (4,4-difluorocyclohexyl)-[5-(3,5-dimethylisoxazol-4-yl)-2-ethyl-1H-pyrrolo[2,3-b]pyridin-3-yl]methanol |
| P-0045 | 4-[3-[(4,4-difluorocyclohexyl)-methoxy-methyl]-2-ethyl-1H-pyrrolo[2,3-b]pyridin-5-yl]-3,5-dimethyl-isoxazole |
| P-0046 | 3,5-dimethyl-4-[3-[[3-(trifluoromethoxy)phenyl]methyl]-1H-pyrrolo[2,3-b]pyridin-5-yl]isoxazole |
| P-0047 | 4-[3-[[2-(difluoromethoxy)phenyl]methyl]-1H-pyrrolo[2,3-b]pyridin-5-yl]-3,5-dimethyl-isoxazole |
| P-0048 | 4-[3-[(2,2-difluoro-1,3-benzodioxol-4-yl)methyl]-1H-pyrrolo[2,3-b]pyridin-5-yl]-3,5-dimethyl-isoxazole |
| P-0049 | 4-[3-[(2-chlorophenyl)methyl]-2-ethyl-1H-pyrrolo[2,3-b]pyridin-5-yl]-3,5-dimethyl-isoxazole |
| P-0050 | 4-[2-ethyl-3-[[3-(trifluoromethoxy)phenyl]methyl]-1H-pyrrolo[2,3-b]pyridin-5-yl]-3,5-dimethyl-isoxazole |
| P-0051 | 4-[3-[(4,4-difluorocyclohexyl)methyl]-2-ethyl-1H-pyrrolo[2,3-b]pyridin-5-yl]-3,5-dimethyl-isoxazole |
| P-0052 | 4-[1-(4-fluorophenyl)sulfonylpyrrolo[3,2-b]pyridin-6-yl]-3,5-dimethyl-isoxazole |
| P-0053 | 4-[1-(4-chlorophenyl)sulfonylpyrrolo[3,2-b]pyridin-6-yl]-3,5-dimethyl-isoxazole |
| P-0054 | 4-[1-[1-(difluoromethyl)pyrazol-4-yl]sulfonylpyrrolo[3,2-b]pyridin-6-yl]-3,5-dimethyl-isoxazole |
| P-0055 | 3,5-dimethyl-4-[1-(2-thienylsulfonyl)pyrrolo[3,2-b]pyridin-6-yl]isoxazole |
| P-0056 | 4-[1-(3-fluorophenyl)sulfonylpyrrolo[3,2-b]pyridin-6-yl]-3,5-dimethyl-isoxazole |
| P-0057 | 4-[1-(3-chlorophenyl)sulfonylpyrrolo[3,2-b]pyridin-6-yl]-3,5-dimethyl-isoxazole |
| P-0058 | 4-[1-[1-(difluoromethyl)-3-methyl-pyrazol-4-yl]sulfonylpyrrolo[3,2-b]pyridin-6-yl]-3,5-dimethyl-isoxazole |
| P-0059 | 3,5-dimethyl-4-[1-[(4-methyl-2-thienyl)sulfonyl]pyrrolo[3,2-b]pyridin-6-yl]isoxazole |
| P-0060 | 4-[1-(2-fluorophenyl)sulfonylpyrrolo[3,2-b]pyridin-6-yl]-3,5-dimethyl-isoxazole |
| P-0061 | 4-[1-[3-(difluoromethoxy)phenyl]sulfonylpyrrolo[3,2-b]pyridin-6-yl]-3,5-dimethyl-isoxazole |
| P-0062 | 3,5-dimethyl-4-[1-[(5-methyl-2-thienyl)sulfonyl]pyrrolo[3,2-b]pyridin-6-yl]isoxazole |
| P-0063 | 4-[3-[1-(4-fluorophenyl)-1-methyl-ethyl]-1H-pyrrolo[2,3-b]pyridin-5-yl]-3,5-dimethyl-isoxazole |

TABLE 27-continued

| | Compound |
|---|---|
| P-0064 | 4-[3-[cyclopropyl-(4-fluorophenyl)methyl]-1H-pyrrolo[2,3-b]pyridin-5-yl]-3,5-dimethyl-isoxazole |
| P-0065 | 4-[1-(2-methoxyphenyl)sulfonylpyrrolo[3,2-b]pyridin-6-yl]-3,5-dimethyl-isoxazole |
| P-0066 | 4-(1-cyclohexylsulfonylpyrrolo[3,2-b]pyridin-6-yl)-3,5-dimethyl-isoxazole |
| P-0067 | 3,5-dimethyl-4-[1-(1-piperidylsulfonyl)pyrrolo[3,2-b]pyridin-6-yl]isoxazole |
| P-0068 | 3,5-dimethyl-4-(1-pyrrolidin-1-ylsulfonylpyrrolo[3,2-b]pyridin-6-yl)isoxazole |
| P-0069 | 4-[3-[cyclopropyl(methoxy)methyl]-1H-pyrrolo[3,2-b]pyridin-6-yl]-3,5-dimethyl-isoxazole |
| P-0070 | 4-[3-(cyclopropylmethyl)-1H-pyrrolo[3,2-b]pyridin-6-yl]-3,5-dimethyl-isoxazole |
| P-0071 | 4-[1-cyclohexylsulfonyl-3-[cyclopropyl(methoxy)methyl]pyrrolo[3,2-b]pyridin-6-yl]-3,5-dimethyl-isoxazole |
| P-0072 | 4-(3-iodo-1H-pyrrolo[3,2-b]pyridin-6-yl)-3,5-dimethyl-isoxazole |
| P-0073 | 4-[3-[(4,4-difluorocyclohexyl)-methoxy-methyl]-1H-pyrrolo[2,3-b]pyridin-5-yl]-3,5-dimethyl-isoxazole |
| P-0074 | 4-[3-(cyclopropylmethyl)-1-(3,3,3-trifluoropropylsulfonyl)pyrrolo[3,2-b]pyridin-6-yl]-3,5-dimethyl-isoxazole |
| P-0075 | 4-[1-cyclohexylsulfonyl-3-(cyclopropylmethyl)pyrrolo[3,2-b]pyridin-6-yl]-3,5-dimethyl-isoxazole |
| P-0076 | 4-[1-(benzenesulfonyl)-3-iodo-pyrrolo[3,2-b]pyridin-6-yl]-3,5-dimethyl-isoxazole |
| P-0077 | 4-[1-(benzenesulfonyl)-3-phenyl-pyrrolo[3,2-b]pyridin-6-yl]-3,5-dimethyl-isoxazole |
| P-0078 | 4-[3-[(4,4-difluorocyclohexyl)-methoxy-methyl]-1-ethylsulfonyl-pyrrolo[2,3-b]pyridin-5-yl]-3,5-dimethyl-isoxazole |
| P-0079 | 4-[3-[(4,4-difluorocyclohexyl)methyl]-1-(trideuteriomethyl)pyrrolo[2,3-b]pyridin-5-yl]-3,5-dimethyl-isoxazole |
| P-0080 | 4-[3-[(4,4-difluorocyclohexyl)-methoxy-methyl]-1-(trideuteriomethyl)pyrrolo[2,3-b]pyridin-5-yl]-3,5-dimethyl-isoxazole |
| P-0081 | 1-(benzenesulfonyl)-6-(3,5-dimethylisoxazol-4-yl)pyrrolo[3,2-b]pyridine-3-carbonitrile |
| P-0082 | 6-(3,5-dimethylisoxazol-4-yl)-1H-pyrrolo[3,2-b]pyridine-3-carbonitrile |
| P-0083 | 3,5-dimethyl-4-[3-(3-pyridyl)-1H-pyrrolo[3,2-b]pyridin-6-yl]isoxazole |
| P-0084 | 4-[1-(benzenesulfonyl)-3-(3-pyridyl)pyrrolo[3,2-b]pyridin-6-yl]-3,5-dimethyl-isoxazole |
| P-0085 | 4-[3-[dicyclopropyl-(4-fluorophenyl)methyl]-1H-pyrrolo[2,3-b]pyridin-5-yl]-3,5-dimethyl-isoxazole |
| P-0086 | 4-(3-iodo-1H-pyrrolo[2,3-b]pyridin-5-yl)-3,5-dimethyl-isoxazole |
| P-0087 | 4-[1-(benzenesulfonyl)-3-iodo-pyrrolo[2,3-b]pyridin-5-yl]-3,5-dimethyl-isoxazole |
| P-0088 | 4-[3-iodo-1-(trideuteriomethyl)pyrrolo[2,3-b]pyridin-5-yl]-3,5-dimethyl-isoxazole |
| P-0089 | 4-[[5-(3,5-dimethylisoxazol-4-yl)-1H-pyrrolo[2,3-b]pyridin-3-yl]-methoxy-methyl]thiane 1,1-dioxide |
| P-0090 | [1-(benzenesulfonyl)-5-(3,5-dimethylisoxazol-4-yl)pyrrolo[2,3-b]pyridin-3-yl]-tetrahydrothiopyran-4-yl-methanol |
| P-0091 | [5-(3,5-dimethylisoxazol-4-yl)-1H-pyrrolo[2,3-b]pyridin-3-yl]-tetrahydrothiopyran-4-yl-methanone |
| P-0092 | benzyl 4-[[5-(3,5-dimethylisoxazol-4-yl)-1-(trideuteriomethyl)pyrrolo[2,3-b]pyridin-3-yl]methyl]piperidine-1-carboxylate |
| P-0093 | 4-[[5-(3,5-dimethylisoxazol-4-yl)-1H-pyrrolo[2,3-b]pyridin-3-yl]methylene]thiane 1-oxide |
| P-0094 | [1-(benzenesulfonyl)-5-(3,5-dimethylisoxazol-4-yl)pyrrolo[2,3-b]pyridin-3-yl]-(1,1-dioxothian-4-yl)methanol |
| P-0095 | 4-[[1-(benzenesulfonyl)-5-(3,5-dimethylisoxazol-4-yl)pyrrolo[2,3-b]pyridin-3-yl]-fluoro-methyl]thiane 1,1-dioxide |
| P-0096 | 4-[[1-(benzenesulfonyl)-5-(3,5-dimethylisoxazol-4-yl)pyrrolo[2,3-b]pyridin-3-yl]methyl]thiane 1,1-dioxide |
| P-0097 | 4-[[1-(benzenesulfonyl)-5-(3,5-dimethylisoxazol-4-yl)pyrrolo[2,3-b]pyridin-3-yl]methylene]thiane 1,1-dioxide |
| P-0098 | 4-[[5-(3,5-dimethylisoxazol-4-yl)-1H-pyrrolo[2,3-b]pyridin-3-yl]methyl]thiane 1,1-dioxide |
| P-0099 | 4-[[5-(3,5-dimethylisoxazol-4-yl)-1H-pyrrolo[2,3-b]pyridin-3-yl]methylene]thiane 1,1-dioxide |
| P-0100 | 3,5-dimethyl-4-[1-methyl-3-(norbornan-2-ylmethyl)pyrrolo[2,3-b]pyridm-5-yl]isoxazole |
| P-0101 | (4,4-difluorocyclohexyl)-[5-(3,5-dimethylisoxazol-4-yl)-1-methyl-pyrrolo[2,3-b]pyridin-3-yl]methanol |
| P-0102 | 4-[1-(benzenesulfonyl)-3-(2-cyclopropylpyrimidin-5-yl)pyrrolo[3,2-b]pyridin-6-yl]-3,5-dimethyl-isoxazole |
| P-0103 | 4-[1-cyclopentylsulfonyl-3-(2-cyclopropylpyrimidin-5-yl)pyrrolo[3,2-b]pyridin-6-yl]-3,5-dimethyl-isoxazole |

TABLE 27-continued

| | Compound |
|---|---|
| P-0104 | 4-[1-(benzenesulfonyl)-3-(2-methoxypyrimidin-5-yl)pyrrolo[3,2-b]pyridin-6-yl]-3,5-dimethyl-isoxazole |
| P-0105 | 4-[1-cyclopentylsulfonyl-3-(2-methoxypyrimidin-5-yl)pyrrolo[3,2-b]pyridin-6-yl]-3,5-dimethyl-isoxazole |
| P-0106 | 1-[4-[[5-(3,5-dimethylisoxazol-4-yl)-1-methyl-pyrrolo[2,3-b]pyridin-3-yl]methyl]-1-piperidyl]-2,2,2-trifluoro-ethanone |
| P-0108 | 1-(4,4-difluorocyclohexyl)-1-[5-(3,5-dimethylisoxazol-4-yl)-1-methyl-pyrrolo[2,3-b]pyridin-3-yl]pentan-1-ol |
| P-0109 | 4-[3-[1-(4,4-difluorocyclohexyl)pentyl]-1-methyl-pyrrolo[2,3-b]pyridin-5-yl]-3,5-dimethyl-isoxazole |
| P-0110 | 4-[1-(benzenesulfonyl)-3-(1-methylpyrazol-4-yl)pyrrolo[3,2-b]pyridin-6-yl]-3,5-dimethyl-isoxazole |
| P-0111 | 3,5-dimethyl-4-[3-(1-methylpyrazol-4-yl)-1-propylsulfonyl-pyrrolo[3,2-b]pyridin-6-yl]isoxazole |
| P-0112 | 4-[1-cyclopentylsulfonyl-3-(1-methylpyrazo1-4-yl)pyrrolo[3,2-b]pyridin-6-yl]-3,5-dimethyl-isoxazole |
| P-0113 | 4-[3-[[1-(benzenesulfonyl)-4-piperidyl]methyl]-1-methyl-pyrrolo[2,3-b]pyridin-5-yl]-3,5-dimethyl-isoxazole |
| P-0114 | 4-[[5-(3,5-dimethylisoxazol-4-yl)-1-methyl-pyrrolo[2,3-b]pyridin-3-yl]methyl]-N-phenyl-piperidine-1-carboxamide |
| P-0115 | [4-[[5-(3,5-dimethylisoxazol-4-yl)-1-methyl-pyrrolo[2,3-b]pyridin-3-yl]methyl]-1-piperidyl]-phenyl-methanone |
| P-0116 | 4-[3-[(1-ethylsulfonyl-4-piperidyl)methyl]-1-methyl-pyrrolo[2,3-b]pyridin-5-yl]-3,5-dimethyl-isoxazole |
| P-0117 | 4-[[5-(3,5-dimethylisoxazol-4-yl)-1-methyl-pyrrolo[2,3-b]pyridin-3-yl]methyl]-N-ethyl-piperidine-1-carboxamide |
| P-0118 | 4-[3-[1-(4,4-difluorocyclohexyl)propyl]-1-methyl-pyrrolo[2,3-b]pyridin-5-yl]-3,5-dimethyl-isoxazole |
| P-0119 | 4-[3-[(1-cyclopentylsulfonyl-4-piperidyl)methyl]-1-methyl-pyrrolo[2,3-b]pyridin-5-yl]-3,5-dimethyl-isoxazole |
| P-0120 | 1-[4-[[5-(3,5-dimethylisoxazol-4-yl)-1-methyl-pyrrolo[2,3-b]pyridin-3-yl]methyl]-1-piperidyl]ethanone |
| P-0121 | 4-[1-(2-fluorophenyl)sulfonyl-3-(1-methylpyrazo1-4-yl)pyrrolo[3,2-b]pyridin-6-yl]-3,5-dimethyl-isoxazole |
| P-0122 | 4-[1-(3-fluorophenyl)sulfonyl-3-(1-methylpyrazo1-4-yl)pyrrolo[3,2-b]pyridin-6-yl]-3,5-dimethyl-isoxazole |
| P-0123 | 4-[1-(4-fluorophenyl)sulfonyl-3-(1-methylpyrazo1-4-yl)pyrrolo[3,2-b]pyridin-6-yl]-3,5-dimethyl-isoxazole |
| P-0124 | 4-[1-(benzenesulfonyl)-3-(1-ethylpyrazol-4-yl)pyrrolo[3,2-b]pyridin-6-yl]-3,5-dimethyl-isoxazole |
| P-0125 | 4-[3-(1-ethylpyrazol-4-yl)-1-(2-fluorophenyl)sulfonyl-pyrrolo[3,2-b]pyridin-6-yl]-3,5-dimethyl-isoxazole |
| P-0126 | 4-[3-(1-allylpyrazol-4-yl)-1-(benzenesulfonyl)pyrrolo[3,2-b]pyridin-6-yl]-3,5-dimethyl-isoxazole |
| P-0127 | 4-[3-(1-allylpyrazol-4-yl)-1-(2-fluorophenyl)sulfonyl-pyrrolo[3,2-b]pyridin-6-yl]-3,5-dimethyl-isoxazole |
| P-0128 | 4-[3-(1-allylpyrazol-4-yl)-1-cyclopentylsulfonyl-pyrrolo[3,2-b]pyridin-6-yl]-3,5-dimethyl-isoxazole |
| P-0129 | 4-[3-(1-allylpyrazol-4-yl)-1-(3,3,3-trifluoropropylsulfonyl)pyrrolo[3,2-b]pyridin-6-yl]-3,5-dimethyl-isoxazole |
| P-0130 | [6-(3,5-dimethylisoxazol-4-yl)-3-iodo-pyrrolo[3,2-b]pyridin-1-yl]-triisopropyl-silane |
| P-0131 | 4-[1-(benzenesulfonyl)-3-[1-(difluoromethyl)pyrazo1-4-yl]pyrrolo[3,2-b]pyridin-6-yl]-3,5-dimethyl-isoxazole |
| P-0132 | 4-[3-[1-(difluoromethyl)pyrazo1-4-yl]-1-(2-fluorophenyl)sulfonyl-pyrrolo[3,2-b]pyridin-6-yl]-3,5-dimethyl-isoxazole |
| P-0133 | 4-[1-cyclopentylsulfonyl-3-[1-(difluoromethyl)pyrazol-4-yl]pyrrolo[3,2-b]pyridin-6-yl]-3,5-dimethyl-isoxazole |
| P-0134 | 4-[1-cyclobutylsulfonyl-3-[1-(difluoromethyl)pyrazol-4-yl]pyrrolo[3,2-b]pyridin-6-yl]-3,5-dimethyl-isoxazole |
| P-0135 | 4-[3-[1-(difluoromethyl)pyrazol-4-yl]-1-propylsulfonyl-pyrrolo[3,2-b]pyridin-6-yl]-3,5-dimethyl-isoxazole |
| P-0136 | 4-[3-[1-(difluoromethyl)pyrazol-4-yl]-1-(3,3,3-trifluoropropylsulfonyl)pyrrolo[3,2-b]pyridin-6-yl]-3,5-dimethyl-isoxazole |
| P-0137 | 4-[3-(1-allylpyrazol-4-yl)-1-propylsulfonyl-pyrrolo[3,2-b]pyridin-6-yl]-3,5-dimethyl-isoxazole |
| P-0138 | 4-[3-(1-allylpyrazol-4-yl)-1-sec-butylsulfonyl-pyrrolo[3,2-b]pyridin-6-yl]-3,5-dimethyl-isoxazole |
| P-0139 | 4-[3-(1-allylpyrazol-4-yl)-1-cyclopropylsulfonyl-pyrrolo[3,2-b]pyridin-6-yl]-3,5-dimethyl-isoxazole |
| P-0140 | 4-[3-(1-allylpyrazol-4-yl)-1-(cyclopropylmethylsulfonyl)pyrrolo[3,2-b]pyridin-6-yl]-3,5-dimethyl-isoxazole |
| P-0141 | 4-[3-(3-fluorophenyl)sulfanyl-1H-pyrrolo[2,3-b]pyridin-5-yl]-3,5-dimethyl-isoxazole |
| P-0142 | 4-[3-(3-fluorophenyl)sulfinyl-1H-pyrrolo[2,3-b]pyridin-5-yl]-3,5-dimethyl-isoxazole |

TABLE 27-continued

| | Compound |
|---|---|
| P-0143 | 4-[3-(3-fluorophenyl)sulfonyl-1H-pyrrolo[2,3-b]pyridin-5-yl]-3,5-dimethyl-isoxazole |
| P-0144 | 3,5-dimethyl-4-(3-phenylsulfanyl-1H-pyrrolo[2,3-b]pyridin-5-yl)isoxazole |
| P-0145 | 4-[3-(benzenesulfonyl)-1H-pyrrolo[2,3-b]pyridin-5-yl]-3,5-dimethyl-isoxazole |
| P-0146 | 4-[1-(benzenesulfonyl)-3-[1-(2,2,2-trifluoroethyl)pyrazol-4-yl]pyrrolo[3,2-b]pyridin-6-yl]-3,5-dimethyl-isoxazole |
| P-0147 | 4-[1-(benzenesulfonyl)-3-[1-(2-methoxyethyl)pyrazol-4-yl]pyrrolo[3,2-b]pyridin-6-yl]-3,5-dimethyl-isoxazole |
| P-0148 | 4-[1-(benzenesulfonyl)-3-(1-tetrahydrofuran-3-ylpyrazol-4-yl)pyrrolo[3,2-b]pyridin-6-yl]-3,5-dimethyl-isoxazole |
| P-0149 | 4-[1-cyclopentylsulfonyl-3-[1-(2,2,2-trifluoroethyl)pyrazol-4-yl]pyrrolo[3,2-b]pyridin-6-yl]-3,5-dimethyl-isoxazole |
| P-0150 | 3,5-dimethyl-4-[1-propylsulfonyl-3-[1-(2,2,2-trifluoroethyl)pyrazol-4-yl]pyrrolo[3,2-b]pyridin-6-yl]isoxazole |
| P-0151 | 4-[1-cyclopentylsulfonyl-3-[1-(2-methoxyethyl)pyrazol-4-yl]pyrrolo[3,2-b]pyridin-6-yl]-3,5-dimethyl-isoxazole |
| P-0152 | 4-[3-[1-(2-methoxyethyl)pyrazol-4-yl]-1-propylsulfonyl-pyrrolo[3,2-b]pyridin-6-yl]-3,5-dimethyl-isoxazole |
| P-0153 | 4-[1-cyclopentylsulfonyl-3-(1-tetrahydrofuran-3-ylpyrazol-4-yl)pyrrolo[3,2-b]pyridin-6-yl]-3,5-dimethyl-isoxazole |
| P-0154 | 3,5-dimethyl-4-[1-propylsulfonyl-3-(1-tetrahydrofuran-3-ylpyrazol-4-yl)pyrrolo[3,2-b]pyridin-6-yl]isoxazole |
| P-0155 | 3-[1-(benzenesulfonyl)-6-(3,5-dimethylisoxazol-4-yl)pyrrolo[3,2-b]pyridin-3-yl]prop-2-yn-1-ol |
| P-0156 | 3-[1-cyclopentylsulfonyl-6-(3,5-dimethylisoxazol-4-yl)pyrrolo[3,2-b]pyridin-3-yl]prop-2-yn-1-ol |
| P-0157 | 4-[1-(benzenesulfonyl)-3-(3-fluoroprop-1-ynyl)pyrrolo[3,2-b]pyridin-6-yl]-3,5-dimethyl-isoxazole |
| P-0158 | 4-[1-cyclopentylsulfonyl-3-(3-fluoroprop-1-ynyl)pyrrolo[3,2-b]pyridin-6-yl]-3,5-dimethyl-isoxazole |
| P-0159 | 3,5-dimethyl-4-[1-(1-phenylethyl)pyrrolo[3,2-b]pyridin-6-yl]isoxazole |
| P-0160 | 4-[3-(1-allylpyrazol-4-yl)-1-benzyl-pyrrolo[3,2-b]pyridin-6-yl]-3,5-dimethyl-isoxazole |
| P-0161 | 3,5-dimethyl-4-[3-(1-methylpyrazol-4-yl)-1-(1-phenylethyl)pyrrolo[3,2-b]pyridin-6-yl]isoxazole |
| P-0162 | 4-(1-benzylpyrrolo[3,2-b]pyridin-6-yl)-3,5-dimethyl-isoxazole |
| P-0163 | 4-[1-(benzenesulfonyl)-3-(1H-pyrazol-4-yl)pyrrolo[3,2-b]pyridin-6-yl]-3,5-dimethyl-isoxazole |
| P-0164 | 4-[1-(benzenesulfonyl)-3-(3-methyl-1H-pyrazol-5-yl)pyrrolo[3,2-b]pyridin-6-yl]-3,5-dimethyl-isoxazole |
| P-0165 | 3,5-dimethyl-4-[3-[methyl(phenyl)phosphoryl]-1H-pyrrolo[2,3-b]pyridin-5-yl]isoxazole |
| P-0166 | 4-(3-diphenylphosphoryl-1H-pyrrolo[2,3-b]pyridin-5-yl)-3,5-dimethyl-isoxazole |
| P-0167 | 4-[1-cyclopentylsulfonyl-3-(1H-pyrazol-4-yl)pyrrolo[3,2-b]pyridin-6-yl]-3,5-dimethyl-isoxazole |
| P-0168 | 4-[1-(benzenesulfonyl)-3-(1-tetrahydropyran-2-ylpyrazol-4-yl)pyrrolo[3,2-b]pyridin-6-yl]-3,5-dimethyl-isoxazole |
| P-0169 | 1-(benzenesulfonyl)-6-(3,5-dimethylisoxazol-4-yl)pyrrolo[3,2-b]pyridine-3-carboxylic acid |
| P-0170 | 3,5-dimethyl-4-[3-(1-methylpyrazol-4-yl)-1-[(2-methylthiazol-4-yl)methyl]pyrrolo[3,2-b]pyridin-6-yl]isoxazole |
| P-0171 | 3,5-dimethyl-4-[3-(1-methylpyrazol-4-yl)-1-(thiazol-4-ylmethyl)pyrrolo[3,2-b]pyridin-6-yl]isoxazole |
| P-0172 | 4-[1-[(2-fluorophenyl)methyl]-3-(1-methylpyrazol-4-yl)pyrrolo[3,2-b]pyridin-6-yl]-3,5-dimethyl-isoxazole |
| P-0173 | 4-[1-[(2,6-difluorophenyl)methyl]-3-(1-methylpyrazol-4-yl)pyrrolo[3,2-b]pyridin-6-yl]-3,5-dimethyl-isoxazole |
| P-0174 | 3-[1-(benzenesulfonyl)-6-(3,5-dimethylisoxazol-4-yl)pyrrolo[3,2-b]pyridin-3-yl]propanoic acid |
| P-0175 | 3-[1-(benzenesulfonyl)-6-(3,5-dimethylisoxazol-4-yl)-2,3-dihydropyrrolo[3,2-b]pyridin-3-yl]propanoic acid |
| P-0176 | 4-[3-[1-(difluoromethyl)pyrazol-4-yl]-1-[(2-fluorophenyl)methyl]pyrrolo[3,2-b]pyridin-6-yl]-3,5-dimethyl-isoxazole |
| P-0177 | 4-[3-[1-(difluoromethyl)pyrazol-4-yl]-1-(1-phenylethyl)pyrrolo[3,2-b]pyridin-6-yl]-3,5-dimethyl-isoxazole |
| P-0178 | 3,5-dimethyl-4-[1-(oxetan-3-yl)-3-phenylsulfanyl-pyrrolo[2,3-b]pyridin-5-yl]isoxazole |
| P-0179 | 4-[3-(benzenesulfonyl)-1-(oxetan-3-yl)pyrrolo[2,3-b]pyridin-5-yl]-3,5-dimethyl-isoxazole |
| P-0180 | 3,5-dimethyl-4-(3-phenylsulfanyl-1-tetrahydrofuran-3-yl-pyrrolo[2,3-b]pyridm-5-yl)isoxazole |

TABLE 27-continued

| | Compound |
|---|---|
| P-0181 | 4-[3-(benzenesulfonyl)-1-tetrahydrofuran-3-yl-pyrrolo[2,3-b]pyridin-5-yl]-3,5-dimethyl-isoxazole |
| P-0182 | 3,5-dimethyl-4-(3-phenylsulfanyl-1-tetrahydropyran-4-yl-pyrrolo[2,3-b]pyridm-5-yl)isoxazole |
| P-0183 | 4-[3-(benzenesulfonyl)-1-tetrahydropyran-4-yl-pyrrolo[2,3-b]pyridin-5-yl]-3,5-dimethyl-isoxazole |
| P-0184 | 3,5-dimethyl-4-[1-(1-methylpyrazol-4-yl)-3-phenylsulfanyl-pyrrolo[2,3-b]pyridin-5-yl]isoxazole |
| P-0185 | 4-[3-(benzenesulfonyl)-1-(1-methylpyrazol-4-yl)pyrrolo[2,3-b]pyridin-5-yl]-3,5-dimethyl-isoxazole |
| P-0186 | ethyl 2-[6-(3,5-dimethylisoxazol-4-yl)-3-(1-methylpyrazol-4-yl)pyrrolo[3,2-b]pyridin-1-yl]-2-phenyl-acetate |
| P-0187 | 4-[1-(2-fluoro-1-phenyl-ethyl)-3-(1-methylpyrazol-4-yl)pyrrolo[3,2-b]pyridin-6-yl]-3,5-dimethyl-isoxazole |
| P-0188 | 3,5-dimethyl-4-[3-(1-methylpyrazol-4-yl)-1-[[2-(trifluoromethyl)phenyl]methyl]pyrrolo[3,2-b]pyridin-6-yl]isoxazole |
| P-0189 | 4-[1-[(2,6-dichlorophenyl)methyl]-3-(1-methylpyrazol-4-yl)pyrrolo[3,2-b]pyridin-6-yl]-3,5-dimethyl-isoxazole |
| P-0190 | 4-[1-[(2-chloro-5-fluoro-phenyl)methyl]-3-(1-methylpyrazol-4-yl)pyrrolo[3,2-b]pyridin-6-yl]-3,5-dimethyl-isoxazole |
| P-0191 | 4-[1-(benzenesulfonyl)-3-(2-methylthiazol-4-yl)pyrrolo[3,2-b]pyridin-6-yl]-3,5-dimethyl-isoxazole |
| P-0192 | 2-[6-(3,5-dimethylisoxazol-4-yl)-3-(1-methylpyrazol-4-yl)pyrrolo[3,2-b]pyridin-1-yl]-2-phenyl-ethanol |
| P-0193 | 4-[1-[(2-chlorophenyl)methyl]-3-(1-methylpyrazol-4-yl)pyrrolo[3,2-b]pyridin-6-yl]-3,5-dimethyl-isoxazole |
| P-0194 | 3,5-dimethyl-4-[3-(1-methylpyrazol-4-yl)-1-[[2-(trifluoromethoxy)phenyl]methyl]pyrrolo[3,2-b]pyridin-6-yl]isoxazole |
| P-0195 | 3,5-dimethyl-4-[3-(1-methylpyrazol-4-yl)-1-(3-pyridylmethyl)pyrrolo[3,2-b]pyridin-6-yl]isoxazole |
| P-0196 | 3-cyclopentyl-3-[6-(3,5-dimethylisoxazol-4-yl)pyrrolo[3,2-b]pyridin-1-yl]propanenitrile |
| P-0197 | 3-cyclopentyl-3-[6-(3,5-dimethylisoxazol-4-yl)-3-(1-methylpyrazol-4-yl)pyrrolo[3,2-b]pyridin-1-yl]propanenitrile |
| P-0198 | 3,5-dimethyl-4-[3-(1-methylpyrazol-4-yl)-1-(2-pyridylmethyl)pyrrolo[3,2-b]pyridin-6-yl]isoxazole |
| P-0199 | 3,5-dimethyl-4-[1-(1-phenylethyl)-3-(1H-pyrazol-4-yl)pyrrolo[3,2-b]pyridin-6-yl]isoxazole |
| P-0200 | 4-[3-(1-ethylpyrazol-4-yl)-1-(1-phenylethyl)pyrrolo[3,2-b]pyridin-6-yl]-3,5-dimethyl-isoxazole |
| P-0201 | 4-[3-(1-allylpyrazol-4-yl)-1-(1-phenylethyl)pyrrolo[3,2-b]pyridin-6-yl]-3,5-dimethyl-isoxazole |
| P-0202 | 3,5-dimethyl-4-[1-(1-phenylethyl)-3-[1-(2,2,2-trifluoroethyl)pyrazol-4-yl]pyrrolo[3,2-b]pyridin-6-yl]isoxazole |
| P-0203 | 4-[3-[1-(2-methoxyethyl)pyrazol-4-yl]-1-(1-phenylethyl)pyrrolo[3,2-b]pyridin-6-yl]-3,5-dimethyl-isoxazole |
| P-0204 | 3,5-dimethyl-4-[1-(1-phenylethyl)-3-(1-tetrahydrofuran-3-ylpyrazol-4-yl)pyrrolo[3,2-b]pyridin-6-yl]isoxazole |
| P-0205 | 4-[3-(1,3-dimethylpyrazol-4-yl)-1-(1-phenylethyl)pyrrolo[3,2-b]pyridin-6-yl]-3,5-dimethyl-isoxazole |
| P-0206 | 2-[6-(3,5-dimethylisoxazol-4-yl)-3-(1-methylpyrazol-4-yepyrrolo[3,2-b]pyridin-1-yl]-2-phenyl-aceticacid |
| P-0207 | N-cyclopropyl-2-[6-(3,5-dimethylisoxazol-4-yl)-3-(1-methylpyrazol-4-yl)pyrrolo[3,2-b]pyridin-1-yl]-2-phenyl-acetamide |
| P-0208 | (4,4-difluorocyclohexyl)-[6-(3,5-dimethylisoxazol-4-yl)-3-(1-methylpyrazol-4-yl)pyrrolo[3,2-b]pyridin-1-yl]methanone |
| P-0209 | 4-[1-[(4,4-difluorocyclohexyl)methyl]-3-(1-methylpyrazol-4-yl)pyrrolo[3,2-b]pyridin-6-yl]-3,5-dimethyl-isoxazole |
| P-0210 | 4-[1-[(4,4-difluorocyclohexyl)methyl]-3-[1-(difluoromethyl)pyrazol-4-yl]pyrrolo[3,2-b]pyridin-6-yl]-3,5-dimethyl-isoxazole |
| P-0211 | 4-[1-[dideuterio-(4,4-difluorocyclohexyl)methyl]-3-(1-methylpyrazol-4-yl)pyrrolo[3,2-b]pyridin-6-yl]-3,5-dimethyl-isoxazole |
| P-0212 | 4-[1-[(1-fluorocyclohexyl)methyl]-3-(1-methylpyrazol-4-yl)pyrrolo[3,2-b]pyridin-6-yl]-3,5-dimethyl-isoxazole |
| P-0213 | 4-[1-[(3,3-difluorocyclobutyl)methyl]-3-(1-methylpyrazol-4-yl)pyrrolo[3,2-b]pyridin-6-yl]-3,5-dimethyl-isoxazole |
| P-0214 | 4-[1-[dideuterio-(3,3-difluorocyclobutyl)methyl]-3-(1-methylpyrazol-4-yl)pyrrolo[3,2-b]pyridin-6-yl]-3,5-dimethyl-isoxazole |
| P-0215 | 3,5-dimethyl-4-[1-(1-phenylethyl)-3-[3-(trifluoromethyl)-1H-pyrazol-5-yl]pyrrolo[3,2-b]pyridin-6-yl]isoxazole |
| P-0216 | 4-[3-(1-cyclopropylpyrazol-4-yl)-1-(1-phenylethyl)pyrrolo[3,2-b]pyridin-6-yl]-3,5-dimethyl-isoxazole |
| P-0217 | 3,5-dimethyl-4-[3-(1-methylpyrazol-4-yl)-1-[1-(2-pyridyl)ethyl]pyrrolo[3,2-b]pyridin-6-yl]isoxazole |

TABLE 27-continued

| | Compound |
|---|---|
| P-0218 | 1,1-dideuterio-2-[6-(3,5-dimethylisoxazol-4-yl)-3-(1-methylpyrazol-4-yl)pyrrolo[3,2-b]pyridin-1-yl]-2-phenyl-ethanol |
| P-0219 | 4-[1-[dideuterio-(4,4-difluorocyclohexyl)methyl]-3-[1-(difluoromethyl)pyrazol-4-yl]pyrrolo[3,2-b]pyridin-6-yl]-3,5-dimethyl-isoxazole |
| P-0220 | 4-[3-(1-cyclopropylpyrazol-4-yl)-1-[dideuterio-(4,4-difluorocyclohexyl)methyl]pyrrolo[3,2-b]pyridin-6-yl]-3,5-dimethyl-isoxazole |
| P-0221 | 4-[1-[dideuterio-(4,4-difluorocyclohexyl)methyl]-3-[1-(2,2,2-trifluoroethyl)pyrazol-4-yl]pyrrolo[3,2-b]pyridin-6-yl]-3,5-dimethyl-isoxazole |
| P-0222 | 3,5-dimethyl-4-[3-(1-methylpyrazol-4-yl)-1-[(1S)-1-phenylethyl]pyrrolo[3,2-b]pyridin-6-yl]isoxazole |
| P-0223 | 3,5-dimethyl-4-[3-(1-methylpyrazol-4-yl)-1-[(1R)-1-phenylethyl]pyrrolo[3,2-b]pyridin-6-yl]isoxazole |
| P-0224 | 4-[3-iodo-1-(1-phenylethyl)pyrrolo[3,2-b]pyridin-6-yl]-3,5-dimethyl-isoxazole |
| P-0225 | 4-[3-iodo-2-(trifluoromethyl)-1H-pyrrolo[3,2-b]pyridin-6-yl]-3,5-dimethyl-isoxazole |
| P-0226 | 4-[1-[(2-fluorophenyl)methyl]-3-(1-methylpyrazol-4-yl)indol-6-yl]-3,5-dimethyl-isoxazole |
| P-0227 | 4-[1-[(2-chlorophenyl)methyl]-3-(1-methylpyrazol-4-yl)indol-6-yl]-3,5-dimethyl-isoxazole |
| P-0228 | 3,5-dimethyl-4-[3-(1-methylpyrazol-4-yl)-1-[[2-(trifluoromethyl)phenyl]methyl]indol-6-yl]isoxazole |
| P-0229 | 4-[1-[(2,6-difluorophenyl)methyl]-3-(1-methylpyrazol-4-yl)indol-6-yl]-3,5-dimethyl-isoxazole |
| P-0230 | 4-[1-(benzenesulfonyl)-3-(1-methylpyrazol-4-yl)indol-6-yl]-3,5-dimethyl-isoxazole |
| P-0231 | 4-[1-cyclopentylsulfonyl-3-(1-methylpyrazol-4-yl)indol-6-yl]-3,5-dimethyl-isoxazole |
| P-0232 | 3,5-dimethyl-4-[3-(1-methylpyrazol-4-yl)-1-(1-phenylethyl)indol-6-yl]isoxazole |
| P-0233 | 4-[1-(2,2-dideuterio-2-fluoro-1-phenyl-ethyl)-3-(1-methylpyrazol-4-yl)pyrrolo[3,2-b]pyridin-6-yl]-3,5-dimethyl-isoxazole |
| P-0234 | 4-[1-[(1-fluorocyclohexyl)methyl]-3-iodo-pyrrolo[3,2-b]pyridin-6-yl]-3,5-dimethyl-isoxazole |
| P-0235 | 4-[3-[1-(difluoromethyl)pyrazol-4-yl]-1-[(1-fluorocyclohexyl)methyl]pyrrolo[3,2-b]pyridin-6-yl]-3,5-dimethyl-isoxazole |
| P-0236 | 4-[3-(1-cyclopropylpyrazol-4-yl)-1-[(1-fluorocyclohexyl)methyl]pyrrolo[3,2-b]pyridin-6-yl]-3,5-dimethyl-isoxazole |
| P-0237 | 4-[1-[(1-fluorocyclohexyl)methyl]-3-[1-(2,2,2-trifluoroethyl)pyrazol-4-yl]pyrrolo[3,2-b]pyridin-6-yl]-3,5-dimethyl-isoxazole |
| P-0238 | 4-[1-[(1-fluorocyclohexyl)methyl]-3-[1-(2-methoxyethyl)pyrazol-4-yl]pyrrolo[3,2-b]pyridin-6-yl]-3,5-dimethyl-isoxazole |
| P-0239 | 4-[1-[(1-fluorocyclohexyl)methyl]-3-(1H-pyrazol-4-yl)pyrrolo[3,2-b]pyridin-6-yl]-3,5-dimethyl-isoxazole |
| P-0240 | 4-[1-[(8-fluoro-1,4-dioxaspiro[4.5]decan-8-yl)methyl]-3-iodo-pyrrolo[3,2-b]pyridin-6-yl]-3,5-dimethyl-isoxazole |
| P-0241 | 4-[3-[1-(difluoromethyl)pyrazol-4-yl]-1-[(8-fluoro-1,4-dioxaspiro[4.5]decan-8-yl)methyl]pyrrolo[3,2-b]pyridin-6-yl]-3,5-dimethyl-isoxazole |
| P-0242 | 4-[[3-[1-(difluoromethyl)pyrazol-4-yl]-6-(3,5-dimethylisoxazol-4-yl)pyrrolo[3,2-b]pyridin-1-yl]methyl]-4-fluoro-cyclohexanone |
| P-0243 | 4-[3-[1-(difluoromethyl)pyrazol-4-yl]-1-[(1,4,4-trifluorocyclohexyl)methyl]pyrrolo[3,2-b]pyridin-6-yl]-3,5-dimethyl-isoxazole |
| P-0244 | 4-[1-[(1,4-difluorocyclohex-3-en-1-yl)methyl]-3-[1-(difluoromethyl)pyrazol-4-yl]pyrrolo[3,2-b]pyridin-6-yl]-3,5-dimethyl-isoxazole |
| P-0245 | 4-[3-iodo-1-(1-phenylethyl)-2-(trifluoromethyl)pyrrolo[3,2-b]pyridin-6-yl]-3,5-dimethyl-isoxazole |
| P-0246 | 3,5-dimethyl-4-(1H-pyrrolo[2,3-b]pyridin-5-yl)isoxazole |

Compounds listed in Table 28 below, e.g., compounds P-0250 to P-0372 were prepared according to the protocols set forth in Examples 1 to 39 or Examples 40 to 56. The $^1H$ NMR and mass spectroscopy data were consistent with the structures of the compounds.

TABLE 28

| Compound No. | Structure | Name | MS(ESI) [M + H+]+ observed |
|---|---|---|---|
| P-0250 | 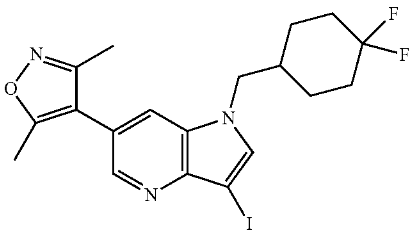 [SMILES: Cc1noc(C)c1-c1cnc2c(I)cn(CC3CCC(F)(F)CC3)c2c1] | 4-[1-[(4,4-difluorocyclohexyl)methyl]-3-iodo-pyrrolo[3,2-b]pyridin-6-yl]-3,5-dimethyl-isoxazole | 472.1 |
| P-0251 | 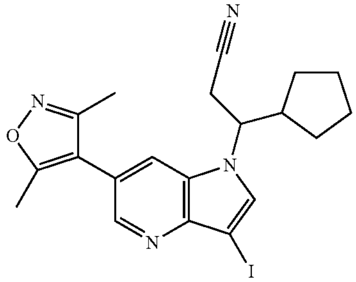 [SMILES: Cc1noc(C)c1-c1cnc2c(I)cn(C(CC#N)C3CCCC3)c2c1] | 3-cyclopentyl-3-[6-(3,5-dimethylisoxazol-4-yl)-3-iodo-pyrrolo[3,2-b]pyridin-1-yl]propanenitrile | 461.2 |
| P-0252 | 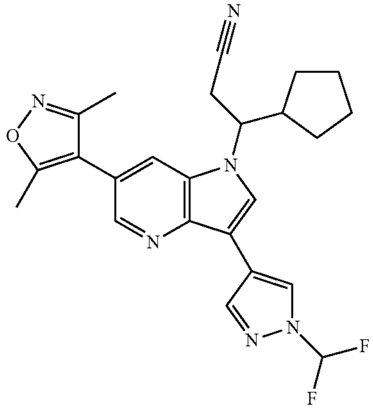 [SMILES: Cc1noc(C)c1-c1cnc2c(-c3cnn(C(F)F)c3)cn(C(CC#N)C3CCCC3)c2c1] | 3-cyclopentyl-3-[3-[1-(difluoromethyl)pyrazol-4-yl]-6-(3,5-dimethylisoxazol-4-yl)pyrrolo[3,2-b]pyridin-1-yl]propanenitrile | 451.0 |
| P-0253 | 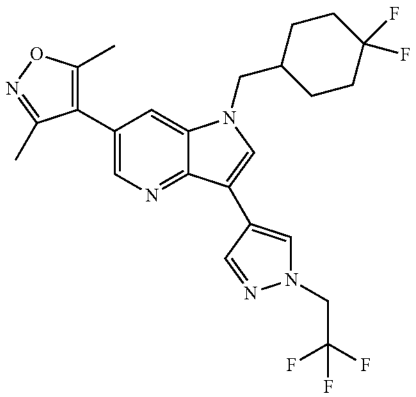 [SMILES: Cc1noc(C)c1-c1cnc2c(-c3cnn(CC(F)(F)F)c3)cn(CC3CCC(F)(F)CC3)c2c1] | 4-[1-[(4,4-difluorocyclohexyl)methyl]-3-[1-(2,2,2-trifluoroethyl)pyrazol-4-yl]pyrrolo[3,2-b]pyridin-6-yl]-3,5-dimethyl-isoxazole | 494.3 |

TABLE 28-continued

| Compound No. | Structure | Name | MS(ESI) [M + H+]+ observed |
|---|---|---|---|
| P-0254 | 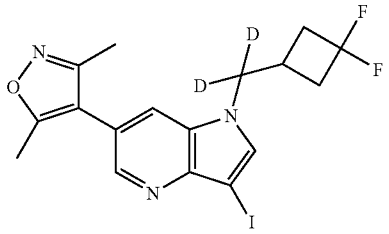 [SMILES: [2H]C([2H])(C1CC(F)(F)C1)n1cc(I)c2ncc(-c3c(C)noc3C)cc21] | 4-[1-[dideuterio-(3,3-difluorocyclobutyl)methyl]-3-iodo-pyrrolo[3,2-b]pyridin-6-yl]-3,5-dimethyl-isoxazole | 446.0 |
| P-0255 | 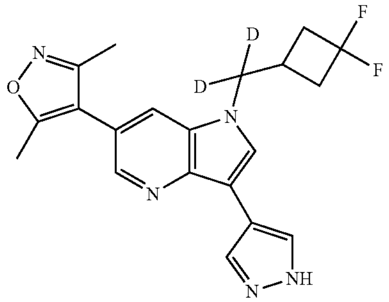 [SMILES: [2H]C([2H])(C1CC(F)(F)C1)n1cc(-c2cn[nH]c2)c2ncc(-c3c(C)noc3C)cc21] | 4-[1-[dideuterio-(3,3-difluorocyclobutyl)methyl]-3-(1H-pyrazol-4-yl)pyrrolo[3,2-b]pyridin-6-yl]-3,5-dimethyl-isoxazole | 386.0 |
| P-0256 | 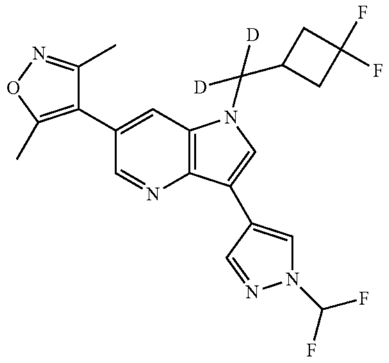 [SMILES: [2H]C([2H])(C1CC(F)(F)C1)n1cc(-c2cnn(C(F)F)c2)c2ncc(-c3c(C)noc3C)cc21] | 4-[1-[dideuterio-(3,3-difluorocyclobutyl)methyl]-3-[1-(difluoromethyl)pyrazol-4-yl]pyrrolo[3,2-b]pyridin-6-yl]-3,5-dimethyl-isoxazole | 436.4 |
| P-0257 | 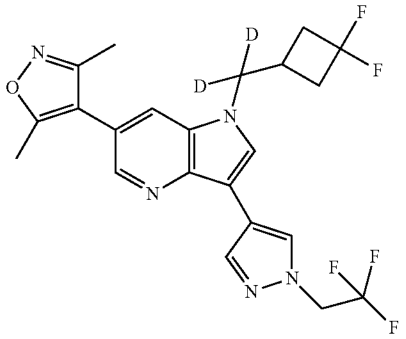 [SMILES: [2H]C([2H])(C1CC(F)(F)C1)n1cc(-c2cnn(CC(F)(F)F)c2)c2ncc(-c3c(C)noc3C)cc21] | 4-[1-[dideuterio-(3,3-difluorocyclobutyl)methyl]-3-[1-(2,2,2-trifluoroethyl)pyrazol-4-yl]pyrrolo[3,2-b]pyridin-6-yl]-3,5-dimethyl-isoxazole | 468.4 |

TABLE 28-continued

| Compound No. | Structure | Name | MS(ESI) [M + H+]+ observed |
|---|---|---|---|
| P-0258 | 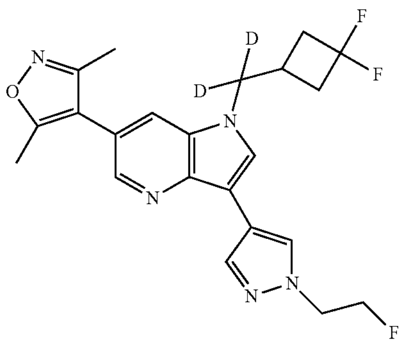 [SMILES: [2H]C([2H])(C1CC(F)(F)C1)n1cc(-c2cnn(CCF)c2)c2ncc(-c3c(C)noc3C)cc21] | 4-[1-[dideuterio-(3,3-difluorocyclobutyl)methyl]-3-[1-(2-fluoroethyl)pyrazol-4-yl]pyrrolo[3,2-b]pyridin-6-yl]-3,5-dimethyl-isoxazole | 432.0 |
| P-0259 | 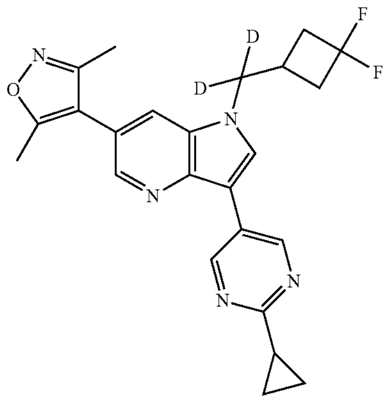 [SMILES: [2H]C([2H])(C1CC(F)(F)C1)n1cc(-c2cnc(C3CC3)nc2)c2ncc(-c3c(C)noc3C)cc21] | 4-[3-(2-cyclopropylpyrimidin-5-yl)-1-[dideuterio-(3,3-difluorocyclobutyl)methyl]pyrrolo[3,2-b]pyridin-6-yl]-3,5-dimethyl-isoxazole | 438.4 |
| P-0260 | 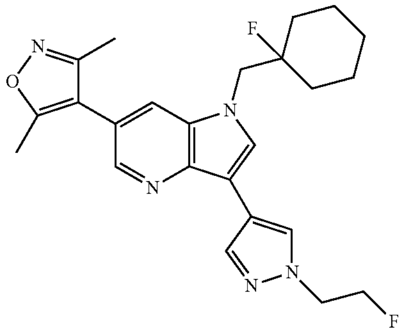 [SMILES: Cc1noc(C)c1-c1cnc2c(-c3cnn(CCF)c3)cn(CC3(F)CCCCC3)c2c1] | 4-[1-[(1-fluorocyclohexyl)methyl]-3-[1-(2-fluoroethyl)pyrazol-4-yl]pyrrolo[3,2-b]pyridin-6-yl]-3,5-dimethyl-isoxazole | 440.3 |
| P-0261 | 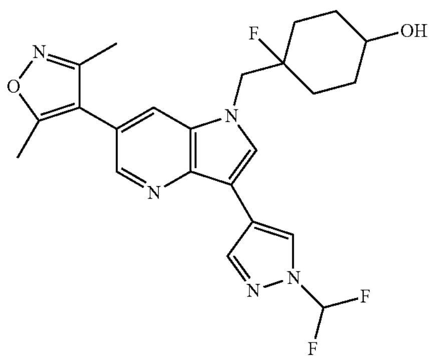 [SMILES: Cc1noc(C)c1-c1cnc2c(-c3cnn(C(F)F)c3)cn(CC3(F)CCC(O)CC3)c2c1] | 4-[[3-[1-(difluoromethyl)pyrazol-4-yl]-6-(3,5-dimethylisoxazol-4-yl)pyrrolo[3,2-b]pyridin-1-yl]methyl]-4-fluoro-cyclohexanol | 460.2 |

TABLE 28-continued

| Compound No. | Structure | Name | MS(ESI) [M + H+]+ observed |
| --- | --- | --- | --- |
| P-0262 | 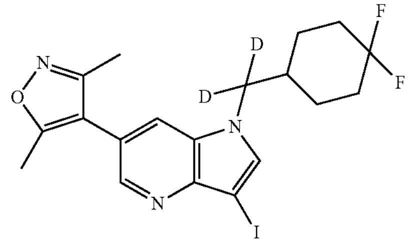 [SMILES: [2H]C([2H])(C1CCC(F)(F)CC1)n1cc(I)c2ncc(-c3c(C)noc3C)cc21] | 4-[1-[dideuterio-(4,4-difluorocyclohexyl)methyl]-3-iodo-pyrrolo[3,2-b]pyridin-6-yl]-3,5-dimethyl-isoxazole | 474.0 |
| P-0263 | 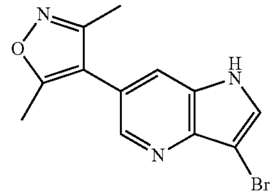 [SMILES: Cc1noc(C)c1-c1cnc2c(Br)c[nH]c2c1] | 4-(3-bromo-1H-pyrrolo[3,2-b]pyridin-6-yl)-3,5-dimethyl-isoxazole | 291.9, 294.0 |
| P-0264 | 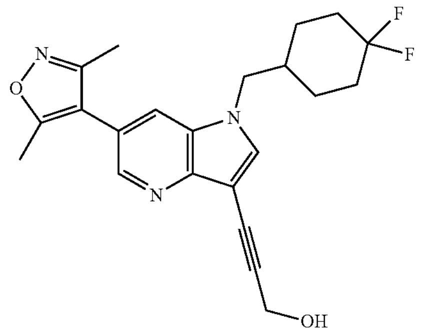 [SMILES: Cc1noc(C)c1-c1cnc2c(C#CCO)cn(CC3CCC(F)(F)CC3)c2c1] | 3-[1-[(4,4-difluorocyclohexyl)methyl]-6-(3,5-dimethylisoxazol-4-yl)pyrrolo[3,2-b]pyridin-3-yl]prop-2-yn-1-ol | 399.9 |
| P-0265 | 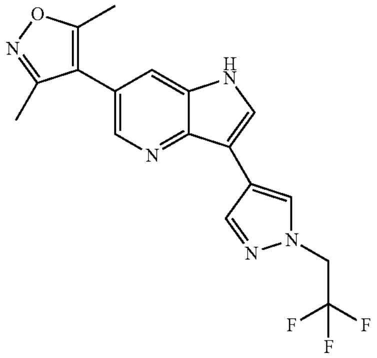 [SMILES: Cc1noc(C)c1-c1cnc2c(-c3cnn(CC(F)(F)F)c3)c[nH]c2c1] | 3,5-dimethyl-4-[3-[1-(2,2,2-trifluoroethyl)pyrazol-4-yl]-1H-pyrrolo[3,2-b]pyridin-6-yl]isoxazole | 362.0 |
| P-0266 | 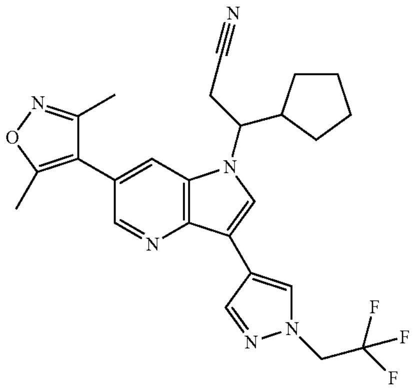 [SMILES: Cc1noc(C)c1-c1cnc2c(-c3cnn(CC(F)(F)F)c3)cn(C(CC#N)C3CCCC3)c2c1] | 3-cyclopentyl-3-[6-(3,5-dimethylisoxazol-4-yl)-3-[1-(2,2,2-trifluoroethyl)pyrazol-4-yl]pyrrolo[3,2-b]pyridin-1-yl]propanenitrile | 483.0 |

TABLE 28-continued
| Compound No. | Structure | Name | MS(ESI) [M + H+]+ observed |
|---|---|---|---|
| P-0267 | 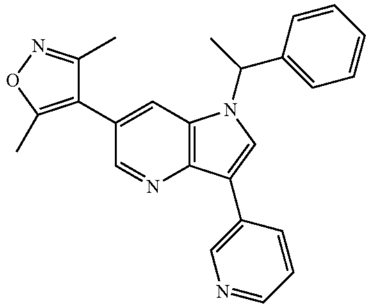 [SMILES: Cc1noc(C)c1-c1cnc2c(-c3cccnc3)cn(C(C)c3ccccc3)c2c1] | 3,5-dimethyl-4-[1-(1-phenylethyl)-3-(3-pyridyl)pyrrolo[3,2-b]pyridin-6-yl]isoxazole | 395.2 |
| P-0268 | 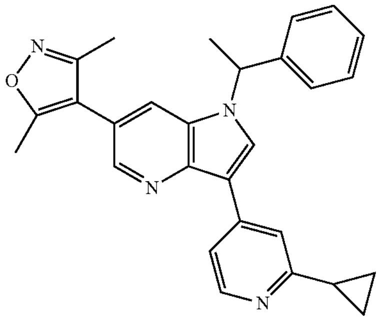 [SMILES: Cc1noc(C)c1-c1cnc2c(-c3ccnc(C4CC4)c3)cn(C(C)c3ccccc3)c2c1] | 4-[3-(2-cyclopropyl-4-pyridyl)-1-(1-phenylethyl)pyrrolo[3,2-b]pyridin-6-yl]-3,5-dimethyl-isoxazole | 435.4 |
| P-0269 | 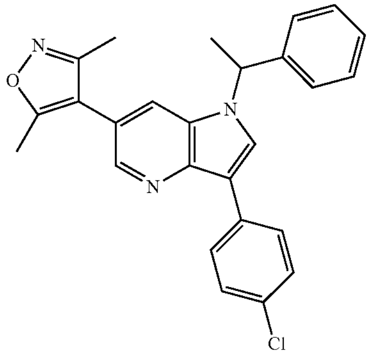 [SMILES: Cc1noc(C)c1-c1cnc2c(-c3ccc(Cl)cc3)cn(C(C)c3ccccc3)c2c1] | 4-[3-(4-chlorophenyl)-1-(1-phenylethyl)pyrrolo[3,2-b]pyridin-6-yl]-3,5-dimethyl-isoxazole | 428.2 |
| P-0270 | 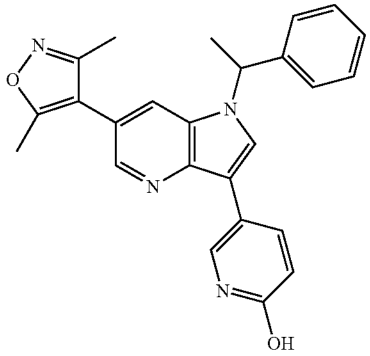 [SMILES: Cc1noc(C)c1-c1cnc2c(-c3ccc(O)nc3)cn(C(C)c3ccccc3)c2c1] | 5-[6-(3,5-dimethylisoxazol-4-yl)-1-(1-phenylethyl)pyrrolo[3,2-b]pyridin-3-yl]pyridin-2-ol | 411.1 |

TABLE 28-continued
| Compound No. | Structure | Name | MS(ESI) [M + H+]+ observed |
|---|---|---|---|
| P-0271 | 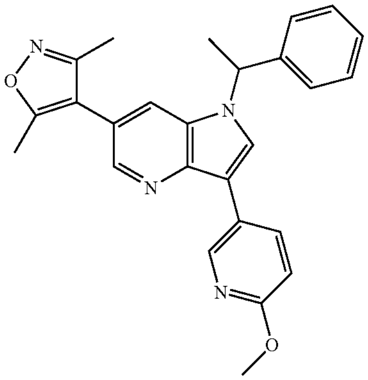 [SMILES: COc1ccc(-c2cn(C(C)c3ccccc3)c3cc(-c4c(C)noc4C)cnc23)cn1] | 4-[3-(6-methoxy-3-pyridyl)-1-(1-phenylethyl)pyrrolo[3,2-b]pyridin-6-yl]-3,5-dimethyl-isoxazole | 425.2 |
| P-0272 | 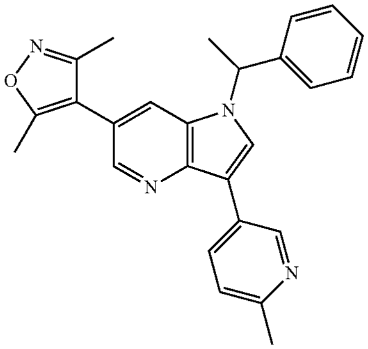 [SMILES: Cc1ccc(-c2cn(C(C)c3ccccc3)c3cc(-c4c(C)noc4C)cnc23)cn1] | 3,5-dimethyl-4-[3-(6-methyl-3-pyridyl)-1-(1-phenylethyl)pyrrolo[3,2-b]pyridin-6-yl]isoxazole | 409.3 |
| P-0273 | 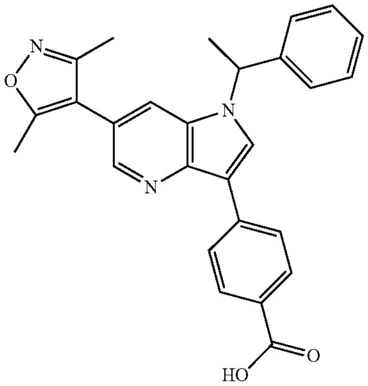 [SMILES: Cc1noc(C)c1-c1cnc2c(-c3ccc(C(=O)O)cc3)cn(C(C)c3ccccc3)c2c1] | 4-[6-(3,5-dimethylisoxazol-4-yl)-1-(1-phenylethyl)pyrrolo[3,2-b]pyridin-3-yl]benzoic acid | 438.1 |
| P-0274 | 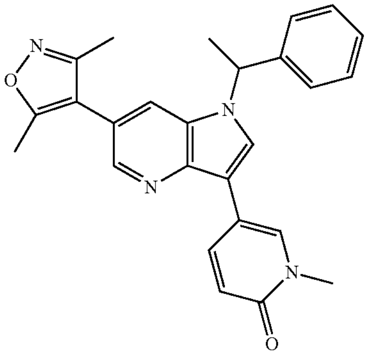 [SMILES: Cc1noc(C)c1-c1cnc2c(-c3ccc(=O)n(C)c3)cn(C(C)c3ccccc3)c2c1] | 5-[6-(3,5-dimethylisoxazol-4-yl)-1-(1-phenylethyl)pyrrolo[3,2-b]pyridin-3-yl]-1-methyl-pyridin-2-one | 425.2 |

TABLE 28-continued

| Compound No. | Structure | Name | MS(ESI) [M + H+]+ observed |
|---|---|---|---|
| P-0275 | 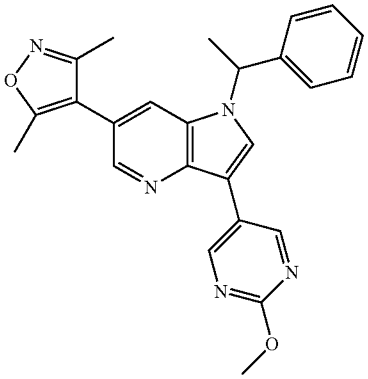 [SMILES: COc1ncc(-c2cn(C(C)c3ccccc3)c3cc(-c4c(C)noc4C)cnc23)cn1] | 4-[3-(2-methoxypyrimidin-5-yl)-1-(1-phenylethyl)pyrrolo[3,2-b]pyridin-6-yl]-3,5-dimethyl-isoxazole | 426.1 |
| P-0276 | 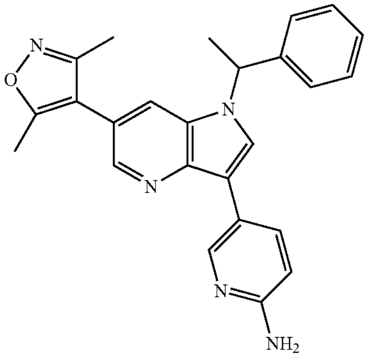 [SMILES: Cc1noc(C)c1-c1cnc2c(-c3ccc(N)nc3)cn(C(C)c3ccccc3)c2c1] | 5-[6-(3,5-dimethylisoxazol-4-yl)-1-(1-phenylethyl)pyrrolo[3,2-b]pyridin-3-yl]pyridin-2-amine | 410.2 |
| P-0277 | 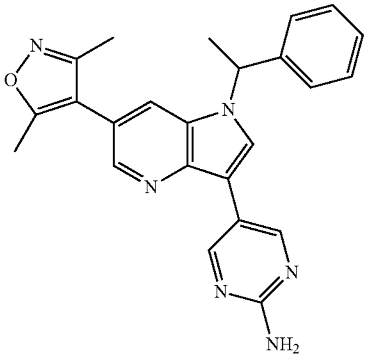 [SMILES: Cc1noc(C)c1-c1cnc2c(-c3cnc(N)nc3)cn(C(C)c3ccccc3)c2c1] | 5-[6-(3,5-dimethylisoxazol-4-yl)-1-(1-phenylethyl)pyrrolo[3,2-b]pyridin-3-yl]pyrimidin-2-amine | 411.1 |
| P-0278 | 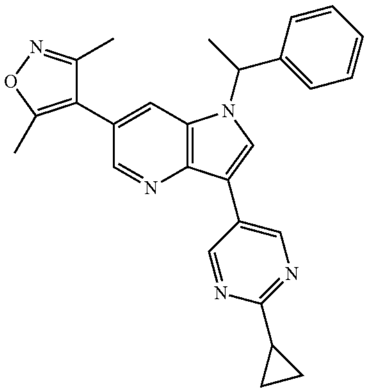 [SMILES: Cc1noc(C)c1-c1cnc2c(-c3cnc(C4CC4)nc3)cn(C(C)c3ccccc3)c2c1] | 4-[3-(2-cyclopropylpyrimidin-5-yl)-1-(1-phenylethyl)pyrrolo[3,2-b]pyridin-6-yl]-3,5-dimethyl-isoxazole | 436.3 |

TABLE 28-continued

| Compound No. | Structure | Name | MS(ESI) [M + H+]+ observed |
| --- | --- | --- | --- |
| P-0279 | 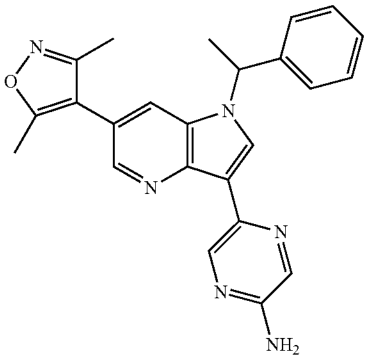 [SMILES: Cc1noc(C)c1-c1cnc2c(-c3cnc(N)cn3)cn(C(C)c3ccccc3)c2c1] | 5-[6-(3,5-dimethylisoxazol-4-yl)-1-(1-phenylethyl)pyrrolo[3,2-b]pyridin-3-yl]pyrazin-2-amine | 411.1 |
| P-0280 | 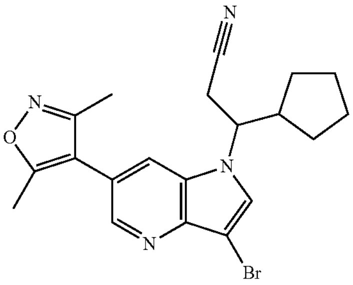 | 3-[3-bromo-6-(3,5-dimethylisoxazol-4-yl)pyrrolo[3,2-b]pyridin-1-yl]-3-cyclopentyl-propanenitrile | 412.9 |
| P-0281 | 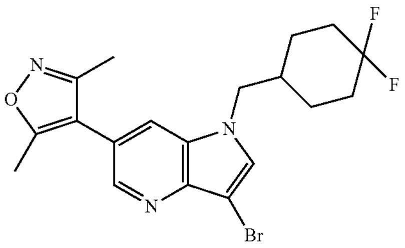 | 4-[3-bromo-1-[(4,4-difluorocyclohexyl)methyl]pyrrolo[3,2-b]pyridin-6-yl]-3,5-dimethyl-isoxazole | 423.9 |
| P-0282 | 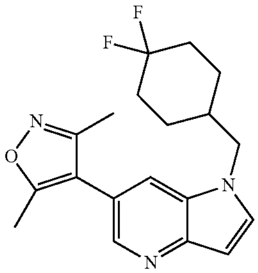 [SMILES: Cc1noc(C)c1-c1cnc2ccn(CC3CCC(F)(F)CC3)c2c1] | 4-[1-[(4,4-difluorocyclohexyl)methyl]pyrrolo[3,2-b]pyridin-6-yl]-3,5-dimethyl-isoxazole | 346.1 |
| P-0283 | 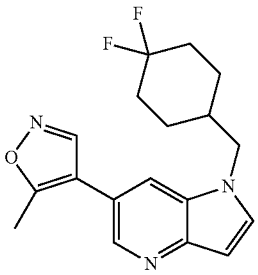 [SMILES: Cc1oncc1-c1cnc2ccn(CC3CCC(F)(F)CC3)c2c1] | 4-[1-[(4,4-difluorocyclohexyl)methyl]pyrrolo[3,2-b]pyridin-6-yl]-5-methyl-isoxazole | 331.9 |

TABLE 28-continued

| Compound No. | Structure | Name | MS(ESI) [M + H+]+ observed |
|---|---|---|---|
| P-0284 | 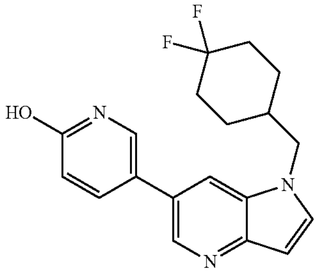 [SMILES: Oc1ccc(-c2cnc3ccn(CC4CCC(F)(F)CC4)c3c2)cn1] | 5-[1-[(4,4-difluorocyclohexyl)methyl]pyrrolo[3,2-b]pyridin-6-yl]pyridin-2-ol | 343.9 |
| P-0285 | 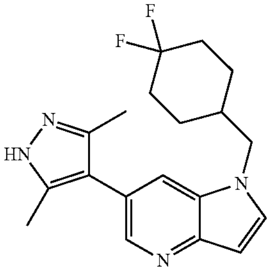 [SMILES: Cc1n[nH]c(C)c1-c1cnc2ccn(CC3CCC(F)(F)CC3)c2c1] | 1-[(4,4-difluorocyclohexyl)methyl]-6-(3,5-dimethyl-1H-pyrazol-4-yl)pyrrolo[3,2-b]pyridine | 345.2 |
| P-0286 | 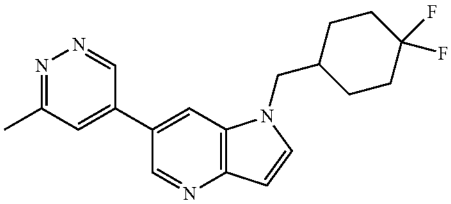 [SMILES: Cc1cc(-c2cnc3ccn(CC4CCC(F)(F)CC4)c3c2)cnn1] | 1-[(4,4-difluorocyclohexyl)methyl]-6-(6-methylpyridazin-4-yl)pyrrolo[3,2-b]pyridine | 342.9 |
| P-0287 | 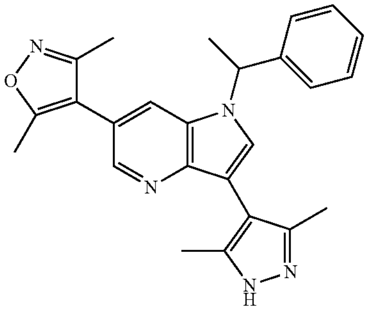 [SMILES: Cc1n[nH]c(C)c1-c1cn(C(C)c2ccccc2)c2cc(-c3c(C)noc3C)cnc12] | 4-[3-(3,5-dimethyl-1H-pyrazol-4-yl)-1-(1-phenylethyl)pyrrolo[3,2-b]pyridin-6-yl]-3,5-dimethyl-isoxazole | 412.3 |
| P-0288 | 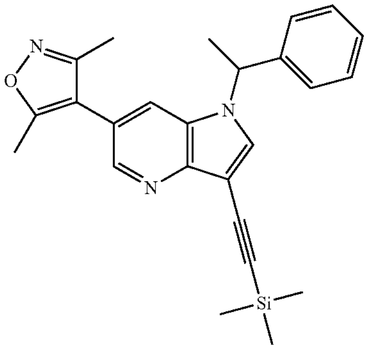 [SMILES: Cc1noc(C)c1-c1cnc2c(C#C[Si](C)(C)C)cn(C(C)c3ccccc3)c2c1] | 2-[6-(3,5-dimethylisoxazol-4-yl)-1-(1-phenylethyl)pyrrolo[3,2-b]pyridin-3-yl]ethynyl-trimethyl-silane | 414.1 |

TABLE 28-continued

| Compound No. | Structure | Name | MS(ESI) [M + H+]+ observed |
|---|---|---|---|
| P-0289 | 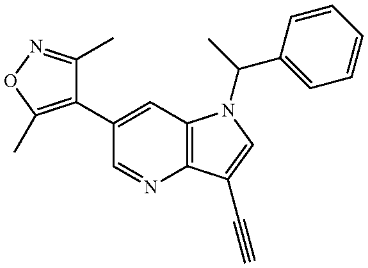 [SMILES: C#Cc1cn(C(C)c2ccccc2)c2cc(-c3c(C)noc3C)cnc12] | 4-[3-ethynyl-1-(1-phenylethyl)pyrrolo[3,2-b]pyridin-6-yl]-3,5-dimethyl-isoxazole | 342.3 |
| P-0290 | 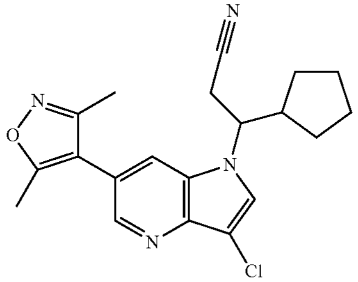 [SMILES: Cc1noc(C)c1-c1cnc2c(Cl)cn(C(CC#N)C3CCCC3)c2c1] | 3-[3-chloro-6-(3,5-dimethylisoxazol-4-yl)pyrrolo[3,2-b]pyridin-1-yl]-3-cyclopentyl-propanenitrile | 368.9 |
| P-0291 | 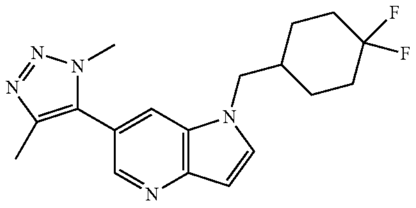 [SMILES: Cc1nnn(C)c1-c1cnc2ccn(CC3CCC(F)(F)CC3)c2c1] | 1-[(4,4-difluorocyclohexyl)methyl]-6-(3,5-dimethyltriazol-4-yl)pyrrolo[3,2-b]pyridine | 346.2 |
| P-0292 | 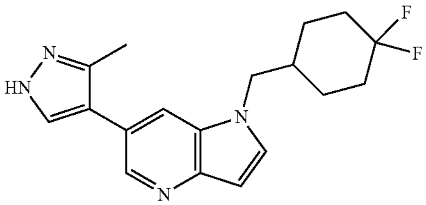 [SMILES: Cc1n[nH]cc1-c1cnc2ccn(CC3CCC(F)(F)CC3)c2c1] | 1-[(4,4-difluorocyclohexyl)methyl]-6-(3-methyl-1H-pyrazol-4-yl)pyrrolo[3,2-b]pyridine | 331.2 |
| P-0293 | 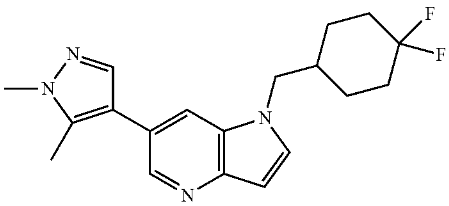 [SMILES: Cc1c(-c2cnc3ccn(CC4CCC(F)(F)CC4)c3c2)cnn1C] | 1-[(4,4-difluorocyclohexyl)methyl]-6-(1,5-dimethylpyrazol-4-yl)pyrrolo[3,2-b]pyridine | 346.1 |
| P-0294 | 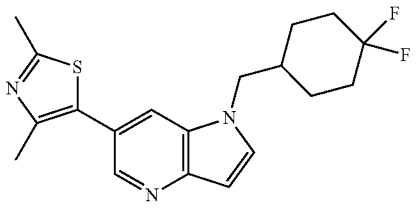 [SMILES: Cc1nc(C)c(-c2cnc3ccn(CC4CCC(F)(F)CC4)c3c2)s1] | 5-[1-[(4,4-difluorocyclohexyl)methyl]pyrrolo[3,2-b]pyridin-6-yl]-2,4-dimethyl-thiazole | 362.5 |

TABLE 28-continued

| Compound No. | Structure | Name | MS(ESI) [M + H+]+ observed |
|---|---|---|---|
| P-0295 | 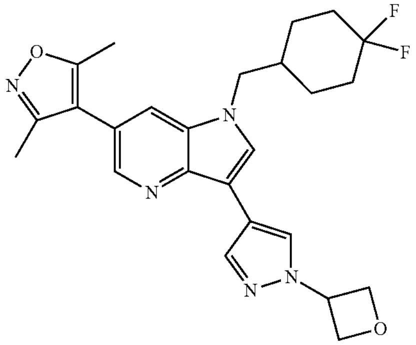 [SMILES: Cc1noc(C)c1-c1cnc2c(-c3cnn(C4COC4)c3)cn(CC3CCC(F)(F)CC3)c2c1] | 4-[1-[(4,4-difluorocyclohexyl)methyl]-3-[1-(oxetan-3-yl)pyrazol-4-yl]pyrrolo[3,2-b]pyridin-6-yl]-3,5-dimethyl-isoxazole | 468.0 |
| P-0296 | 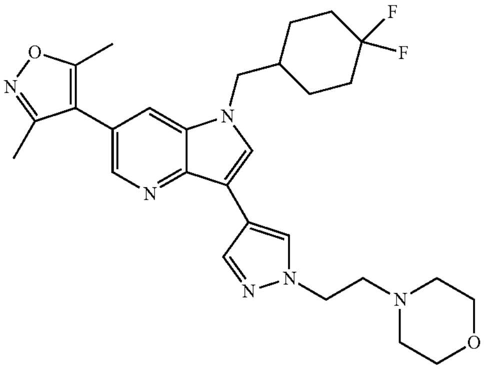 [SMILES: Cc1noc(C)c1-c1cnc2c(-c3cnn(CCN4CCOCC4)c3)cn(CC3CCC(F)(F)CC3)c2c1] | 4-[2-[4-[1-[(4,4-difluorocyclohexyl)methyl]-6-(3,5-dimethylisoxazol-4-yl)pyrrolo[3,2-b]pyridin-3-yl]pyrazol-1-yl]ethyl]morpholine | 525.1 |
| P-0297 | 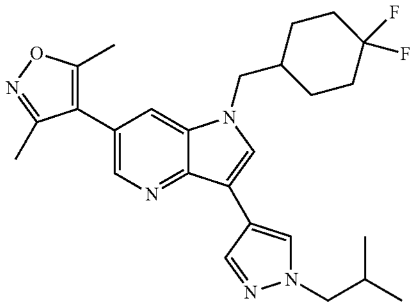 [SMILES: Cc1noc(C)c1-c1cnc2c(-c3cnn(CC(C)C)c3)cn(CC3CCC(F)(F)CC3)c2c1] | 4-[1-[(4,4-difluorocyclohexyl)methyl]-3-(1-isobutylpyrazol-4-yl)pyrrolo[3,2-b]pyridin-6-yl]-3,5-dimethyl-isoxazole | 468.1 |
| P-0298 | 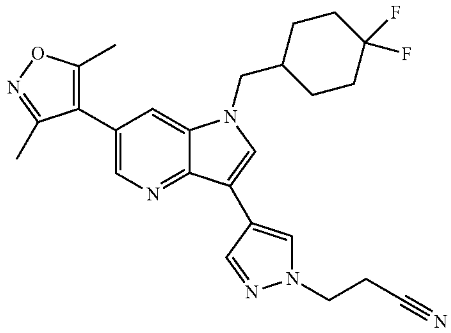 [SMILES: Cc1noc(C)c1-c1cnc2c(-c3cnn(CCC#N)c3)cn(CC3CCC(F)(F)CC3)c2c1] | 3-[4-[1-[(4,4-difluorocyclohexyl)methyl]-6-(3,5-dimethylisoxazol-4-yl)pyrrolo[3,2-b]pyridin-3-yl]pyrazol-1-yl]propanenitrile | 465.0 |

TABLE 28-continued

| Compound No. | Structure | Name | MS(ESI) [M + H+]+ observed |
|---|---|---|---|
| P-0299 | 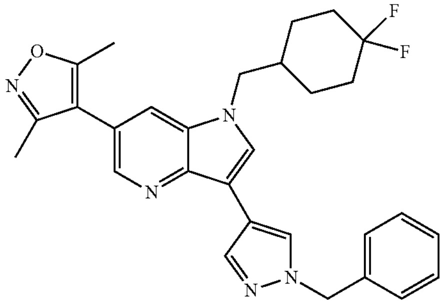 [SMILES: Cc1noc(C)c1-c1cnc2c(-c3cnn(Cc4ccccc4)c3)cn(CC3CCC(F)(F)CC3)c2c1] | 4-[3-(1-benzylpyrazol-4-yl)-1-[(4,4-difluorocyclohexyl)methyl]pyrrolo[3,2-b]pyridin-6-yl]-3,5-dimethyl-isoxazole | 502.1 |
| P-0300 | 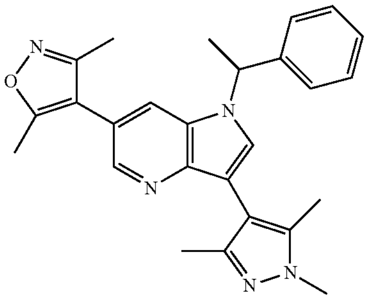 [SMILES: Cc1noc(C)c1-c1cnc2c(-c3c(C)nn(C)c3C)cn(C(C)c3ccccc3)c2c1] | 3,5-dimethyl-4-[1-(1-phenylethyl)-3-(1,3,5-trimethylpyrazol-4-yl)pyrrolo[3,2-b]pyridin-6-yl]isoxazole | 426.4 |
| P-0301 | 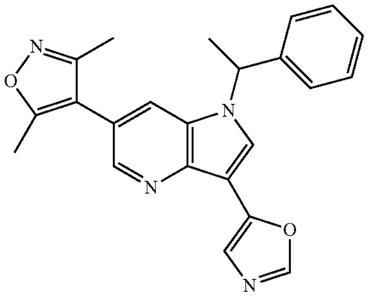 [SMILES: Cc1noc(C)c1-c1cnc2c(-c3cnco3)cn(C(C)c3ccccc3)c2c1] | 3,5-dimethyl-4-[3-oxazol-5-yl-1-(1-phenylethyl)pyrrolo[3,2-b]pyridin-6-yl]isoxazole | 385.2 |
| P-0302 | 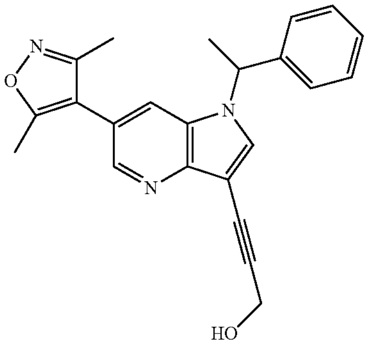 [SMILES: Cc1noc(C)c1-c1cnc2c(C#CCO)cn(C(C)c3ccccc3)c2c1] | 3-[6-(3,5-dimethylisoxazol-4-yl)-1-(1-phenylethyl)pyrrolo[3,2-b]pyridin-3-yl]prop-2-yn-1-ol | 372.3 |
| P-0303 | 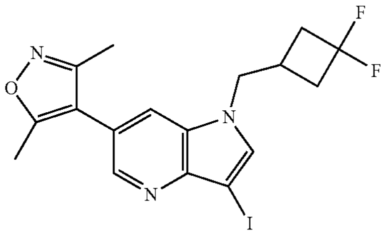 [SMILES: Cc1noc(C)c1-c1cnc2c(I)cn(CC3CC(F)(F)C3)c2c1] | 4-[1-[(3,3-difluorocyclobutyl)methyl]-3-iodo-pyrrolo[3,2-b]pyridin-6-yl]-3,5-dimethyl-isoxazole | 444.0 |

TABLE 28-continued

| Compound No. | Structure | Name | MS(ESI) [M + H+]+ observed |
|---|---|---|---|
| P-0304 | 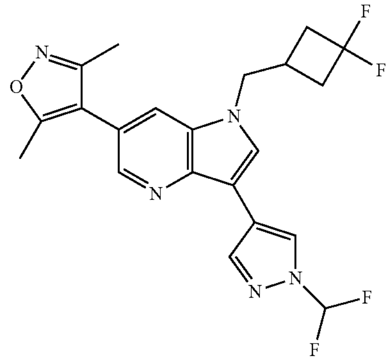 [SMILES: Cc1noc(C)c1-c1cnc2c(-c3cnn(C(F)F)c3)cn(CC3CC(F)(F)C3)c2c1] | 4-[1-[(3,3-difluorocyclobutyl)methyl]-3-[1-(2,2,2-trifluoroethyl)pyrazol-4-yl]pyrrolo[3,2-b]pyridin-6-yl]-3,5-dimethyl-isoxazole | 434.2 |
| P-0305 | 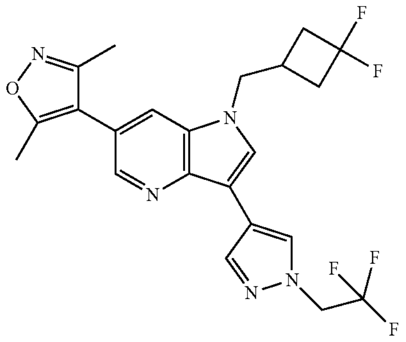 [SMILES: Cc1noc(C)c1-c1cnc2c(-c3cnn(CC(F)(F)F)c3)cn(CC3CC(F)(F)C3)c2c1] | 4-[1-[(3,3-difluorocyclobutyl)methyl]-3-[1-(2,2,2-trifluoroethyl)pyrazol-4-yl]pyrrolo[3,2-b]pyridin-6-yl]-3,5-dimethyl-isoxazole | 466.2 |
| P-0306 | 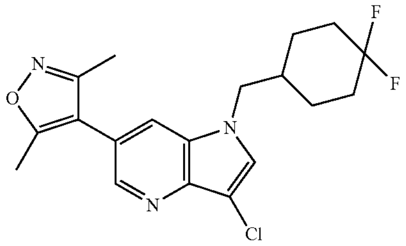 [SMILES: Cc1noc(C)c1-c1cnc2c(Cl)cn(CC3CCC(F)(F)CC3)c2c1] | 4-[3-chloro-1-[(4,4-difluorocyclohexyl)methyl]pyrrolo[3,2-b]pyridin-6-yl]-3,5-dimethyl-isoxazole | 379.9 |
| P-0307 | 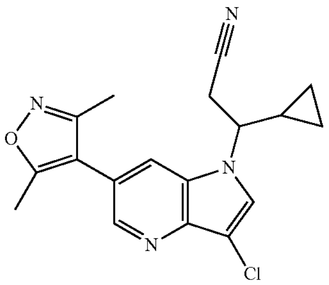 [SMILES: Cc1noc(C)c1-c1cnc2c(Cl)cn(C(CC#N)C3CC3)c2c1] | 3-[3-chloro-6-(3,5-dimethylisoxazol-4-yl)pyrrolo[3,2-b]pyridin-1-yl]-3-cyclopropyl-propanenitrile | 340.8 |
| P-0308 | 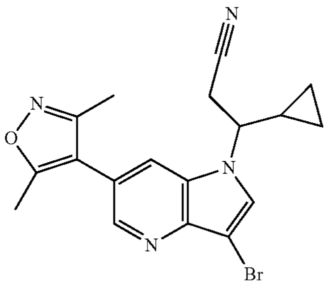 [SMILES: Cc1noc(C)c1-c1cnc2c(Br)cn(C(CC#N)C3CC3)c2c1] | 3-[3-bromo-6-(3,5-dimethylisoxazol-yl)pyrrolo[3,2-b]pyridin-1-yl]-3-cyclopropyl-propanenitrile | 384.8 |

TABLE 28-continued

| Compound No. | Structure | Name | MS(ESI) [M + H+]+ observed |
|---|---|---|---|
| P-0309 | 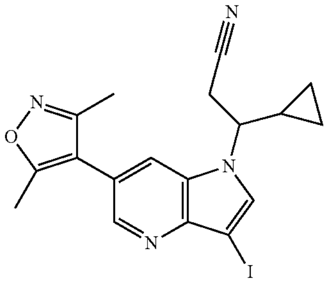 [SMILES: Cc1noc(C)c1-c1cnc2c(I)cn(C(CC#N)C3CC3)c2c1] | 3-cyclopropyl-3-[6-(3,5-dimethylisoxazol-4-yl)-3-iodo-pyrrolo[3,2-b]pyridin-1-yl]propanenitrile | 432.8 |
| P-0310 | 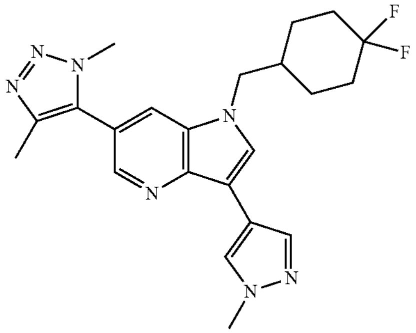 [SMILES: Cc1nnn(C)c1-c1cnc2c(-c3cnn(C)c3)cn(CC3CCC(F)(F)CC3)c2c1] | 1-[(4,4-difluorocyclohexyl)methyl]-6-(3,5-dimethyltriazol-4-yl)-3-(1-methylpyrazol-4-yl)pyrrolo[3,2-b]pyridine | 425.9 |
| P-0311 | 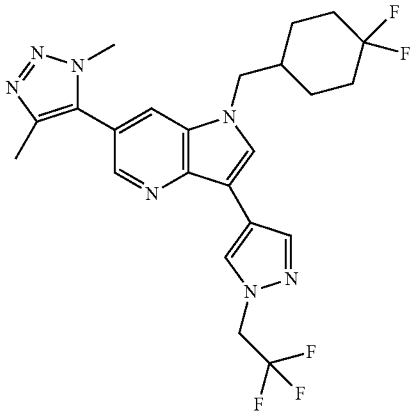 [SMILES: Cc1nnn(C)c1-c1cnc2c(-c3cnn(CC(F)(F)F)c3)cn(CC3CCC(F)(F)CC3)c2c1] | 1-[(4,4-difluorocyclohexyl)methyl]-6-(3,5-dimethyltriazol-4-yl)-3-[1-(2,2,2-trifluoroethyl)pyrazol-4-yl]pyrrolo[3,2-b]pyridine | 494.0 |
| P-0312 | 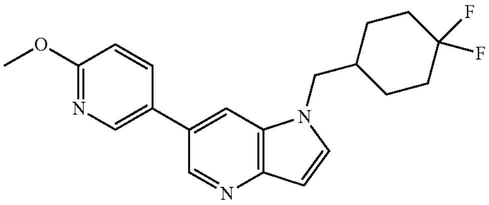 [SMILES: COc1ccc(-c2cnc3ccn(CC4CCC(F)(F)CC4)c3c2)cn1] | 1-[(4,4-difluorocyclohexyl)methyl]-6-(6-methoxy-3-pyridyl)pyrrolo[3,2-b]pyridine | 359.1 |
| P-0313 | 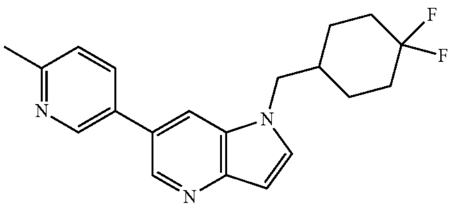 [SMILES: Cc1ccc(-c2cnc3ccn(CC4CCC(F)(F)CC4)c3c2)cn1] | 1-[(4,4-difluorocyclohexyl)methyl]-6-(6-methyl-3-pyridyl)pyrrolo[3,2-b]pyridine | 341.9 |

TABLE 28-continued

| Compound No. | Structure | Name | MS(ESI) [M + H+]+ observed |
|---|---|---|---|
| P-0314 | 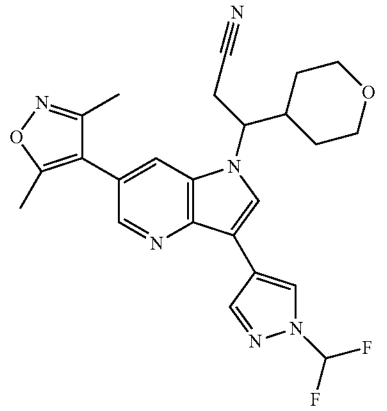 [SMILES: Cc1noc(C)c1-c1cnc2c(-c3cnn(C(F)F)c3)cn(C(CC#N)C3CCOCC3)c2c1] | 3-[3-[1-(difluoromethyl)pyrazol-4-yl]-6-(3,5-dimethylisoxazol-4-yl)pyrrolo[3,2-b]pyridin-1-yl]-3-tetrahydropyran-4-yl-propanenitrile | 467.1 |
| P-0315 | 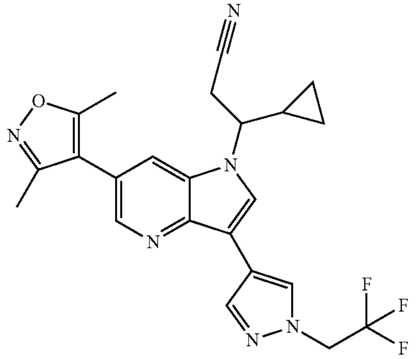 [SMILES: Cc1noc(C)c1-c1cnc2c(-c3cnn(CC(F)(F)F)c3)cn(C(CC#N)C3CC3)c2c1] | 3-cyclopropyl-3-[6-(3,5-dimethylisoxazol-4-yl)-3-[1-(2,2,2-trifluoroethyl)pyrazol-4-yl]pyrrolo[3,2-b]pyridin-1-yl]propanenitrile | 455.3 |
| P-0316 | 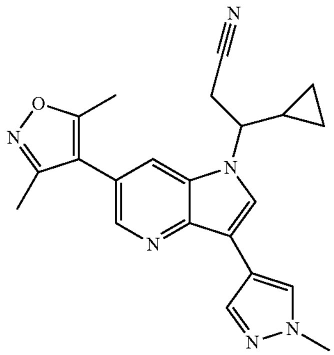 [SMILES: Cc1noc(C)c1-c1cnc2c(-c3cnn(C)c3)cn(C(CC#N)C3CC3)c2c1] | 3-cyclopropyl-3-[6-(3,5-dimethylisoxazol-4-yl)-3-(1-methylpyrazol-4-yl)pyrrolo[3,2-b]pyridin-1-yl]propanenitrile | 386.9 |
| P-0317 | 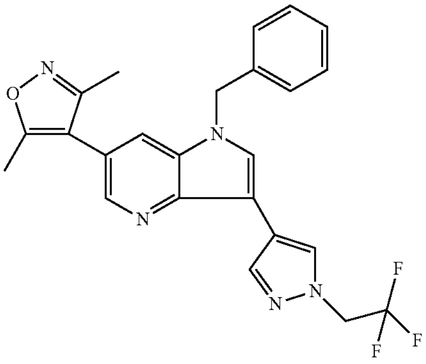 [SMILES: Cc1noc(C)c1-c1cnc2c(-c3cnn(CC(F)(F)F)c3)cn(Cc3ccccc3)c2c1] | 4-[1-benzyl-3-[1-(2,2,2-trifluoroethyl)pyrazol-4-yl]pyrrolo[3,2-b]pyridin-6-yl]-3,5-dimethyl-isoxazole | 452.2 |

TABLE 28-continued

| Compound No. | Structure | Name | MS(ESI) [M + H+]+ observed |
|---|---|---|---|
| P-0318 | 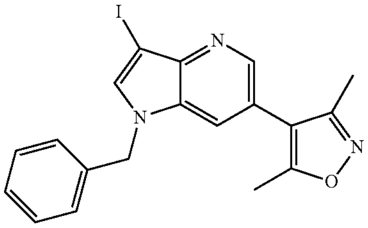 [SMILES: Cc1noc(C)c1-c1cnc2c(I)cn(Cc3ccccc3)c2c1] | 4-(1-benzyl-3-iodo-pyrrolo[3,2-b]pyridin-6-yl)-3,5-dimethyl-isoxazole | 430.0 |
| P-0319 | 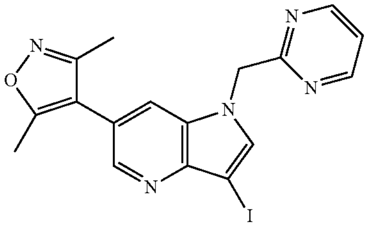 [SMILES: Cc1noc(C)c1-c1cnc2c(I)cn(Cc3ncccn3)c2c1] | 4-[3-iodo-1-(pyrimidin-2-ylmethyl)pyrrolo[3,2-b]pyridin-6-yl]-3,5-dimethyl-isoxazole | 432.0 |
| P-0320 | 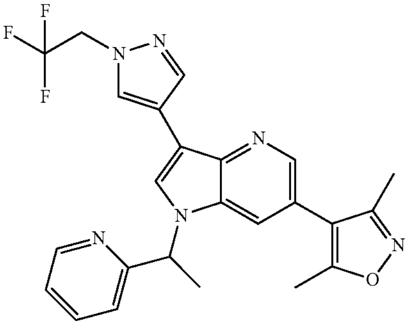 [SMILES: Cc1noc(C)c1-c1cnc2c(-c3cnn(CC(F)(F)F)c3)cn(C(C)c3ccccn3)c2c1] | 3,5-dimethyl-4-[1-[1-(2-pyridyl)ethyl]-3-[1-(2,2,2-trifluoroethyl)pyrazol-4-yl]pyrrolo[3,2-b]pyridin-6-yl]isoxazole | 467.2 |
| P-0321 | 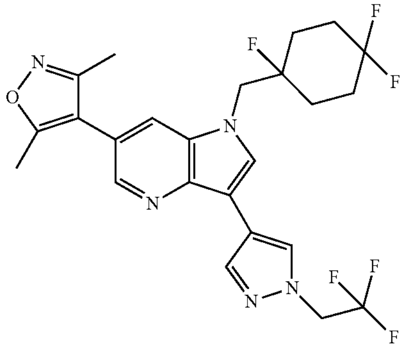 [SMILES: Cc1noc(C)c1-c1cnc2c(-c3cnn(CC(F)(F)F)c3)cn(CC3(F)CCC(F)(F)CC3)c2c1] | 3,5-dimethyl-4-[1-[(1,4,4-trifluorocyclohexyl)methyl]-3-[1-(2,2,2-trifluoroethyl)pyrazol-4-yl]pyrrolo[3,2-b]pyridin-6-yl]isoxazole | 512.0 |
| P-0322 | 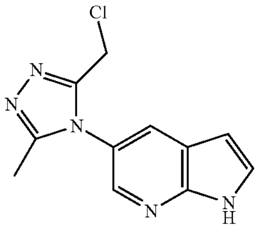 [SMILES: Cc1nnc(CCl)n1-c1cnc2[nH]ccc2c1] | 5-[3-(chloromethyl)-5-methyl-1,2,4-triazol-4-yl]-1H-pyrrolo[2,3-b]pyridine | 247.8 |

TABLE 28-continued

| Compound No. | Structure | Name | MS(ESI) [M + H+]+ observed |
|---|---|---|---|
| P-0323 | 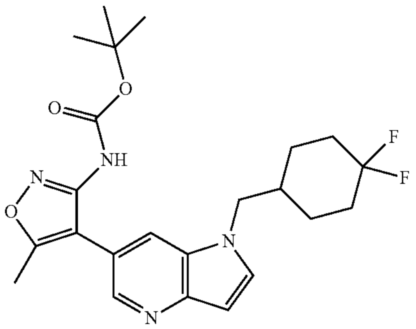 [SMILES: Cc1onc(NC(=O)OC(C)(C)C)c1-c1cnc2ccn(CC3CCC(F)(F)CC3)c2c1] | tert-butyl N-[4-[1-[(4,4-difluorocyclohexyl)methyl]pyrrolo[3,2-b]pyridin-6-yl]-5-methyl-isoxazol-3-yl]carbamate | 447.2 |
| P-0324 | 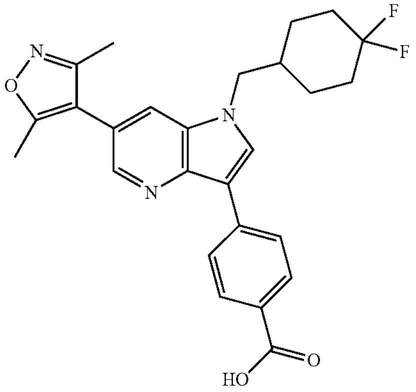 [SMILES: Cc1noc(C)c1-c1cnc2c(-c3ccc(C(=O)O)cc3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]benzoic acid | 466.0 |
| P-0325 | 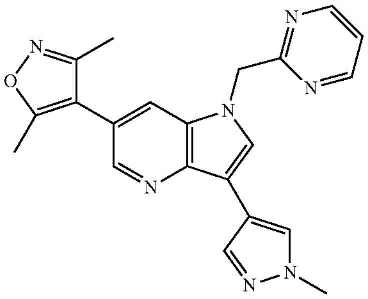 | 3,5-dimethyl-4-[3-(1-methylpyrazol-4-yl)-1-(pyrimidin-2-ylmethyl)pyrrolo[3,2-b]pyridin-6-yl]isoxazole | 386.2 |
| P-0326 | 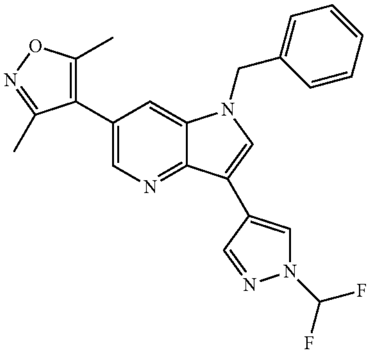 [SMILES: Cc1noc(C)c1-c1cnc2c(-c3cnn(C(F)F)c3)cn(Cc3ccccc3)c2c1] | 4-[1-benzyl-3-[1-(difluoromethyl)pyrazol-4-yl]pyrrolo[3,2-b]pyridin-6-yl]-3,5-dimethyl-isoxazole | 419.9 |

TABLE 28-continued

| Compound No. | Structure | Name | MS(ESI) [M + H+]+ observed |
|---|---|---|---|
| P-0327 | 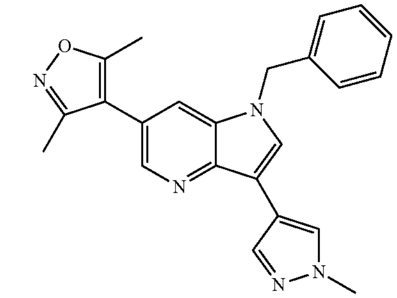 [SMILES: Cc1noc(C)c1-c1cnc2c(-c3cnn(C)c3)cn(Cc3ccccc3)c2c1] | 4-[1-benzyl-3-(1-methylpyrazol-4-yl)pyrrolo[3,2-b]pyridin-6-yl]-3,5-dimethyl-isoxazole | 383.9 |
| P-0328 | 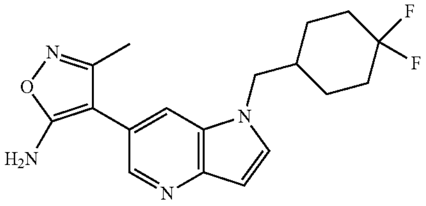 [SMILES: Cc1noc(N)c1-c1cnc2ccn(CC3CCC(F)(F)CC3)c2c1] | 4-[1-[(4,4-difluorocyclohexyl)methyl]pyrrolo[3,2-b]pyridin-6-yl]-3-methyl-isoxazol-5-amine | 347.1 |
| P-0329 | 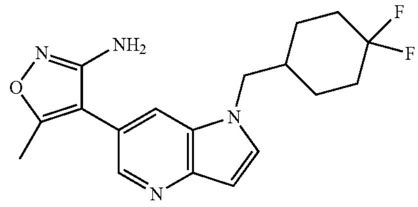 [SMILES: Cc1onc(N)c1-c1cnc2ccn(CC3CCC(F)(F)CC3)c2c1] | 4-[1-[(4,4-difluorocyclohexyl)methyl]pyrrolo[3,2-b]pyridin-6-yl]-5-methyl-isoxazol-3-amine | 347.1 |
| P-0330 | 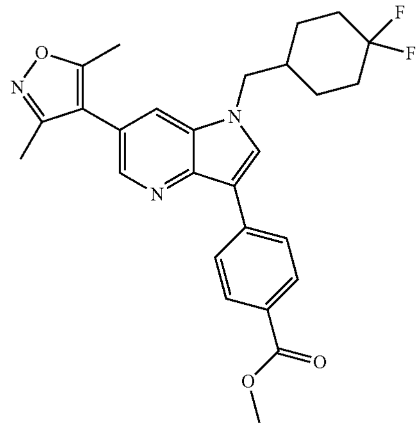 [SMILES: COC(=O)c1ccc(-c2cn(CC3CCC(F)(F)CC3)c3cc(-c4c(C)noc4C)cnc23)cc1] | methyl 4-[1-[(4,4-difluorocyclohexyl)methyl]-6-(3,5-dimethylisoxazol-4-yl)pyrrolo[3,2-b]pyridin-3-yl]benzoate | 480.1 |
| P-0331 | 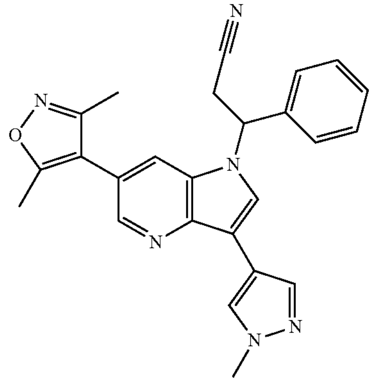 [SMILES: Cc1noc(C)c1-c1cnc2c(-c3cnn(C)c3)cn(C(CC#N)c3ccccc3)c2c1] | 3-[6-(3,5-dimethylisoxazol-4-yl)-3-(1-methylpyrazol-4-yl)pyrrolo[3,2-b]pyridin-1-yl]-3-phenyl-propanenitrile | 423.0 |

TABLE 28-continued

| Compound No. | Structure | Name | MS(ESI) [M + H+]+ observed |
|---|---|---|---|
| P-0332 | 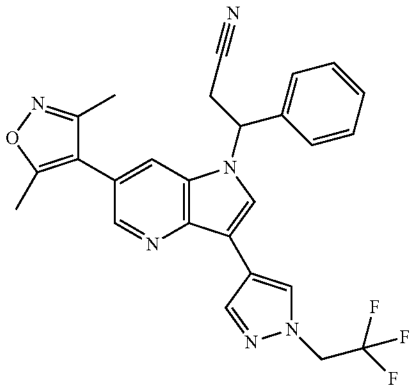 [SMILES: Cc1noc(C)c1-c1cnc2c(-c3cnn(CC(F)(F)F)c3)cn(C(CC#N)c3ccccc3)c2c1] | 3-[6-(3,5-dimethylisoxazol-4-yl)-3-[1-(2,2,2-trifluoroethyl)pyrazol-4-yl]pyrrolo[3,2-b]pyridin-1-yl]-3-phenyl-propanenitrile | 491.0 |
| P-0333 | 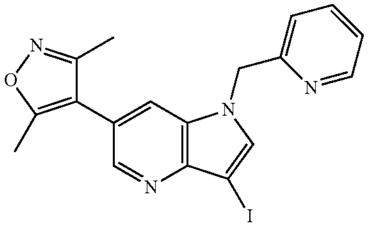 [SMILES: Cc1noc(C)c1-c1cnc2c(I)cn(Cc3ccccn3)c2c1] | 4-[3-iodo-1-(2-pyridylmethyl)pyrrolo[3,2-b]pyridin-6-yl]-3,5-dimethyl-isoxazole | 430.8 |
| P-0334 | 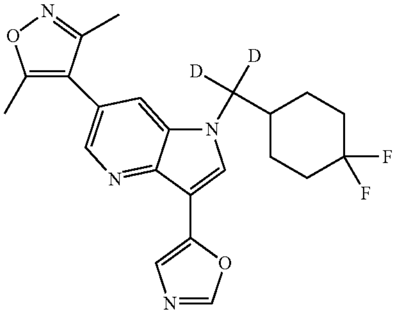 [SMILES: [2H]C([2H])(C1CCC(F)(F)CC1)n1cc(-c2cnco2)c2ncc(-c3c(C)noc3C)cc21] | 4-[1-[dideuterio-(4,4-difluorocyclohexyl)methyl]-3-oxazol-5-yl-pyrrolo[3,2-b]pyridin-6-yl]-3,5-dimethyl-isoxazole | 415.3 |
| P-0335 | 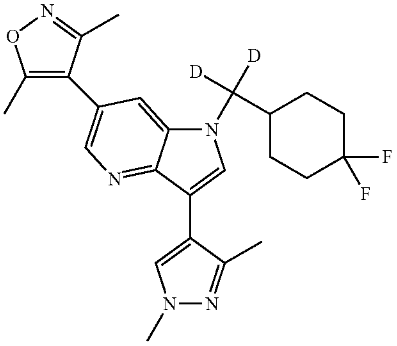 [SMILES: [2H]C([2H])(C1CCC(F)(F)CC1)n1cc(-c2cn(C)nc2C)c2ncc(-c3c(C)noc3C)cc21] | 4-[1-[dideuterio-(4,4-difluorocyclohexyl)methyl]-3-(1,3-dimethylpyrazol-4-yl)pyrrolo[3,2-b]pyridin-6-yl]-3,5-dimethyl-isoxazole | 442.3 |

TABLE 28-continued

| Compound No. | Structure | Name | MS(ESI) [M + H+]+ observed |
|---|---|---|---|
| P-0336 | 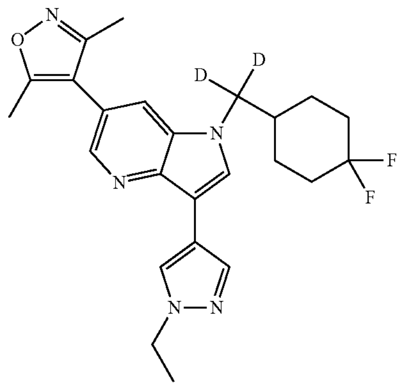 [SMILES: [2H]C([2H])(C1CCC(F)(F)CC1)n1cc(-c2cnn(CC)c2)c2ncc(-c3c(C)noc3C)cc21] | 4-[1-[dideuterio-(4,4-difluorocyclohexyl)methyl]-3-(1-ethylpyrazol-4-yl)pyrrolo[3,2-b]pyridin-6-yl]-3,5-dimethyl-isoxazole | 442.3 |
| P-0337 | 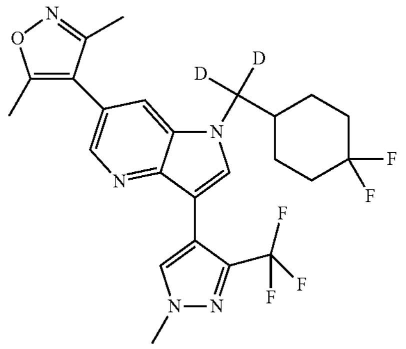 [SMILES: [2H]C([2H])(C1CCC(F)(F)CC1)n1cc(-c2cn(C)nc2C(F)(F)F)c2ncc(-c3c(C)noc3C)cc21] | 4-[1-[dideuterio-(4,4-difluorocyclohexyl)methyl]-3-[1-methyl-3-(trifluoromethyl)pyrazol-4-yl]pyrrolo[3,2-b]pyridin-6-yl]-3,5-dimethyl-isoxazole | 496.6 |
| P-0338 | 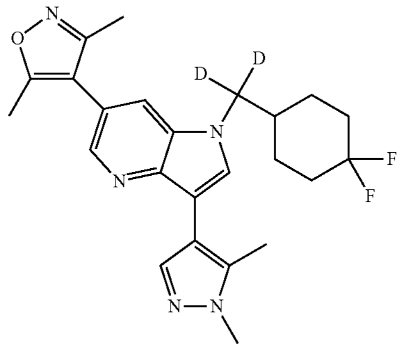 [SMILES: [2H]C([2H])(C1CCC(F)(F)CC1)n1cc(-c2cnn(C)c2C)c2ncc(-c3c(C)noc3C)cc21] | 4-[1-[dideuterio-(4,4-difluorocyclohexyl)methyl]-3-(1,5-dimethylpyrazol-4-yl)pyrrolo[3,2-b]pyridin-6-yl]-3,5-dimethyl-isoxazole | 442.3 |
| P-0339 | 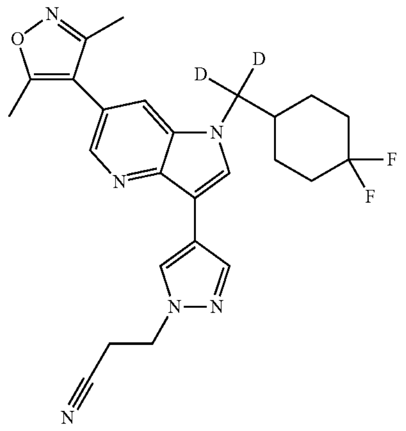 [SMILES: [2H]C([2H])(C1CCC(F)(F)CC1)n1cc(-c2cnn(CCC#N)c2)c2ncc(-c3c(C)noc3C)cc21] | 3-[4-[1-[dideuterio-(4,4-difluorocyclohexyl)methyl]-6-(3,5-dimethylisoxazol-4-yl)pyrrolo[3,2-b]pyridin-3-yl]pyrazol-1-yl]propanenitrile | 467.2 |

TABLE 28-continued

| Compound No. | Structure | Name | MS(ESI) [M + H+]+ observed |
|---|---|---|---|
| P-0340 | 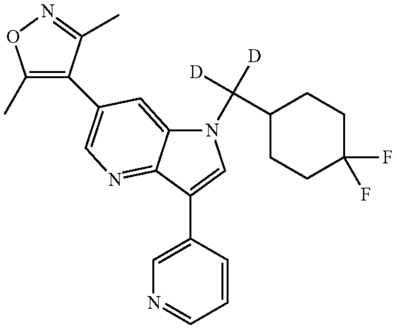 [SMILES: [2H]C([2H])(C1CCC(F)(F)CC1)n1cc(-c2cccnc2)c2ncc(-c3c(C)noc3C)cc21] | 4-[1-[dideuterio-(4,4-difluorocyclohexyl)methyl]-3-(3-pyridyl)pyrrolo[3,2-b]pyridin-6-yl]-3,5-dimethyl-isoxazole | 425.2 |
| P-0341 | 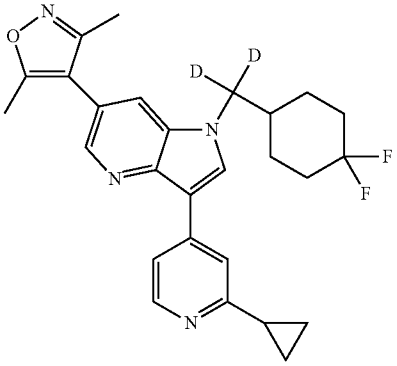 [SMILES: [2H]C([2H])(C1CCC(F)(F)CC1)n1cc(-c2ccnc(C3CC3)c2)c2ncc(-c3c(C)noc3C)cc21] | 4-[3-(2-cyclopropyl-4-pyridyl)-1-[dideuterio-(4,4-difluorocyclohexyl)methyl]pyrrolo[3,2-b]pyridin-6-yl]-3,5-dimethyl-isoxazole | 465.4 |
| P-0342 | 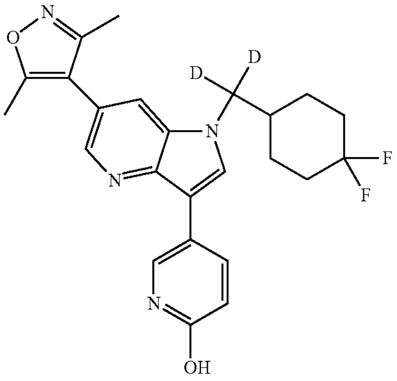 [SMILES: [2H]C([2H])(C1CCC(F)(F)CC1)n1cc(-c2ccc(O)nc2)c2ncc(-c3c(C)noc3C)cc21] | 5-[1-[dideuterio-(4,4-difluorocyclohexyl)methyl]-6-(3,5-dimethylisoxazol-4-yl)pyrrolo[3,2-b]pyridin-3-yl]pyridin-2-ol | 441.4 |
| P-0343 | 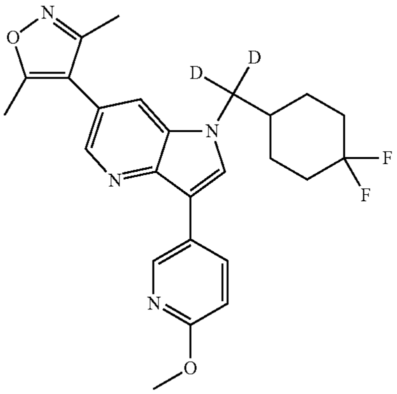 [SMILES: [2H]C([2H])(C1CCC(F)(F)CC1)n1cc(-c2ccc(OC)nc2)c2ncc(-c3c(C)noc3C)cc21] | 4-[1-[dideuterio-(4,4-difluorocyclohexyl)methyl]-3-(6-methoxy-3-pyridyl)pyrrolo[3,2-b]pyridin-6-yl]-3,5-dimethyl-isoxazole | 455.2 |

TABLE 28-continued

| Compound No. | Structure | Name | MS(ESI) [M + H+]+ observed |
|---|---|---|---|
| P-0344 | 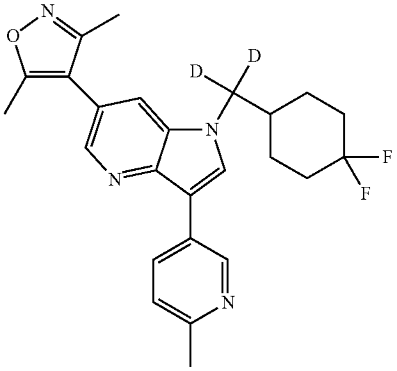 [SMILES: [2H]C([2H])(C1CCC(F)(F)CC1)n1cc(-c2ccc(C)nc2)c2ncc(-c3c(C)noc3C)cc21] | 4-[1-[dideuterio-(4,4-difluorocyclohexyl)methyl]-3-(6-methyl-3-pyridyl)pyrrolo[3,2-b]pyridin-6-yl]-3,5-dimethyl-isoxazole | 439.3 |
| P-0345 | 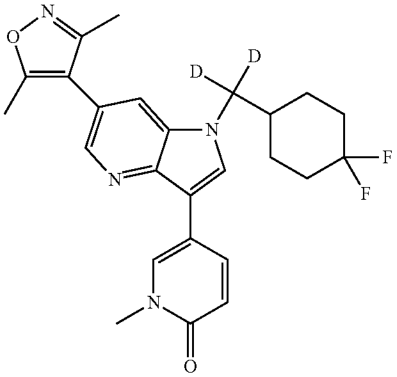 [SMILES: [2H]C([2H])(C1CCC(F)(F)CC1)n1cc(-c2ccc(=O)n(C)c2)c2ncc(-c3c(C)noc3C)cc21] | 5-[1-[dideuterio-(4,4-difluorocyclohexyl)methyl]-6-(3,5-dimethylisoxazol-4-yl)pyrrolo[3,2-b]pyridin-3-yl]-1-methyl-pyridin-2-one | 455.2 |
| P-0346 | 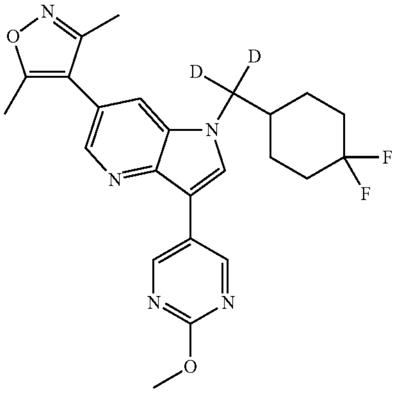 | 4-[1-[dideuterio-(4,4-difluorocyclohexyl)methyl]-3-(2-methoxypyrimidin-5-yl)pyrrolo[3,2-b]pyridin-6-yl]-3,5-dimethyl-isoxazole | 456.4 |
| P-0347 | 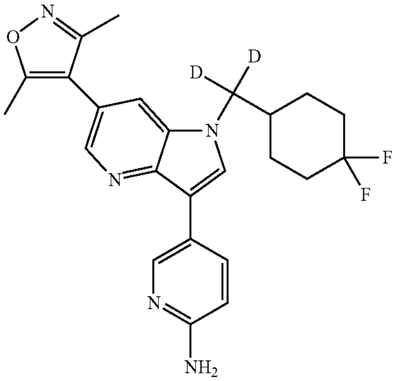 [SMILES: [2H]C([2H])(C1CCC(F)(F)CC1)n1cc(-c2ccc(N)nc2)c2ncc(-c3c(C)noc3C)cc21] | 5-[1-[dideuterio-(4,4-difluorocyclohexyl)methyl]-6-(3,5-dimethylisoxazol-4-yl)pyrrolo[3,2-b]pyridin-3-yl]pyridin-2-amine | 440.2 |

TABLE 28-continued

| Compound No. | Structure | Name | MS(ESI) [M + H+]+ observed |
|---|---|---|---|
| P-0348 | 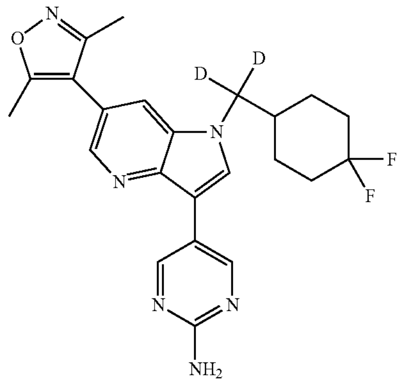 [SMILES: [2H]C([2H])(C1CCC(F)(F)CC1)n1cc(-c2cnc(N)nc2)c2ncc(-c3c(C)noc3C)cc21] | 5-[1-[dideuterio-(4,4-difluorocyclohexyl)methyl]-6-(3,5-dimethylisoxazol-4-yl)pyrrolo[3,2-b]pyridin-3-yl]pyrimidin-2-amine | 441.4 |
| P-0349 | 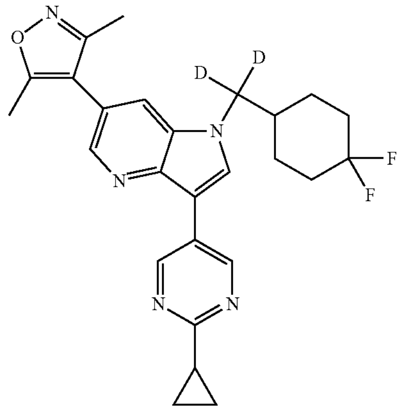 [SMILES: [2H]C([2H])(C1CCC(F)(F)CC1)n1cc(-c2cnc(C3CC3)nc2)c2ncc(-c3c(C)noc3C)cc21] | 4-[3-(2-cyclopropylpyrimidin-5-yl)-1-[dideuterio-(4,4-difluorocyclohexyl)methyl]pyrrolo[3,2-b]pyridin-6-yl]-3,5-dimethyl-isoxazole | 466.3 |
| P-0350 | 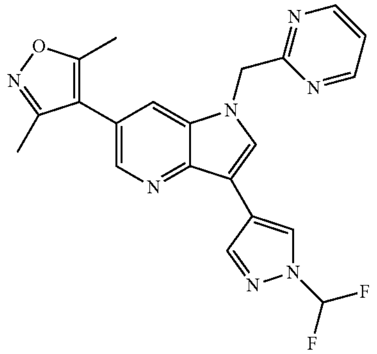 | 4-[3-[1-(difluoromethyl)pyrazol-4-yl]-1-(pyrimidin-2-ylmethyl)pyrrolo[3,2-b]pyridin-6-yl]-3,5-dimethyl-isoxazole | 422.1 |
| P-0351 | 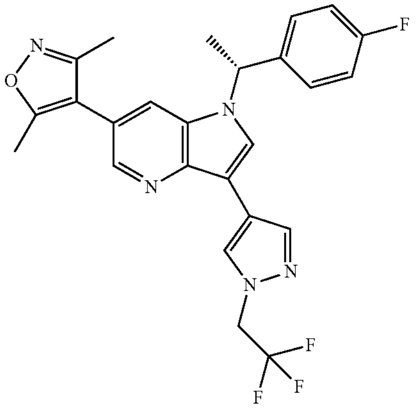 [SMILES: Cc1noc(C)c1-c1cnc2c(-c3cnn(CC(F)(F)F)c3)cn([C@H](C)c3ccc(F)cc3)c2c1] | 4-[1-[(1R)-1-(4-fluorophenyl)ethyl]-3-[1-(2,2,2-trifluoroethyl)pyrazol-4-yl]pyrrolo[3,2-b]pyridin-6-yl]-3,5-dimethyl-isoxazole | 484.0 |

TABLE 28-continued

| Compound No. | Structure | Name | MS(ESI) [M + H+]+ observed |
| --- | --- | --- | --- |
| P-0352 | 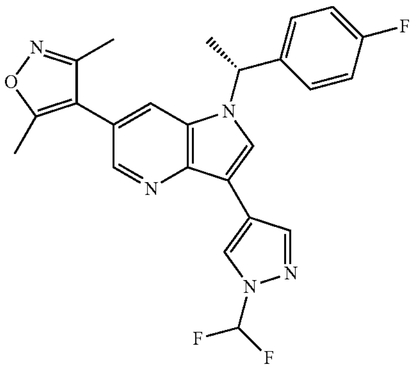 [SMILES: Cc1noc(C)c1-c1cnc2c(-c3cnn(C(F)F)c3)cn([C@H](C)c3ccc(F)cc3)c2c1] | 4-[3-[1-(difluoromethyl)pyrazol-4-yl]-1-[(1R)-1-(4-fluorophenyl)ethyl]pyrrolo[3,2-b]pyridin-6-yl]-3,5-dimethyl-isoxazole | 452.2 |
| P-0353 | 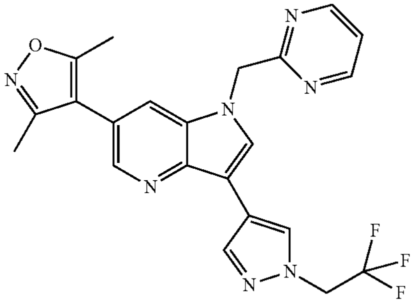 [SMILES: Cc1noc(C)c1-c1cnc2c(-c3cnn(CC(F)(F)F)c3)cn(Cc3ncccn3)c2c1] | 3,5-dimethyl-4-[1-(pyrimidin-2-ylmethyl)-3-[1-(2,2,2-trifluoroethyl)pyrazol-4-yl]pyrrolo[3,2-b]pyridin-6-yl]isoxazole | 454.2 |
| P-0354 | 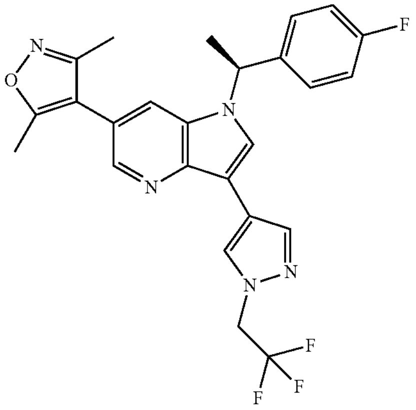 [SMILES: Cc1noc(C)c1-c1cnc2c(-c3cnn(CC(F)(F)F)c3)cn([C@@H](C)c3ccc(F)cc3)c2c1] | 4-[1-[(1S)-1-(4-fluorophenyl)ethyl]-3-[1-(2,2,2-trifluoroethyl)pyrazol-4-yl]pyrrolo[3,2-b]pyridin-6-yl]-3,5-dimethyl-isoxazole | 484.2 |
| P-0355 | 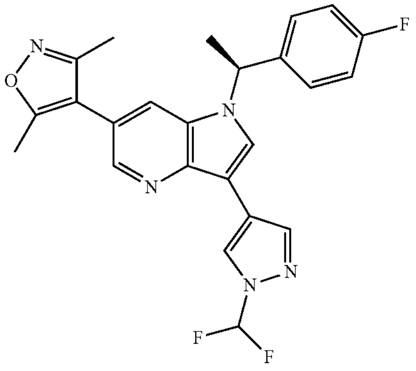 [SMILES: Cc1noc(C)c1-c1cnc2c(-c3cnn(C(F)F)c3)cn([C@@H](C)c3ccc(F)cc3)c2c1] | 4-[3-[1-(difluoromethyl)pyrazol-4-yl]-1-[(1S)-1-(4-fluorophenyl)ethyl]pyrrolo[3,2-b]pyridin-6-yl]-3,5-dimethyl-isoxazole | 452.2 |

TABLE 28-continued

| Compound No. | Structure | Name | MS(ESI) [M + H+]+ observed |
|---|---|---|---|
| P-0356 | 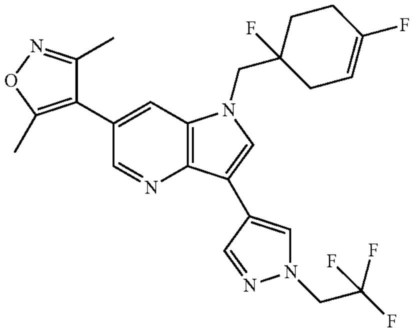 [SMILES: Cc1noc(C)c1-c1cnc2c(-c3cnn(CC(F)(F)F)c3)cn(CC3(F)CC=C(F)CC3)c2c1] | 4-[1-[(1,4-(difluorocyclohex-3-en-1-yl)methyl]-3-[1-(2,2,2-trifluoroethyl)pyrazol-4-yl]pyrrolo[3,2-b]pyridin-6-yl]-3,5-dimethyl-isoxazole | 492.0 |
| P-0357 | 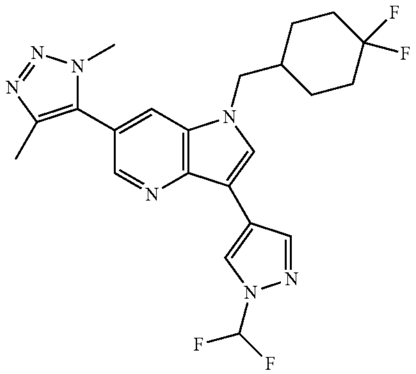 [SMILES: Cc1nnn(C)c1-c1cnc2c(-c3cnn(C(F)F)c3)cn(CC3CCC(F)(F)CC3)c2c1] | 1-[(4,4-difluorocyclohexyl)methyl]-3-[1-(difluoromethyl)pyrazol-4-yl]-6-(3,5-dimethyltriazol-4-yl)pyrrolo[3,2-b]pyridine | 462.4 |
| P-0358 | 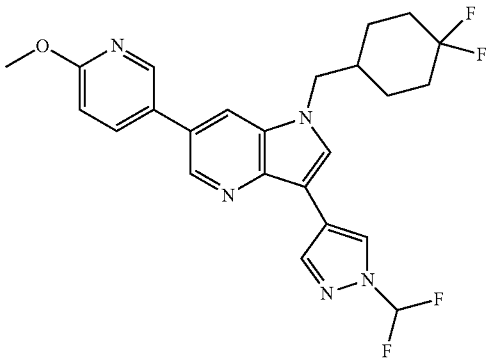 [SMILES: COc1ccc(-c2cnc3c(-c4cnn(C(F)F)c4)cn(CC4CCC(F)(F)CC4)c3c2)cn1] | 1-[(4,4-difluorocyclohexyl)methyl]-3-[1-(difluoromethyl)pyrazol-4-yl]-6-(6-methoxy-3-pyridyl)pyrrolo[3,2-b] pyridine | 474.5 |
| P-0359 | 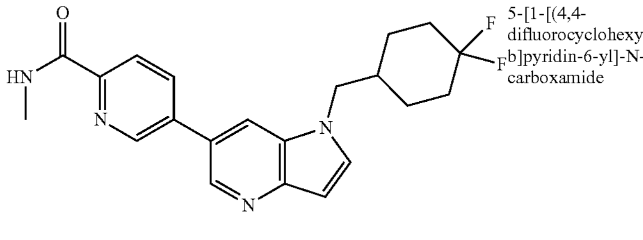 | 5-[1-[(4,4-difluorocyclohexyl)methyl]pyrrolo[3,2-b]pyridin-6-yl]-N-methyl-pyridine-2-carboxamide | 385.2 |
| P-0360 | 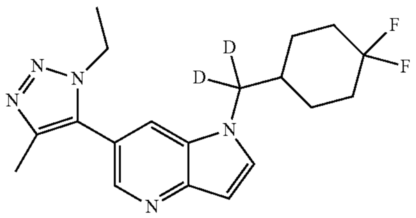 [SMILES: [2H]C([2H])(C1CCC(F)(F)CC1)n1ccc2ncc(-c3c(C)nnn3CC)cc21] | 1-[dideuterio-(4,4-difluorocyclohexyl)methyl]-6-(3-ethyl-5-methyl-triazol-4-yl)pyrrolo[3,2-b]pyridine | 362.4 |

TABLE 28-continued

| Compound No. | Structure | Name | MS(ESI) [M + H+]+ observed |
|---|---|---|---|
| P-0361 | 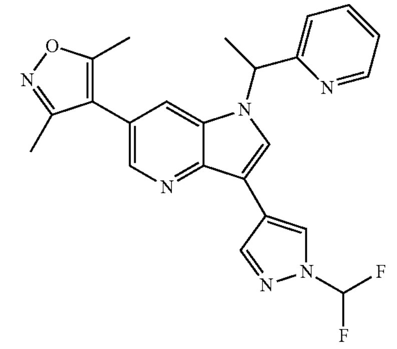 [SMILES: Cc1noc(C)c1-c1cnc2c(-c3cnn(C(F)F)c3)cn(C(C)c3ccccn3)c2c1] | 4-[3-[1-(difluoromethyl)pyrazol-4-yl]-1-[1-(2-pyridyl)ethyl]pyrrolo[3,2-b]pyridin-6-yl]-3,5-dimethyl-isoxazole | 435.0 |
| P-0362 | 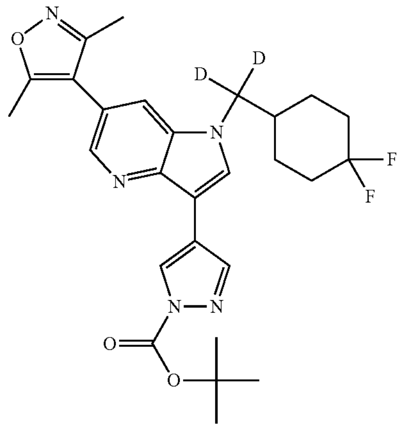 [SMILES: [2H]C([2H])(C1CCC(F)(F)CC1)n1cc(-c2cnn(C(=O)OC(C)(C)C)c2)c2ncc(-c3c(C)noc3C)cc21] | tert-butyl 4-[1-[dideuterio-(4,4-difluorocyclohexyl)methyl]-6-(3,5-dimethylisoxazol-4-yl)pyrrolo[3,2-b]pyridin-3-yl]pyrazole-1-carboxylate | 414.4 (M-BOC) |
| P-0363 | 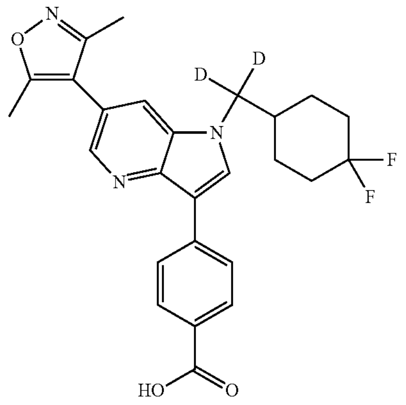 [SMILES: [2H]C([2H])(C1CCC(F)(F)CC1)n1cc(-c2ccc(C(=O)O)cc2)c2ncc(-c3c(C)noc3C)cc21] | 4-[1-[dideuterio-(4,4-difluorocyclohexyl)methyl]-6-(3,5-dimethylisoxazol-4-yl)pyrrolo[3,2-b]pyridin-3-yl]benzoic acid | 468.4 |
| P-0364 | 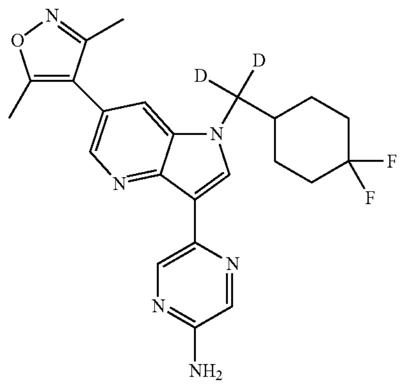 | 5-[1-[dideuterio-(4,4-difluorocyclohexyl)methyl]-6-(3,5-dimethylisoxazol-4-yl)pyrrolo[3,2-b]pyridin-3-yl]pyrazin-2-amine | 441.4 |

TABLE 28-continued

| Compound No. | Structure | Name | MS(ESI) [M + H+]+ observed |
|---|---|---|---|
| P-0365 | 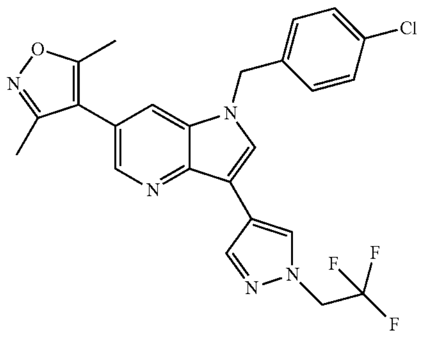 [SMILES: Cc1noc(C)c1-c1cnc2c(-c3cnn(CC(F)(F)F)c3)cn(Cc3ccc(Cl)cc3)c2c1] | 4-[1-[(4-chlorophenyl)methyl]-3-[1-(2,2,2-trifluoroethyl)pyrazol-4-yl]pyrrolo[3,2-b]pyridin-6-yl]-3,5-dimethyl-isoxazole | 485.9 |
| P-0366 | 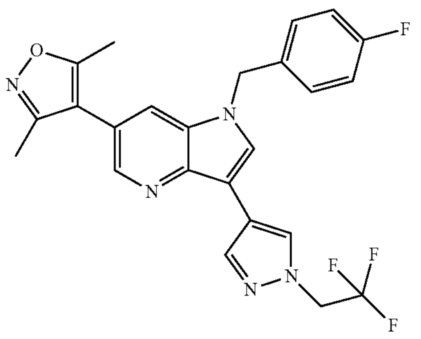 [SMILES: Cc1noc(C)c1-c1cnc2c(-c3cnn(CC(F)(F)F)c3)cn(Cc3ccc(F)cc3)c2c1] | 4-[1-[(4-fluorophenyl)methyl]-3-[1-(2,2,2-trifluoroethyl)pyrazol-4-yl]pyrrolo[3,2-b]pyridin-6-yl]-3,5-dimethyl-isoxazole | 470.0 |
| P-0367 | 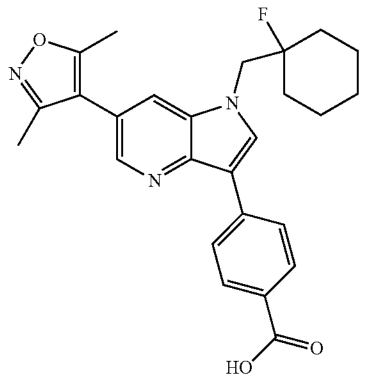 [SMILES: Cc1noc(C)c1-c1cnc2c(-c3ccc(C(=O)O)cc3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]benzoic acid | 448.3 |
| P-0368 | 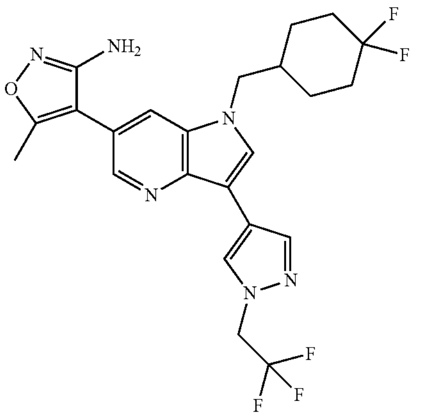 [SMILES: Cc1onc(N)c1-c1cnc2c(-c3cnn(CC(F)(F)F)c3)cn(CC3CCC(F)(F)CC3)c2c1] | 4-[1-[(4,4-difluorocyclohexyl)methyl]-3-[1-(2,2,2-trifluoroethyl)pyrazol-4-yl]pyrrolo[3,2-b]pyridin-6-yl]-5-methyl-isoxazol-3-amine | 495.1 |

TABLE 28-continued

| Compound No. | Structure | Name | MS(ESI) [M + H+]+ observed |
|---|---|---|---|
| P-0369 | 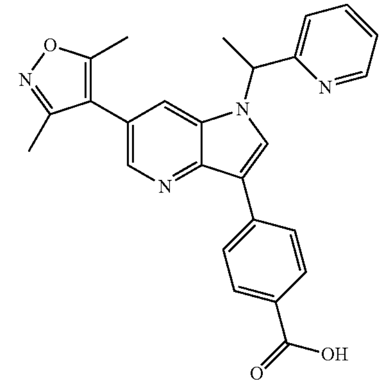 [SMILES: Cc1noc(C)c1-c1cnc2c(-c3ccc(C(=O)O)cc3)cn(C(C)c3ccccn3)c2c1] | 4-[6-(3,5-dimethylisoxazol-4-yl)-1-[1-(2-pyridyl)ethyl]pyrrolo[3,2-b]pyridin-3-yl]benzoic acid | 439.3 |
| P-0370 | 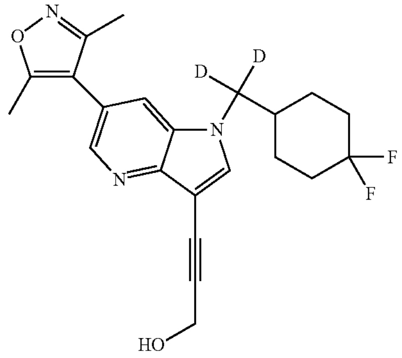 [SMILES: [2H]C([2H])(C1CCC(F)(F)CC1)n1cc(C#CCO)c2ncc(-c3c(C)noc3C)cc21] | 3-[1-[dideuterio-(4,4-difluorocyclohexyl)methyl]-6-(3,5-dimethylisoxazol-4-yl)pyrrolo[3,2-b]pyridin-3-yl]prop-2-yn-1-ol | 402.4 |
| P-0371 | 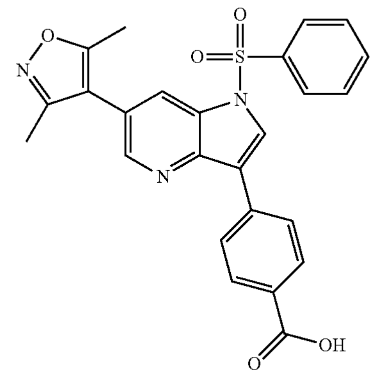 [SMILES: Cc1noc(C)c1-c1cnc2c(-c3ccc(C(=O)O)cc3)cn(S(=O)(=O)c3ccccc3)c2c1] | 4-[1-(benzenesulfonyl)-6-(3,5-dimethylisoxazol-4-yl)pyrrolo[3,2-b]pyridin-3-yl]benzoic acid | 474.3 |
| P-0372 | 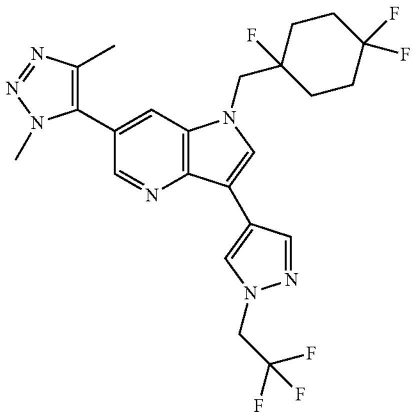 [SMILES: Cc1nnn(C)c1-c1cnc2c(-c3cnn(CC(F)(F)F)c3)cn(CC3(F)CCC(F)(F)CC3)c2c1] | 6-(3,5-dimethyltriazol-4-yl)-1-[(1,4,4-trifluorocyclohexyl)methyl]-3-[1-(2,2,2-trifluoroethyl)pyrazol-4-yl]pyrrolo[3,2-b]pyridine | 512.0 |

Example 40

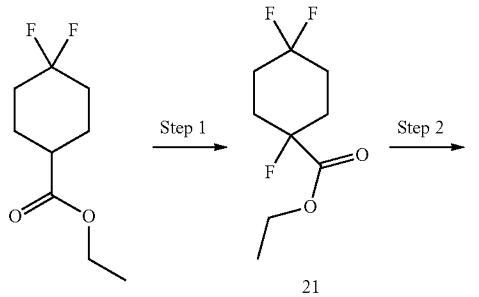

21

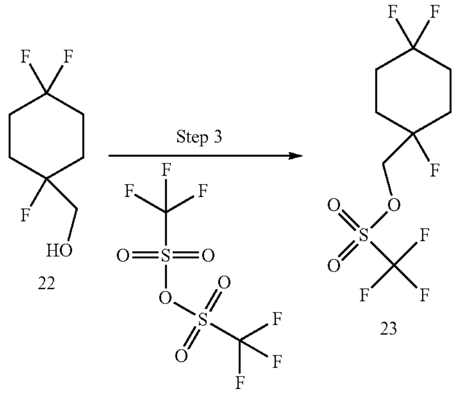

22

23

Step 1—Synthesis of ethyl 1,4,4-trifluorocyclohexanecarboxylate (21): To the solution of ethyl 4,4-difluorocyclohexanecarboxylate (5.00 g, 26 mmol) in tetrahydrofuran (50 ml) chilled to −78° C. under nitrogen gas was added slowly a solution of 2M lithium diisopropylamide in tetrahydrofuran (19.5 ml, 1.5 eq). After stirring at −78° C. for one hour, a solution of N-fluorobenzenesulfonimide (9.84 g, 31.2 mmol) in tetrahydrofuran (30 mL) was added slowly to the reaction. The mixture was allowed to stir and reach room temperature and then continued for 15 hours. The mixture was quenched slowly with saturated ammonium chloride then extracted with ethyl acetate which was washed with water and brine. The organic layer was dried over sodium sulfate, filtered and concentrated down. The crude material was purified by flash chromatography eluting with 0-5% ethyl acetate in hexane to provide product as a clear oil (21, 3.89 g, 64.1%).

Step 2—Preparation of (1,4,4-trifluorocyclohexyl)methanol (22): To an ice cold solution of ethyl 1,4,4-trifluorocyclohexanecarboxylate (21, 3.89 g, 16.66 mmol) in tetrahydrofuran (80 ml) was added slowly the solution of 1M lithium aluminum hydride (18.32 ml, 1.1 eq) in tetrahydrofuran. The mixture was stirred at 0° C. for two hours then quenched sequentially with 0.600 mL water, 1.33 mL 10% aqueous sodium hydroxide, and 0.900 mL water. The mixture was diluted with ethyl acetate and dried over magnesium sulfate, filtered and concentrated down. The residue was purified by flash chromatography eluting with 10% ethyl acetate in hexane. The sample was triturated with hexane to provide product as a white solid (22, 1.67 g, 59.6%).

Step 3—Preparation of (1,4,4-trifluorocyclohexyl)methyl trifluoromethanesulfonate (3): To an ice cold solution of (1,4,4-trifluorocyclohexyl)methanol (22, 1.51 g, 9 mmol) and triethylamine (1.5 mL, 10.8 mmol, 1.2 eq) in dichloromethane (45 ml) was added slowly the solution of trifluoromethane sulfonic anhydride (1.62 ml, 9.9 mmol, 1.1 eq) in 10 mL dichloromethane. The mixture was stirred at 0° C. for three hours then quenched with water. The mixture was extracted with ethyl acetate which was washed with water, saturated sodium bicarbonate and brine. The organic layer was dried over sodium sulfate, filtered and concentrated down to provide product as a pale solid which was used without further purification. (23, 2.55 g, 94.4%).

Example 41

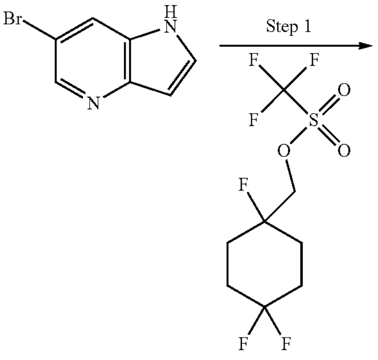

23

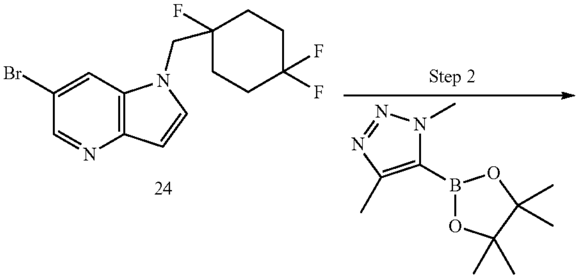

24

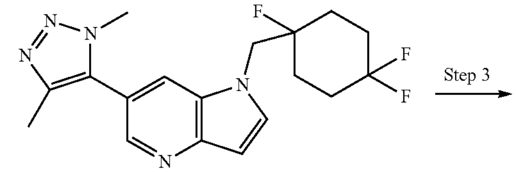

25

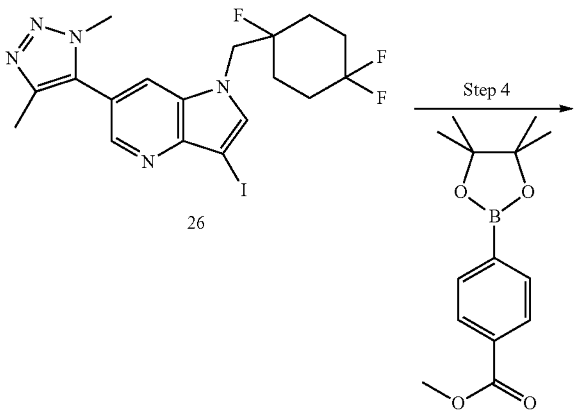

26

-continued

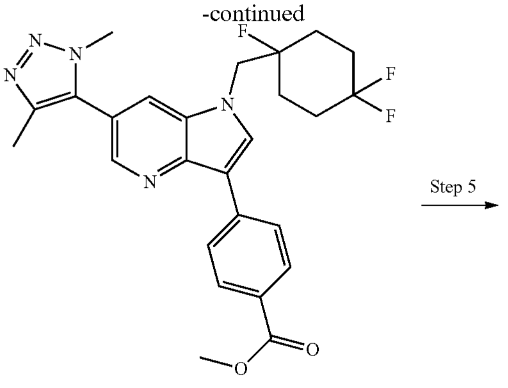

27

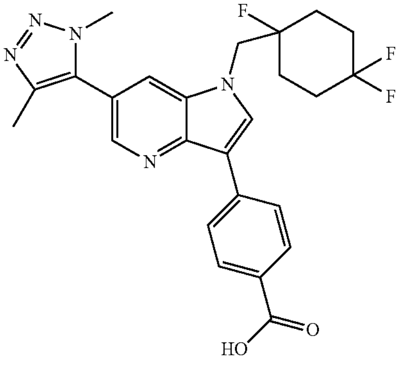

P-0373

Step 1—Synthesis of 6-bromo-1-[(1,4,4-trifluorocyclohexyl)methyl]pyrrolo[3,2-b]pyridine 24: To a mixture of 6-bromo-1H-pyrrolo[3,2-b]pyridine (0.985 g, 5 mmol, 1 eq) in N,N-dimethylformamide (25 ml) was added cesium carbonate (1.79 g, 5.5 mmol, 1.1 eq), followed by (1,4,4-trifluorocyclohexyl)methyl trifluoromethanesulfonate (1.50 g, 5 mmol, 1 eq). The mixture was stirred at 70° C. for five hours. The mixture was quenched with water, and extracted with ethyl acetate which was washed with water and brine. The organic layer was dried over sodium sulfate, filtered and concentrated down. The sample was purified by flash chromatography eluting with 40% ethyl acetate in hexane, then triturated with hexanes to provide 1.63 g (93.9%) of product as a solid (24, 1.63 g, 93.9%), MS (ESI) $[M+H^+]^+$=347.0, 349.0.

Step 2—Preparation of 6-(3,5-dimethyltriazol-4-yl)-1-[(1,4,4-trifluorocyclohexyl)methyl]pyrrolo[3,2-b]pyridine (25): A mixture of 6-bromo-1-[(1,4,4-trifluorocyclohexyl)methyl]pyrrolo[3,2-b]pyridine (24, 833 mg, 2.4 mmol, 1 eq), 1,4-dimethyl-5-(4,4,5,5-tetramethyl-1,3,2-dioxaborolan-2-yl)triazole (803 mg, 3.6 mmol, 1.5 eq), [1,1'-bis(diphenylphosphino)ferrocene]dichloropalladium(II) (351 mg, 0.48 mmol, 0.2 eq) in acetonitrile (24 ml) was purged with nitrogen gas then 2.88 mL of 2.5M aqueous potassium carbonate (3eq) was added. The resulting mixture was irradiated in a microwave vessel at 140° C. for one hour. The resulting mixture was cooled & filtered through a pad of celite. The filtrate was concentrated down and purified by flash chromatography eluting with 80-100% ethylacetate in dichloromethane. The purified sample was triturated with 5% dichloromethane/hexane to provide product (25, 436 mg, 50%), MS (ESI) $[M+H^+]^+$=364.2.

Step 3—Preparation of 6-(3,5-dimethyltriazol-4-yl)-3-iodo-1-[(1,4,4-trifluoro cyclohexyl)methyl]pyrrolo[3,2-b]pyridine 26: To an ice cold mixture of 6-(3,5-dimethyltriazol-4-yl)-1-[(1,4,4-trifluorocyclohexyl)methyl]pyrrolo[3,2-b]pyridine (25, 436 mg, 1.2 mmol, 1 eq) in acetonitrile (12 ml) was added N-iodosuccinimide (0.13 ml, 1.32 mmol, 1.1 eq). The mixture was stirred to reach room temperature for 15 hours then cooled and quenched with IN aqueous potassium carbonate. The mixture was extracted with ethyl acetate which was washed with water followed by brine. The organic layer was dried over sodium sulfate, filtered and concentrated down. The sample was purified by flash chromatography eluting with 30-50% ethyl acetate in hexane to yield product (26, 166.2 mg, 28.3%) MS (ESI) $[M+H^+]^+$=490.1.

Step 4—Preparation of methyl 4-[6-(3,5-dimethyltriazol-4-yl)-1-[(1,4,4-trifluorocyclohexyl)methyl]pyrrolo[3,2-b]pyridin-3-yl]benzoate (27): A mixture of 6-(3,5-dimethyltriazol-4-yl)-3-iodo-1-[(1,4,4-trifluorocyclohexyl)methyl]pyrrolo[3,2-b]pyridine (26, 166 mg, 0.34 mmol, 1 eq), methyl 4-(4,4,5,5-tetramethyl-1,3,2-dioxaborolan-2-yl)benzoate (133.68 mg, 0.51 mmol, 1.5 eq) and [1,1'-bis(diphenylphosphino) ferrocene]dichloropalladium(II) (24 mg, 0.034 mmol, 0.1 eq) in acetonitrile (5 ml) was purged with nitrogen gas then 0.48 mL of 2.5M aqueous potassium carbonate (3eq) was added. The resulting mixture was irradiated in a microwave vessel at 100° C. for 30 minutes. The resulting mixture was cooled & filtered through a pad of celite, concentrated down and purified by flash chromatography eluting with 30-40% ethyl acetate in dichloromethane to provide product (27, 88 mg, 52%) MS (ESI) $[M+H^+]^+$=498.5.

Step 5—Preparation of 4-[6-(3,5-dimethyltriazol-4-yl)-1-[(1,4,4-trifluorocyclohexyl)methyl]pyrrolo[3,2-b]pyridin-3-yl]benzoic acid (P-0373): To a mixture of methyl 4-[6-(3,5-dimethyltriazol-4-yl)-1-[(1,4,4-trifluorocyclohexyl)methyl]pyrrolo[3,2-b]pyridin-3-yl]benzoate (27, 88 mg, 0.18 mmol, 1 eq) in tetrahydrofuran (4 ml) was added 4.18M lithium hydroxide (0.2 ml, 4 eq). The mixture was stirred at 50° C. for 15 hours, followed by cooling and acidifying with 1N hydrochloric acid. The mixture was extracted with ethyl acetate which was washed with water, followed by brine. The organic layer was dried over sodium sulfate, filtered and concentrated down. The crude sample was purified by reversed phase chromatography (C18) to provide the product as a light yellow solid (P-0373, 55 mg, 63.3%) MS (ESI) $[M+H^+]^+$=484.0.

Example 42

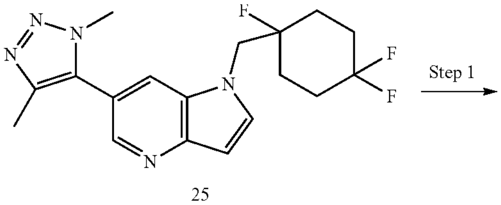

25

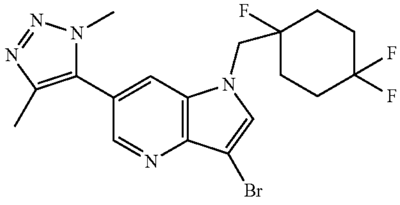

29

Step 1—Synthesis of 3-bromo-6-(3,5-dimethyltriazol-4-yl)-1-[(1,4,4-trifluorocyclohexyl)methyl]pyrrolo[3,2-b]pyridine (29): To an ice cold mixture of 6-(3,5-dimethyltriazol-4-yl)-1-[(1,4,4-trifluorocyclohexyl)methyl]pyrrolo[3,2-b]pyridine (25, 211 mg, 0.58 mmol) in N,N-dimethylformamide (6 ml) was added a solution of N-bromosuccinimide (114 mg, 0.64 mmol) in N,N-dimethylformamide (1 mL). The mixture was stirred at 0° C. for 3 hrs then quenched with 1N potassium carbonate. The mixture was extracted with ethyl acetate which was washed with water, followed by brine. The organic layer was dried over sodium sulfate, filtered and concentrated. The crude product was triturated with 5% ethyl acetate in hexane to yield solid product (29, 179 mg, 69.6%). MS (ESI) [M+H$^+$]$^+$=442.2.

Example 43

Preparation of 6-(3,5-dimethyltriazol-4-yl)-1-[(1,4,4-trifluorocyclohexyl)methyl]-3-[1-(2,2,2-trifluoroethyl)pyrazol-4-yl]pyrrolo[3,2-b]pyridine (P-0372)

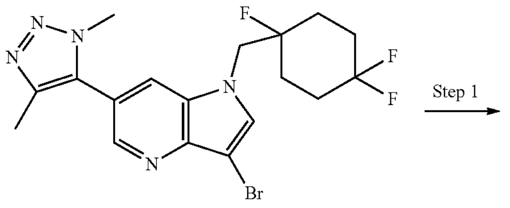

29

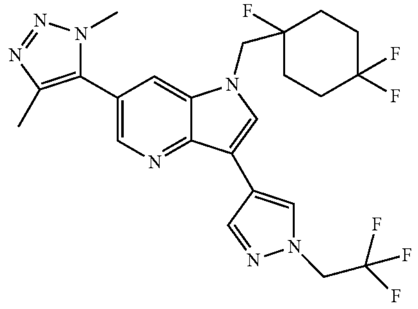

P-0372

Step 1—Synthesis of 6-(3,5-dimethyltriazol-4-yl)-1-[(1,4,4-trifluorocyclohexyl)methyl]-3-[1-(2,2,2-trifluoroethyl)pyrazol-4-yl]pyrrolo[3,2-b]pyridine (P-0372):A mixture of 3-bromo-6-(3,5-dimethyltriazol-4-yl)-1-[(1,4,4-trifluorocyclohexyl)methyl]pyrrolo[3,2-b]pyridine (29, 63 mg, 0.142 mmol), 4-(4,4,5,5-tetramethyl-1,3,2-dioxaborolan-2-yl)-1-(2,2,2-trifluoroethyl)pyrazole (90 mg, 0.33 mmol) and [1,1'-bis(diphenylphosphino) ferrocene]dichloropalladium(II) (16 mg, 0.021 mmol) in acetonitrile (2 ml) was purged with nitrogen gas then 0.43 mL of 1M aqueous degassed potassium carbonate was added. The resulting mixture was irradiated in a microwave vessel at 140° C. for 25 minutes. The resulting mixture was cooled & filtered through a pad of celite, concentrated down and purified by flash chromatography eluting with 50-90% ethyl acetate in hexane to provide product (P-0372, 33 mg, 45%) MS (ESI) [M+H$^+$]$^+$=512.3.

Example 44

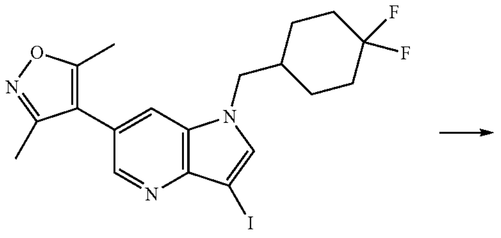

15

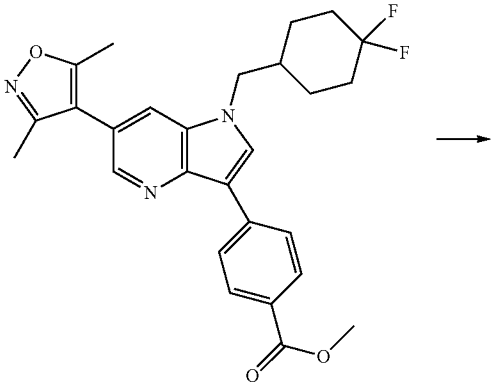

P-0330

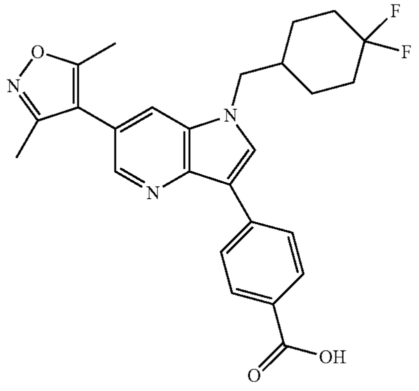

P-0324

Step 1—Synthesis of methyl 4-[1-[(4,4-difluorocyclohexyl)methyl]-6-(3,5-dimethylisoxazol-4-yl)pyrrolo[3,2-b]pyridin-3-yl]benzoate (P-0330):To a 10 mL of microwave tube was added 4-[1-[(4,4-difluorocyclohexyl)methyl]-3-iodo-pyrrolo[3,2-b]pyridin-6-yl]-3,5-dimethyl-isoxazole (15, 0.15 g, 0.32 mmol), acetonitrile (4 ml), methyl 4-(4,4,5,5-tetramethyl-1,3,2-dioxaborolan-2-yl)benzoate (0.13 g, 0.5 mmol), 1M potassium carbonate in water (2 ml), and [1,1'-bis(diphenylphosphino) ferrocene]dichloropalladium (II) (0.02 g, 0.03 mmol). The resulting mixture was irradiated in a microwave vessel at 140° C. for 30 minutes. The reaction mixture was diluted with 1N aqueous HCl water and extracted with ethyl acetate. The organic layer was washed with water and brine, dried over magnesium sulfate, filtered and concentrated. The crude material was purified flash chromatography eluting with 0-100% ethyl acetate in hexane to provide product as a light tan solid (P-0330, 65 mg, 43%). MS (ESI) [M+H$^+$]$^+$=480.1.

Step 2—Synthesis of 4-[1-[(4,4-difluorocyclohexyl)methyl]-6-(3,5-dimethylisoxazol-4-yl)pyrrolo[3,2-b]pyridin-3-yl]benzoic acid (P-0324): In a screw-cap vial was added a solution of methyl 4-[1-[(4,4-difluorocyclohexyl)methyl]-6-(3,5-dimethylisoxazol-4-yl)pyrrolo[3,2-b]pyridin-3-yl]benzoate (P-0330, 50 mg, 0.1 mmol) in THF (8 ml) followed by 1M aqueous sodium hydroxide (3 ml). The mixture was heated and stirred at 75° C. for overnight. The reaction mixture was extracted with 1N aqueous HCl and ethyl acetate. The organic layer was washed with water and brine, dried over magnesium sulfate, filtered and concentrated. The volatiles were removed under vacuum. The crude material was purified by flash chromatography eluting with 0-15% methanol in dichloromethane to provide product as an off-white solid (P-0324, 32 mg, 66%). MS (ESI) $[M+H^+]^+$=466.4.

Example 45A

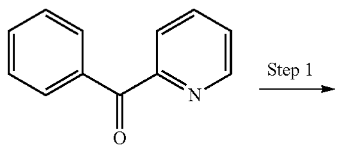

31

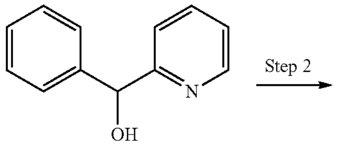

32

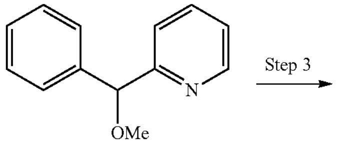

33

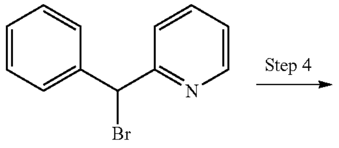

34

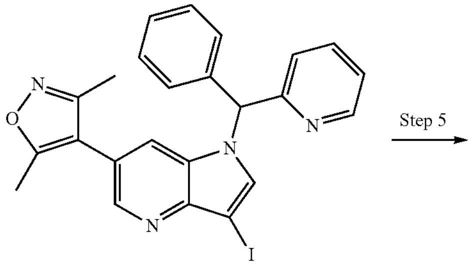

35

-continued

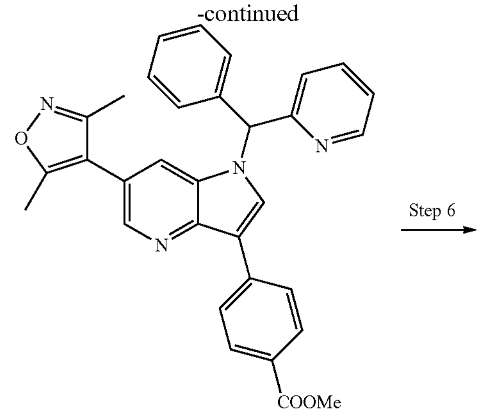

P-0610

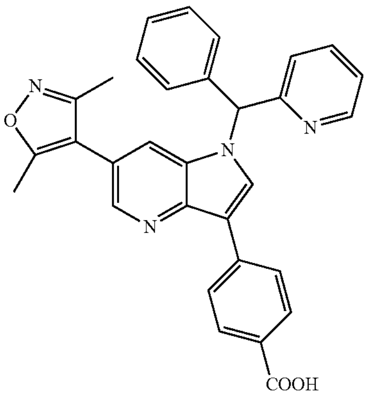
P-0611

Step 1—Preparation phenyl(2-pyridyl)methanol (32): To phenyl(2-pyridyl)methanone (31, 5.1 g, 27.84 mmol) in methanol (100 ml), was added sodium borohydride (1.16 g, 30.62 mmol) keeping the temperature below 0° C. The reaction was allowed to warm to room temperature overnight. The reaction was concentrated, following by adding 1 N HCl to dissolve the crude product. The crude product was poured into aqueous potassium carbonate, and extracted with ethyl acetate. The organic layer was washed with brine, dried over sodium sulfate, and filtered. The filtrate was concentrated give product (32 4.9 g, 95.0%).

Step 2—Preparation [phenyl(2-pyridyl)methyl]methanesulfonate 33: To phenyl(2-pyridyl)methanol (32, 1 g, 5.4 mmol) in methylene chloride (20 ml) was added triethylamine (1.13 ml, 8.1 mmol) and methanesulfonyl chloride (0.4 ml, 5.94 mmol) at 0° C. The reaction was allowed to warm to room temperature for 2 hours. The reaction was poured into water, and extracted with ethyl acetate. The organic layer was washed with brine, dried over sodium sulfate, and filtered. The filtrate was concentrated to give crude product (33, 1.3 g, 91.5%) that was used in the next step directly.

Step 3—Preparation of 2-[bromo(phenyl)methyl]pyridine 34: To [phenyl(2-pyridyl)methyl]methanesulfonate (33, 1.3 g, 4.94 mmol) in DMF (25 ml) was added bromolithium (1.4 g, 16.12 mmol). The reaction was stirred at room temperature overnight. The reaction was poured into water, and extracted with ethyl acetate. The organic layer was washed with brine, dried over sodium sulfate, and filtered. The filtrate was concentrated to give crude product (34, 1.2 g, 98%) that was used directly in the next step without further purification.

Step 4—Preparation of 4-[3-iodo-1-[phenyl(2-pyridyl)methyl]pyrrolo[3,2-b]pyridin-6-yl]-3,5-dimethyl-isoxazole (35): To 4-(3-iodo-1H-pyrrolo[3,2-b]pyridin-6-yl)-3,5-dimethyl-isoxazole (P-0072, 0.54 g, 1.59 mmol) in THF (20 ml), was added cesium carbonate (1.2 g, 3.68 mmol) at room temperature. After 10 minutes, 2-[bromo(phenyl)methyl]pyridine (34, 0.7 g, 2.82 mmol) was added. The reaction was stirred at 65° C. for 5 hours. The reaction was poured into water, extracted with ethyl acetate. The organic layer was washed with brine, and the organic layer was dried over sodium sulfate, filtered, concentrated, and purified with silica gel column chromatography eluting with 10-100% ethyl acetate in hexane to give product (35, 0.5 g, 62%).

Step 5—Preparation of methyl 4-[6-(3,5-dimethylisoxazol-4-yl)-1-[phenyl(2-pyridyl)methyl]pyrrolo[3,2-b]pyridin-3-yl]benzoate (P-0610)

To 4-[3-iodo-1-[phenyl(2-pyridyl)methyl]pyrrolo[3,2-b]pyridin-6-yl]-3,5-dimethyl-isoxazole (35, 0.45 g, 0.89 mmol) in THF (25 ml) were added [1,1'-bis(diphenylphosphino)ferrocene]dichloropalladium(II) (0.05 g, 0.07 mmol), methyl 4-(4,4,5,5-tetramethyl-1,3,2-dioxaborolan-2-yl)benzoate (0.38 g, 1.45 mmol), and 1M potassium carbonate in water (10 ml). The reaction was heated to 70° C. for 50 minutes. The reaction was poured into water, and extracted with ethyl acetate. The organic layer was washed with brine, dried over sodium sulfate, and filtered. The filtrate was concentrated, and purified by flash chromatography eluting with 20-100% ethyl acetate in hexane to give product (P-0610, 0.32 g, 70%).

Step 6—Preparation of 4-[6-(3,5-dimethylisoxazol-4-yl)-1-[phenyl(2-pyridyl)methyl]pyrrolo[3,2-b]pyridin-3-yl]benzoic acid (P-0611): To methyl 4-[6-(3,5-dimethylisoxazol-4-yl)-1-[phenyl(2-pyridyl)methyl]pyrrolo[3,2-b]pyridin-3-yl]benzoate (P-0610. 0.32 g, 0.62 mmol) in THF (10 ml) was added 2M lithium hydroxide (5 ml). The reaction mixture was stirred at 50° C. overnight. The reaction was poured into water, acidified to a pH of about 6 with 1N of HCl (10 mL), and extracted with ethyl acetate. The organic layer was washed with brine, and the organic layer was dried over sodium sulfate, filtered, concentrated, and washed with ethyl acetate and hexane to give product (P-0611, 280 mg, 90%). MS (ESI) $[M+H^+]^+=501.0$.

Example 45B

Preparation of [2-[4-[1-[(4,4-difluorocyclohexyl)methyl]-6-(3,5-dimethylisoxazol-4-yl)pyrrolo[3,2-b]pyridin-3-yl]phenyl]acetyl]oxysodium (38)

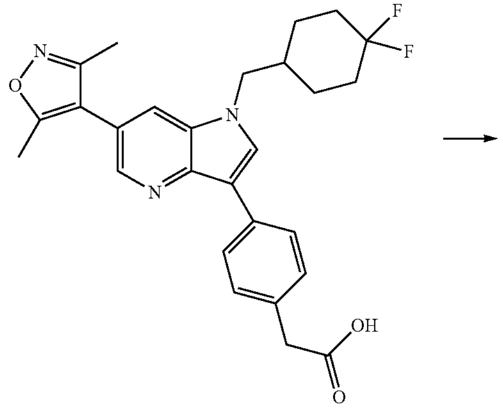

P-0413

-continued

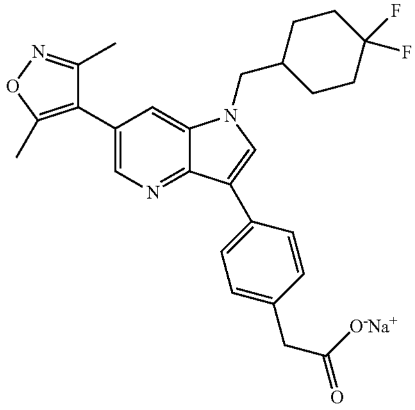

38

Step 1—Synthesis of [2-[4-[1-[(4,4-difluorocyclohexyl)methyl]-6-(3,5-dimethylisoxazol-4-yl)pyrrolo[3,2-b]pyridin-3-yl]phenyl]acetyl]oxysodium (38)

To a solution of 2-[4-[1-[(4,4-difluorocyclohexyl)methyl]-6-(3,5-dimethylisoxazol-4-yl)pyrrolo[3,2-b]pyridin-3-yl]phenyl]acetic acid (P-0413, 0.25 g, 0.52 mmol) in acetone (15 mL) was added 1.8M aqueous sodium hydroxide (0.29 ml). The reaction mixture was concentrated to a solid and dried overnight in a vacuum oven to give product (38, 261 mg, 100%). LCMS (ESI) [M+H+]+=480.5.

Example 46

Preparation of 5-[1-[(4,4-difluorocyclohexyl)methyl]-3-[1-(2,2,2-trifluoroethyl)pyrazol-4-yl]pyrrolo[3,2-b]pyridin-6-yl]-1,3-dimethyl-pyridin-2-one (P-0541)

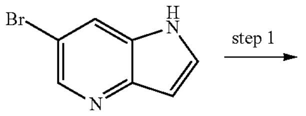

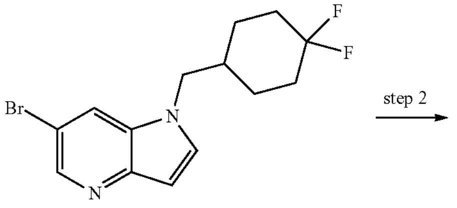

40

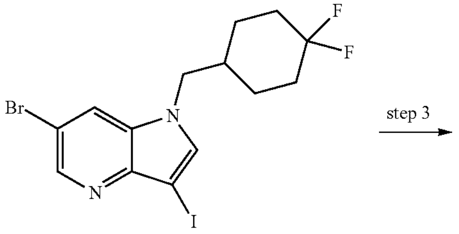

41

-continued

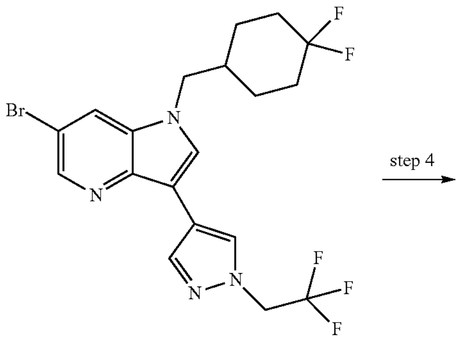

42

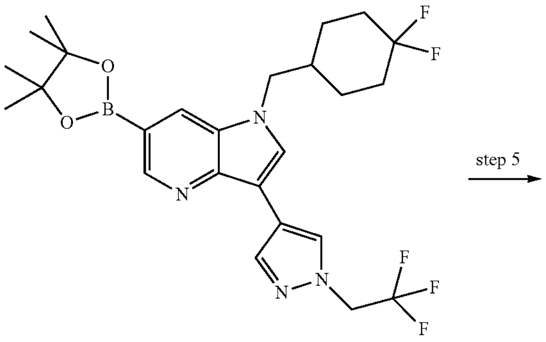

43

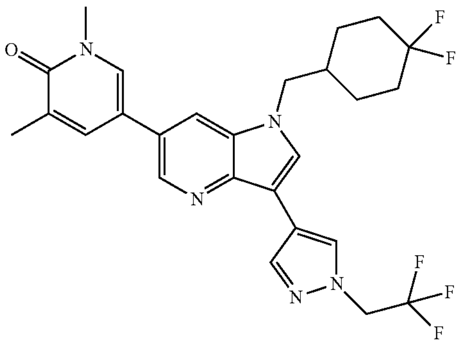

P-0541

Step 1—Synthesis of 6-bromo-1-[(4,4-difluorocyclohexyl)methyl]pyrrolo[3,2-b]pyridine 40: To a round bottom flask was added 6-bromo-1H-pyrrolo[3,2-b]pyridine (1.78 g, 9.03 mmol) in dimethylformamide (20 ml). Then, sodium hydride (60%, 0.51 g, 12.65 mmol) was added and the mixture was stirred at room temperature for 1 hour. Then (4,4-difluorocyclohexyl)methyl 4-nitrobenzenesulfonate (14, 3.61 g, 10.71 mmol) was added and stirred overnight. The reaction mixture was partitioned between ethyl acetate, washed with brine, and dried over sodium sulfate. After removal of drying agent and solvent, the residue was purified by column chromatography (0-50% ethyl acetate/hexane). The desired fractions were combined and concentrated under reduced pressure to afford product as a white/yellow solid (40, 2.38 g, 80%). MS (ESI) $[M+H^+]^+$=328.7/330.7.

Step 2—Synthesis of 6-bromo-1-[(4,4-difluorocyclohexyl)methyl]-3-iodo-pyrrolo[3,2-b]pyridine 41: To 6-bromo-1-[(4,4-difluorocyclohexyl)methyl]pyrrolo[3,2-b]pyridine (40, 1 g, 3.04 mmol) in dimethylformamide (20 ml) was added N-iodosuccinimide (0.75 g, 3.34 mmol) as a dimethylformamide solution and allowed to stir overnight at room temperature. The reaction mixture was partitioned between ethyl acetate and water, washed with brine, and dried under sodium sulfate. After removal of drying agent and solvent, the residue was purified by flash chromatography. Desired fractions were concentrated and the product was triturated with ethyl acetate to afford product as a yellow/tan solid (41, 1.35 g, 97.7%). MS (ESI) $[M+H^+]^+$=453.2/455.2.

Step 3—Synthesis of 6-bromo-1-[(4,4-difluorocyclohexyl)methyl]-3-[1-(2,2,2-trifluoroethyl)pyrazol-4-yl]pyrrolo[3,2-b]pyridine 42: To 6-bromo-1-[(4,4-difluorocyclohexyl)methyl]-3-iodo-pyrrolo[3,2-b]pyridine (41, 1 g, 2.2 mmol), 4-(4,4,5,5-tetramethyl-1,3,2-dioxaborolan-2-yl)-1-(2,2,2-trifluoroethyl)pyrazole (0.64 g, 2.31 mmol) and tetrakis(triphenylphosphine)palladium(0) (0.22 g, 0.19 mmol) in 1,4 dioxane (20 ml) was added 1M aqueous potassium carbonate (4.5 ml). The reaction was allowed to stir at 60° C. for 5 hours. The reaction mixture was partitioned between ethyl acetate and water, washed with brine, and dried over sodium sulfate. After removal of drying agent and solvent, the residue was purified by flash chromatography (0-30% ethyl acetate in hexane). Desired fractions were collected and concentrated to afford product as a yellow solid (42, 392 mg, 37.4%) MS (ESI) $[M+H^+]^+$=478.9.

Step 4—Preparation of 1-[(4,4-difluorocyclohexyl)methyl]-6-(4,4,5,5-tetramethyl-1,3,2-dioxaborolan-2-yl)-3-[1-(2,2,2-trifluoroethyl)pyrazol-4-yl]pyrrolo[3,2-b]pyridine 43: To 6-bromo-1-[(4,4-difluorocyclohexyl)methyl]-3-[1-(2,2,2-trifluoroethyl)pyrazol-4-yl]pyrrolo[3,2-b]pyridine (42, 0.39 g, 0.82 mmol), 4,4,5,5-tetramethyl-2-(4,4,5,5-tetramethyl-1,3,2-dioxaborolan-2-yl)-1,3,2-dioxaborolane (250.28 mg, 0.99 mmol), [1,1'-bis(diphenylphosphino)ferrocene]dichloropalladium(II) (0.13 g, 0.16 mmol) was added potassium acetate (1.64 mmol) in dimethylformamide (10 ml). The reaction was allowed to stir at 90° C. overnight. The reaction mixture was neutralized with 1N HCl, partitioned between ethyl acetate and water, washed with brine, and dried over sodium sulfate. After removal of drying agent and solvent, the residue was purified by flash chromatography (0-70% ethyl acetate in hexane). The desired fractions were combined and concentrated to provide product as a solid (43, 80 mg, 18.6%) LCMS (ESI) $[M(\text{boronic acid})+H^+]^+$=443.3.

Step 5—Preparation of 5-[1-[(4,4-difluorocyclohexyl)methyl]-3-[1-(2,2,2-trifluoroethyl)pyrazol-4-yl]pyrrolo[3,2-b]pyridin-6-yl]-1,3-dimethyl-pyridin-2-one (P-0541): A microwave vial was charged with 1-[(4,4-difluorocyclohexyl)methyl]-6-(4,4,5,5-tetramethyl-1,3,2-dioxaborolan-2-yl)-3-[1-(2,2,2-trifluoroethyl)pyrazol-4-yl]pyrrolo[3,2-b]pyridine (43, 50 mg, 0.1 mmol), 5-iodo-1,3-dimethyl-pyridin-2-one (45, 0.03 g, 0.11 mmol), [1,1'-bis(diphenylphosphino)ferrocene]dichloropalladium(II) (8.07 mg, 0.01 mmol) and 1M aqueous potassium carbonate (0.29 ml) in acetonitrile (3 ml). The reaction was allowed to stir at 120° C. for 15 minutes. The reaction mixture was neutralized with 1N HCl, partitioned between ethyl acetate and water, washed with brine, and dried over sodium sulfate.

After removal of drying agent and solvent, and the residue was purified by flash chromatography (0-10% methanol in dichloromethane) followed by RP-HPLC (20-70% acetonitrile in water, 0.1% formic acid) to provide product after lyophilization as a light yellowish/white solid (P-0541, 18 mg, 36.3%) MS (ESI) $[M+H^{+}]^{+}$=520.4.

Preparation 5-iodo-1,3-dimethyl-pyridin-2-one 25

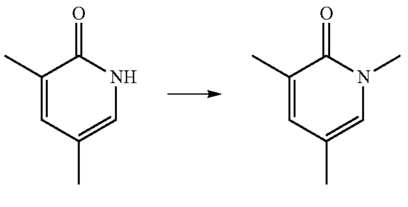

44 45

In round bottom flask charged with 5-iodo-3-methyl-1H-pyridin-2-one (44, 65 mg, 0.28 mmol), potassium carbonate (0.06 g, 0.41 mmol), and iodomethane (0.03 ml, 0.41 mmol) was added acetonitrile (3 ml). The reaction was allowed to stir overnight at room temperature. The reaction was concentrated under reduced pressure and diluted with dichloromethane/methanol. Potassium carbonate was removed by filtration, and the filtrate was concentrated to afford desired product 45 as a white solid. This material was used without further purification.

Example 47

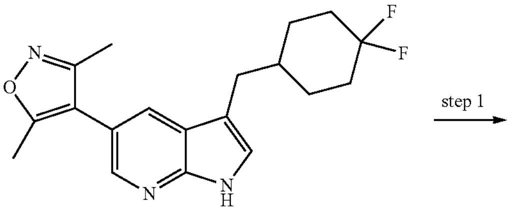

P-0034

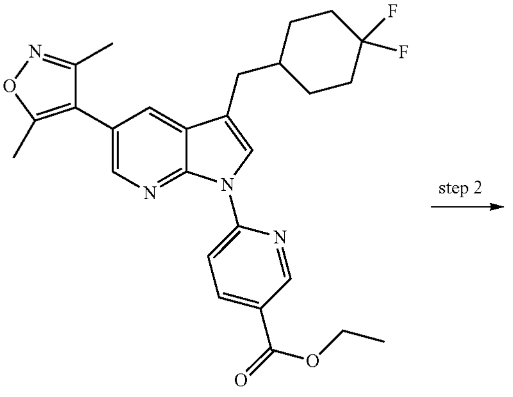

P-0429

-continued

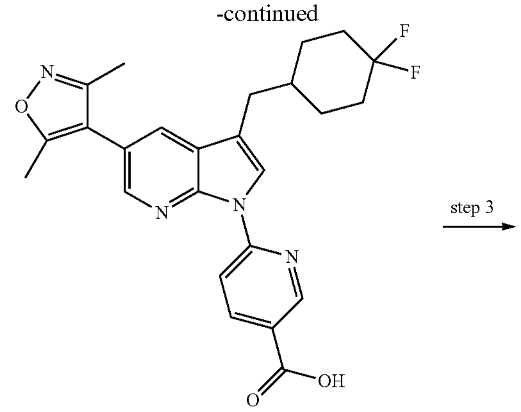

P-0430

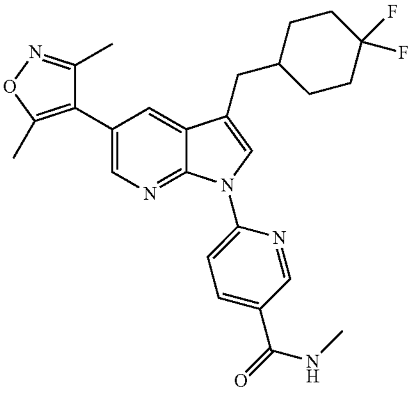

P-0532

Step 1—Preparation of ethyl 6-[3-[(4,4-difluorocyclohexyl)methyl]-5-(3,5-dimethylisoxazol-4-yl)pyrrolo[2,3-b]pyridin-1-yl]pyridine-3-carboxylate (P-0429): To 4-[3-[(4,4-difluorocyclohexyl)methyl]-1H-pyrrolo[2,3-b]pyridin-5-yl]-3,5-dimethyl-isoxazole (P-0034, 0.35 g, 1.01 mmol) in NMP (3 ml) was added ethyl 6-chloropyridine-3-carboxylate (0.23 g, 1.22 mmol) followed by cesium carbonate (0.6 g, 1.84 mmol). The reaction was heated at 140° C. in a microwave reactor for 40 minutes. The reaction was poured into water, and extracted with ethyl acetate. The organic layer was washed with brine, dried over sodium sulfate, and filtered. The filtrate was concentrated and purified by silica gel flash chromatography eluting with 20-100% ethyl acetate in hexane to give product (P-0429, 0.27 g, 53.9%) MS (ESI) $[M+H^{+}]^{+}$=495.0.

Step 2—Preparation of 6-[3-[(4,4-difluorocyclohexyl)methyl]-5-(3,5-dimethylisoxazol-4-yl)pyrrolo[2,3-b]pyridin-1-yl]pyridine-3-carboxylic acid (P-0430): To ethyl 6-[3-[(4,4-difluorocyclohexyl)methyl]-5-(3,5-dimethylisoxazol-4-yl)pyrrolo[2,3-b]pyridin-1-yl]pyridine-3-carboxylate (P-0429), 0.23 g, 0.47 mmol) in THF (10 ml) was added aqueous lithium hydroxide (10 ml, 1060.62 mmol). The reaction mixture was allowed to stir at 80° C. for 5 hours. The reaction was poured into water and extracted with ethyl acetate. The organic layer was washed with brine and the organic layer was dried over sodium sulfate, concentrated, and washed with ethyl acetate and hexane to give product (P-0430, 138 mg, 63.5%) MS (ESI) $[M+H^{+}]^{+}$=466.9.

Step 3—Preparation of 6-[3-[(4,4-difluorocyclohexyl)methyl]-5-(3,5-dimethylisoxazol-4-yl)pyrrolo[2,3-b]pyridin-1-yl]-N-methyl-pyridine-3-carboxamide (P-0532): To 6-[3-[(4,4-difluorocyclohexyl)methyl]-5-[3,5-dimethylisoxazol-4-yl)pyrrolo[2,3-b]pyridin-1-yl]pyridine-3-carboxylic acid (P-0430, 0.06 g, 0.13 mmol) in dimethylacetamide ("DMA") (2 mL) was added PYBOP (0.1 g, 0.2 mmol). The reaction was allowed to stir at room temperature for 40 minutes, followed by the addition of 2M methanamine in THF (0.1 ml) and N,N-diisopropylethylamine (0.03 ml, 0.2 mmol). The reaction was allowed to stir at room temperature for 3 hours. The reaction was poured into water, and extracted with ethyl acetate. The organic layer was washed with brine, dried over sodium sulfate, and filtered. The filtrate was concentrated, and purified by flash silica gel column chromatography eluting with 20-100% ethyl acetate in hexane to give product (P-0532, 36.3 mg, 58.9%) MS (ESI) $[M+H^+]^+=480.1$.

Example 48

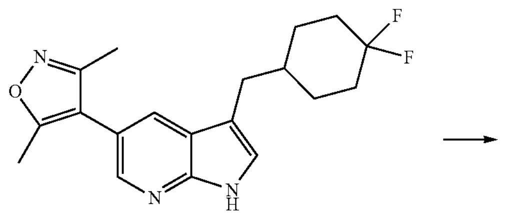

P-0034

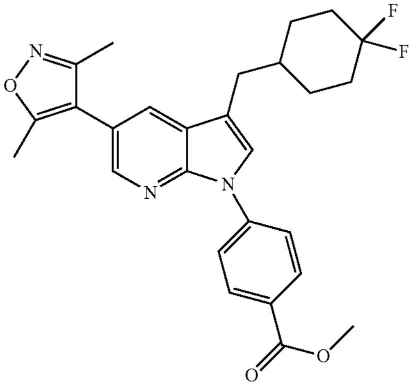

P-0544

Preparation of methyl 4-[3-[(4,4-difluorocyclohexyl)methyl]-5-(3,5-dimethylisoxazol-4-yl)pyrrolo[2,3-b]pyridin-1-yl]benzoate (P-0544): To 4-[3-[(4,4-difluorocyclohexyl)methyl]-1H-pyrrolo[2,3-b]pyridin-5-yl]-3,5-dimethyl-isoxazole (P-0034, 0.08 g, 0.23 mmol) in DMSO (3 ml), was added methyl 4-fluorobenzoate (0.05 g, 0.32 mmol), and dibenzo-18-crown-6 (0.08 g, 0.23 mmol). The reaction was allowed to stir at 160° C. for 1 hour and 40 minutes in a microwave reactor, at 150° C. for two days, and then at 175° C. for an additional 2 hours. The reaction was poured into water and extracted with ethyl acetate. The organic layer was washed with brine, dried over sodium sulfate, and filtered. The filtrate was concentrated and purified by silica gel flash chromatography eluting with 20-100% ethyl acetate in hexane to give product which contained some starting material. The product was obtained by RP-HPLC (P-0544, 4.6 mg, 4%) MS (ESI) $[M+H^+]^+=480.0$.

Example 49

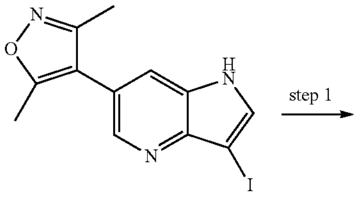

P-0072

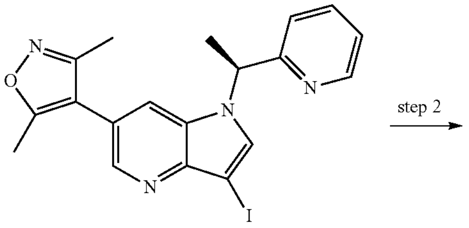

46

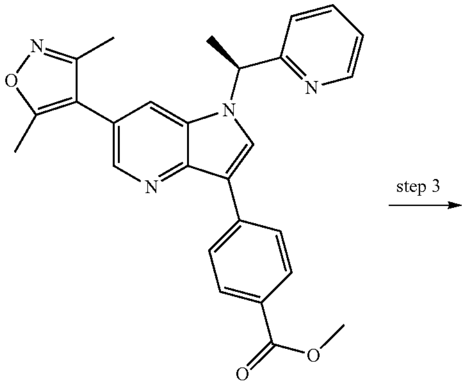

P-0509

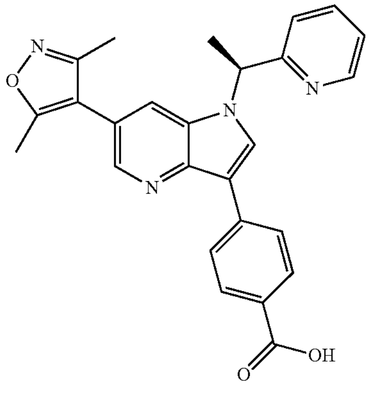

P-0511

Step 1—Preparation of 4-[3-iodo-1-[(1S)-1-(2-pyridyl)ethyl]pyrrolo[3,2-b]pyridin-6-yl]-3,5-dimethyl-isoxazole (46): To 4-(3-iodo-1H-pyrrolo[3,2-b]pyridin-6-yl)-3,5-dimethyl-isoxazole (P-0072, 0.92 g, 2.71 mmol) in THF (20 ml) was added (1R)-1-(2-pyridyl)ethanol (0.38 g, 3.09 mmol) and triphenylphosphine (0.8 ml, 3.65 mmol). The reaction was cooled to 0° C., followed by the dropwise addition of diisopropylazodicarboxylate (0.47 ml, 2.38 mmol) over a period of 15 minutes. After 1 hour at 0° C., the reaction was removed from the cooling bath and allowed to stir for an additional hour while warming to room temperature. The reaction was concentrated and purified by silica gel flash chromatography eluting with 20-100% ethyl acetate in hexane to give product (46, 0.91 g, 75.5%).

Step 2—Preparation of methyl 4-[6-(3,5-dimethylisoxazol-4-yl)-1-[(1S)-1-(2-pyridyl)ethyl]pyrrolo[3,2-b]pyridin-3-yl]benzoate (P-0509): To 4-[3-iodo-1-[(1S)-1-(2-pyridyl)ethyl]pyrrolo[3,2-b]pyridin-6-yl]-3,5-dimethyl-isoxazole (46, 0.5 g, 1.13 mmol) in THF (16 ml) was added methyl 4-(4,4,5,5-tetramethyl-1,3,2-dioxaborolan-2-yl)benzoate (0.38 g, 1.46 mmol), [1,1'-bis(diphenylphosphino)ferrocene]dichloropalladium(II) (0.05 g, 0.07 mmol), and 1M aqueous potassium carbonate (8 ml). The reaction was allowed to stir for 2 hours at 70° C. The reaction was poured into water and extracted with ethyl acetate. The organic layer was washed with brine, dried over sodium sulfate, and filtered. The filtrate was concentrated and purified by silica gel flash chromatography eluting with 20-100% ethyl acetate in hexane to give product (P-0509, 0.37 g, 72.7%) MS (ESI) $[M+H^+]^+=453.3$.

Step 3—Preparation of 4-[6-(3,5-dimethylisoxazol-4-yl)-1-[(1S)-1-(2-pyridyl)ethyl]pyrrolo[3,2-b]pyridin-3-yl]benzoic acid (P-0511): To methyl 4-[6-(3,5-dimethylisoxazol-4-yl)-1-[(1S)-1-(2-pyridyl)ethyl]pyrrolo[3,2-b]pyridin-3-yl]benzoate (P-0509, 0.32 g, 0.71 mmol) in THF (ml) was added 2M aqueous lithium hydroxide (3 ml). The reaction mixture was allowed to stir at 60° C. overnight. The reaction was poured into water, acidified to an approximate pH of 6 with 1N aqueous HCl (6 mL) and extracted with ethyl acetate. The organic layer was washed with brine, dried over sodium sulfate, concentrated, and washed with ethyl acetate and hexane to give product (P-0511, 261.1 mg, 84.2%) MS (ESI) $[M+H^+]^+=438.9$.

Example 50

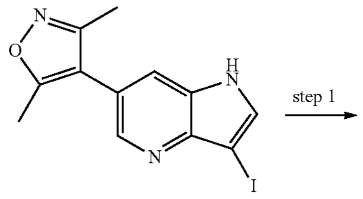

P-0072

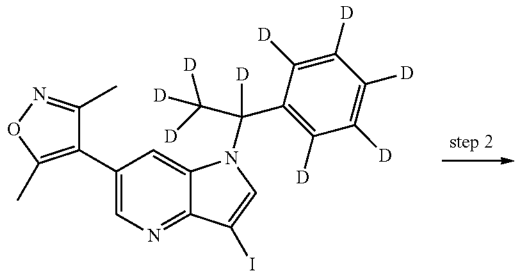

47

-continued

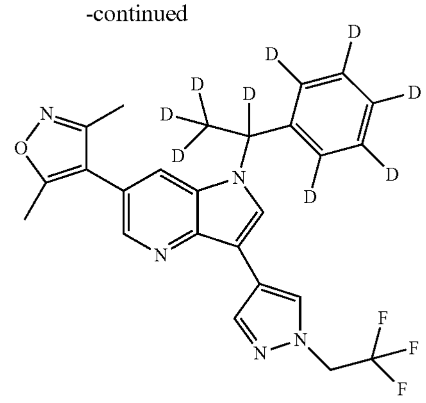

P-0606

Step 1—Preparation of 4-[3-iodo-1-[1,2,2,2-tetradeuterio-1-(2,3,4,5,6-pentadeuteriophenyl)ethyl]pyrrolo[3,2-b]pyridin-6-yl]-3,5-dimethyl-isoxazole (47): To a round bottom flask charged with 1,2,2,2-tetradeuterio-1-(2,3,4,5,6-pentadeuteriophenyl)ethanol (0.18 g, 1.37 mmol), 4-(3-iodo-1H-pyrrolo[3,2-b]pyridin-6-yl)-3,5-dimethyl-isoxazole (P-0072, 0.52 g, 1.53 mmol), and triphenylphosphine (0.58 g, 2.19 mmol) was added THF (10 ml) and the reaction mixture was cooled to between −20° C. and −10° C. in a dry ice/acetone bath. Then, diethylazodicarboxylate (1 ml, 2.19 mmol) in toluene was added dropwise. The reaction mixture was allowed to stir while maintaining a temperature between −20° C. and −10° C. for 6 hours and then allowed to warm to room temperature. The reaction was allowed to stir at room temperature for another 1 hr. The reaction was concentrated and purified by silica gel flash chromatography eluting with 0-40% ethyl acetate in hexane. The pure fractions were combined and concentrated under reduced pressure to provide product as a slightly yellowish solid (47, 152 mg, 24.5%) MS (ESI) $[M+H^+]^+=453.1$.

Step 2—Preparation of 3,5-dimethyl-4-[1-[1,2,2,2-tetradeuterio-1-(2,3,4,5,6-pentadeuteriophenyl)ethyl]-3-[1-(2,2,2-trifluoroethyl)pyrazol-4-yl]pyrrolo[3,2-b]pyridin-6-yl]isoxazole (P-0606): To a 10 mL microwave vial charged with 4-[3-iodo-1-[1,2,2,2-tetradeuterio-1-(2,3,4,5,6-pentadeuteriophenyl)ethyl]pyrrolo[3,2-b]pyridin-6-yl]-3,5-dimethyl-isoxazole (47, 0.06 g, 0.12 mmol) in acetonitrile (6 ml) was added 4-(4,4,5,5-tetramethyl-1,3,2-dioxaborolan-2-yl)-1-(2,2,2-trifluoroethyl)pyrazole (0.04 g, 0.16 mmol), 1M aqueous potassium carbonate in water (3 ml), and [1,1'-bis(diphenylphosphino)ferrocene]dichloropalladium(II) (0.01 g, 0.01 mmol). The reaction mixture was heated at 75° C. for 5 hrs. The reaction mixture was diluted with water and extracted with ethyl acetate. The organic layer was washed with water, brine, dried over magnesium sulfate, filtered and the volatiles were removed under reduced pressure. The product was purified by silica gel flash chromatography eluting with 20-100% ethyl acetate in hexane. Fractions that contained product were combined and further purified by RP-HPLC to provide pure product after lyophilization (P-0606, 23 mg, 39.2%) MS (ESI) $[M+H^+]^+=474.9$.

Example 51

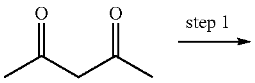

-continued

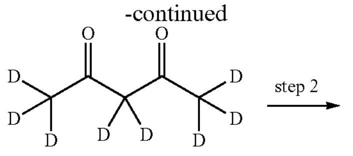

48

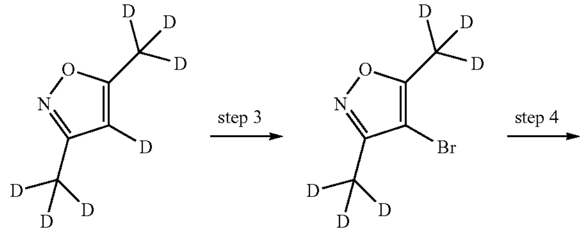

49
50

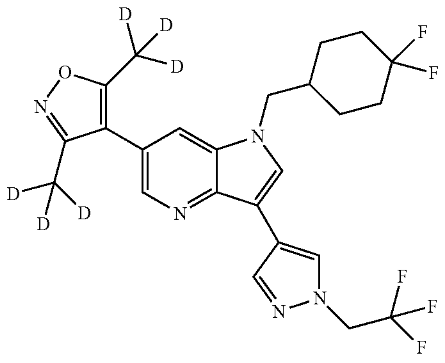

P-0615

Step 1—Preparation of 1,1,1,3,3,5,5,5-octadeuteriopentane-2,4-dione (48): A reaction flask was charged with pentane-2,4-dione (10 mL, 97.19 mmol), potassium carbonate (1 gram, 7.24 mmol) and deuterium oxide (50 mL). The reaction flask was sealed and allowed to stir at 120° C. for 3 days. The reaction mixture was extracted with dichloromethane (2×150 mL) and the combined organic layers were dried over sodium sulfate. The dichloromethane was removed under reduced pressure (~150 mbar) to provide brown liquid. This material was subjected to the above procedure a second time to provide a brown liquid (48, 11.4 g, 108%) that was used without further purification.

Step 2—Preparation of 4-deuterio-3,5-bis(trideuteriomethyl)isoxazole (49): In a microwave vial charged with 1,1,1,3,3,5,5,5-octadeuteriopentane-2,4-dione (48, 1500 mg, 14 mmol) and MeOH-d4 (10 mL) was added Hydroxylamine-D3 DCl (1200 mg, 16.3 mmol) and Trifluoroacetic acid-D (1 mL). The reaction mixture was heated to 90° C. in an oil bath for 2 hrs. The reaction mixture was diluted with water and extracted with dichloromethane. The organic layer was washed with aqueous sodium bicarbonate, followed by brine and then dried over sodium sulfate. The volatiles were removed under reduced pressure to provide product as a brown oil (49, 1.5 g, 104%) that was used without further purification.

Step 3—Preparation of 4-bromo-3,5-bis(trideuteriomethyl)isoxazole (50): To a solution of 4-deuterio-3,5-bis(trideuteriomethyl)isoxazole (49, 0.25 g, 2.4 mmol) in N,N-dimethylformamide (5 mL) was added N-bromosuccinimide (0.64 g, 3.6 mmol). The reaction was allowed to stir at 60° C. for 4 hours. The reaction mixture was poured into aqueous potassium carbonate and extracted with dichloromethane. The organic layer was washed with water and brine and then dried over sodium sulfate. The volatiles were removed under reduced pressure to provide the product as a yellow liquid (50, 0.43 g, 98.4%) MS (ESI) $[M+H^+]^+=182.2$ and 184.2.

Step 4—Preparation of 4-[1-[(4,4-difluorocyclohexyl)methyl]-3-[1-(2,2,2-trifluoroethyl)pyrazol-4-yl]pyrrolo[3,2-b]pyridin-6-yl]-3,5-bis(trideuteriomethyl)isoxazole (P-0615): In a 10 mL microwave vial charged with 4-bromo-3,5-bis(trideuteriomethyl)isoxazole (50, 0.1 g, 0.54 mmol) and acetonitrile (4 mL) was added 1-[(4,4-difluorocyclohexyl)methyl]-6-(4,4,5,5-tetramethyl-1,3,2-dioxaborolan-2-yl)-3-[1-(2,2,2-trifluoroethyl)pyrazol-4-yl]pyrrolo[3,2-b]pyridine (43, 0.09 g, 0.17 mmol), 1M aqueous potassium carbonate (2 mL) and [1,1'-bis(diphenylphosphino)ferrocene]dichloropalladium(II) (0.04 g, 0.05 mmol). The reaction mixture was allowed to stir at 100° C. for 90 min. The reaction mixture was diluted with water and extracted with ethyl acetate. The organic layer was washed with water followed by brine. The organic layer was dried over magnesium sulfate and filtered. The volatiles were removed from the filtrate under reduced pressure and the resulting crude material was purified by RP-HPLC to give the product as a white solid after lyophilization (P-0615, 7 mg, 8%) MS (ESI) $[M+H^+]^+=500.3$.

Example 52

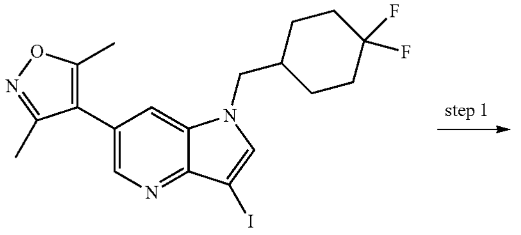

15

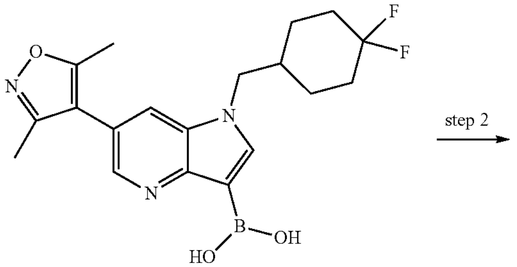

51

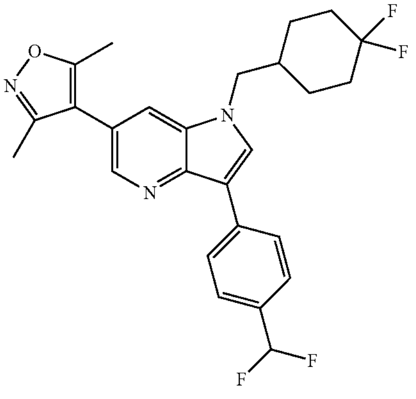

P-0608

Step 1—Preparation of [1-[(4,4-difluorocyclohexyl)methyl]-6-(3,5-dimethylisoxazol-4-yl)pyrrolo[3,2-b]pyridin-3-yl]boronic acid 31: In a vial, to a solution of 4-[1-[(4,4-difluorocyclohexyl)methyl]-3-iodo-pyrrolo[3,2-b]pyridin-6-yl]-3,5-dimethyl-isoxazole (15, 0.65 g, 1.38 mmol) in 15 mL of THF at −78° C. under nitrogen was added 2M chloro(isopropyl)magnesium (1.06 ml, 2.12 mmol). The reaction was allowed to warm to 5° C. over 2-3 hrs. Then, the reaction was cooled to -78° C., followed by the addition of 4,4,5,5-tetramethyl-1,3,2-dioxaborolane (0.35 g, 2.76 mmol) in THF (1.0 mL). The reaction mixture was slowly warmed to room temperature over 2-3 hours. The reaction mixture was quenched with methanol. The volatiles were removed under reduced pressure. The crude was purified by silica gel flash chromatography eluting with 0-70% ethyl acetate in hexane followed by 0-20% methanol in dichloromethane to provide product as a slightly yellowish solid (51, 173 mg, 32.2%) MS (ESI) $[M+H^+]^+$=390.1.

Step 2—Preparation of 4-[1-[(4,4-difluorocyclohexyl)methyl]-3-[4-(difluoromethyl)phenyl]pyrrolo[3,2-b]pyridin-6-yl]-3,5-dimethyl-isoxazole (P-0608): In a 10 mL vial charged with [1-[(4,4-difluorocyclohexyl)methyl]-6-(3,5-dimethylisoxazol-4-yl)pyrrolo[3,2-b]pyridin-3-yl]boronic acid (51, 0.05 g, 0.13 mmol) and acetonitrile (4 ml) was added 1-bromo-4-(difluoromethyl)benzene (0.05 g, 0.24 mmol), 1M aqueous potassium carbonate (2 ml), and [1,1'-bis(diphenylphosphino)ferrocene]dichloropalladium(II) (0.01 g, 0.01 mmol). The reaction mixture was heated at 140° C. in a microwave reactor for 30 min. The reaction mixture was diluted with water and extracted with ethyl acetate. The organic layer was washed with water and brine. Then, the organic layer was dried over magnesium sulfate and the drying agent removed by filtration. The volatiles were removed from the filtrate under reduced pressure and the crude material was purified by silica gel flash chromatography eluting with 0-50% ethyl acetate in hexane to provide product as a tan solid (P-0608, 18 mg, 28.6%) MS (ESI) $[M+H^+]^+$=472.0.

Example 53

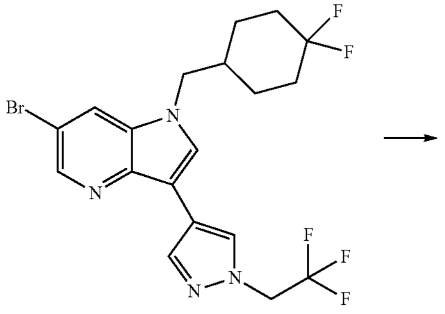

42

-continued

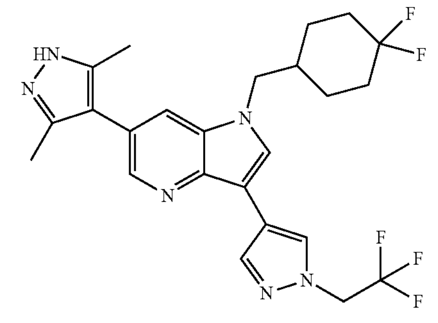

P-0440

Step 1—Preparation of 1-[(4,4-difluorocyclohexyl)methyl]-6-(3,5-dimethyl-1H-pyrazol-4-yl)-3-[1-(2,2,2-trifluoroethyl)pyrazol-4-yl]pyrrolo[3,2-b]pyridine (P-0440): To 6-bromo-1-[(4,4-difluorocyclohexyl)methyl]-3-[1-(2,2,2-trifluoroethyl)pyrazol-4-yl]pyrrolo[3,2-b]pyridine (42, 0.06 g, 0.12 mmol) in acetonitrile (3 ml) was added tert-butyl 3,5-dimethyl-4-(4,4,5,5-tetramethyl-1,3,2-dioxaborolan-2-yl)pyrazole-1-carboxylate (0.08 g, 0.25 mmol), [1,1'-bis(diphenylphosphino)ferrocene]dichloropalladium(II) (0.02 g, 0.13 mmol), and 1M aqueous potassium carbonate (1.2 ml). The reaction was heated under at 140° C. for 40 minutes in a microwave reactor. The reaction was poured into water, and extracted with ethyl acetate. The organic layer was washed with brine, dried over sodium sulfate, and filtered. The filtrate was concentrated, and purified by silica gel flash chromatography eluting with 20-100% ethyl acetate in hexane, and then further purified with RP-HPLC to give product (P-0440, 25.5 mg, 44.9%) MS (ESI) [M+H+]+=493.3.

Example 54

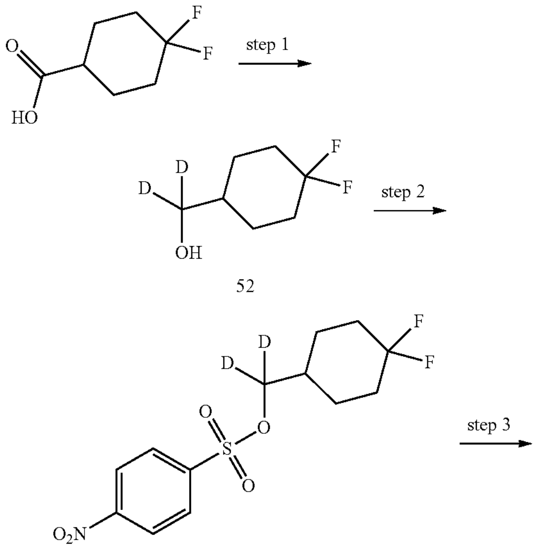

52

53

-continued

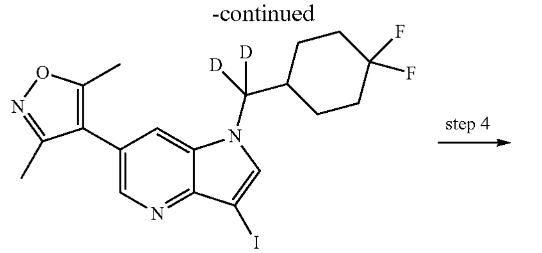

54

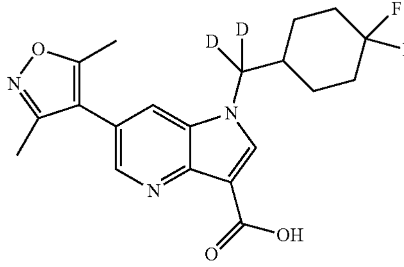

P-0459

Step 1—Preparation of dideuterio-(4,4-difluorocyclohexyl)methanol 52: To 4,4-difluorocyclohexanecarboxylic acid (2.45 g, 14.93 mmol) in THF (160 ml) was added lithium aluminum deuteride (0.8 g, 19.06 mmol) at room temperature. The reaction was stirred at room temperature overnight. To the reaction mixture was added sodium sulfate decahydrate (~10 g). After 2 hours, the reaction was filtered and the resulting solid was washed with ethyl acetate. The combined filtrates were concentrated under reduced pressure to give product (52, 2.0 g, 88.1%)

Step 2—Preparation of [dideuterio-(4,4-difluorocyclohexyl)methyl] 4-nitrobenzenesulfonate (53): To dideuterio-(4,4-difluorocyclohexyl)methanol (52, 1 g, 6.57 mmol) in methylene chloride (25 mL) were added triethylamine (4 ml, 28.7 mmol), and 4-nitrobenzenesulfonyl chloride (1.66 g, 7.49 mmol). The reaction was stirred at room temperature overnight. The reaction was poured into water and extracted with ethyl acetate. The organic layer was washed with brine, dried over sodium sulfate, and filtered. The filtrate was concentrated and purified by silica gel flash chromatography eluting with 10-100% ethyl acetate in hexane to give pure product (53, 1.0 g, 45.1%)

Step 3—Preparation of 4-[1-[dideuterio-(4,4-difluorocyclohexyl)methyl]-3-iodo-pyrrolo[3,2-b]pyridin-6-yl]-3,5-dimethyl-isoxazole (54): To 4-(3-iodo-1H-pyrrolo[3,2-b]pyridin-6-yl)-3,5-dimethyl-isoxazole (P-0072, 0.35 g, 1.03 mmol) in DMF (10 ml), was added sodium hydride (60%, 49.54 mg, 1.24 mmol) at room temperature. After 10 minutes, [dideuterio-(4,4-difluorocyclohexyl)methyl] 4-nitrobenzenesulfonate (53, 0.42 g, 1.24 mmol) was added. The reaction was allowed to stir at room temperature for 4 hours. The reaction did not go to completion, so additional [dideuterio-(4,4-difluorocyclohexyl)methyl] 4-nitrobenzenesulfonate (33, 0.6 g, 1.8 mmol) was added and the reaction was allowed to stir overnight. The reaction was poured into water and extracted with ethyl acetate. The organic layer was washed with brine, dried over sodium sulfate, filtered, concentrated, and purified by silica gel flash chromatography eluting with 2-20% methanol in methylene chloride to give crude product, which was then further purified with RP-HPLC to give pure product (54, 200 mg, 40.9%)

Step 4—Preparation of 1-[dideuterio-(4,4-difluorocyclohexyl)methyl]-6-(3,5-dimethylisoxazol-4-yl)pyrrolo[3,2-b]pyridine-3-carboxylic acid (P-0459): To 4-[1-[dideuterio-(4,4-difluorocyclohexyl)methyl]-3-iodo-pyrrolo[3,2-b]pyridin-6-yl]-3,5-dimethyl-isoxazole (54, 0.21 g, 0.43 mmol) in THF (5 mL) under an atmosphere of nitrogen and cooled to −40° C., was added 2M i-PrMgCl in THF (0.3 ml). The reaction was allowed to warm to 5° C. in 1 hour. Then, the reaction was cooled to -40° C., followed by the addition of carbon dioxide (dry ice, 0.5 g, 11.36 mmol). The reaction was allowed to warm to room temperature in 1 hour. The reaction was poured into water, acidified to pH around 6, and extracted with ethyl acetate. The organic layer was washed with brine, dried over sodium sulfate, filtered, concentrated and purified by silica gel flash chromatography eluting 20-100% ethyl acetate in hexane to give product (P-0459, 0.060 g, 35.2%) MS (ESI) $[M+H^+]^+=392.1$.

Example 55

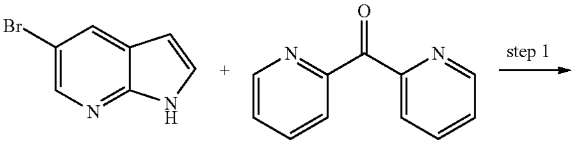

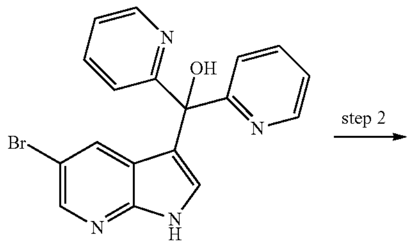

55

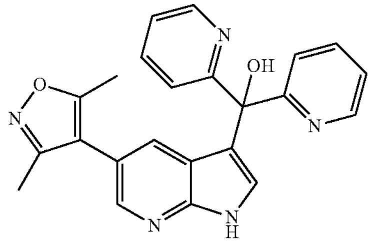

P-0545

Step 1—Preparation of (5-bromo-1H-pyrrolo[2,3-b]pyridin-3-yl)-bis(2-pyridyl)methanol (55): To 5-bromo-1H-pyrrolo[2,3-b]pyridine (1.15 g, 5.84 mmol) in DMSO (3 ml) was added bis(2-pyridyl)methanone (1.37 g, 7.44 mmol) and potassium hydroxide (1.2 g, 21.39 mmol). The reaction was allowed to stir at room temperature over 3 days. The reaction was poured into water and extracted with ethyl acetate. The organic layer was washed with brine, dried over sodium sulfate, and filtered to give product (55, 1.95 g, 87.6%).

Step 2—Preparation of (5-(3,5-dimethylisoxazol-4-yl)-1H-pyrrolo[2,3-b]pyridin-3-yl)di(pyridin-2-yl)methanol (P-0545): To (5-bromo-1H-pyrrolo[2,3-b]pyridin-3-yl)-bis(2-pyridyl)methanol (55, 0.78 g, 2.05 mmol) in tetrahydrofuran (50 ml) was added [1,1'-bis(diphenylphosphino)ferrocene]dichloropalladium(II) (0.1 g, 0.13 mmol), 3,5-dimethyl-4-(4,4,5,5-tetramethyl-1,3,2-dioxaborolan-2-yl) isoxazole (0.55 g, 2.46 mmol), and 1M aqueous potassium carbonate (25 ml). The reaction was heated and stirred at 70° C. for 1 hour. The reaction was poured into water and extracted with ethyl acetate. The organic layer was washed with brine, dried over sodium sulfate, and filtered. The filtrate was concentrated and purified by silica gel flash chromatography eluting 2-15% methanol in dichloromethane to give product (P-0545, 0.3 g, 36.9%) MS (ESI) $[M+H^+]^+=397.8$.

Example 56

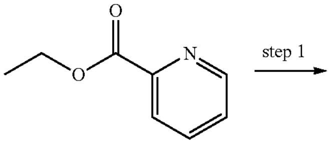

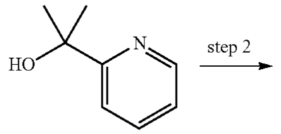

56

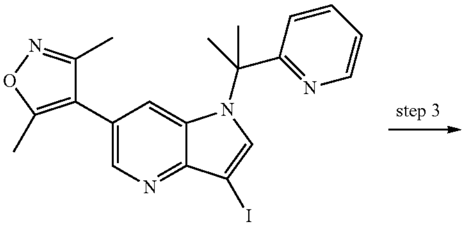

57

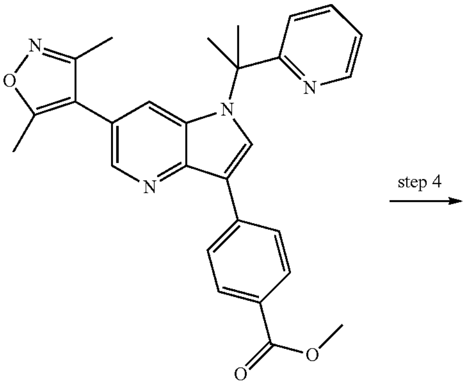

P-0547

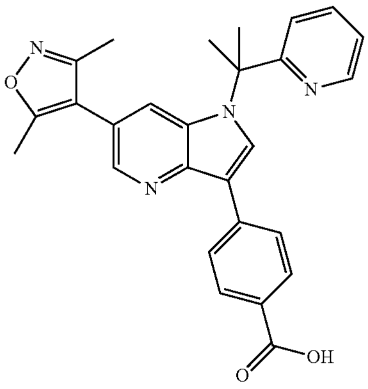

P-0548

Step 1—Preparation of 2-(2-pyridyl)propan-2-ol (56): To a solution of ethyl pyridine-2-carboxylate (5 g, 33.08 mmol) in THF (50 ml) cooled to −78° C. was added 1.6M methyllithium in ether (50 ml) slowly. After 3 hours, the reaction mixture was allowed to warm to room temperature for 10 minutes. The reaction was poured into water and extracted with ethyl acetate. The organic layer was washed with brine, dried over sodium sulfate and concentrated to give crude product (56, 4.0 g, 88.2%) which was used in the next step without further purification.

Step 2—Preparation of 4-[3-iodo-1-[1-methyl-1-(2-pyridyl)ethyl]pyrrolo[3,2-b]pyridin-6-yl]-3,5-dimethyl-isoxazole (57): To 4-(3-iodo-1H-pyrrolo[3,2-b]pyridin-6-yl)-3,5-dimethyl-isoxazole (P-0072, 1.26 g, 3.73 mmol) in THF (20 ml) was added 2-(2-pyridyl)propan-2-ol (56) (0.91 g, 6.63 mmol) and phenoxy(diphenyl)phosphane (1.89 g, 6.77 mmol). The reaction was cooled with an ice water bath, followed by the addition of 2.3M ethyl (NE)-N-ethoxycarbonyliminocarbamate in toluene (2.94 ml) dropwise over 15 minutes. After 1 hour, the reaction was removed from the ice bath and allowed to warm to room temperature for 1 hour. The reaction was heated to 65° C. for 2 hours. The reaction was poured into water and extracted with ethyl acetate. The organic layer was washed with brine, dried over sodium sulfate, and filtered. The filtrate was concentrated, and purified by silica gel flash chromatography eluting with 20-100% ethyl acetate in hexane to give impure product that was used without further purification (57, 0.6 g, ~35%).

Step 3—Preparation of methyl 4-[6-(3,5-dimethylisoxazol-4-yl)-1-[1-methyl-1-(2-pyridyl)ethyl]pyrrolo[3,2-b]pyridin-3-yl]benzoate (P-0547): To 4-[3-iodo-1-[I-methyl-1-(2-pyridyl)ethyl]pyrrolo[3,2-b]pyridin-6-yl]-3,5-dimethyl-isoxazole (57, 0.5 g, 1.09 mmol) in THF (80 ml) was added methyl 4-(4,4,5,5-tetramethyl-1,3,2-dioxaborolan-2-yl)benzoate (0.38 g, 1.43 mmol), [1,1'-bis(diphenylphosphino)ferrocene]dichloropalladium(II) (0.1 g, 0.13 mmol), and 1M aqueous potassium carbonate in water (40 ml). The reaction was allowed to stir for 2 hours at 70° C. The reaction was poured into water and extracted with ethyl acetate. The organic layer was washed with brine, dried over sodium sulfate, and filtered. The filtrate was concentrated and purified by silica gel flash chromatography eluting 20-100% ethyl acetate in hexane to give product (P-0547, 0.05 g, 9.8%) MS (ESI) $[M+H^+]^+=466.9$.

Step 4—Preparation of 4-[6-(3,5-dimethylisoxazol-4-yl)-1-[1-methyl-1-(2-pyridyl)ethyl]pyrrolo[3,2-b]pyridin-3-yl]benzoic acid (P-0548): To methyl 4-[6-(3,5-dimethylisoxazol-4-yl)-1-[1-methyl-1-(2-pyridyl)ethyl]pyrrolo[3,2-b]pyridin-3-yl]benzoate (P-0547) (0.04 g, 0.09 mmol) in THF (5 ml) was added 2M aqueous lithium hydroxide (2 ml). The reaction mixture was allowed to stir at 60° C. overnight. The reaction was poured into water, acidified to around pH 6 with 1N aqueous HCl (~4 mL) and extracted with ethyl acetate. The organic layer was washed with brine, dried over sodium sulfate, concentrated and then purified by RP-HPLC to give product (P-0548, 3.6 mg, 92.3%) MS (ESI) $[M+H^+]^+=452.9$.

Compounds listed in Table 29 below, e.g., compounds P-0373 to P-0420, P-0424, P-0427 to P-0443, P-0448, and P-0451 to P-0622 were prepared according to the protocols set forth in Examples 1 to 56. The $^1H$ NMR and mass spectroscopy data were consistent with the structures of the compounds

TABLE 29

| Compound No. | Structure | Name | MS(ESI) [M + H+]+ or [M − H+]− observed |
|---|---|---|---|
| P-0373 | 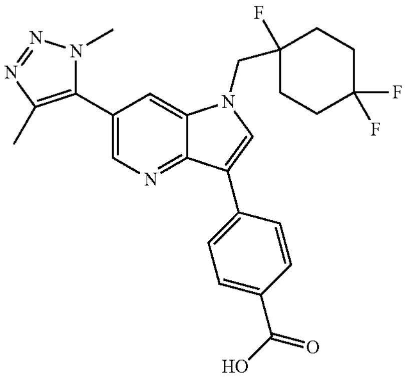 [SMILES: Cc1nnn(C)c1-c1cnc2c(-c3ccc(C(=O)O)cc3)cn(CC3(F)CCC(F)(F)CC3)c2c1] | 4-[6-(3,5-dimethyltriazol-4-yl)-1-[(1,4,4-trifluorocyclohexyl)methyl]pyrrolo[3,2-b]pyridin-3-yl]benzoic acid | 484.3 |
| P-0374 | 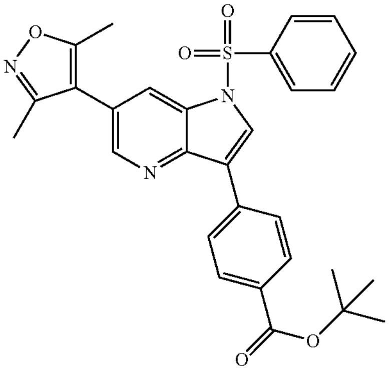 [SMILES: Cc1noc(C)c1-c1cnc2c(-c3ccc(C(=O)OC(C)(C)C)cc3)cn(S(=O)(=O)c3ccccc3)c2c1] | tert-butyl 4-[1-(benzenesulfonyl)-6-(3,5-dimethylisoxazol-4-yl)pyrrolo[3,2-b]pyridin-3-yl]benzoate | 530.0 |
| P-0375 | 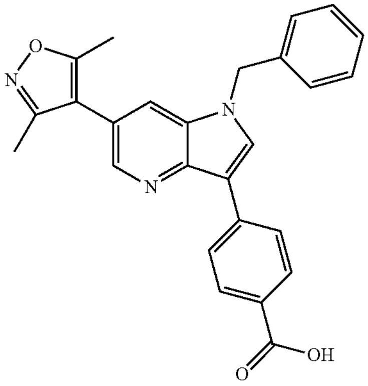 [SMILES: Cc1noc(C)c1-c1cnc2c(-c3ccc(C(=O)O)cc3)cn(Cc3ccccc3)c2c1] | 4-[1-benzyl-6-(3,5-dimethylisoxazol-4-yl)pyrrolo[3,2-b]pyridin-3-yl]benzoic acid | 424.0 |
| P-0376 | 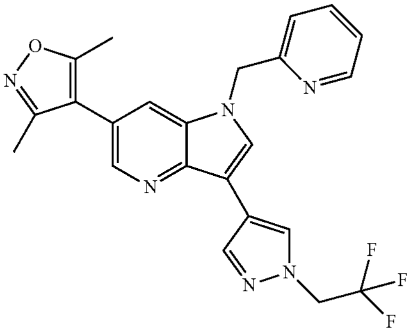 [SMILES: Cc1noc(C)c1-c1cnc2c(-c3cnn(CC(F)(F)F)c3)cn(Cc3ccccn3)c2c1] | 3,5-dimethyl-4-[1-(2-pyridylmethyl)-3-[1-(2,2,2-trifluoroethyl)pyrazol-4-yl]pyrrolo[3,2-b]pyridin-6-yl]isoxazole | 453.2 |

TABLE 29-continued
| Compound No. | Structure | Name | MS(ESI) [M + H+]+ or [M − H+]− observed |
|---|---|---|---|
| P-0377 | 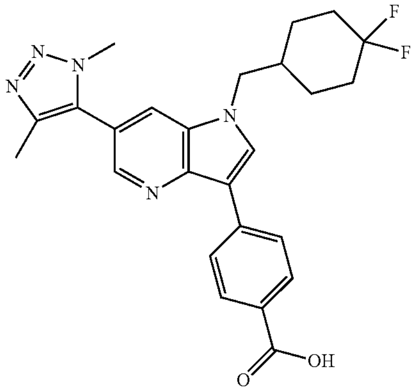 [SMILES: Cc1nnn(C)c1-c1cnc2c(-c3ccc(C(=O)O)cc3)cn(CC3CCC(F)(F)CC3)c2c1] | 4-[1-[(4,4-difluorocyclohexyl)methyl]-6-(3,5-dimethyltriazol-4-yl)pyrrolo[3,2-b]pyridin-3-yl]benzoic acid | 466.0 |
| P-0378 | 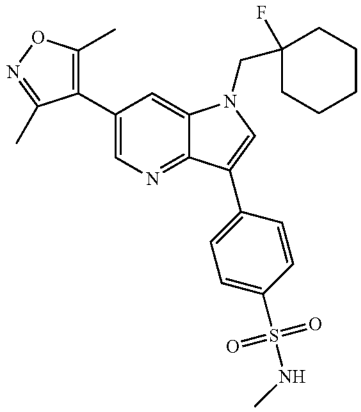 [SMILES: CNS(=O)(=O)c1ccc(-c2cn(CC3(F)CCCCC3)c3cc(-c4c(C)noc4C)cnc23)cc1] | 4-[6-(3,5-dimethylisoxazol-4-yl)-1-[(1-fluorocyclohexyl)methyl]pyrrolo[3,2-b]pyridin-3-yl]-N-methyl-benzenesulfonamide | 497.4 |
| P-0379 | 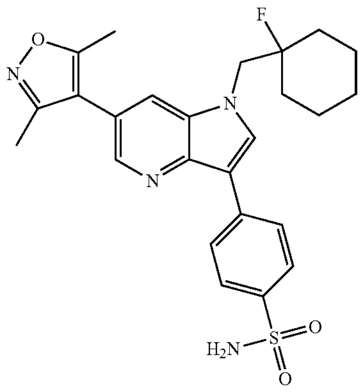 [SMILES: Cc1noc(C)c1-c1cnc2c(-c3ccc(S(N)(=O)=O)cc3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]benzenesulfonamide | 483.3 |

TABLE 29-continued

| Compound No. | Structure | Name | MS(ESI) [M + H+]+ or [M − H+]− observed |
|---|---|---|---|
| P-0380 | 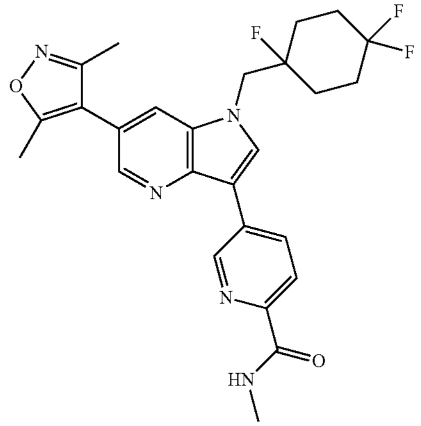 [SMILES: CNC(=O)c1ccc(-c2cn(CC3(F)CCC(F)(F)CC3)c3cc(-c4c(C)noc4C)cnc23)cn1] | 5-[6-(3,5-dimethylisoxazol-4-yl)-1-[(1,4,4-trifluorocyclohexyl)methyl]pyrrolo[3,2-b]pyridin-3-yl]-N-methyl-pyridine-2-carboxamide | 498.4 |
| P-0381 | 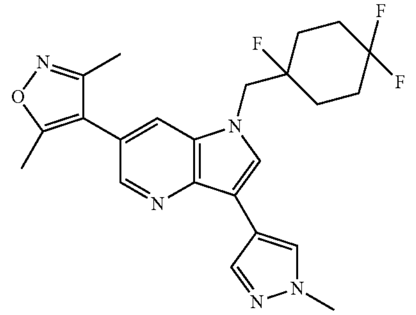 [SMILES: Cc1noc(C)c1-c1cnc2c(-c3cnn(C)c3)cn(CC3(F)CCC(F)(F)CC3)c2c1] | 3,5-dimethyl-4-[3-(1-methylpyrazol-4-yl)-1-[(1,4,4-trifluorocyclohexyl)methyl]pyrrolo[3,2-b]pyridin-6-yl]isoxazole | 444.3 |
| P-0382 | 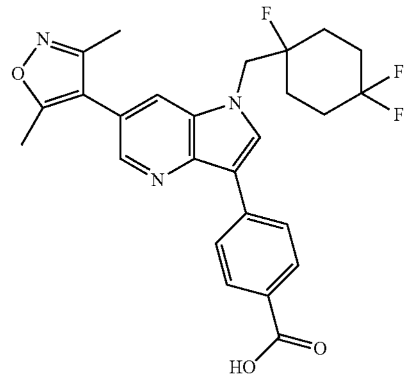 [SMILES: Cc1noc(C)c1-c1cnc2c(-c3ccc(C(=O)O)cc3)cn(CC3(F)CCC(F)(F)CC3)c2c1] | 4-[6-(3,5-dimethylisoxazol-4-yl)-1-trifluorocyclohexyl)methyl]pyrrolo[3,2-b]pyridin-3-yl]benzoic acid | 482.3* |
| P-0383 | 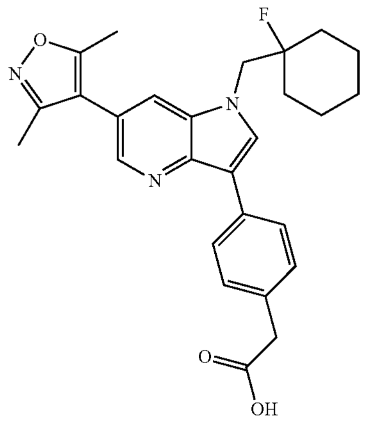 [SMILES: Cc1noc(C)c1-c1cnc2c(-c3ccc(CC(=O)O)cc3)cn(CC3(F)CCCCC3)c2c1] | 2-[4-[6-(3,5-dimethylisoxazol-4-yl)-1-[(1-fluorocyclohexyl)methyl]pyrrolo[3,2-b]pyridin-3-yl]phenyl]acetic acid | 462.4 |

TABLE 29-continued

| Compound No. | Structure | Name | MS(ESI) [M + H+]+ or [M − H+]− observed |
|---|---|---|---|
| P-0384 | 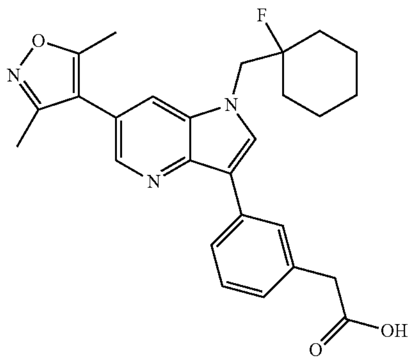 [SMILES: Cc1noc(C)c1-c1cnc2c(-c3cccc(CC(=O)O)c3)cn(CC3(F)CCCCC3)c2c1] | 2-[3-[6-(3,5-dimethylisoxazol-4-yl)-1-[(1-fluorocyclohexyl)methyl]pyrrolo[3,2-b]pyridin-3-yl]phenyl]acetic acid | 462.4 |
| P-0385 | 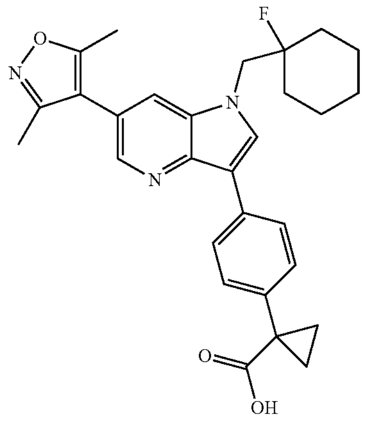 [SMILES: Cc1noc(C)c1-c1cnc2c(-c3ccc(C4(C(=O)O)CC4)cc3)cn(CC3(F)CCCCC3)c2c1] | 1-[4-[6-(3,5-dimethylisoxazol-4-yl)-1-[(1-fluorocyclohexyl)methyl]pyrrolo[3,2-b]pyridin-3-yl]phenyl]cyclopropanecarboxylic acid | 488.4 |
| P-0386 | 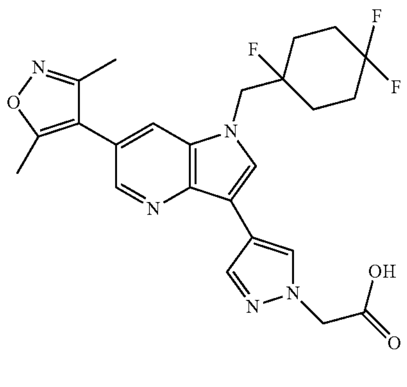 [SMILES: Cc1noc(C)c1-c1cnc2c(-c3cnn(CC(=O)O)c3)cn(CC3(F)CCC(F)(F)CC3)c2c1] | 2-[4-[6-(3,5-dimethylisoxazol-4-yl)-1-[(1,4,4-trifluorocyclohexyl)methyl]pyrrolo[3,2-b]pyridin-3-yl]pyrazol-1-yl]acetic acid | 488.0 |

TABLE 29-continued

| Compound No. | Structure | Name | MS(ESI) [M + H+]+ or [M − H+]− observed |
|---|---|---|---|
| P-0387 | 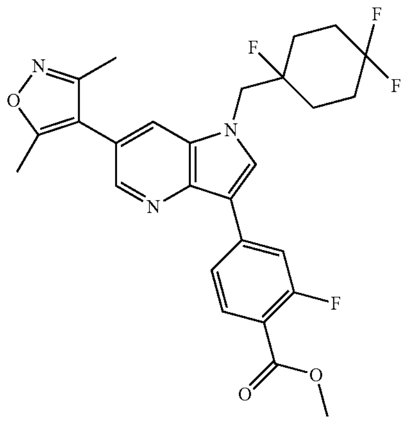 [SMILES: COC(=O)c1ccc(-c2cn(CC3(F)CCC(F)(F)CC3)c3cc(-c4c(C)noc4C)cnc23)cc1F] | methyl 4-[6-(3,5-dimethylisoxazol-4-yl)-1-[(1,4,4-trifluorocyclohexyl)methyl]pyrrolo[3,2-b]pyridin-3-yl]-2-fluoro-benzoate | 516 |
| P-0388 | 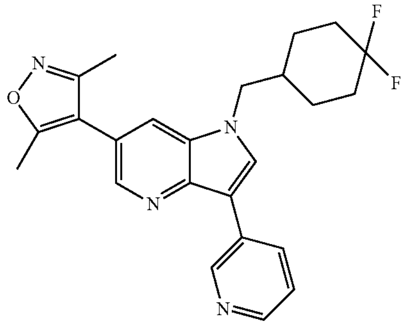 [SMILES: Cc1noc(C)c1-c1cnc2c(-c3cccnc3)cn(CC3CCC(F)(F)CC3)c2c1] | 4-[1-[(4,4-difluorocyclohexyl)methyl]-3-(3-pyridyl)pyrrolo[3,2-b]pyridin-6-yl]-3,5-dimethyl-isoxazole | 423.1 |
| P-0389 | 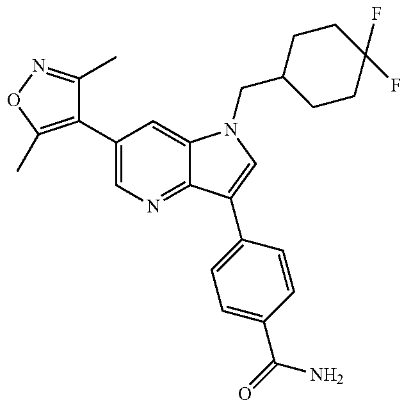 [SMILES: Cc1noc(C)c1-c1cnc2c(-c3ccc(C(N)=O)cc3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]benzamide | 465.1 |
| P-0390 | 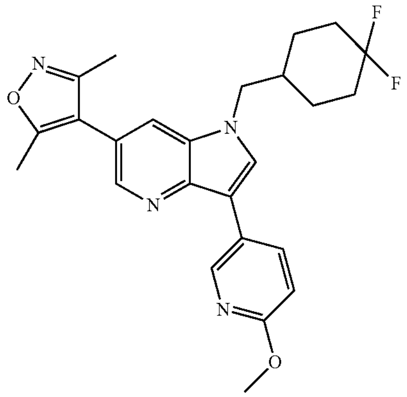 [SMILES: COc1ccc(-c2cn(CC3CCC(F)(F)CC3)c3cc(-c4c(C)noc4C)cnc23)cn1] | 4-[1-[(4,4-difluorocyclohexyl)methyl]-3-(6-methoxy-3-pyridyl)pyrrolo[3,2-b]pyridin-6-yl]-3,5-dimethyl-isoxazole | 453.1 |

TABLE 29-continued

| Compound No. | Structure | Name | MS(ESI) [M + H+]+ or [M − H+]− observed |
|---|---|---|---|
| P-0391 | 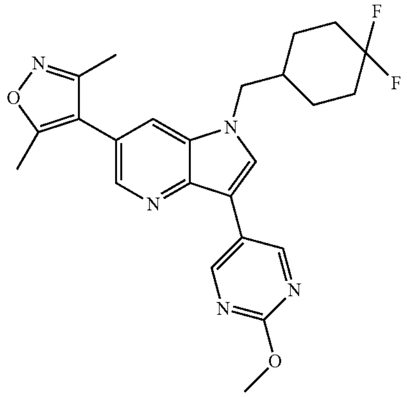 [SMILES: COc1ncc(-c2cn(CC3CCC(F)(F)CC3)c3cc(-c4c(C)noc4C)cnc23)cn1] | 4-[1-[(4,4-difluorocyclohexyl)methyl]-3-(2-methoxypyrimidin-5-yl)pyrrolo[3,2-b]pyridin-6-yl]-3,5-dimethyl-isoxazole | 454.3 |
| P-0392 | 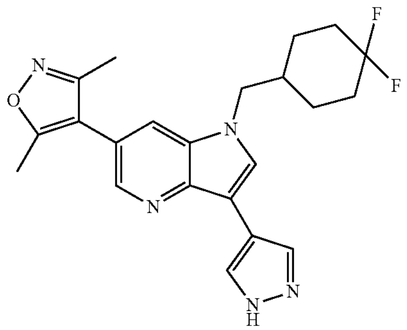 [SMILES: Cc1noc(C)c1-c1cnc2c(-c3cn[nH]c3)cn(CC3CCC(F)(F)CC3)c2c1] | 4-[1-[(4,4-trifluorocyclohexyl)methyl]-3-(1H-pyrazol-4-yl)pyrrolo[3,2-b]pyridin-6-yl]-3,5-dimethyl-isoxazole | 412.3 |
| P-0393 | 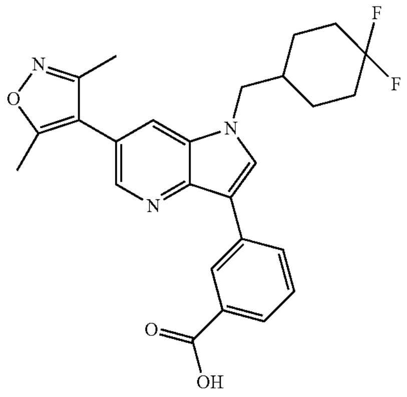 [SMILES: Cc1noc(C)c1-c1cnc2c(-c3cccc(C(=O)O)c3)cn(CC3CCC(F)(F)CC3)c2c1] | 3-[1-[(4,4-difluorocyclohexyl)methyl]-6-(3,5-dimethylisoxazol-4-yl)pyrrolo[3,2-b]pyridin-3-yl]benzoic acid | 466.3 |
| P-0394 | 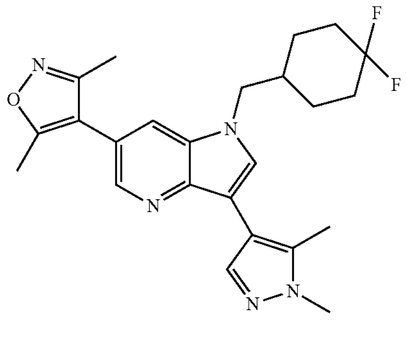 [SMILES: Cc1noc(C)c1-c1cnc2c(-c3cnn(C)c3C)cn(CC3CCC(F)(F)CC3)c2c1] | 4-[1-[(4,4-difluorocyclohexyl)methyl]-3-(1,5-dimethylpyrazol-4-yl)pyrrolo[3,2-b]pyridin-6-yl]-3,5-dimethyl-isoxazole | 440.2 |

TABLE 29-continued

| Compound No. | Structure | Name | MS(ESI) [M + H+]+ or [M − H+]− observed |
|---|---|---|---|
| P-0395 | 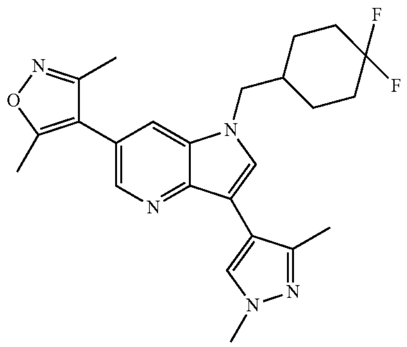 [SMILES: Cc1nn(C)cc1-c1cn(CC2CCC(F)(F)CC2)c2cc(-c3c(C)noc3C)cnc12] | 4-[1-[(4,4-difluorocyclohexyl)methyl]-3-(1,3-dimethylpyrazol-4-yl)pyrrolo[3,2-b]pyridin-6-yl]-3,5-dimethyl-isoxazole | 440.2 |
| P-0396 | 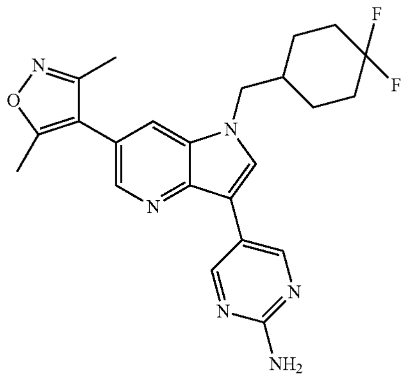 [SMILES: Cc1noc(C)c1-c1cnc2c(-c3cnc(N)nc3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]pyrimidin-2-amine | 439.3 |
| P-0397 | 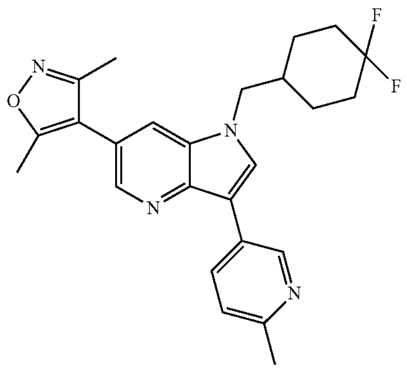 [SMILES: Cc1ccc(-c2cn(CC3CCC(F)(F)CC3)c3cc(-c4c(C)noc4C)cnc23)cn1] | 4-[1-[(4,4-difluorocyclohexyl)methyl]-3-(6-methyl-3-pyridyl)pyrrolo[3,2-b]pyridin-6-yl]-3,5-dimethyl-isoxazole | 437.2 |
| P-0399 | 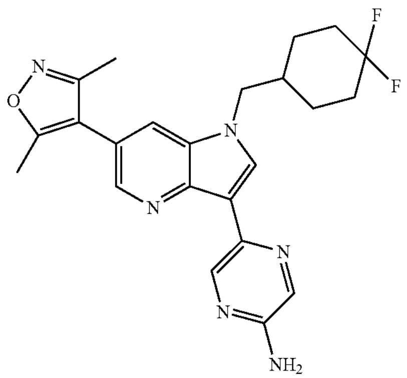 [SMILES: Cc1noc(C)c1-c1cnc2c(-c3cnc(N)cn3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]pyrazin-2-amine | 439.3 |

TABLE 29-continued

| Compound No. | Structure | Name | MS(ESI) [M + H+]+ or [M − H+]− observed |
|---|---|---|---|
| P-0400 | 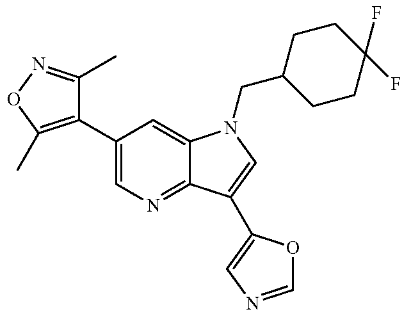 [SMILES: Cc1noc(C)c1-c1cnc2c(-c3cnco3)cn(CC3CCC(F)(F)CC3)c2c1] | 4-[1-[(4,4-difluorocyclohexyl)methyl]-3-oxazol-5-yl-pyrrolo[3,2-b]pyridin-6-yl]-3,5-dimethyl-isoxazole | 413.2 |
| P-0401 | 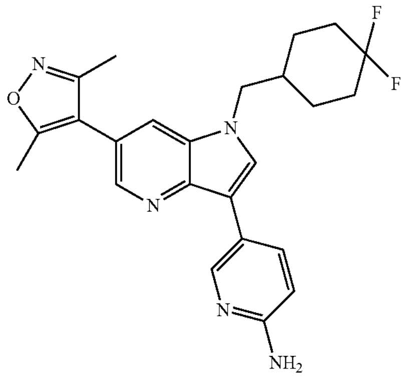 [SMILES: Cc1noc(C)c1-c1cnc2c(-c3ccc(N)nc3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]pyridin-2-amine | 438.1 |
| P-0402 | 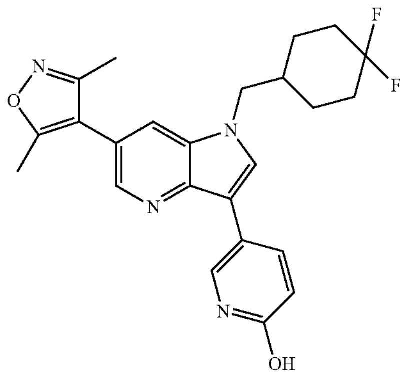 [SMILES: Cc1noc(C)c1-c1cnc2c(-c3ccc(O)nc3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]pyridin-2-ol | 439.0 |
| P-0403 | 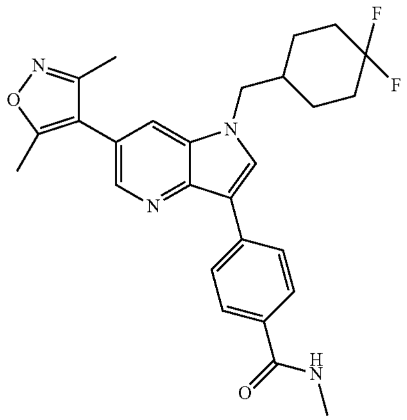 [SMILES: CNC(=O)c1ccc(-c2cn(CC3CCC(F)(F)CC3)c3cc(-c4c(C)noc4C)cnc23)cc1] | 4-[1-[(4,4-difluorocyclohexyl)methyl]-6-(3,5-dimethylisoxazol-4-yl)pyrrolo[3,2-b]pyridin-3-yl]-N-methyl-benzamide | 479.2 |

TABLE 29-continued
| Compound No. | Structure | Name | MS(ESI) [M + H+]+ or [M − H+]− observed |
|---|---|---|---|
| P-0404 | 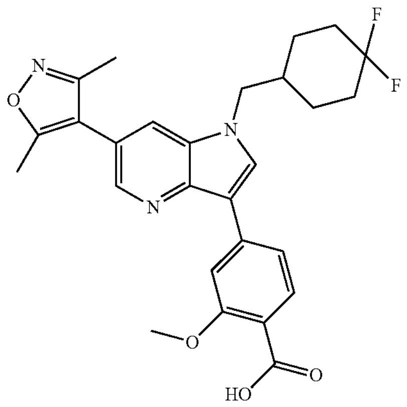 [SMILES: COc1cc(-c2cn(CC3CCC(F)(F)CC3)c3cc(-c4c(C)noc4C)cnc23)ccc1C(=O)O] | 4-[1-[(4,4-difluorocyclohexyl)methyl]-6-(3,5-dimethylisoxazol-4-yl)pyrrolo[3,2-b]pyridin-3-yl]-2-methoxy-benzoic acid | 496.6 |
| P-0405 | 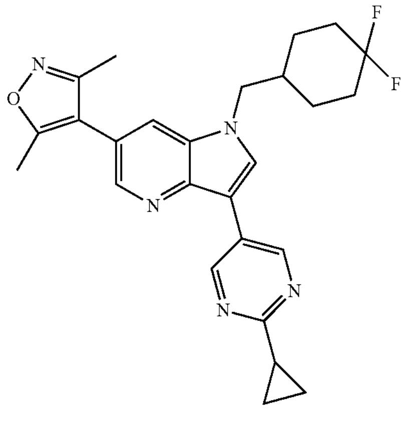 [SMILES: Cc1noc(C)c1-c1cnc2c(-c3cnc(C4CC4)nc3)cn(CC3CCC(F)(F)CC3)c2c1] | 4-[3-(2-cyclopropylpyrimidin-5-yl)-1-[(4,4-difluorocyclohexyl)methyl]pyrrolo[3,2-b]pyridin-6-yl]-3,5-dimethyl-isoxazole | 464.2 |
| P-0406 | 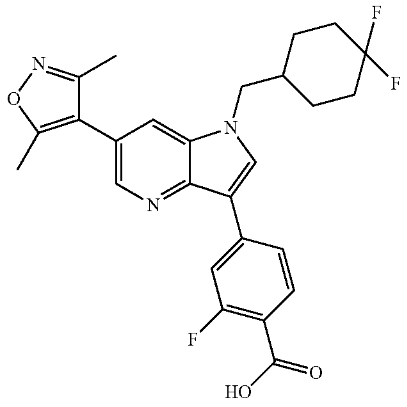 [SMILES: Cc1noc(C)c1-c1cnc2c(-c3ccc(C(=O)O)c(F)c3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]-2-fluoro-benzoic acid | 484.3 |

TABLE 29-continued

| Compound No. | Structure | Name | MS(ESI) [M + H+]+ or [M − H+]− observed |
|---|---|---|---|
| P-0407 | 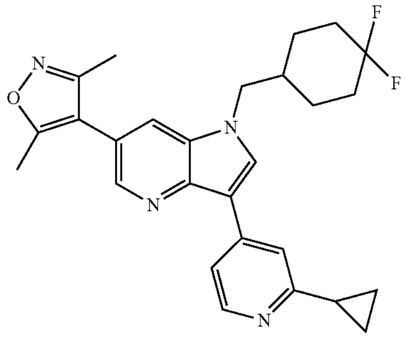 [SMILES: Cc1noc(C)c1-c1cnc2c(-c3ccnc(C4CC4)c3)cn(CC3CCC(F)(F)CC3)c2c1] | 4-[3-(2-cyclopropyl-4-pyridyl)-1-[(4,4-difluorocyclohexyl)methyl]pyrrolo[3,2-b]pyridin-6-yl]-3,5-dimethyl-isoxazole | 463.3 |
| P-0408 | 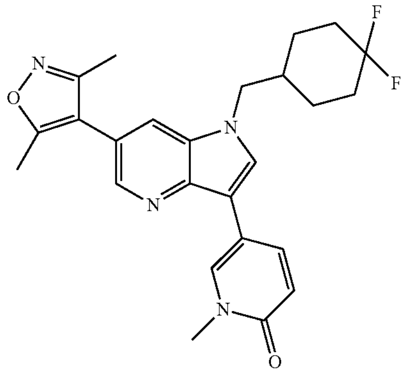 [SMILES: Cc1noc(C)c1-c1cnc2c(-c3ccc(=O)n(C)c3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]-1-methyl-pyridin-2-one | 453.1 |
| P-0409 | 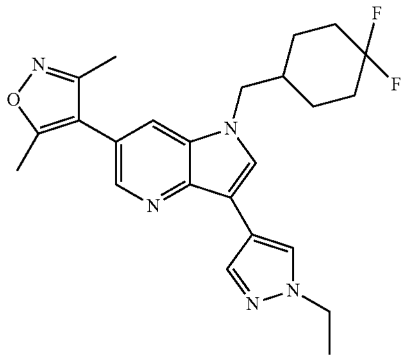 [SMILES: CCn1cc(-c2cn(CC3CCC(F)(F)CC3)c3cc(-c4c(C)noc4C)cnc23)cn1] | 4-[1-[(4,4-difluorocyclohexyl)methyl]-3-(1-ethylpyrazol-4-yl)pyrrolo[3,2-b]pyridin-6-yl]-3,5-dimethyl-isoxazole | 440.2 |
| P-0410 | 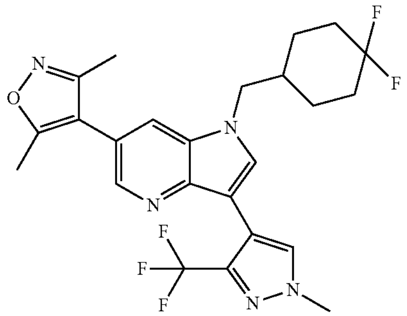 [SMILES: Cc1noc(C)c1-c1cnc2c(-c3cn(C)nc3C(F)(F)F)cn(CC3CCC(F)(F)CC3)c2c1] | 4-[1-[(4,4-difluorocyclohexyl)methyl]-3-[1-methyl-3-(trifluoromethyl)pyrazol-4-yl]pyrrolo[3,2-b]pyridin-6-yl]-3,5-dimethyl-isoxazole | 494.2 |

TABLE 29-continued

| Compound No. | Structure | Name | MS(ESI) [M + H+]+ or [M − H+]− observed |
|---|---|---|---|
| P-0411 | 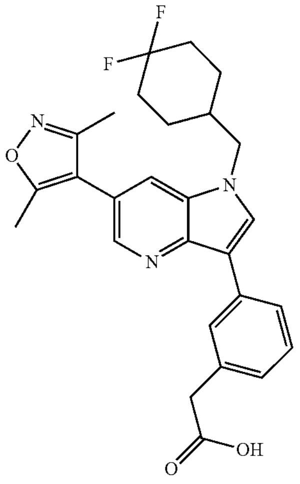 [SMILES: Cc1noc(C)c1-c1cnc2c(-c3cccc(CC(=O)O)c3)cn(CC3CCC(F)(F)CC3)c2c1] | 2-[3-[1-[(4,4-difluorocyclohexyl)methyl]-6-(3,5-dimethylisoxazol-4-yl)pyrrolo[3,2-b]pyridin-3-yl]phenyl]acetic acid | 480.1 |
| P-0412 | 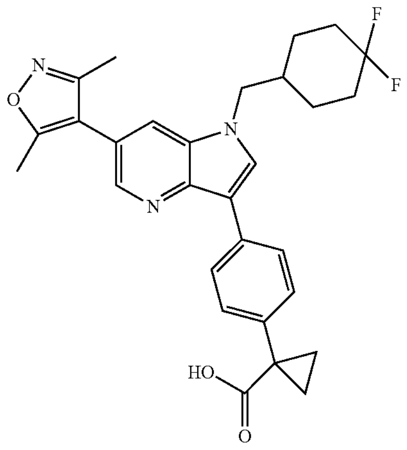 [SMILES: Cc1noc(C)c1-c1cnc2c(-c3ccc(C4(C(=O)O)CC4)cc3)cn(CC3CCC(F)(F)CC3)c2c1] | 1-[4-[1-[(4,4-difluorocyclohexyl)methyl]-6-(3,5-dimethylisoxazol-4-yl)pyrrolo[3,2-b]pyridin-3-yl]phenyl]cyclopropanecarboxylic acid | 506.2 |
| P-0413 | 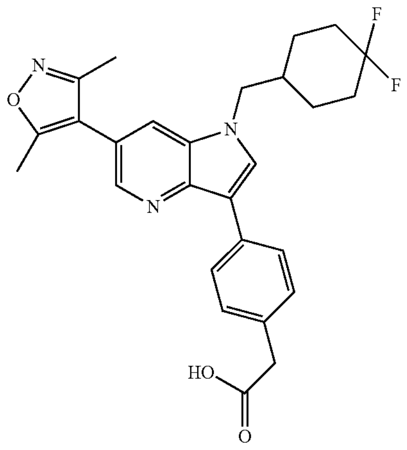 [SMILES: Cc1noc(C)c1-c1cnc2c(-c3ccc(CC(=O)O)cc3)cn(CC3CCC(F)(F)CC3)c2c1] | 2-[4-[1-[(4,4-difluorocyclohexyl)methyl]-6-(3,5-dimethylisoxazol-4-yl)pyrrolo[3,2-b]pyridin-3-yl]phenyl]acetic acid | 480.5 |

TABLE 29-continued
| Compound No. | Structure | Name | MS(ESI) [M + H+]+ or [M − H+]− observed |
|---|---|---|---|
| P-0414 | 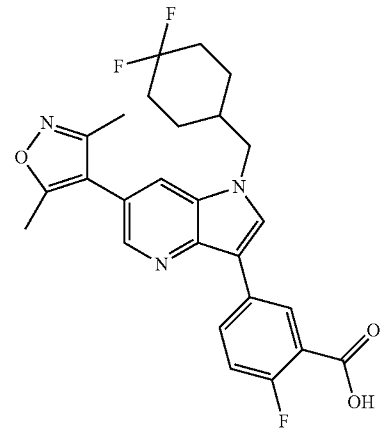 [SMILES: Cc1noc(C)c1-c1cnc2c(-c3ccc(F)c(C(=O)O)c3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]-2-fluoro-benzoic acid | 484.3 |
| P-0415 | 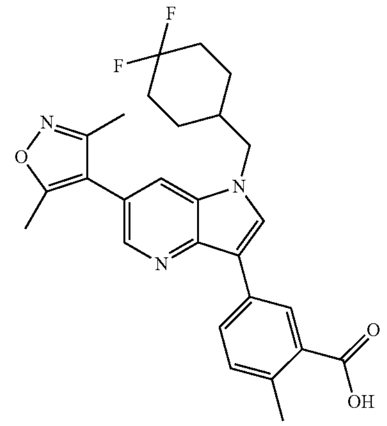 [SMILES: Cc1ccc(-c2cn(CC3CCC(F)(F)CC3)c3cc(-c4c(C)noc4C)cnc23)cc1C(=O)O] | 5-[1-[(4,4-difluorocyclohexyl)methyl]-6-(3,5-dimethylisoxazol-4-yl)pyrrolo[3,2-b]pyridin-3-yl]-2-methyl-benzoic acid | 480.1 |
| P-0416 | 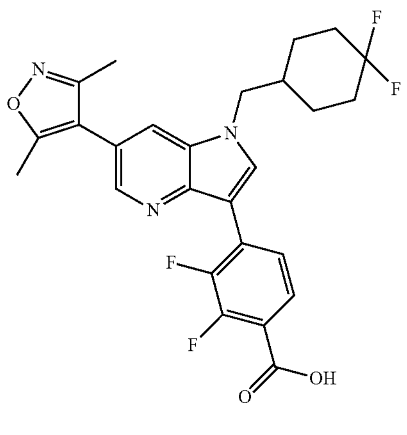 [SMILES: Cc1noc(C)c1-c1cnc2c(-c3ccc(C(=O)O)c(F)c3F)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]-2,3-difluoro-benzoic acid | 502.3 |

TABLE 29-continued

| Compound No. | Structure | Name | MS(ESI) [M + H+]+ or [M − H+]− observed |
|---|---|---|---|
| P-0417 | 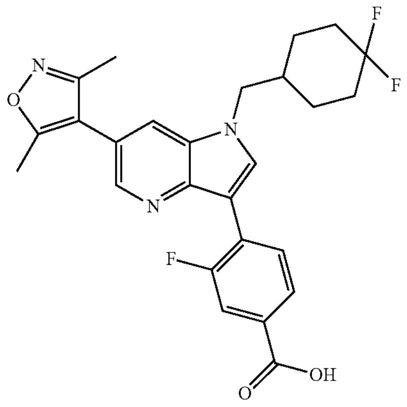 [SMILES: Cc1noc(C)c1-c1cnc2c(-c3ccc(C(=O)O)cc3F)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]-3-fluoro-benzoic acid | 484.3 |
| P-0418 | 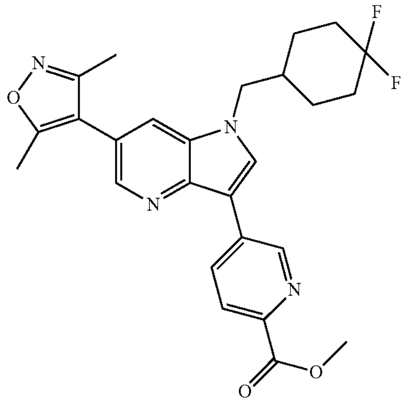 [SMILES: COC(=O)c1ccc(-c2cn(CC3CCC(F)(F)CC3)c3cc(-c4c(C)noc4C)cnc23)cn1] | methyl 5-[1-[(4,4-difluorocyclohexyl)methyl]-6-(3,5-dimethylisoxazol-4-yl)pyrrolo[3,2-b]pyridin-3-yl]pyridine-2-carboxylate | 481.3 |
| P-0419 | 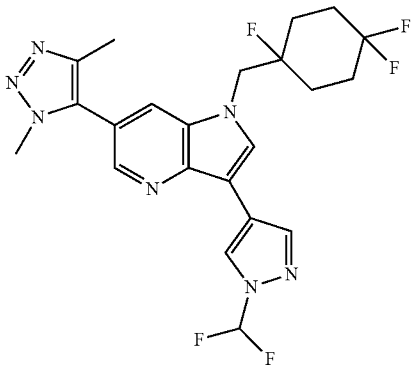 [SMILES: Cc1nnn(C)c1-c1cnc2c(-c3cnn(C(F)F)c3)cn(CC3(F)CCC(F)(F)CC3)c2c1] | 3-[1-(difluoromethyl)pyrazol-4-yl]-6-(3,5-dimethyltriazol-4-yl)-1-[(1,4,4-trifluorocyclohexyl)methyl]pyrrolo[3,2-b]pyridine | 480.0 |

TABLE 29-continued

| Compound No. | Structure | Name | MS(ESI) [M + H+]+ or [M − H+]− observed |
|---|---|---|---|
| P-0420 | 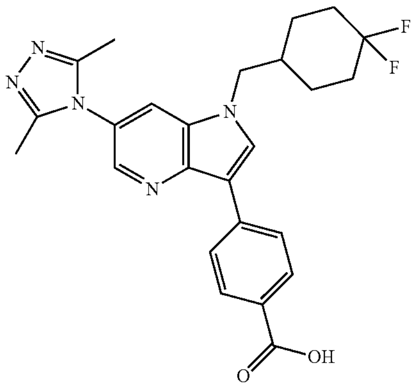 [SMILES: Cc1nnc(C)n1-c1cnc2c(-c3ccc(C(=O)O)cc3)cn(CC3CCC(F)(F)CC3)c2c1] | 4-[1-[(4,4-difluorocyclohexyl)methyl]-6-(3,5-dimethyl-1,2,4-triazol-4-yl)pyrrolo[3,2-b]pyridin-3-yl]benzoic acid | 466.2 |
| P-0424 | 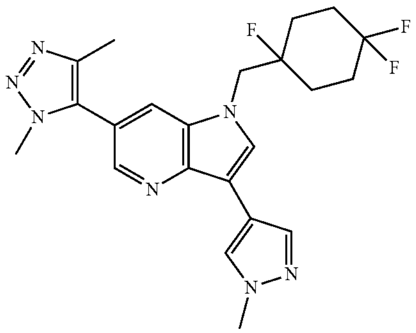 [SMILES: Cc1nnn(C)c1-c1cnc2c(-c3cnn(C)c3)cn(CC3(F)CCC(F)(F)CC3)c2c1] | 6-(3,5-dimethyltriazol-4-yl)-3-(1-methylpyrazol-4-yl)-1-[(1,4,4-trifluorocyclohexyl)methyl]pyrrolo[3,2-b]pyridine | 444.0 |
| P-0427 | 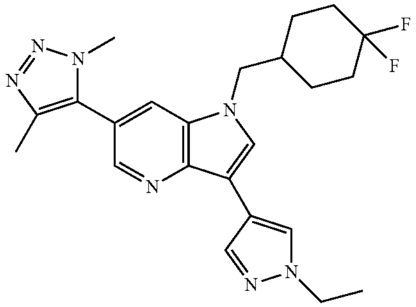 [SMILES: CCn1cc(-c2cn(CC3CCC(F)(F)CC3)c3cc(-c4c(C)nnn4C)cnc23)cn1] | 1-[(4,4-difluorocyclohexyl)methyl]-6-(3,5-dimethyltriazol-4-yl)-3-(1-ethylpyrazol-4-yl)pyrrolo[3,2-b]pyridine | 440.0 |
| P-0428 | 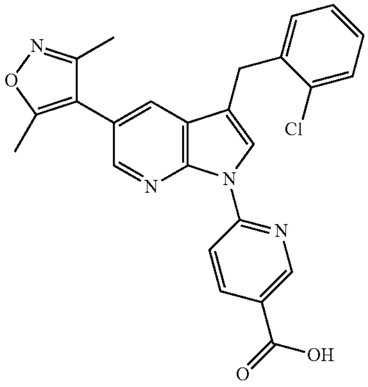 [SMILES: Cc1noc(C)c1-c1cnc2c(c1)c(Cc1ccccc1Cl)cn2-c1ccc(C(=O)O)cn1] | 6-[3-[(2-chlorophenyl)methyl]-5-(3,5-dimethylisoxazol-4-yl)pyrrolo[2,3-b]pyridin-1-yl]pyridine-3-carboxylic acid | 459.1 |

TABLE 29-continued
| Compound No. | Structure | Name | MS(ESI) [M + H+]+ or [M − H+]− observed |
|---|---|---|---|
| P-0429 | 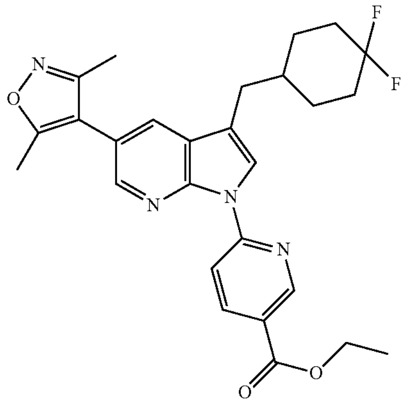 [SMILES: CCOC(=O)c1ccc(-n2cc(CC3CCC(F)(F)CC3)c3cc(-c4c(C)noc4C)cnc32)nc1] | ethyl 6-[3-[(4,4-difluorocyclohexyl)methyl]-5-(3,5-dimethylisoxazol-4-yl)pyrrolo[2,3-b]pyridin-1-yl]pyridine-3-carboxylate | 495.0 |
| P-0430 | 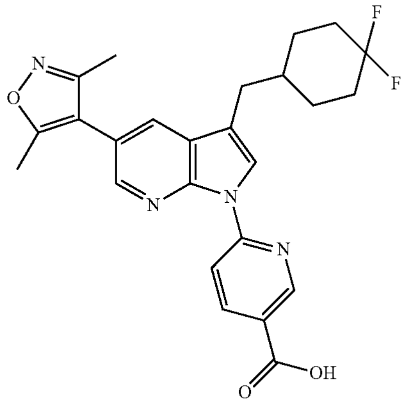 [SMILES: Cc1noc(C)c1-c1cnc2c(c1)c(CC1CCC(F)(F)CC1)cn2-c1ccc(C(=O)O)cn1] | 6-[3-[(4,4-difluorocyclohexyl)methyl]-5-(3,5-dimethylisoxazol-4-yl)pyrrolo[2,3-b]pyridin-1-yl]pyridine-3-carboxylic acid | 466.9 |
| P-0431 | 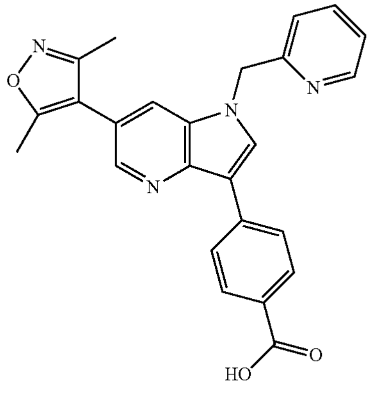 [SMILES: Cc1noc(C)c1-c1cnc2c(-c3ccc(C(=O)O)cc3)cn(Cc3ccccn3)c2c1] | 4-[6-(3,5-dimethylisoxazol-4-yl)-1-(2-pyridylmethyl)pyrrolo[3,2-b]pyridin-3-yl]benzoic acid | 424.9 |

TABLE 29-continued
| Compound No. | Structure | Name | MS(ESI) [M + H+]+ or [M − H+]− observed |
|---|---|---|---|
| P-0432 | 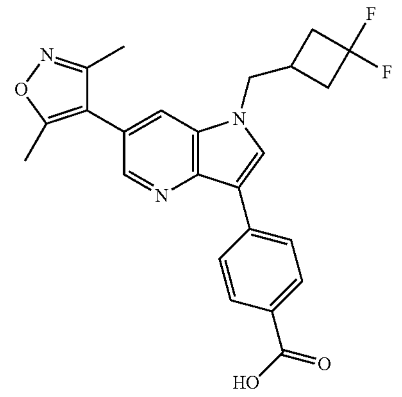 [SMILES: Cc1noc(C)c1-c1cnc2c(-c3ccc(C(=O)O)cc3)cn(CC3CC(F)(F)C3)c2c1] | 4-[1-[(3,3-difluorocyclobutyl)methyl]-6-(3,5-dimethylisoxazol-4-yl)pyrrolo[3,2-b]pyridin-3-yl]benzoic acid | 438.0 |
| P-0433 | 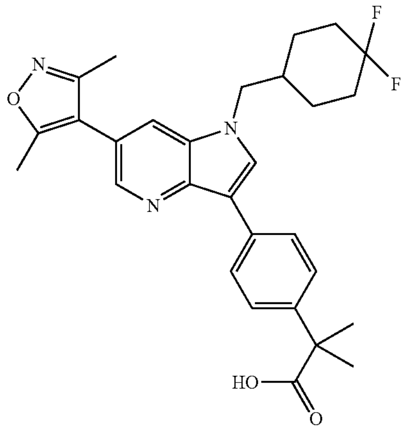 [SMILES: Cc1noc(C)c1-c1cnc2c(-c3ccc(C(C)(C)C(=O)O)cc3)cn(CC3CCC(F)(F)CC3)c2c1] | 2-[4-[1-[(4,4-difluorocyclohexyl)methyl]-6-(3,5-dimethylisoxazol-4-yl)pyrrolo[3,2-b]pyridin-3-yl]phenyl]-2-methyl-propanoic acid | 508.31 |
| P-0434 | 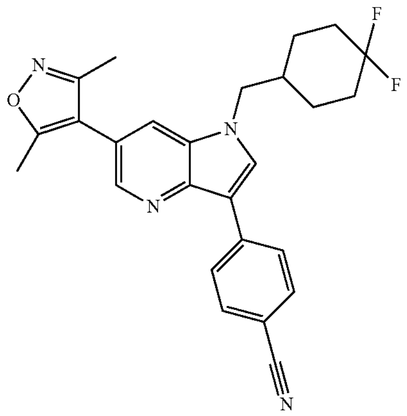 [SMILES: Cc1noc(C)c1-c1cnc2c(-c3ccc(C#N)cc3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]benzonitrile | 447.08 |

TABLE 29-continued

| Compound No. | Structure | Name | MS(ESI) [M + H+]+ or [M − H+]− observed |
|---|---|---|---|
| P-0435 | 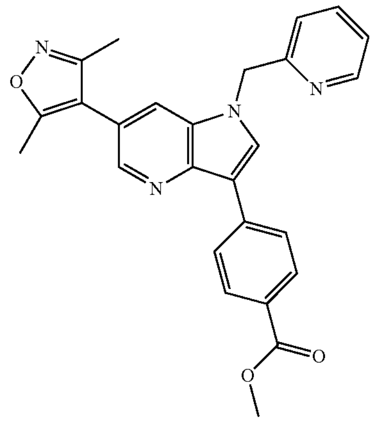 [SMILES: COC(=O)c1ccc(-c2cn(Cc3ccccn3)c3cc(-c4c(C)noc4C)cnc23)cc1] | methyl 4-[6-(3,5-dimethylisoxazol-4-yl)-1-(2-pyridylmethyl)pyrrolo[3,2-b]pyridin-3-yl]benzoate | 438.9 |
| P-0436 | 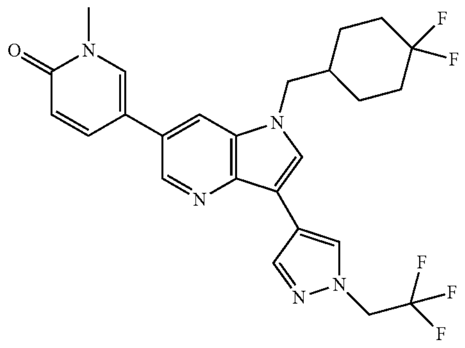 [SMILES: Cn1cc(-c2cnc3c(-c4cnn(CC(F)(F)F)c4)cn(CC4CCC(F)(F)CC4)c3c2)ccc1=O] | 5-[1-[(4,4-difluorocyclohexyl)methyl]-3-[1-(2,2,2-trifluoroethyl)pyrazol-4-yl]pyrrolo[3,2-b]pyridin-6-yl]-1-methyl-pyridin-2-one | 506.1 |
| P-0437 | 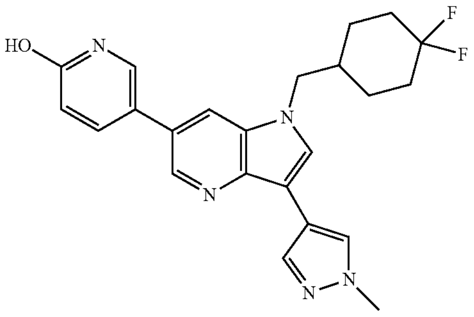 [SMILES: Cn1cc(-c2cn(CC3CCC(F)(F)CC3)c3cc(-c4ccc(O)nc4)cnc23)cn1] | 5-[1-[(4,4-difluorocyclohexyl)methyl]-3-(1-methylpyrazol-4-yl)pyrrolo[3,2-b]pyridin-6-yl]pyridin-2-ol | 423.9 |
| P-0438 | 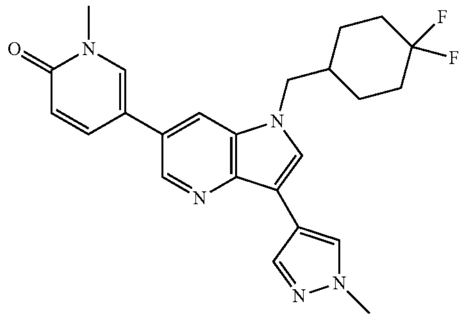 [SMILES: Cn1cc(-c2cn(CC3CCC(F)(F)CC3)c3cc(-c4ccc(=O)n(C)c4)cnc23)cn1] | 5-[1-[(4,4-difluorocyclohexyl)methyl]-3-(1-methylpyrazol-4-yl)pyrrolo[3,2-b]pyridin-6-yl]-1-methyl-pyridin-2-one | 438.0 |

TABLE 29-continued

| Compound No. | Structure | Name | MS(ESI) [M + H+]+ or [M − H+]− observed |
|---|---|---|---|
| P-0440 | 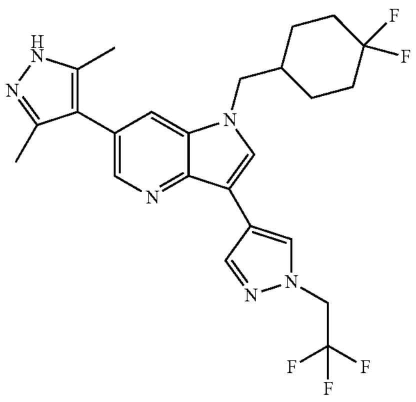 [SMILES: Cc1n[nH]c(C)c1-c1cnc2c(-c3cnn(CC(F)(F)F)c3)cn(CC3CCC(F)(F)CC3)c2c1] | 1-[(4,4-difluorocyclohexyl)methyl]-6-(3,5-dimethyl-1H-pyrazol-4-yl)-3-[1-(2,2,2-trifluoroethyl)pyrazol-4-yl]pyrrolo[3,2-b]pyridine | 494.3 |
| P-0441 | 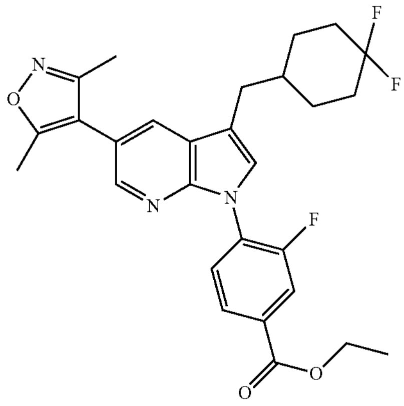 [SMILES: CCOC(=O)c1ccc(-n2cc(CC3CCC(F)(F)CC3)c3cc(-c4c(C)noc4C)cnc32)c(F)c1] | ethyl 4-[3-[(4,4-difluorocyclohexyl)methyl]-5-(3,5-dimethylisoxazol-4-yl)pyrrolo[2,3-b]pyridin-1-yl]-3-fluoro-benzoate | 512.0 |
| P-0442 | 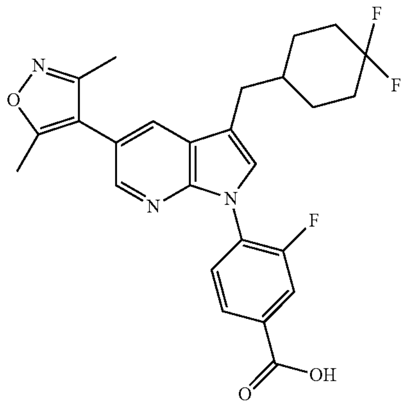 [SMILES: Cc1noc(C)c1-c1cnc2c(c1)c(CC1CCC(F)(F)CC1)cn2-c1ccc(C(=O)O)cc1F] | 4-[3-[(4,4-difluorocyclohexyl)methyl]-5-(3,5-dimethylisoxazol-4-yl)pyrrolo[2,3-b]pyridin-1-yl]-3-fluoro-benzoic acid | 484.0 |

TABLE 29-continued

| Compound No. | Structure | Name | MS(ESI) [M + H+]+ or [M − H+]− observed |
|---|---|---|---|
| P-0443 | 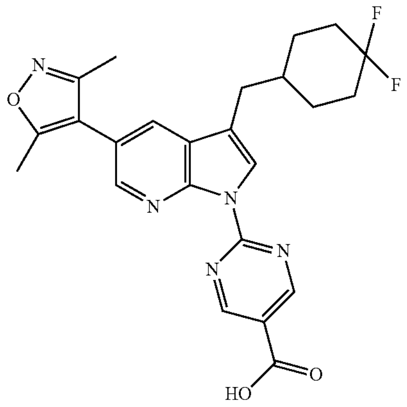 [SMILES: Cc1noc(C)c1-c1cnc2c(c1)c(CC1CCC(F)(F)CC1)cn2-c1ncc(C(=O)O)cn1] | 2-[3-[(4,4-difluorocyclohexyl)methyl]-5-(3,5-dimethylisoxazol-4-yl)pyrrolo[2,3-b]pyridin-1-yl]pyrimidine-5-carboxylic acid | 468.0 |
| P-0448 | 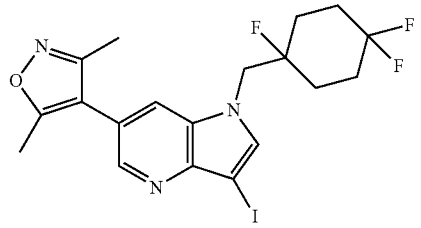 [SMILES: Cc1noc(C)c1-c1cnc2c(I)cn(CC3(F)CCC(F)(F)CC3)c2c1] | 4-[3-iodo-1-[(1,4,4-trifluorocyclohexyl)methyl]pyrrolo[3,2-b]pyridin-6-yl]-3,5-dimethyl-isoxazole | 490.1 |
| P-0451 | 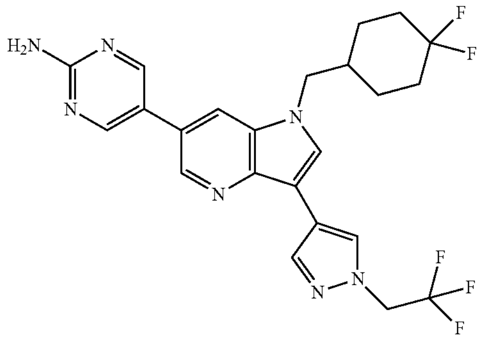 [SMILES: Nc1ncc(-c2cnc3c(-c4cnn(CC(F)(F)F)c4)cn(CC4CCC(F)(F)CC4)c3c2)cn1] | 5-[1-[(4,4-difluorocyclohexyl)methyl]-3-[1-(2,2,2-trifluoroethyl)pyrazol-4-yl]pyrrolo[3,2-b]pyridin-6-yl]pyrimidin-2-amine | 492.0 |
| P-0452 | 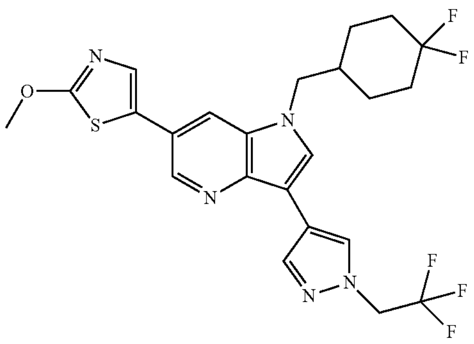 [SMILES: COc1ncc(-c2cnc3c(-c4cnn(CC(F)(F)F)c4)cn(CC4CCC(F)(F)CC4)c3c2)s1] | 5-[1-[(4,4-difluorocyclohexyl)methyl]-3-[1-(2,2,2-trifluoroethyl)pyrazol-4-yl]pyrrolo[3,2-b]pyridin-6-yl]-2-methoxy-thiazole | 512.2 |

TABLE 29-continued

| Compound No. | Structure | Name | MS(ESI) [M + H+]+ or [M − H+]− observed |
|---|---|---|---|
| P-0453 | 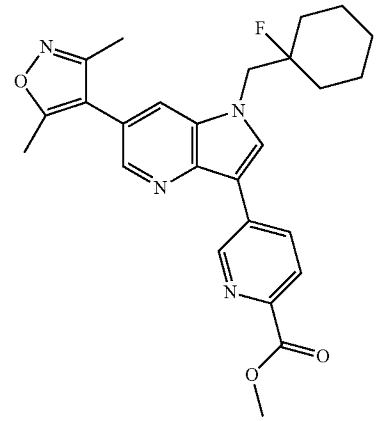 [SMILES: COC(=O)c1ccc(-c2cn(CC3(F)CCCCC3)c3cc(-c4c(C)noc4C)cnc23)cn1] | methyl 5-[6-(3,5-dimethylisoxazol-4-yl)-1-[(1-fluorocyclohexyl)methyl]pyrrolo[3,2-b]pyridin-3-yl]pyridine-2-carboxylate | 463.3 |
| P-0454 | 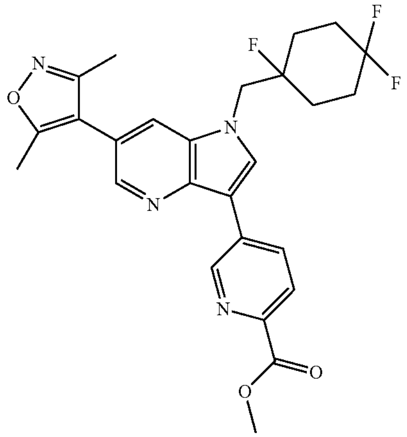 [SMILES: COC(=O)c1ccc(-c2cn(CC3(F)CCC(F)(F)CC3)c3cc(-c4c(C)noc4C)cnc23)cn1] | methyl 5-[6-(3,5-dimethylisoxazol-4-yl)-1-[(1,4,4-trifluorocyclohexyl)methyl]pyrrolo[3,2-b]pyridin-3-yl]pyridine-2-carboxylate | 499.3 |
| P-0455 | 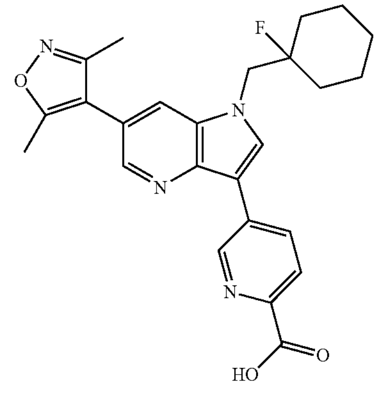 [SMILES: Cc1noc(C)c1-c1cnc2c(-c3ccc(C(=O)O)nc3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]pyridine-2-carboxylic acid | 449.3 |

TABLE 29-continued

| Compound No. | Structure | Name | MS(ESI) [M + H+]+ or [M − H+]− observed |
|---|---|---|---|
| P-0456 | 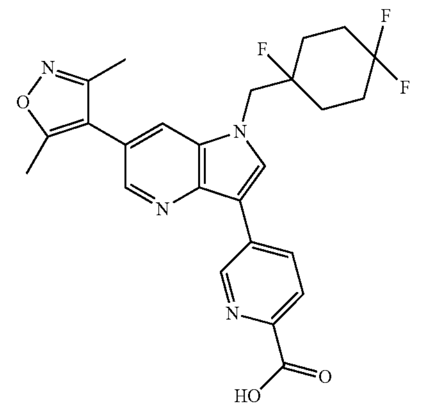 [SMILES: Cc1noc(C)c1-c1cnc2c(-c3ccc(C(=O)O)nc3)cn(CC3(F)CCC(F)(F)CC3)c2c1] | 5-[6-(3,5-dimethylisoxazol-4-yl)-1-[(1,4,4-trifluorocyclohexyl)methyl]pyrrolo[3,2-b]pyridin-3-yl]pyridine-2-carboxylic acid | 485.0 |
| P-0457 | 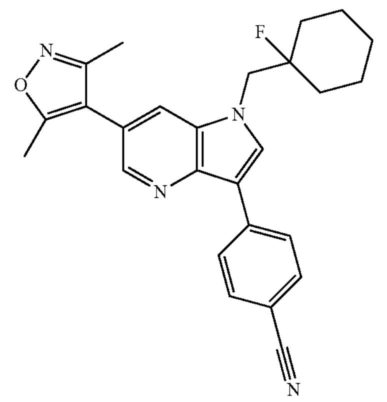 [SMILES: Cc1noc(C)c1-c1cnc2c(-c3ccc(C#N)cc3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]benzonitrile | 429.4 |
| P-0458 | 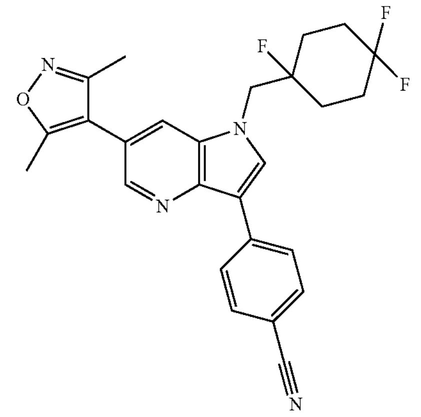 [SMILES: Cc1noc(C)c1-c1cnc2c(-c3ccc(C#N)cc3)cn(CC3(F)CCC(F)(F)CC3)c2c1] | 4-[6-(3,5-dimethylisoxazol-4-yl)-1-[(1,4,4-trifluorocyclohexyl)methyl]pyrrolo[3,2-b]pyridin-3-yl]benzonitrile | 465.3 |
| P-0459 | 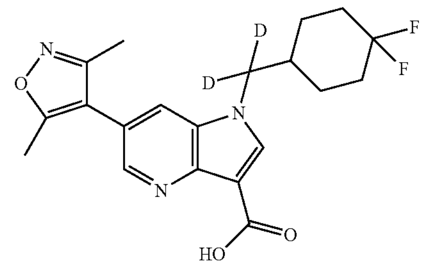 [SMILES: [2H]C([2H])(C1CCC(F)(F)CC1)n1cc(C(=O)O)c2ncc(-c3c(C)noc3C)cc21] | 1-[dideuterio-(4,4-difluorocyclohexyl)methyl]-6-(3,5-dimethylisoxazol-4-yl)pyrrolo[3,2-b]pyridine-3-carboxylic acid | 392.1 |

TABLE 29-continued
| Compound No. | Structure | Name | MS(ESI) [M + H+]+ or [M − H+]− observed |
|---|---|---|---|
| P-0460 | 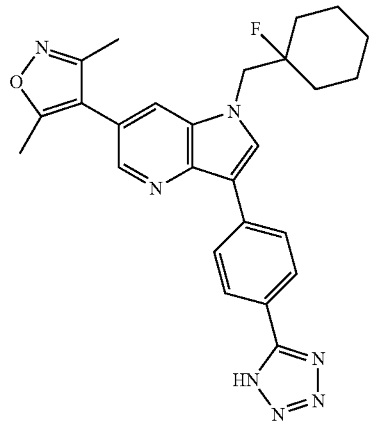 [SMILES: Cc1noc(C)c1-c1cnc2c(-c3ccc(-c4nnn[nH]4)cc3)cn(CC3(F)CCCCC3)c2c1] | 4-[1-[(1-fluorocyclohexyl)methyl]-3-[4-(1H-tetrazol-5-yl)phenyl]pyrrolo[3,2-b]pyridin-6-yl]-3,5-dimethyl-isoxazole | 472.3 |
| P-0461 | 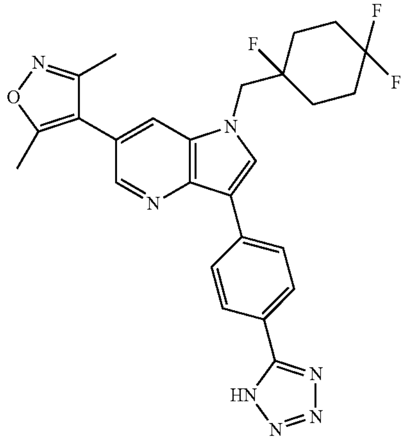 [SMILES: Cc1noc(C)c1-c1cnc2c(-c3ccc(-c4nnn[nH]4)cc3)cn(CC3(F)CCC(F)(F)CC3)c2c1] | 3,5-dimethyl-4-[3-[4-(1H-tetrazol-5-yl)phenyl]-1-[(1,4,4-trifluorocyclohexyl)methyl]pyrrolo[3,2-b]pyridin-6-yl]isoxazole | 508.3 |
| P-0462 | 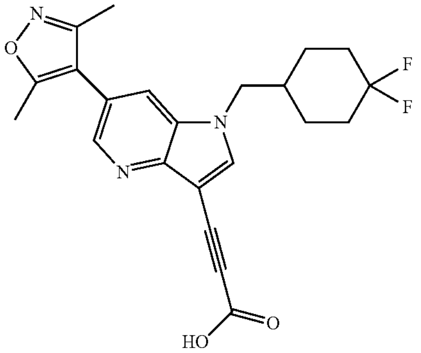 [SMILES: Cc1noc(C)c1-c1cnc2c(C#CC(=O)O)cn(CC3CCC(F)(F)CC3)c2c1] | 3-[1-[(4,4-difluorocyclohexyl)methyl]-6-(3,5-dimethylisoxazol-4-yl)pyrrolo[3,2-b]pyridin-3-yl]prop-2-ynoic acid | 413.9 |

TABLE 29-continued

| Compound No. | Structure | Name | MS(ESI) [M + H+]+ or [M − H+]− observed |
|---|---|---|---|
| P-0463 | 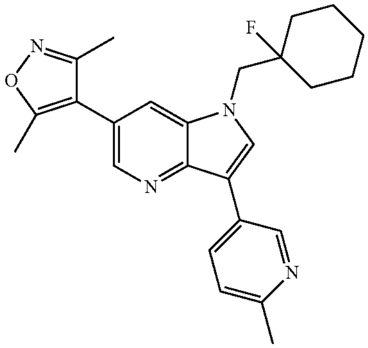 [SMILES: Cc1ccc(-c2cn(CC3(F)CCCCC3)c3cc(-c4c(C)noc4C)cnc23)cn1] | 4-[1-[(1-fluorocyclohexyl)methyl]-3-(6-methyl-3-pyridyl)pyrrolo[3,2-b]pyridin-6-yl]-3,5-dimethyl-isoxazole | 419.2 |
| P-0464 | 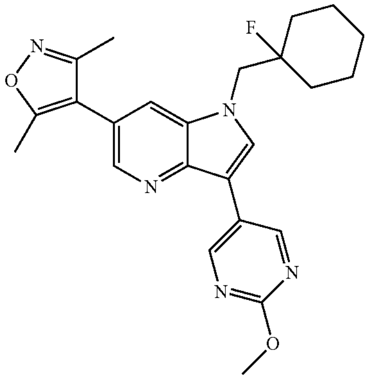 | 4-[1-[(1-fluorocyclohexyl)methyl]-3-(2-methoxypyrimidin-5-yl)pyrrolo[3,2-b]pyridin-6-yl]-3,5-dimethyl-isoxazole | 436.3 |
| P-0465 | 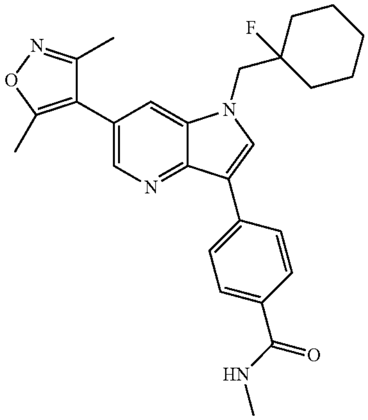 [SMILES: CNC(=O)c1ccc(-c2cn(CC3(F)CCCCC3)c3cc(-c4c(C)noc4C)cnc23)cc1] | 4-[6-(3,5-dimethylisoxazol-4-yl)-1-[(1-fluorocyclohexyl)methyl]pyrrolo[3,2-b]pyridin-3-yl]-N-methyl-benzamide | 461.5 |
| P-0466 | 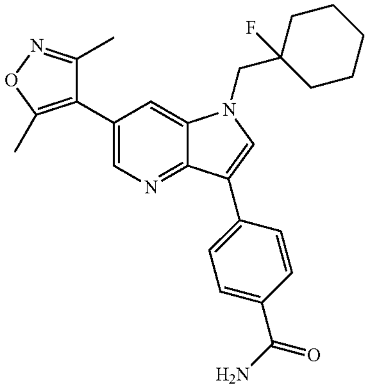 [SMILES: Cc1noc(C)c1-c1cnc2c(-c3ccc(C(N)=O)cc3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]benzamide | 447.4 |

TABLE 29-continued

| Compound No. | Structure | Name | MS(ESI) [M + H+]+ or [M − H+]− observed |
|---|---|---|---|
| P-0467 | 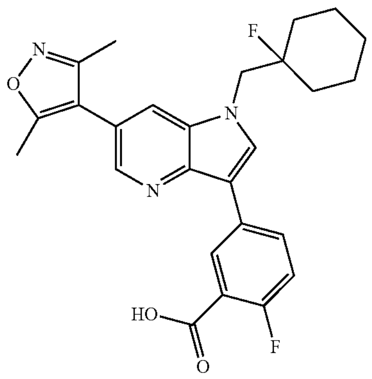 [SMILES: Cc1noc(C)c1-c1cnc2c(-c3ccc(F)c(C(=O)O)c3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]-2-fluoro-benzoic acid | 466.3 |
| P-0468 | 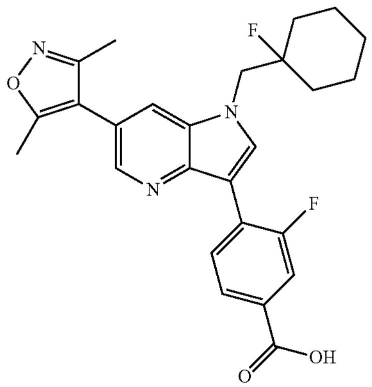 [SMILES: Cc1noc(C)c1-c1cnc2c(-c3ccc(C(=O)O)cc3F)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]-3-fluoro-benzoic acid | 466.3 |
| P-0469 | 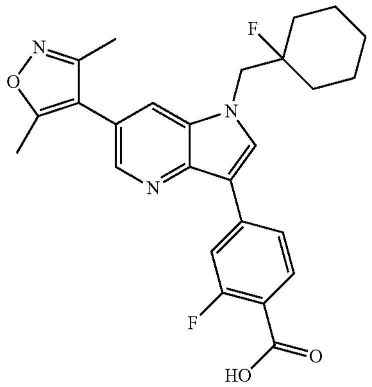 [SMILES: Cc1noc(C)c1-c1cnc2c(-c3ccc(C(=O)O)c(F)c3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]-2-fluoro-benzoic acid | 466.3 |
| P-0470 | 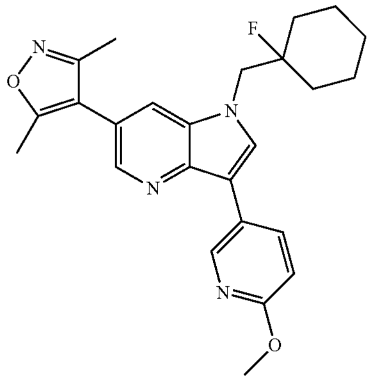 [SMILES: COc1ccc(-c2cn(CC3(F)CCCCC3)c3cc(-c4c(C)noc4C)cnc23)cn1] | 4-[1-[(1-fluorocyclohexyl)methyl]-3-(6-methoxy-3-pyridyl)pyrrolo[3,2-b]pyridin-6-yl]-3,5-dimethyl-isoxazole | 435.4 |

TABLE 29-continued

| Compound No. | Structure | Name | MS(ESI) [M + H+]+ or [M − H+]− observed |
|---|---|---|---|
| P-0471 | 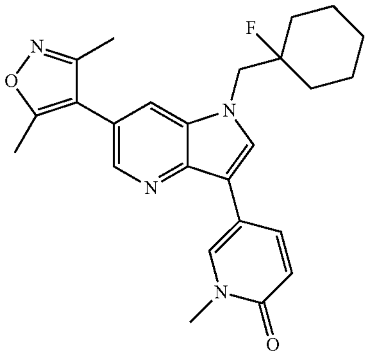 [SMILES: Cc1noc(C)c1-c1cnc2c(-c3ccc(=O)n(C)c3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]-1-methyl-pyridin-2-one | 435.4 |
| P-0472 | 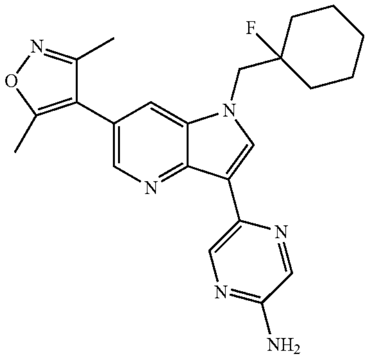 [SMILES: Cc1noc(C)c1-c1cnc2c(-c3cnc(N)cn3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]pyrazin-2-amine | 421.3 |
| P-0473 | 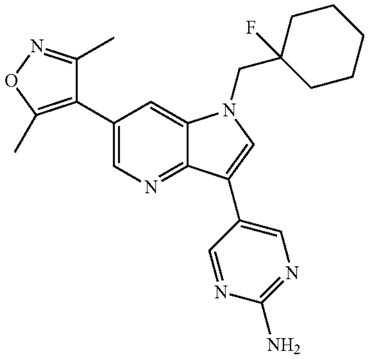 [SMILES: Cc1noc(C)c1-c1cnc2c(-c3cnc(N)nc3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]pyrimidin-2-amine | 421.3 |
| P-0474 | 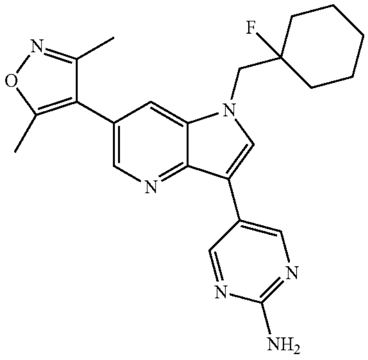 [SMILES: Cc1noc(C)c1-c1cnc2c(-c3cnc(N)nc3)cn(CC3(F)CCCCC3)c2c1] | 4-[3-(2-cyclopropylpyrimidin-5-yl)-1-[(1-fluorocyclohexyl)methyl]pyrrolo[3,2-b]pyridin-6-yl]-3,5-dimethyl-isoxazole | 446.5 |

TABLE 29-continued

| Compound No. | Structure | Name | MS(ESI) [M + H+]+ or [M − H+]− observed |
|---|---|---|---|
| P-0475 | 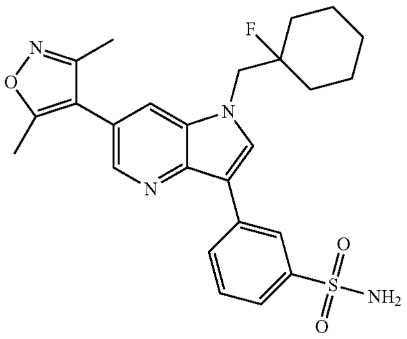 [SMILES: Cc1noc(C)c1-c1cnc2c(-c3cccc(S(N)(=O)=O)c3)cn(CC3(F)CCCCC3)c2c1] | 3-[6-(3,5-dimethylisoxazol-4-yl)-1-[(1-fluorocyclohexyl)methyl]pyrrolo[3,2-b]pyridin-3-yl]benzenesulfonamide | 483.4 |
| P-0476 | 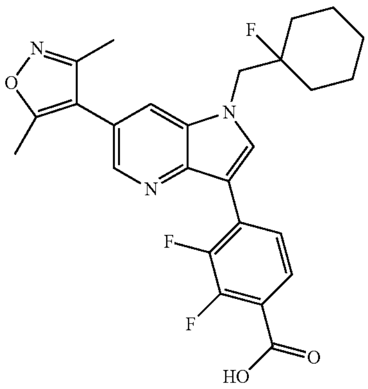 [SMILES: Cc1noc(C)c1-c1cnc2c(-c3ccc(C(=O)O)c(F)c3F)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]-2,3-difluoro-benzoic acid | 484.3 |
| P-0477 | 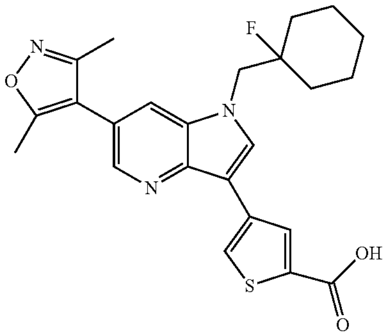 [SMILES: Cc1noc(C)c1-c1cnc2c(-c3csc(C(=O)O)c3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]thiophene-2-carboxylic acid | 45403.0 |
| P-0478 | 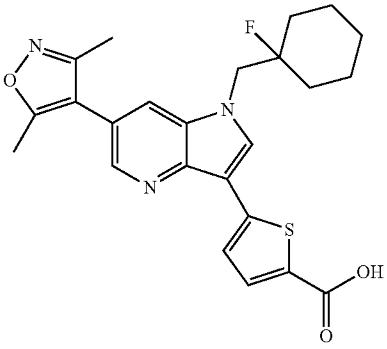 [SMILES: Cc1noc(C)c1-c1cnc2c(-c3ccc(C(=O)O)s3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]thiophene-2-carboxylic acid | 454.3 |

TABLE 29-continued
| Compound No. | Structure | Name | MS(ESI) [M + H+]+ or [M − H+]− observed |
|---|---|---|---|
| P-0479 | 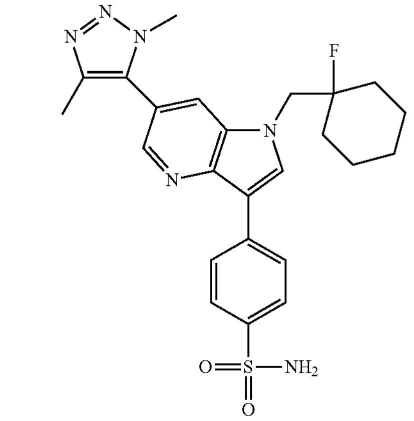 [SMILES: Cc1nnn(C)c1-c1cnc2c(-c3ccc(S(N)(=O)=O)cc3)cn(CC3(F)CCCCC3)c2c1] | 4-[6-(3,5-dimethyltriazol-4-yl)-1-[(1-fluorocyclohexyl)methyl]pyrrolo[3,2-b]pyridin-3-yl]benzenesulfonamide | 483.0 |
| P-0480 | 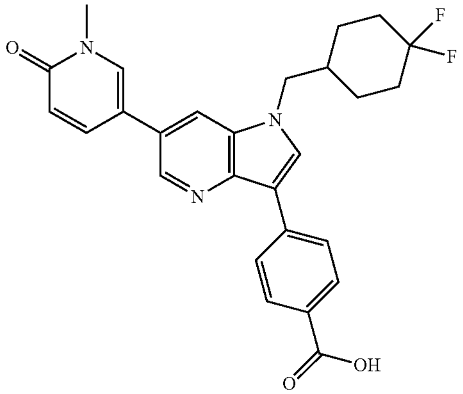 [SMILES: Cn1cc(-c2cnc3c(-c4ccc(C(=O)O)cc4)cn(CC4CCC(F)(F)CC4)c3c2)ccc1=O] | 4-[1-[(4,4-difluorocyclohexyl)methyl]-6-(1-methyl-6-oxo-3-pyridyl)pyrrolo[3,2-b]pyridin-3-yl]benzoic acid | 477.9 |
| P-0481 | 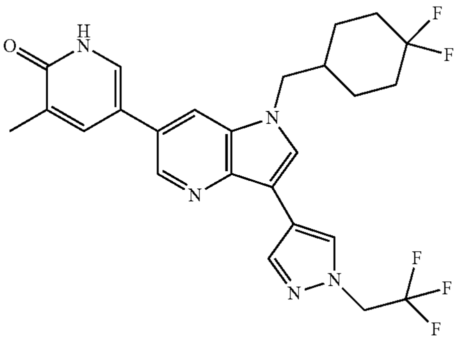 [SMILES: Cc1cc(-c2cnc3c(-c4cnn(CC(F)(F)F)c4)cn(CC4CCC(F)(F)CC4)c3c2)c[nH]c1=O] | 5-[1-[(4,4-difluorocyclohexyl)methyl]-3-[1-(2,2,2-trifluoroethyl)pyrazol-4-yl]pyrrolo[3,2-b]pyridin-6-yl]-3-methyl-1H-pyridin-2-one | 506.0 |

TABLE 29-continued

| Compound No. | Structure | Name | MS(ESI) [M + H+]+ or [M − H+]− observed |
|---|---|---|---|
| P-0482 | 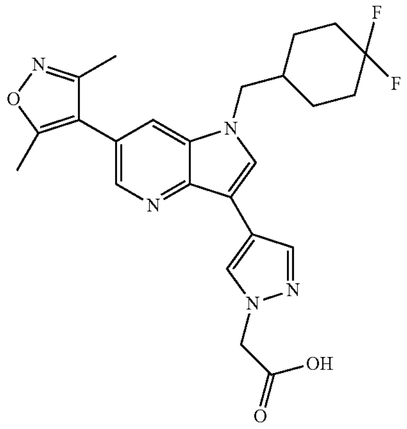 [SMILES: Cc1noc(C)c1-c1cnc2c(-c3cnn(CC(=O)O)c3)cn(CC3CCC(F)(F)CC3)c2c1] | 2-[4-[1-[(4,4-difluorocyclohexyl)methyl]-6-(3,5-dimethylisoxazol-4-yl)pyrrolo[3,2-b]pyridin-3-yl]pyrazol-1-yl]acetic acid | 470.5 |
| P-0483 | 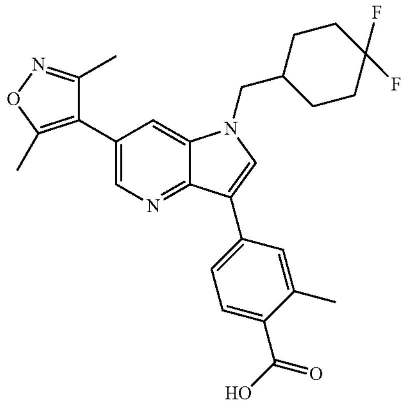 [SMILES: Cc1cc(-c2cn(CC3CCC(F)(F)CC3)c3cc(-c4c(C)noc4C)cnc23)ccc1C(=O)O] | 4-[1-[(4,4-difluorocyclohexyl)methyl]-6-(3,5-dimethylisoxazol-4-yl)pyrrolo[3,2-b]pyridin-3-yl]-2-methyl-benzoic acid | 480.4 |
| P-0484 | 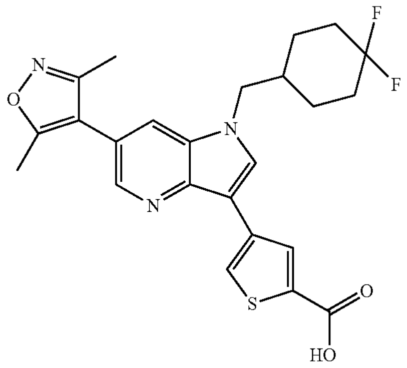 [SMILES: Cc1noc(C)c1-c1cnc2c(-c3csc(C(=O)O)c3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]thiophene-2-carboxylic acid | 472.3 |

TABLE 29-continued

| Compound No. | Structure | Name | MS(ESI) [M + H+]+ or [M − H+]− observed |
|---|---|---|---|
| P-0485 | 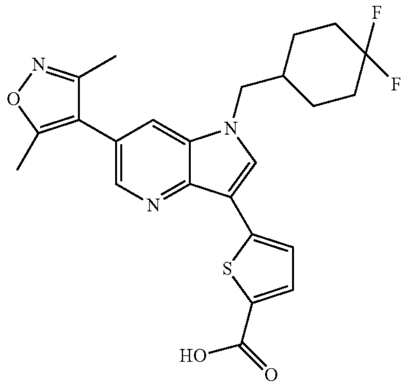 [SMILES: Cc1noc(C)c1-c1cnc2c(-c3ccc(C(=O)O)s3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]thiophene-2-carboxylic acid | 472.3 |
| P-0486 | 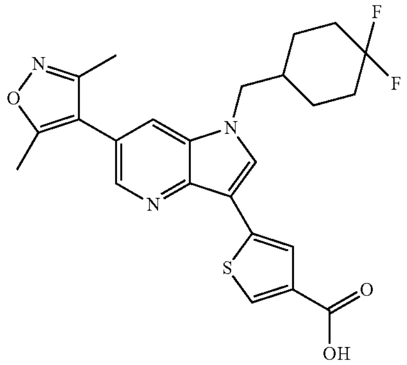 [SMILES: Cc1noc(C)c1-c1cnc2c(-c3cc(C(=O)O)cs3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]thiophene-3-carboxylic acid | 472.3 |
| P-0487 | 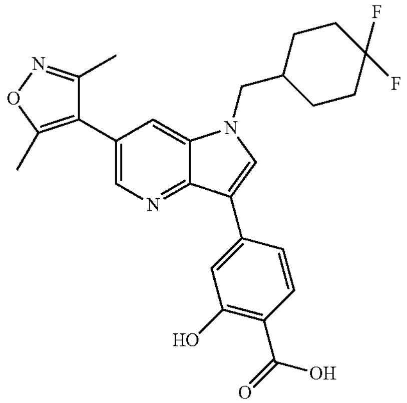 [SMILES: Cc1noc(C)c1-c1cnc2c(-c3ccc(C(=O)O)c(O)c3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]-2-hydroxy-benzoic acid | 482.2 |
| P-0488 | 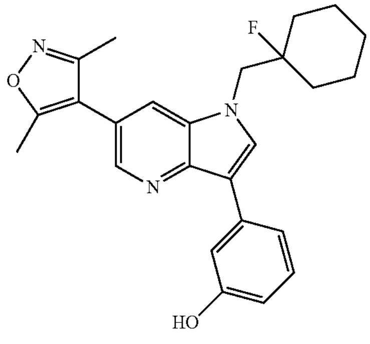 [SMILES: Cc1noc(C)c1-c1cnc2c(-c3cccc(O)c3)cn(CC3(F)CCCCC3)c2c1] | 3-[6-(3,5-dimethylisoxazol-4-yl)-1-[(1-fluorocyclohexyl)methyl]pyrrolo[3,2-b]pyridin-3-yl]phenol | 420.4 |

TABLE 29-continued

| Compound No. | Structure | Name | MS(ESI) [M + H+]+ or [M − H+]− observed |
|---|---|---|---|
| P-0489 | 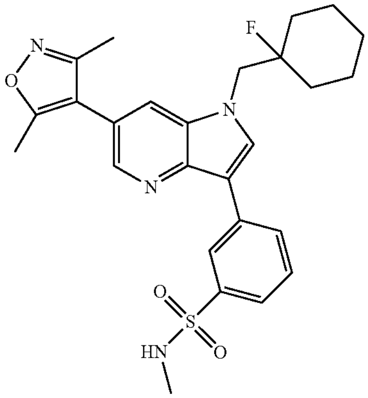 [SMILES: CNS(=O)(=O)c1cccc(-c2cn(CC3(F)CCCCC3)c3cc(-c4c(C)noc4C)cnc23)c1] | 3-[6-(3,5-dimethylisoxazol-4-yl)-1-[(1-fluorocyclohexyl)methyl]pyrrolo[3,2-b]pyridin-3-yl]-N-methyl-benzenesulfonamide | 497.5 |
| P-0490 | 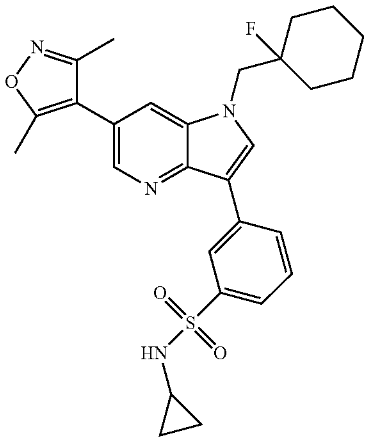 [SMILES: Cc1noc(C)c1-c1cnc2c(-c3cccc(S(=O)(=O)NC4CC4)c3)cn(CC3(F)CCCCC3)c2c1] | N-cyclopropyl-3-[6-(3,5-dimethylisoxazol-4-yl)-1-[(1-fluorocyclohexyl)methyl]pyrrolo[3,2-b]pyridin-3-yl]benzenesulfonamide | 523.6 |
| P-0491 | 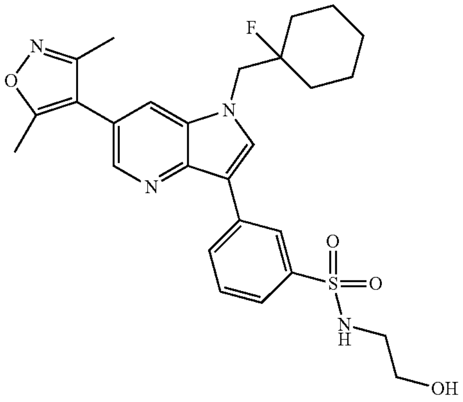 [SMILES: Cc1noc(C)c1-c1cnc2c(-c3cccc(S(=O)(=O)NCCO)c3)cn(CC3(F)CCCCC3)c2c1] | 3-[6-(3,5-dimethylisoxazol-4-yl)-1-[(1-fluorocyclohexyl)methyl]pyrrolo[3,2-b]pyridin-3-yl]-N-(2-hydroxyethyl)benzenesulfonamide | 527.2 |

TABLE 29-continued

| Compound No. | Structure | Name | MS(ESI) [M + H+]+ or [M − H+]− observed |
|---|---|---|---|
| P-0492 | 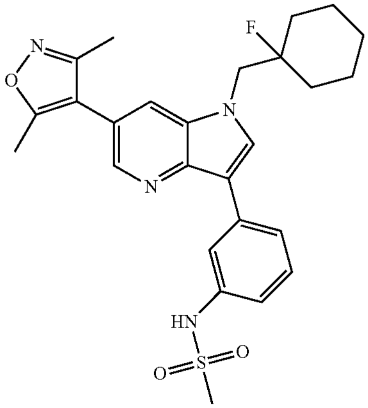 [SMILES: Cc1noc(C)c1-c1cnc2c(-c3cccc(NS(C)(=O)=O)c3)cn(CC3(F)CCCCC3)c2c1] | N-[3-[6-(3,5-dimethylisoxazol-4-yl)-1-[(1-fluorocyclohexyl)methyl]pyrrolo[3,2-b]pyridin-3-yl]phenyl]methanesulfonamide | 497.5 |
| P-0493 | 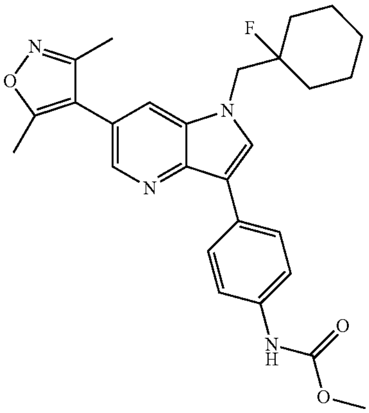 [SMILES: COC(=O)Nc1ccc(-c2cn(CC3(F)CCCCC3)c3cc(-c4c(C)noc4C)cnc23)cc1] | methyl N-[4-[6-(3,5-dimethylisoxazol-4-yl)-1-[(1-fluorocyclohexyl)methyl]pyrrolo[3,2-b]pyridin-3-yl]phenyl]carbamate | 477.4 |
| P-0494 | 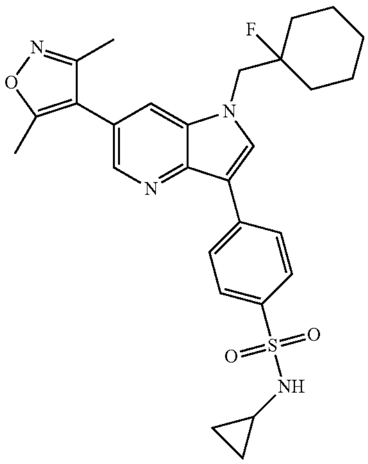 [SMILES: Cc1noc(C)c1-c1cnc2c(-c3ccc(S(=O)(=O)NC4CC4)cc3)cn(CC3(F)CCCCC3)c2c1] | N-cyclopropyl-4-[6-(3,5-dimethylisoxaxol-4-yl)-1-[(1-fluorocyclohexyl)methyl]pyrrolo[3,2-b]pyridin-3-yl]benzenesulfonamide | 523.3 |

TABLE 29-continued
| Compound No. | Structure | Name | MS(ESI) [M + H+]+ or [M − H+]− observed |
|---|---|---|---|
| P-0495 | 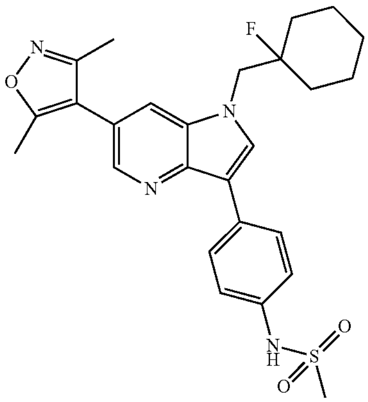 [SMILES: Cc1noc(C)c1-c1cnc2c(-c3ccc(NS(C)(=O)=O)cc3)cn(CC3(F)CCCCC3)c2c1] | N-[4-[6-(3,5-dimethylisoxazol-4-yl)-1-[(1-fluorocyclohexyl)methyl]pyrrolo[3,2-b]pyridin-3-yl]phenyl]methanesulfonamide | 497.5 |
| P-0496 | 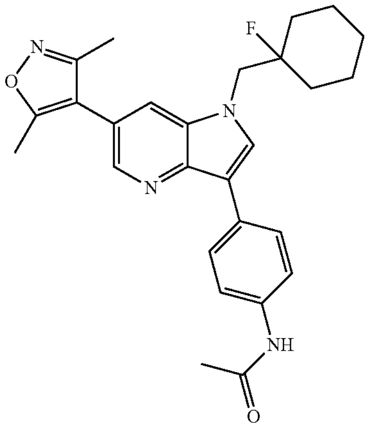 [SMILES: CC(=O)Nc1ccc(-c2cn(CC3(F)CCCCC3)c3cc(-c4c(C)noc4C)cnc23)cc1] | N-[4-[6-(3,5-dimethylisoxazol-4-yl)-1-[(1-fluorocyclohexyl)methyl]pyrrolo[3,2-b]pyridin-3-yl]phenyl]acetamide | 461.2 |
| P-0497 | 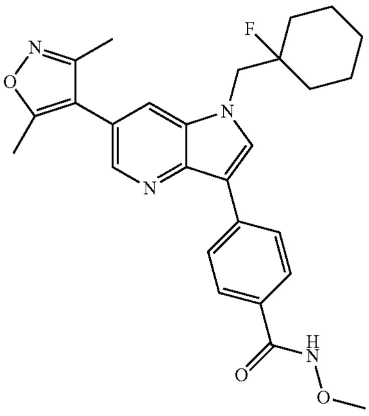 [SMILES: CONC(=O)c1ccc(-c2cn(CC3(F)CCCCC3)c3cc(-c4c(C)noc4C)cnc23)cc1] | 4-[6-(3,5-dimethylisoxazol-4-yl)-1-[(1-fluorocyclohexyl)methyl]pyrrolo[3,2-b]pyridin-3-yl]-N-methoxy-benzamide | 477.4 |

TABLE 29-continued

| Compound No. | Structure | Name | MS(ESI) [M + H+]+ or [M − H+]− observed |
|---|---|---|---|
| P-0498 | 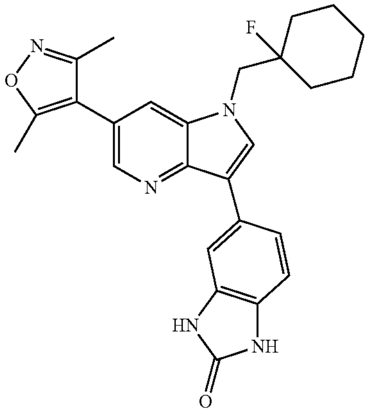 [SMILES: Cc1noc(C)c1-c1cnc2c(-c3ccc4[nH]c(=O)[nH]c4c3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]-1,3-dihydrobenzimidazol-2-one | 460.3 |
| P-0499 | 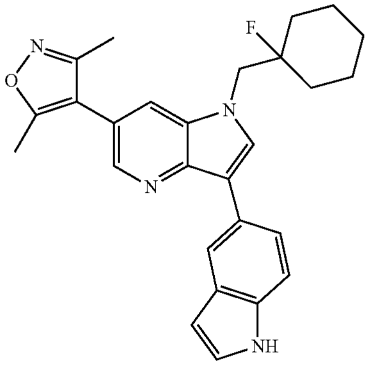 [SMILES: Cc1noc(C)c1-c1cnc2c(-c3ccc4[nH]ccc4c3)cn(CC3(F)CCCCC3)c2c1] | 4-[1-[(1-fluorocyclohexyl)methyl]-3-(1H-indazol-5-yl)pyrrolo[3,2-b]pyridin-6-yl]-3,5-dimethyl-isoxazole | 444.4 |
| P-0500 | 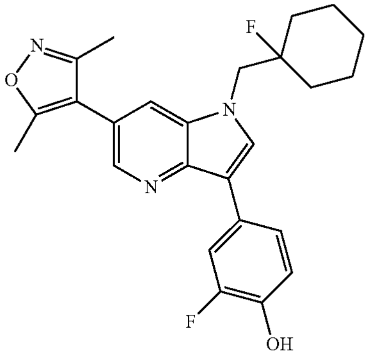 [SMILES: Cc1noc(C)c1-c1cnc2c(-c3ccc(O)c(F)c3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]-2-fluoro-phenol | 438.4 |
| P-0502 | 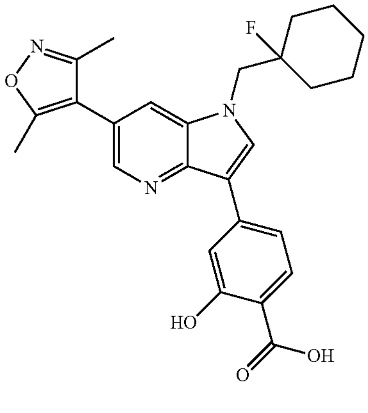 [SMILES: Cc1noc(C)c1-c1cnc2c(-c3ccc(C(=O)O)c(O)c3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]-2-hydroxy-benzoic acid | 464.2 |

TABLE 29-continued
| Compound No. | Structure | Name | MS(ESI) [M + H+]+ or [M − H+]− observed |
|---|---|---|---|
| P-0503 | 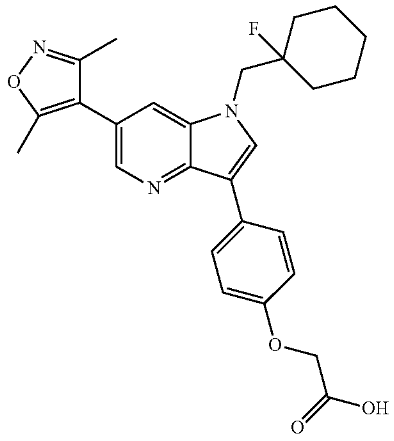 [SMILES: Cc1noc(C)c1-c1cnc2c(-c3ccc(OCC(=O)O)cc3)cn(CC3(F)CCCCC3)c2c1] | 2-[4-[6-(3,5-dimethylisoxazol-4-yl)-1-[(1-fluorocyclohexyl)methyl]pyrrolo[3,2-b]pyridin-3-yl]phenoxy]acetic acid | 478.3 |
| P-0504 | 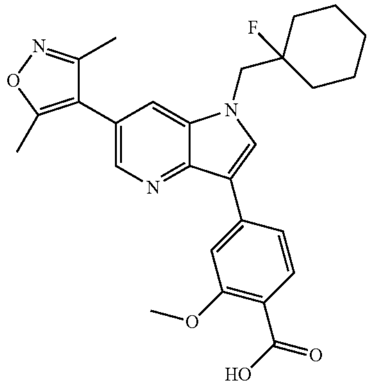 [SMILES: COc1cc(-c2cn(CC3(F)CCCCC3)c3cc(-c4c(C)noc4C)cnc23)ccc1C(=O)O] | 4-[6-(3,5-dimethylisoxazol-4-yl)-1-[(1-fluorocyclohexyl)methyl]pyrrolo[3,2-b]pyridin-3-yl]-2-methoxy-benzoic acid | 478.3 |
| P-0505 | 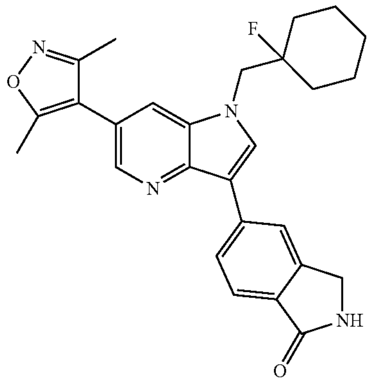 [SMILES: Cc1noc(C)c1-c1cnc2c(-c3ccc4c(c3)CNC4=O)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]isoindolin-1-one | 459.4 |

TABLE 29-continued
| Compound No. | Structure | Name | MS(ESI) [M + H+]+ or [M − H+]− observed |
|---|---|---|---|
| P-0506 | 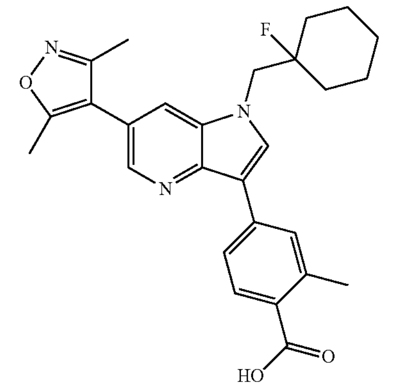 [SMILES: Cc1cc(-c2cn(CC3(F)CCCCC3)c3cc(-c4c(C)noc4C)cnc23)ccc1C(=O)O] | 4-[6-(3,5-dimethylisoxazol-4-yl)-1-[(1-fluorocyclohexyl)methyl]pyrrolo[3,2-b]pyridin-3-yl]-2-methyl-benzoic acid | 462.4 |
| P-0507 | 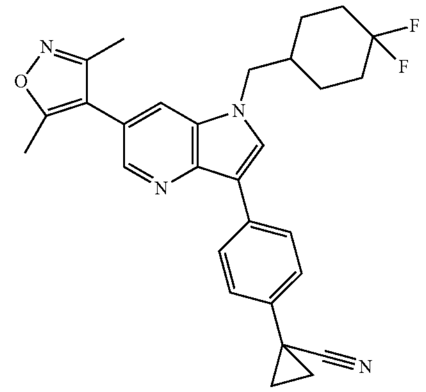 [SMILES: Cc1noc(C)c1-c1cnc2c(-c3ccc(C4(C#N)CC4)cc3)cn(CC3CCC(F)(F)CC3)c2c1] | 1-[4-[1-[(4,4-difluorocyclohexyl)methyl]-6-(3,5-dimethylisoxazol-4-yl)pyrrolo[3,2-b]pyridin-3-yl]phenyl]cyclopropanecarbonitrile | 487.3 |
| P-0508 | 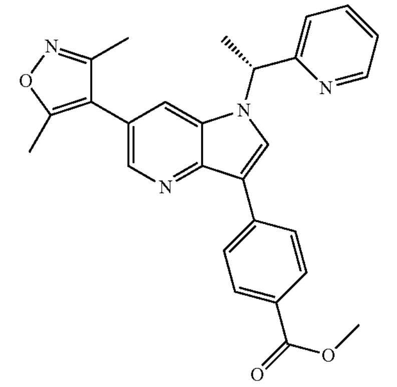 [SMILES: COC(=O)c1ccc(-c2cn([C@H](C)c3ccccn3)c3cc(-c4c(C)noc4C)cnc23)cc1] | methyl 4-[6-(3,5-dimethylisoxazol-4-yl)-1-[(1R)-1-(2-pyridyl)ethyl]pyrrolo[3,2-b]pyridin-3-yl]benzoate | 453.0 |

TABLE 29-continued

| Compound No. | Structure | Name | MS(ESI) [M + H+]+ or [M − H+]− observed |
|---|---|---|---|
| P-0509 | 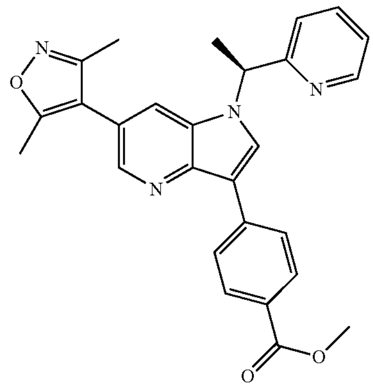 [SMILES: COC(=O)c1ccc(-c2cn([C@@H](C)c3ccccn3)c3cc(-c4c(C)noc4C)cnc23)cc1] | methyl 4-[6-(3,5-dimethylisoxazol-4-yl)-1-[(1S)-1-(2-pyridyl)ethyl]pyrrolo[3,2-b]pyridin-3-yl]benzoate | 453.3 |
| P-0510 | 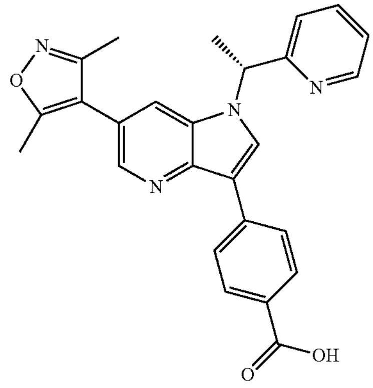 [SMILES: Cc1noc(C)c1-c1cnc2c(-c3ccc(C(=O)O)cc3)cn([C@H](C)c3ccccn3)c2c1] | 4-[6-(3,5-dimethylisoxazol-4-yl)-1-[(1R)-1-(2-pyridyl)ethyl]pyrrolo[3,2-b]pyridin-3-yl]benzoic acid | 439.0 |
| P-0511 | 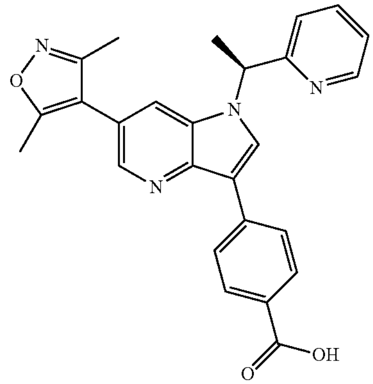 [SMILES: Cc1noc(C)c1-c1cnc2c(-c3ccc(C(=O)O)cc3)cn([C@@H](C)c3ccccn3)c2c1] | 4-[6-(3,5-dimethylisoxazol-4-yl)-1-[(1S)-1-(2-pyridyl)ethyl]pyrrolo[3,2-b]pyridin-3-yl]benzoic acid | 438.9 |
| P-0512 | 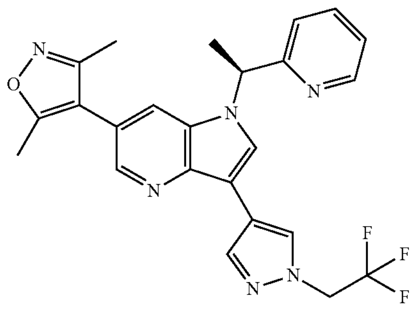 [SMILES: Cc1noc(C)c1-c1cnc2c(-c3cnn(CC(F)(F)F)c3)cn([C@@H](C)c3ccccn3)c2c1] | 3,5-dimethyl-4-[1-[(1S)-1-(2-pyridyl)ethyl]-3-[1-(2,2,2-trifluoroethyl)pyrazol-4-yl]pyrrolo[3,2-b]pyridin-6-yl]isoxazole | 467.3 |

TABLE 29-continued

| Compound No. | Structure | Name | MS(ESI) [M + H+]+ or [M − H+]− observed |
|---|---|---|---|
| P-0513 | 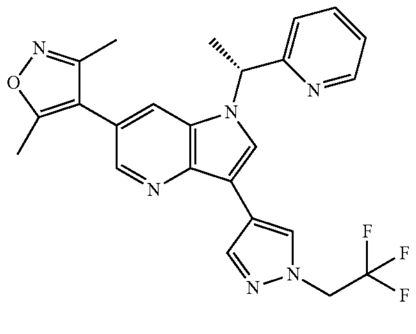 [SMILES: Cc1noc(C)c1-c1cnc2c(-c3cnn(CC(F)(F)F)c3)cn([C@H](C)c3ccccn3)c2c1] | 3,5-dimethyl-4-[1-[(1R)-1-(2-pyridyl)ethyl]-3-[1-(2,2,2-trifluoroethyl)pyrazol-4-yl]pyrrolo[3,2-b]pyridin-6-yl]isoxazole | 467.3 |
| P-0514 | 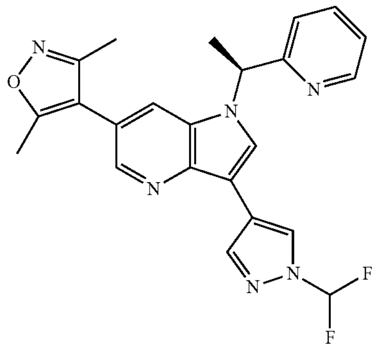 [SMILES: Cc1noc(C)c1-c1cnc2c(-c3cnn(C(F)F)c3)cn([C@@H](C)c3ccccn3)c2c1] | 4-[3-[1-(difluoromethyl)pyrazol-4-yl]-1-[(1S)-1-(2-pyridyl)ethyl]pyrrolo[3,2-b]pyridin-6-yl]-3,5-dimethyl-isoxazole | 435.3 |
| P-0515 | 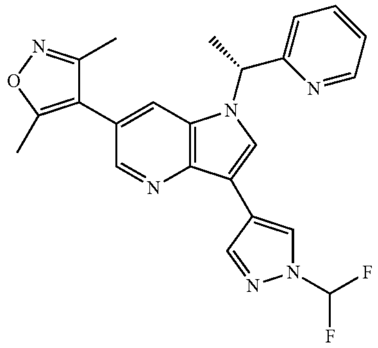 [SMILES: Cc1noc(C)c1-c1cnc2c(-c3cnn(C(F)F)c3)cn([C@H](C)c3ccccn3)c2c1] | 4-[3-[1-(difluoromethyl)pyrazol-4-yl]-1-[(1R)-1-(2-pyridyl)ethyl]pyrrolo[3,2-b]pyridin-6-yl]-3,5-dimethyl-isoxazole | 435.2 |
| P-0516 | 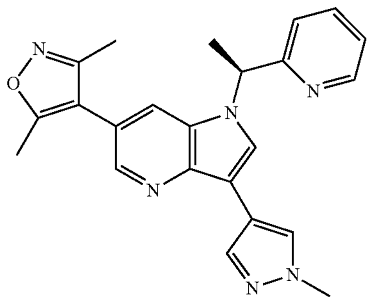 | 3,5-dimethyl-4-[3-(1-methylpyrazol-4-yl)-1-[(1S)-1-(2-pyridyl)ethyl]pyrrolo[3,2-b]pyridin-6-yl]isoxazole | 399.3 |

TABLE 29-continued

| Compound No. | Structure | Name | MS(ESI) [M + H+]+ or [M − H+]− observed |
|---|---|---|---|
| P-0517 | 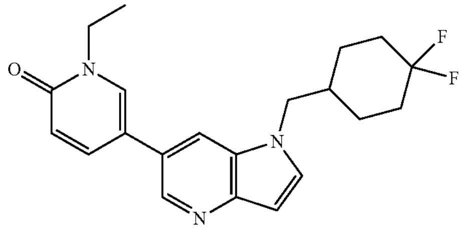 [SMILES: CCn1cc(-c2cnc3ccn(CC4CCC(F)(F)CC4)c3c2)ccc1=O] | 5-[1-[(4,4-difluorocyclohexyl)methyl]pyrrolo[3,2-b]pyridin-6-yl]-1-ethyl-pyridin-2-one | 372.2 |
| P-0518 | 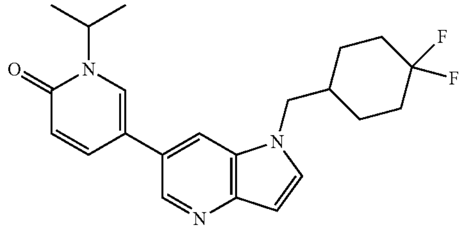 [SMILES: CC(C)n1cc(-c2cnc3ccn(CC4CCC(F)(F)CC4)c3c2)ccc1=O] | 5-[1-[(4,4-difluorocyclohexyl)methyl]pyrrolo[3,2-b]pyridin-6-yl]-1-isopropyl-pyridin-2-one | 386.3 |
| P-0519 | 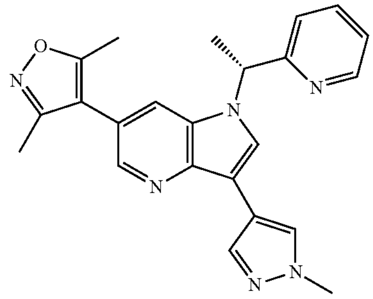 [SMILES: Cc1noc(C)c1-c1cnc2c(-c3cnn(C)c3)cn([C@H](C)c3ccccn3)c2c1] | 3,5-dimethyl-4-[3-(1-methylpyrazol-4-yl)-1-[(1R)-1-(2-pyridyl)ethyl]pyrrolo[3,2-b]pyridin-6-yl]isoxazole | 399.0 |
| P-0520 | 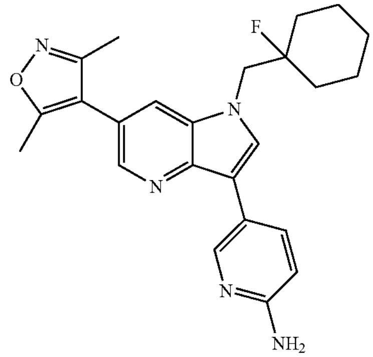 [SMILES: Cc1noc(C)c1-c1cnc2c(-c3ccc(N)nc3)cn(CC3(F)CCCCC3)c2c1] | 5-[6-(3,5-dimethylisoxazol-4-yl)-1-[(1-fluorocyclohexyl)methyl]pyrrolo[3,2-b]pyridin-3-yl]pyridin-2-amine | 420.1 |
| P-0521 | 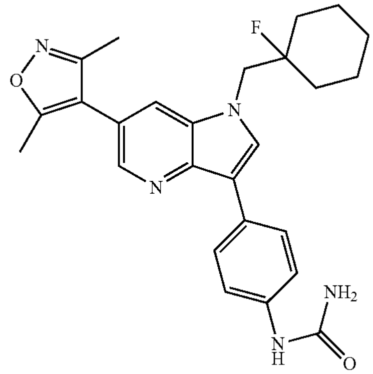 [SMILES: Cc1noc(C)c1-c1cnc2c(-c3ccc(NC(N)=O)cc3)cn(CC3(F)CCCCC3)c2c1] | [4-[6-(3,5-dimethylisoxazol-4-yl)-1-[(1-fluorocyclohexyl)methyl]pyrrolo[3,2-b]pyridin-3-yl]phenyl]urea | 462.4 |

TABLE 29-continued

| Compound No. | Structure | Name | MS(ESI) [M + H+]+ or [M − H+]− observed |
|---|---|---|---|
| P-0522 | 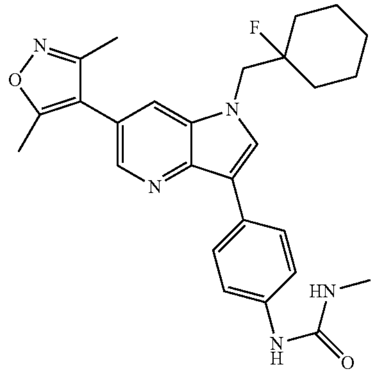 [SMILES: CNC(=O)Nc1ccc(-c2cn(CC3(F)CCCCC3)c3cc(-c4c(C)noc4C)cnc23)cc1] | 1-[4-[6-(3,5-dimethylisoxazol-4-yl)-1-[(1-fluorocyclohexyl)methyl]pyrrolo[3,2-b]pyridin-3-yl]phenyl]-3-methyl-urea | 476.2 |
| P-0523 | 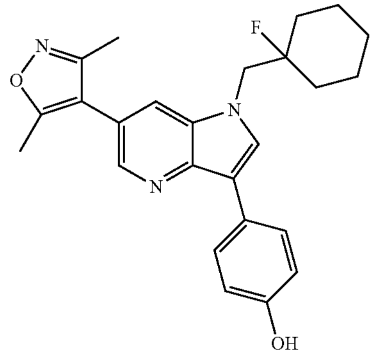 [SMILES: Cc1noc(C)c1-c1cnc2c(-c3ccc(O)cc3)cn(CC3(F)CCCCC3)c2c1] | 4-[6-(3,5-dimethylisoxazol-4-yl)-1-[(1-fluorocyclohexyl)methyl]pyrrolo[3,2-b]pyridin-3-yl]phenol | 420.4 |
| P-0524 | 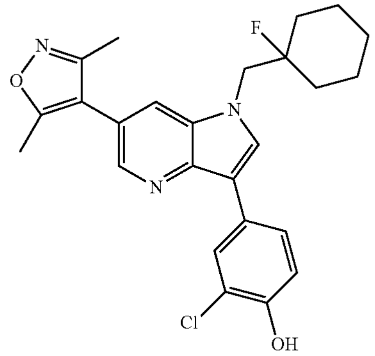 [SMILES: Cc1noc(C)c1-c1cnc2c(-c3ccc(O)c(Cl)c3)cn(CC3(F)CCCCC3)c2c1] | 2-chloro-4-[6-(3,5-dimethylisoxazol-4-yl)-1-[(1-fluorocyclohexyl)methyl]pyrrolo[3,2-b]pyridin-3-yl]phenol | 454.3 |
| P-0525 | 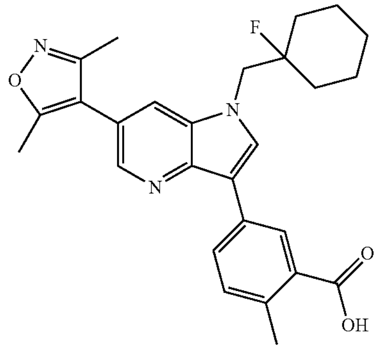 [SMILES: Cc1ccc(-c2cn(CC3(F)CCCCC3)c3cc(-c4c(C)noc4C)cnc23)cc1C(=O)O] | 5-[6-(3,5-dimethylisoxazol-4-yl)-1-[(1-fluorocyclohexyl)methyl]pyrrolo[3,2-b]pyridin-3-yl]-2-methyl-benzoic acid | 462.4 |

TABLE 29-continued
| Compound No. | Structure | Name | MS(ESI) [M + H+]+ or [M − H+]− observed |
|---|---|---|---|
| P-0526 | 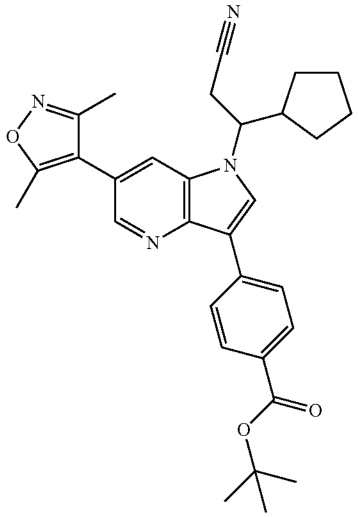 [SMILES: Cc1noc(C)c1-c1cnc2c(-c3ccc(C(=O)OC(C)(C)C)cc3)cn(C(CC#N)C3CCCC3)c2c1] | tert-butyl 4-[1-(2-cyano-1-cyclopentyl-ethyl)-6-(3,5-dimethylisoxazol-4-yl)pyrrolo[3,2-b]pyridin-3-yl]benzoate | 511.4 |
| P-0527 | 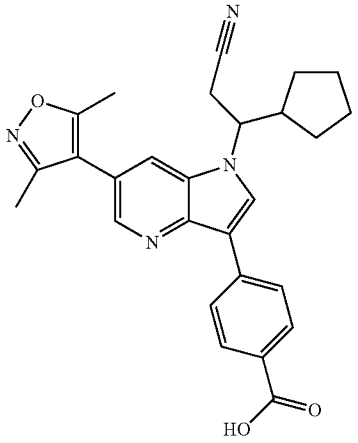 [SMILES: Cc1noc(C)c1-c1cnc2c(-c3ccc(C(=O)O)cc3)cn(C(CC#N)C3CCCC3)c2c1] | 4-[1-(2-cyano-1-cyclopentyl-ethyl)-6-(3,5-dimethylisoxazol-4-yl)pyrrolo[3,2-b]pyridin-3-yl]benzoic acid | 455.5 |
| P-0528 | 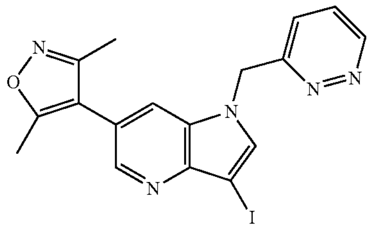 [SMILES: Cc1noc(C)c1-c1cnc2c(I)cn(Cc3cccnn3)c2c1] | 4-[3-iodo-1-(pyridazin-3-ylmethyl)pyrrolo[3,2-b]pyridin-6-yl]-3,5-dimethyl-isoxazole | 432.0 |

TABLE 29-continued
| Compound No. | Structure | Name | MS(ESI) [M + H+]+ or [M − H+]− observed |
|---|---|---|---|
| P-0529 | 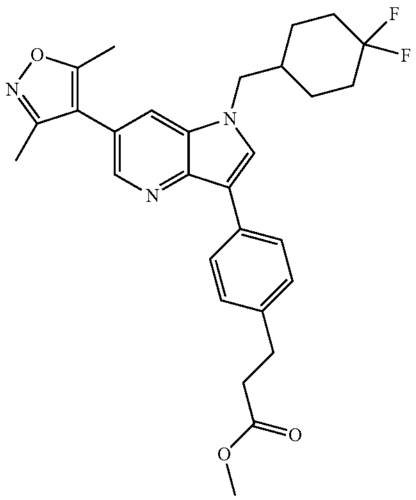 [SMILES: COC(=O)CCc1ccc(-c2cn(CC3CCC(F)(F)CC3)c3cc(-c4c(C)noc4C)cnc23)cc1] | methyl 3-[4-[1-[(4,4-difluorocyclohexyl)methyl]-6-(3,5-dimethylisoxazol-4-yl)pyrrolo[3,2-b]pyridin-3-yl]phenyl]propanoate | 508.0 |
| P-0530 | 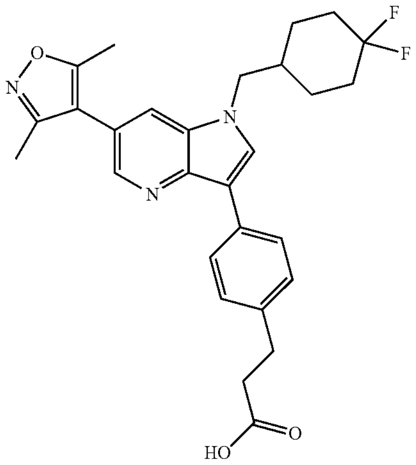 [SMILES: Cc1noc(C)c1-c1cnc2c(-c3ccc(CCC(=O)O)cc3)cn(CC3CCC(F)(F)CC3)c2c1] | 3-[4-[1-[(4,4-difluorocyclohexyl)methyl]-6-(3,5-dimethylisoxazol-4-yl)pyrrolo[3,2-b]pyridin-3-yl]phenyl]propanoic acid | 494.0 |
| P-0531 | 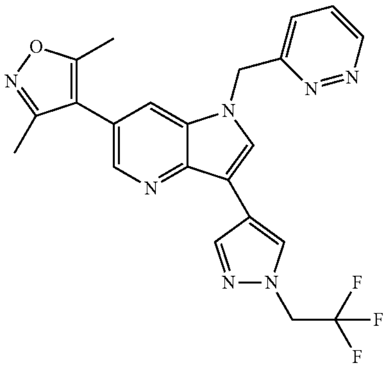 [SMILES: Cc1noc(C)c1-c1cnc2c(-c3cnn(CC(F)(F)F)c3)cn(Cc3cccnn3)c2c1] | 3,5-dimethyl-4-[1-(pyridazin-3-ylmethyl)-3-[1-(2,2,2-trifluoroethyl)pyrazol-4-yl]pyrrolo[3,2-b]pyridin-6-yl]isoxazole | 453.9 |

TABLE 29-continued

| Compound No. | Structure | Name | MS(ESI) [M + H+]+ or [M − H+]− observed |
|---|---|---|---|
| P-0532 | 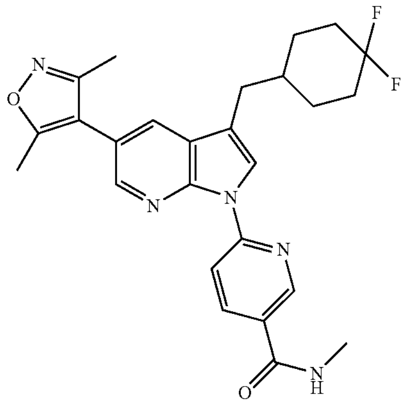 [SMILES: CNC(=O)c1ccc(-n2cc(CC3CCC(F)(F)CC3)c3cc(-c4c(C)noc4C)cnc32)nc1] | 6-[3-[(4,4-difluorocyclohexyl)methyl]-5-(3,5-dimethylisoxazol-4-yl)pyrrolo[2,3-b]pyridin-1-yl]-N-methyl-pyridine-3-carboxamide | 480.1 |
| P-0533 | 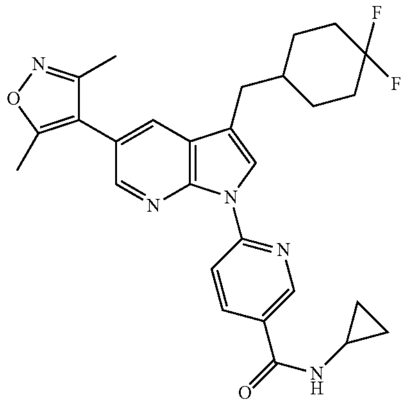 [SMILES: Cc1noc(C)c1-c1cnc2c(c1)c(CC1CCC(F)(F)CC1)cn2-c1ccc(C(=O)NC2CC2)cn1] | N-cyclopropyl-6-[3-[(4,4-difluorocyclohexyl)methyl]-5-(3,5-dimethylisoxazol-4-yl)pyrrolo[2,3-b]pyridin-1-yl]pyridine-3-carboxamide | 506.0 |
| P-0534 | 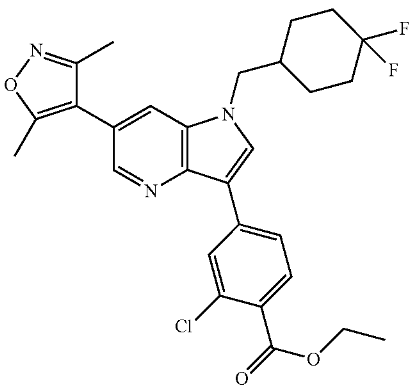 [SMILES: CCOC(=O)c1ccc(-c2cn(CC3CCC(F)(F)CC3)c3cc(-c4c(C)noc4C)cnc23)cc1Cl] | ethyl 2-chloro-4-[1-[(4,4-difluorocyclohexyl)methyl]-6-(3,5-dimethylisoxazol-4-yl)pyrrolo[3,2-b]pyridin-3-yl]benzoate | 528.0 |

TABLE 29-continued

| Compound No. | Structure | Name | MS(ESI) [M + H+]+ or [M − H+]− observed |
|---|---|---|---|
| P-0535 | 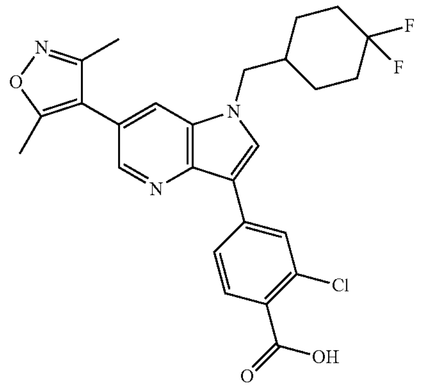 [SMILES: Cc1noc(C)c1-c1cnc2c(-c3ccc(C(=O)O)c(Cl)c3)cn(CC3CCC(F)(F)CC3)c2c1] | 2-chloro-4-[1-[(4,4-difluorocyclohexyl)methyl]-6-(3,5-dimethylisoxazol-4-yl)pyrrolo[3,2-b]pyridin-3-yl]benzoic acid | 499.9 |
| P-0536 | 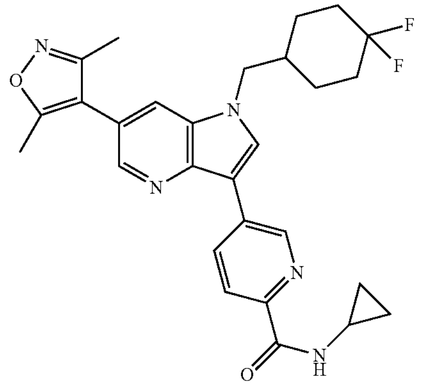 [SMILES: Cc1noc(C)c1-c1cnc2c(-c3ccc(C(=O)NC4CC4)nc3)cn(CC3CCC(F)(F)CC3)c2c1] | N-cyclopropyl-5-[1-[(4,4-difluorocyclohexyl)methyl]-6-(3,5-dimethylisoxazol-4-yl)pyrrolo[3,2-b]pyridin-3-yl]pyridine-2-carboxamide | 506.3 |
| P-0537 | 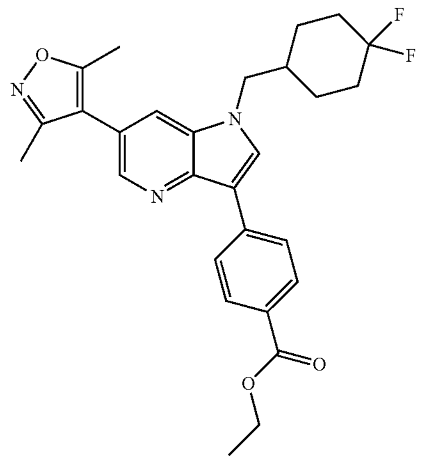 [SMILES: CCOC(=O)c1ccc(-c2cn(CC3CCC(F)(F)CC3)c3cc(-c4c(C)noc4C)cnc23)cc1] | ethyl 4-[1-[(4,4-difluorocyclohexyl)methyl]-6-(3,5-dimethylisoxazol-4-yl)pyrrolo[3,2-b]pyridin-3-yl]benzoate | 494.5 |

TABLE 29-continued
| Compound No. | Structure | Name | MS(ESI) [M + H+]+ or [M − H+]− observed |
|---|---|---|---|
| P-0538 | 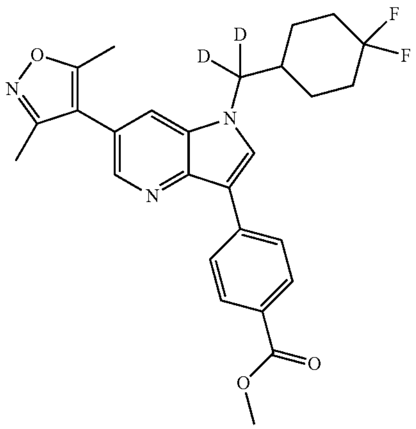 [SMILES: [2H]C([2H])(C1CCC(F)(F)CC1)n1cc(-c2ccc(C(=O)OC)cc2)c2ncc(-c3c(C)noc3C)cc21] | methyl 4-[1-[dideuterio-(4,4-difluorocyclohexyl)methyl]-6-(3,5-dimethylisoxazol-4-yl)pyrrolo[3,2-b]pyridin-3-yl]benzoate | 482.1 |
| P-0539 | 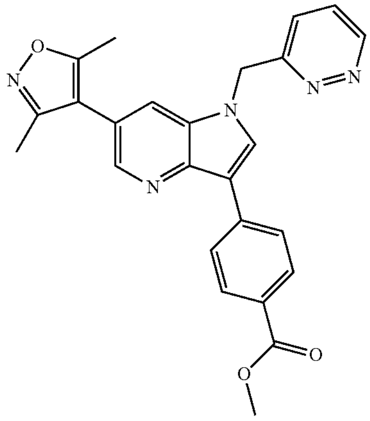 [SMILES: COC(=O)c1ccc(-c2cn(Cc3cccnn3)c3cc(-c4c(C)noc4C)cnc23)cc1] | methyl 4-[6-(3,5-dimethylisoxazol-4-yl)-1-(pyridazin-3-ylmethyl)pyrrolo[3,2-b]pyridin-3-yl]benzoate | 439.9 |
| P-0540 | 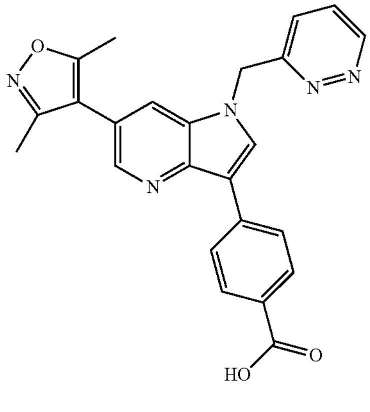 [SMILES: Cc1noc(C)c1-c1cnc2c(-c3ccc(C(=O)O)cc3)cn(Cc3cccnn3)c2c1] | 4-[6-(3,5-dimethylisoxazol-4-yl)-1-(pyridazin-3-ylmethyl)pyrrolo[3,2-b]pyridin-3-yl]benzoic acid | 425.9 |

TABLE 29-continued

| Compound No. | Structure | Name | MS(ESI) [M + H+]+ or [M − H+]− observed |
|---|---|---|---|
| P-0541 | 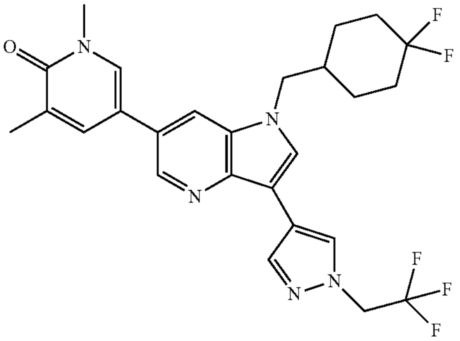 [SMILES: Cc1cc(-c2cnc3c(-c4cnn(CC(F)(F)F)c4)cn(CC4CCC(F)(F)CC4)c3c2)cn(C)c1=O] | 5-[1-[(4,4-difluorocyclohexyl)methyl]-3-[1-(2,2,2-trifluoroethyl)pyrazol-4-yl]pyrrolo[3,2-b]pyridin-6-yl]-1,3-dimethyl-pyridin-2-one | 520.4 |
| P-0542 | 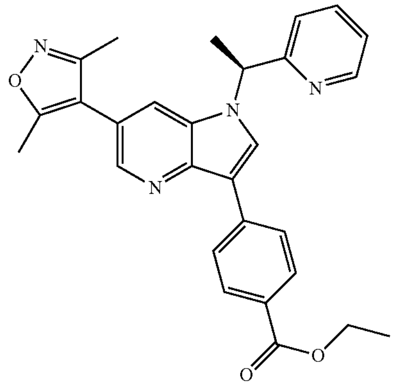 [SMILES: CCOC(=O)c1ccc(-c2cn([C@@H](C)c3ccccn3)c3cc(-c4c(C)noc4C)cnc23)cc1] | ethyl 4-[6-(3,5-dimethylisoxazol-4-yl)-1-[(1S)-1-(2-pyridyl)ethyl]pyrrolo[3,2-b]pyridin-3-yl]benzoate | 467.0 |
| P-0543 | 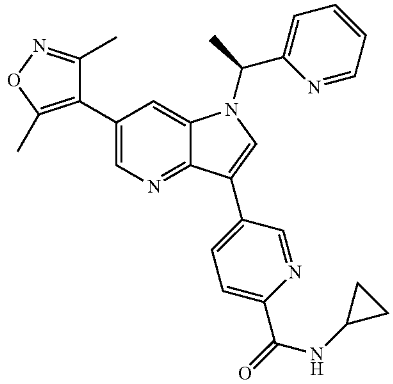 [SMILES: Cc1noc(C)c1-c1cnc2c(-c3ccc(C(=O)NC4CC4)nc3)cn([C@@H](C)c3ccccn3)c2c1] | N-cyclopropyl-5-[6-(3,5-dimethylisoxazol-4-yl)-1-[(1S)-1-(2-pyridyl)ethyl]pyrrolo[3,2-b]pyridin-3-yl]pyridine-2-carboxamide | 478.9 |
| P-0544 | 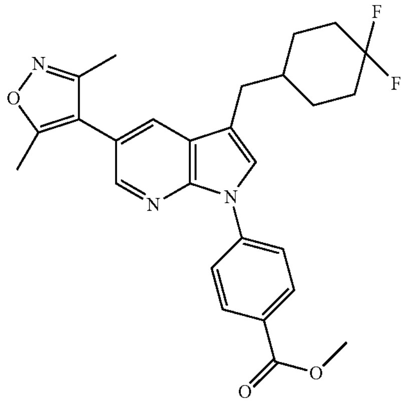 [SMILES: COC(=O)c1ccc(-n2cc(CC3CCC(F)(F)CC3)c3cc(-c4c(C)noc4C)cnc32)cc1] | methyl 4-[3-[(4,4-difluorocyclohexyl)methyl]-5-(3,5-dimethylisoxazol-4-yl)pyrrolo[2,3-b]pyridin-1-yl]benzoate | 480.0 |

TABLE 29-continued

| Compound No. | Structure | Name | MS(ESI) [M + H+]+ or [M − H+]− observed |
|---|---|---|---|
| P-0545 | 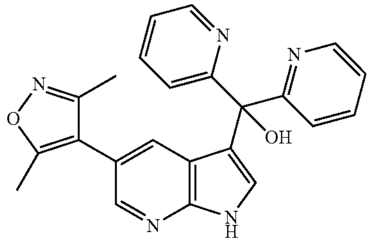 [SMILES: Cc1noc(C)c1-c1cnc2[nH]cc(C(O)(c3ccccn3)c3ccccn3)c2c1] | [5-(3,5-dimethylisoxazol-4-yl)-1H-pyrrolo[2,3-b]pyridin-3-yl]-bis(2-pyridyl)methanol | 397.8 |
| P-0546 | 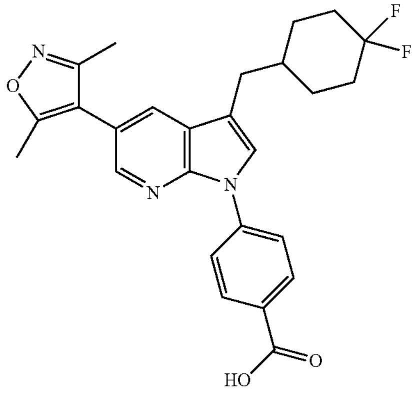 [SMILES: Cc1noc(C)c1-c1cnc2c(c1)c(CC1CCC(F)(F)CC1)cn2-c1ccc(C(=O)O)cc1] | 4-[3-[(4,4-difluorocyclohexyl)methyl]-5-(3,5-dimethylisoxazol-4-yl)pyrrolo[2,3-b]pyridin-1-yl]benzoic acid | 465.9 |
| P-0547 | 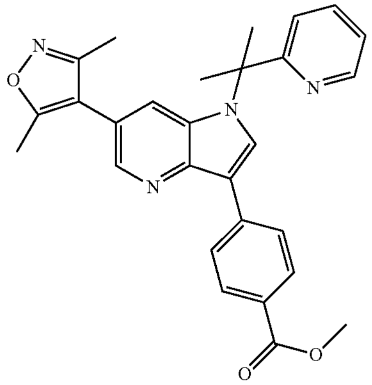 [SMILES: COC(=O)c1ccc(-c2cn(C(C)(C)c3ccccn3)c3cc(-c4c(C)noc4C)cnc23)cc1] | methyl 4-[6-(3,5-dimethylisoxazol-4-yl)-1-[1-methyl-1-(2-pyridyl)ethyl]pyrrolo[3,2-b]pyridin-3-yl]benzoate | 466.9 |
| P-0548 | 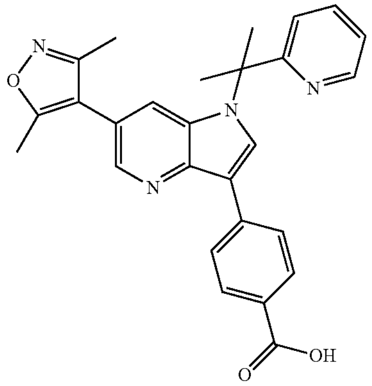 [SMILES: Cc1noc(C)c1-c1cnc2c(-c3ccc(C(=O)O)cc3)cn(C(C)(C)c3ccccn3)c2c1] | 4-[6-(3,5-dimethylisoxazol-4-yl)-1-[1-methyl-1-(2-pyridyl)ethyl]pyrrolo[3,2-b]pyridin-3-yl]benzoic acid | 452.9 |

TABLE 29-continued

| Compound No. | Structure | Name | MS(ESI) [M + H+]+ or [M − H+]− observed |
|---|---|---|---|
| P-0549 | 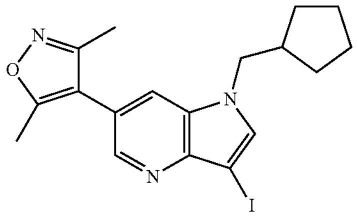 [SMILES: Cc1noc(C)c1-c1cnc2c(I)cn(CC3CCCC3)c2c1] | 4-[1-(cyclopentylmethyl)-3-iodo-pyrrolo[3,2-b]pyridin-6-yl]-3,5-dimethyl-isoxazole | 422.1 |
| P-0550 | 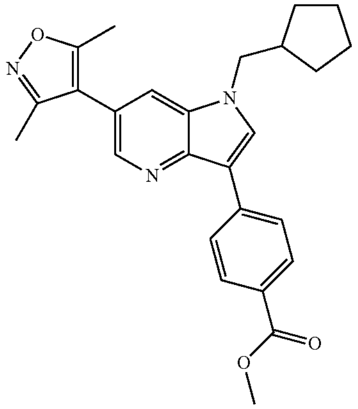 [SMILES: COC(=O)c1ccc(-c2cn(CC3CCCC3)c3cc(-c4c(C)noc4C)cnc23)cc1] | methyl 4-[1-(cyclopentylmethyl)-6-(3,5-dimethylisoxazol-4-yl)pyrrolo[3,2-b]pyridin-3-yl]benzoate | 430.0 |
| P-0551 | 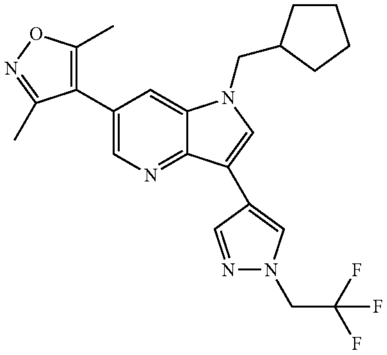 [SMILES: Cc1noc(C)c1-c1cnc2c(-c3cnn(CC(F)(F)F)c3)cn(CC3CCCC3)c2c1] | 4-[1-(cyclopentylmethyl)-3-[1-(2,2,2-trifluoroethyl)pyrazol-4-yl]pyrrolo[3,2-b]pyridin-6-yl]-3,5-dimethyl-isoxazole | 444.3 |
| P-0552 | 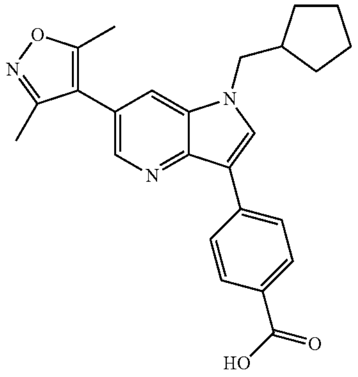 [SMILES: Cc1noc(C)c1-c1cnc2c(-c3ccc(C(=O)O)cc3)cn(CC3CCCC3)c2c1] | 4-[1-(cyclopentylmethyl)-6-(3,5-dimethylisoxazol-4-yl)pyrrolo[3,2-b]pyridin-3-yl]benzoic acid | 416.2 |

TABLE 29-continued

| Compound No. | Structure | Name | MS(ESI) [M + H+]+ or [M − H+]− observed |
|---|---|---|---|
| P-0553 | 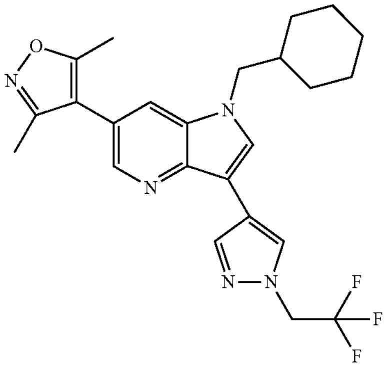 [SMILES: Cc1noc(C)c1-c1cnc2c(-c3cnn(CC(F)(F)F)c3)cn(CC3CCCCC3)c2c1] | 4-[1-(cyclohexylmethyl)-3-[1-(2,2,2-trifluoroethyl)pyrazol-4-yl]pyrrolo[3,2-b]pyridin-6-yl]-3,5-dimethyl-isoxazole | 458.0 |
| P-0554 | 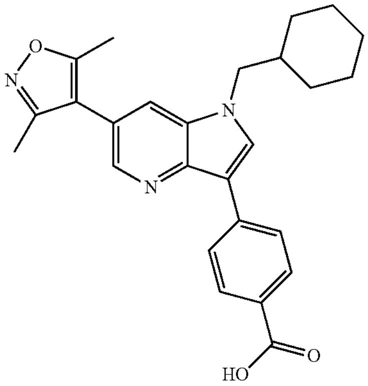 [SMILES: Cc1noc(C)c1-c1cnc2c(-c3ccc(C(=O)O)cc3)cn(CC3CCCCC3)c2c1] | 4-[1-(cyclohexylmethyl)-6-(3,5-dimethylisoxazol-4-yl)pyrrolo[3,2-b]pyridin-3-yl]benzoic acid | 429.9 |
| P-0555 | 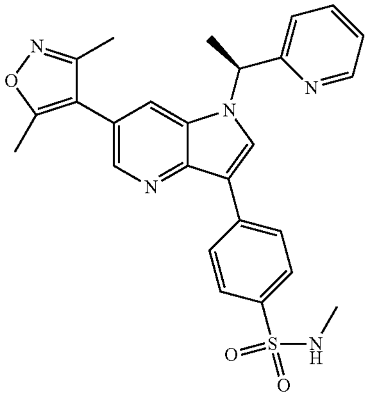 [SMILES: CNS(=O)(=O)c1ccc(-c2cn([C@@H](C)c3ccccn3)c3cc(-c4c(C)noc4C)cnc23)cc1] | 4-[6-(3,5-dimethylisoxazol-4-yl)-1-[(1S)-1-(2-pyridyl)ethyl]pyrrolo[3,2-b]pyridin-3-yl]-N-methyl-benzenesulfonamide | 487.9 |
| P-0556 | 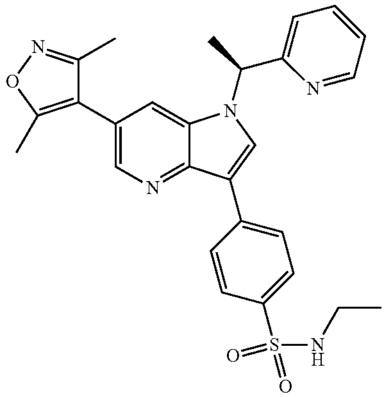 [SMILES: CCNS(=O)(=O)c1ccc(-c2cn([C@@H](C)c3ccccn3)c3cc(-c4c(C)noc4C)cnc23)cc1] | 4-[6-(3,5-dimethylisoxazol-4-yl)-1-[(1S)-1-(2-pyridyl)ethyl]pyrrolo[3,2-b]pyridin-3-yl]-N-ethyl-benzenesulfonamide | 502.0 |

TABLE 29-continued
| Compound No. | Structure | Name | MS(ESI) [M + H+]+ or [M − H+]− observed |
|---|---|---|---|
| P-0557 | 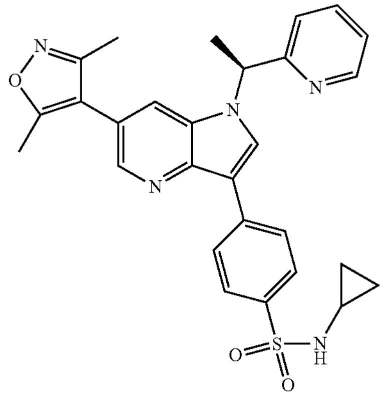 [SMILES: Cc1noc(C)c1-c1cnc2c(-c3ccc(S(=O)(=O)NC4CC4)cc3)cn([C@@H](C)c3ccccn3)c2c1] | N-cyclopropyl-4-[6-(3,5-dimethylisoxazol-4-yl)-1-[(1S)-1-(2-pyridyl)ethyl]pyrrolo[3,2-b]pyridin-3-yl]benzenesulfonamide | 513.9 |
| P-0558 | 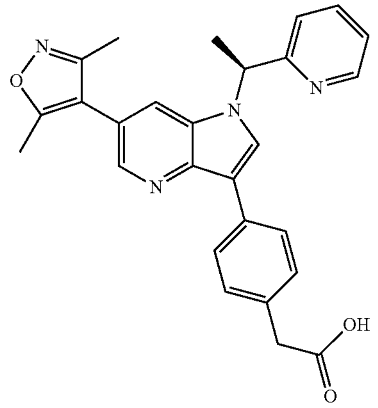 [SMILES: Cc1noc(C)c1-c1cnc2c(-c3ccc(CC(=O)O)cc3)cn([C@@H](C)c3ccccn3)c2c1] | 2-[4-[6-(3,5-dimethylisoxazol-4-yl)-1-[(1S)-1-(2-pyridyl)ethyl]pyrrolo[3,2-b]pyridin-3-yl]phenyl]acetic acid | 453.4 |
| P-0559 | 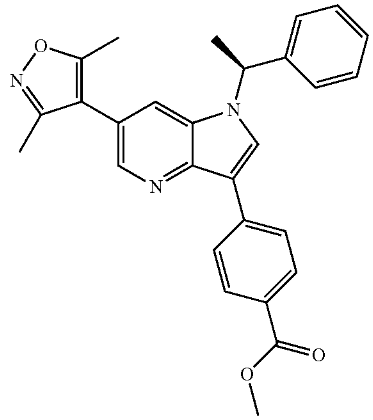 [SMILES: COC(=O)c1ccc(-c2cn([C@@H](C)c3ccccc3)c3cc(-c4c(C)noc4C)cnc23)cc1] | methyl 4-[6-(3,5-dimethylisoxazol-4-yl)-1-[(1S)-1-phenylethyl]pyrrolo[3,2-b]pyridin-3-yl]benzoate | 452.0 |

TABLE 29-continued
| Compound No. | Structure | Name | MS(ESI) [M + H+]+ or [M − H+]− observed |
|---|---|---|---|
| P-0560 | 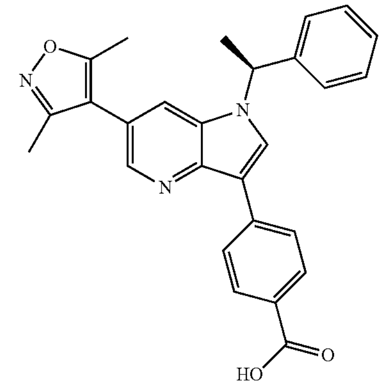 [SMILES: Cc1noc(C)c1-c1cnc2c(-c3ccc(C(=O)O)cc3)cn([C@@H](C)c3ccccc3)c2c1] | 4-[6-(3,5-dimethylisoxazol-4-yl)-1-[(1S)-1-phenylethyl]pyrrolo[3,2-b]pyridin-3-yl]benzoic acid | 438.3 |
| P-0561 | 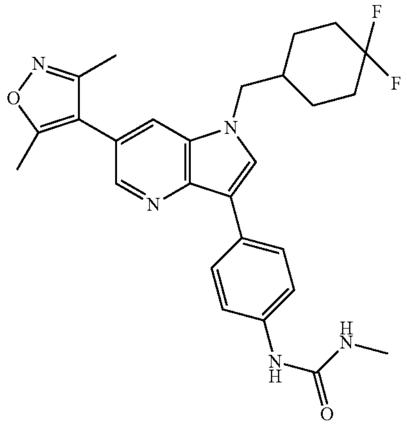 [SMILES: CNC(=O)Nc1ccc(-c2cn(CC3CCC(F)(F)CC3)c3cc(-c4c(C)noc4C)cnc23)cc1] | 1-[4-[1-[(4,4-difluorocyclohexyl)methyl]-6-(3,5-dimethylisoxazol-4-yl)pyrrolo[3,2-b]pyridin-3-yl]phenyl]-3-methyl-urea | 494.1 |
| P-0562 | 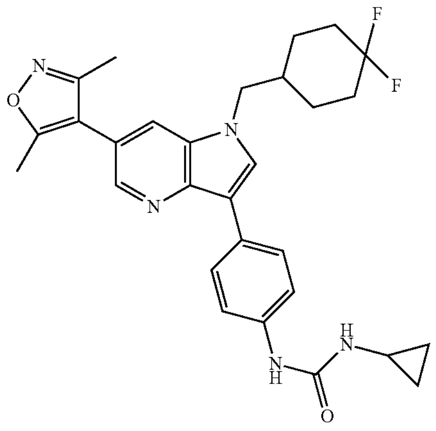 [SMILES: Cc1noc(C)c1-c1cnc2c(-c3ccc(NC(=O)NC4CC4)cc3)cn(CC3CCC(F)(F)CC3)c2c1] | 1-cyclopropyl-3-[4-[1-[(4,4-difluorocyclohexyl)methyl]-6-(3,5-dimethylisoxazol-4-yl)pyrrolo[3,2-b]pyridin-3-yl]phenyl]urea | 520.1 |

TABLE 29-continued
| Compound No. | Structure | Name | MS(ESI) [M + H+]+ or [M − H+]− observed |
|---|---|---|---|
| P-0563 | 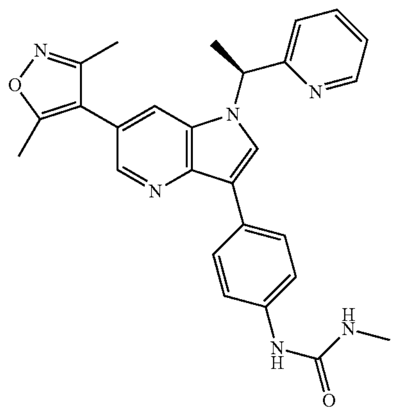 [SMILES: CNC(=O)Nc1ccc(-c2cn([C@@H](C)c3ccccn3)c3cc(-c4c(C)noc4C)cnc23)cc1] | 1-[4-[6-(3,5-dimethylisoxazol-4-yl)-1-[(1S)-1-(2-pyridyl)ethyl]pyrrolo[3,2-b]pyridin-3-yl]phenyl]-3-methyl-urea | 467.0 |
| P-0564 | 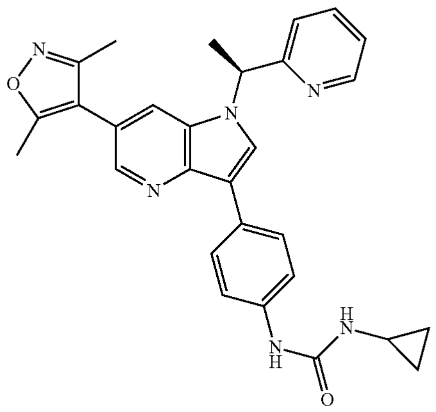 [SMILES: Cc1noc(C)c1-c1cnc2c(-c3ccc(NC(=O)NC4CC4)cc3)cn([C@@H](C)c3ccccn3)c2c1] | 1-cyclopropyl-3-[4-[6-(3,5-dimethylisoxazol-4-yl)-1-[(1S)-1-(2-pyridyl)ethyl]pyrrolo[3,2-b]pyridin-3-yl]phenyl]urea | 493.0 |
| P-0565 | 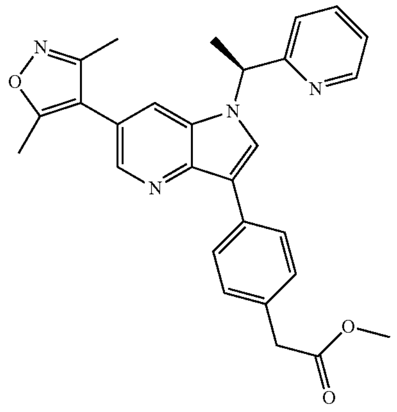 [SMILES: COC(=O)Cc1ccc(-c2cn([C@@H](C)c3ccccn3)c3cc(-c4c(C)noc4C)cnc23)cc1] | methyl 2-[4-[6-(3,5-dimethylisoxazol-4-yl)-1-[(1S)-1-(2-pyridyl)ethyl]pyrrolo[3,2-b]pyridin-3-yl]phenyl]acetate | 467.0 |

TABLE 29-continued
| Compound No. | Structure | Name | MS(ESI) [M + H+]+ or [M − H+]− observed |
|---|---|---|---|
| P-0566 | 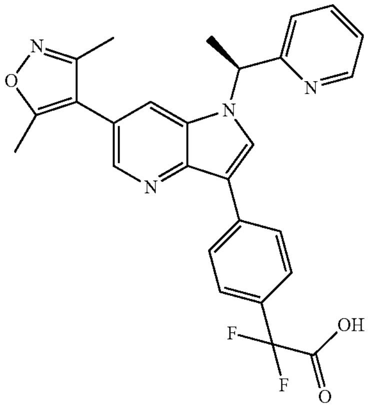 [SMILES: Cc1noc(C)c1-c1cnc2c(-c3ccc(C(F)(F)C(=O)O)cc3)cn([C@@H](C)c3ccccn3)c2c1] | 2,2-difluoro-2-(4-(6-(3,5-dimethylisoxazol-4-yl)-1-((S)-1-(pyridin-2-yl)ethyl)-1H-pyrrolo[3,2-b]pyridin-3-yl)phenyl)acetic acid | 488.9 |
| P-0567 | 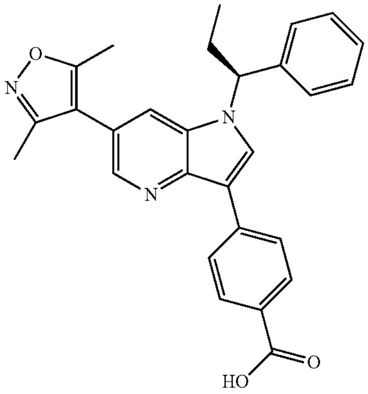 [SMILES: CC[C@@H](c1ccccc1)n1cc(-c2ccc(C(=O)O)cc2)c2ncc(-c3c(C)noc3C)cc21] | 4-[6-(3,5-dimethylisoxazol-4-yl)-1-[(1S)-1-phenylpropyl]pyrrolo[3,2-b]pyridin-3-yl]benzoic acid | 451.9 |
| P-0568 | 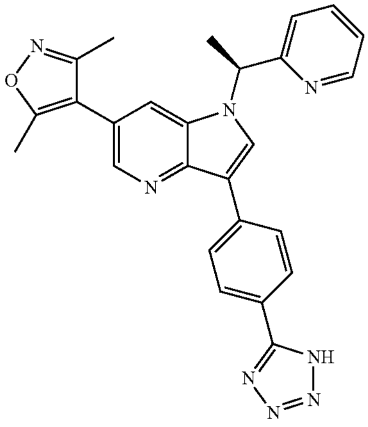 [SMILES: Cc1noc(C)c1-c1cnc2c(-c3ccc(-c4nnn[nH]4)cc3)cn([C@@H](C)c3ccccn3)c2c1] | 3,5-dimethyl-4-[1-[(1S)-1-(2-pyridyl)ethyl]-3-[4-(1H-tetrazol-5-yl)phenyl]pyrrolo[3,2-b]pyridin-6-yl]isoxazole | 463.0 |

TABLE 29-continued

| Compound No. | Structure | Name | MS(ESI) [M + H+]+ or [M − H+]− observed |
|---|---|---|---|
| P-0569 | 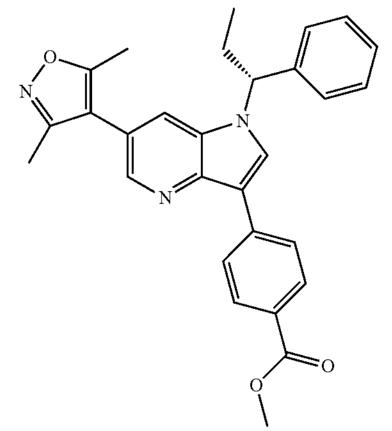 [SMILES: CC[C@H](c1ccccc1)n1cc(-c2ccc(C(=O)OC)cc2)c2ncc(-c3c(C)noc3C)cc21] | methyl 4-[6-(3,5-dimethylisoxazol-4-yl)-1-[(1R)-1-phenylpropyl]pyrrolo[3,2-b]pyridin-3-yl]benzoate | 466.0 |
| P-0570 | 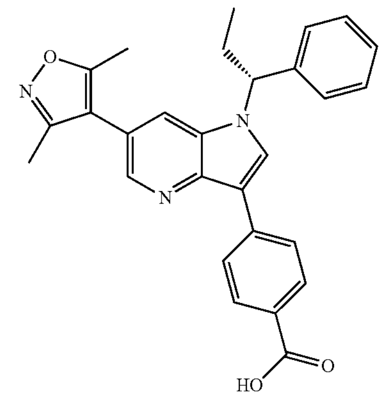 [SMILES: CC[C@H](c1ccccc1)n1cc(-c2ccc(C(=O)O)cc2)c2ncc(-c3c(C)noc3C)cc21] | 4-[6-(3,5-dimethylisoxazol-4-yl)-1-[(1R)-1-phenylpropyl]pyrrolo[3,2-b]pyridin-3-yl]benzoic acid | 451.9 |
| P-0571 | 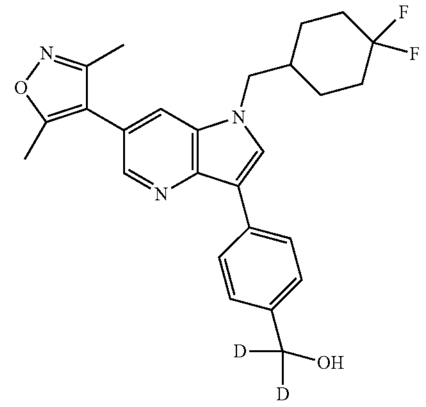 [SMILES: [2H]C([2H])(O)c1ccc(-c2cn(CC3CCC(F)(F)CC3)c3cc(-c4c(C)noc4C)cnc23)cc1] | dideuterio-[4-[1-[(4,4-difluorocyclohexyl)methyl]-6-(3,5-dimethylisoxazol-4-yl)pyrrolo[3,2-b]pyridin-3-yl]phenyl]methanol | 454.5 |
| P-0572 | 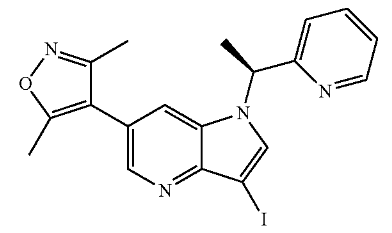 [SMILES: Cc1noc(C)c1-c1cnc2c(I)cn([C@@H](C)c3ccccn3)c2c1] | 4-[3-iodo-1-[(1S)-1-(2-pyridyl)ethyl]pyrrolo[3,2-b]pyridin-6-yl]-3,5-dimethyl-isoxazole | 445.0 |

TABLE 29-continued

| Compound No. | Structure | Name | MS(ESI) [M + H+]+ or [M − H+]− observed |
|---|---|---|---|
| P-0573 | 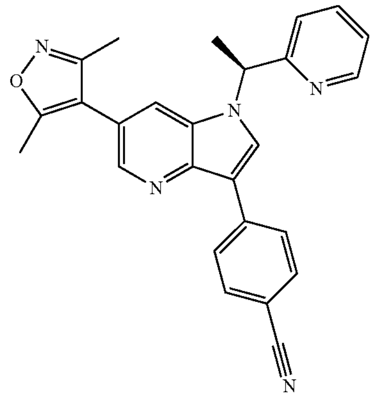 [SMILES: Cc1noc(C)c1-c1cnc2c(-c3ccc(C#N)cc3)cn([C@@H](C)c3ccccn3)c2c1] | 4-[6-(3,5-dimethylisoxazol-4-yl)-1-[(1S)-1-(2-pyridyl)ethyl]pyrrolo[3,2-b]pyridin-3-yl]benzonitrile | 419.9 |
| P-0574 | 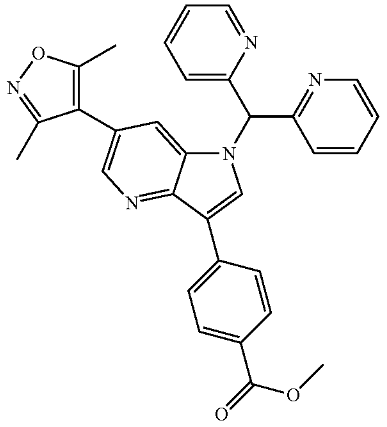 [SMILES: COC(=O)c1ccc(-c2cn(C(c3ccccn3)c3ccccn3)c3cc(-c4c(C)noc4C)cnc23)cc1] | methyl 4-[1-[bis(2-pyridyl)methyl]-6-(3,5-dimethylisoxazol-4-yl)pyrrolo[3,2-b]pyridin-3-yl]benzoate | 516.0 |
| P-0575 | 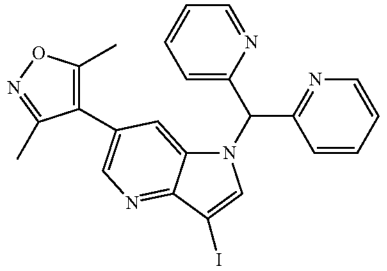 [SMILES: Cc1noc(C)c1-c1cnc2c(I)cn(C(c3ccccn3)c3ccccn3)c2c1] | 4-[1-[bis(2-pyridyl)methyl]-3-iodo-pyrrolo[3,2-b]pyridin-6-yl]-3,5-dimethyl-isoxazole | 508.2 |
| P-0576 | 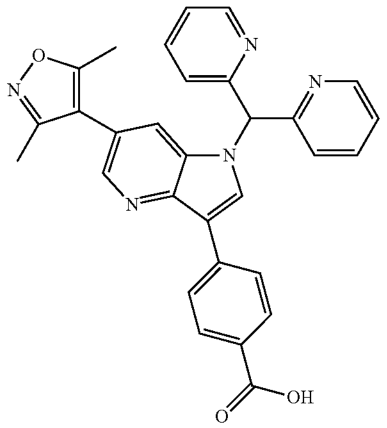 [SMILES: Cc1noc(C)c1-c1cnc2c(-c3ccc(C(=O)O)cc3)cn(C(c3ccccn3)c3ccccn3)c2c1] | 4-[1-[bis(2-pyridyl)methyl]-6-(3,5-dimethylisoxazol-4-yl)pyrrolo[3,2-b]pyridin-3-yl]benzoic acid | 502.4 |

TABLE 29-continued

| Compound No. | Structure | Name | MS(ESI) [M + H+]+ or [M − H+]− observed |
|---|---|---|---|
| P-0577 | 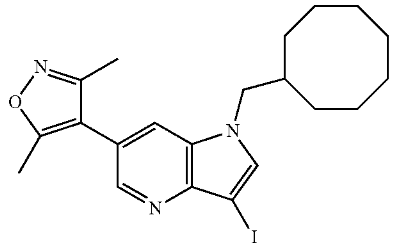 [SMILES: Cc1noc(C)c1-c1cnc2c(I)cn(CC3CCCCCCC3)c2c1] | 4-[1-(cyclooctylmethyl)-3-iodo-pyrrolo[3,2-b]pyridin-6-yl]-3,5-dimethyl-isoxazole | 463.9 |
| P-0578 | 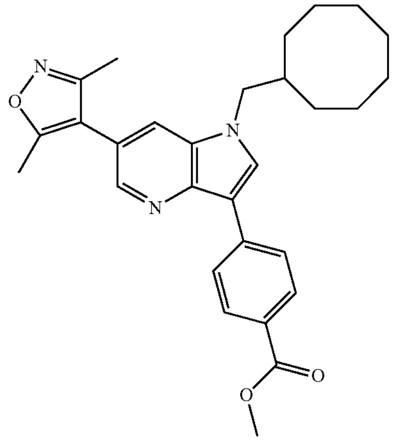 [SMILES: COC(=O)c1ccc(-c2cn(CC3CCCCCCC3)c3cc(-c4c(C)noc4C)cnc23)cc1] | methyl 4-[1-(cyclooctylmethyl)-6-(3,5-dimethylisoxazol-4-yl)pyrrolo[3,2-b]pyridin-3-yl]benzoate | 472.0 |
| P-0579 | 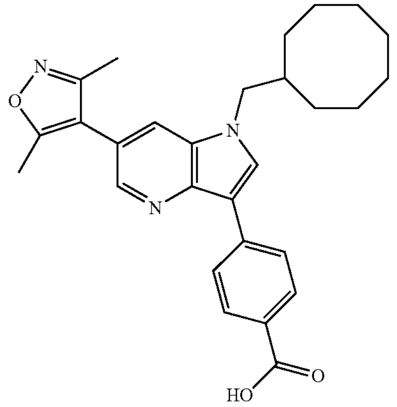 [SMILES: Cc1noc(C)c1-c1cnc2c(-c3ccc(C(=O)O)cc3)cn(CC3CCCCCCC3)c2c1] | 4-[1-(cyclooctylmethyl)-6-(3,5-dimethylisoxazol-4-yl)pyrrolo[3,2-b]pyridin-3-yl]benzoic acid | 458.0 |
| P-0580 | 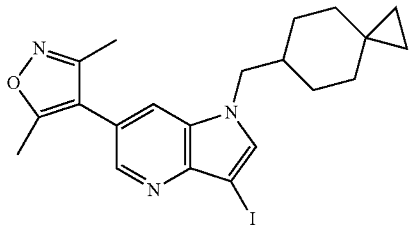 [SMILES: Cc1noc(C)c1-c1cnc2c(I)cn(CC3CCC4(CC3)CC4)c2c1] | 4-[3-iodo-1-(spiro[2.5]octan-6-ylmethyl)pyrrolo[3,2-b]pyridin-6-yl]-3,5-dimethyl-isoxazole | 461.9 |

TABLE 29-continued
| Compound No. | Structure | Name | MS(ESI) [M + H+]+ or [M − H+]− observed |
|---|---|---|---|
| P-0581 | 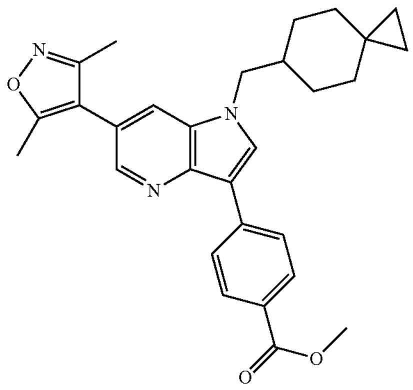 [SMILES: COC(=O)c1ccc(-c2cn(CC3CCC4(CC3)CC4)c3cc(-c4c(C)noc4C)cnc23)cc1] | methyl 4-[6-(3,5-dimethylisoxazol-4-yl)-1-(spiro[2.5]octan-6-ylmethyl)pyrrolo[3,2-b]pyridin-3-yl]benzoate | 470.0 |
| P-0582 | 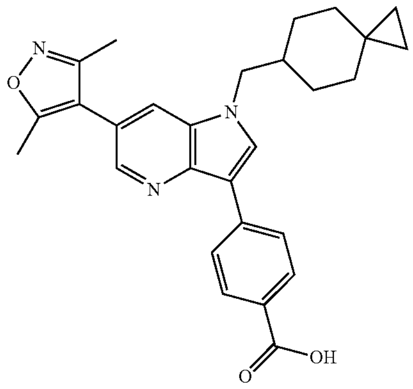 [SMILES: Cc1noc(C)c1-c1cnc2c(-c3ccc(C(=O)O)cc3)cn(CC3CCC4(CC3)CC4)c2c1] | 4-[6-(3,5-dimethylisoxazol-4-yl)-1-(spiro[2.5]octan-6-ylmethyl)pyrrolo[3,2-b]pyridin-3-yl]benzoic acid | 455.9 |
| P-0583 | 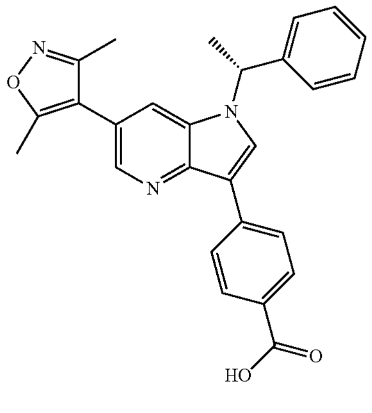 [SMILES: Cc1noc(C)c1-c1cnc2c(-c3ccc(C(=O)O)cc3)cn([C@H](C)c3ccccc3)c2c1] | 4-[6-(3,5-dimethylisoxazol-4-yl)-1-[(1R)-1-phenylethyl]pyrrolo[3,2-b]pyridin-3-yl]benzoic acid | 437.9 |

TABLE 29-continued
| Compound No. | Structure | Name | MS(ESI) [M + H+]+ or [M − H+]− observed |
|---|---|---|---|
| P-0584 | 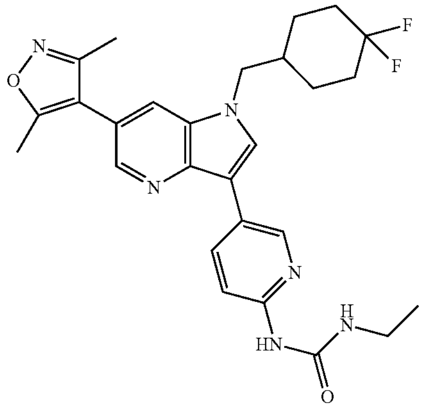 [SMILES: CCNC(=O)Nc1ccc(-c2cn(CC3CCC(F)(F)CC3)c3cc(-c4c(C)noc4C)cnc23)cn1] | 1-[5-[1-[(4,4-difluorocyclohexyl)methyl]-6-(3,5-dimethylisoxazol-4-yl)pyrrolo[3,2-b]pyridin-3-yl]-2-pyridyl]-3-ethyl-urea | 509.5 |
| P-0585 | 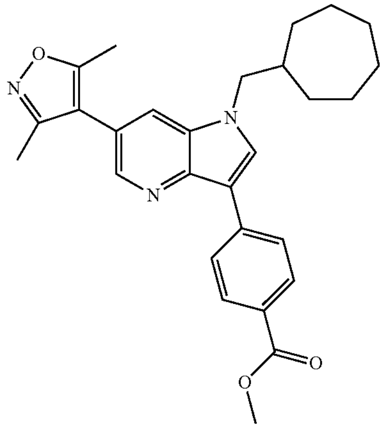 [SMILES: COC(=O)c1ccc(-c2cn(CC3CCCCCC3)c3cc(-c4c(C)noc4C)cnc23)cc1] | methyl 4-[1-(cycloheptylmethyl)-6-(3,5-dimethylisoxazol-4-yl)pyrrolo[3,2-b]pyridin-3-yl]benzoate | 458.0 |
| P-0586 | 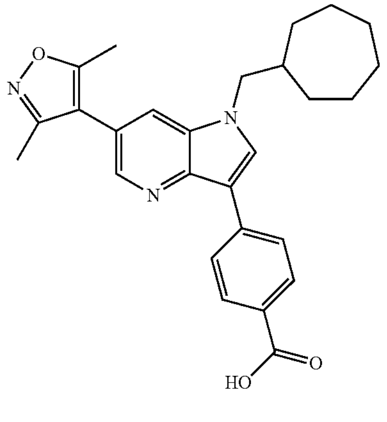 [SMILES: Cc1noc(C)c1-c1cnc2c(-c3ccc(C(=O)O)cc3)cn(CC3CCCCCC3)c2c1] | 4-[1-(cycloheptylmethyl)-6-(3,5-dimethylisoxazol-4-yl)pyrrolo[3,2-b]pyridin-3-yl]benzoic acid | 444.0 |

TABLE 29-continued
| Compound No. | Structure | Name | MS(ESI) [M + H+]+ or [M − H+]− observed |
|---|---|---|---|
| P-0587 | 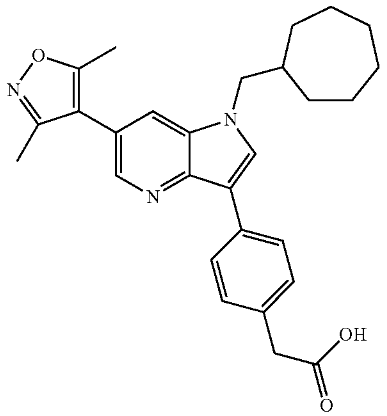 [SMILES: Cc1noc(C)c1-c1cnc2c(-c3ccc(CC(=O)O)cc3)cn(CC3CCCCCC3)c2c1] | 2-[4-[1-(cycloheptylmethyl)-6-(3,5-dimethylisoxazol-4-yl)pyrrolo[3,2-b]pyridin-3-yl]phenyl]acetic acid | 458.0 |
| P-0588 | 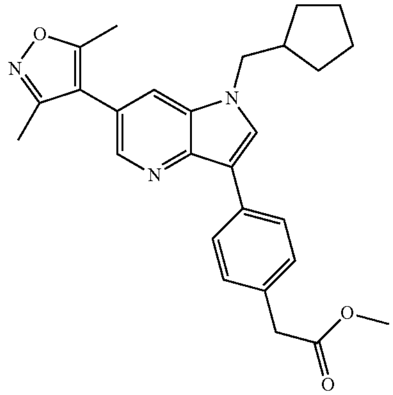 [SMILES: COC(=O)Cc1ccc(-c2cn(CC3CCCC3)c3cc(-c4c(C)noc4C)cnc23)cc1] | methyl 2-[4-[1-(cyclopentylmethyl)-6-(3,5-dimethylisoxazol-4-yl)pyrrolo[3,2-b]pyridin-3-yl]phenyl]acetate | 444.2 |
| P-0589 | 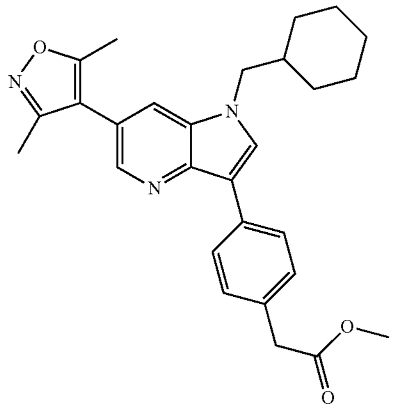 [SMILES: COC(=O)Cc1ccc(-c2cn(CC3CCCCC3)c3cc(-c4c(C)noc4C)cnc23)cc1] | methyl 2-[4-[1-(cyclohexylmethyl)-6-(3,5-dimethylisoxazol-4-yl)pyrrolo[3,2-b]pyridin-3-yl]phenyl]acetate | 458.5 |

TABLE 29-continued
| Compound No. | Structure | Name | MS(ESI) [M + H+]+ or [M − H+]− observed |
|---|---|---|---|
| P-0590 | 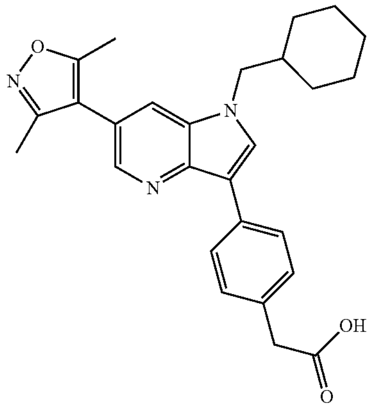 [SMILES: Cc1noc(C)c1-c1cnc2c(-c3ccc(CC(=O)O)cc3)cn(CC3CCCCC3)c2c1] | 2-[4-[1-(cyclohexylmethyl)-6-(3,5-dimethylisoxazol-4-yl)pyrrolo[3,2-b]pyridin-3-yl]phenyl]acetic acid | 444.0 |
| P-0591 | 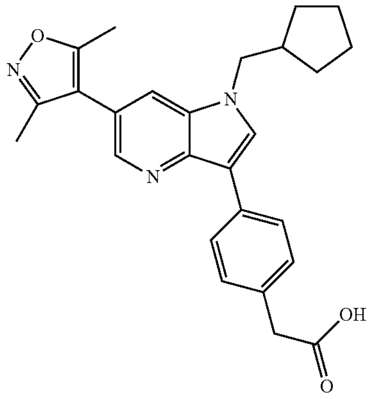 [SMILES: Cc1noc(C)c1-c1cnc2c(-c3ccc(CC(=O)O)cc3)cn(CC3CCCC3)c2c1] | 2-[4-[1-(cyclopentylmethyl)-6-(3,5-dimethylisoxazol-4-yl)pyrrolo[3,2-b]pyridin-3-yl]phenyl]acetic acid | 429.2 |
| P-0592 | 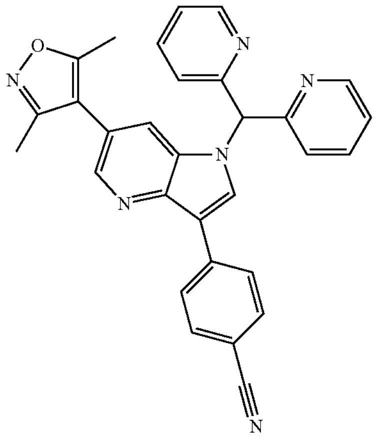 [SMILES: Cc1noc(C)c1-c1cnc2c(-c3ccc(C#N)cc3)cn(C(c3ccccn3)c3ccccn3)c2c1] | 4-[1-[bis(2-pyridyl)methyl]-6-(3,5-dimethylisoxazol-4-yl)pyrrolo[3,2-b]pyridin-3-yl]benzonitrile | 482.9 |

TABLE 29-continued

| Compound No. | Structure | Name | MS(ESI) [M + H+]+ or [M − H+]− observed |
|---|---|---|---|
| P-0593 | 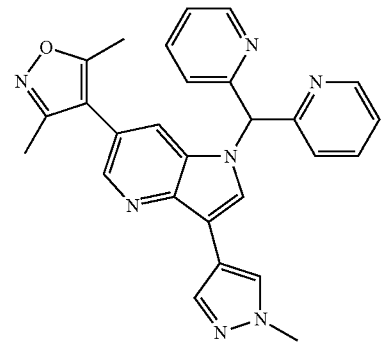 [SMILES: Cc1noc(C)c1-c1cnc2c(-c3cnn(C)c3)cn(C(c3ccccn3)c3ccccn3)c2c1] | 4-[1-[bis(2-pyridyl)methyl]-3-(1-methylpyrazol-4-yl)pyrrolo[3,2-b]pyridin-6-yl]-3,5-dimethyl-isoxazole | 462.0 |
| P-0594 | 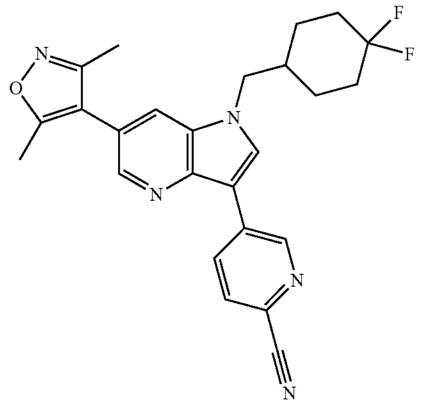 [SMILES: Cc1noc(C)c1-c1cnc2c(-c3ccc(C#N)nc3)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]pyridine-2-carbonitrile | 448.4 |
| P-0595 | 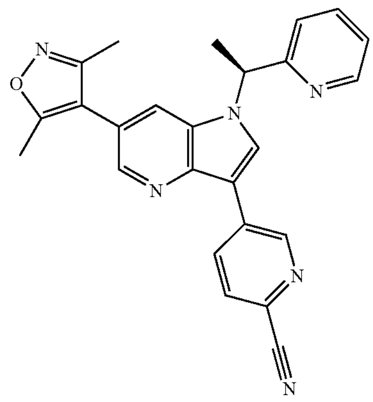 [SMILES: Cc1noc(C)c1-c1cnc2c(-c3ccc(C#N)nc3)cn([C@@H](C)c3ccccn3)c2c1] | 5-[6-(3,5-dimethylisoxazol-4-yl)-1-[(1S)-1-(2-pyridyl)ethyl]pyrrolo[3,2-b]pyridin-3-yl]pyridine-2-carbonitrile | 420.9 |
| P-0596 | 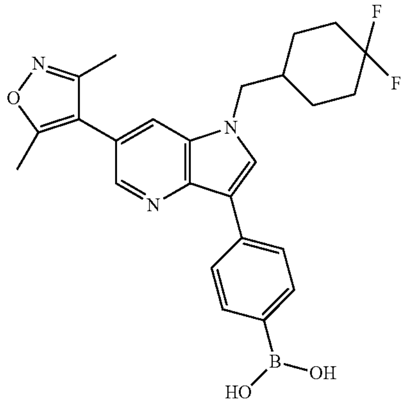 [SMILES: Cc1noc(C)c1-c1cnc2c(-c3ccc(B(O)O)cc3)cn(CC3CCC(F)(F)CC3)c2c1] | [4-[1-[(4,4-difluorocyclohexyl)methyl]-6-(3,5-dimethylisoxazol-4-yl)pyrrolo[3,2-b]pyridin-3-yl]phenyl]boronic acid | 465.8 |

TABLE 29-continued
| Compound No. | Structure | Name | MS(ESI) [M + H+]+ or [M − H+]− observed |
|---|---|---|---|
| P-0597 | 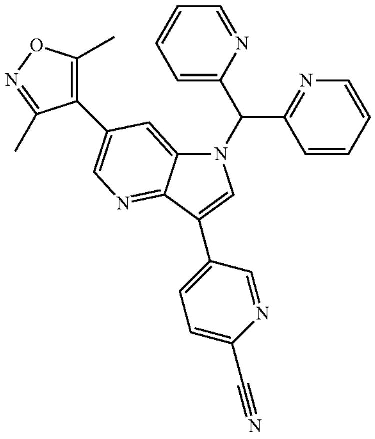 [SMILES: Cc1noc(C)c1-c1cnc2c(-c3ccc(C#N)nc3)cn(C(c3ccccn3)c3ccccn3)c2c1] | 5-[1-[bis(2-pyridyl)methyl]-6-(3,5-dimethylisoxazol-4-yl)pyrrolo[3,2-b]pyridin-3-yl]pyridine-2-carbonitrile | 484.0 |
| P-0598 | 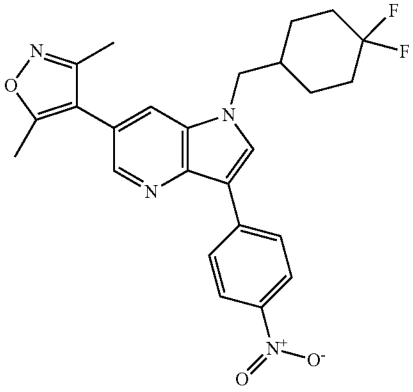 [SMILES: Cc1noc(C)c1-c1cnc2c(-c3ccc([N+](=O)[O-])cc3)cn(CC3CCC(F)(F)CC3)c2c1] | 4-[1-[(4,4-difluorocyclohexyl)methyl]-3-(4-nitrophenyl)pyrrolo[3,2-b]pyridin-6-yl]-3,5-dimethyl-isoxazole | 466.9 |
| P-0599 | 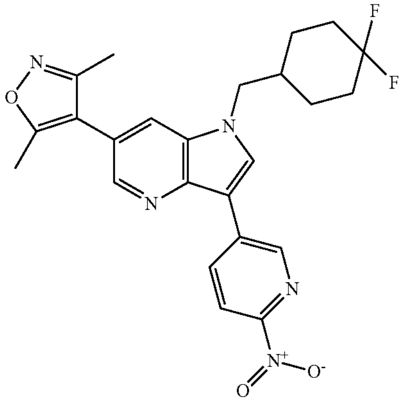 [SMILES: Cc1noc(C)c1-c1cnc2c(-c3ccc([N+](=O)[O-])nc3)cn(CC3CCC(F)(F)CC3)c2c1] | 4-[1-[(4,4-difluorocyclohexyl)methyl]-3-(6-nitro-3-pyridyl)pyrrolo[3,2-b]pyridin-6-yl]-3,5-dimethyl-isoxazole | 467.9 |

TABLE 29-continued

| Compound No. | Structure | Name | MS(ESI) [M + H+]+ or [M − H+]− observed |
|---|---|---|---|
| P-0600 | 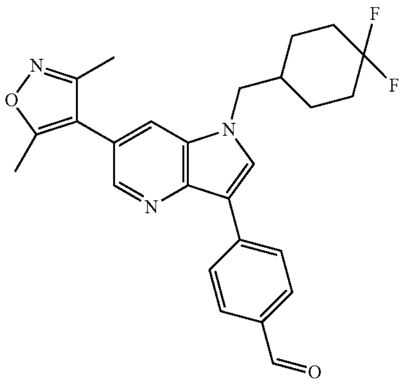 [SMILES: Cc1noc(C)c1-c1cnc2c(-c3ccc(C=O)cc3)cn(CC3CCC(F)(F)CC3)c2c1] | 4-[1-[(4,4-difluorocyclohexyl)methyl]-6-(3,5-dimethylisoxazol-4-yl)pyrrolo[3,2-b]pyridin-3-yl]benzaldehyde | 449.9 |
| P-0601 | 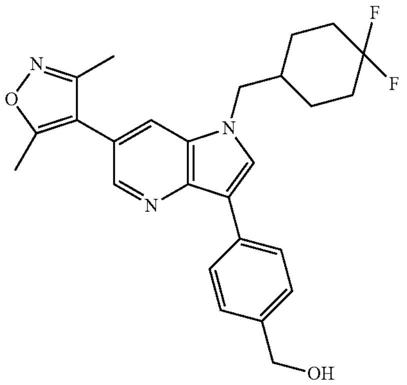 [SMILES: Cc1noc(C)c1-c1cnc2c(-c3ccc(CO)cc3)cn(CC3CCC(F)(F)CC3)c2c1] | [4-[1-[(4,4-difluorocyclohexyl)methyl]-6-(3,5-dimethylisoxazol-4-yl)pyrrolo[3,2-b]pyridin-3-yl]phenyl]methanol | 452.3 |
| P-0602 | 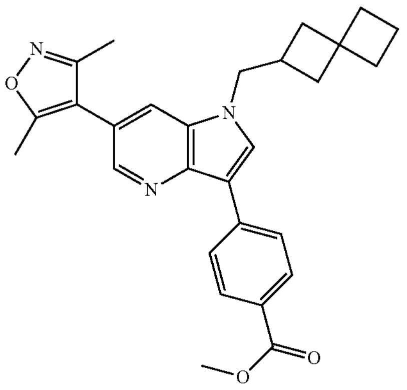 [SMILES: COC(=O)c1ccc(-c2cn(CC3CC4(CCC4)C3)c3cc(-c4c(C)noc4C)cnc23)cc1] | methyl 4-[6-(3,5-dimethylisoxazol-4-yl)-1-(spiro[3.3]heptan-6-ylmethyl)pyrrolo[3,2-b]pyridin-3-yl]benzoate | 456.3 |
| P-0603 | 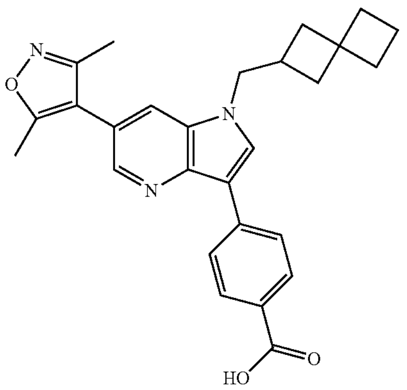 [SMILES: Cc1noc(C)c1-c1cnc2c(-c3ccc(C(=O)O)cc3)cn(CC3CC4(CCC4)C3)c2c1] | 4-[6-(3,5-dimethylisoxazol-4-yl)-1-(spiro[3.3]heptan-6-ylmethyl)pyrrolo[3,2-b]pyridin-3-yl]benzoic acid | 441.9 |

TABLE 29-continued

| Compound No. | Structure | Name | MS(ESI) [M + H+]+ or [M − H+]− observed |
|---|---|---|---|
| P-0604 | 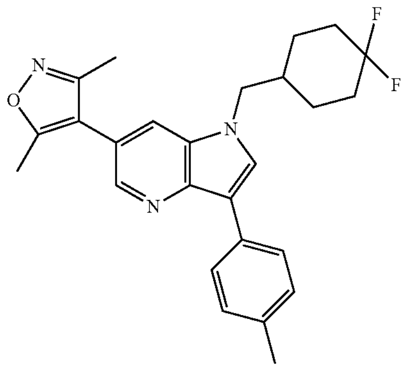 [SMILES: Cc1ccc(-c2cn(CC3CCC(F)(F)CC3)c3cc(-c4c(C)noc4C)cnc23)cc1] | 4-[1-[(4,4-difluorocyclohexyl)methyl]-3-(p-tolyl)pyrrolo[3,2-b]pyridin-6-yl]-3,5-dimethyl-isoxazole | 436.0 |
| P-0605 | 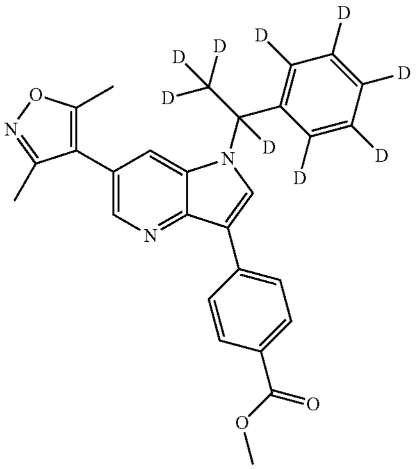 [SMILES: [2H]c1c([2H])c([2H])c(C([2H])(n2cc(-c3ccc(C(=O)OC)cc3)c3ncc(-c4c(C)noc4C)cc32)C([2H])([2H])[2H])c([2H])c1[2H]] | methyl 4-[6-(3,5-dimethylisoxazol-4-yl)-1-[1,2,2,2-tetradeuterio-1-(2,3,4,5,6-pentadeuteriophenyl)ethyl]pyrrolo[3,2-b]pyridin-3-yl]benzoate | 460.9 |
| P-0606 | 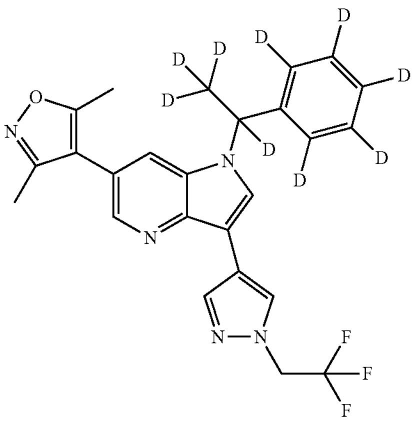 [SMILES: [2H]c1c([2H])c([2H])c(C([2H])(n2cc(-c3cnn(CC(F)(F)F)c3)c3ncc(-c4c(C)noc4C)cc32)C([2H])([2H])[2H])c([2H])c1[2H]] | 3,5-dimethyl-4-[1-[1,2,2,2-tetradeuterio-1-(2,3,4,5,6-pentadeuteriophenyl)ethyl]-3-[1-(2,2,2-trifluoroethyl)pyrazol-4-yl]pyrrolo[3,2-b]pyridin-6-yl]isoxazole | 474.9 |

TABLE 29-continued
| Compound No. | Structure | Name | MS(ESI) [M + H+]+ or [M − H+]− observed |
|---|---|---|---|
| P-0607 | 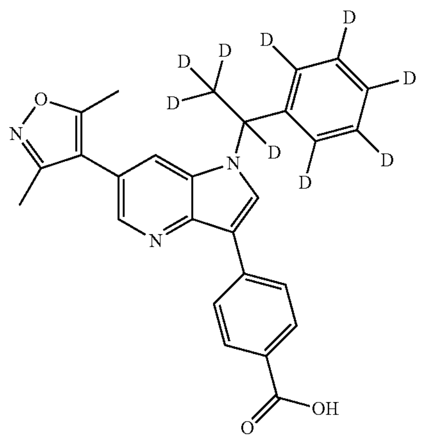 [SMILES: [2H]c1c([2H])c([2H])c(C([2H])(n2cc(-c3ccc(C(=O)O)cc3)c3ncc(-c4c(C)noc4C)cc32)C([2H])([2H])[2H])c([2H])c1[2H]] | 4-[6-(3,5-dimethylisoxazol-4-yl)-1-[1,2,2,2-tetradeuterio-1-(2,3,4,5,6-pentadeuteriophenyl)ethyl]pyrrolo[3,2-b]pyridin-3-yl]benzoic acid | 446.8 |
| P-0608 | 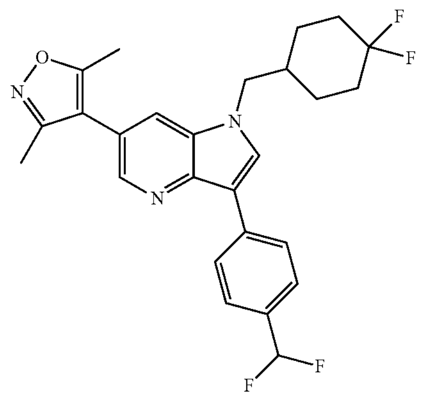 [SMILES: Cc1noc(C)c1-c1cnc2c(-c3ccc(C(F)F)cc3)cn(CC3CCC(F)(F)CC3)c2c1] | 4-[1-[(4,4-difluorocyclohexyl)methyl]-3-[4-(difluoromethyl)phenyl]pyrrolo[3,2-b]pyridin-6-yl]-3,5-dimethyl-isoxazole | 472.0 |
| P-0609 | 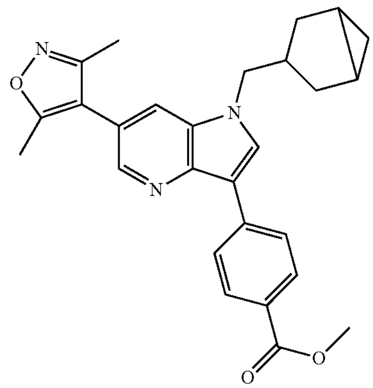 [SMILES: COC(=O)c1ccc(-c2cn(CC3CC4CC4C3)c3cc(-c4c(C)noc4C)cnc23)cc1] | methyl 4-[1-(3-bicyclo[3.1.0]hexanylmethyl)-6-(3,5-dimethylisoxazol-4-yl)pyrrolo[3,2-b]pyridin-3-yl]benzoate | 442.3 |

TABLE 29-continued
| Compound No. | Structure | Name | MS(ESI) [M + H+]+ or [M − H+]− observed |
|---|---|---|---|
| P-0610 | 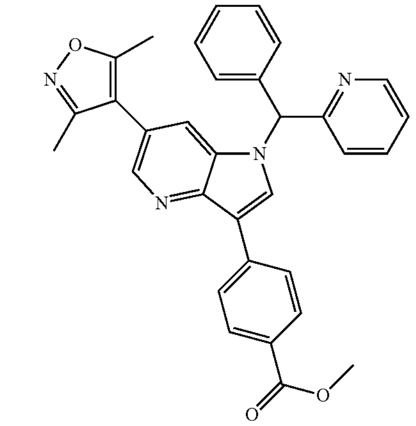 [SMILES: COC(=O)c1ccc(-c2cn(C(c3ccccc3)c3ccccn3)c3cc(-c4c(C)noc4C)cnc23)cc1] | methyl 4-[6-(3,5-dimethylisoxazol-4-yl)-1-[phenyl(2-pyridyl)methyl]pyrrolo[3,2-b]pyridin-3-yl]benzoate | 515.1 |
| P-0611 | 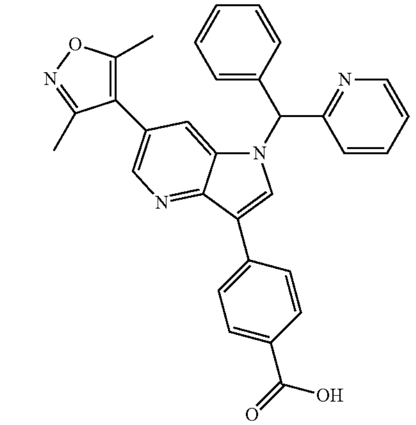 [SMILES: Cc1noc(C)c1-c1cnc2c(-c3ccc(C(=O)O)cc3)cn(C(c3ccccc3)c3ccccn3)c2c1] | 4-[6-(3,5-dimethylisoxazol-4-yl)-1-[phenyl(2-pyridyl)methyl]pyrrolo[3,2-b]pyridin-3-yl]benzoic acid | 501.0 |
| P-0612 | 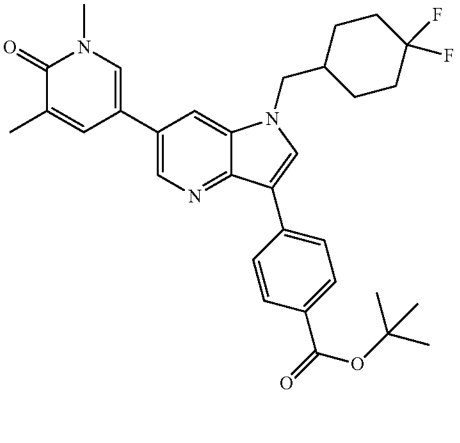 [SMILES: Cc1cc(-c2cnc3c(-c4ccc(C(=O)OC(C)(C)C)cc4)cn(CC4CCC(F)(F)CC4)c3c2)cn(C)c1=O] | tert-butyl 4-[1-[(4,4-difluorocyclohexyl)methyl]-6-(1,5-dimethyl-6-oxo-3-pyridyl)pyrrolo[3,2-b]pyridin-3-yl]benzoate | 548.0 |

TABLE 29-continued

| Compound No. | Structure | Name | MS(ESI) [M + H+]+ or [M − H+]− observed |
|---|---|---|---|
| P-0613 | 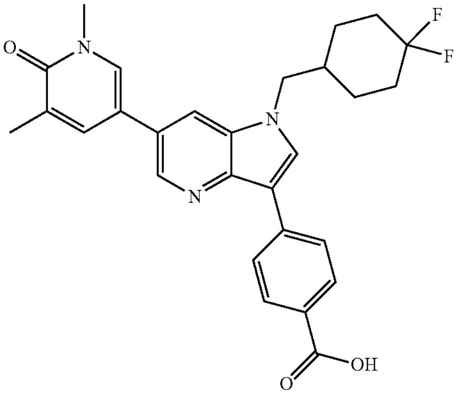 [SMILES: Cc1cc(-c2cnc3c(-c4ccc(C(=O)O)cc4)cn(CC4CCC(F)(F)CC4)c3c2)cn(C)c1=O] | 4-[1-[(4,4-difluorocyclohexyl)methyl]-6-(1,5-dimethyl-6-oxo-3-pyridyl)pyrrolo[3,2-b]pyridin-3-yl]benzoic acid | 492.0 |
| P-0614 | 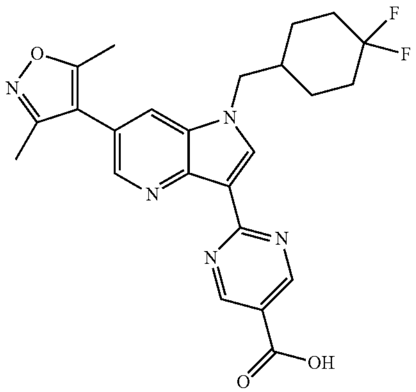 [SMILES: Cc1noc(C)c1-c1cnc2c(-c3ncc(C(=O)O)cn3)cn(CC3CCC(F)(F)CC3)c2c1] | 2-[1-[(4,4-difluorocyclohexyl)methyl]-6-(3,5-dimethylisoxazol-4-yl)pyrrolo[3,2-b]pyridin-3-yl]pyrimidine-5-carboxylic acid | 468.3 |
| P-0615 | 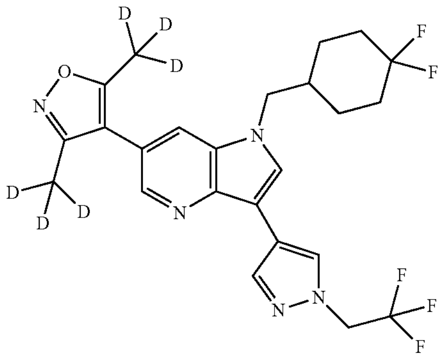 [SMILES: [2H]C([2H])([2H])c1noc(C([2H])([2H])[2H])c1-c1cnc2c(-c3cnn(CC(F)(F)F)c3)cn(CC3CCC(F)(F)CC3)c2c1] | 4-[1-[(4,4-difluorocyclohexyl)methyl]-3-[1-(2,2,2-trifluoroethyl)pyrazol-4-yl]pyrrolo[3,2-b]pyridin-6-yl]-3,5-bis(trideuteriomethyl)isoxazole | 500.3 |
| P-0616 | 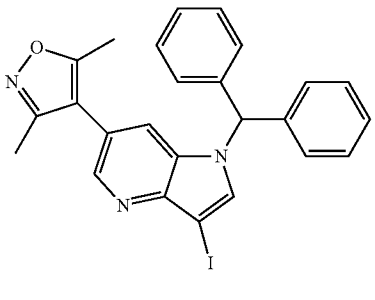 [SMILES: Cc1noc(C)c1-c1cnc2c(I)cn(C(c3ccccc3)c3ccccc3)c2c1] | 4-(1-benzhydryl-3-iodo-pyrrolo[3,2-b]pyridin-6-yl)-3,5-dimethyl-isoxazole | 505.9 |

TABLE 29-continued
| Compound No. | Structure | Name | MS(ESI) [M + H+]+ or [M − H+]− observed |
|---|---|---|---|
| P-0617 | 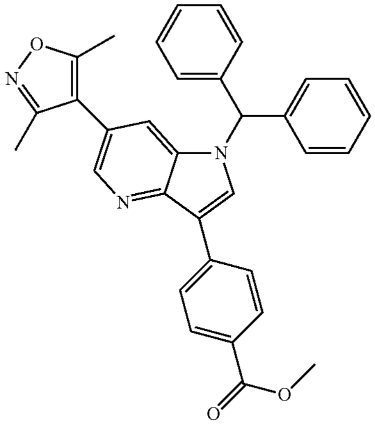 [SMILES: COC(=O)c1ccc(-c2cn(C(c3ccccc3)c3ccccc3)c3cc(-c4c(C)noc4C)cnc23)cc1] | methyl 4-[1-benzhydryl-6-(3,5-dimethylisoxazol-4-yl)pyrrolo[3,2-b]pyridin-3-yl]benzoate | 514.0 |
| P-0618 | 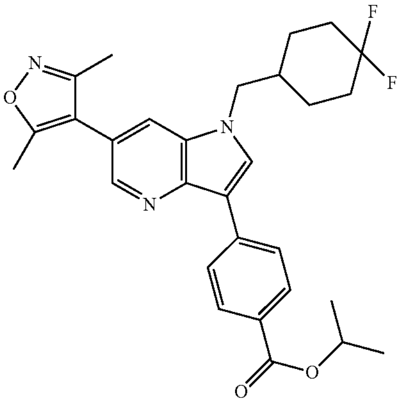 [SMILES: Cc1noc(C)c1-c1cnc2c(-c3ccc(C(=O)OC(C)C)cc3)cn(CC3CCC(F)(F)CC3)c2c1] | isopropyl 4-[1-[(4,4-difluorocyclohexyl)methyl]-6-(3,5-dimethylisoxazol-4-yl)pyrrolo[3,2-b]pyridin-3-yl]benzoate | 508.0 |
| P-0619 | 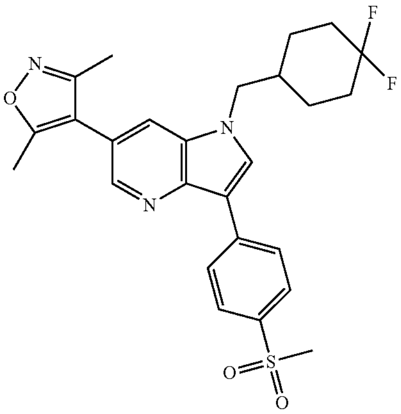 [SMILES: Cc1noc(C)c1-c1cnc2c(-c3ccc(S(C)(=O)=O)cc3)cn(CC3CCC(F)(F)CC3)c2c1] | 4-[1-[(4,4-difluorocyclohexyl)methyl]-3-(4-methylsulfonylphenyl)pyrrolo[3,2-b]pyridin-6-yl]-3,5-dimethyl-isoxazole | 500.2 |

TABLE 29-continued

| Compound No. | Structure | Name | MS(ESI) [M + H+]+ or [M − H+]− observed |
|---|---|---|---|
| P-0620 | 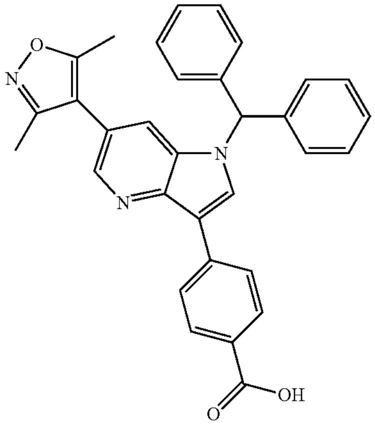 | 4-[1-benzhydryl-6-(3,5-dimethylisoxazol-4-yl)pyrrolo[3,2-b]pyridin-3-yl]benzoic acid | 500.0 |
| P-0621 | 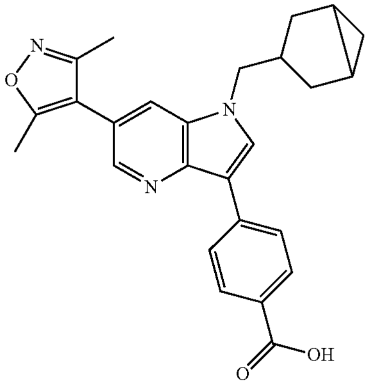 [SMILES: Cc1noc(C)c1-c1cnc2c(-c3ccc(C(=O)O)cc3)cn(CC3CC4CC4C3)c2c1] | 4-[1-(3-bicyclo[3.1.0]hexanylmethyl)-6-(3,5-dimethylisoxazol-4-yl)pyrrolo[3,2-b]pyridin-3-yl]benzoic acid | 428.4 |
| P-0622 | 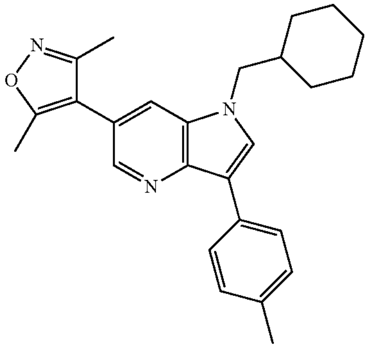 [SMILES: Cc1ccc(-c2cn(CC3CCCCC3)c3cc(-c4c(C)noc4C)cnc23)cc1] | 4-[1-(cyclohexylmethyl)-3-(p-tolyl)pyrrolo[3,2-b]pyridin-6-yl]-3,5-dimethyl-isoxazole | 400.1 |
| P-0398 | 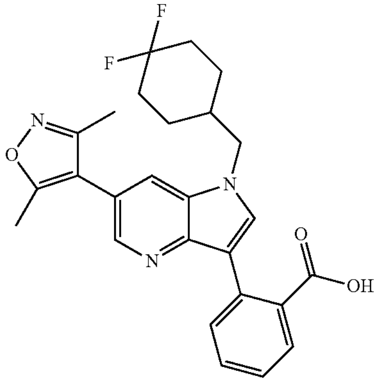 [SMILES: Cc1noc(C)c1-c1cnc2c(-c3ccccc3C(=O)O)cn(CC3CCC(F)(F)CC3)c2c1] | 2-[1-[(4,4-difluorocyclohexyl)methyl]-6-(3,5-dimethylisoxazol-4-yl)pyrrolo[3,2-b]pyridin-3-yl]benzoic acid | 466.3 |

TABLE 29-continued

| Compound No. | Structure | Name | MS(ESI) [M + H+]+ or [M − H+]− observed |
|---|---|---|---|
| P-0501 | 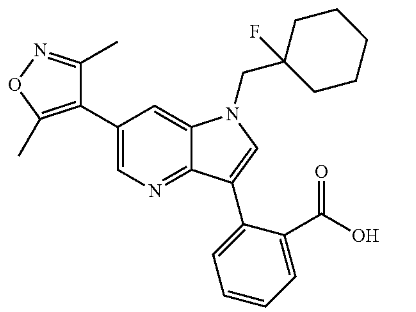 [SMILES: Cc1noc(C)c1-c1cnc2c(-c3ccccc3C(=O)O)cn(CC3(F)CCCCC3)c2c1] | 2-[6-(3,5-dimethylisoxazol-4-yl)-1-[(1-fluorocyclohexyl)methyl]pyrrolo[3,2-b]pyridin-3-yl]benzoic acid | 448.3 |

* MS(ESI) [M − H+]− observed.

Compounds listed in Table 30 below, e.g., compounds P-0700 to P-0822 are prepared according to the protocols set forth in Examples 1 to 56. The $^1$H NMR and mass spectroscopy data are consistent with the structures of the compounds

TABLE 30

| Compound No. | Structure | Name | MS(ESI) [M + H+]+ or [M − H+]− observed |
|---|---|---|---|
| P-0700 | 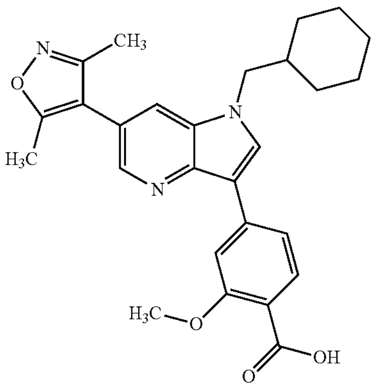 [SMILES: COc1cc(-c2cn(CC3CCCCC3)c3cc(-c4c(C)noc4C)cnc23)ccc1C(=O)O] | 4-[1-(cyclohexylmethyl)-6-(3,5-dimethylisoxazol-4-yl)pyrrolo[3,2-b]pyridin-3-yl]-2-methoxy-benzoic acid | 459.9 |
| P-0701 | 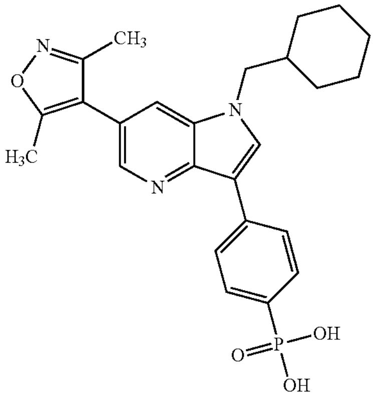 [SMILES: Cc1noc(C)c1-c1cnc2c(-c3ccc(P(=O)(O)O)cc3)cn(CC3CCCCC3)c2c1] | [4-[1-(cyclohexylmethyl)-6-(3,5-dimethylisoxazol-4-yl)pyrrolo[3,2-b]pyridin-3-yl]phenyl]phosphonic acid | |

TABLE 30-continued
| Compound No. | Structure | Name | MS(ESI) [M + H+]+ or [M − H+]− observed |
|---|---|---|---|
| P-0702 | 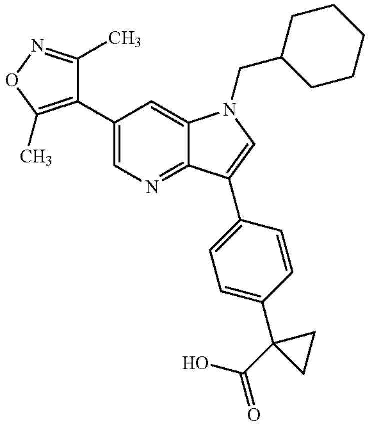 [SMILES: Cc1noc(C)c1-c1cnc2c(-c3ccc(C4(C(=O)O)CC4)cc3)cn(CC3CCCCC3)c2c1] | 1-[4-[1-(cyclohexylmethyl)-6-(3,5-dimethylisoxazol-4-yl)pyrrolo[3,2-b]pyridin-3-yl]phenyl]cyclopropanecarboxylic acid | |
| P-0703 | 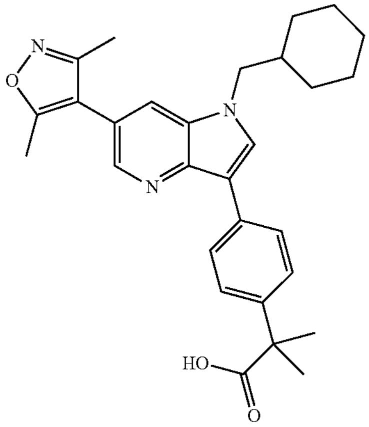 [SMILES: Cc1noc(C)c1-c1cnc2c(-c3ccc(C(C)(C)C(=O)O)cc3)cn(CC3CCCCC3)c2c1] | 2-[4-[1-(cyclohexylmethyl)-6-(3,5-dimethylisoxazol-4-yl)pyrrolo[3,2-b]pyridin-3-yl]phenyl]-2-methyl-propanoic acid | |
| P-0704 | 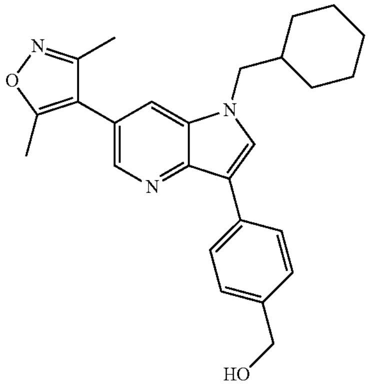 [SMILES: Cc1noc(C)c1-c1cnc2c(-c3ccc(CO)cc3)cn(CC3CCCCC3)c2c1] | [4-[1-(cyclohexylmethyl)-6-(3,5-dimethylisoxazol-4-yl)pyrrolo[3,2-b]pyridin-3-yl]phenyl]methanol | |

TABLE 30-continued
| Compound No. | Structure | Name | MS(ESI) [M + H+]+ or [M − H+]− observed |
|---|---|---|---|
| P-0705 | 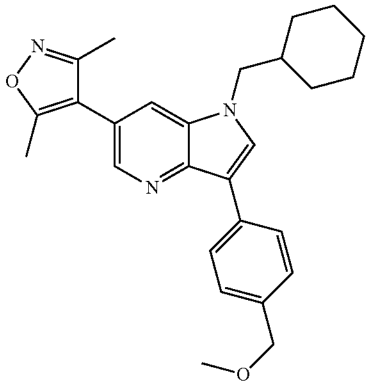 [SMILES: COCc1ccc(-c2cn(CC3CCCCC3)c3cc(-c4c(C)noc4C)cnc23)cc1] | 4-[1-(cyclohexylmethyl)-3-[4-(methoxymethyl)phenyl]pyrrolo[3,2-b]pyridin-6-yl]-3,5-dimethyl-isoxazole | 429.9 |
| P-0706 | 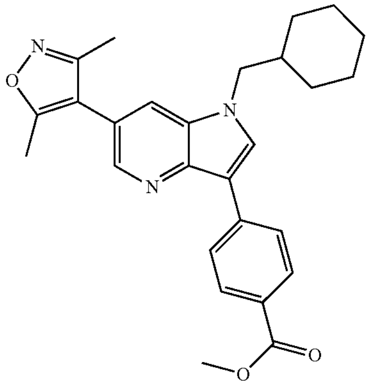 [SMILES: COC(=O)c1ccc(-c2cn(CC3CCCCC3)c3cc(-c4c(C)noc4C)cnc23)cc1] | methyl 4-[1-(cyclohexylmethyl)-6-(3,5-dimethylisoxazol-4-yl)pyrrolo[3,2-b]pyridin-3-yl]benzoate | |
| P-0707 | 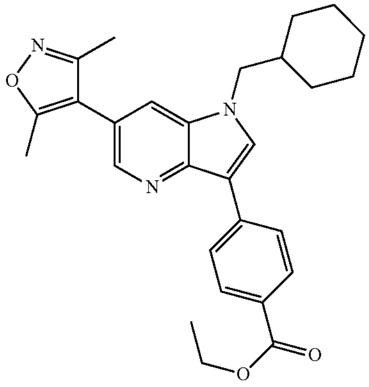 [SMILES: CCOC(=O)c1ccc(-c2cn(CC3CCCCC3)c3cc(-c4c(C)noc4C)cnc23)cc1] | ethyl 4-[1-(cyclohexylmethyl)-6-(3,5-dimethylisoxazol-4-yl)pyrrolo[3,2-b]pyridin-3-yl]benzoate | |

TABLE 30-continued
| Compound No. | Structure | Name | MS(ESI) [M + H+]+ or [M − H+]− observed |
|---|---|---|---|
| P-0708 | 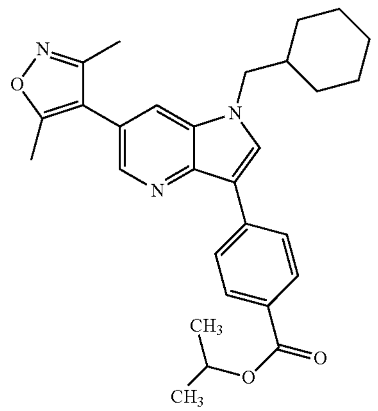 [SMILES: Cc1noc(C)c1-c1cnc2c(-c3ccc(C(=O)OC(C)C)cc3)cn(CC3CCCCC3)c2c1] | isopropyl 4-[1-(cyclohexylmethyl)-6-(3,5-dimethylisoxazol-4-yl)pyrrolo[3,2-b]pyridin-3-yl]benzoate | 472.1 |
| P-0709 | 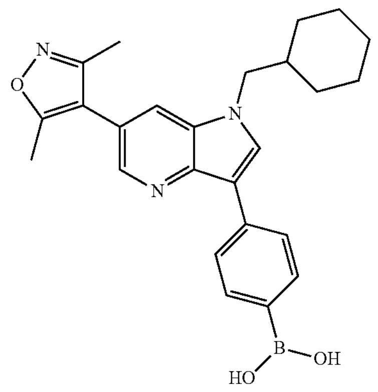 [SMILES: Cc1noc(C)c1-c1cnc2c(-c3ccc(B(O)O)cc3)cn(CC3CCCCC3)c2c1] | [4-[1-(cyclohexylmethyl)-6-(3,5-dimethylisoxazol-4-yl)pyrrolo[3,2-b]pyridin-3-yl]phenyl]boronic acid | |
| P-0710 | 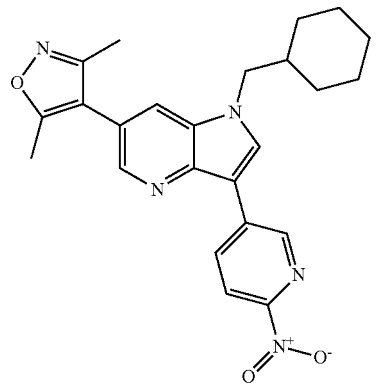 [SMILES: Cc1noc(C)c1-c1cnc2c(-c3ccc([N+](=O)[O-])nc3)cn(CC3CCCCC3)c2c1] | 4-[1-(cyclohexylmethyl)-3-(6-nitro-3-pyridyl)pyrrolo[3,2-b]pyridin-6-yl]-3,5-dimethyl-isoxazole | 432.2 |

TABLE 30-continued

| Compound No. | Structure | Name | MS(ESI) [M + H+]+ or [M − H+]− observed |
|---|---|---|---|
| P-0711 | 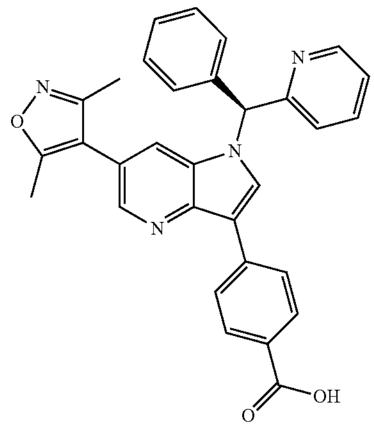 | 4-[6-(3,5-dimethylisoxazol-4-yl)-1-[(S)-phenyl(2-pyridyl)methyl]pyrrolo[3,2-b]pyridin-3-yl]benzoic acid | 501.3 |
| P-0712 | 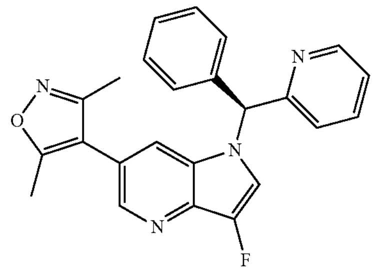 [SMILES: Cc1noc(C)c1-c1cnc2c(F)cn([C@@H](c3ccccc3)c3ccccn3)c2c1] | 4-[3-fluoro-1-[(S)-phenyl(2-pyridyl)methyl]pyrrolo[3,2-b]pyridin-6-yl]-3,5-dimethyl-isoxazole | |
| P-0713 | 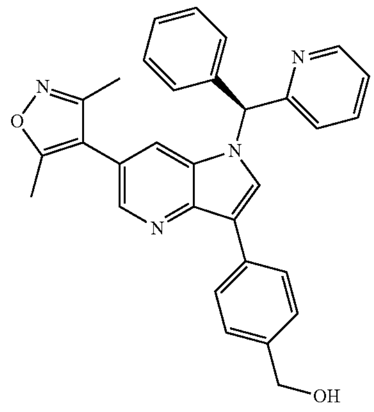 | [4-[6-(3,5-dimethylisoxazol-4-yl)-1-[(S)-phenyl(2-pyridyl)methyl]pyrrolo[3,2-b]pyridin-3-yl]phenyl]methanol | |
| P-0714 | 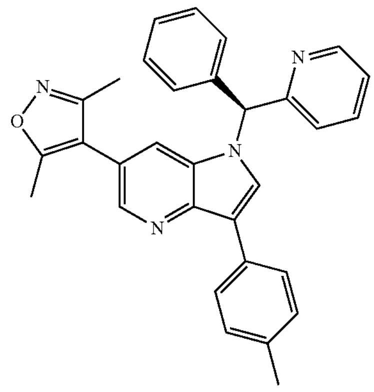 [SMILES: Cc1ccc(-c2cn([C@@H](c3ccccc3)c3ccccn3)c3cc(-c4c(C)noc4C)cnc23)cc1] | 3,5-dimethyl-4-[1-[(S)-phenyl(2-pyridyl)methyl]-3-(p-tolyl)pyrrolo[3,2-b]pyridin-6-yl]isoxazole | |

TABLE 30-continued
| Compound No. | Structure | Name | MS(ESI) [M + H+]+ or [M − H+]− observed |
|---|---|---|---|
| P-0715 | 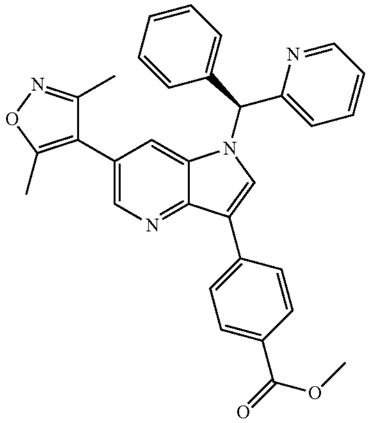 [SMILES: COC(=O)c1ccc(-c2cn([C@@H](c3ccccc3)c3ccccn3)c3cc(-c4c(C)noc4C)cnc23)cc1] | methyl 4-[6-(3,5-dimethylisoxazol-4-yl)-1-[(S)-phenyl(2-pyridyl)methyl]pyrrolo[3,2-b]pyridin-3-yl]benzoate | |
| P-0716 | 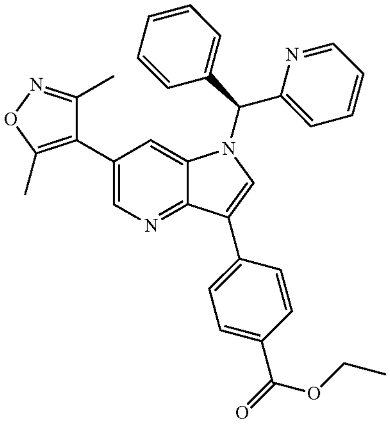 [SMILES: CCOC(=O)c1ccc(-c2cn([C@@H](c3ccccc3)c3ccccn3)c3cc(-c4c(C)noc4C)cnc23)cc1] | ethyl 4-[6-(3,5-dimethylisoxazol-4-yl)-1-[(S)-phenyl(2-pyridyl)methyl]pyrrolo[3,2-b]pyridin-3-yl]benzoate | |
| P-0717 | 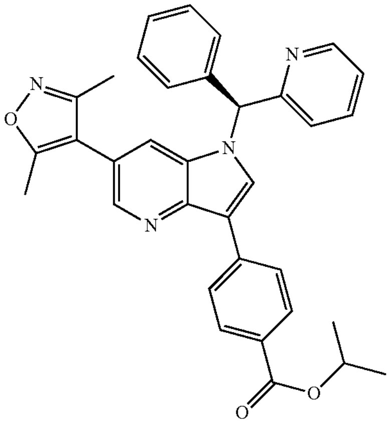 [SMILES: Cc1noc(C)c1-c1cnc2c(-c3ccc(C(=O)OC(C)C)cc3)cn([C@@H](c3ccccc3)c3ccccn3)c2c1] | isopropyl 4-[6-(3,5-dimethylisoxazol-4-yl)-1-[(S)-phenyl(2-pyridyl)methyl]pyrrolo[3,2-b]pyridin-3-yl]benzoate | |

TABLE 30-continued
| Compound No. | Structure | Name | MS(ESI) [M + H+]+ or [M − H+]− observed |
|---|---|---|---|
| P-0718 | 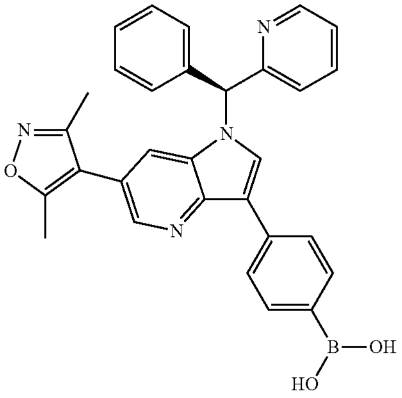 [SMILES: Cc1noc(C)c1-c1cnc2c(-c3ccc(B(O)O)cc3)cn([C@@H](c3ccccc3)c3ccccn3)c2c1] | [4-[6-(3,5-dimethylisoxazol-4-yl)-1-[(S)-phenyl(2-pyridyl)methyl]pyrrolo[3,2-b]pyridin-3-yl]phenyl]boronic acid | |
| P-0719 | 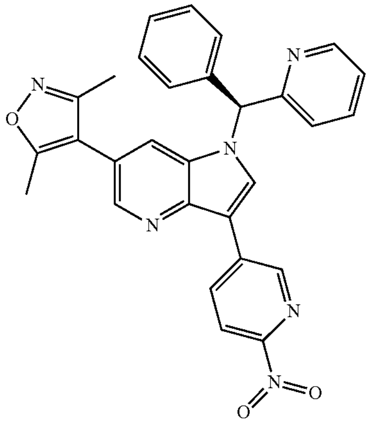 [SMILES: Cc1noc(C)c1-c1cnc2c(-c3ccc([N+](=O)[O-])nc3)cn([C@@H](c3ccccc3)c3ccccn3)c2c1] | 3,5-dimethyl-4-[3-(6-nitro-3-pyridyl)-1-[(S)-phenyl(2-pyridyl)methyl]pyrrolo[3,2-b]pyridin-6-yl]isoxazole | |
| P-0720 | 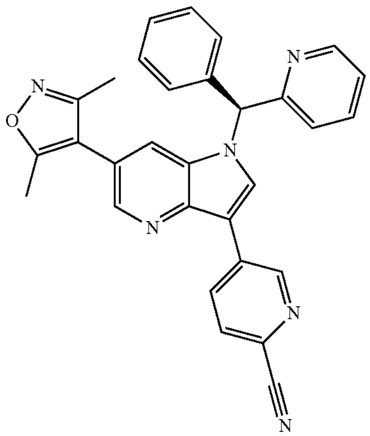 [SMILES: Cc1noc(C)c1-c1cnc2c(-c3ccc(C#N)nc3)cn([C@@H](c3ccccc3)c3ccccn3)c2c1] | 5-[6-(3,5-dimethylisoxazol-4-yl)-1-[(S)-phenyl(2-pyridyl)methyl]pyrrolo[3,2-b]pyridin-3-yl]pyridine-2-carbonitrile | |

TABLE 30-continued

| Compound No. | Structure | Name | MS(ESI) [M + H+]+ or [M − H+]− observed |
|---|---|---|---|
| P-0721 | 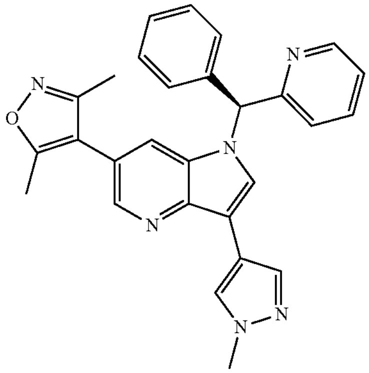 [SMILES: Cc1noc(C)c1-c1cnc2c(-c3cnn(C)c3)cn([C@@H](c3ccccc3)c3ccccn3)c2c1] | 3,5-dimethyl-4-[3-(1-methylpyrazol-4-yl)-1-[(S)-phenyl(2-pyridyl)methyl]pyrrolo[3,2-b]pyridin-6-yl]isoxazole | |
| P-0722 | 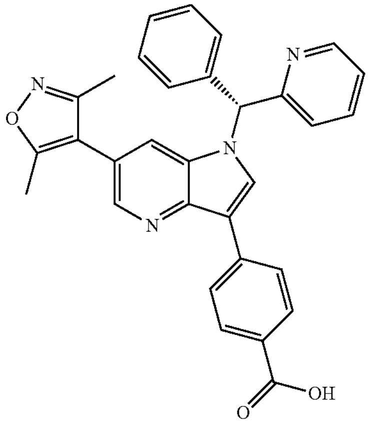 | 4-[6-(3,5-dimethylisoxazol-4-yl)-1-[(R)-phenyl(2-pyridyl)methyl]pyrrolo[3,2-b]pyridin-3-yl]benzoic acid | 501.3 |
| P-0723 | 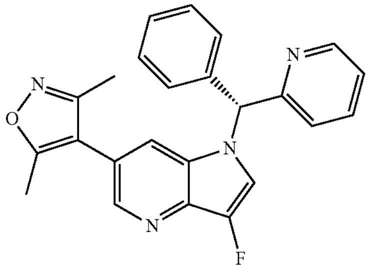 [SMILES: Cc1noc(C)c1-c1cnc2c(F)cn([C@H](c3ccccc3)c3ccccn3)c2c1] | 4-[3-fluoro-1-[(R)-phenyl(2-pyridyl)methyl]pyrrolo[3,2-b]pyridin-6-yl]-3,5-dimethyl-isoxazole | |
| P-0724 | 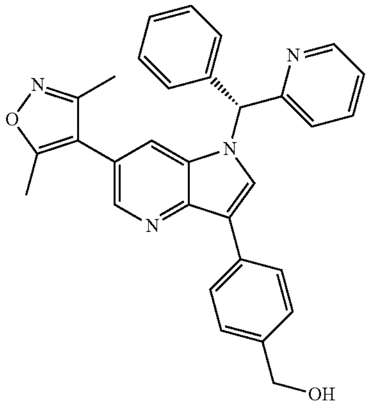 | [4-[6-(3,5-dimethylisoxazol-4-yl)-1-[(R)-phenyl(2-pyridyl)methyl]pyrrolo[3,2-b]pyridin-3-yl]phenyl]methanol | |

TABLE 30-continued
| Compound No. | Structure | Name | MS(ESI) [M + H+]+ or [M − H+]− observed |
|---|---|---|---|
| P-0725 | 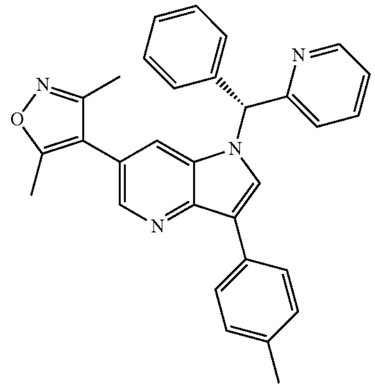 [SMILES: Cc1ccc(-c2cn([C@H](c3ccccc3)c3ccccn3)c3cc(-c4c(C)noc4C)cnc23)cc1] | 3,5-dimethyl-4-[1-[(R)-phenyl(2-pyridyl)methyl]-3-(p-tolyl)pyrrolo[3,2-b]pyridin-6-yl]isoxazole | |
| P-0726 | 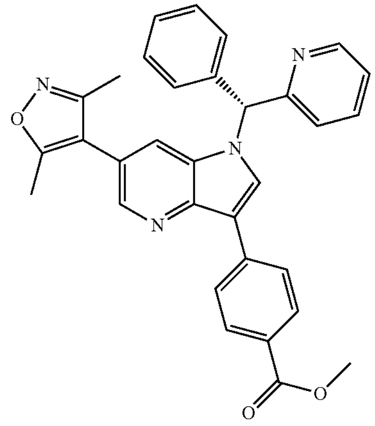 [SMILES: COC(=O)c1ccc(-c2cn([C@H](c3ccccc3)c3ccccn3)c3cc(-c4c(C)noc4C)cnc23)cc1] | methyl 4-[6-(3,5-dimethylisoxazol-4-yl)-1-[(R)-phenyl(2-pyridyl)methyl]pyrrolo[3,2-b]pyridin-3-yl]benzoate | |
| P-0727 | 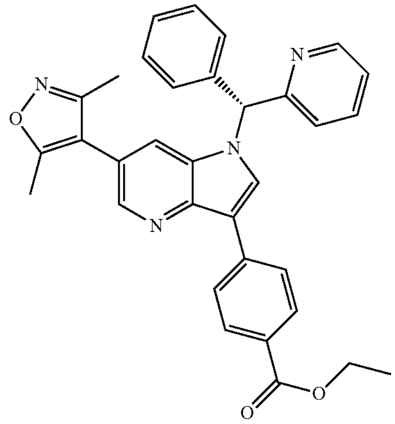 [SMILES: CCOC(=O)c1ccc(-c2cn([C@H](c3ccccc3)c3ccccn3)c3cc(-c4c(C)noc4C)cnc23)cc1] | ethyl 4-[6-(3,5-dimethylisoxazol-4-yl)-1-[(R)-phenyl(2-pyridyl)methyl]pyrrolo[3,2-b]pyridin-3-yl]benzoate | |

TABLE 30-continued
| Compound No. | Structure | Name | MS(ESI) [M + H+]+ or [M − H+]− observed |
|---|---|---|---|
| P-0728 | 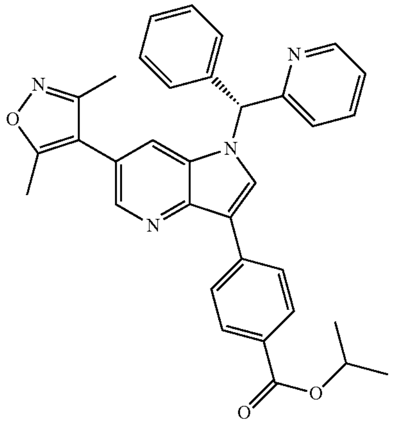 [SMILES: Cc1noc(C)c1-c1cnc2c(-c3ccc(C(=O)OC(C)C)cc3)cn([C@H](c3ccccc3)c3ccccn3)c2c1] | isopropyl 4-[6-(3,5-dimethylisoxazol-4-yl)-1-[(R)-phenyl(2-pyridyl)methyl]pyrrolo[3,2-b]pyridin-3-yl]benzoate | |
| P-0729 | 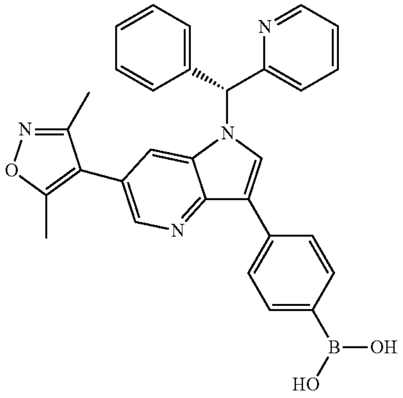 [SMILES: Cc1noc(C)c1-c1cnc2c(-c3ccc(B(O)O)cc3)cn([C@H](c3ccccc3)c3ccccn3)c2c1] | [4-[6-(3,5-dimethylisoxazol-4-yl)-1-[(R)-phenyl(2-pyridyl)methyl]pyrrolo[3,2-b]pyridin-3-yl]phenyl]boronic acid | |
| P-0730 | 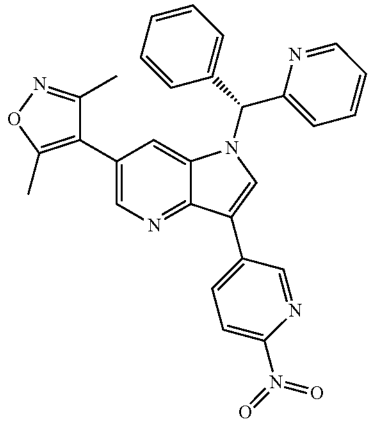 [SMILES: Cc1noc(C)c1-c1cnc2c(-c3ccc([N+](=O)[O-])nc3)cn([C@H](c3ccccc3)c3ccccn3)c2c1] | 3,5-dimethyl-4-[3-(6-nitro-3-pyridyl)-1-[(R)-phenyl(2-pyridyl)methyl]pyrrolo[3,2-b]pyridin-6-yl]isoxazole | |

TABLE 30-continued

| Compound No. | Structure | Name | MS(ESI) [M + H+]+ or [M − H+]− observed |
|---|---|---|---|
| P-0731 | 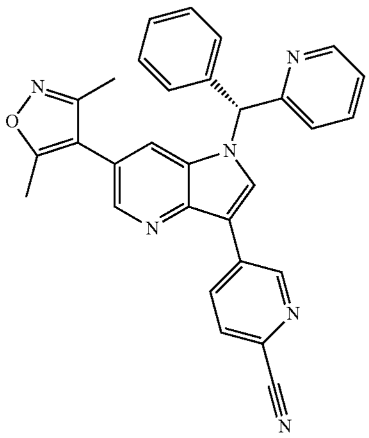 [SMILES: Cc1noc(C)c1-c1cnc2c(-c3ccc(C#N)nc3)cn([C@H](c3ccccc3)c3ccccn3)c2c1] | 5-[6-(3,5-dimethylisoxazol-4-yl)-1-[(R)-phenyl(2-pyridyl)methyl]pyrrolo[3,2-b]pyridin-3-yl]pyridine-2-carbonitrile | |
| P-0732 | 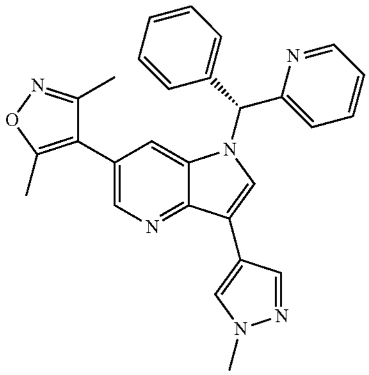 [SMILES: Cc1noc(C)c1-c1cnc2c(-c3cnn(C)c3)cn([C@H](c3ccccc3)c3ccccn3)c2c1] | 3,5-dimethyl-4-[3-(1-methylpyrazol-4-yl)-1-[(R)-phenyl(2-pyridyl)methyl]pyrrolo[3,2-b]pyridin-6-yl]isoxazole | |
| P-0733 | 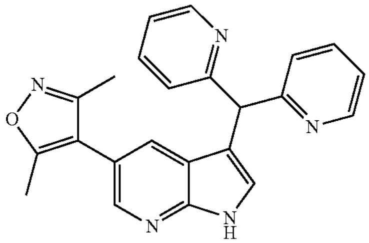 | 4-[3-[bis(2-pyridyl)methyl]-1H-pyrrolo[2,3-b]pyridin-5-yl]-3,5-dimethyl-isoxazole | |
| P-0734 | 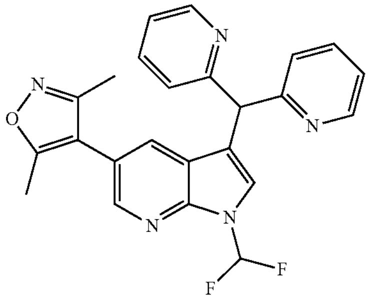 [SMILES: Cc1noc(C)c1-c1cnc2c(c1)c(C(c1ccccn1)c1ccccn1)cn2C(F)F] | 4-[3-[bis(2-pyridyl)methyl]-1-(difluoromethyl)pyrrolo[2,3-b]pyridin-5-yl]-3,5-dimethyl-isoxazole | |

TABLE 30-continued

| Compound No. | Structure | Name | MS(ESI) [M + H+]+ or [M − H+]− observed |
|---|---|---|---|
| P-0735 | 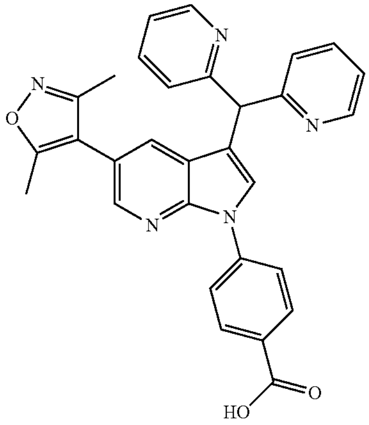 [SMILES: Cc1noc(C)c1-c1cnc2c(c1)c(C(c1ccccn1)c1ccccn1)cn2-c1ccc(C(=O)O)cc1] | 4-[3-[bis(2-pyridyl)methyl]-5-(3,5-dimethylisoxazol-4-yl)pyrrolo[2,3-b]pyridin-1-yl]benzoic acid | |
| P-0736 | 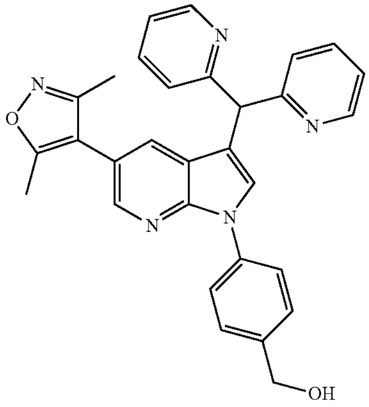 [SMILES: Cc1noc(C)c1-c1cnc2c(c1)c(C(c1ccccn1)c1ccccn1)cn2-c1ccc(CO)cc1] | [4-[3-[bis(2-pyridyl)methyl]-5-(3,5-dimethylisoxazol-4-yl)pyrrolo[2,3-b]pyridin-1-yl]phenyl]methanol | |
| P-0737 | 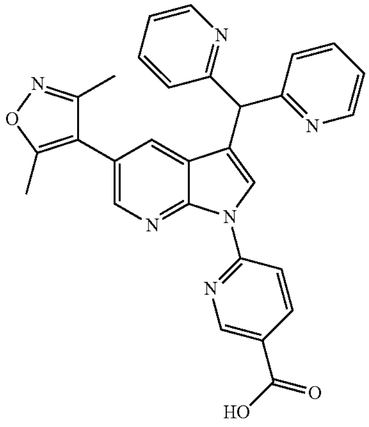 [SMILES: Cc1noc(C)c1-c1cnc2c(c1)c(C(c1ccccn1)c1ccccn1)cn2-c1ccc(C(=O)O)cn1] | 6-[3-[bis(2-pyridyl)methyl]-5-(3,5-dimethylisoxazol-4-yl)pyrrolo[2,3-b]pyridin-1-yl]pyridine-3-carboxylic acid | |
| P-0738 | 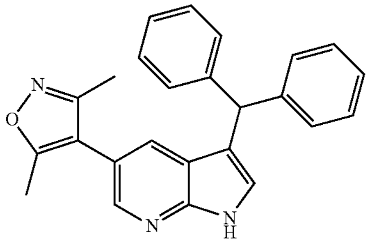 [SMILES: Cc1noc(C)c1-c1cnc2[nH]cc(C(c3ccccc3)c3ccccc3)c2c1] | 4-(3-benzhydryl-1H-pyrrolo[2,3-b]pyridin-5-yl)-3,5-dimethyl-isoxazole | |

TABLE 30-continued
| Compound No. | Structure | Name | MS(ESI) [M + H+]+ or [M − H+]− observed |
| --- | --- | --- | --- |
| P-0739 | 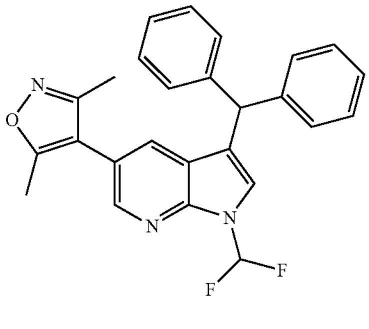 [SMILES: Cc1noc(C)c1-c1cnc2c(c1)c(C(c1ccccc1)c1ccccc1)cn2C(F)F] | 4-[3-benzhydryl-1-(difluoromethyl)pyrrolo[2,3-b]pyridin-5-yl]-3,5-dimethyl-isoxazole | |
| P-0740 | 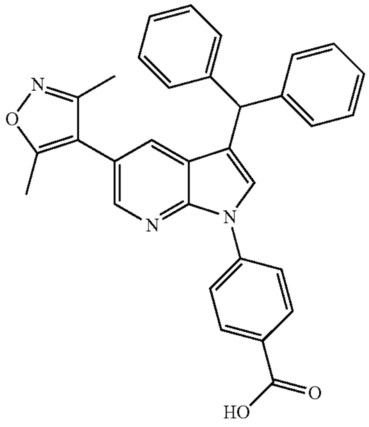 [SMILES: Cc1noc(C)c1-c1cnc2c(c1)c(C(c1ccccc1)c1ccccc1)cn2-c1ccc(C(=O)O)cc1] | 4-[3-benzhydryl-5-(3,5-dimethylisoxazol-4-yl)pyrrolo[2,3-b]pyridin-1-yl]benzoic acid | |
| P-0741 | 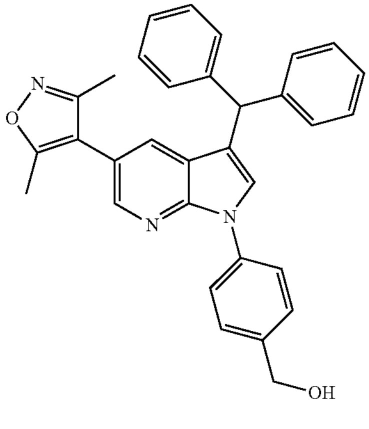 [SMILES: Cc1noc(C)c1-c1cnc2c(c1)c(C(c1ccccc1)c1ccccc1)cn2-c1ccc(CO)cc1] | [4-[3-benzhydryl-5-(3,5-dimethylisoxazol-4-yl)pyrrolo[2,3-b]pyridin-1-yl]phenyl]methanol | |

TABLE 30-continued
| Compound No. | Structure | Name | MS(ESI) [M + H+]+ or [M − H+]− observed |
|---|---|---|---|
| P-0742 | 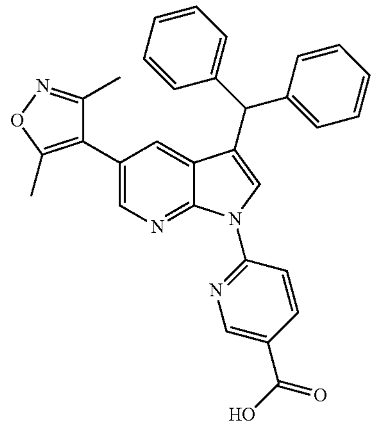 [SMILES: Cc1noc(C)c1-c1cnc2c(c1)c(C(c1ccccc1)c1ccccc1)cn2-c1ccc(C(=O)O)cn1] | 6-[3-benzhydryl-5-(3,5-dimethylisoxazol-4-yl)pyrrolo[2,3-b]pyridin-1-yl]pyridine-3-carboxylic acid | |
| P-0743 | 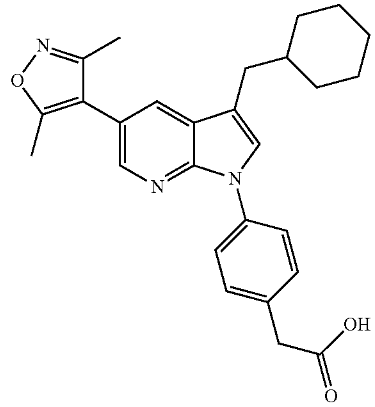 [SMILES: Cc1noc(C)c1-c1cnc2c(c1)c(CC1CCCCC1)cn2-c1ccc(CC(=O)O)cc1] | 2-[4-[3-(cyclohexylmethyl)-5-(3,5-dimethylisoxazol-4-yl)pyrrolo[2,3-b]pyridin-1-yl]phenyl]acetic acid | |
| P-0744 | 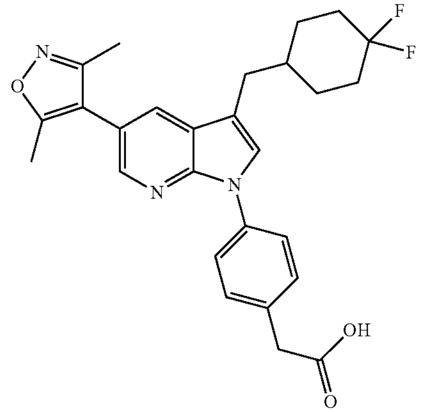 [SMILES: Cc1noc(C)c1-c1cnc2c(c1)c(CC1CCC(F)(F)CC1)cn2-c1ccc(CC(=O)O)cc1] | 2-[4-[3-[(4,4-difluorocyclohexyl)methyl]-5-(3,5-dimethylisoxazol-4-yl)pyrrolo[2,3-b]pyridin-1-yl]phenyl]acetic acid | |

TABLE 30-continued
| Compound No. | Structure | Name | MS(ESI) [M + H+]+ or [M − H+]− observed |
|---|---|---|---|
| P-0745 | 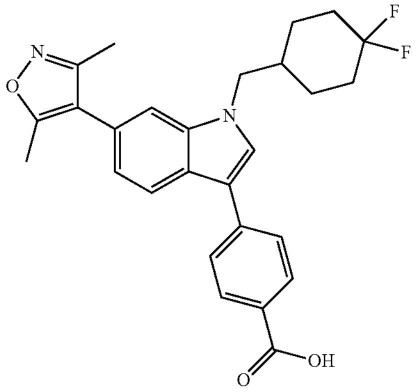 [SMILES: Cc1noc(C)c1-c1ccc2c(-c3ccc(C(=O)O)cc3)cn(CC3CCC(F)(F)CC3)c2c1] | 4-[1-[(4,4-difluorocyclohexyl)methyl]-6-(3,5-dimethylisoxazol-4-yl)indol-3-yl]benzoic acid | |
| P-0746 | 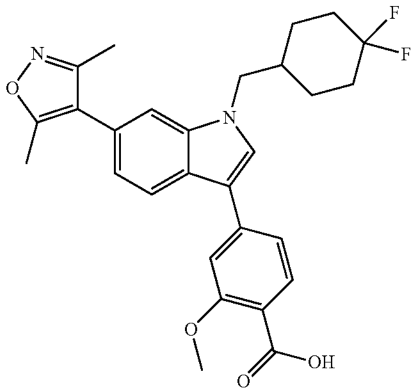 [SMILES: COc1cc(-c2cn(CC3CCC(F)(F)CC3)c3cc(-c4c(C)noc4C)ccc23)ccc1C(=O)O] | 4-[1-[(4,4-difluorocyclohexyl)methyl]-6-(3,5-dimethylisoxazol-4-yl)indol-3-yl]-2-methoxy-benzoic acid | |
| P-0747 | 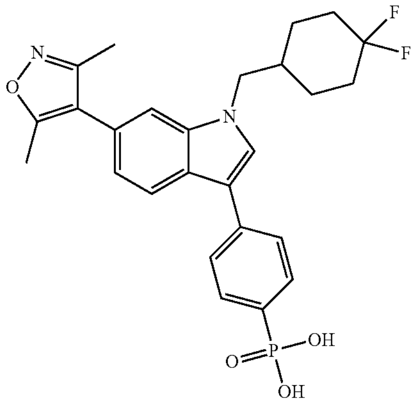 [SMILES: Cc1noc(C)c1-c1ccc2c(-c3ccc(P(=O)(O)O)cc3)cn(CC3CCC(F)(F)CC3)c2c1] | [4-[1-[(4,4-difluorocyclohexyl)methyl]-6-(3,5-dimethylisoxazol-4-yl)indol-3-yl]phenyl]phosphonic acid | |

TABLE 30-continued
| Compound No. | Structure | Name | MS(ESI) [M + H+]+ or [M − H+]− observed |
|---|---|---|---|
| P-0748 | 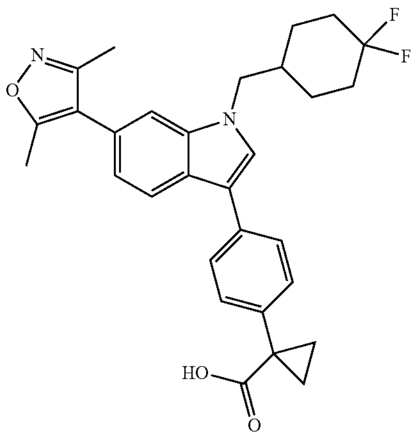 [SMILES: Cc1noc(C)c1-c1ccc2c(-c3ccc(C4(C(=O)O)CC4)cc3)cn(CC3CCC(F)(F)CC3)c2c1] | 1-[4-[1-[(4,4-difluorocyclohexyl)methyl]-6-(3,5-dimethylisoxazol-4-yl)indol-3-yl]phenyl]cyclopropanecarboxylic acid | |
| P-0749 | 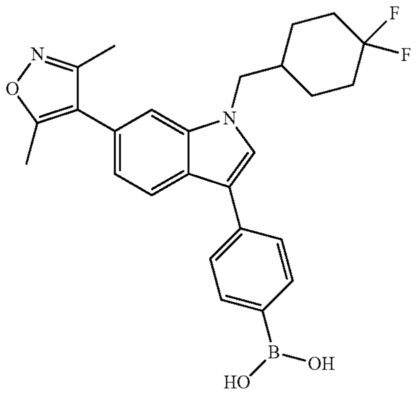 [SMILES: Cc1noc(C)c1-c1ccc2c(-c3ccc(B(O)O)cc3)cn(CC3CCC(F)(F)CC3)c2c1] | [4-[1-[(4,4-difluorocyclohexyl)methyl]-6-(3,5-dimethylisoxazol-4-yl)indol-3-yl]phenyl]boronic acid | |
| P-0750 | 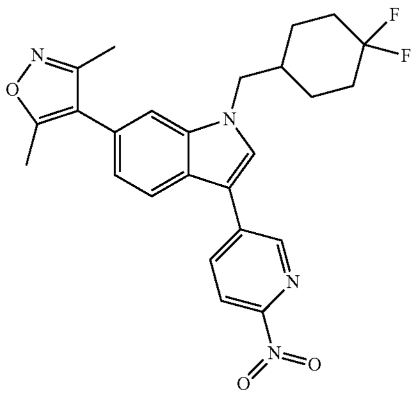 [SMILES: Cc1noc(C)c1-c1ccc2c(-c3ccc([N+](=O)[O-])nc3)cn(CC3CCC(F)(F)CC3)c2c1] | 4-[1-[(4,4-difluorocyclohexyl)methyl]-3-(6-nitro-3-pyridyl)indol-6-yl]-3,5-dimethyl-isoxazole | |

TABLE 30-continued
| Compound No. | Structure | Name | MS(ESI) [M + H+]+ or [M − H+]− observed |
|---|---|---|---|
| P-0751 | 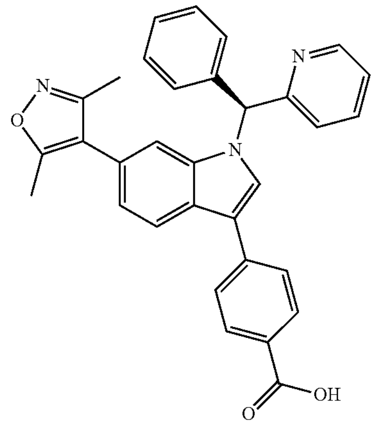 [SMILES: Cc1noc(C)c1-c1ccc2c(-c3ccc(C(=O)O)cc3)cn([C@@H](c3ccccc3)c3ccccn3)c2c1] | 4-[6-(3,5-dimethylisoxazol-4-yl)-1-[(S)-phenyl(2-pyridyl)methyl]indol-3-yl]benzoic acid | |
| P-0752 | 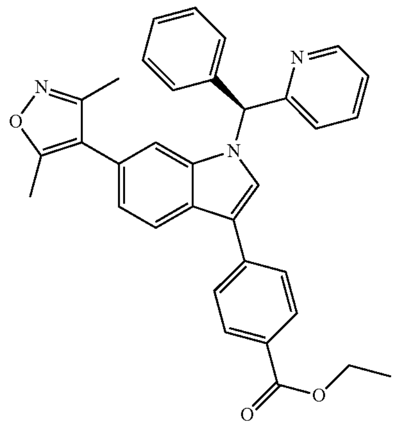 [SMILES: CCOC(=O)c1ccc(-c2cn([C@@H](c3ccccc3)c3ccccn3)c3cc(-c4c(C)noc4C)ccc23)cc1] | ethyl 4-[6-(3,5-dimethylisoxazol-4-yl)-1-[(S)-phenyl(2-pyridyl)methyl]indol-3-yl]benzoate | |
| P-0753 | 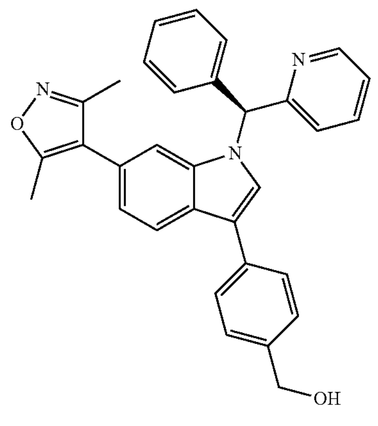 [SMILES: Cc1noc(C)c1-c1ccc2c(-c3ccc(CO)cc3)cn([C@@H](c3ccccc3)c3ccccn3)c2c1] | [4-[6-(3,5-dimethylisoxazol-4-yl)-1-[(S)-phenyl(2-pyridyl)methyl]indol-3-yl]phenyl]methanol | |

TABLE 30-continued
| Compound No. | Structure | Name | MS(ESI) [M + H+]+ or [M − H+]− observed |
|---|---|---|---|
| P-0754 | 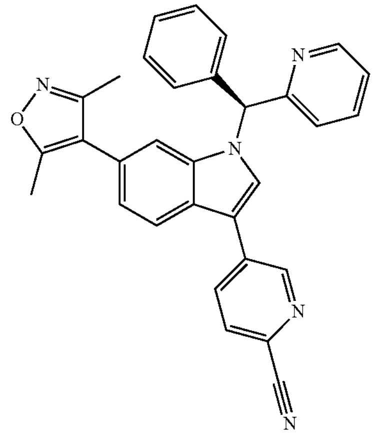 [SMILES: Cc1noc(C)c1-c1ccc2c(-c3ccc(C#N)nc3)cn([C@@H](c3ccccc3)c3ccccn3)c2c1] | 5-[6-(3,5-dimethylisoxazol-4-yl)-1-[(S)-phenyl(2-pyridyl)methyl]indol-3-yl]pyridine-2-carbonitrile | |
| P-0755 | 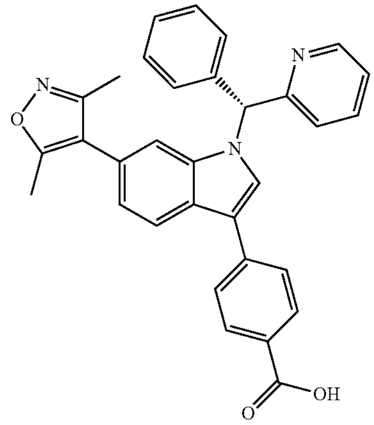 [SMILES: Cc1noc(C)c1-c1ccc2c(-c3ccc(C(=O)O)cc3)cn([C@H](c3ccccc3)c3ccccn3)c2c1] | 4-[6-(3,5-dimethylisoxazol-4-yl)-1-[(R)-phenyl(2-pyridyl)methyl]indol-3-yl]benzoic acid | |
| P-0756 | 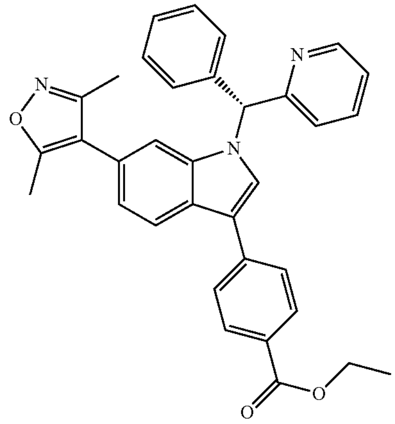 [SMILES: CCOC(=O)c1ccc(-c2cn([C@H](c3ccccc3)c3ccccn3)c3cc(-c4c(C)noc4C)ccc23)cc1] | ethyl 4-[6-(3,5-dimethylisoxazol-4-yl)-1-[(R)-phenyl(2-pyridyl)methyl]indol-3-yl]benzoate | |

TABLE 30-continued
| Compound No. | Structure | Name | MS(ESI) [M + H+]+ or [M − H+]− observed |
|---|---|---|---|
| P-0757 | 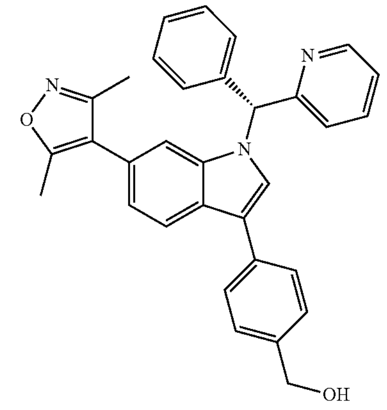 [SMILES: Cc1noc(C)c1-c1ccc2c(-c3ccc(CO)cc3)cn([C@H](c3ccccc3)c3ccccn3)c2c1] | [4-[6-(3,5-dimethylisoxazol-4-yl)-1-[(R)-phenyl(2-pyridyl)methyl]indol-3-yl]phenyl]methanol | |
| P-0758 | 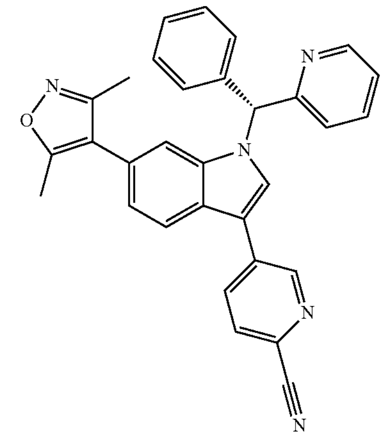 [SMILES: Cc1noc(C)c1-c1ccc2c(-c3ccc(C#N)nc3)cn([C@H](c3ccccc3)c3ccccn3)c2c1] | 5-[6-(3,5-dimethylisoxazol-4-yl)-1-[(R)-phenyl(2-pyridyl)methyl]indol-3-yl]pyridine-2-carbonitrile | |
| P-0759 | 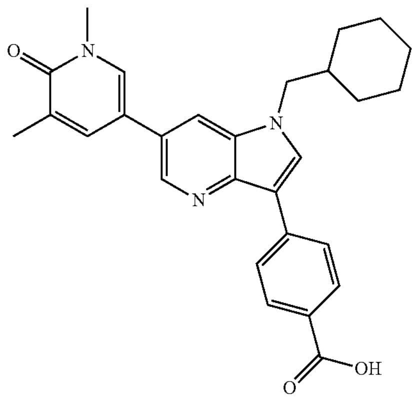 [SMILES: Cc1cc(-c2cnc3c(-c4ccc(C(=O)O)cc4)cn(CC4CCCCC4)c3c2)cn(C)c1=O] | 4-[1-(cyclohexylmethyl)-6-(1,5-dimethyl-6-oxo-3-pyridyl)pyrrolo[3,2-b]pyridin-3-yl]benzoic acid | |

TABLE 30-continued
| Compound No. | Structure | Name | MS(ESI) [M + H+]+ or [M − H+]− observed |
|---|---|---|---|
| P-0760 | 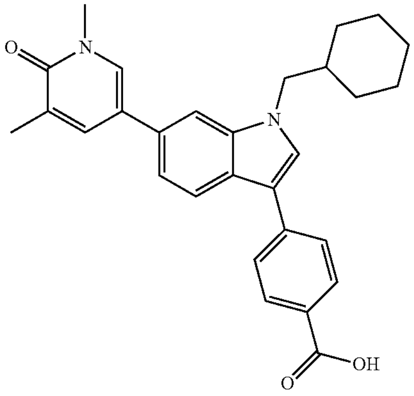 [SMILES: Cc1cc(-c2ccc3c(-c4ccc(C(=O)O)cc4)cn(CC4CCCCC4)c3c2)cn(C)c1=O] | 4-[1-(cyclohexylmethyl)-6-(1,5-dimethyl-6-oxo-3-pyridyl)indol-3-yl]benzoic acid | |
| P-0761 | 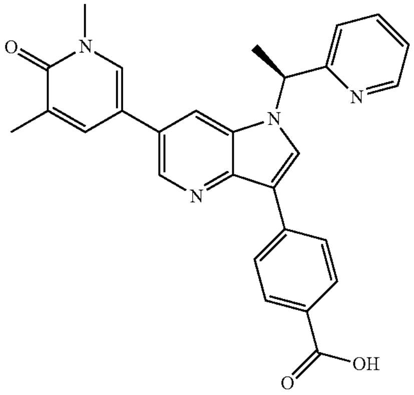 [SMILES: Cc1cc(-c2cnc3c(-c4ccc(C(=O)O)cc4)cn([C@@H](C)c4ccccn4)c3c2)cn(C)c1=O] | 4-[6-(1,5-dimethyl-6-oxo-3-pyridyl)-1-[(1S)-1-(2-pyridyl)ethyl]pyrrolo[3,2-b]pyridin-3-yl]benzoic acid | |
| P-0762 | 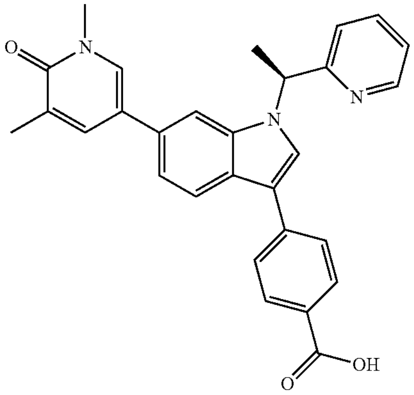 [SMILES: Cc1cc(-c2ccc3c(-c4ccc(C(=O)O)cc4)cn([C@@H](C)c4ccccn4)c3c2)cn(C)c1=O] | 4-[6-(1,5-dimethyl-6-oxo-3-pyridyl)-1-[(1S)-1-(2-pyridyl)ethyl]indol-3-yl]benzoic acid | |

TABLE 30-continued
| Compound No. | Structure | Name | MS(ESI) [M + H+]+ or [M − H+]− observed |
|---|---|---|---|
| P-0763 | 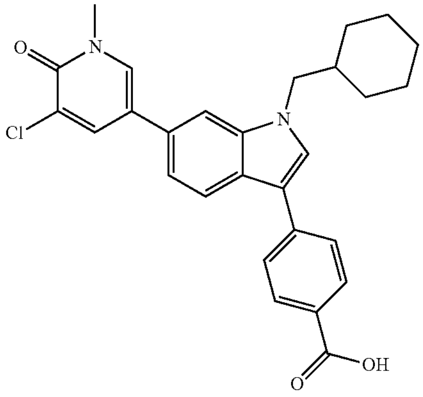 [SMILES: Cn1cc(-c2ccc3c(-c4ccc(C(=O)O)cc4)cn(CC4CCCCC4)c3c2)cc(Cl)c1=O] | 4-[6-(5-chloro-1-methyl-6-oxo-3-pyridyl)-1-(cyclohexylmethyl)indol-3-yl]benzoic acid | |
| P-0764 | 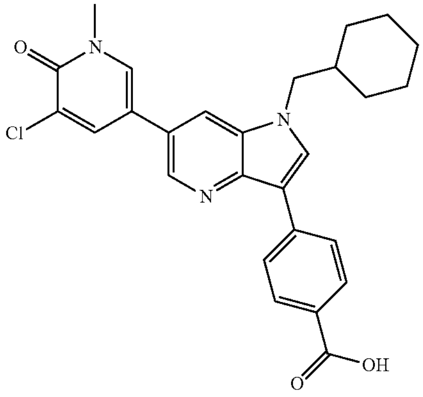 [SMILES: Cn1cc(-c2cnc3c(-c4ccc(C(=O)O)cc4)cn(CC4CCCCC4)c3c2)cc(Cl)c1=O] | 4-[6-(5-chloro-1-methyl-6-oxo-3-pyridyl)-1-(cyclohexylmethyl)pyrrolo[3,2-b]pyridin-3-yl]benzoic acid | |
| P-0765 | 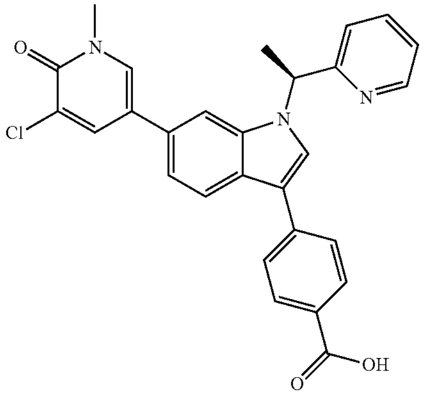 [SMILES: C[C@@H](c1ccccn1)n1cc(-c2ccc(C(=O)O)cc2)c2ccc(-c3cc(Cl)c(=O)n(C)c3)cc21] | 4-[6-(5-chloro-1-methyl-6-oxo-3-pyridyl)-1-[(1S)-1-(2-pyridyl)ethyl]indol-3-yl]benzoic acid | |

TABLE 30-continued
| Compound No. | Structure | Name | MS(ESI) [M + H+]+ or [M − H+]− observed |
|---|---|---|---|
| P-0766 | 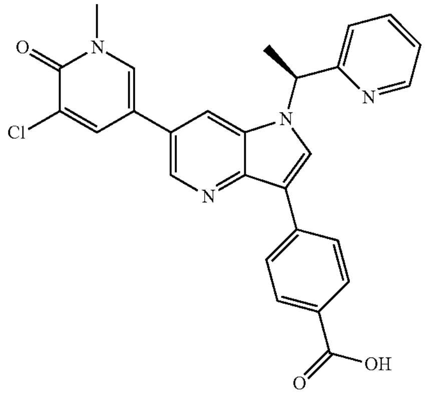 [SMILES: C[C@@H](c1ccccn1)n1cc(-c2ccc(C(=O)O)cc2)c2ncc(-c3cc(Cl)c(=O)n(C)c3)cc21] | 4-[6-(5-chloro-1-methyl-6-oxo-3-pyridyl)-1-[(1S)-1-(2-pyridyl)ethyl]pyrrolo[3,2-b]pyridin-3-yl]benzoic acid | |
| P-0767 | 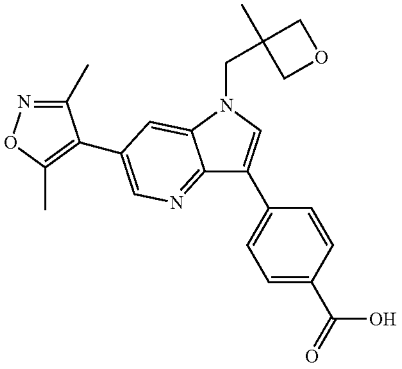 [SMILES: Cc1noc(C)c1-c1cnc2c(-c3ccc(C(=O)O)cc3)cn(CC3(C)COC3)c2c1] | 4-[6-(3,5-dimethylisoxazol-4-yl)-1-[(3-methyloxetan-3-yl)methyl]pyrrolo[3,2-b]pyridin-3-yl]benzoic acid | |
| P-0768 | 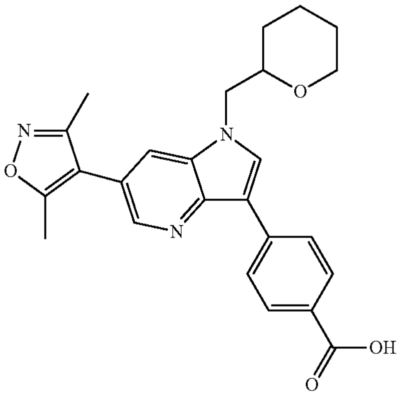 [SMILES: Cc1noc(C)c1-c1cnc2c(-c3ccc(C(=O)O)cc3)cn(CC3CCCCO3)c2c1] | 4-[6-(3,5-dimethylisoxazol-4-yl)-1-(tetrahydropyran-2-ylmethyl)pyrrolo[3,2-b]pyridin-3-yl]benzoic acid | |

TABLE 30-continued
| Compound No. | Structure | Name | MS(ESI) [M + H+]+ or [M − H+]− observed |
|---|---|---|---|
| P-0769 | 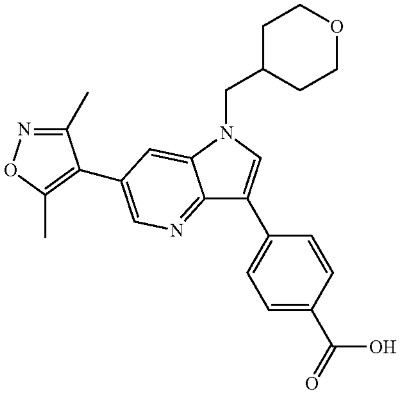 [SMILES: Cc1noc(C)c1-c1cnc2c(-c3ccc(C(=O)O)cc3)cn(CC3CCOCC3)c2c1] | 4-[6-(3,5-dimethylisoxazol-4-yl)-1-(tetrahydropyran-4-ylmethyl)pyrrolo[3,2-b]pyridin-3-yl]benzoic acid | |
| P-0770 | 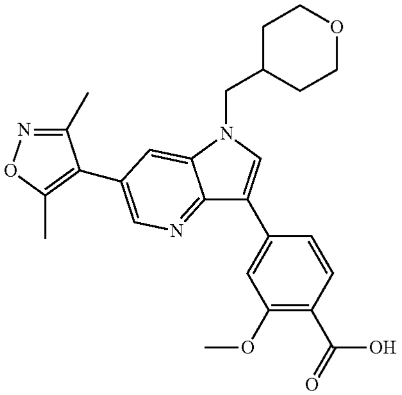 [SMILES: COc1cc(-c2cn(CC3CCOCC3)c3cc(-c4c(C)noc4C)cnc23)ccc1C(=O)O] | 4-[6-(3,5-dimethylisoxazol-4-yl)-1-(tetrahydropyran-4-ylmethyl)pyrrolo[3,2-b]pyridin-3-yl]benzoic acid | |
| P-0771 | 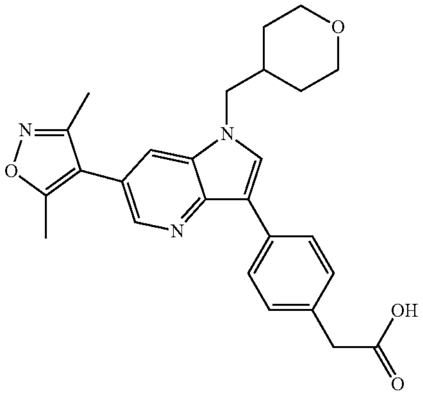 [SMILES: Cc1noc(C)c1-c1cnc2c(-c3ccc(CC(=O)O)cc3)cn(CC3CCOCC3)c2c1] | 2-[4-[6-(3,5-dimethylisoxazol-4-yl)-1-(tetrahydropyran-4-ylmethyl)pyrrolo[3,2-b]pyridin-3-yl]phenyl]acetic acid | |

TABLE 30-continued

| Compound No. | Structure | Name | MS(ESI) [M + H+]+ or [M − H+]− observed |
|---|---|---|---|
| P-0772 | 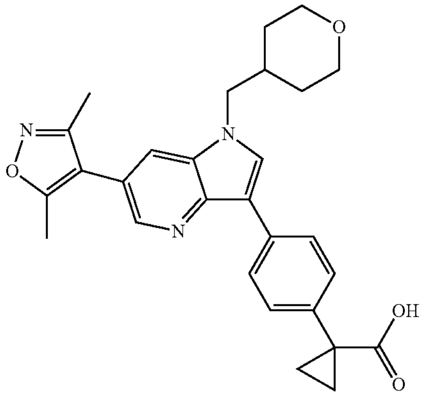 [SMILES: Cc1noc(C)c1-c1cnc2c(-c3ccc(C4(C(=O)O)CC4)cc3)cn(CC3CCOCC3)c2c1] | 1-[4-[6-(3,5-dimethylisoxazol-4-yl)-1-(tetrahydropyran-4-ylmethyl)pyrrolo[3,2-b]pyridin-3-yl]phenyl]cyclopropanecarboxylic acid | |
| P-0773 | 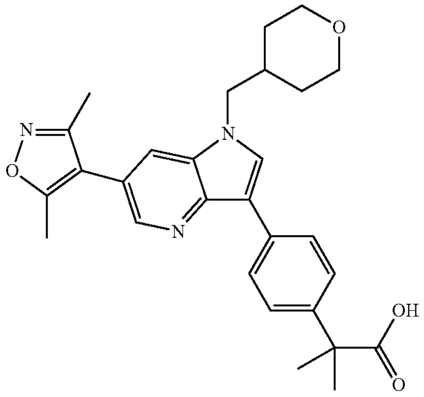 [SMILES: Cc1noc(C)c1-c1cnc2c(-c3ccc(C(C)(C)C(=O)O)cc3)cn(CC3CCOCC3)c2c1] | 2-[4-[6-(3,5-dimethylisoxazol-4-yl)-1-(tetrahydropyran-4-ylmethyl)pyrrolo[3,2-b]pyridin-3-yl]phenyl]-2-methyl-propanoic acid | |
| P-0774 | 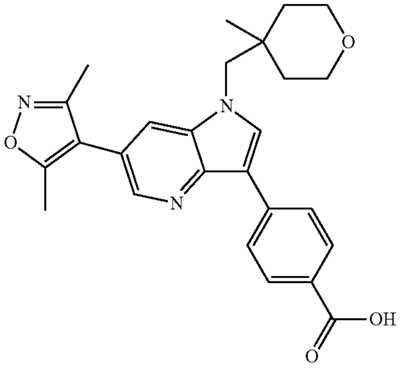 [SMILES: Cc1noc(C)c1-c1cnc2c(-c3ccc(C(=O)O)cc3)cn(CC3(C)CCOCC3)c2c1] | 4-[6-(3,5-dimethylisoxazol-4-yl)-1-[(4-methyltetrahydropyran-4-yl)methyl]pyrrolo[3,2-b]pyridin-3-yl]benzoic acid | 446.5 |

TABLE 30-continued

| Compound No. | Structure | Name | MS(ESI) [M + H+]+ or [M − H+]− observed |
|---|---|---|---|
| P-0775 | 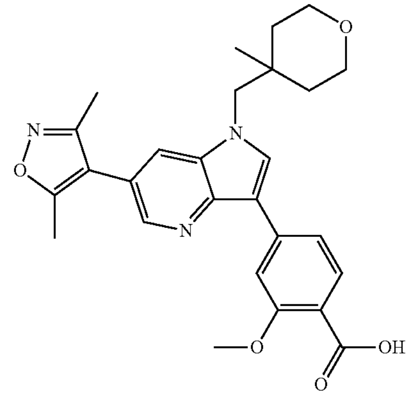 | 4-[6-(3,5-dimethylisoxazol-4-yl)-1-[(4-methyltetrahydropyran-4-yl)methyl]pyrrolo[3,2-b]pyridin-3-yl]-2-methoxy-benzoic acid | 476.2 |
| P-0776 | 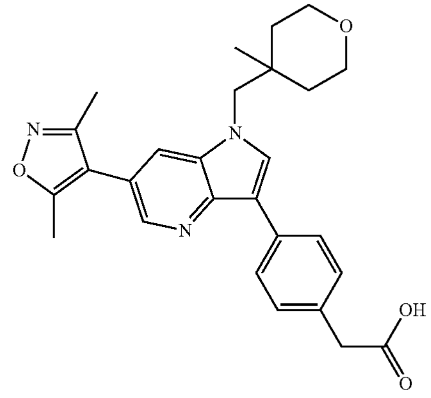 [SMILES: Cc1noc(C)c1-c1cnc2c(-c3ccc(CC(=O)O)cc3)cn(CC3(C)CCOCC3)c2c1] | 2-[4-[6-(3,5-dimethylisoxazol-4-yl)-1-[(4-methyltetrahydropyran-4-yl)methyl]pyrrolo[3,2-b]pyridin-3-yl]phenyl]acetic acid | 460.6 |
| P-0777 | 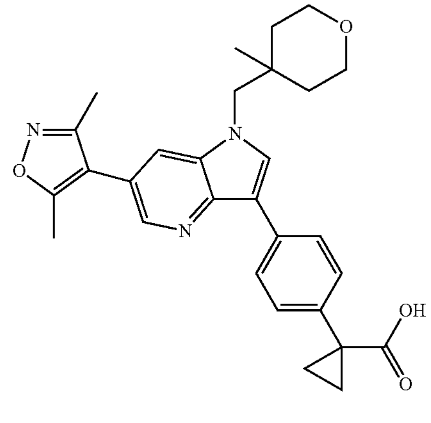 [SMILES: Cc1noc(C)c1-c1cnc2c(-c3ccc(C4(C(=O)O)CC4)cc3)cn(CC3(C)CCOCC3)c2c1] | 1-[4-[6-(3,5-dimethylisoxazol-4-yl)-1-[(4-methyltetrahydropyran-4-yl)methyl]pyrrolo[3,2-b]pyridin-3-yl]phenyl]cyclopropanecarboxylic acid | |

TABLE 30-continued
| Compound No. | Structure | Name | MS(ESI) [M + H+]+ or [M − H+]− observed |
|---|---|---|---|
| P-0778 | 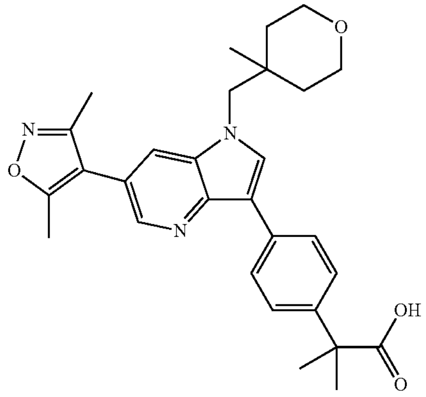 [SMILES: Cc1noc(C)c1-c1cnc2c(-c3ccc(C(C)(C)C(=O)O)cc3)cn(CC3(C)CCOCC3)c2c1] | 2-[4-[6-(3,5-dimethylisoxazol-4-yl)-1-[(4-methyltetrahydropyran-4-yl)methyl]pyrrolo[3,2-b]pyridin-3-yl]phenyl]-2-methyl-propanoic acid | 488.2 |
| P-0779 | 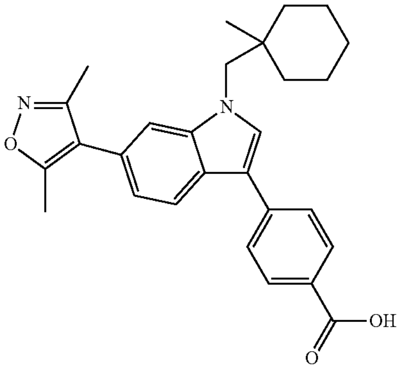 [SMILES: Cc1noc(C)c1-c1ccc2c(-c3ccc(C(=O)O)cc3)cn(CC3(C)CCCCC3)c2c1] | 4-[6-(3,5-dimethylisoxazol-4-yl)-1-[(1-methylcyclohexyl)methyl]indol-3-yl]benzoic acid | |
| P-0780 | 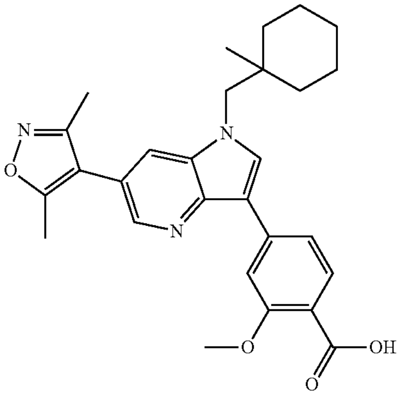 [SMILES: COc1cc(-c2cn(CC3(C)CCCCC3)c3cc(-c4c(C)noc4C)cnc23)ccc1C(=O)O] | 4-[6-(3,5-dimethylisoxazol-4-yl)-1-[(1-methylcyclohexyl)methyl]pyrrolo[3,2-b]pyridin-3-yl]-2-methoxy-benzoic acid | |

TABLE 30-continued

| Compound No. | Structure | Name | MS(ESI) [M + H+]+ or [M − H+]− observed |
|---|---|---|---|
| P-0781 | 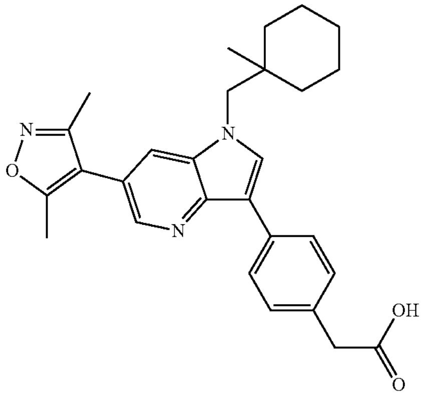 [SMILES: Cc1noc(C)c1-c1cnc2c(-c3ccc(CC(=O)O)cc3)cn(CC3(C)CCCCC3)c2c1] | 2-[4-[6-(3,5-dimethylisoxazol-4-yl)-1-[(1-methylcyclohexyl)methyl]pyrrolo[3,2-b]pyridin-3-yl]phenyl]acetic acid | |
| P-0782 | 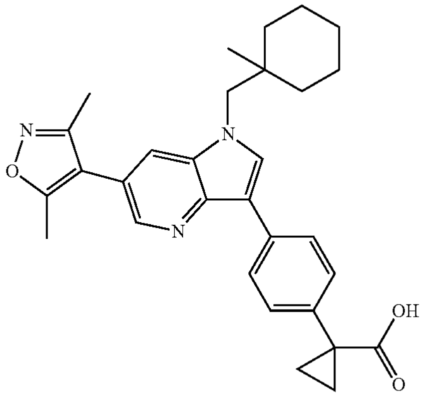 | 1-[4-[6-(3,5-dimethylisoxazol-4-yl)-1-[(1-methylcyclohexyl)methyl]pyrrolo[3,2-b]pyridin-3-yl]phenyl]cyclopropanecarboxylic acid | |
| P-0783 | 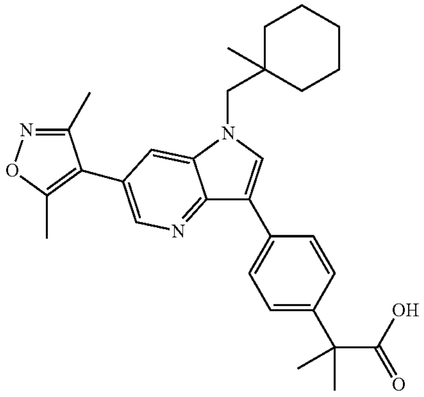 [SMILES: Cc1noc(C)c1-c1cnc2c(-c3ccc(C(C)(C)C(=O)O)cc3)cn(CC3(C)CCCCC3)c2c1] | 2-[4-[6-(3,5-dimethylisoxazol-4-yl)-1-[(1-methylcyclohexyl)methyl]pyrrolo[3,2-b]pyridin-3-yl]phenyl]-2-methyl-propanoic acid | |

TABLE 30-continued

| Compound No. | Structure | Name | MS(ESI) [M + H+]+ or [M − H+]− observed |
|---|---|---|---|
| P-0784 | 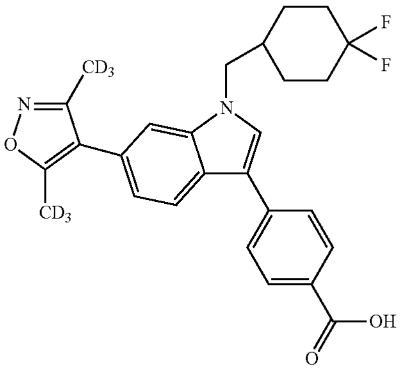 [SMILES: [2H]C([2H])([2H])c1noc(C([2H])([2H])[2H])c1-c1ccc2c(-c3ccc(C(=O)O)cc3)cn(CC3CCC(F)(F)CC3)c2c1] | 4-[6-[3,5-bis(trideuteriomethyl)isoxazol-4-yl]-1-[(4,4-difluorocyclohexyl)methyl]indol-3-yl]benzoic acid | |
| P-0785 | 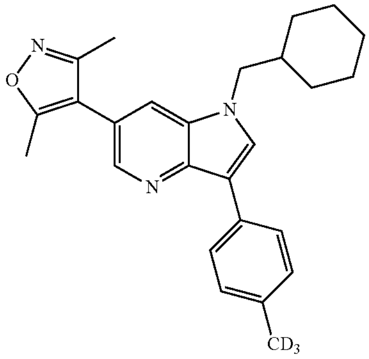 [SMILES: [2H]C([2H])([2H])c1ccc(-c2cn(CC3CCCCC3)c3cc(-c4c(C)noc4C)cnc23)cc1] | 4-[1-(cyclohexylmethyl)-3-[4-(trideuteriomethyl)phenyl]pyrrolo[3,2-b]pyridin-6-yl]-3,5-dimethyl-isoxazole | |
| P-0786 | 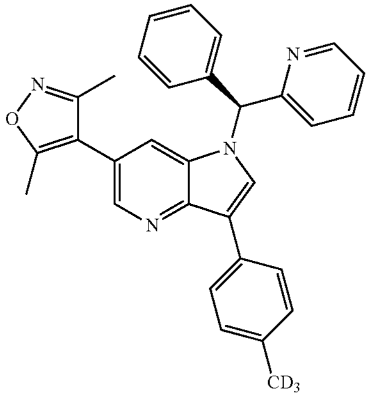 [SMILES: [2H]C([2H])([2H])c1ccc(-c2cn([C@@H](c3ccccc3)c3ccccn3)c3cc(-c4c(C)noc4C)cnc23)cc1] | 3,5-dimethyl-4-[1-[(S)-phenyl(2-pyridyl)methyl]-3-[4-(trideuteriomethyl)phenyl]pyrrolo[3,2-b]pyridin-6-yl]isoxazole | |
| P-0787 | 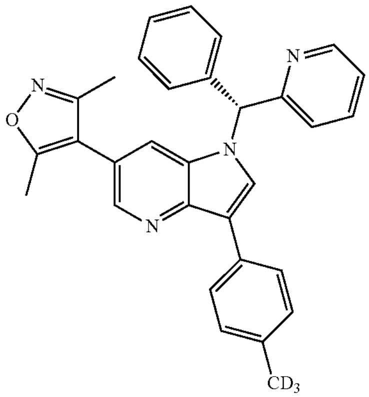 [SMILES: [2H]C([2H])([2H])c1ccc(-c2cn([C@H](c3ccccc3)c3ccccn3)c3cc(-c4c(C)noc4C)cnc23)cc1] | 3,5-dimethyl-4-[1-[(R)-phenyl(2-pyridyl)methyl]-3-[4-(trideuteriomethyl)phenyl]pyrrolo[3,2-b]pyridin-6-yl]isoxazole | |

TABLE 30-continued
| Compound No. | Structure | Name | MS(ESI) [M + H+]+ or [M − H+]− observed |
|---|---|---|---|
| P-0788 | 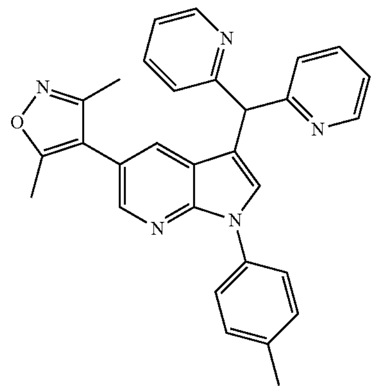 [SMILES: Cc1ccc(-n2cc(C(c3ccccn3)c3ccccn3)c3cc(-c4c(C)noc4C)cnc32)cc1] | 4-[3-[bis(2-pyridyl)methyl]-1-(p-tolyl)pyrrolo[2,3-b]pyridin-5-yl]-3,5-dimethyl-isoxazole | |
| P-0789 | 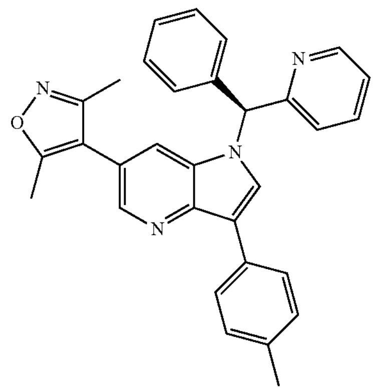 [SMILES: Cc1ccc(-c2cn([C@@H](c3ccccc3)c3ccccn3)c3cc(-c4c(C)noc4C)cnc23)cc1] | 3,5-dimethyl-4-[1-[(S)-phenyl(2-pyridyl)methyl]-3-(p-tolyl)indol-6-yl]isoxazole | |
| P-0790 | 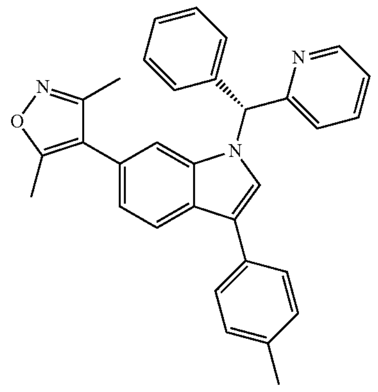 [SMILES: Cc1ccc(-c2cn([C@H](c3ccccc3)c3ccccn3)c3cc(-c4c(C)noc4C)ccc23)cc1] | 3,5-dimethyl-4-[1-[(R)-phenyl(2-pyridyl)methyl]-3-(p-tolyl)indol-6-yl]isoxazole | |
| P-0791 | 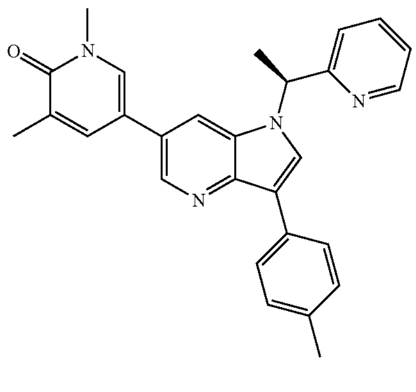 [SMILES: Cc1ccc(-c2cn([C@@H](C)c3ccccn3)c3cc(-c4cc(C)c(=O)n(C)c4)cnc23)cc1] | 1,3-dimethyl-5-[3-(p-tolyl)-1-[(1S)-1-(2-pyridyl)ethyl]pyrrolo[3,2-b]pyridin-6-yl]pyridin-2-one | |

TABLE 30-continued

| Compound No. | Structure | Name | MS(ESI) [M + H+]+ or [M − H+]− observed |
|---|---|---|---|
| P-0792 | 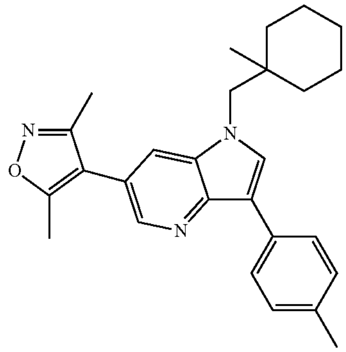 [SMILES: Cc1ccc(-c2cn(CC3(C)CCCCC3)c3cc(-c4c(C)noc4C)cnc23)cc1] | 3,5-dimethyl-4-[1-[(1-methylcyclohexyl)methyl]-3-(p-tolyl)pyrrolo[3,2-b]pyridin-6-yl]isoxazole | |
| P-0793 | 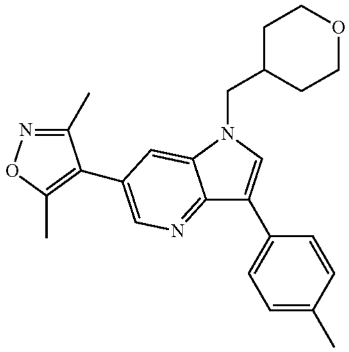 [SMILES: Cc1ccc(-c2cn(CC3CCOCC3)c3cc(-c4c(C)noc4C)cnc23)cc1] | 3,5-dimethyl-4-[3-(p-tolyl)-1-(tetrahydropyran-4-ylmethyl)pyrrolo[3,2-b]pyridin-6-yl]isoxazole | |
| P-0794 | 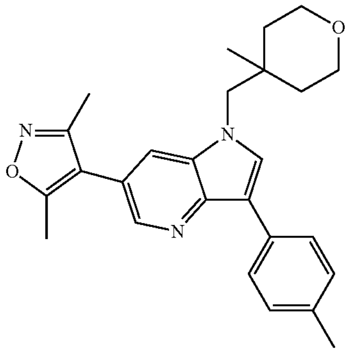 [SMILES: Cc1ccc(-c2cn(CC3(C)CCOCC3)c3cc(-c4c(C)noc4C)cnc23)cc1] | 3,5-dimethyl-4-[1-[(4-methyltetrahydropyran-4-yl)methyl]-3-(p-tolyl)pyrrolo[3,2-b]pyridin-6-yl]isoxazole | 416.5 |
| P-0795 | 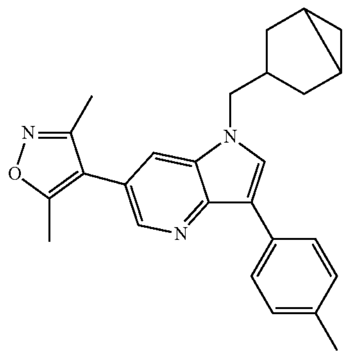 [SMILES: Cc1ccc(-c2cn(CC3CC4CC4C3)c3cc(-c4c(C)noc4C)cnc23)cc1] | 4-[1-(3-bicyclo[3.1.0]hexanylmethyl)-3-(p-tolyl)pyrrolo[3,2-b]pyridin-6-yl]-3,5-dimethyl-isoxazole | |

TABLE 30-continued
| Compound No. | Structure | Name | MS(ESI) [M + H+]+ or [M − H+]− observed |
|---|---|---|---|
| P-0796 | 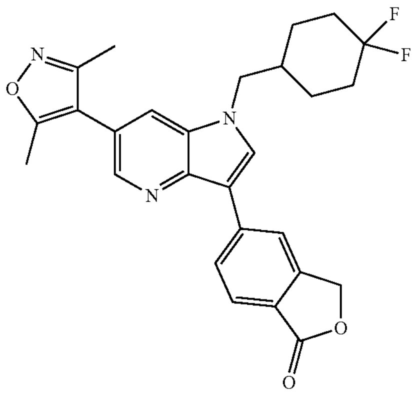 [SMILES: Cc1noc(C)c1-c1cnc2c(-c3ccc4c(c3)COC4=O)cn(CC3CCC(F)(F)CC3)c2c1] | 5-[1-[(4,4-difluorocyclohexyl)methyl]-6-(3,5-dimethylisoxazol-4-yl)pyrrolo[3,2-b]pyridin-3-yl]-3H-isobenzofuran-1-one | |
| P-0797 | 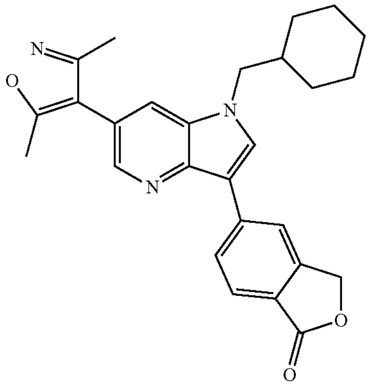 [SMILES: CC(=N)/C(=C(/C)O)c1cnc2c(-c3ccc4c(c3)COC4=O)cn(CC3CCCCC3)c2c1] | 5-[1-(cyclohexylmethyl)-6-(3,5-dimethylisoxazol-4-yl)pyrrolo[3,2-b]pyridin-3-yl]-3H-isobenzofuran-1-one | |
| P-0798 | 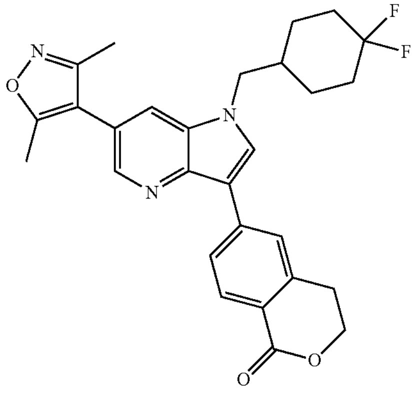 [SMILES: Cc1noc(C)c1-c1cnc2c(-c3ccc4c(c3)CCOC4=O)cn(CC3CCC(F)(F)CC3)c2c1] | 6-[1-[(4,4-difluorocyclohexyl)methyl]-6-(3,5-dimethylisoxazol-4-yl)pyrrolo[3,2-b]pyridin-3-yl]isochroman-1-one | |

TABLE 30-continued

| Compound No. | Structure | Name | MS(ESI) [M + H+]+ or [M − H+]− observed |
|---|---|---|---|
| P-0799 | 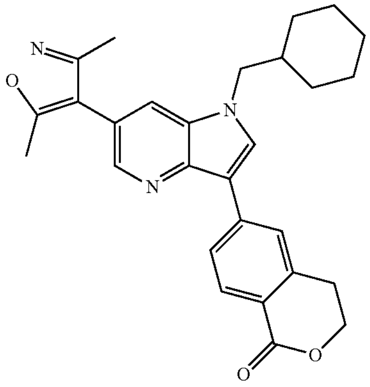 [SMILES: CC(=N)/C(=C(/C)O)c1cnc2c(-c3ccc4c(c3)CCOC4=O)cn(CC3CCCCC3)c2c1] | 6-[1-(cyclohexylmethyl)-6-(3,5-dimethylisoxazol-4-yl)pyrrolo[3,2-b]pyridin-3-yl]isochroman-1-one | |
| P-0800 | 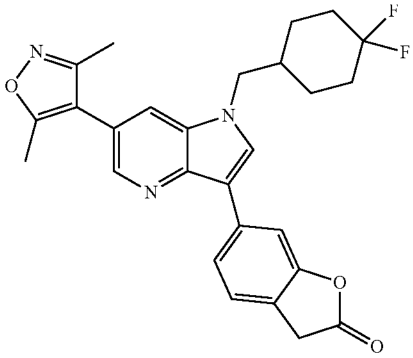 [SMILES: Cc1noc(C)c1-c1cnc2c(-c3ccc4c(c3)OC(=O)C4)cn(CC3CCC(F)(F)CC3)c2c1] | 6-[1-[(4,4-difluorocyclohexyl)methyl]-6-(3,5-dimethylisoxazol-4-yl)pyrrolo[3,2-b]pyridin-3-yl]-3H-benzofuran-2-one | |
| P-0801 | 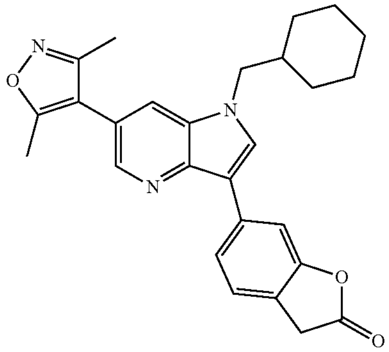 [SMILES: Cc1noc(C)c1-c1cnc2c(-c3ccc4c(c3)OC(=O)C4)cn(CC3CCCCC3)c2c1] | 6-[1-(cyclohexylmethyl)-6-(3,5-dimethylisoxazol-4-yl)pyrrolo[3,2-b]pyridin-3-yl]-3H-benzofuran-2-one | |
| P-0802 | 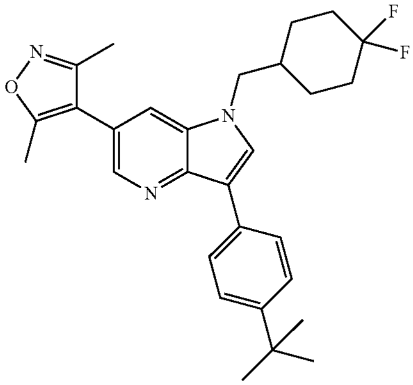 [SMILES: Cc1noc(C)c1-c1cnc2c(-c3ccc(C(C)(C)C)cc3)cn(CC3CCC(F)(F)CC3)c2c1] | 4-[3-(4-tert-butylphenyl)-1-[(4,4-difluorocyclohexyl)methyl]pyrrolo[3,2-b]pyridin-6-yl]-3,5-dimethyl-isoxazole | 478.0 |

TABLE 30-continued

| Compound No. | Structure | Name | MS(ESI) [M + H+]+ or [M − H+]− observed |
| --- | --- | --- | --- |
| P-0803 | 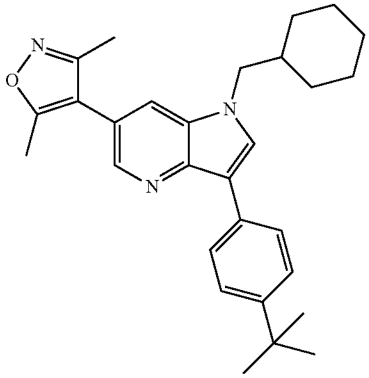 [SMILES: Cc1noc(C)c1-c1cnc2c(-c3ccc(C(C)(C)C)cc3)cn(CC3CCCCC3)c2c1] | 4-[3-(4-tert-butylphenyl)-1-(cyclohexylmethyl)pyrrolo[3,2-b]pyridin-6-yl]-3,5-dimethyl-isoxazole | |
| P-0804 | 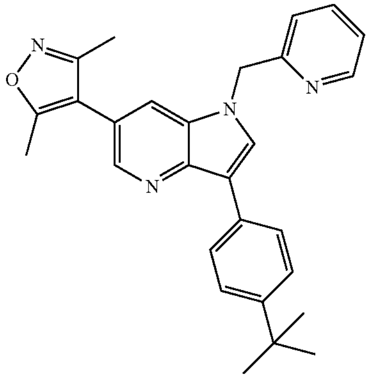 [SMILES: Cc1noc(C)c1-c1cnc2c(-c3ccc(C(C)(C)C)cc3)cn(Cc3ccccn3)c2c1] | 4-[3-(4-tert-butylphenyl)-1-(2-pyridylmethyl)pyrrolo[3,2-b]pyridin-6-yl]-3,5-dimethyl-isoxazole | |
| P-0805 | 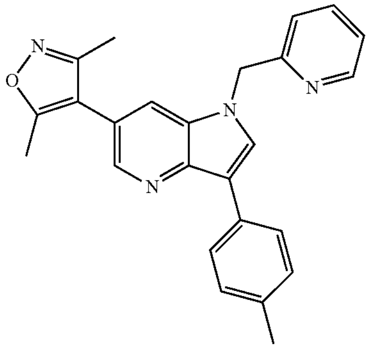 [SMILES: Cc1ccc(-c2cn(Cc3ccccn3)c3cc(-c4c(C)noc4C)cnc23)cc1] | 3,5-dimethyl-4-[3-(p-tolyl)-1-(2-pyridylmethyl)pyrrolo[3,2-b]pyridin-6-yl]isoxazole | 395.3 |
| P-0806 | 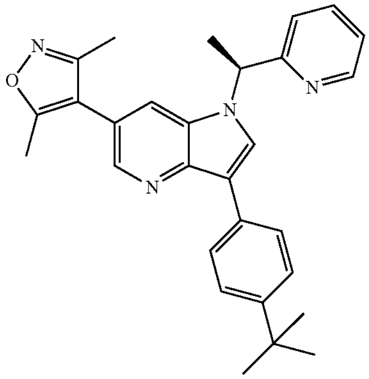 [SMILES: Cc1noc(C)c1-c1cnc2c(-c3ccc(C(C)(C)C)cc3)cn([C@@H](C)c3ccccn3)c2c1] | 4-[3-(4-tert-butylphenyl)-1-[(1S)-1-(2-pyridyl)ethyl]pyrrolo[3,2-b]pyridin-6-yl]-3,5-dimethyl-isoxazole | 451.0 |

TABLE 30-continued

| Compound No. | Structure | Name | MS(ESI) [M + H+]+ or [M − H+]− observed |
|---|---|---|---|
| P-0807 | 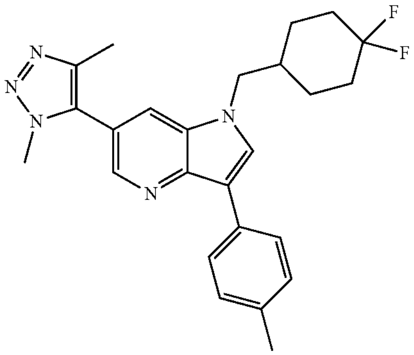 [SMILES: Cc1ccc(-c2cn(CC3CCC(F)(F)CC3)c3cc(-c4c(C)nnn4C)cnc23)cc1] | 1-[(4,4-difluorocyclohexyl)methyl]-6-(3,5-dimethyltriazol-4-yl)-3-(p-tolyl)pyrrolo[3,2-b]pyridine | |
| P-0808 | 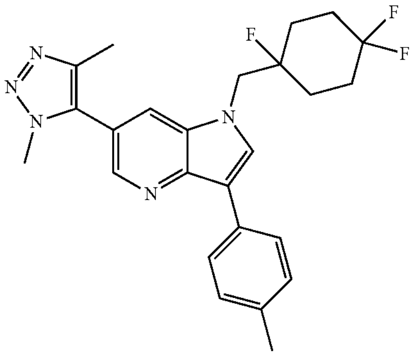 [SMILES: Cc1ccc(-c2cn(CC3(F)CCC(F)(F)CC3)c3cc(-c4c(C)nnn4C)cnc23)cc1] | 6-(3,5-dimethyltriazol-4-yl)-3-(p-tolyl)-1-[(1,4,4-trifluorocyclohexyl)methyl]pyrrolo[3,2-b]pyridine | |
| P-0809 | 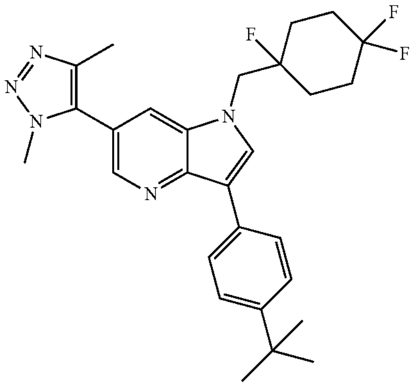 [SMILES: Cc1nnn(C)c1-c1cnc2c(-c3ccc(C(C)(C)C)cc3)cn(CC3(F)CCC(F)(F)CC3)c2c1] | 3-(4-tert-butylphenyl)-6-(3,5-dimethyltriazol-4-yl)-1-[(1,4,4-trifluorocyclohexyl)methyl]pyrrolo[3,2-b]pyridine | |
| P-0810 | 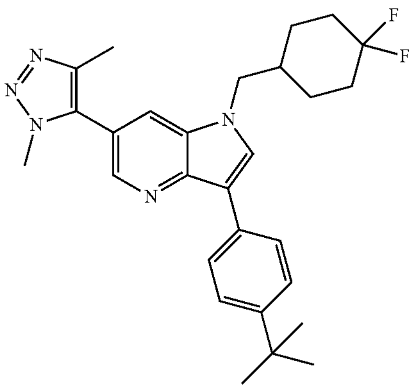 [SMILES: Cc1nnn(C)c1-c1cnc2c(-c3ccc(C(C)(C)C)cc3)cn(CC3CCC(F)(F)CC3)c2c1] | 3-(4-tert-butylphenyl)-1-[(4,4-difluorocyclohexyl)methyl]-6-(3,5-dimethyltriazol-4-yl)pyrrolo[3,2-b]pyridine | |

TABLE 30-continued
| Compound No. | Structure | Name | MS(ESI) [M + H+]+ or [M − H+]− observed |
| --- | --- | --- | --- |
| P-0811 | 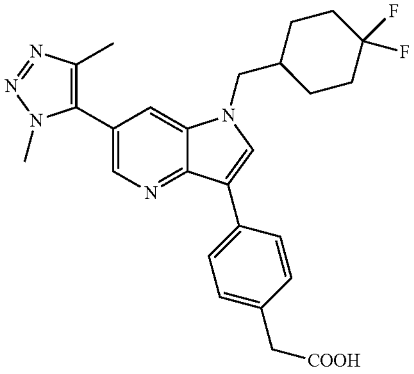 [SMILES: Cc1nnn(C)c1-c1cnc2c(-c3ccc(CC(=O)O)cc3)cn(CC3CCC(F)(F)CC3)c2c1] | 2-[4-[1-[(4,4-difluorocyclohexyl)methyl]-6-(3,5-dimethyltriazol-4-yl)pyrrolo[3,2-b]pyridin-3-yl]phenyl]acetic acid | |
| P-0812 | 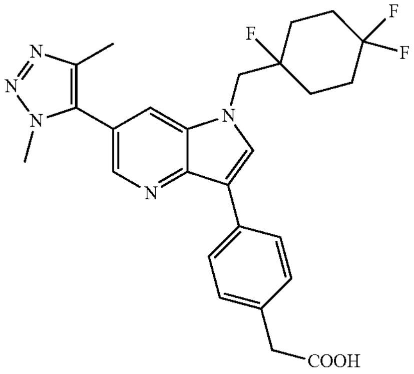 [SMILES: Cc1nnn(C)c1-c1cnc2c(-c3ccc(CC(=O)O)cc3)cn(CC3(F)CCC(F)(F)CC3)c2c1] | 2-[4-[6-(3,5-dimethyltriazol-4-yl)-1-[(1,4,4-trifluorocyclohexyl)methyl]pyrrolo[3,2-b]pyridin-3-yl]phenyl]acetic acid | |
| P-0813 | 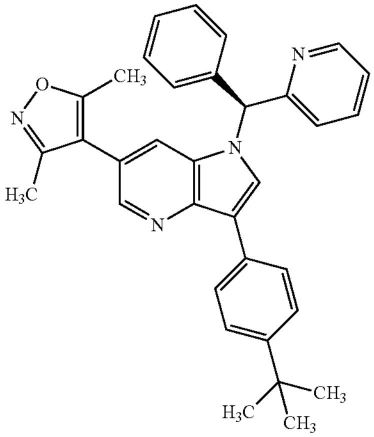 [SMILES: Cc1noc(C)c1-c1cnc2c(-c3ccc(C(C)(C)C)cc3)cn([C@@H](c3ccccc3)c3ccccn3)c2c1] | 4-[3-(4-tert-butylphenyl)-1-[(S)-phenyl(2-pyridyl)methyl]pyrrolo[3,2-b]pyridin-6-yl]-3,5-dimethyl-isoxazole | |

TABLE 30-continued
| Compound No. | Structure | Name | MS(ESI) [M + H+]+ or [M − H+]− observed |
|---|---|---|---|
| P-0814 | 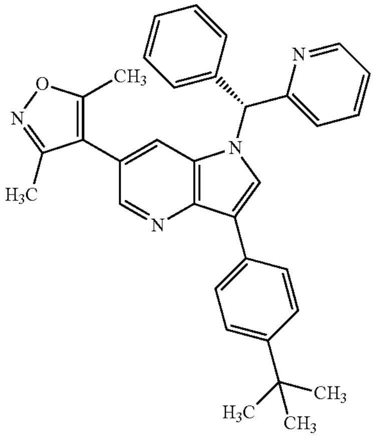 [SMILES: Cc1noc(C)c1-c1cnc2c(-c3ccc(C(C)(C)C)cc3)cn([C@H](c3ccccc3)c3ccccn3)c2c1] | 4-[3-(4-tert-butylphenyl)-1-[(R)-phenyl(2-pyridyl)methyl]pyrrolo[3,2-b]pyridin-6-yl]-3,5-dimethyl-isoxazole | |
| P-0815 | 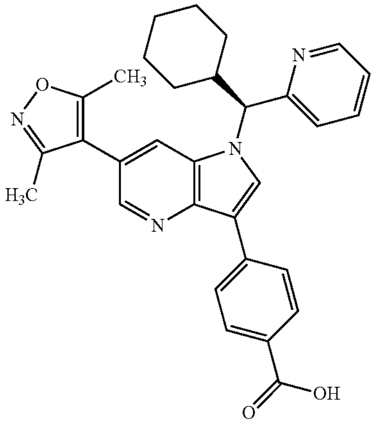 [SMILES: Cc1noc(C)c1-c1cnc2c(-c3ccc(C(=O)O)cc3)cn([C@H](c3ccccn3)C3CCCCC3)c2c1] | 4-[1-[(S)-cyclohexyl(2-pyridyl)methyl]-6-(3,5-dimethylisoxazol-4-yl)pyrrolo[3,2-b]pyridin-3-yl]benzoic acid | |
| P-0816 | 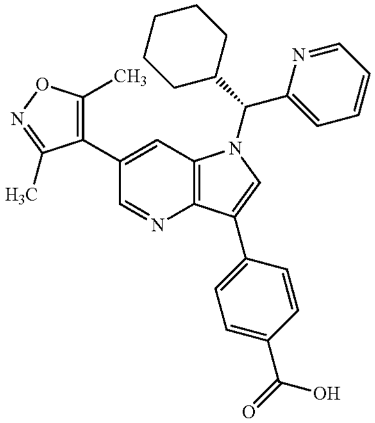 [SMILES: Cc1noc(C)c1-c1cnc2c(-c3ccc(C(=O)O)cc3)cn([C@@H](c3ccccn3)C3CCCCC3)c2c1] | 4-[1-[(R)-cyclohexyl(2-pyridyl)methyl]-6-(3,5-dimethylisoxazol-4-yl)pyrrolo[3,2-b]pyridin-3-yl]benzoic acid | |

TABLE 30-continued
| Compound No. | Structure | Name | MS(ESI) [M + H+]+ or [M − H+]− observed |
|---|---|---|---|
| P-0817 | 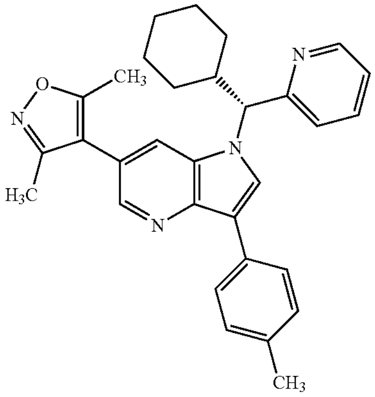 [SMILES: Cc1ccc(-c2cn([C@@H](c3ccccn3)C3CCCCC3)c3cc(-c4c(C)noc4C)cnc23)cc1] | 4-[1-[(R)-cyclohexyl(2-pyridyl)methyl]-3-(p-tolyl)pyrrolo[3,2-b]pyridin-6-yl]-3,5-dimethyl-isoxazole | |
| P-0818 | 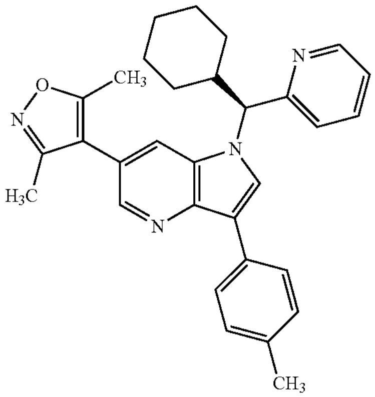 [SMILES: Cc1ccc(-c2cn([C@H](c3ccccn3)C3CCCCC3)c3cc(-c4c(C)noc4C)cnc23)cc1] | 4-[1-[(S)-cyclohexyl(2-pyridyl)methyl]-3-(p-tolyl)pyrrolo[3,2-b]pyridin-6-yl]-3,5-dimethyl-isoxazole | |
| P-0819 | 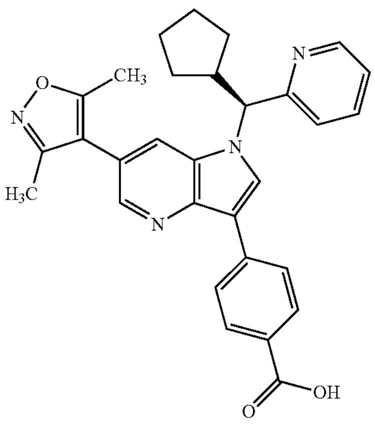 [SMILES: Cc1noc(C)c1-c1cnc2c(-c3ccc(C(=O)O)cc3)cn([C@H](c3ccccn3)C3CCCC3)c2c1] | 4-[1-[(S)-cyclopentyl(2-pyridyl)methyl]-6-(3,5-dimethylisoxazol-4-yl)pyrrolo[3,2-b]pyridin-3-yl]benzoic acid | |

TABLE 30-continued

| Compound No. | Structure | Name | MS(ESI) [M + H+]+ or [M − H+]− observed |
|---|---|---|---|
| P-0820 | 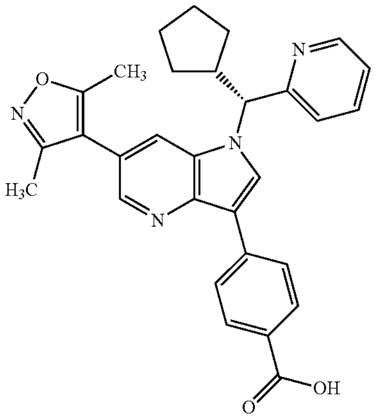 [SMILES: Cc1noc(C)c1-c1cnc2c(-c3ccc(C(=O)O)cc3)cn([C@@H](c3ccccn3)C3CCCC3)c2c1] | 4-[1-[(R)-cyclopentyl(2-pyridyl)methyl]-6-(3,5-dimethylisoxazol-4-yl)pyrrolo[3,2-b]pyridin-3-yl]benzoic acid | |
| P-0821 | 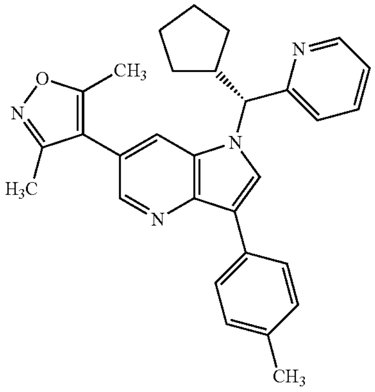 [SMILES: Cc1ccc(-c2cn([C@@H](c3ccccn3)C3CCCC3)c3cc(-c4c(C)noc4C)cnc23)cc1] | 4-[1-[(R)-cyclopentyl(2-pyridyl)methyl]-3-(p-tolyl)pyrrolo[3,2-b]pyridin-6-yl]-3,5-dimethyl-isoxazole | |
| P-0822 | 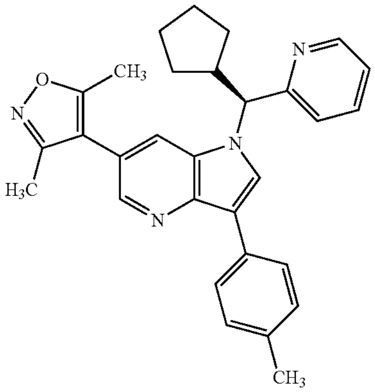 [SMILES: Cc1ccc(-c2cn([C@H](c3ccccn3)C3CCCC3)c3cc(-c4c(C)noc4C)cnc23)cc1] | 4-[1-[(S)-cyclopentyl(2-pyridyl)methyl]-3-(p-tolyl)pyrrolo[3,2-b]pyridin-6-yl]-3,5-dimethyl-isoxazole | |

Compounds listed in Table 31 below, e.g., compounds P-0900 to P-1053 were prepared according to the protocols set forth in Examples 1 to 56. The $^{1}H$ NMR and mass spectroscopy data were consistent with the structures of the compounds.

TABLE 31
| Compound No. | Structure | Name | MS(ESI) [M + H+]+ observed |
|---|---|---|---|
| P-0900 | 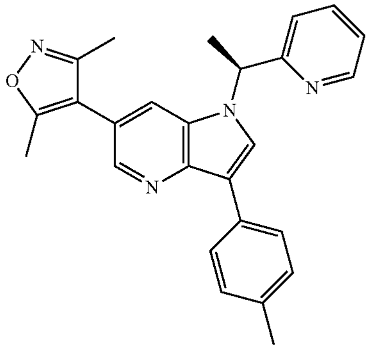 [SMILES: Cc1ccc(-c2cn([C@@H](C)c3ccccn3)c3cc(-c4c(C)noc4C)cnc23)cc1] | 3,5-dimethyl-4-[3-(p-tolyl)-1-[(1S)-1-(2-pyridyl)ethyl]pyrrolo[3,2-b]pyridin-6-yl]isoxazole | 409.4 |
| P-0901 | 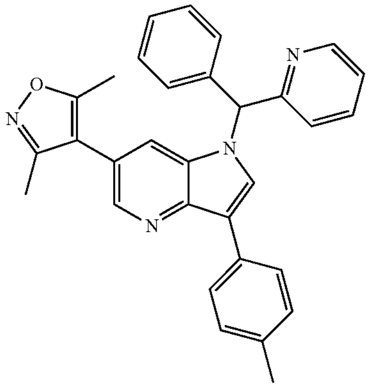 [SMILES: Cc1ccc(-c2cn(C(c3ccccc3)c3ccccn3)c3cc(-c4c(C)noc4C)cnc23)cc1] | 3,5-dimethyl-4-[1-[phenyl(2-pyridyl)methyl]-3-(p-tolyl)pyrrolo[3,2-b]pyridin-6-yl]isoxazole | 471.0 |
| P-0902 | 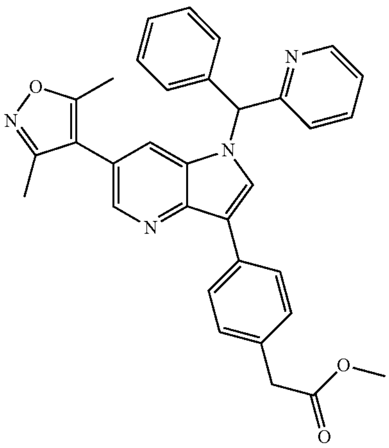 [SMILES: COC(=O)Cc1ccc(-c2cn(C(c3ccccc3)c3ccccn3)c3cc(-c4c(C)noc4C)cnc23)cc1] | methyl 2-[4-[6-(3,5-dimethylisoxazol-4-yl)-1-[phenyl(2-pyridyl)methyl]pyrrolo[3,2-b]pyridin-3-yl]phenyl]acetate | 529.0 |

TABLE 31-continued

| Compound No. | Structure | Name | MS(ESI) [M + H+]+ observed |
|---|---|---|---|
| P-0903 | 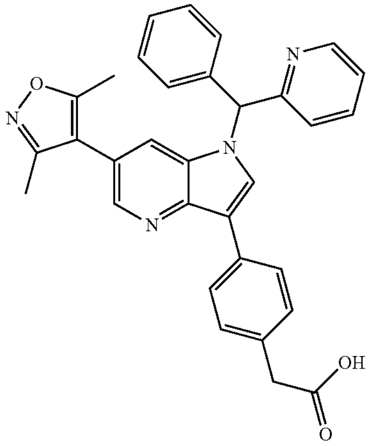 [SMILES: Cc1noc(C)c1-c1cnc2c(-c3ccc(CC(=O)O)cc3)cn(C(c3ccccc3)c3ccccn3)c2c1] | 2-[4-[6-(3,5-dimethylisoxazol-4-yl)-1-[phenyl(2-pyridyl)methyl]pyrrolo[3,2-b]pyridin-3-yl]phenyl]acetic acid | 515.3 |
| P-0904 | 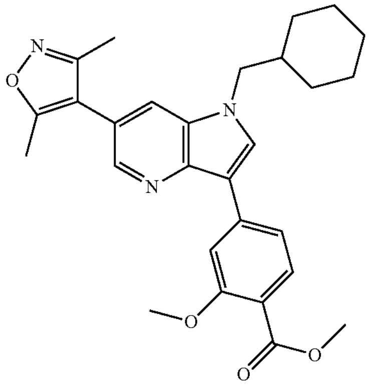 [SMILES: COC(=O)c1ccc(-c2cn(CC3CCCCC3)c3cc(-c4c(C)noc4C)cnc23)cc1OC] | methyl 4-[1-(cyclohexylmethyl)-6-(3,5-dimethylisoxazol-4-yl)pyrrolo[3,2-b]pyridin-3-yl]-2-methoxy-benzoate | 474.0 |
| P-0905 | 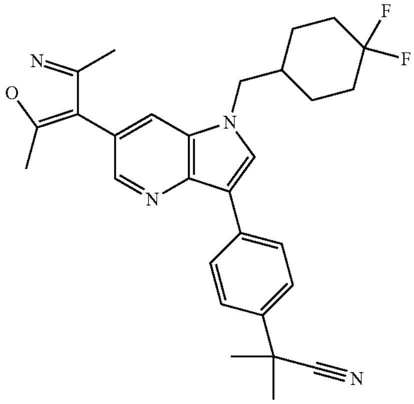 [SMILES: CC(=N)/C(=C(/C)O)c1cnc2c(-c3ccc(C(C)(C)C#N)cc3)cn(CC3CCC(F)(F)CC3)c2c1] | 2-[4-[1-[(4,4-difluorocyclohexyl)methyl]-6-(3,5-dimethylisoxazol-4-yl)pyrrolo[3,2-b]pyridin-3-yl]phenyl]-2-methyl-propanenitrile | 489.0 |
| P-0906 | 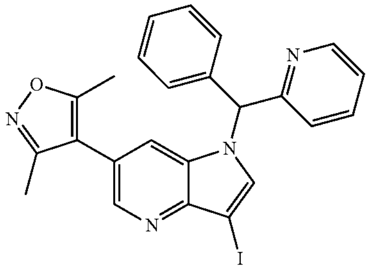 [SMILES: Cc1noc(C)c1-c1cnc2c(I)cn(C(c3ccccc3)c3ccccn3)c2c1] | 4-[3-iodo-1-[phenyl(2-pyridyl)methyl]pyrrolo[3,2-b]pyridin-6-yl]-3,5-dimethyl-isoxazole | 506.8 |

TABLE 31-continued
| Compound No. | Structure | Name | MS(ESI) [M + H+]+ observed |
|---|---|---|---|
| P-0907 | 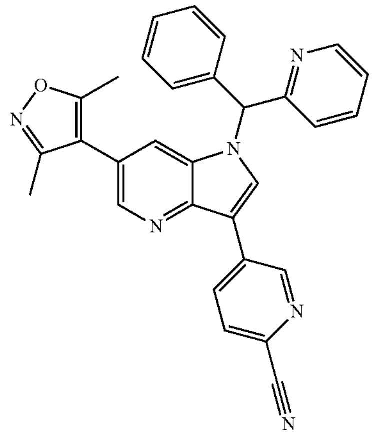 [SMILES: Cc1noc(C)c1-c1cnc2c(-c3ccc(C#N)nc3)cn(C(c3ccccc3)c3ccccn3)c2c1] | 5-[6-(3,5-dimethylisoxazol-4-yl)-1-[phenyl(2-pyridyl)methyl]pyrrolo[3,2-b]pyridin-3-yl]pyridine-2-carbonitrile | 483.2 |
| P-0908 | 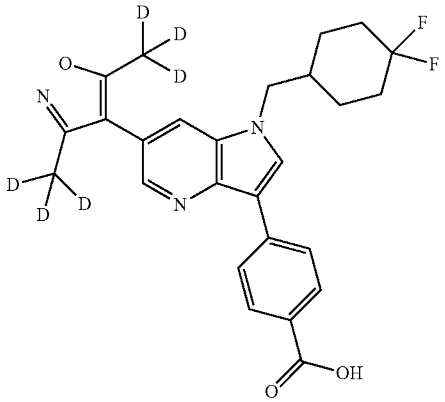 [SMILES: [2H]C([2H])([2H])C(=N)/C(=C(\O)C([2H])([2H])[2H])c1cnc2c(-c3ccc(C(=O)O)cc3)cn(CC3CCC(F)(F)CC3)c2c1] | 4-[6-[3,5-bis(trideuteriomethyl)isoxazol-4-yl]-1-[(4,4-difluorocyclohexyl)methyl]pyrrolo[3,2-b]pyridin-3-yl]benzoic acid | 472.2 |
| P-0909 | 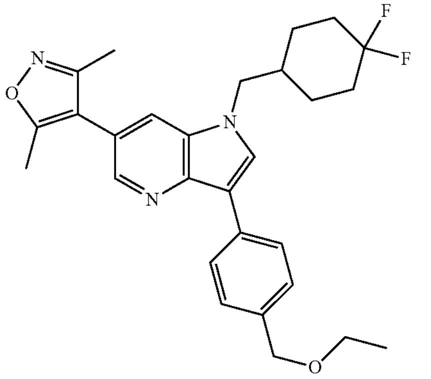 [SMILES: CCOCc1ccc(-c2cn(CC3CCC(F)(F)CC3)c3cc(-c4c(C)noc4C)cnc23)cc1] | 4-[1-[(4,4-difluorocyclohexyl)methyl]-3-[4-(ethoxymethyl)phenyl]pyrrolo[3,2-b]pyridin-6-yl]-3,5-dimethyl-isoxazole | 480.1 |

TABLE 31-continued

| Compound No. | Structure | Name | MS(ESI) [M + H+]+ observed |
| --- | --- | --- | --- |
| P-0910 | 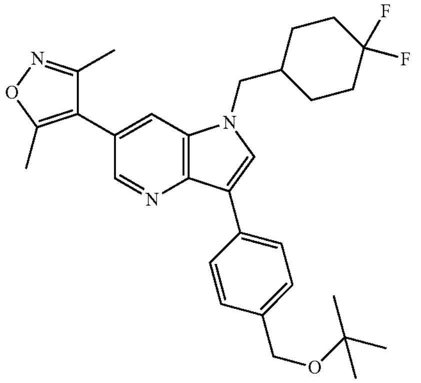 [SMILES: Cc1noc(C)c1-c1cnc2c(-c3ccc(COC(C)(C)C)cc3)cn(CC3CCC(F)(F)CC3)c2c1] | 4-[3-[4-(tert-butoxymethyl)phenyl]-1-[(4,4-difluorocyclohexyl)methyl]pyrrolo[3,2-b]pyridin-6-yl]-3,5-dimethyl-isoxazole | 508.1 |
| P-0911 | 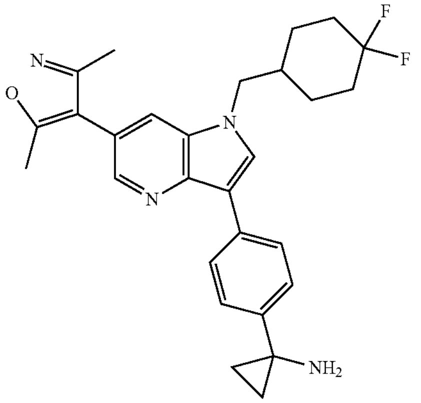 [SMILES: CC(=N)/C(=C(/C)O)c1cnc2c(-c3ccc(C4(N)CC4)cc3)cn(CC3CCC(F)(F)CC3)c2c1] | 1-[4-[1-[(4,4-difluorocyclohexyl)methyl]-6-(3,5-dimethylisoxazol-4-yl)pyrrolo[3,2-b]pyridin-3-yl]phenyl]cyclopropanamine | 477.0 |
| P-0912 | 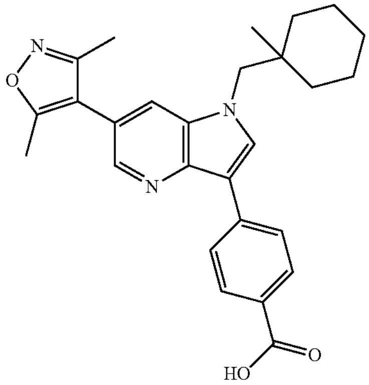 [SMILES: Cc1noc(C)c1-c1cnc2c(-c3ccc(C(=O)O)cc3)cn(CC3(C)CCCCC3)c2c1] | 4-[6-(3,5-dimethylisoxazol-4-yl)-1-[(1-methylcyclohexyl)methyl]pyrrolo[3,2-b]pyridin-3-yl]benzoic acid | 444.2 |
| P-0913 | 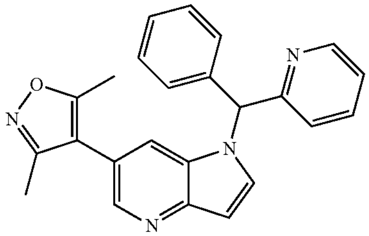 [SMILES: Cc1noc(C)c1-c1cnc2ccn(C(c3ccccc3)c3ccccn3)c2c1] | 3,5-dimethyl-4-[1-[phenyl(2-pyridyl)methyl]pyrrolo[3,2-b]pyridin-6-yl]isoxazole | 380.9 |

TABLE 31-continued

| Compound No. | Structure | Name | MS(ESI) [M + H+]+ observed |
|---|---|---|---|
| P-0914 | 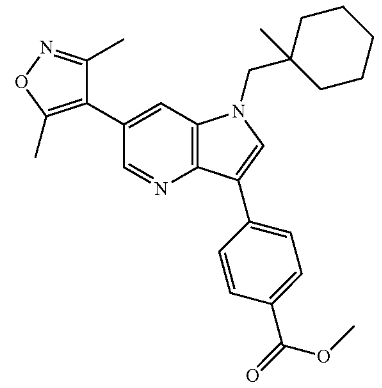 [SMILES: COC(=O)c1ccc(-c2cn(CC3(C)CCCCC3)c3cc(-c4c(C)noc4C)cnc23)cc1] | methyl 4-[6-(3,5-dimethylisoxazol-4-yl)-1-[(1-methylcyclohexyl)methyl]pyrrolo[3,2-b]pyridin-3-yl]benzoate | 458.0 |
| P-0915 | 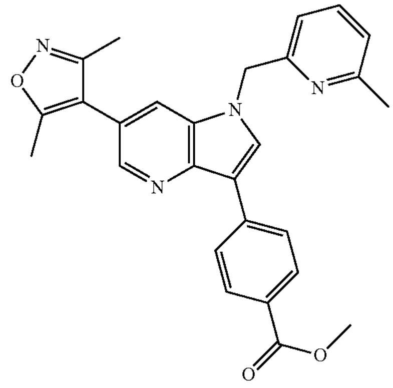 [SMILES: COC(=O)c1ccc(-c2cn(Cc3cccc(C)n3)c3cc(-c4c(C)noc4C)cnc23)cc1] | methyl 4-[6-(3,5-dimethylisoxazol-4-yl)-1-[(6-methyl-2-pyridyl)methyl]pyrrolo[3,2-b]pyridin-3-yl]benzoate | 452.9 |
| P-0916 | 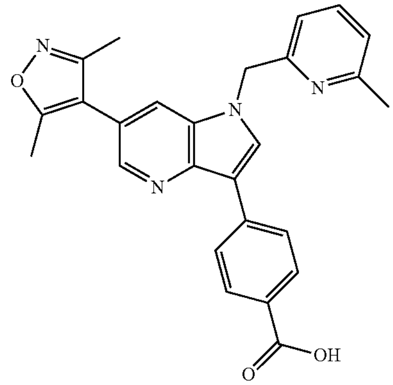 [SMILES: Cc1cccc(Cn2cc(-c3ccc(C(=O)O)cc3)c3ncc(-c4c(C)noc4C)cc32)n1] | 4-[6-(3,5-dimethylisoxazol-4-yl)-1-[(6-methyl-2-pyridyl)methyl]pyrrolo[3,2-b]pyridin-3-yl]benzoic acid | 438.9 |
| P-0917 | 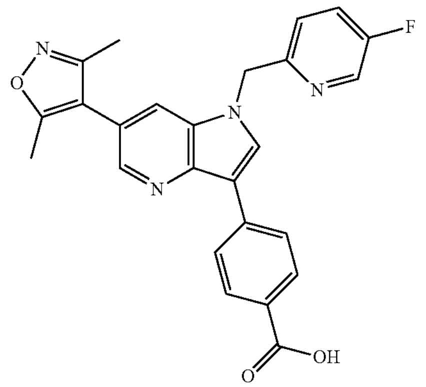 [SMILES: Cc1noc(C)c1-c1cnc2c(-c3ccc(C(=O)O)cc3)cn(Cc3ccc(F)cn3)c2c1] | 4-[6-(3,5-dimethylisoxazol-4-yl)-1-[(5-fluoro-2-pyridyl)methyl]pyrrolo[3,2-b]pyridin-3-yl]benzoic acid | 442.8 |

TABLE 31-continued
| Compound No. | Structure | Name | MS(ESI) [M + H+]+ observed |
|---|---|---|---|
| P-0918 | 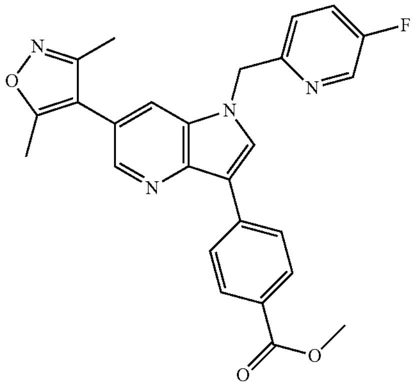 [SMILES: COC(=O)c1ccc(-c2cn(Cc3ccc(F)cn3)c3cc(-c4c(C)noc4C)cnc23)cc1] | methyl 4-[6-(3,5-dimethylisoxazol-4-yl)-1-[(5-fluoro-2-pyridyl)methyl]pyrrolo[3,2-b]pyridin-3-yl]benzoate | 457.3 |
| P-0919 | 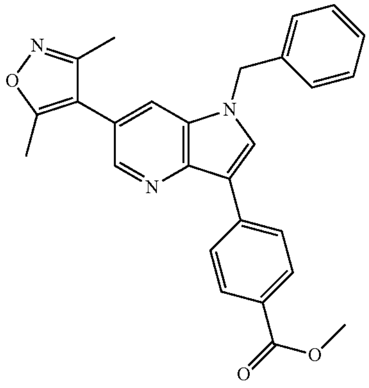 [SMILES: COC(=O)c1ccc(-c2cn(Cc3ccccc3)c3cc(-c4c(C)noc4C)cnc23)cc1] | methyl 4-[1-benzyl-6-(3,5-dimethylisoxazol-4-yl)pyrrolo[3,2-b]pyridin-3-yl]benzoate | 438.3 |
| P-0920 | 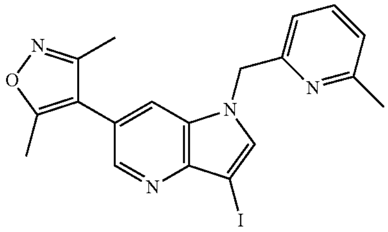 [SMILES: Cc1cccc(Cn2cc(I)c3ncc(-c4c(C)noc4C)cc32)n1] | 4-[3-iodo-1-[(6-methyl-2-pyridyl)methyl]pyrrolo[3,2-b]pyridin-6-yl]-3,5-dimethyl-isoxazole | 445.1 |
| P-0921 | 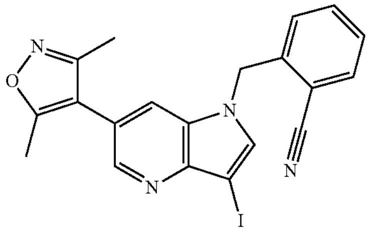 [SMILES: Cc1noc(C)c1-c1cnc2c(I)cn(Cc3ccccc3C#N)c2c1] | 2-[[6-(3,5-dimethylisoxazol-4-yl)-3-iodo-pyrrolo[3,2-b]pyridin-1-yl]methyl]benzonitrile | 455.9 |

TABLE 31-continued

| Compound No. | Structure | Name | MS(ESI) [M + H+]+ observed |
|---|---|---|---|
| P-0922 | 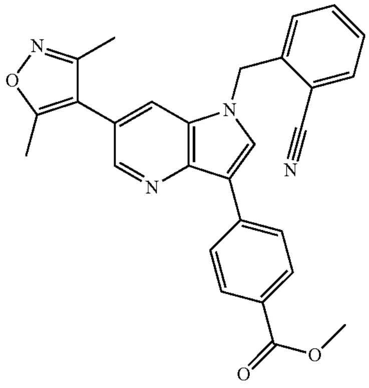 [SMILES: COC(=O)c1ccc(-c2cn(Cc3ccccc3C#N)c3cc(-c4c(C)noc4C)cnc23)cc1] | methyl 4-[1-[(2-cyanophenyl)methyl]-6-(3,5-dimethylisoxazol-4-yl)pyrrolo[3,2-b]pyridin-3-yl]benzoate | 462.9 |
| P-0923 | 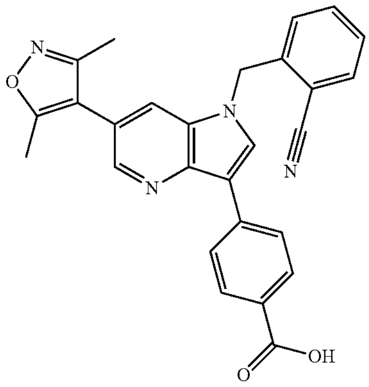 [SMILES: Cc1noc(C)c1-c1cnc2c(-c3ccc(C(=O)O)cc3)cn(Cc3ccccc3C#N)c2c1] | 4-(1-[(2-cyanophenyl)methyl]-6-(3,5-dimethylisoxazol-4-yl)pyrrolo[3,2-b]pyridin-3-yl]benzoic acid | 448.9 |
| P-0924 | 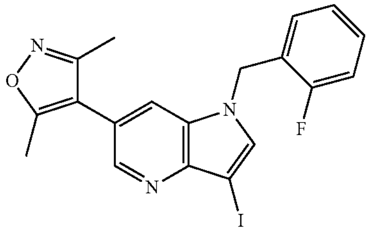 [SMILES: Cc1noc(C)c1-c1cnc2c(I)cn(Cc3ccccc3F)c2c1] | 4-[1-[(2-fluorophenyl)methyl]-3-iodo-pyrrolo[3,2-b]pyridin-6-yl]-3,5-dimethyl-isoxazole | 447.8 |
| P-0925 | 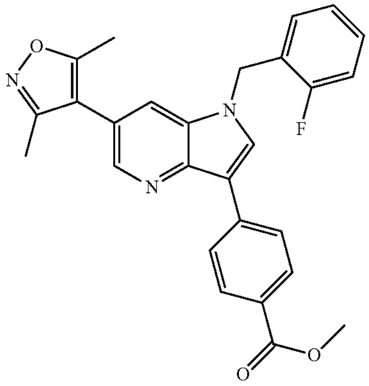 [SMILES: COC(=O)c1ccc(-c2cn(Cc3ccccc3F)c3cc(-c4c(C)noc4C)cnc23)cc1] | methyl 4-[6-(3,5-dimethylisoxazol-4-yl)-1-[(2-fluorophenyl)methyl]pyrrolo[3,2-b]pyridin-3-yl]benzoate | 456.3 |

TABLE 31-continued

| Compound No. | Structure | Name | MS(ESI) [M + H+]+ observed |
|---|---|---|---|
| P-0926 | 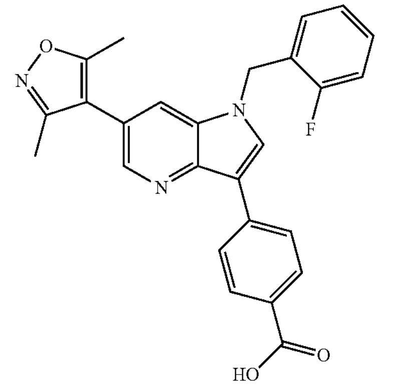 [SMILES: Cc1noc(C)c1-c1cnc2c(-c3ccc(C(=O)O)cc3)cn(Cc3ccccc3F)c2c1] | 4-[6-(3,5-dimethylisoxazol-4-yl)-1-[(2-fluorophenyl)methyl]pyrrolo[3,2-b]pyridin-3-yl]benzoic acid | 441.8 |
| P-0927 | 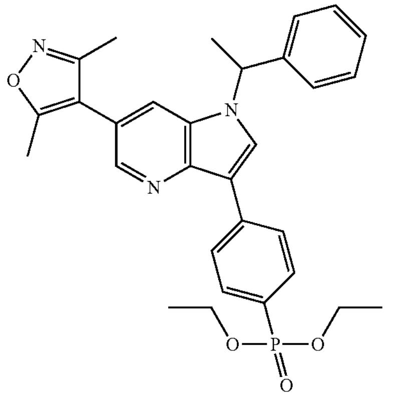 [SMILES: CCOP(=O)(OCC)c1ccc(-c2cn(C(C)c3ccccc3)c3cc(-c4c(C)noc4C)cnc23)cc1] | 4-[3-(4-diethoxyphosphorylphenyl)-1-(1-phenylethyl)pyrrolo[3,2-b]pyridin-6-yl]-3,5-dimethyl-isoxazole | 530.0 |
| P-0928 | 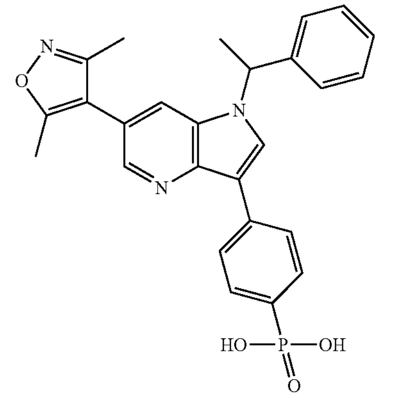 [SMILES: Cc1noc(C)c1-c1cnc2c(-c3ccc(P(=O)(O)O)cc3)cn(C(C)c3ccccc3)c2c1] | [4-[6-(3,5-dimethylisoxazol-4-yl)-1-(1-phenylethyl)pyrrolo[3,2-b]pyridin-3-yl]phenyl]phosphonic acid | 474.0 |
| P-0929 | 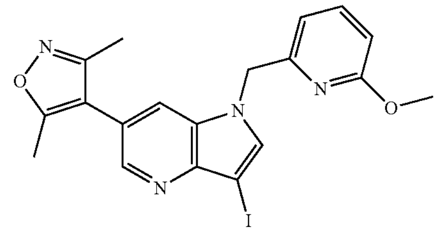 [SMILES: COc1cccc(Cn2cc(I)c3ncc(-c4c(C)noc4C)cc32)n1] | 4-[3-iodo-1-[(6-methoxy-2-pyridyl)methyl]pyrrolo[3,2-b]pyridin-6-yl]-3,5-dimethyl-isoxazole | 461.0 |

TABLE 31-continued

| Compound No. | Structure | Name | MS(ESI) [M + H+]+ observed |
|---|---|---|---|
| P-0930 | 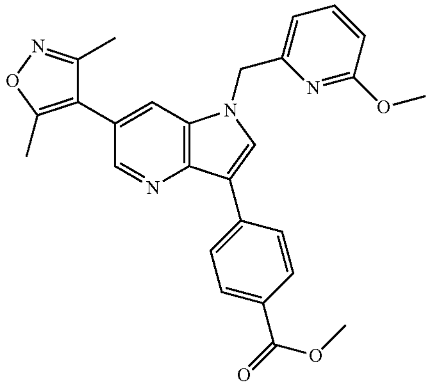 [SMILES: COC(=O)c1ccc(-c2cn(Cc3cccc(OC)n3)c3cc(-c4c(C)noc4C)cnc23)cc1] | methyl 4-[6-(3,5-dimethylisoxazol-4-yl)-1-[(6-methoxy-2-pyridyl)methyl]pyrrolo[3,2-b]pyridin-3-yl]benzoate | 469.0 |
| P-0931 | 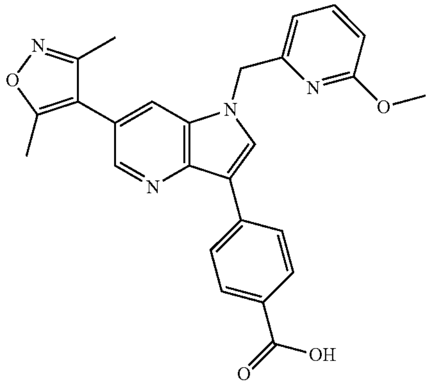 [SMILES: COc1cccc(Cn2cc(-c3ccc(C(=O)O)cc3)c3ncc(-c4c(C)noc4C)cc32)n1] | 4-[6-(3,5-dimethylisoxazol-4-yl)-1-[(6-methoxy-2-pyridyl)methyl]pyrrolo[3,2-b]pyridin-3-yl]benzoic acid | 455.1 |
| P-0932 | 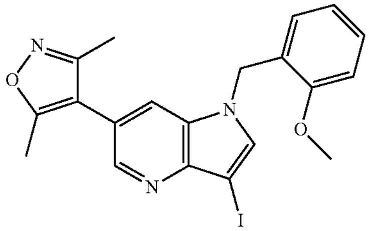 [SMILES: COc1ccccc1Cn1cc(I)c2ncc(-c3c(C)noc3C)cc21] | 4-[3-iodo-1-[(2-methoxyphenyl)methyl]pyrrolo[3,2-b]pyridin-6-yl]-3,5-dimethyl-isoxazole | 459.9 |
| P-0933 | 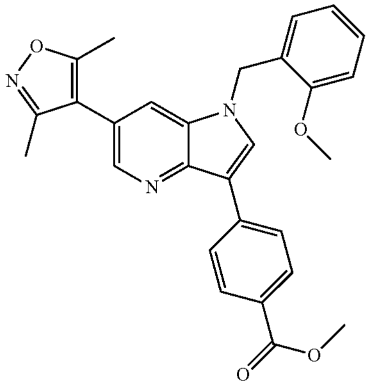 [SMILES: COC(=O)c1ccc(-c2cn(Cc3ccccc3OC)c3cc(-c4c(C)noc4C)cnc23)cc1] | methyl 4-[6-(3,5-dimethylisoxazol-4-yl)-1-[(2-methoxyphenyl)methyl]pyrrolo[3,2-b]pyridin-3-yl]benzoate | 467.9 |

TABLE 31-continued
| Compound No. | Structure | Name | MS(ESI) [M + H+]+ observed |
|---|---|---|---|
| P-0934 | 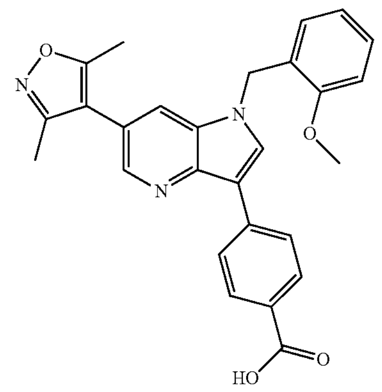 [SMILES: COc1ccccc1Cn1cc(-c2ccc(C(=O)O)cc2)c2ncc(-c3c(C)noc3C)cc21] | 4-[6-(3,5-dimethylisoxazol-4-yl)-1-[(2-methoxyphenyl)methyl]pyrrolo[3,2-b]pyridin-3-yl]benzoic acid | 454.0 |
| P-0935 | 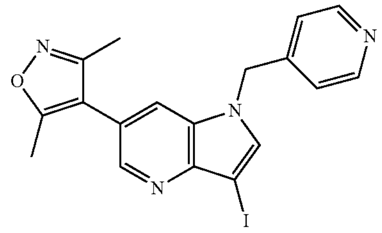 [SMILES: Cc1noc(C)c1-c1cnc2c(I)cn(Cc3ccncc3)c2c1] | 4-[3-iodo-1-(4-pyridylmethyl)pyrrolo[3,2-b]pyridin-6-yl]-3,5-dimethyl-isoxazole | 430.9 |
| P-0936 | 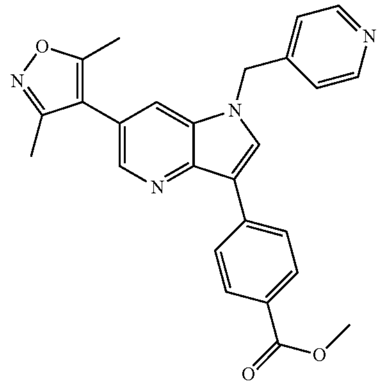 [SMILES: COC(=O)c1ccc(-c2cn(Cc3ccncc3)c3cc(-c4c(C)noc4C)cnc23)cc1] | methyl 4-[6-(3,5-dimethylisoxazol-4-yl)-1-(4-pyridylmethyl)pyrrolo[3,2-b]pyridin-3-yl]benzoate | 438.9 |
| P-0937 | 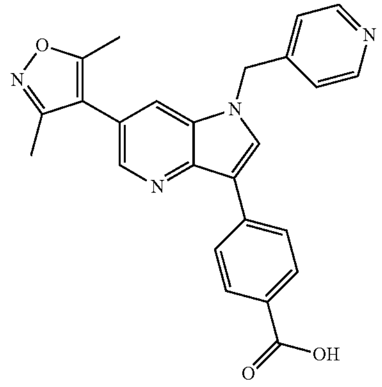 [SMILES: Cc1noc(C)c1-c1cnc2c(-c3ccc(C(=O)O)cc3)cn(Cc3ccncc3)c2c1] | 4-[6-(3,5-dimethylisoxazol-4-yl)-1-(4-pyridylmethyl)pyrrolo[3,2-b]pyridin-3-yl]benzoic acid | 425.1 |

TABLE 31-continued

| Compound No. | Structure | Name | MS(ESI) [M + H+]+ observed |
|---|---|---|---|
| P-0938 | 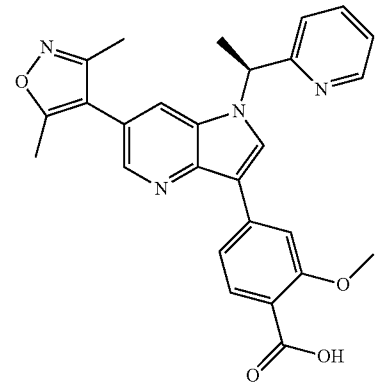 [SMILES: COc1cc(-c2cn([C@@H](C)c3ccccn3)c3cc(-c4c(C)noc4C)cnc23)ccc1C(=O)O] | 4-[6-(3,5-dimethylisoxazol-4-yl)-1-[(1S)-1-(2-pyridyl)ethyl]pyrrolo[3,2-b]pyridin-3-yl]-2-methoxy-benzoic acid | 469.1 |
| P-0939 | 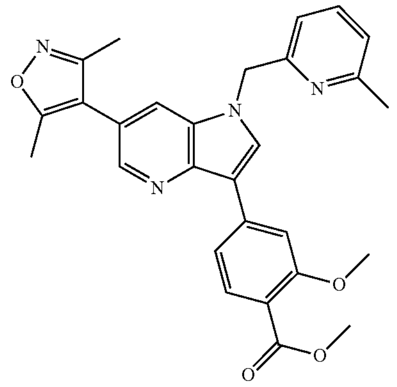 [SMILES: COC(=O)c1ccc(-c2cn(Cc3cccc(C)n3)c3cc(-c4c(C)noc4C)cnc23)cc1OC] | methyl 4-[6-(3,5-dimethylisoxazol-4-yl)-1-[(6-methyl-2-pyridyl)methyl]pyrrolo[3,2-b]pyridin-3-yl]-2-methoxy-benzoate | 482.9 |
| P-0940 | 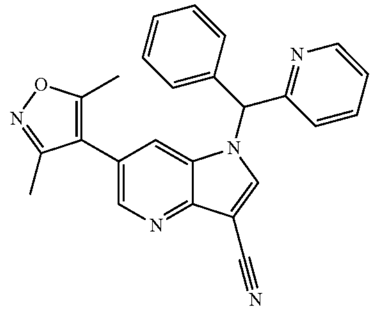 [SMILES: Cc1noc(C)c1-c1cnc2c(C#N)cn(C(c3ccccc3)c3ccccn3)c2c1] | 6-(3,5-dimethylisoxazol-4-yl)-1-[phenyl(2-pyridyl)methyl]pyrrolo[3,2-b]pyridine-3-carbonitrile | 406.1 |
| P-0941 | 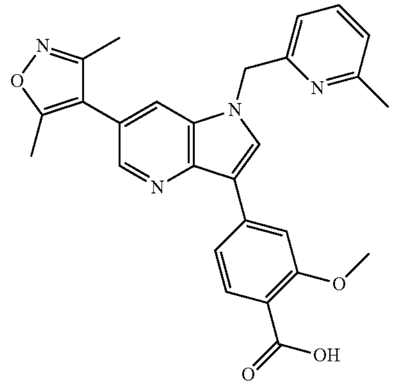 [SMILES: COc1cc(-c2cn(Cc3cccc(C)n3)c3cc(-c4c(C)noc4C)cnc23)ccc1C(=O)O] | 4-[6-(3,5-dimethylisoxazol-4-yl)-1-[(6-methyl-2-pyridyl)methyl]pyrrolo[3,2-b]pyridin-3-yl]-2-methoxy-benzoic acid | 469.0 |

TABLE 31-continued

| Compound No. | Structure | Name | MS(ESI) [M + H+]+ observed |
|---|---|---|---|
| P-0942 | 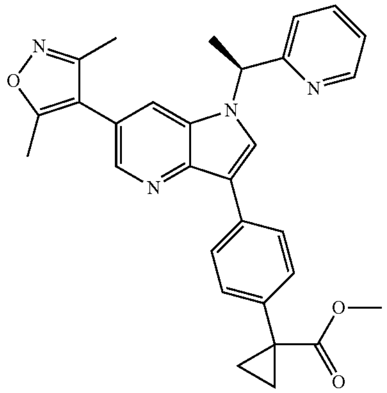 [SMILES: COC(=O)C1(c2ccc(-c3cn([C@@H](C)c4ccccn4)c4cc(-c5c(C)noc5C)cnc34)cc2)CC1] | methyl 1-[4-[6-(3,5-dimethylisoxazol-4-yl)-1-[(1S)-1-(2-pyridyl)ethyl]pyrrolo[3,2-b]pyridin-3-yl]phenyl]cyclopropanecarboxylate | 493.3 |
| P-0943 | 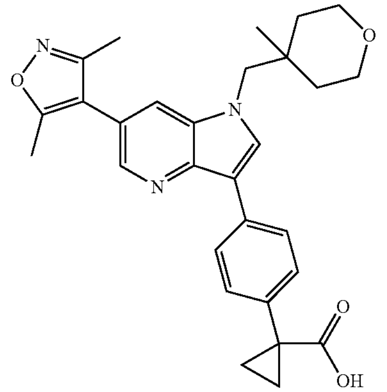 [SMILES: Cc1noc(C)c1-c1cnc2c(-c3ccc(C4(C(=O)O)CC4)cc3)cn(CC3(C)CCOCC3)c2c1] | 1-[4-[6-(3,5-dimethylisoxazol-4-yl)-1-[(4-methyltetrahydropyran-4-yl)methyl]pyrrolo[3,2-b]pyridin-3-yl]phenyl]cyclopropanecarboxylic acid | 486.4 |
| P-0944 | 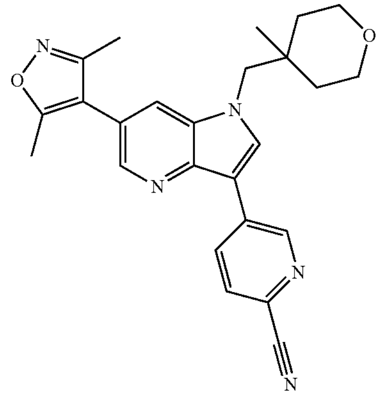 [SMILES: Cc1noc(C)c1-c1cnc2c(-c3ccc(C#N)nc3)cn(CC3(C)CCOCC3)c2c1] | 5-[6-(3,5-dimethylisoxazol-4-yl)-1-[(4-methyltetrahydropyran-4-yl)methyl]pyrrolo[3,2-b]pyridin-3-yl]pyridine-2-carbonitrile | 428.5 |
| P-0945 | 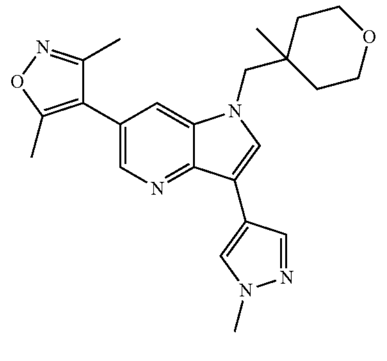 [SMILES: Cc1noc(C)c1-c1cnc2c(-c3cnn(C)c3)cn(CC3(C)CCOCC3)c2c1] | 3,5-dimethyl-4-[3-(1-methylpyrazol-4-yl)-1-[(4-methyltetrahydropyran-4-yl)methyl]pyrrolo[3,2-b]pyridin-6-yl]isoxazole | 406.6 |

TABLE 31-continued

| Compound No. | Structure | Name | MS(ESI) [M + H+]+ observed |
|---|---|---|---|
| P-0946 | 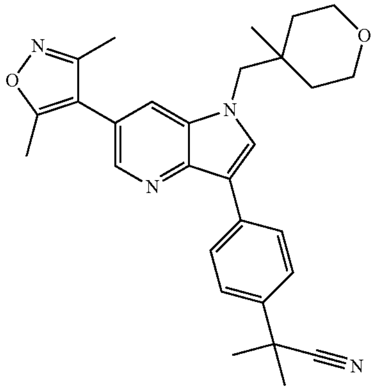 [SMILES: Cc1noc(C)c1-c1cnc2c(-c3ccc(C(C)(C)C#N)cc3)cn(CC3(C)CCOCC3)c2c1] | 2-[4-[6-(3,5-dimethylisoxazol-4-yl)-1-[(4-methyltetrahydropyran-4-yl)methyl]pyrrolo[3,2-b]pyridin-3-yl]phenyl]-2-methyl-propanenitrile | 469.6 |
| P-0947 | 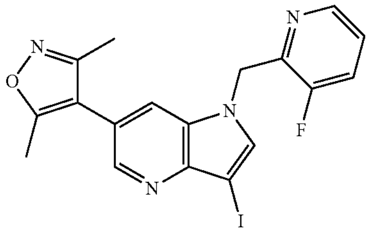 [SMILES: Cc1noc(C)c1-c1cnc2c(I)cn(Cc3ncccc3F)c2c1] | 4-[1-[(3-fluoro-2-pyridyl)methyl]-3-iodo-pyrrolo[3,2-b]pyridin-6-yl]-3,5-dimethyl-isoxazole | 449.0 |
| P-0948 | 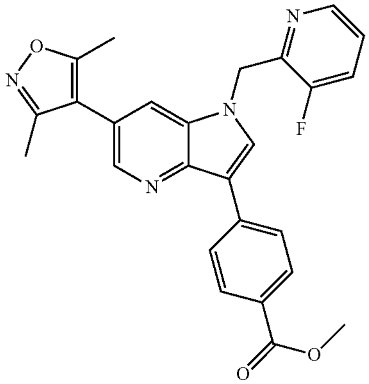 [SMILES: COC(=O)c1ccc(-c2cn(Cc3ncccc3F)c3cc(-c4c(C)noc4C)cnc23)cc1] | methyl 4-[6-(3,5-dimethylisoxazol-4-yl)-1-[(3-fluoro-2-pyridyl)methyl]pyrrolo[3,2-b]pyridin-3-yl]benzoate | 456.9 |
| P-0949 | 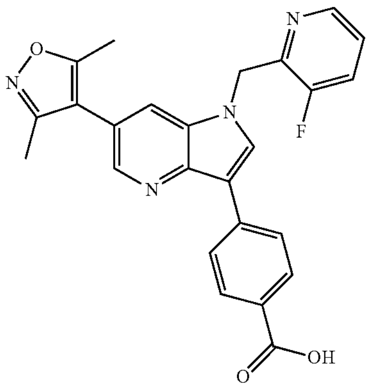 [SMILES: Cc1noc(C)c1-c1cnc2c(-c3ccc(C(=O)O)cc3)cn(Cc3ncccc3F)c2c1] | 4-[6-(3,5-dimethylisoxazol-4-yl)-1-[(3-fluoro-2-pyridyl)methyl]pyrrolo[3,2-b]pyridin-3-yl]benzoic acid | 442.9 |

TABLE 31-continued
| Compound No. | Structure | Name | MS(ESI) [M + H+]+ observed |
|---|---|---|---|
| P-0950 | 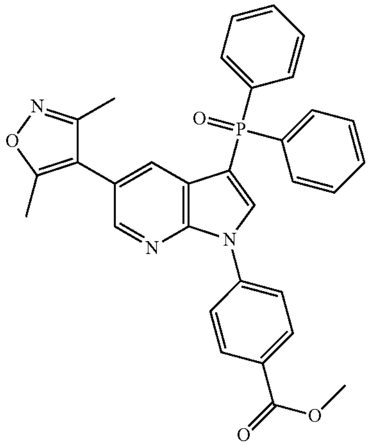 [SMILES: COC(=O)c1ccc(-n2cc(P(=O)(c3ccccc3)c3ccccc3)c3cc(-c4c(C)noc4C)cnc32)cc1] | methyl 4-[5-(3,5-dimethylisoxazol-4-yl)-3-diphenylphosphoryl-pyrrolo[2,3-b]pyridin-1-yl]benzoate | 547.8 |
| P-0951 | 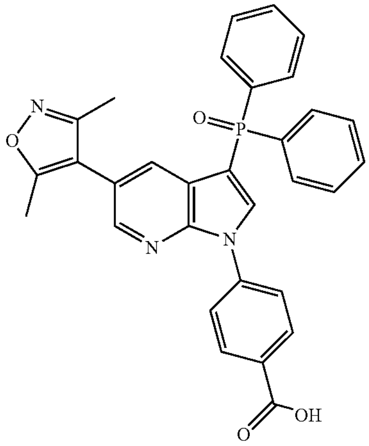 [SMILES: Cc1noc(C)c1-c1cnc2c(c1)c(P(=O)(c1ccccc1)c1ccccc1)cn2-c1ccc(C(=O)O)cc1] | 4-[5-(3,5-dimethylisoxazol-4-yl)-3-diphenylphosphoryl-pyrrolo[2,3-b]pyridin-1-yl]benzoic acid | 534.1 |
| P-0952 | 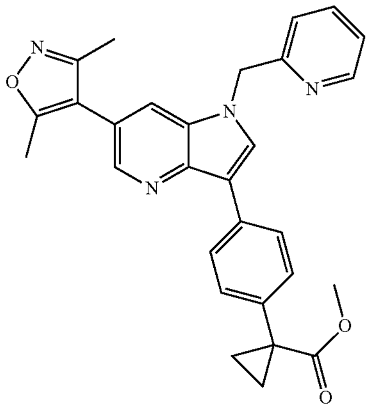 [SMILES: COC(=O)C1(c2ccc(-c3cn(Cc4ccccn4)c4cc(-c5c(C)noc5C)cnc34)cc2)CC1] | methyl 1-[4-[6-(3,5-dimethylisoxazol-4-yl)-1-(2-pyridylmethyl)pyrrolo[3,2-b]pyridin-3-yl]phenyl]cyclopropanecarboxylate | 479.3 |

TABLE 31-continued

| Compound No. | Structure | Name | MS(ESI) [M + H+]+ observed |
|---|---|---|---|
| P-0953 | 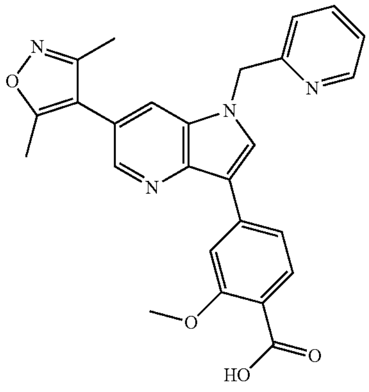 [SMILES: COc1cc(-c2cn(Cc3ccccn3)c3cc(-c4c(C)noc4C)cnc23)ccc1C(=O)O] | 4-[6-(3,5-dimethylisoxazol-4-yl)-1-(2-pyridylmethyl)pyrrolo[3,2-b]pyridin-3-yl]-2-methoxy-benzoic acid | 454.9 |
| P-0954 | 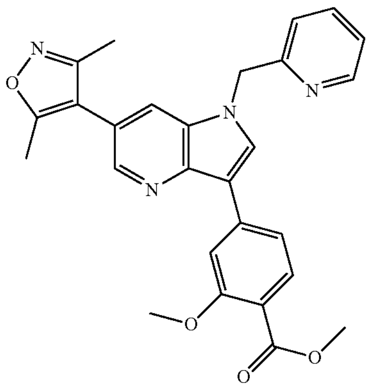 [SMILES: COC(=O)c1ccc(-c2cn(Cc3ccccn3)c3cc(-c4c(C)noc4C)cnc23)cc1OC] | methyl 4-[6-(3,5-dimethylisoxazol-4-yl)-1-(2-pyridylmethyl)pyrrolo[3,2-b]pyridin-3-yl]-2-methoxy-benzoate | 468.9 |
| P-0955 | 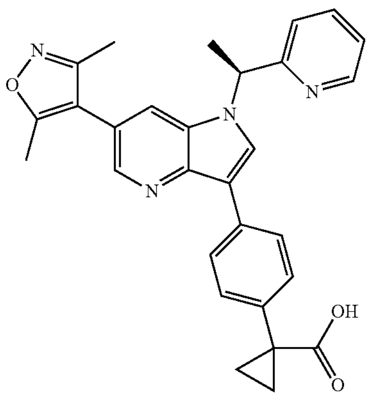 [SMILES: Cc1noc(C)c1-c1cnc2c(-c3ccc(C4(C(=O)O)CC4)cc3)cn([C@@H](C)c3ccccn3)c2c1] | 1-[4-[6-(3,5-dimethylisoxazol-4-yl)-1-[(1S)-1-(2-pyridyl)ethyl]pyrrolo[3,2-b]pyridin-3-yl]phenyl]cyclopropanecarboxylic acid | 478.9 |
| P-0956 | 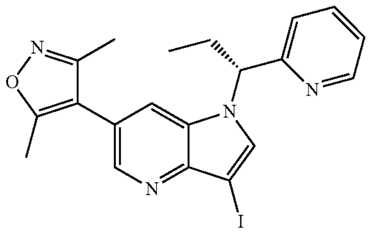 [SMILES: CC[C@H](c1ccccn1)n1cc(I)c2ncc(-c3c(C)noc3C)cc21] | 4-[3-iodo-1-[(1R)-1-(2-pyridyl)propyl]pyrrolo[3,2-b]pyridin-6-yl]-3,5-dimethyl-isoxazole | 458.9 |

TABLE 31-continued
| Compound No. | Structure | Name | MS(ESI) [M + H+]+ observed |
|---|---|---|---|
| P-0957 | 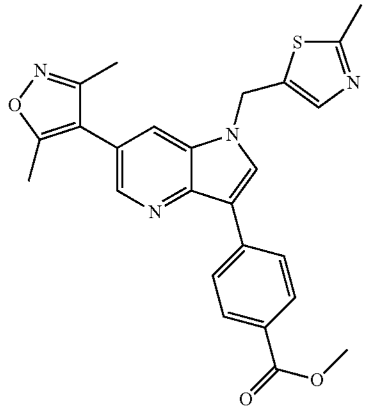 [SMILES: COC(=O)c1ccc(-c2cn(Cc3cnc(C)s3)c3cc(-c4c(C)noc4C)cnc23)cc1] | methyl 4-[6-(3,5-dimethylisoxazol-4-yl)-1-[(2-methylthiazol-5-yl)methyl]pyrrolo[3,2-b]pyridin-3-yl]benzoate | 459.0 |
| P-0958 | 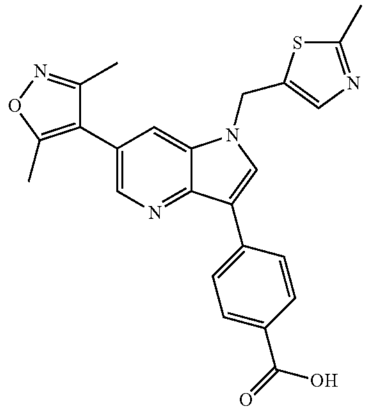 [SMILES: Cc1ncc(Cn2cc(-c3ccc(C(=O)O)cc3)c3ncc(-c4c(C)noc4C)cc32)s1] | 4-[6-(3,5-dimethylisoxazol-4-yl)-1-[(2-methylthiazol-5-yl)methyl]pyrrolo[3,2-b]pyridin-3-yl]benzoic acid | 445.0 |
| P-0959 | 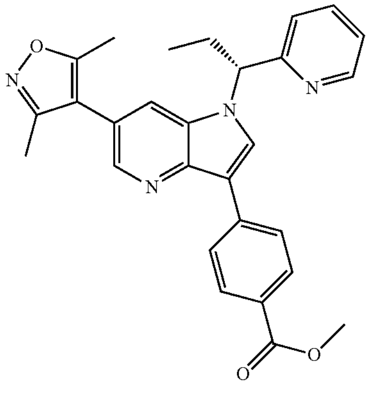 [SMILES: CC[C@H](c1ccccn1)n1cc(-c2ccc(C(=O)OC)cc2)c2ncc(-c3c(C)noc3C)cc21] | methyl 4-[6-(3,5-dimethylisoxazol-4-yl)-1-[(1R)-1-(2-pyridyl)propyl]pyrrolo[3,2-b]pyridin-3-yl]benzoate | 467.0 |

TABLE 31-continued

| Compound No. | Structure | Name | MS(ESI) [M + H+]+ observed |
| --- | --- | --- | --- |
| P-0960 | 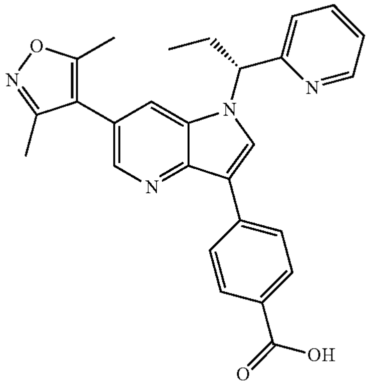 [SMILES: CC[C@H](c1ccccn1)n1cc(-c2ccc(C(=O)O)cc2)c2ncc(-c3c(C)noc3C)cc21] | 4-[6-(3,5-dimethylisoxazol-4-yl)-1-[(1R)-1-(2-pyridyl)propyl]pyrrolo[3,2-b]pyridin-3-yl]benzoic acid | 452.9 |
| P-0961 | 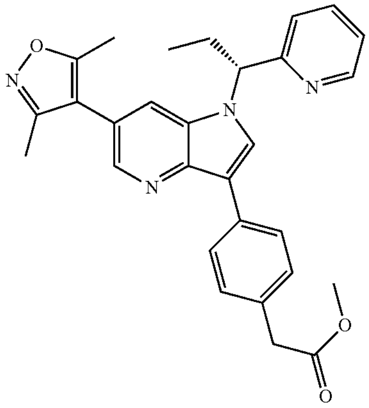 [SMILES: CC[C@H](c1ccccn1)n1cc(-c2ccc(CC(=O)OC)cc2)c2ncc(-c3c(C)noc3C)cc21] | methyl 2-[4-[6-(3,5-dimethylisoxazol-4-yl)-1-[(1R)-1-(2-pyridyl)propyl]pyrrolo[3,2-b]pyridin-3-yl]phenyl]acetate | 481.0 |
| P-0962 | 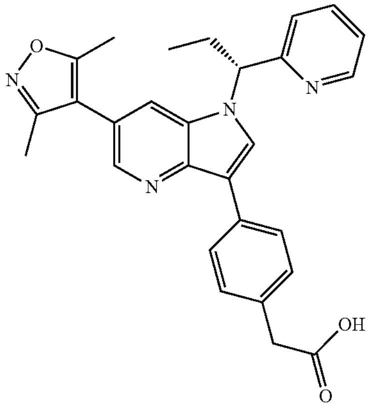 [SMILES: CC[C@H](c1ccccn1)n1cc(-c2ccc(CC(=O)O)cc2)c2ncc(-c3c(C)noc3C)cc21] | 2-[4-[6-(3,5-dimethylisoxazol-4-yl)-1-[(1R)-1-(2-pyridyl)propyl]pyrrolo[3,2-b]pyridin-3-yl]phenyl]acetic acid | 467.0 |
| P-0963 | 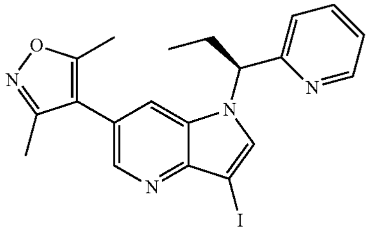 [SMILES: CC[C@@H](c1ccccn1)n1cc(I)c2ncc(-c3c(C)noc3C)cc21] | 4-[3-iodo-1-[(1S)-1-(2-pyridyl)propyl]pyrrolo[3,2-b]pyridin-6-yl]-3,5-dimethyl-isoxazole | 458.9 |

TABLE 31-continued
| Compound No. | Structure | Name | MS(ESI) [M + H+]+ observed |
|---|---|---|---|
| P-0964 | 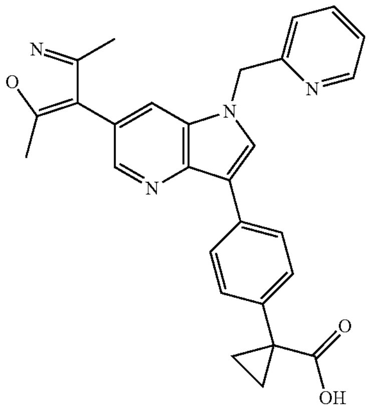 [SMILES: CC(=N)/C(=C(/C)O)c1cnc2c(-c3ccc(C4(C(=O)O)CC4)cc3)cn(Cc3ccccn3)c2c1] | 1-[4-[6-(3,5-dimethylisoxazol-4-yl)-1-(2-pyridylmethyl)pyrrolo[3,2-b]pyridin-3-yl]phenyl]cyclopropanecarboxylic acid | 465.0 |
| P-0965 | 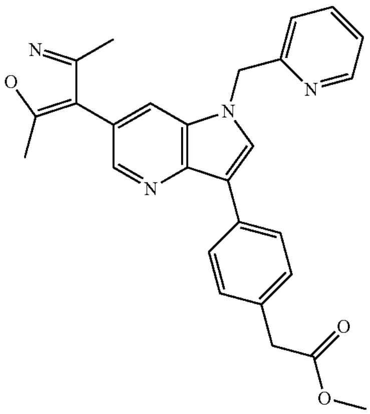 [SMILES: COC(=O)Cc1ccc(-c2cn(Cc3ccccn3)c3cc(/C(C(C)=N)=C(\C)O)cnc23)cc1] | methyl 2-[4-[6-(3,5-dimethylisoxazol-4-yl)-1-(2-pyridylmethyl)pyrrolo[3,2-b]pyridin-3-yl]phenyl]acetate | 452.9 |
| P-0966 | 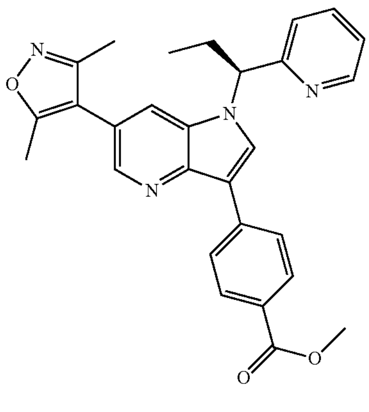 [SMILES: CC[C@@H](c1ccccn1)n1cc(-c2ccc(C(=O)OC)cc2)c2ncc(-c3c(C)noc3C)cc21] | methyl 4-[6-(3,5-dimethylisoxazol-4-yl)-1-[(1S)-1-(2-pyridyl)propyl]pyrrolo[3,2-b]pyridin-3-yl]benzoate | 467.2 |

TABLE 31-continued
| Compound No. | Structure | Name | MS(ESI) [M + H+]+ observed |
|---|---|---|---|
| P-0967 | 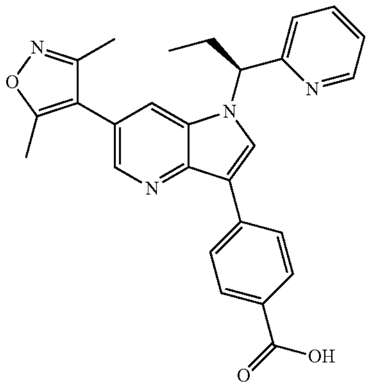 [SMILES: CC[C@@H](c1ccccn1)n1cc(-c2ccc(C(=O)O)cc2)c2ncc(-c3c(C)noc3C)cc21] | 4-[6-(3,5-dimethylisoxazol-4-yl)-1-[(1S)-1-(2-pyridyl)propyl]pyrrolo[3,2-b]pyridin-3-yl]benzoic acid | 452.8 |
| P-0968 | 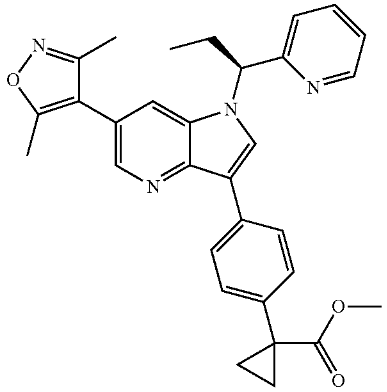 [SMILES: CC[C@@H](c1ccccn1)n1cc(-c2ccc(C3(C(=O)OC)CC3)cc2)c2ncc(-c3c(C)noc3C)cc21] | methyl 1-[4-[6-(3,5-dimethylisoxazol-4-yl)-1-[(1S)-1-(2-pyridyl)propyl]pyrrolo[3,2-b]pyridin-3-yl]phenyl]cyclopropanecarboxylate | 507.0 |
| P-0969 | 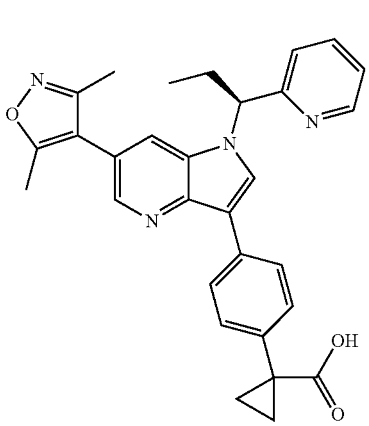 [SMILES: CC[C@@H](c1ccccn1)n1cc(-c2ccc(C3(C(=O)O)CC3)cc2)c2ncc(-c3c(C)noc3C)cc21] | 1-[4-[6-(3,5-dimethylisoxazol-4-yl)-1-[(1S)-1-(2-pyridyl)propyl]pyrrolo[3,2-b]pyridin-3-yl]phenyl]cyclopropanecarboxylic acid | 493.3 |

TABLE 31-continued

| Compound No. | Structure | Name | MS(ESI) [M + H+]+ observed |
|---|---|---|---|
| P-0970 | 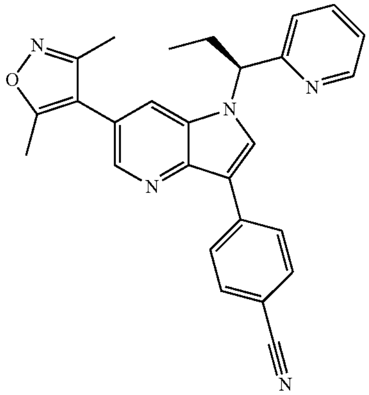 [SMILES: CC[C@@H](c1ccccn1)n1cc(-c2ccc(C#N)cc2)c2ncc(-c3c(C)noc3C)cc21] | 4-[6-(3,5-dimethylisoxazol-4-yl)-1-[(1S)-1-(2-pyridyl)propyl]pyrrolo[3,2-b]pyridin-3-yl]benzonitrile | 434.0 |
| P-0971 | 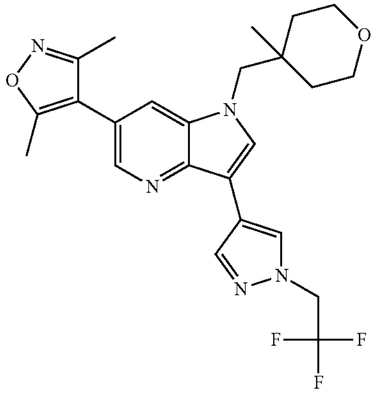 [SMILES: Cc1noc(C)c1-c1cnc2c(-c3cnn(CC(F)(F)F)c3)cn(CC3(C)CCOCC3)c2c1] | 3,5-dimethyl-4-[1-[(4-methyltetrahydropyran-4-yl)methyl]-3-[1-(2,2,2-trifluoroethyl)pyrazol-4-yl]pyrrolo[3,2-b]pyridin-6-yl]isoxazole | 474.1 |
| P-0972 | 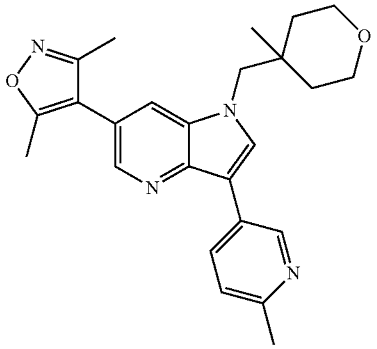 [SMILES: Cc1ccc(-c2cn(CC3(C)CCOCC3)c3cc(-c4c(C)noc4C)cnc23)cn1] | 3,5-dimethyl-4-[3-(6-methyl-3-pyridyl)-1-[(4-methyltetrahydropyran-4-yl)methyl]pyrrolo[3,2-b]pyridin-6-yl]isoxazole | 417.4 |
| P-0973 | 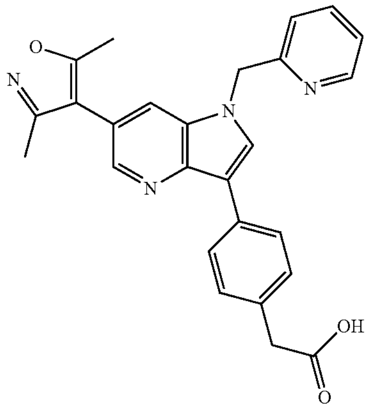 [SMILES: CC(=N)/C(=C(/C)O)c1cnc2c(-c3ccc(CC(=O)O)cc3)cn(Cc3ccccn3)c2c1] | 2-[4-[6-(3,5-dimethylisoxazol-4-yl)-1-(2-pyridylmethyl)pyrrolo[3,2-b]pyridin-3-yl]phenyl]acetic acid | 438.9 |

TABLE 31-continued
| Compound No. | Structure | Name | MS(ESI) [M + H+]+ observed |
|---|---|---|---|
| P-0974 | AND Enantiomer 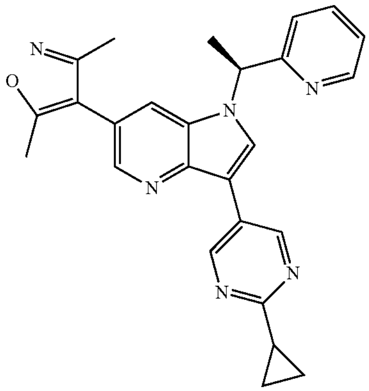 | 4-[3-(2-cyclopropylpyrimidin-5-yl)-1-[(1S)-1-(2-pyridyl)ethyl]pyrrolo[3,2-b]pyridin-6-yl]-3,5-dimethyl-isoxazole | 437.2 |
| P-0975 | AND Enantiomer 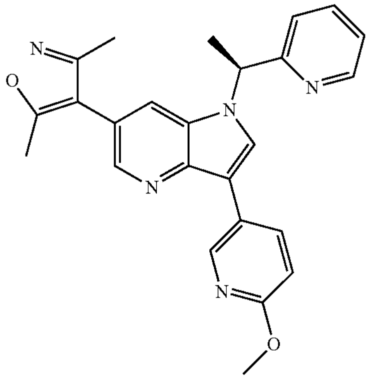 | 4-[3-(6-methoxy-3-pyridyl)-1-[(1S)-1-(2-pyridyl)ethyl]pyrrolo[3,2-b]pyridin-6-yl]-3,5-dimethyl-isoxazole | 426.4 |
| P-0976 | AND Enantiomer 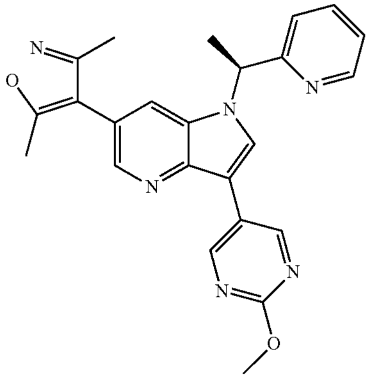 | 4-[3-(2-methoxypyrimidin-5-yl)-1-[(1S)-1-(2-pyridyl)ethyl]pyrrolo[3,2-b]pyridin-6-yl]-3,5-dimethyl-isoxazole | 427.3 |

TABLE 31-continued

| Compound No. | Structure | Name | MS(ESI) [M + H+]+ observed |
|---|---|---|---|
| P-0977 | AND Enantiomer 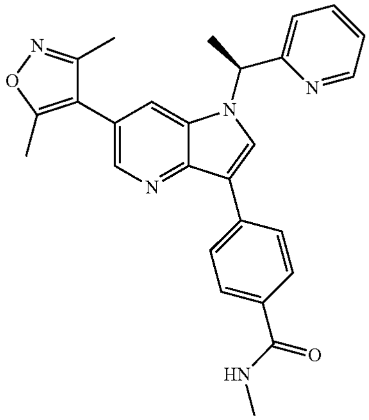 | 4- [6-(3,5-dimethylisoxazol-4-yl)-1-[(1S)-1-(2-pyridyl)ethyl]pyrrolo[3,2-b]pyridin-3-yl]-N-methyl-benzamide | 452.2 |
| P-0978 | AND Enantiomer 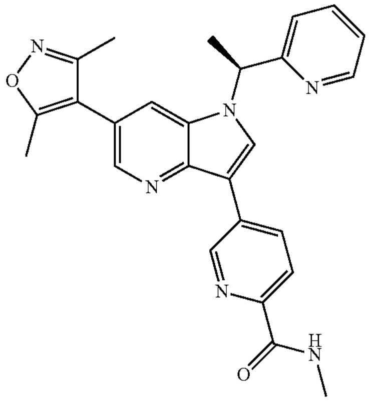 | 5- [6-(3,5-dimethylisoxazol-4-yl)-1-[(1S)-1-(2-pyridyl)ethyl]pyrrolo[3,2-b]pyridin-3-yl]-N-methyl-pyridine-2-carboxamide | 453.1 |
| P-0979 | AND Enantiomer 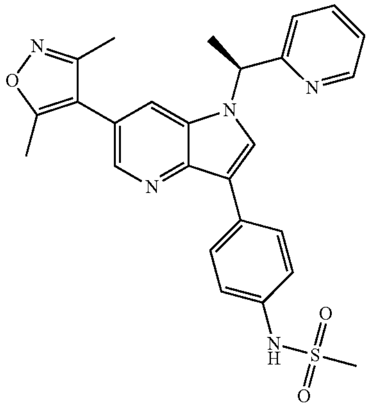 | N-[4-[6-(3,5-dimethylisoxazol-4-yl)-1-[(1S)-1-(2-pyridyl)ethyl]pyrrolo[3,2-b]pyridin-3-yl]phenyl]methanesulfonamide | 488.2 |

TABLE 31-continued

| Compound No. | Structure | Name | MS(ESI) [M + H+]+ observed |
| --- | --- | --- | --- |
| P-0980 | AND Enantiomer 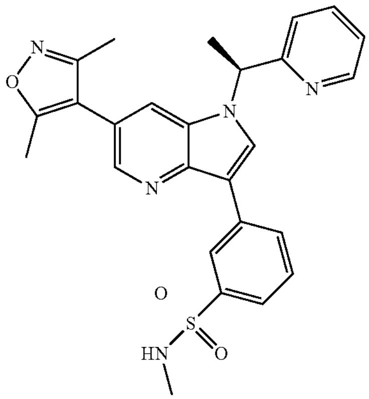 | 3-[6-(3,5-dimethylisoxazol-4-yl)-1-[(1S)-1-(2-pyridyl)ethyl]pyrrolo[3,2-b]pyridin-3-yl]-N-methyl-benzenesulfonamide | 488.2 |
| P-0981 | AND Enantiomer 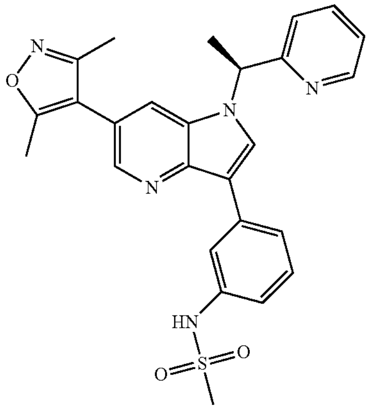 | N-[3-[6-(3,5-dimethylisoxazol-4-yl)-1-[(1S)-1-(2-pyridyl)ethyl]pyrrolo[3,2-b]pyridin-3-yl]phenyl]methanesulfonamide | 488.2 |
| P-0982 | AND Enantiomer 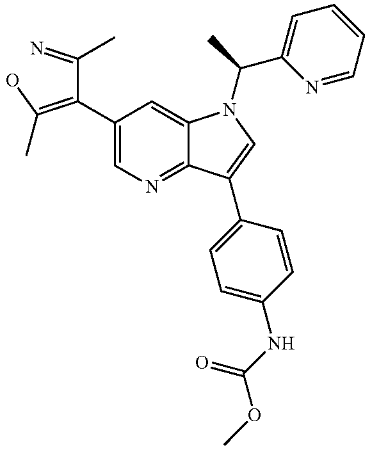 | methyl N-[4-[6-(3,5-dimethylisoxazol-4-yl)-1-[(1S)-1-(2-pyridyl)ethyl]pyrrolo[3,2-b]pyridin-3-yl]phenyl]carbamate | 468.4 |

TABLE 31-continued

| Compound No. | Structure | Name | MS(ESI) [M + H+]+ observed |
|---|---|---|---|
| P-0983 | AND Enantiomer 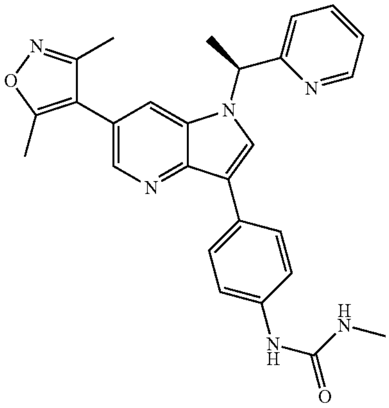 | 1-[4-[6-(3,5-dimethylisoxazol-4-yl)-1-[(1S)-1-(2-pyridyl)ethyl]pyrrolo[3,2-b]pyridin-3-yl]phenyl]-3-methyl-urea | 467.5 |
| P-0984 | AND Enantiomer 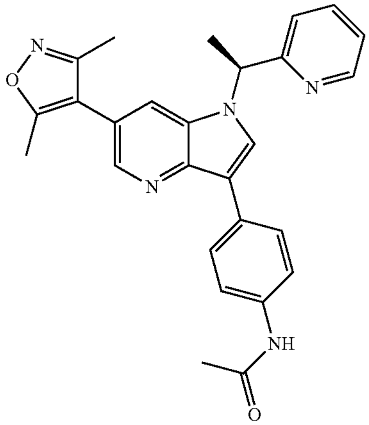 | N-[4-[6-(3,5-dimethylisoxazol-4-yl)-1-[(1S)-1-(2-pyridyl)ethyl]pyrrolo[3,2-b]pyridin-3-yl]phenyl]acetamide | 452.2 |
| P-0985 | 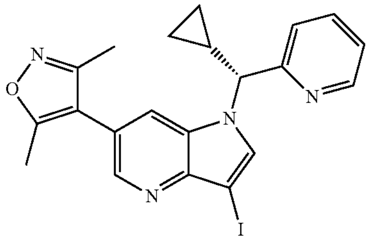 [SMILES: Cc1noc(C)c1-c1cnc2c(I)cn([C@@H](c3ccccn3)C3CC3)c2c1] | 4-[1-[(R)-cyclopropyl(2-pyridyl)methyl]-3-iodo-pyrrolo[3,2-b]pyridin-6-yl]-3,5-dimethyl-isoxazole | 471.1 |
| P-0986 | 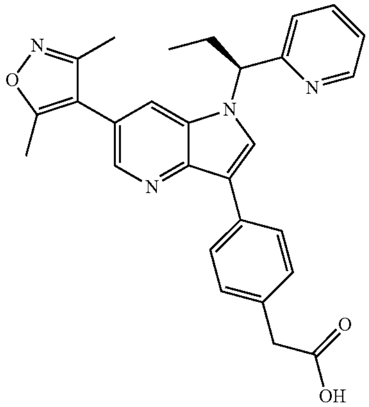 [SMILES: CC[C@@H](c1ccccn1)n1cc(-c2ccc(CC(=O)O)cc2)c2ncc(-c3c(C)noc3C)cc21] | 2-[4-[6-(3,5-dimethylisoxazol-4-yl)-1-[(1S)-1-(2-pyridyl)propyl]pyrrolo[3,2-b]pyridin-3-yl]phenyl]acetic acid | 467.0 |

TABLE 31-continued

| Compound No. | Structure | Name | MS(ESI) [M + H+]+ observed |
|---|---|---|---|
| P-0987 | 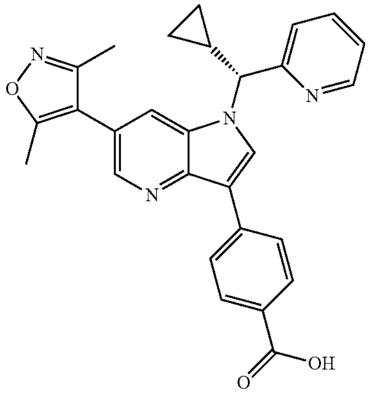 [SMILES: Cc1noc(C)c1-c1cnc2c(-c3ccc(C(=O)O)cc3)cn([C@@H](c3ccccn3)C3CC3)c2c1] | 4-[1-[(R)-cyclopropyl(2-pyridyl)methyl]-6-(3,5-dimethylisoxazol-4-yl)pyrrolo[3,2-b]pyridin-3-yl]benzoic acid | 465.0 |
| P-0988 | 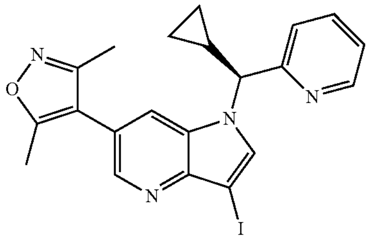 [SMILES: Cc1noc(C)c1-c1cnc2c(I)cn([C@H](c3ccccn3)C3CC3)c2c1] | 4-[1-[(S)-cyclopropyl(2-pyridyl)methyl]-3-iodo-pyrrolo[3,2-b]pyridin-6-yl]-3,5-dimethyl-isoxazole | 470.8 |
| P-0989 | 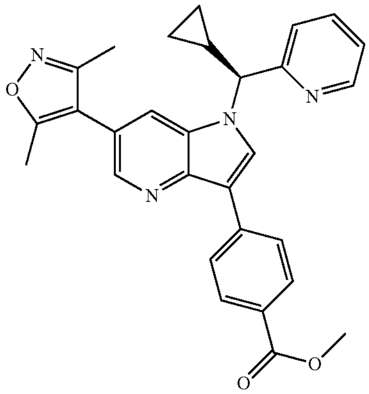 [SMILES: COC(=O)c1ccc(-c2cn([C@H](c3ccccn3)C3CC3)c3cc(-c4c(C)noc4C)cnc23)cc1] | methyl 4-[1-[(S)-cyclopropyl(2-pyridyl)methyl]-6-(3,5-dimethylisoxazol-4-yl)pyrrolo[3,2-b]pyridin-3-yl]benzoate | 479.0 |
| P-0990 | 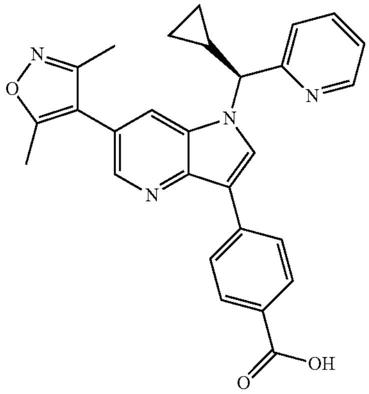 [SMILES: Cc1noc(C)c1-c1cnc2c(-c3ccc(C(=O)O)cc3)cn([C@H](c3ccccn3)C3CC3)c2c1] | 4-[1-[(S)-cyclopropyl(2-pyridyl)methyl]-6-(3,5-dimethylisoxazol-4-yl)pyrrolo[3,2-b]pyridin-3-yl]benzoic acid | 465.0 |

TABLE 31-continued

| Compound No. | Structure | Name | MS(ESI) [M + H+]+ observed |
|---|---|---|---|
| P-0991 | 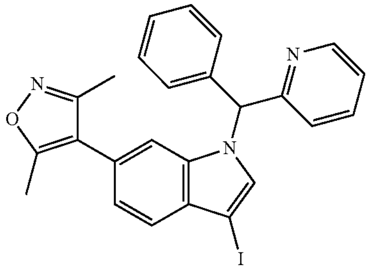 [SMILES: Cc1noc(C)c1-c1ccc2c(I)cn(C(c3ccccc3)c3ccccn3)c2c1] | 4-[3-iodo-1-[phenyl(2-pyridyl)methyl]indol-6-yl]-3,5-dimethyl-isoxazole | 505.8 |
| P-0992 | 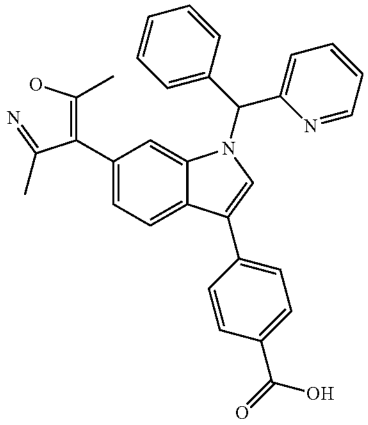 [SMILES: CC(=N)/C(=C(/C)O)c1ccc2c(-c3ccc(C(=O)O)cc3)cn(C(c3ccccc3)c3ccccn3)c2c1] | 4-[6-(3,5-dimethylisoxazol-4-yl)-1-[phenyl(2-pyridyl)methyl]indol-3-yl]benzoic acid | 500.4 |
| P-0993 | 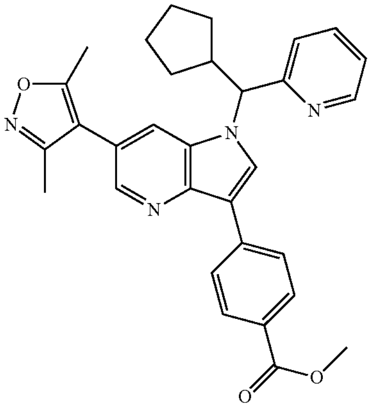 [SMILES: COC(=O)c1ccc(-c2cn(C(c3ccccn3)C3CCCC3)c3cc(-c4c(C)noc4C)cnc23)cc1] | methyl 4-[1-[cyclopentyl(2-pyridyl)methyl]-6-(3,5-dimethylisoxazol-4-yl)pyrrolo[3,2-b]pyridin-3-yl]benzoate | 507.1 |
| P-0994 | 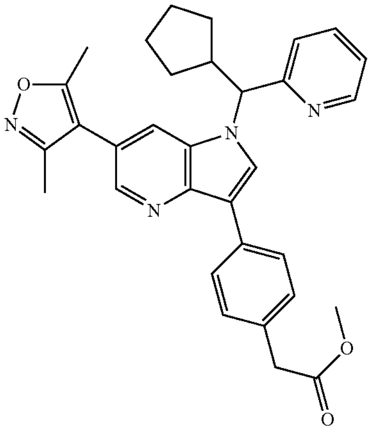 [SMILES: COC(=O)Cc1ccc(-c2cn(C(c3ccccn3)C3CCCC3)c3cc(-c4c(C)noc4C)cnc23)cc1] | methyl 2-[4-[1-[cyclopentyl(2-pyridyl)methyl]-6-(3,5-dimethylisoxazol-4-yl)pyrrolo[3,2-b]pyridin-3-yl]phenyl]acetate | 521.6 |

TABLE 31-continued

| Compound No. | Structure | Name | MS(ESI) [M + H+]+ observed |
|---|---|---|---|
| P-0995 | 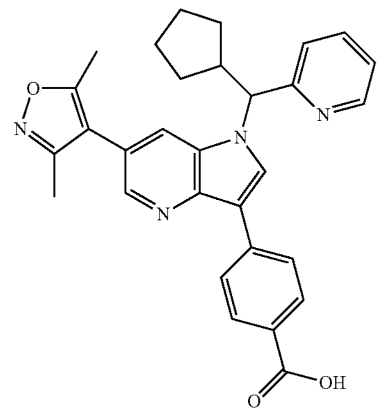 [SMILES: Cc1noc(C)c1-c1cnc2c(-c3ccc(C(=O)O)cc3)cn(C(c3ccccn3)C3CCCC3)c2c1] | 4-[1-[cyclopentyl(2-pyridyl)methyl]-6-(3,5-dimethylisoxazol-4-yl)pyrrolo[3,2-b]pyridin-3-yl]benzoic acid | 493.5 |
| P-0996 | 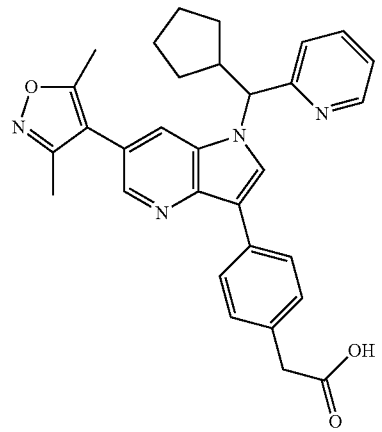 [SMILES: Cc1noc(C)c1-c1cnc2c(-c3ccc(CC(=O)O)cc3)cn(C(c3ccccn3)C3CCCC3)c2c1] | 2-[4-[1-[cyclopentyl(2-pyridyl)methyl]-6-(3,5-dimethylisoxazol-4-yl)pyrrolo[3,2-b]pyridin-3-yl]phenyl]acetic acid | 507.7 |
| P-0997 | 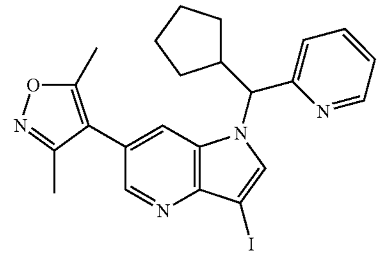 [SMILES: Cc1noc(C)c1-c1cnc2c(I)cn(C(c3ccccn3)C3CCCC3)c2c1] | 4-[1-[cyclopentyl(2-pyridyl)methyl]-3-iodo-pyrrolo[3,2-b]pyridin-6-yl]-3,5-dimethyl-isoxazole | 498.9 |
| P-0998 | AND Enantiomer 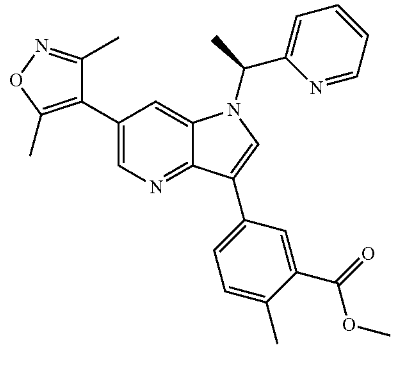 | methyl 5-[6-(3,5-dimethylisoxazol-4-yl)-1-[(1S)-1-(2-pyridyl)ethyl]pyrrolo[3,2-b]pyridin-3-yl]-2-methyl-benzoate | 467.5 |

TABLE 31-continued
| Compound No. | Structure | Name | MS(ESI) [M + H+]+ observed |
|---|---|---|---|
| P-0999 | AND Enantiomer 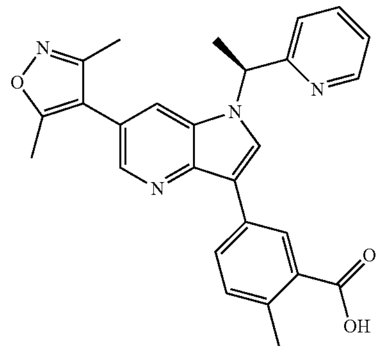 | 5-[6-(3,5-dimethylisoxazol-4-yl)-1-[(1S)-1-(2-pyridyl)ethyl]pyrrolo[3,2-b]pyridin-3-yl]-2-methyl-benzoic acid | 453.4 |
| P-1000 | AND Enantiomer 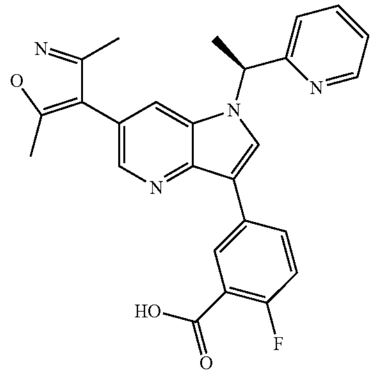 | 5-[6-(3,5-dimethylisoxazol-4-yl)-1-[(1S)-1-(2-pyridyl)ethyl]pyrrolo[3,2-b]pyridin-3-yl]-2-fluoro-benzoic acid | 457.6 |
| P-1001 | AND Enantiomer 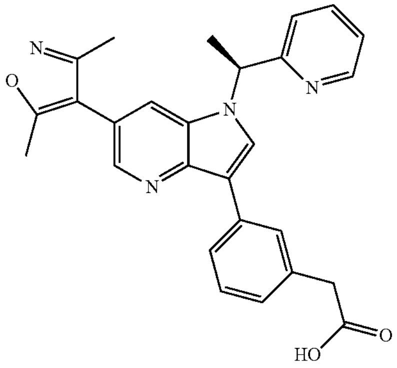 | 2-[3-[6-(3,5-dimethylisoxazol-4-yl)-1-[(1S)-1-(2-pyridyl)ethyl]pyrrolo[3,2-b]pyridin-3-yl]phenyl]acetic acid | 453.4 |

TABLE 31-continued
| Compound No. | Structure | Name | MS(ESI) [M + H+]+ observed |
|---|---|---|---|
| P-1002 | AND Enantiomer 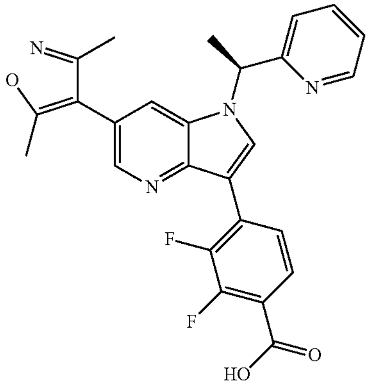 | 4-[6-(3,5-dimethylisoxazol-4-yl)-1-[(1S)-1-(2-pyridyl)ethyl]pyrrolo[3,2-b]pyridin-3-yl]-2,3-difluoro-benzoic acid | 475.3 |
| P-1003 | AND Enantiomer 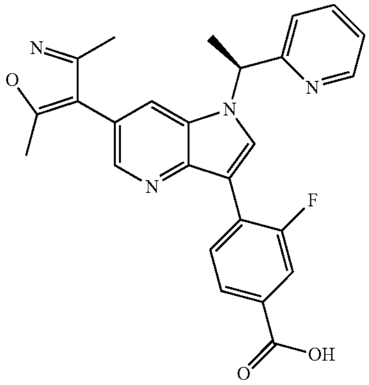 | 4-[6-(3,5-dimethylisoxazol-4-yl)-1-[(1S)-1-(2-pyridyl)ethyl]pyrrolo[3,2-b]pyridin-3-yl]-3-fluoro-benzoic acid | 457.6 |
| P-1004 | AND Enantiomer 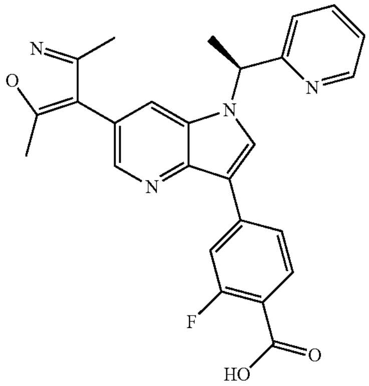 | 4-[6-(3,5-dimethylisoxazol-4-yl)-1-[(1S)-1-(2-pyridyl)ethyl]pyrrolo[3,2-b]pyridin-3-yl]-2-fluoro-benzoic acid | 457.6 |

TABLE 31-continued

| Compound No. | Structure | Name | MS(ESI) [M + H+]+ observed |
|---|---|---|---|
| P-1005 | AND Enantiomer 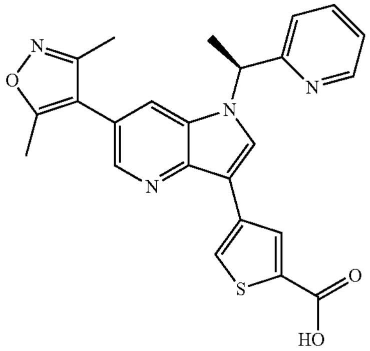 | 4-[6-(3,5-dimethylisoxazol-4-yl)-1-[(1S)-1-(2-pyridyl)ethyl]pyrrolo[3,2-b]pyridin-3-yl]thiophene-2-carboxylic acid | 445.6 |
| P-1006 | AND Enantiomer 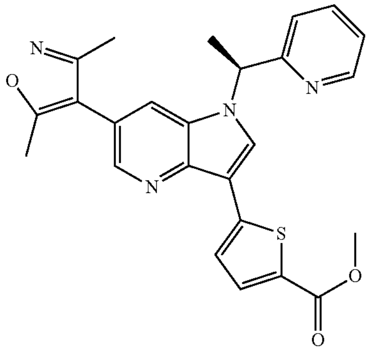 | methyl 5-[6-(3,5-dimethylisoxazol-4-yl)-1-[(1S)-1-(2-pyridyl)ethyl]pyrrolo[3,2-b]pyridin-3-yl]thiophene-2-carboxylate | 459.4 |
| P-1007 | AND Enantiomer 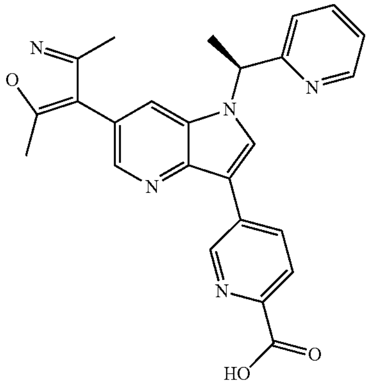 | 5-[6-(3,5-dimethylisoxazol-4-yl)-1-[(1S)-1-(2-pyridyl)ethyl]pyrrolo[3,2-b]pyridin-3-yl]pyridine-2-carboxylic acid | 440.5 |

TABLE 31-continued
| Compound No. | Structure | Name | MS(ESI) [M + H+]+ observed |
|---|---|---|---|
| P-1008 | AND Enantiomer 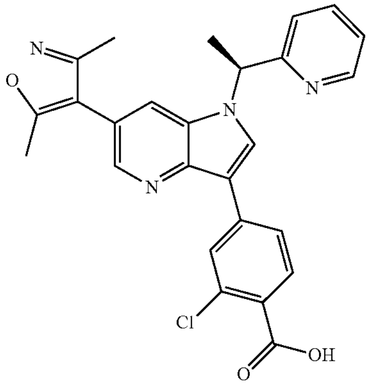 | 2-chloro-4-[6-(3,5-dimethylisoxazol-4-yl)-1-[(1S)-1-(2-pyridyl)ethyl]pyrrolo[3,2-b]pyridin-3-yl]benzoic acid | 473.5 |
| P-1009 | AND Enantiomer 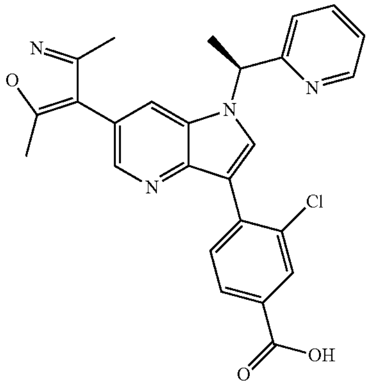 | 3-chloro-4-[6-(3,5-dimethylisoxazol-4-yl)-1-[(1S)-1-(2-pyridyl)ethyl]pyrrolo[3,2-b]pyridin-3-yl]benzoic acid | 473.5 |
| P-1010 | AND Enantiomer 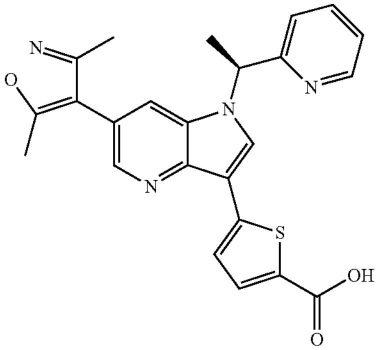 | 5-[6-(3,5-dimethylisoxazol-4-yl)-1-[(1S)-1-(2-pyridyl)ethyl]pyrrolo[3,2-b]pyridin-3-yl]thiophene-2-carboxylic acid | 445.6 |

TABLE 31-continued
| Compound No. | Structure | Name | MS(ESI) [M + H+]+ observed |
|---|---|---|---|
| P-1011 | 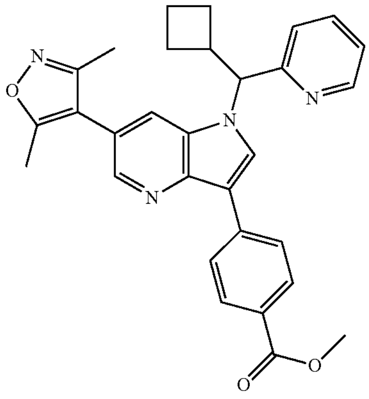 [SMILES: COC(=O)c1ccc(-c2cn(C(c3ccccn3)C3CCC3)c3cc(-c4c(C)noc4C)cnc23)cc1] | methyl 4-[1-[cyclobutyl(2-pyridyl)methyl]-6-(3,5-dimethylisoxazol-4-yl)pyrrolo[3,2-b]pyridin-3-yl]benzoate | 492.9 |
| P-1012 | 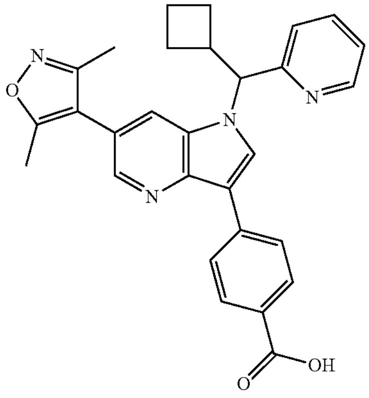 [SMILES: Cc1noc(C)c1-c1cnc2c(-c3ccc(C(=O)O)cc3)cn(C(c3ccccn3)C3CCC3)c2c1] | 4-[1-[cyclobutyl(2-pyridyl)methyl]-6-(3,5-dimethylisoxazol-4-yl)pyrrolo[3,2-b]pyridin-3-yl]benzoic acid | 478.9 |
| P-1013 | 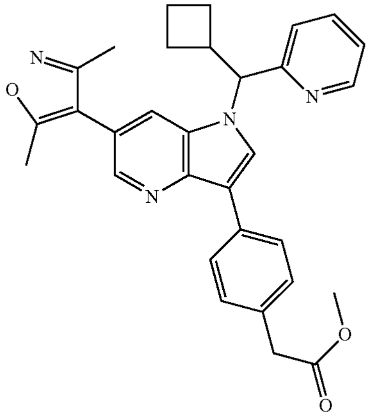 [SMILES: COC(=O)Cc1ccc(-c2cn(C(c3ccccn3)C3CCC3)c3cc(/C(C(C)=N)=C(\C)O)cnc23)cc1] | methyl 2-[4-[1-[cyclobutyl(2-pyridyl)methyl]-6-(3,5-dimethylisoxazol-4-yl)pyrrolo[3,2-b]pyridin-3-yl]phenyl]acetate | 506.9 |

TABLE 31-continued
| Compound No. | Structure | Name | MS(ESI) [M + H+]+ observed |
|---|---|---|---|
| P-1014 | 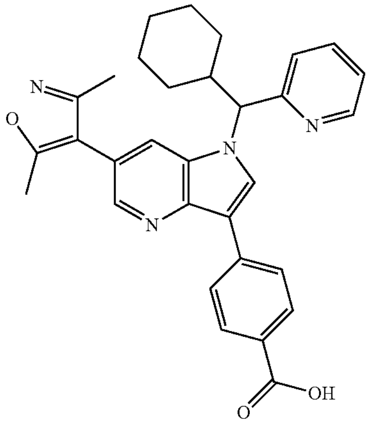 [SMILES: CC(=N)/C(=C(/C)O)c1cnc2c(-c3ccc(C(=O)O)cc3)cn(C(c3ccccn3)C3CCCCC3)c2c1] | 4-[1-[cyclohexyl(2-pyridyl)methyl]-6-(3,5-dimethylisoxazol-4-yl)pyrrolo[3,2-b]pyridin-3-yl]benzoic acid | 506.8 |
| P-1015 | 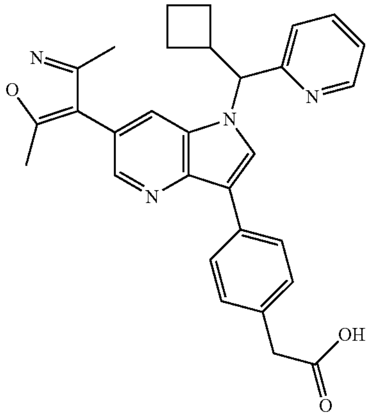 [SMILES: CC(=N)/C(=C(/C)O)c1cnc2c(-c3ccc(CC(=O)O)cc3)cn(C(c3ccccn3)C3CCC3)c2c1] | 2-[4-[1-[cyclobutyl(2-pyridyl)methyl]-6-(3,5-dimethylisoxazol-4-yl)pyrrolo[3,2-b]pyridin-3-yl]phenyl]acetic acid | 492.9 |
| P-1016 | 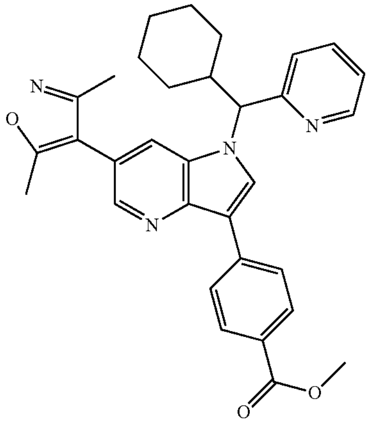 [SMILES: COC(=O)c1ccc(-c2cn(C(c3ccccn3)C3CCCCC3)c3cc(/C(C(C)=N)=C(\C)O)cnc23)cc1] | methyl 4-[1-[cyclohexyl(2-pyridyl)methyl]-6-(3,5-dimethylisoxazol-4-yl)pyrrolo[3,2-b]pyridin-3-yl]benzoate | 520.9 |

TABLE 31-continued
| Compound No. | Structure | Name | MS(ESI) [M + H+]+ observed |
| --- | --- | --- | --- |
| P-1017 | 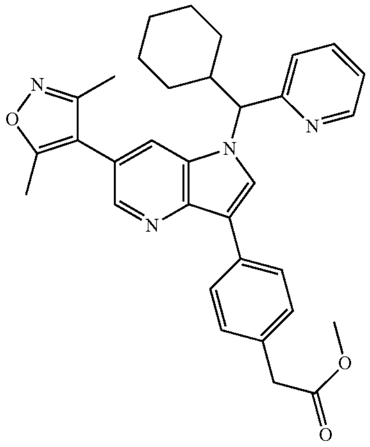 [SMILES: COC(=O)Cc1ccc(-c2cn(C(c3ccccn3)C3CCCCC3)c3cc(-c4c(C)noc4C)cnc23)cc1] | methyl 2-[4-[1-[cyclohexyl(2-pyridyl)methyl]-6-(3,5-dimethylisoxazol-4-yl)pyrrolo[3,2-b]pyridin-3-yl]phenyl]acetate | 534.9 |
| P-1018 | 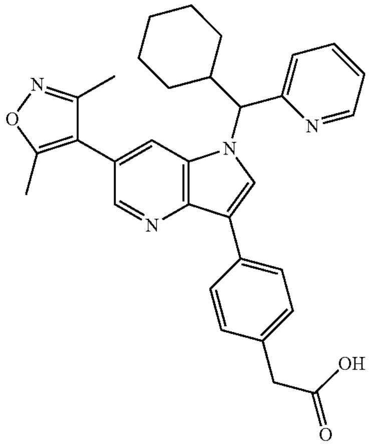 [SMILES: Cc1noc(C)c1-c1cnc2c(-c3ccc(CC(=O)O)cc3)cn(C(c3ccccn3)C3CCCCC3)c2c1] | 2-[4-[1-[cyclohexyl(2-pyridyl)methyl]-6-(3,5-dimethylisoxazol-4-yl)pyrrolo[3,2-b]pyridin-3-yl]phenyl]acetic acid | 520.9 |
| P-1019 | AND Enantiomer 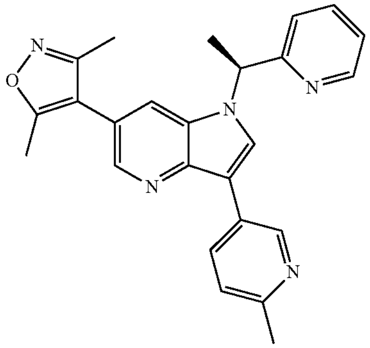 | 3,5-dimethyl-4-[3-(6-methyl-3-pyridyl)-1-[(1S)-1-(2-pyridyl)ethyl]pyrrolo[3,2-b]pyridin-6-yl]isoxazole | 410.5 |

TABLE 31-continued

| Compound No. | Structure | Name | MS(ESI) [M + H+]+ observed |
|---|---|---|---|
| P-1020 | AND Enantiomer 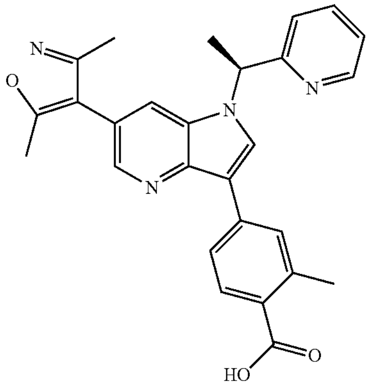 | 4-[6-(3,5-dimethylisoxazol-4-yl)-1-[(1S)-1-(2-pyridyl)ethyl]pyrrolo[3,2-b]pyridin-3-yl]-2-methyl-benzoic acid | 453.4 |
| P-1021 | AND Enantiomer 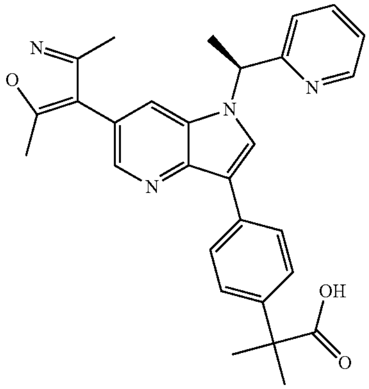 | 2-[4-[6-(3,5-dimethylisoxazol-4-yl)-1-[(1S)-1-(2-pyridyl)ethyl]pyrrolo[3,2-b]pyridin-3-yl]phenyl]-2-methyl-propanoic acid | 481.6 |
| P-1022 | AND Enantiomer 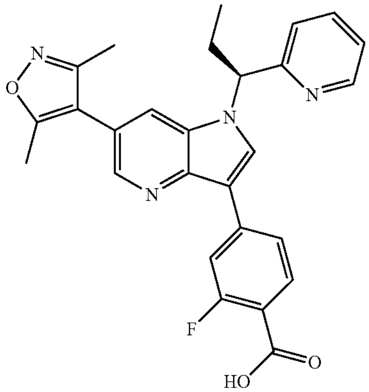 | 4-[6-(3,5-dimethylisoxazol-4-yl)-1-[(1S)-1-(2-pyridyl)propyl]pyrrolo[3,2-b]pyridin-3-yl]-2-fluoro-benzoic acid | 471.7 |

TABLE 31-continued
| Compound No. | Structure | Name | MS(ESI) [M + H+]+ observed |
|---|---|---|---|
| P-1023 | AND Enantiomer 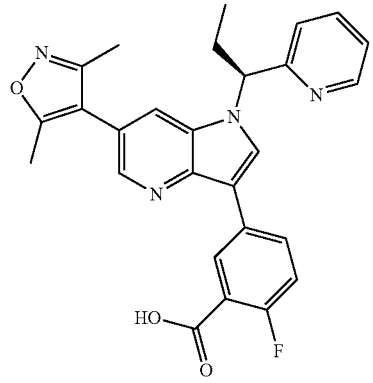 | 5-[6-(3,5-dimethylisoxazol-4-yl)-1-[(1S)-1-(2-pyridyl)propyl]pyrrolo[3,2-b]pyridin-3-yl]-2-fluoro-benzoic acid | 471.7 |
| P-1024 | AND Enantiomer 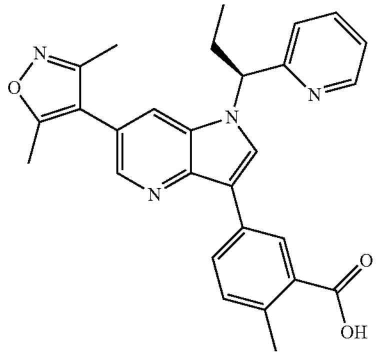 | 5-[6-(3,5-dimethylisoxazol-4-yl)-1-[(1S)-1-(2-pyridyl)propyl]pyrrolo[3,2-b]pyridin-3-yl]-2-methyl-benzoic acid | 467.5 |
| P-1025 | AND Enantiomer 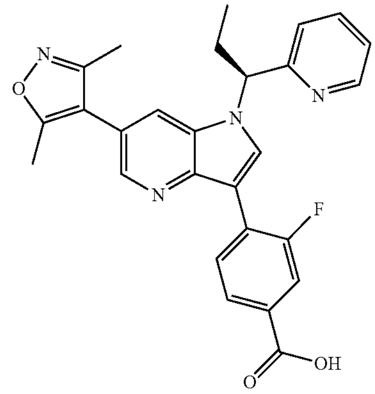 | 4-[6-(3,5-dimethylisoxazol-4-yl)-1-[(1S)-1-(2-pyridyl)propyl]pyrrolo[3,2-b]pyridin-3-yl]-3-fluoro-benzoic acid | 471.7 |

TABLE 31-continued
| Compound No. | Structure | Name | MS(ESI) [M + H+]+ observed |
|---|---|---|---|
| P-1026 | AND Enantiomer 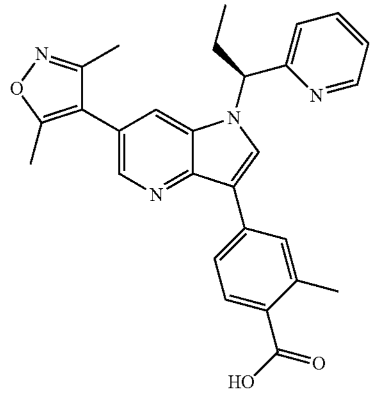 | 4-[6-(3,5-dimethylisoxazol-4-yl)-1-[(1S)-1-(2-pyridyl)propyl]pyrrolo[3,2-b]pyridin-3-yl]-2-methyl-benzoic acid | 467.5 |
| P-1027 | AND Enantiomer 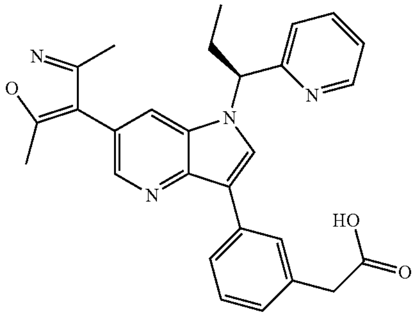 | 2-[3-[6-(3,5-dimethylisoxazol-4-yl)-1-[(1S)-1-(2-pyridyl)propyl]pyrrolo[3,2-b]pyridin-3-yl]phenyl]acetic acid | 467.5 |
| P-1028 | AND Enantiomer 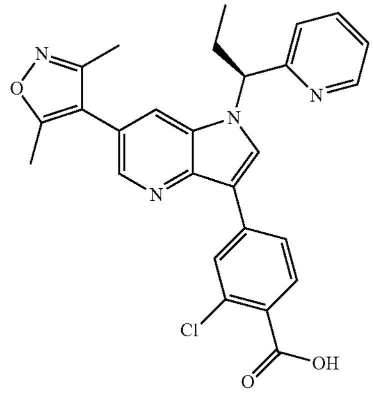 | 2-chloro-4-[6-(3,5-dimethylisoxazol-4-yl)-1-[(1S)-1-(2-pyridyl)propyl]pyrrolo[3,2-b]pyridin-3-yl]benzoic acid | 487.6 |

TABLE 31-continued
| Compound No. | Structure | Name | MS(ESI) [M + H+]+ observed |
|---|---|---|---|
| P-1029 | AND Enantiomer 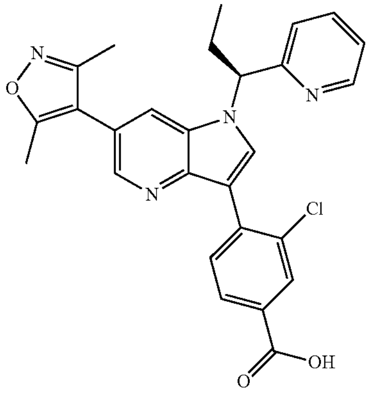 | 3-chloro-4-[6-(3,5-dimethylisoxazol-4-yl)-1-[(1S)-1-(2-pyridyl)propyl]pyrrolo[3,2-b]pyridin-3-yl]benzoic acid | 487.6 |
| P-1030 | 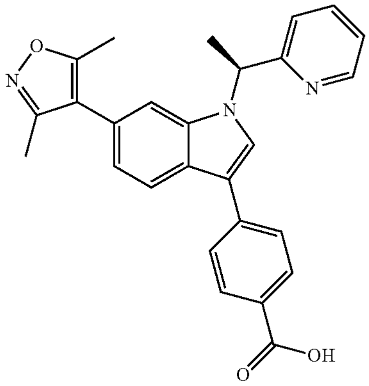 [SMILES: Cc1noc(C)c1-c1ccc2c(-c3ccc(C(=O)O)cc3)cn([C@@H](C)c3ccccn3)c2c1] | 4-[6-(3,5-dimethylisoxazol-4-yl)-1-[(1S)-1-(2-pyridyl)ethyl]indol-3-yl]benzoic acid | 437.9 |
| P-1031 | 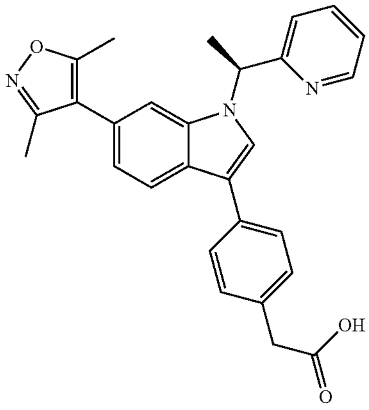 [SMILES: Cc1noc(C)c1-c1ccc2c(-c3ccc(CC(=O)O)cc3)cn([C@@H](C)c3ccccn3)c2c1] | 2-[4-[6-(3,5-dimethylisoxazol-4-yl)-1-[(1S)-1-(2-pyridyl)ethyl]indol-3-yl]phenyl]acetic acid | 452.0 |

TABLE 31-continued

| Compound No. | Structure | Name | MS(ESI) [M + H+]+ observed |
|---|---|---|---|
| P-1032 | 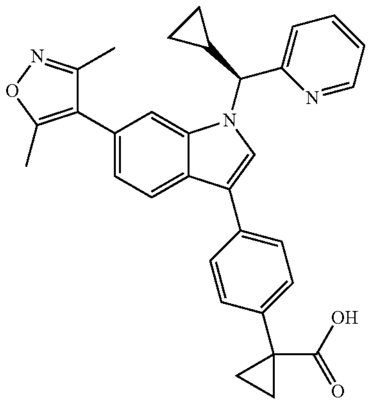 [SMILES: Cc1noc(C)c1-c1ccc2c(-c3ccc(C4(C(=O)O)CC4)cc3)cn([C@H](c3ccccn3)C3CC3)c2c1] | 1-[4-[1-[(S)-cyclopropyl(2-pyridyl)methyl]-6-(3,5-dimethylisoxazol-4-yl)pyrrolo[3,2-b]pyridin-3-yl]phenyl]cyclopropanecarboxylic acid | 505.1 |
| P-1033 | 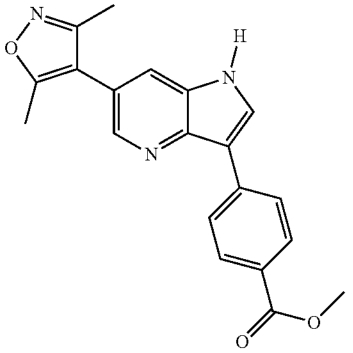 [SMILES: COC(=O)c1ccc(-c2c[nH]c3cc(-c4c(C)noc4C)cnc23)cc1] | methyl 4-[6-(3,5-dimethylisoxazol-4-yl)-1H-pyrrolo[3,2-b]pyridin-3-yl]benzoate | 348.9 |
| P-1034 | 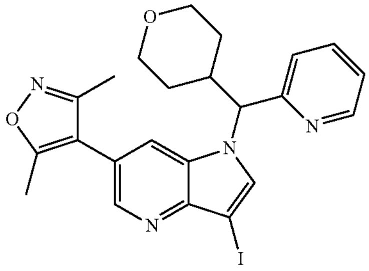 [SMILES: Cc1noc(C)c1-c1cnc2c(I)cn(C(c3ccccn3)C3CCOCC3)c2c1] | 4-[3-iodo-1-[2-pyridyl(tetrahydropyran-4-yl)methyl]pyrrolo[3,2-b]pyridin-6-yl]-3,5-dimethyl-isoxazole | 514.9 |
| P-1035 | 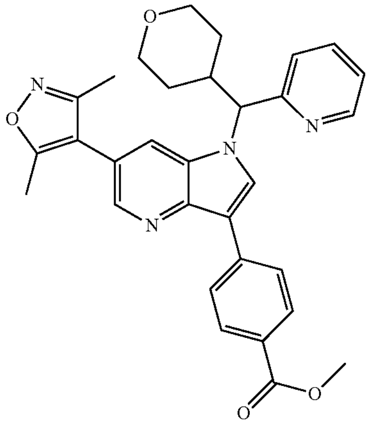 [SMILES: COC(=O)c1ccc(-c2cn(C(c3ccccn3)C3CCOCC3)c3cc(-c4c(C)noc4C)cnc23)cc1] | methyl 4-[6-(3,5-dimethylisoxazol-4-yl)-1-[2-pyridyl(tetrahydropyran-4-yl)methyl]pyrrolo[3,2-b]pyridin-3-yl]benzoate | 523.0 |

TABLE 31-continued
| Compound No. | Structure | Name | MS(ESI) [M + H+]+ observed |
|---|---|---|---|
| P-1036 | 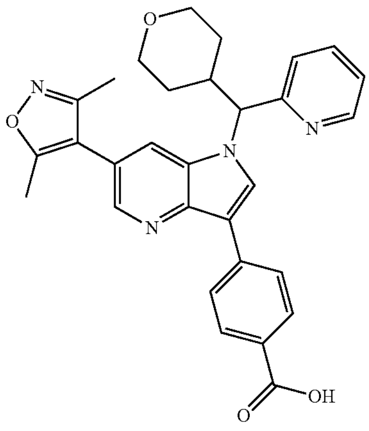 [SMILES: Cc1noc(C)c1-c1cnc2c(-c3ccc(C(=O)O)cc3)cn(C(c3ccccn3)C3CCOCC3)c2c1] | 4-[6-(3,5-dimethylisoxazol-4-yl)-1-[2-pyridyl(tetrahydropyran-4-yl)methyl]pyrrolo[3,2-b]pyridin-3-yl]benzoic acid | 509.6 |
| P-1037 | 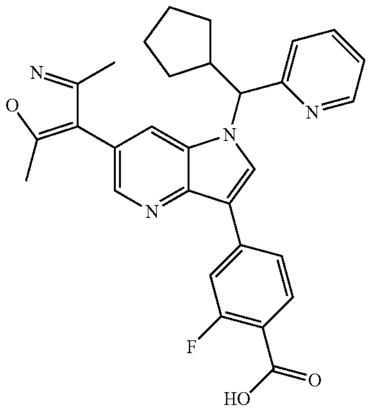 [SMILES: CC(=N)/C(=C(/C)O)c1cnc2c(-c3ccc(C(=O)O)c(F)c3)cn(C(c3ccccn3)C3CCCC3)c2c1] | 4-[1-[cyclopentyl(2-pyridyl)methyl]-6-(3,5-dimethylisoxazol-4-yl)pyrrolo[3,2-b]pyridin-3-yl]-2-fluoro-benzoic acid | 511.6 |
| P-1038 | 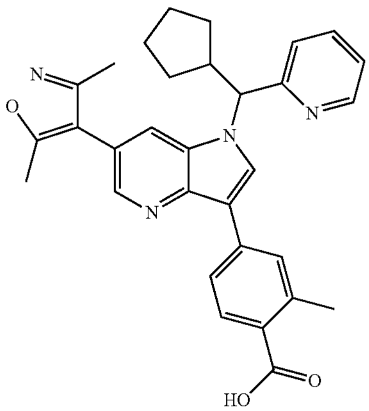 [SMILES: CC(=N)/C(=C(/C)O)c1cnc2c(-c3ccc(C(=O)O)c(C)c3)cn(C(c3ccccn3)C3CCCC3)c2c1] | 4-[1-[cyclopentyl(2-pyridyl)methyl]-6-(3,5-dimethylisoxazol-4-yl)pyrrolo[3,2-b]pyridin-3-yl]-2-methyl-benzoic acid | 507.4 |

TABLE 31-continued
| Compound No. | Structure | Name | MS(ESI) [M + H+]+ observed |
|---|---|---|---|
| P-1039 | 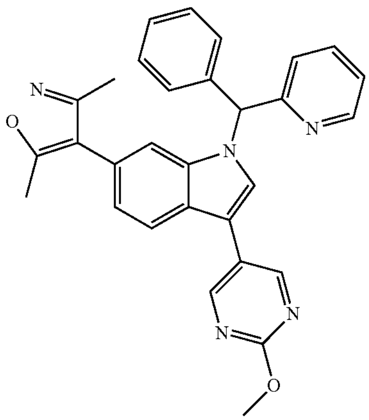 [SMILES: COc1ncc(-c2cn(C(c3ccccc3)c3ccccn3)c3cc(/C(C(C)=N)=C(\C)O)ccc23)cn1] | 4-[3-(2-methoxypyrimidin-5-yl)-1-[phenyl(2-pyridyl)methyl]indol-6-yl]-3,5-dimethyl-isoxazole | 488.5 |
| P-1040 | 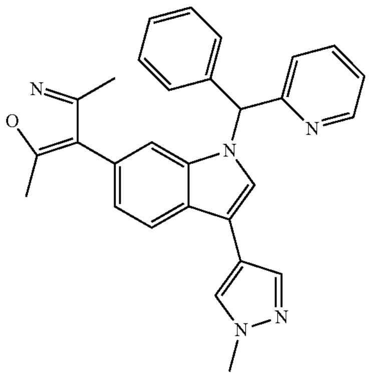 [SMILES: CC(=N)/C(=C(/C)O)c1ccc2c(-c3cnn(C)c3)cn(C(c3ccccc3)c3ccccn3)c2c1] | 3,5-dimethyl-4-[3-(1-methylpyrazol-4-yl)-1-[phenyl(2-pyridyl)methyl]indol-6-yl]isoxazole | 460.6 |
| P-1041 | 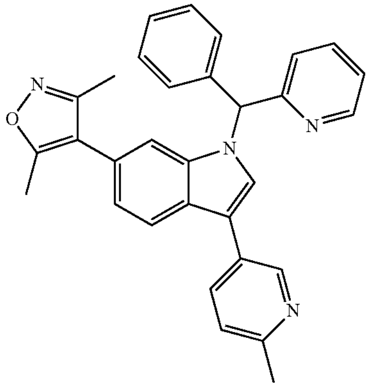 [SMILES: Cc1ccc(-c2cn(C(c3ccccc3)c3ccccn3)c3cc(-c4c(C)noc4C)ccc23)cn1] | 3,5-dimethyl-4-[3-(6-methyl-3-pyridyl)-1-[phenyl(2-pyridyl)methyl]indol-6-yl]isoxazole | 471.7 |

TABLE 31-continued
| Compound No. | Structure | Name | MS(ESI) [M + H+]+ observed |
|---|---|---|---|
| P-1042 | 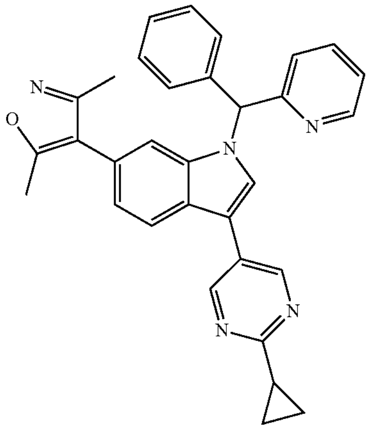 [SMILES: CC(=N)/C(=C(/C)O)c1ccc2c(-c3cnc(C4CC4)nc3)cn(C(c3ccccc3)c3ccccn3)c2c1] | 4-[3-(2-cyclopropylpyrimidin-5-yl)-1-[phenyl(2-pyridyl)methyl]indol-6-yl]-3,5-dimethyl-isoxazole | 498.7 |
| P-1043 | 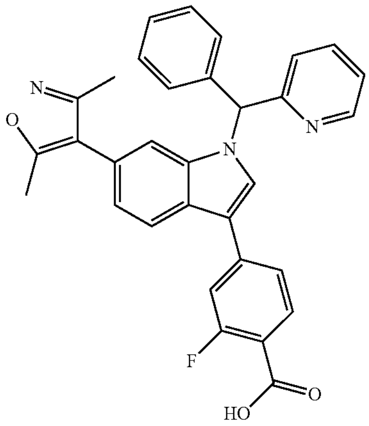 [SMILES: CC(=N)/C(=C(/C)O)c1ccc2c(-c3ccc(C(=O)O)c(F)c3)cn(C(c3ccccc3)c3ccccn3)c2c1] | 4-[6-(3,5-dimethylisoxazol-4-yl)-1-[phenyl(2-pyridyl)methyl]indol-3-yl]-2-fluoro-benzoic acid | 518.5 |
| P-1044 | 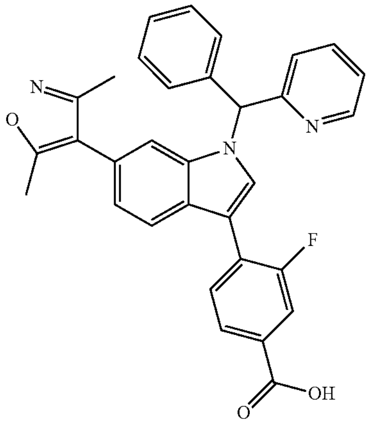 [SMILES: CC(=N)/C(=C(/C)O)c1ccc2c(-c3ccc(C(=O)O)cc3F)cn(C(c3ccccc3)c3ccccn3)c2c1] | 4-[6-(3,5-dimethylisoxazol-4-yl)-1-[phenyl(2-pyridyl)methyl]indol-3-yl]-3-fluoro-benzoic acid | 518.5 |

TABLE 31-continued
| Compound No. | Structure | Name | MS(ESI) [M + H+]+ observed |
|---|---|---|---|
| P-1045 | 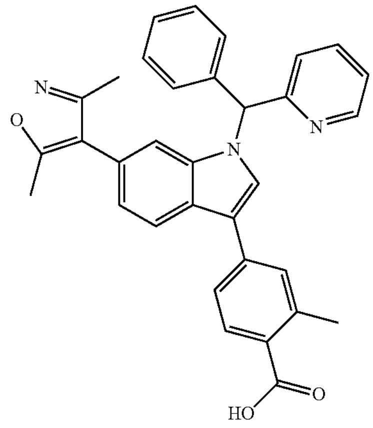 [SMILES: CC(=N)/C(=C(/C)O)c1ccc2c(-c3ccc(C(=O)O)c(C)c3)cn(C(c3ccccc3)c3ccccn3)c2c1] | 4-[6-(3,5-dimethylisoxazol-4-yl)-1-[phenyl(2-pyridyl)methyl]indol-3-yl]-2-methyl-benzoic acid | 514.3 |
| P-1046 | 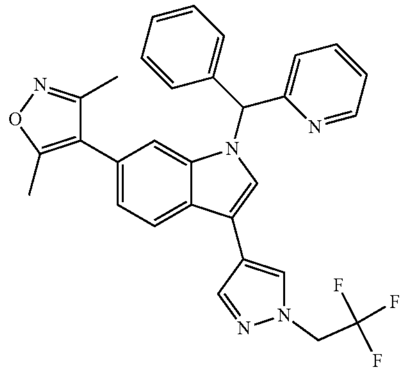 [SMILES: Cc1noc(C)c1-c1ccc2c(-c3cnn(CC(F)(F)F)c3)cn(C(c3ccccc3)c3ccccn3)c2c1] | 3,5-dimethyl-4-[1-[phenyl(2-pyridyl)methyl]-3-[1-(2,2,2-trifluoroethyl)pyrazol-4-yl]indol-6-yl]isoxazole | 528.4 |
| P-1047 | 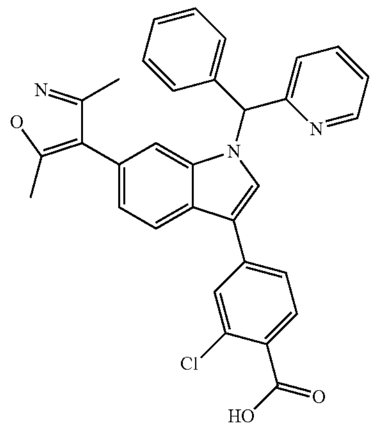 [SMILES: CC(=N)/C(=C(/C)O)c1ccc2c(-c3ccc(C(=O)O)c(Cl)c3)cn(C(c3ccccc3)c3ccccn3)c2c1] | 2-chloro-4-[6-(3,5-dimethylisoxazol-4-yl)-1-[phenyl(2-pyridyl)methyl]indol-3-yl]benzoic acid | 534.4 |

TABLE 31-continued

| Compound No. | Structure | Name | MS(ESI) [M + H+]+ observed |
|---|---|---|---|
| P-1048 | 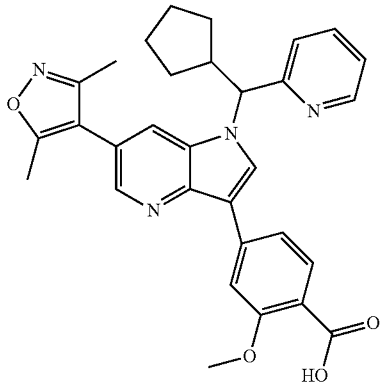 [SMILES: COc1cc(-c2cn(C(c3ccccn3)C3CCCC3)c3cc(-c4c(C)noc4C)cnc23)ccc1C(=O)O] | 4-[1-[cyclopentyl(2-pyridyl)methyl]-6-(3,5-dimethylisoxazol-4-yl)pyrrolo[3,2-b]pyridin-3-yl]-2-methoxy-benzoic acid | 523.6 |
| P-1049 | 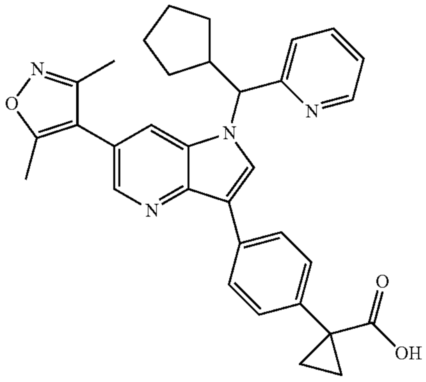 [SMILES: Cc1noc(C)c1-c1cnc2c(-c3ccc(C4(C(=O)O)CC4)cc3)cn(C(c3ccccn3)C3CCCC3)c2c1] | 1-[4-[1-[cyclopentyl(2-pyridyl)methyl]-6-(3,5-dimethylisoxazol-4-yl)pyrrolo[3,2-b]pyridin-3-yl]phenyl]cyclopropanecarboxylic acid | 533.2 |
| P-1050 | 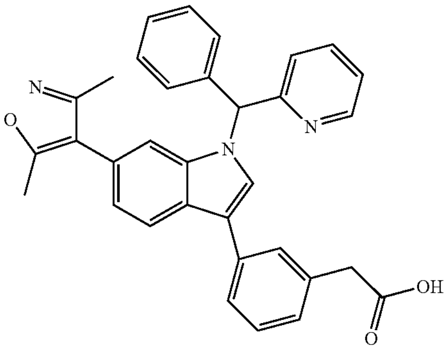 [SMILES: CC(=N)/C(=C(/C)O)c1ccc2c(-c3cccc(CC(=O)O)c3)cn(C(c3ccccc3)c3ccccn3)c2c1] | 2-[3-[6-(3,5-dimethylisoxazol-4-yl)-1-[phenyl(2-pyridyl)methyl]indol-3-yl]phenyl]acetic acid | 514.3 |
| P-1051 | 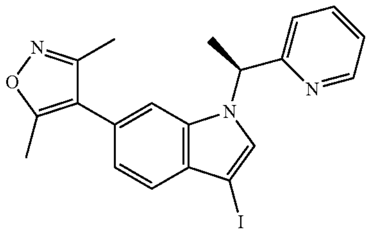 [SMILES: Cc1noc(C)c1-c1ccc2c(I)cn([C@@H](C)c3ccccn3)c2c1] | 4-[3-iodo-1-[(1S)-1-(2-pyridyl)ethyl]indol-6-yl]-3,5-dimethyl-isoxazole | 443.9 |

TABLE 31-continued

| Compound No. | Structure | Name | MS(ESI) [M + H+]+ observed |
|---|---|---|---|
| P-1052 | 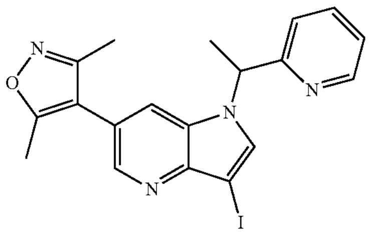 [SMILES: Cc1noc(C)c1-c1cnc2c(I)cn(C(C)c3ccccn3)c2c1] | 4-[3-iodo-1-[1-(2-pyridyl)ethyl]pyrrolo[3,2-b]pyridin-6-yl]-3,5-dimethyl-isoxazole | 444.9 |
| P-1053 | 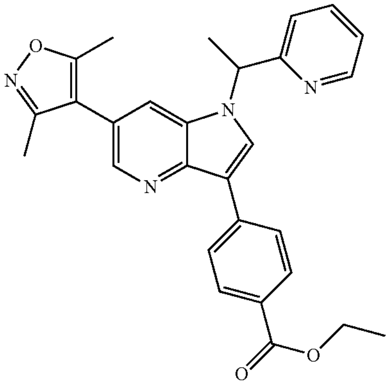 [SMILES: CCOC(=O)c1ccc(-c2cn(C(C)c3ccccn3)c3cc(-c4c(C)noc4C)cnc23)cc1] | ethyl 4-[6-(3,5-dimethylisoxazol-4-yl)-1-[1-(2-pyridyl)ethyl]pyrrolo[3,2-b]pyridin-3-yl]benzoate | 467.0 |

Example 57

Compound Properties

While the inhibitory activity of the compounds on any bromodomain and mutants thereof is important to their activity in treating of disease, the compounds described herein show favorable properties that provide advantages as a pharmaceutical as well.

The compounds described herein are useful for treating disorders related to bromodomain proteins and mutants thereof.

Alphascreen Binding Assay

Binding of compounds of formula (I) with bromodomain 2, 3 4 was assessed using Alphascreen binding assay. The inhibition of the interaction between bromodomain and its acetylated target protein (Filippakopoulos P et al. 2012) was measured quantitatively using recombinant BRD proteins, an acetylated Histone 4 peptide and AlphaScreen™ technology. In absence of inhibition the BRD protein bound to AlphaScreen™ nickel chelate acceptor beads can interact with the acetylated Histone 4 peptide which is immobilized by the AlphaScreen™ Streptavidin coated beads. This interaction brings donor and acceptor beads in proximity. The close proximity allows the singlet oxygen produced by laser excitation of the donor beads to reach the acceptor beads and generate a luminescence signal. BRD inhibitors result in a decrease in the proximity signal through an inhibition of the BRD—acetylated peptide interaction.

Recombinant human bromodomains containing the N-terminal bromodomain (BRD2-BD1 (71-194), BRD3-BD1 (24-144) and BRD4-BD1 (44-164)) or dual bromodomains (BRD4-BD12 (1-477), BRD4-BD12 (1-472)) were prepared and purified as described in protein expression and purification session. The peptide is human Histone $H4_{1-21}$ $K5_{Ac}K8_{Ac}K12_{Ac}K16_{Ac}$-Biotin (Anaspec Calif., USA).

Protocol for BRD2, BRD3 and BRD4 assay: All components are prepared in buffer composed of 50 mM HEPES pH 7.5, 100 mM NaCl, 0.01% bovine serum albumin ("BSA"), 0.01% Triton X-100, 2 mM dithiothreitol ("DTT"). 7 μL of Bromodomain protein and 7 μL of peptide are added to wells containing 1 μL of various concentrations of test compounds of formula (I) or DMSO vehicle in an Alphaplate (PerkinElmer Ga., USA) and incubated for 1 hour at room temperature. 4 μL donor and acceptor bead mixture is then added with final concentrations of 7.5 μg/ml. 30 minutes after bead addition, Alpha signal is read on the Envision spectrometer ($\lambda_{Ex}$ 680 nm, $\lambda_{Em}$520-620 nm). Final concentrations of bromodomain proteins and peptide are as shown below.

| Assay name | BRD protein (nM) | Peptide (nM) |
|---|---|---|
| BRD2-BD1 | 6 | 41 |
| BRD3-BD1 | 4 | 41 |
| BRD4-BD1 | 6 | 41 |
| BRD2-BD12 | 1 | 10 |
| BRD4-BD12 | 3.7 | 37 |

All data was normalized to the mean of 16 high and 16 low control wells on each plate. A four parameter curve fit of the following formula was then applied:

$$Y=a+(b-a)/(1+(x/c)^d)$$

Where 'a' is the minimum, 'b' is the maximum, 'c' is the pIC50 and 'd' is the Hill slope.

Protein Expression and Purification

Recombinant human bromodomains containing the N-terminal bromodomain (BRD2-BD1 (71-194), BRD3-BD1 (24-144) and BRD4-BD1 (44-164)) or dual bromodomains (BRD4-BD12 (1-477), BRD4-BD12 (1-472)) were expressed in *E. coli* cells (in a modified pET vector) with an N-terminal six-His tag and purified using a combination of both IMAC (Ni-affinity) and size exclusion chromatography steps.

Recombinant BRD proteins were expressed using the *E. coli* strain BL21-CodonPlus (DE3) (Agilent Technologies Calif., USA). Cells were grown in Terrific Broth (TB) media to an OD600 of 1.2 at 37° C. at which temperature was reduced to 25° C., protein was induced with 1.0 mM ispropyl-13-D-thiogalactopyranoside ("IPTG") for 12-18 hours and harvested by centrifugation at 8000×g for 20 minutes. Cells were re-suspended in 0.1M $K_2PO_4$ pH 8.0, 250 mM NaCl, 10% Glycerol, 0.75% NP-40, 25 mM Imidazole, 5 mM beta-mercaptoethanol ("BME") with 0.2 mg/ml Lysosyme, 2.0 mM phenylmethanesulfonyl fluoride ("PMSF"), 25 μg/ml DNAse I, incubated on ice for 30 minutes and lyzed with a cell disruptor (MicroFluidics Mass., USA). The lysate was clarified by centrifugation at 20,000×g for 2 hours. The protein was captured with Ni-NTA resin (Life Technologies, USA). Contaminating proteins were washed off with 25 mM Tris-HCl pH 8.3, 250 mM NaCl, 12% Glycerol and 50 mM Imidazole. Following 3× wash steps, protein was eluted step wise using a 50 mM HEPES pH 7.5, 500 mM NaCl and 400 mM Imidazole. The protein was further purified using Gel Filtration column 26/600 Superdex 200 (GE Biosciences N.J., USA) in 50 mM HEPES pH 7.5, 250 mM NaCl. The protein was aliquoted and flash-frozen in liquid Nitrogen.

Oncology Cell Growth Assay

Published bromodomain inhibitors JQ1 and iBET 151 have shown activity in variety of cancer cells such leukemia and lymphoma, multiple myeloma cells, NUT midline carcinoma and glioblastoma cells (Dawson M A et al. 2011; Delmore J E 2011; Chen Z et al. 2013; Filippakopoulos P et al. 2010; Mertz J A et al. 2011; Ott C J et al. 2012). In this study, we test compounds in different cancer cell lines. MV-4-11 and MOLM-13 are AML cell lines harboring a MLL-AF4 and MLL-AF9 translocation, respectively. MM.1S is a multiple myeloma cell line. SK-N-AS, IMR-32 and SK-N-BE(2) are neuroblastoma cell lines. IMR-32 and SK-N-BE(2) cell lines harbor MYCN amplifications.

MV-4-11, MM.1S, IMR-32, SK-N-AS and SK-N-BE(2) were obtained from ATCC (IL, USA) and MOLM-13 were purchased from DSMZ(Braunschweig, German). Cells are cultured as recommended by their sources. For growth inhibition studies 3000 cells are seeded in wells of a 96-well plate in 75 μL of culture media. After several hours, growth media containing compounds of formula (I) are added to the wells. Compound at a maximal concentration of 5 mM was serially diluted 1:3 for a total of 8 point titration with DMSO as a control. A 1 μL aliquot of each dilution point is added to 249 μL growth media and 75 μL is added to each well containing cells, providing 10 μM compound at the maximum concentration point. The final concentration of DMSO in all wells is 0.2%. Cells are incubated for 72 hours, and 25 μL of CellTiter Glo Reagent (Promega Ga., USA) is added to each well. Plates are shaken for approximately 10 minutes and chemiluminescent signal is read on Tecan microplate reader. The measured luminescence correlates directly with cell number.

All data is normalized to the mean of eight DMSO high control wells on each plate. A four parameter curve fit of the following formula was then applied:

$$Y=a+(b-a)/(1+(x/c)^d)$$

Where 'a' is the minimum, 'b' is the maximum, 'c' is the pIC50 and 'd' is the Hill slope. These data demonstrate that the bromodomain inhibitors tested in the above assays inhibit cell growth in oncology cell lines.

Myc Reporter Assay

In MV-4-11 cells, BRD2, BRD3 and BRD4 bind to the promoter region of MYC and regulate its transcription (Dawson M A et al. 2011). The literature bromodomain inhibitor iBET 151 could disrupt BRD4 recruitment to the MYC promoter and subsequently downregulate c-myc transcription (Dawson M A et al. 2011). Myc protein is a transcription factor that heterodimerizes with an obligatory partner Max and regulates the transcription of genes important for cell proliferation, differentiation, and apoptosis. This Myc reporter assay is used to monitor the inhibitory effect of compound of formula (I) on Myc dependent gene expression. Effective compounds could have potential therapeutic effects in Myc-driven tumors.

The MV-4-11 Myc reporter cell line is established by infecting MV-4-11 with VSV-g pseudotyped lentivirus expressing the firefly luciferase gene under the control of a minimal (m) CMV promoter and tandem repeats of the E-box transcriptional response element (TRE) (Qiagen IL, USA) and selecting cells in 2.5 μg/ml Puromycin.

The MV-4-11 Myc reporter cell line is maintained in Iscove's Modified Dulbecco's Medium containing 10% FBS, 1% PenStep and 2.5 μg/ml Puromycin. Cells are incubated at 37° C. in a humidified atmosphere with 5% $CO_2$. 25,000 cells are seeded in 96-well plate in 50 μL of culture media. After several hours, growth media containing 2× compounds are added to the wells. Compound at a maximal concentration of 5 mM is serially diluted 1:3 for a total of 8 point titration. A 1 μl aliquot of each dilution point is added to 249 μl growth media and 50 μl is added to each well containing cells, providing 10 μM compound at the maximum concentration point. DMSO treated cells serve as a high control and 10 μM JQ1 treated cells serve as a low control. Cells are incubated for a further 24 hours and 25 μL of CellTiter-Fluo Reagent (Promega Ga., USA) is added to each well. Plates are shaken for approximately 2 minutes and incubated at 37° C. for 0.5 hour. Fluorescence signal is read in a Tecan Plate reader (λex=400 nm, λem=505 nm). 25 μL of One-Glo Reagent (Promega Ga., USA) is then added to the plates. Chemiluminescent signal is read on Tecan plate reader. Values from the wells with no cells are subtracted from all samples for background correction. The background corrected fluorescence correlates directly with cell number, and luminescence correlates directly with Myc reporter activity.

All data is normalized to the mean of 8 high control and 4 low control wells on each plate. A four parameter curve fit of the following formula was then applied:

$$Y=a+(b-a)/(1+(x/c)^d)$$

Where 'a' is the minimum, 'b' is the maximum, 'c' is the pIC50 and 'd' is the Hill slope.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. In some instances, the compounds were not tested in all of the assays, or assay results were not valid.

The following table provides data indicating the BRD4 biochemical inhibitory activity and MV-4-11 cell growth inhibitory activity for exemplary compounds as described herein. In the table below, activity in the bromodomain assays is provided as follows: +++=$IC_{50}$≤1 μM; ++=1 μM<$IC_{50}$≤10 μM; +=10 μM<$IC_{50}$≤200 μM.

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0001 | ++ | | |
| P-0002 | ++ | | |
| P-0003 | +++ | | +++ |
| P-0004 | ++ | | |
| P-0005 | +++ | | +++ |
| P-0006 | ++ | | |
| P-0007 | +++ | | +++ |
| P-0008 | ++ | | |
| P-0009 | +++ | | +++ |
| P-0010 | ++ | | |
| P-0011 | +++ | | +++ |
| P-0012 | +++ | | ++ |
| P-0013 | +++ | | +++ |
| P-0014 | +++ | | +++ |
| P-0015 | ++ | | |
| P-0016 | ++ | | |
| P-0017 | ++ | | ++ |
| P-0018 | ++ | | |
| P-0019 | +++ | | +++ |
| P-0020 | +++ | | +++ |
| P-0021 | +++ | | +++ |
| P-0022 | +++ | | +++ |
| P-0023 | ++ | | ++ |
| P-0024 | +++ | | ++ |
| P-0025 | +++ | | ++ |
| P-0026 | +++ | | ++ |
| P-0027 | +++ | | ++ |
| P-0028 | +++ | | +++ |
| P-0029 | +++ | | ++ |
| P-0030 | +++ | | +++ |
| P-0031 | +++ | | ++ |
| P-0032 | ++ | | ++ |
| P-0033 | ++ | | ++ |
| P-0034 | +++ | | +++ |
| P-0035 | ++ | | ++ |
| P-0036 | +++ | | ++ |
| P-0037 | +++ | | +++ |
| P-0038 | +++ | | +++ |
| P-0039 | +++ | | ++ |
| P-0040 | +++ | | +++ |
| P-0041 | +++ | | ++ |
| P-0042 | +++ | | +++ |
| P-0043 | +++ | | ++ |
| P-0044 | +++ | | +++ |
| P-0045 | +++ | | +++ |
| P-0046 | ++ | | ++ |
| P-0047 | +++ | | ++ |
| P-0048 | +++ | | ++ |
| P-0049 | +++ | | ++ |
| P-0050 | + | | |
| P-0051 | +++ | | |
| P-0052 | ++ | | ++ |
| P-0053 | ++ | | ++ |
| P-0054 | ++ | | ++ |
| P-0055 | ++ | | ++ |
| P-0056 | ++ | | ++ |
| P-0057 | ++ | | +++ |
| P-0058 | ++ | | ++ |
| P-0059 | ++ | | ++ |
| P-0060 | +++ | | ++ |
| P-0061 | ++ | | ++ |
| P-0062 | +++ | | ++ |
| P-0063 | +++ | | +++ |
| P-0064 | +++ | | +++ |
| P-0065 | ++ | | |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0066 | +++ | | +++ |
| P-0067 | +++ | | |
| P-0068 | ++ | | |
| P-0069 | ++ | | |
| P-0070 | ++ | | |
| P-0071 | +++ | | ++ |
| P-0072 | ++ | | |
| P-0073 | +++ | | +++ |
| P-0074 | ++ | | |
| P-0075 | +++ | | ++ |
| P-0076 | +++ | | +++ |
| P-0077 | +++ | | ++ |
| P-0078 | +++ | | ++ |
| P-0079 | +++ | | ++ |
| P-0080 | +++ | | +++ |
| P-0081 | +++ | | |
| P-0082 | ++ | | |
| P-0083 | ++ | | ++ |
| P-0084 | +++ | | +++ |
| P-0085 | +++ | | ++ |
| P-0086 | ++ | | |
| P-0087 | ++ | | |
| P-0088 | ++ | | |
| P-0089 | +++ | | ++ |
| P-0090 | +++ | | ++ |
| P-0091 | +++ | | ++ |
| P-0092 | +++ | | ++ |
| P-0093 | ++ | | ++ |
| P-0094 | ++ | | |
| P-0095 | ++ | | |
| P-0096 | ++ | | |
| P-0097 | ++ | | ++ |
| P-0098 | +++ | | ++ |
| P-0099 | ++ | | ++ |
| P-0100 | ++ | | ++ |
| P-0101 | +++ | | +++ |
| P-0102 | ++ | | ++ |
| P-0103 | +++ | | ++ |
| P-0104 | +++ | | ++ |
| P-0105 | +++ | | ++ |
| P-0106 | +++ | | +++ |
| P-0108 | +++ | | +++ |
| P-0109 | +++ | | ++ |
| P-0110 | +++ | | +++ |
| P-0111 | +++ | | +++ |
| P-0112 | +++ | | +++ |
| P-0113 | +++ | | ++ |
| P-0114 | +++ | | +++ |
| P-0115 | +++ | | +++ |
| P-0116 | +++ | | ++ |
| P-0117 | +++ | | +++ |
| P-0118 | +++ | | +++ |
| P-0119 | ++ | | ++ |
| P-0120 | +++ | | ++ |
| P-0121 | +++ | | +++ |
| P-0122 | +++ | | +++ |
| P-0123 | +++ | | +++ |
| P-0124 | +++ | | +++ |
| P-0125 | +++ | | +++ |
| P-0126 | +++ | | +++ |
| P-0127 | +++ | | +++ |
| P-0128 | +++ | | +++ |
| P-0129 | +++ | | +++ |
| P-0130 | ++ | | |
| P-0131 | +++ | | +++ |
| P-0132 | +++ | | +++ |
| P-0133 | +++ | | +++ |
| P-0134 | +++ | | +++ |
| P-0135 | +++ | | +++ |
| P-0136 | +++ | | ++ |
| P-0137 | +++ | | +++ |
| P-0138 | +++ | | +++ |
| P-0139 | +++ | | +++ |
| P-0140 | +++ | | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0141 | +++ | | ++ |
| P-0142 | +++ | | ++ |
| P-0143 | +++ | | +++ |
| P-0144 | +++ | | ++ |
| P-0145 | +++ | | +++ |
| P-0146 | +++ | | +++ |
| P-0147 | +++ | | +++ |
| P-0148 | +++ | | +++ |
| P-0149 | +++ | | +++ |
| P-0150 | +++ | | +++ |
| P-0151 | +++ | | +++ |
| P-0152 | +++ | | +++ |
| P-0153 | +++ | | +++ |
| P-0154 | +++ | | +++ |
| P-0155 | +++ | | +++ |
| P-0156 | +++ | | +++ |
| P-0157 | +++ | | +++ |
| P-0158 | +++ | | +++ |
| P-0159 | +++ | | +++ |
| P-0160 | +++ | | +++ |
| P-0161 | +++ | | +++ |
| P-0162 | +++ | | +++ |
| P-0163 | +++ | | +++ |
| P-0164 | +++ | | +++ |
| P-0165 | +++ | | +++ |
| P-0166 | +++ | | +++ |
| P-0167 | +++ | | +++ |
| P-0168 | +++ | | +++ |
| P-0169 | +++ | | |
| P-0170 | +++ | | +++ |
| P-0171 | +++ | | +++ |
| P-0172 | +++ | | +++ |
| P-0173 | +++ | | +++ |
| P-0174 | ++ | | ++ |
| P-0175 | ++ | | |
| P-0176 | +++ | | +++ |
| P-0177 | +++ | | +++ |
| P-0178 | ++ | | ++ |
| P-0179 | ++ | | ++ |
| P-0180 | ++ | | ++ |
| P-0181 | ++ | | +++ |
| P-0182 | ++ | | +++ |
| P-0183 | ++ | | +++ |
| P-0184 | +++ | | +++ |
| P-0185 | +++ | | +++ |
| P-0186 | +++ | | +++ |
| P-0187 | +++ | | +++ |
| P-0188 | +++ | | +++ |
| P-0189 | +++ | | +++ |
| P-0190 | +++ | | +++ |
| P-0191 | ++ | | +++ |
| P-0192 | +++ | | +++ |
| P-0193 | +++ | | +++ |
| P-0194 | +++ | | +++ |
| P-0195 | +++ | | +++ |
| P-0196 | +++ | | +++ |
| P-0197 | +++ | | +++ |
| P-0198 | +++ | | +++ |
| P-0199 | +++ | | +++ |
| P-0200 | +++ | | +++ |
| P-0201 | +++ | | +++ |
| P-0202 | +++ | | +++ |
| P-0203 | +++ | | +++ |
| P-0204 | +++ | | +++ |
| P-0205 | +++ | | +++ |
| P-0206 | +++ | | ++ |
| P-0207 | +++ | | +++ |
| P-0208 | +++ | | ++ |
| P-0209 | +++ | | +++ |
| P-0210 | +++ | | +++ |
| P-0211 | +++ | | +++ |
| P-0212 | +++ | | +++ |
| P-0213 | +++ | | +++ |
| P-0214 | +++ | | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0215 | +++ | | +++ |
| P-0216 | +++ | | +++ |
| P-0217 | +++ | | +++ |
| P-0218 | +++ | | +++ |
| P-0219 | +++ | | +++ |
| P-0220 | +++ | | +++ |
| P-0221 | +++ | | +++ |
| P-0222 | +++ | | +++ |
| P-0223 | | | +++ |
| P-0224 | +++ | | +++ |
| P-0250 | | +++ | +++ |
| P-0251 | | +++ | +++ |
| P-0252 | | +++ | +++ |
| P-0253 | | +++ | +++ |
| P-0254 | | +++ | +++ |
| P-0255 | | +++ | +++ |
| P-0256 | | +++ | +++ |
| P-0257 | +++ | +++ | +++ |
| P-0258 | | +++ | +++ |
| P-0259 | | +++ | +++ |
| P-0260 | | +++ | +++ |
| P-0261 | | +++ | +++ |
| P-0262 | +++ | +++ | +++ |
| P-0263 | | +++ | |
| P-0264 | +++ | ++ | +++ |
| P-0265 | +++ | +++ | +++ |
| P-0266 | +++ | +++ | +++ |
| P-0267 | +++ | +++ | +++ |
| P-0268 | +++ | +++ | +++ |
| P-0269 | +++ | +++ | ++ |
| P-0270 | +++ | +++ | +++ |
| P-0271 | +++ | +++ | +++ |
| P-0272 | +++ | +++ | +++ |
| P-0273 | +++ | +++ | +++ |
| P-0274 | +++ | +++ | +++ |
| P-0275 | +++ | +++ | +++ |
| P-0276 | +++ | +++ | +++ |
| P-0277 | +++ | +++ | +++ |
| P-0278 | +++ | +++ | +++ |
| P-0279 | +++ | +++ | +++ |
| P-0280 | +++ | +++ | +++ |
| P-0281 | +++ | +++ | +++ |
| P-0282 | +++ | ++ | +++ |
| P-0283 | ++ | ++ | ++ |
| P-0284 | +++ | ++ | ++ |
| P-0285 | ++ | + | ++ |
| P-0286 | | +++ | + |
| P-0287 | +++ | +++ | +++ |
| P-0288 | +++ | +++ | +++ |
| P-0289 | +++ | +++ | +++ |
| P-0290 | +++ | +++ | +++ |
| P-0291 | +++ | + | ++ |
| P-0292 | + | | ++ |
| P-0293 | + | + | + |
| P-0294 | + | +++ | ++ |
| P-0295 | +++ | +++ | +++ |
| P-0296 | +++ | +++ | +++ |
| P-0297 | +++ | +++ | +++ |
| P-0298 | +++ | +++ | +++ |
| P-0299 | +++ | +++ | +++ |
| P-0300 | +++ | +++ | +++ |
| P-0301 | +++ | +++ | +++ |
| P-0302 | +++ | +++ | +++ |
| P-0303 | +++ | +++ | +++ |
| P-0304 | +++ | +++ | +++ |
| P-0305 | +++ | +++ | +++ |
| P-0306 | +++ | +++ | +++ |
| P-0307 | +++ | +++ | ++ |
| P-0308 | +++ | +++ | +++ |
| P-0309 | +++ | +++ | +++ |
| P-0310 | +++ | +++ | +++ |
| P-0311 | +++ | ++ | +++ |
| P-0312 | ++ | + | + |
| P-0313 | + | +++ | + |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0314 | +++ | +++ | +++ |
| P-0315 | +++ | +++ | +++ |
| P-0316 | +++ | +++ | +++ |
| P-0317 | +++ | +++ | +++ |
| P-0318 | +++ | +++ | +++ |
| P-0319 | +++ | +++ | +++ |
| P-0320 | +++ | +++ | +++ |
| P-0321 | +++ | ++ | +++ |
| P-0322 | + | + | ++ |
| P-0323 | + | +++ | + |
| P-0324 | +++ | +++ | +++ |
| P-0325 | +++ | +++ | +++ |
| P-0326 | +++ | +++ | +++ |
| P-0327 | +++ | +++ | +++ |
| P-0328 | +++ | +++ | ++ |
| P-0329 | +++ | +++ | ++ |
| P-0330 | +++ | +++ | +++ |
| P-0331 | +++ | +++ | +++ |
| P-0332 | +++ | +++ | +++ |
| P-0333 | +++ | +++ | +++ |
| P-0334 | | +++ | +++ |
| P-0335 | | +++ | +++ |
| P-0336 | | +++ | +++ |
| P-0337 | | +++ | +++ |
| P-0338 | | +++ | +++ |
| P-0339 | | +++ | +++ |
| P-0340 | | +++ | +++ |
| P-0341 | | +++ | +++ |
| P-0342 | | +++ | +++ |
| P-0343 | | +++ | +++ |
| P-0344 | | +++ | +++ |
| P-0345 | | +++ | +++ |
| P-0346 | | +++ | +++ |
| P-0347 | | +++ | +++ |
| P-0348 | | +++ | +++ |
| P-0349 | | +++ | +++ |
| P-0350 | | +++ | +++ |
| P-0351 | | +++ | +++ |
| P-0352 | | +++ | +++ |
| P-0353 | | +++ | +++ |
| P-0354 | | +++ | +++ |
| P-0355 | | +++ | +++ |
| P-0356 | | +++ | +++ |
| P-0357 | | +++ | +++ |
| P-0358 | | | + |
| P-0359 | | | + |
| P-0360 | | ++ | + |
| P-0361 | | +++ | +++ |
| P-0362 | | +++ | +++ |
| P-0363 | | +++ | +++ |
| P-0364 | | +++ | +++ |
| P-0365 | | +++ | +++ |
| P-0366 | | +++ | +++ |
| P-0367 | | +++ | +++ |
| P-0368 | | +++ | +++ |
| P-0369 | +++ | +++ | +++ |
| P-0370 | +++ | +++ | +++ |
| P-0371 | +++ | +++ | +++ |
| P-0372 | +++ | +++ | +++ |
| P-0373 | | +++ | +++ |
| P-0374 | | ++ | + |
| P-0375 | | +++ | +++ |
| P-0376 | | +++ | +++ |
| P-0377 | | +++ | +++ |
| P-0378 | | +++ | +++ |
| P-0379 | | +++ | +++ |
| P-0380 | | +++ | +++ |
| P-0381 | | +++ | +++ |
| P-0382 | | +++ | +++ |
| P-0383 | | +++ | +++ |
| P-0384 | | +++ | +++ |
| P-0385 | | +++ | +++ |
| P-0386 | | +++ | + |
| P-0387 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0388 | | +++ | +++ |
| P-0389 | | +++ | +++ |
| P-0390 | | +++ | +++ |
| P-0391 | | +++ | +++ |
| P-0392 | | +++ | +++ |
| P-0393 | | +++ | +++ |
| P-0394 | | +++ | +++ |
| P-0395 | | +++ | +++ |
| P-0396 | | +++ | +++ |
| P-0397 | | +++ | +++ |
| P-0398 | | +++ | +++ |
| P-0399 | | +++ | +++ |
| P-0400 | | +++ | +++ |
| P-0401 | | +++ | +++ |
| P-0402 | | +++ | +++ |
| P-0403 | | +++ | +++ |
| P-0404 | | +++ | +++ |
| P-0405 | | +++ | +++ |
| P-0406 | | +++ | +++ |
| P-0407 | | +++ | +++ |
| P-0408 | | +++ | +++ |
| P-0409 | | +++ | +++ |
| P-0410 | | +++ | +++ |
| P-0411 | | +++ | +++ |
| P-0412 | | +++ | +++ |
| P-0413 | | +++ | +++ |
| P-0414 | | +++ | +++ |
| P-0415 | | +++ | +++ |
| P-0416 | | +++ | +++ |
| P-0417 | | +++ | +++ |
| P-0418 | | +++ | +++ |
| P-0419 | | +++ | +++ |
| P-0420 | | +++ | + |
| P-0424 | | +++ | +++ |
| P-0427 | | +++ | +++ |
| P-0428 | | +++ | ++ |
| P-0429 | | +++ | ++ |
| P-0430 | | +++ | +++ |
| P-0431 | | +++ | +++ |
| P-0432 | | +++ | +++ |
| P-0433 | | +++ | +++ |
| P-0434 | | +++ | +++ |
| P-0435 | | +++ | +++ |
| P-0436 | | +++ | +++ |
| P-0437 | | +++ | +++ |
| P-0438 | | +++ | +++ |
| P-0440 | | +++ | +++ |
| P-0441 | | +++ | ++ |
| P-0442 | | +++ | +++ |
| P-0443 | | +++ | ++ |
| P-0448 | | +++ | +++ |
| P-0451 | | ++ | + |
| P-0452 | | +++ | ++ |
| P-0453 | | +++ | +++ |
| P-0454 | | +++ | +++ |
| P-0455 | | +++ | +++ |
| P-0456 | | +++ | +++ |
| P-0457 | | +++ | +++ |
| P-0458 | | +++ | +++ |
| P-0459 | | +++ | ++ |
| P-0460 | | +++ | +++ |
| P-0461 | | +++ | +++ |
| P-0462 | | +++ | ++ |
| P-0463 | | +++ | +++ |
| P-0464 | | +++ | +++ |
| P-0465 | | +++ | +++ |
| P-0466 | | +++ | +++ |
| P-0467 | | +++ | +++ |
| P-0468 | | +++ | +++ |
| P-0469 | | +++ | +++ |
| P-0470 | | +++ | +++ |
| P-0471 | | +++ | +++ |
| P-0472 | | +++ | +++ |
| P-0473 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0474 | | +++ | +++ |
| P-0475 | | +++ | +++ |
| P-0476 | | +++ | +++ |
| P-0477 | | +++ | ++ |
| P-0478 | | +++ | +++ |
| P-0479 | | +++ | +++ |
| P-0480 | | +++ | ++ |
| P-0481 | | +++ | +++ |
| P-0482 | | +++ | + |
| P-0483 | | +++ | +++ |
| P-0484 | | +++ | +++ |
| P-0485 | | +++ | +++ |
| P-0486 | | +++ | +++ |
| P-0487 | | +++ | +++ |
| P-0488 | | +++ | +++ |
| P-0489 | | +++ | +++ |
| P-0490 | | +++ | +++ |
| P-0491 | | +++ | +++ |
| P-0492 | | +++ | +++ |
| P-0493 | | +++ | +++ |
| P-0494 | | +++ | +++ |
| P-0495 | | +++ | +++ |
| P-0496 | | +++ | +++ |
| P-0497 | | +++ | +++ |
| P-0498 | | +++ | +++ |
| P-0499 | | +++ | +++ |
| P-0500 | | +++ | +++ |
| P-0501 | | +++ | +++ |
| P-0502 | | +++ | +++ |
| P-0503 | | +++ | +++ |
| P-0504 | | +++ | +++ |
| P-0505 | | +++ | +++ |
| P-0506 | | +++ | +++ |
| P-0507 | | +++ | +++ |
| P-0508 | | +++ | +++ |
| P-0509 | | +++ | +++ |
| P-0510 | | +++ | +++ |
| P-0511 | | +++ | +++ |
| P-0512 | | +++ | +++ |
| P-0513 | | +++ | +++ |
| P-0514 | | +++ | +++ |
| P-0515 | | +++ | +++ |
| P-0516 | | +++ | +++ |
| P-0517 | | ++ | ++ |
| P-0518 | | ++ | + |
| P-0519 | | +++ | +++ |
| P-0520 | | +++ | +++ |
| P-0521 | | +++ | +++ |
| P-0522 | | +++ | +++ |
| P-0523 | | +++ | +++ |
| P-0524 | | +++ | +++ |
| P-0525 | | +++ | +++ |
| P-0526 | | +++ | +++ |
| P-0527 | | +++ | +++ |
| P-0528 | | +++ | +++ |
| P-0529 | | +++ | +++ |
| P-0530 | | +++ | +++ |
| P-0531 | | +++ | +++ |
| P-0532 | | +++ | +++ |
| P-0533 | | +++ | +++ |
| P-0534 | | +++ | ++ |
| P-0535 | | +++ | +++ |
| P-0536 | | +++ | +++ |
| P-0537 | | +++ | +++ |
| P-0538 | | +++ | +++ |
| P-0539 | | +++ | +++ |
| P-0540 | | +++ | +++ |
| P-0541 | | +++ | +++ |
| P-0542 | | +++ | +++ |
| P-0543 | | +++ | +++ |
| P-0544 | | +++ | ++ |
| P-0545 | | +++ | +++ |
| P-0546 | | +++ | +++ |
| P-0547 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0548 | | +++ | +++ |
| P-0549 | | +++ | +++ |
| P-0550 | | +++ | ++ |
| P-0551 | | +++ | +++ |
| P-0552 | | +++ | +++ |
| P-0553 | | +++ | +++ |
| P-0554 | | +++ | +++ |
| P-0555 | | +++ | +++ |
| P-0556 | | +++ | +++ |
| P-0557 | | +++ | +++ |
| P-0558 | | +++ | +++ |
| P-0559 | | +++ | +++ |
| P-0560 | | +++ | +++ |
| P-0561 | | +++ | +++ |
| P-0562 | | +++ | +++ |
| P-0563 | | +++ | +++ |
| P-0564 | | +++ | +++ |
| P-0565 | | +++ | +++ |
| P-0566 | | +++ | ++ |
| P-0567 | | +++ | +++ |
| P-0568 | | +++ | +++ |
| P-0569 | | +++ | +++ |
| P-0570 | | +++ | +++ |
| P-0571 | | +++ | +++ |
| P-0572 | | +++ | +++ |
| P-0573 | | +++ | +++ |
| P-0574 | | +++ | +++ |
| P-0575 | | +++ | +++ |
| P-0576 | | +++ | +++ |
| P-0577 | | +++ | +++ |
| P-0578 | | +++ | ++ |
| P-0579 | | +++ | +++ |
| P-0580 | | +++ | +++ |
| P-0581 | | +++ | ++ |
| P-0582 | | +++ | +++ |
| P-0583 | | +++ | +++ |
| P-0584 | | +++ | +++ |
| P-0585 | | +++ | ++ |
| P-0586 | | +++ | +++ |
| P-0587 | | +++ | +++ |
| P-0588 | | +++ | +++ |
| P-0589 | | +++ | +++ |
| P-0590 | | +++ | +++ |
| P-0591 | | +++ | +++ |
| P-0592 | | +++ | +++ |
| P-0593 | | +++ | +++ |
| P-0594 | | +++ | +++ |
| P-0595 | | +++ | +++ |
| P-0596 | | +++ | +++ |
| P-0597 | | +++ | +++ |
| P-0598 | | +++ | +++ |
| P-0599 | | +++ | +++ |
| P-0600 | | +++ | +++ |
| P-0601 | | +++ | +++ |
| P-0602 | | +++ | +++ |
| P-0603 | | +++ | +++ |
| P-0604 | | +++ | +++ |
| P-0605 | | | +++ |
| P-0606 | | | +++ |
| P-0607 | | | +++ |
| P-0608 | | | +++ |
| P-0700 | | +++ | +++ |
| P-0705 | | +++ | +++ |
| P-0708 | | +++ | +++ |
| P-0710 | | +++ | +++ |
| P-0711 | | +++ | +++ |
| P-0722 | | +++ | +++ |
| P-0774 | | +++ | +++ |
| P-0775 | | +++ | +++ |
| P-0776 | | +++ | ++ |
| P-0778 | | +++ | ++ |
| P-0794 | | +++ | ++ |
| P-0802 | | +++ | ++ |
| P-0805 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0806 | | +++ | ++ |
| P-0900 | | +++ | +++ |
| P-0901 | | +++ | +++ |
| P-0902 | | +++ | +++ |
| P-0903 | | +++ | +++ |
| P-0904 | | +++ | +++ |
| P-0905 | | +++ | +++ |
| P-0906 | | +++ | +++ |
| P-0907 | | +++ | +++ |
| P-0908 | | +++ | +++ |
| P-0909 | | +++ | +++ |
| P-0910 | | +++ | +++ |
| P-0911 | | +++ | +++ |
| P-0912 | | +++ | +++ |
| P-0913 | | +++ | +++ |
| P-0914 | | +++ | ++ |
| P-0915 | | +++ | +++ |
| P-0916 | | +++ | +++ |
| P-0917 | | +++ | +++ |
| P-0918 | | +++ | +++ |
| P-0919 | | +++ | +++ |
| P-0920 | | +++ | +++ |
| P-0921 | | +++ | +++ |
| P-0922 | | +++ | +++ |
| P-0923 | | +++ | +++ |
| P-0924 | | +++ | +++ |
| P-0925 | | +++ | +++ |
| P-0926 | | +++ | +++ |
| P-0927 | | +++ | +++ |
| P-0928 | | +++ | ++ |
| P-0929 | | +++ | +++ |
| P-0930 | | +++ | ++ |
| P-0931 | | +++ | +++ |
| P-0932 | | +++ | +++ |
| P-0933 | | +++ | ++ |
| P-0934 | | +++ | +++ |
| P-0935 | | +++ | +++ |
| P-0936 | | +++ | +++ |
| P-0937 | | +++ | +++ |
| P-0938 | | +++ | +++ |
| P-0939 | | +++ | +++ |
| P-0940 | | +++ | +++ |
| P-0941 | | +++ | +++ |
| P-0942 | | +++ | +++ |
| P-0943 | | +++ | ++ |
| P-0944 | | +++ | +++ |
| P-0945 | | +++ | +++ |
| P-0946 | | +++ | +++ |
| P-0947 | | +++ | +++ |
| P-0948 | | +++ | +++ |
| P-0949 | | +++ | +++ |
| P-0950 | | +++ | +++ |
| P-0951 | | +++ | +++ |
| P-0952 | | +++ | +++ |
| P-0953 | | +++ | +++ |
| P-0954 | | +++ | |
| P-0955 | | +++ | +++ |
| P-0956 | | +++ | +++ |
| P-0957 | | +++ | +++ |
| P-0958 | | +++ | +++ |
| P-0959 | | +++ | +++ |
| P-0960 | | +++ | +++ |
| P-0961 | | +++ | +++ |
| P-0962 | | +++ | +++ |
| P-0963 | | +++ | +++ |
| P-0964 | | +++ | +++ |
| P-0965 | | +++ | +++ |
| P-0966 | | +++ | +++ |
| P-0967 | | +++ | +++ |
| P-0968 | | +++ | +++ |
| P-0969 | | +++ | +++ |
| P-0970 | | +++ | +++ |
| P-0971 | | +++ | +++ |
| P-0972 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-0973 | | +++ | +++ |
| P-0974 | | +++ | +++ |
| P-0975 | | +++ | +++ |
| P-0976 | | +++ | +++ |
| P-0977 | | +++ | +++ |
| P-0978 | | +++ | +++ |
| P-0979 | | +++ | +++ |
| P-0980 | | +++ | +++ |
| P-0981 | | +++ | +++ |
| P-0982 | | +++ | +++ |
| P-0983 | | +++ | +++ |
| P-0984 | | +++ | +++ |
| P-0985 | | +++ | +++ |
| P-0986 | | +++ | +++ |
| P-0987 | | +++ | +++ |
| P-0988 | | +++ | +++ |
| P-0989 | | +++ | +++ |
| P-0990 | | +++ | +++ |
| P-0991 | | +++ | +++ |
| P-0992 | | +++ | +++ |
| P-0993 | | +++ | +++ |
| P-0994 | | +++ | +++ |
| P-0995 | | +++ | +++ |
| P-0996 | | +++ | +++ |
| P-0997 | | +++ | +++ |
| P-0998 | | +++ | +++ |
| P-0999 | | +++ | +++ |
| P-1000 | | +++ | ++ |
| P-1001 | | +++ | ++ |
| P-1002 | | +++ | +++ |
| P-1003 | | +++ | +++ |
| P-1004 | | +++ | +++ |
| P-1005 | | +++ | ++ |
| P-1006 | | +++ | +++ |
| P-1007 | | +++ | +++ |
| P-1008 | | +++ | +++ |
| P-1009 | | +++ | +++ |
| P-1010 | | +++ | ++ |
| P-1011 | | +++ | +++ |
| P-1012 | | +++ | +++ |
| P-1013 | | +++ | +++ |
| P-1014 | | +++ | +++ |
| P-1015 | | +++ | +++ |
| P-1016 | | +++ | +++ |
| P-1017 | | +++ | +++ |
| P-1018 | | +++ | +++ |
| P-1019 | | +++ | +++ |
| P-1020 | | +++ | +++ |
| P-1021 | | +++ | +++ |
| P-1022 | | +++ | +++ |
| P-1023 | | +++ | +++ |
| P-1024 | | +++ | +++ |
| P-1025 | | +++ | +++ |
| P-1026 | | +++ | +++ |
| P-1027 | | +++ | +++ |
| P-1028 | | +++ | +++ |
| P-1029 | | +++ | +++ |
| P-1030 | | +++ | +++ |
| P-1031 | | +++ | +++ |
| P-1032 | | +++ | +++ |
| P-1033 | | +++ | ++ |
| P-1034 | | +++ | +++ |
| P-1035 | | +++ | +++ |
| P-1036 | | +++ | +++ |
| P-1037 | | +++ | +++ |
| P-1038 | | +++ | +++ |
| P-1039 | | +++ | +++ |
| P-1040 | | +++ | +++ |
| P-1041 | | +++ | +++ |
| P-1042 | | +++ | +++ |
| P-1043 | | +++ | +++ |
| P-1044 | | +++ | +++ |
| P-1045 | | +++ | +++ |
| P-1046 | | +++ | +++ |

-continued

| Compound number | Biochemical activity ($IC_{50}$ μM) BRD4(1) H4 | Biochemical activity ($IC_{50}$ μM) BRD4(1 2) H4 | Cell activity ($IC_{50}$ μM) MV-4-11 3d-Growth |
|---|---|---|---|
| P-1047 | | +++ | +++ |
| P-1048 | | +++ | +++ |
| P-1049 | | +++ | +++ |
| P-1050 | | +++ | +++ |
| P-1051 | | | ++ |

Compounds P-0001 to P-0106, P-0108 to P-0246 and P-0250-0372, e.g., compounds P-0001, P-0002, P-0003, P-0004, P-0005, P-0006, P-0007, P-0008, P-0009, P-0010, P-0011, P-0012, P-0013, P-0014, P-0015, P-0016, P-0017, P-0018, P-0019, P-0020, P-0021, P-0022, P-0023, P-0024, P-0025, P-0026, P-0027, P-0028, P-0029, P-0030, P-0031, P-0032, P-0033, P-0034, P-0035, P-0036, P-0037, P-0038, P-0039, P-0040, P-0041, P-0042, P-0043, P-0044, P-0045, P-0046, P-0047, P-0048, P-0049, P-0050, P-0051, P-0052, P-0053, P-0054, P-0055, P-0056, P-0057, P-0058, P-0059, P-0060, P-0061, P-0062, P-0063, P-0064, P-0065, P-0066, P-0067, P-0068, P-0069, P-0070, P-0071, P-0072, P-0073, P-0074, P-0075, P-0076, P-0077, P-0078, P-0079, P-0080, P-0081, P-0082, P-0083, P-0084, P-0085, P-0086, P-0087, P-0088, P-0089, P-0090, P-0091, P-0092, P-0093, P-0094, P-0095, P-0096, P-0097, P-0098, P-0099, P-0100, P-0101, P-0102, P-0103, P-0104, P-0105, P-0106, P-0108, P-0109, P-0110, P-0111, P-0112, P-0113, P-0114, P-0115, P-0116, P-0117, P-0118, P-0119, P-0120, P-0121, P-0122, P-0123, P-0125, P-0126, P-0127, P-0128, P-0129, P-0130, P-0131, P-0132, P-0134, P-0135, P-0136, P-0137, P-0138, P-0139, P-0140, P-0141, P-0142, P-0143, P-0144, P-0145, P-0146, P-0147, P-0148, P-0149, P-0150, P-0151, P-0152, P-0153, P-0154, P-0156, P-0157, P-0158, P-0159, P-0160, P-0161, P-0163, P-0164, P-0165, P-0167, P-0168, P-0169, P-0170, P-0171, P-0172, P-0173, P-0174, P-0175, P-0176, P-0179, P-0180, P-0181, P-0182, P-0183, P-0185, P-0186, P-0187, P-0188, P-0189, P-0190, P-0191, P-0192, P-0193, P-0194, P-0195, P-0196, P-0197, P-0198, P-0199, P-0200, P-0201, P-0202, P-0203, P-0204, P-0205, P-0206, P-0207, P-0208, P-0209, P-0210, P-0211, P-0212, P-0213, P-0214, P-0215, P-0216, P-0217, P-0218, P-0219, P-0220, P-0221, P-0222, P-0223, P-0224, P-0225, P-0226, P-0227, P-0228, P-0229, P-0230, P-0231, P-0232, P-0233, P-0234, P-0235, P-0236, P-0237, P-0238, P-0239, P-0240, P-0241, P-0242, P-0243, P-0244, P-0245, P-0246, P-0250, P-0251, P-0252, P-0253, P-0254, P-0255, P-0256, P-0257, P-0258, P-0259, P-0260, P-0261, P-0262, P-0263, P-0264, P-0265, P-0266, P-0267, P-0268, P-0269, P-0270, P-0271, P-0272, P-0273, P-0274, P-0275, P-0276, P-0277, P-0278, P-0279, P-0280, P-0281, P-0282, P-0283, P-0284, P-0285, P-0286, P-0287, P-0288, P-0289, P-0290, P-0291, P-0292, P-0293, P-0294, P-0295, P-0296, P-0297, P-0298, P-0299, P-0300, P-0301, P-0302, P-0303, P-0304, P-0305, P-0306, P-0307, P-0308, P-0309, P-0310, P-0311, P-0312, P-0313, P-0314, P-0315, P-0316, P-0317, P-0318, P-0319, P-0320, P-0321, P-0322, P-0323, P-0324, P-0325, P-0326, P-0327, P-0328, P-0329, P-0330, P-0331, P-0332, P-0333, P-0334, P-0335, P-0336, P-0337, P-0338, P-0339, P-0340, P-0341, P-0342, P-0343, P-0344, P-0345, P-0346, P-0347, P-0348, P-0349, P-0350, P-0351, P-0352, P-0353, P-0354, P-0355, P-0356, P-0357, P-0358, P-0359, P-0360, P-0361, P-0362, P-0363, P-0364, P-0365, P-0366, P-0367, P-0368, P-0369, P-0370, P-0371 or P-0372 had $IC_{50}$ of less than 10 μM in at least one of the bromodomain cell assays described above in Example 57.

Compounds P-0373 to P-0420, P-0424, P-0427 to P-0438, P-0440 to P-0443, P-0448, and P-0451 to P-0622, e.g., compounds P-0373, P-0374, P-0375, P-0376, P-0377, P-0378, P-0378, P-0379, P-0381, P-0382, P-0383, P-0384, P-0385, P-0386, P-0387, P-0388, P-0389, P-0390, P-0391, P-0392, P-0393, P-0394, P-0395, P-0396, P-0397, P-0399, P-0400, P-0401, P-0402, P-0403, P-0404, P-0405, P-0406, P-0407, P-0408, P-0409, P-0410, P-0411, P-0412, P-0413, P-0414, P-0415, P-0416, P-0417, P-0418, P-0419, P-0420, P-0424, P-0427, P-0428, P-0429, P-0430, P-0431, P-0432, P-0433, P-0434, P-0435, P-0436, P-0437, P-0438, P-0440, P-0441, P-0442, P-0443, P-0448, P-0451, P-0452, P-0453, P-0454, P-0455, P-0456, P-0457, P-0458, P-0459, P-0460, P-0461, P-0462, P-0463, P-0464, P-0465, P-0466, P-0467, P-0468, P-0469, P-0470, P-0471, P-0472, P-0473, P-0474, P-0475, P-0476, P-0477, P-0478, P-0479, P-0480, P-0481, P-0482, P-0483, P-0484, P-0485, P-0486, P-0487, P-0488, P-0489, P-0490, P-0491, P-0492, P-0493, P-0494, P-0495, P-0496, P-0497, P-0498, P-0499, P-0500, P-0501, P-0502, P-0503, P-0504, P-0505, P-0506, P-0507, P-0508, P-0509, P-0510, P-0511, P-0512, P-0513, P-0514, P-0515, P-0516, P-0517, P-0518, P-0519, P-0520, P-0521, P-0522, P-0523, P-0524, P-0525, P-0526, P-0527, P-0528, P-0529, P-0530, P-0531, P-0532, P-0533, P-0534, P-0535, P-0536, P-0537, P-0538, P-0539, P-0540, P-0541, P-0542, P-0543, P-0544, P-0545, P-0546, P-0547, P-0548, P-0549, P-0550, P-0551, P-0552, P-0553, P-0554, P-0555, P-0556, P-0557, P-0558, P-0559, P-0560, P-0561, P-0562, P-0563, P-0564, P-0565, P-0566, P-0567, P-0568, P-0569, P-0570, P-0571, P-0572, P-0573, P-0574, P-0575, P-0576, P-0577, P-0578, P-0579, P-0580, P-0581, P-0582, P-0583, P-0584, P-0585, P-0586, P-0587, P-0588, P-0589, P-0590, P-0591, P-0592, P-0593, P-0594, P-0595, P-0596, P-0597, P-0598, P-0599, P-0600, P-0601, P-0602, P-0603, P-0604, P-0605, P-0606, P-0607, P-0608, P-0609, P-0610, P-0611, P-0612, P-0613, P-0614, P-0615, P-0616, P-0617, P-0618, P-0619, P-0620, P-0621 or P-0622 had $IC_{50}$ of less than 10 μM in at least one of the bromodomain cell assays described above in Example 57.

Compounds P-0700 to P-0822, e.g., compounds P-0700, P-0701, P-0702, P-0703, P-0704, P-0705, P-0706, P-0707, P-0708, P-0709, P-0710, P-0711, P-0712, P-0713, P-0714, P-0715, P-0716, P-0717, P-0718, P-0719, P-0720, P-0721, P-0722, P-0723, P-0724, P-0725, P-0726, P-0727, P-0728, P-0729, P-0730, P-0731, P-0732, P-0733, P-0734, P-0735, P-0736, P-0737, P-0738, P-0739, P-0740, P-0741, P-0742, P-0743, P-0744, P-0745, P-0746, P-0747, P-0748, P-0749, P-0750, P-0751, P-0752, P-0753, P-0754, P-0755, P-0756, P-0757, P-0758, P-0759, P-0760, P-0761, P-0762, P-0763, P-0764, P-0765, P-0766, P-0767, P-0768, P-0769, P-0770, P-0771, P-0772, P-0773, P-0774, P-0775, P-0776, P-0777, P-0778, P-0779, P-0780, P-0781, P-0782, P-0783, P-0784, P-0785, P-0786, P-0787, P-0788, P-0789, P-0790, P-0791, P-0792, P-0793, P-0794, P-0795, P-0796, P-0797, P-0798, P-0799, P-0800, P-0801, P-0802, P-0803, P-0804, P-0805, P-0806, P-807, P-0808, P-0809, P-0810, P-0811, P-0812, P-0813 P-0814, P-0815, P-0816, P-0817, P-0818, P-0819, P-0820, P-0821 or P-0822 have $IC_{50}$ of less than 10 μM in at least one of the bromodomain cell assays described above in Example 57.

All patents, patent applications and other references cited in the specification are indicative of the level of skill of those skilled in the art to which the present disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the present disclosure. Changes therein and other uses will occur to those skilled in the art, which are encompassed within the spirit of the present disclosure, are defined by the scope of the claims.

While this disclosure has been made with reference to specific embodiments, it is apparent that other embodiments and variations of the present disclosure may be devised by others skilled in the art without departing from the true spirit and scope of the present disclosure.

In addition, where features or aspects of the present disclosure are described in terms of Markush groups or other grouping of alternatives, those skilled in the art will recognize that the present disclosure is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the present disclosure.

What is claimed is:

1. A compound having formula (Va):

(Va)

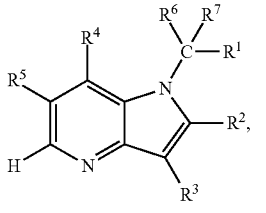

or a pharmaceutically acceptable salt, a solvate, a tautomer, a stereoisomer or a deuterated analog thereof, wherein:

$R^2$ is H;

$R^4$ is H;

$R^6$ is H;

$R^7$ is H, —OH, $C_{1-6}$ alkyl, aryl, heteroaryl, cycloalkyl, or heterocycloalkyl;

$R^1$ is heteroaryl optionally substituted with from 1-3 $R^j$ groups;

each $R^j$ independently selected from halogen, —CN, —OH, —$NH_2$, —$NO_2$, —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —CH═C($R^k$)($R^k$), —$OR^k$, —$SR^k$, —OC(O)$R^k$, —OC(S)$R^k$, —P(═O)H$R^k$, —P(═O)$R^kR^k$, —PH(═O)$OR^k$, —P(═O)$(OR^k)_2$, —OP(═O)$(OR^k)_2$, —C(O)H, —O(CO)$OR^k$, —C(O)$R^k$, —C(S)$R^k$, —C(O)$OR^k$, —C(S)$OR^k$, —S(O)$R^k$, —$S(O)_2R^k$, —C(O)$NHR^k$, —C(S)$NHR^k$, —C(O)$NR^kR^k$, —C(S)$NR^kR^k$, —$S(O)_2NHR^k$, —$S(O)_2NR^kR^k$, —C(NH)$NHR^k$, —C(NH)$NR^kR^k$, —NHC(O)$R^k$, —NHC(S)$R^k$, —$NR^k$C(O)$R^k$, —$NR^k$C(S)$R^k$, —$NHS(O)_2R^k$, —$NR^kS(O)_2R^k$, —NHC(O)$NHR^k$, —NHC(S)$NHR^k$, —$NR^k$C(O)$NH_2$, —$NR^k$C(S)$NH_2$, —$NR^k$C(O)$NHR^k$, —$NR^k$C(S)$NHR^k$, —NHC(O)$NR^kR^k$, —NHC(S)$NR^kR^k$, —$NR^k$C(O)$NR^kR^k$, —NR $^k$C(S)$NR^kR^k$, —$NHS(O)_2NHR^k$, —$NR^kS(O)_2NH_2$, —$NR^kS(O)_2NHR^k$, —$NHS(O)_2NR^kR^k$, —$NR^k$S(O)$_2$ $NR^kR^k$, —$NHR^k$ or —$NR^kR^k$;

each $R^k$ is independently H, $C_{1-6}$alkyl, aryl, arylalkyl, heteroaryl, heteroarylalkyl, heterocycloalkyl, heterocycloalkylalkyl, cycloalkyl or cycloalkylalkyl; or two $R^k$ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized;

$R^3$ is H, halogen, —CN, optionally substituted $C_{1-6}$alkyl, optionally substituted deuterated $C_{1-6}$alkyl, optionally substituted aryl, optionally substituted aryl-$C_{1-4}$alkyl, optionally substituted heteroaryl, optionally substituted heteroaryl-$C_{1-4}$alkyl, optionally substituted $C_{3-8}$ cycloalkyl, optionally substituted $C_{3-8}$ cycloalkyl-$C_{1-4}$ alkyl, optionally substituted heterocycloalkyl, or optionally substituted heterocycloalkyl-$C_{1-4}$alkyl; and $R^5$ is

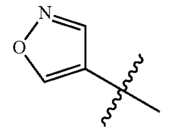 [SMILES: *c1cnoc1]

optionally substituted with from 1 to 2 $R^{11}$ groups independently selected from D, halogen, $C_{1-6}$alkyl, $C_{1-4}$haloalkyl, $C_{1-4}$haloalkoxy or —CN;

wherein the wavy line indicates the point of attachment to the rest of molecule.

2. The compound of claim 1, wherein $R^3$ is halogen, —CN, optionally substituted $C_{1-6}$alkyl, optionally substituted aryl, optionally substituted aryl-$C_{1-4}$alkyl, optionally substituted heteroaryl, optionally substituted heteroaryl-$C_{1-4}$ alkyl, optionally substituted $C_{3-8}$ cycloalkyl, optionally substituted $C_{3-8}$ cycloalkyl-$C_{1-4}$alkyl, optionally substituted heterocycloalkyl, or optionally substituted heterocycloalkyl-$C_{1-4}$alkyl.

3. The compound of claim 1, wherein $R^3$ is deuterated $C_{1-6}$alkyl, $C_{1-6}$alkyl, aryl, heteroaryl, $C_{3-8}$ cycloalkyl, or heterocycloalkyl, wherein each $R^3$ is optionally substituted with from 1-3 substituents independently selected from CN, —OH, —$NH_2$, —$NO_2$, —C(O)OH, —C(S)OH, —C(O)$NH_2$, —C(S)$NH_2$, —$S(O)_2NH_2$, —NHC(O)$NH_2$, —NHC(S)$NH_2$, —$NHS(O)_2NH_2$, —C(NH)$NH_2$, —$B(OH)_2$, —Si$(R'')_3$, —CH═C(R″)(R″), —OR″, —OC(O)R″, —OC(S)R″, —P(═O)R″R″, —P(═O)R″R″, —PH(═O)OR″, —P(═O)$(OR'')_2$, —OP(═O)$(OR'')_2$, —C(O)H, —O(CO)OR″, —C(O)R″, —C(S)R″, —C(O)OR″, —C(S)OR″, —S(O)R″, —$S(O)_2$R″, —C(O)NHR″, —C(S)NHR″, —C(O)NR″R″, —C(S)NR″R″, —$S(O)_2$NHR″, —$S(O)_2$NHR″, —C(NH)NHR″, —C(NH)NR″R″, —NHC(O)R″, —NHC(S)R″, —NR″C(O)R″, —NR″C(S)R″, —$NHS(O)_2$R″, —NR″$S(O)_2$ R″, —NHC(O)NHR″, —NHC(S)NHR″, —NR″C(O)$NH_2$, —NR″C(S)$NH_2$, —NR″C(O)NHR″, —N R″C(S)NHR″, —NHC(O)NR″R″, —NHC(S)NR″R″, —NR″C(O)NR″R″, —NR″C(S)NR″R″, —$NHS(O)_2$NH R″, —NR″$S(O)_2NH_2$, —NR″$S(O)_2$NHR″, —$NHS(O)_2$NR″R″, —NR″$S(O)_2$ NR″R″, —NHR″, R″ or —NR″R″, wherein each R″ is independently selected from H, $C_{1-6}$alkyl or aryl, arylalkyl, heteroaryl, heteroarylalkyl, heterocycloalkyl, heterocycloalkylalkyl, cycloalkyl or cycloalkylalkyl; or two R″ groups when attached to the same carbon or nitrogen atom are taken together to form a 3- to 6-membered carbocyclic ring or 3- to 8-membered heterocyclic ring having from 1-2 heteroatoms as ring members selected from O, N or S, wherein the nitrogen or sulfur ring atoms are optionally oxidized.

4. The compound of claim 1, wherein $R^3$ is aryl or heteroaryl, wherein each $R^3$ is optionally substituted with from 1-3 substituents independently selected from halogen, vinyl, $C_{1-6}$alkyl, —OH, $C_{1-6}$alkoxy, $C_{1-6}$haloalkyl, $C_{1-6}$haloalkoxy, —CN, —$NH_2$, —NH($C_{1-6}$alkyl), —N($C_{1-6}$alkyl)$_2$, $C_{3-6}$cycloalkyl, heterocycloalkyl, aryl, or heteroaryl.

5. The compound of claim 1, wherein $R^3$ is aryl or heteroaryl, each of which is optionally substituted with from 1-5 substituents independently selected from halogen, —CN, —OH, —$NH_2$, —$NO_2$, —CH═C($R^i$)($R^i$), —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^i$, —$SR^i$, —OC(O)$R^i$, —OC(S)$R^i$, —P(═O)$HR^i$, —P(═O)$R^iR^i$, —PH(═O)$OR^i$, —P(═)($OR^i$)$_2$, —OP(═O)($OR^i$)$_2$, —C(O)H, —O(CO)$OR^i$, —C(O)$R^i$, —C(S)$R^i$, —C(O)$OR^i$, —C(S)$OR^i$, —S(O)$R^i$, —S(O)$_2R^i$, —C(O)$NHR^i$, —C(S)$NHR^i$, —C(O)$NR^iR^i$, —C(S)$NR^iR^i$, —S(O)$_2NHR^i$, —S(O)$_2NR^iR^i$, —C(NH)$NHR^i$, —C(NH)$NR^iR^i$, —NH C(O)$R^i$, —NHC(S)$R^i$, —$NR^i$C(O)$R^i$, —$NR^i$C(S)$R^i$, —NHS(O)$_2R^i$, —$NR^i$S(O)$_2R^i$, —NHC(O)$NHR^i$, —NHC(S) $NHR^i$, —$NR^i$C(O)$NH_2$, —$NR^i$C(S)$NH_2$, —$NR^i$C(O)$NHR^i$, —$NR^i$C(S)$NHR^i$, —NHC(O)$NR^iR^i$, —NHC(S)N $R^iR^i$, —$NR^i$C(O)$NR^iR^i$, —$NR^i$C(S)$NR^iR^i$, —NHS(O)$_2NHR^i$, —$NR^i$S(O)$_2NH_2$, —$NR^i$S(O)$_2NHR^i$, —NHS(O)$_2NR^iR^i$, —$NR^i$S(O)$_2NR^iR^i$, $R^i$, —$NHR^i$ or —$NR^iR^i$, wherein each $R^i$ is independently $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl or heterocycloalkyl-$C_{1-4}$alkyl, wherein each $R^i$ is further optionally substituted with from 1-3 $R^p$ groups independently selected from halogen, CN, —OH, —$NH_2$, —N($R^q$)($R^q$), —$NO_2$, —C(O)OH, —C(O)$NH_2$, —S(O)$_2NH_2$, —NHC(O)$NH_2$, —C(NH)$NH_2$, —P(═O)$HR^q$, —P(═O)$R^qR^q$, —PH(═O)$OR^q$, —P(═O)($OR^q$)$_2$, —OP(═O)($OR^q$)$_2$, —OC(O)$R^q$, —OC(S)$R^q$, —C(O)$R^q$, —C(S)$R^q$, —C(O)$OR^q$, —S(O)$_2R^q$, —C(O)$NHR^q$, $C_{1-6}$alkyl, $C_{1-6}$alkoxy, halogen, $C_{1-6}$ haloalkyl or $C_{1-6}$ haloalkoxy, and wherein $R^q$ is $C_{1-6}$alkyl.

6. The compound of claim 1, wherein $R^7$ is H, D, $C_{1-6}$alkyl, or deuterated $C_{1-6}$alkyl.

7. The compound of claim 1, wherein $R^{11}$ is halogen, $CH_3$, $CD_3$, $CF_3$, $CHF_2$, $CH_2F$, $CH_2Cl$ or —CN.

8. The compound of claim 1, wherein $R^1$ is 2-pyridyl, 3-pyridyl, 4-pyridyl, 3-pyridazinyl, or 4-pyridazinyl.

9. A pharmaceutical composition comprising a compound of claim 1 and a pharmaceutical acceptable excipient or carrier.

10. A compound selected from:

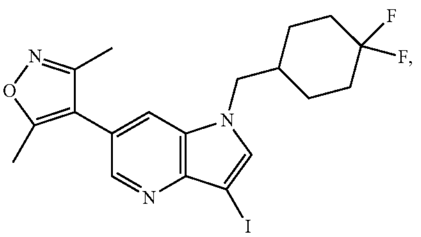

-continued

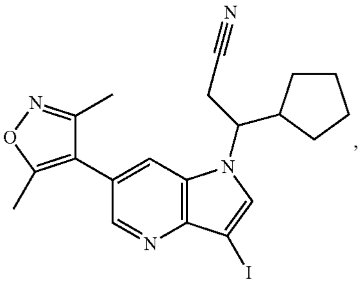
,

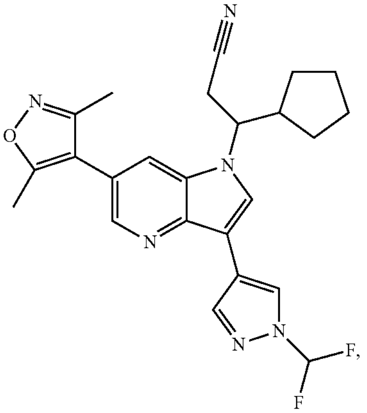

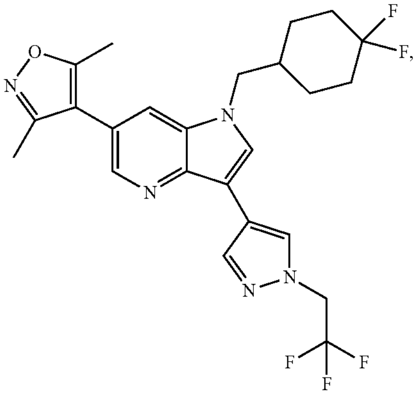

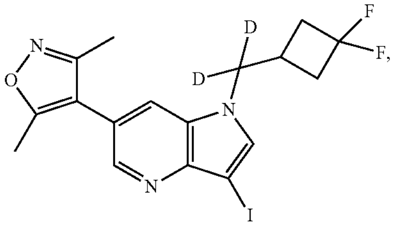

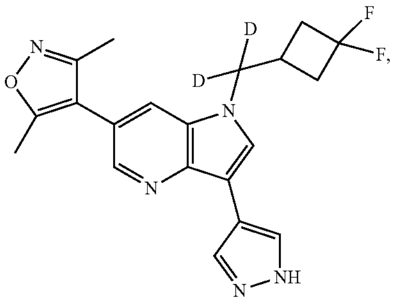

-continued
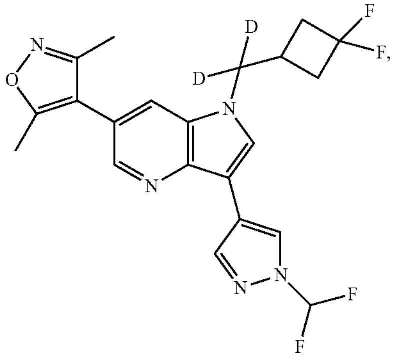
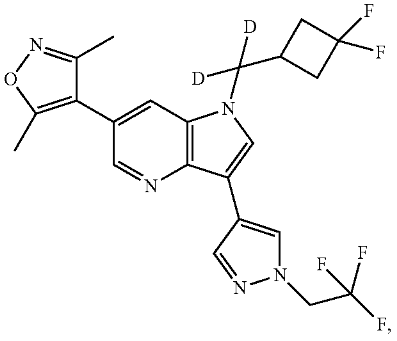
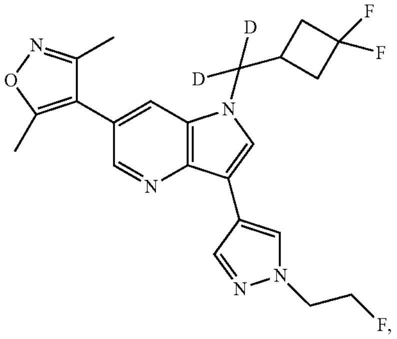
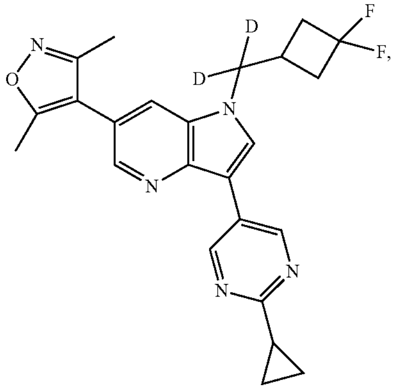
-continued
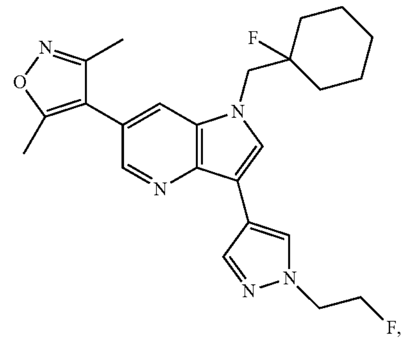
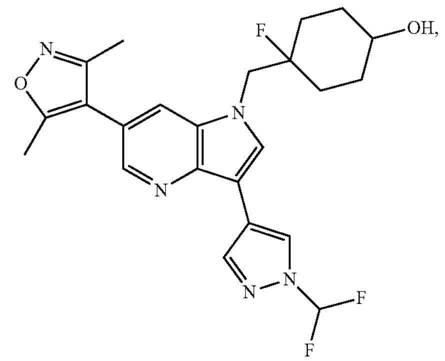
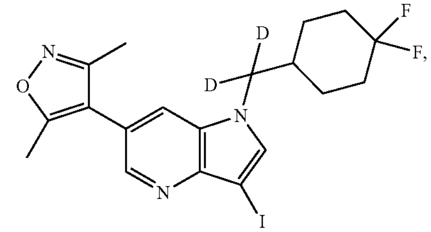
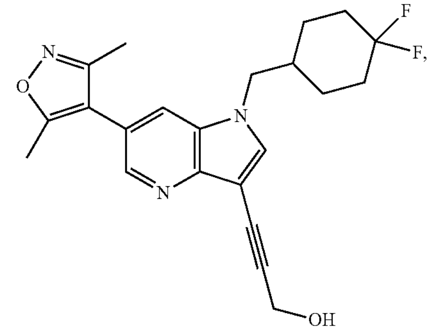
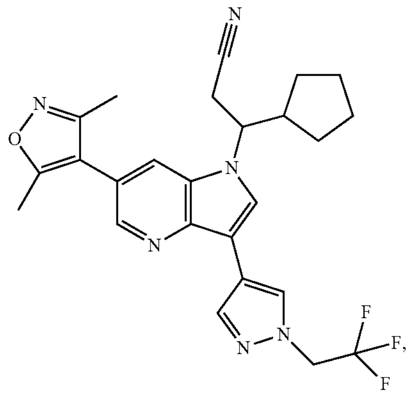

-continued
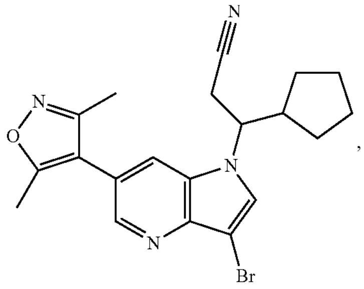
,
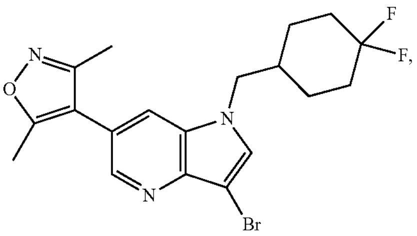
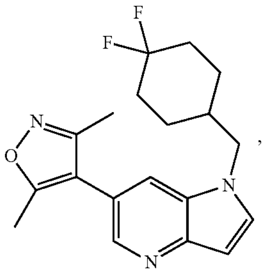
,
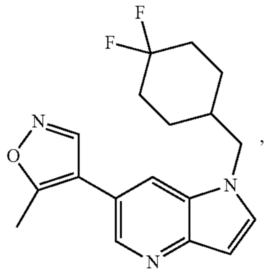
,
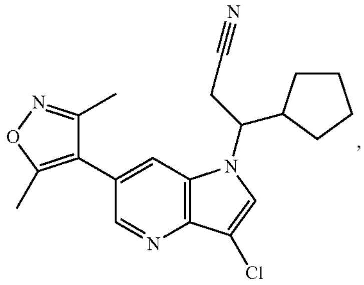
,
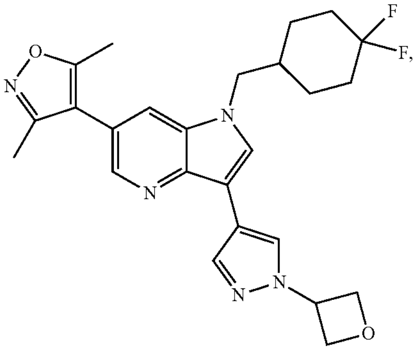
-continued
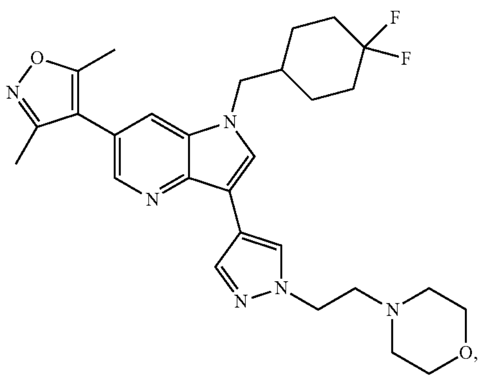
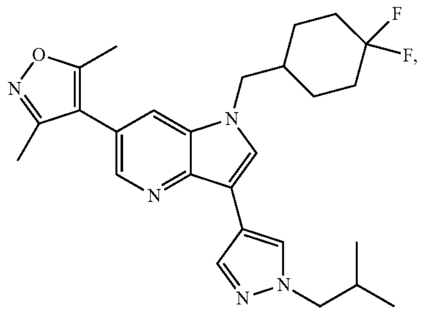
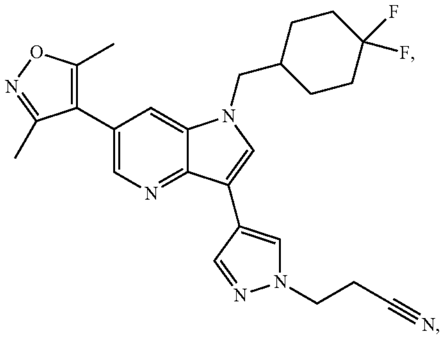 [SMILES: Cc1noc(C)c1-c1cnc2c(-c3cnn(CCC#N)c3)cn(CC3CCC(F)(F)CC3)c2c1]
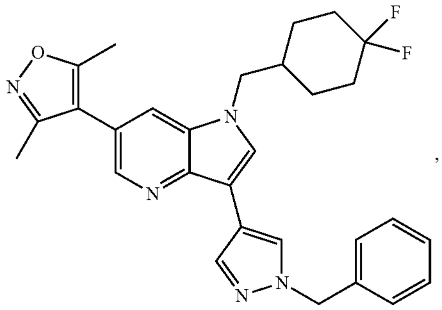
,
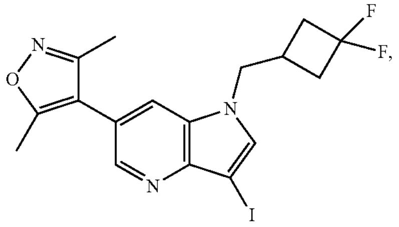

-continued
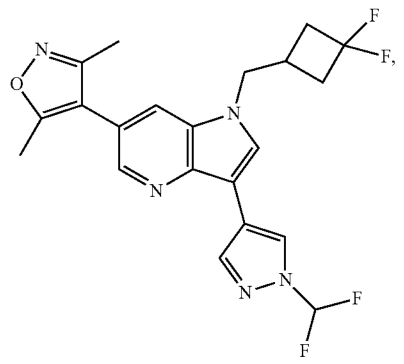
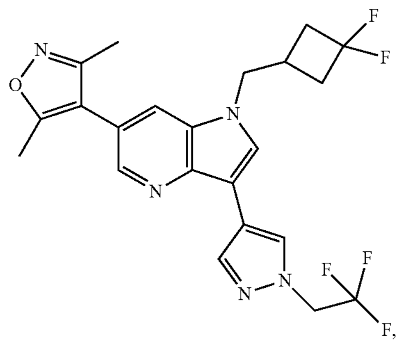
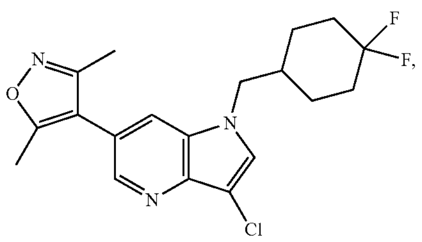
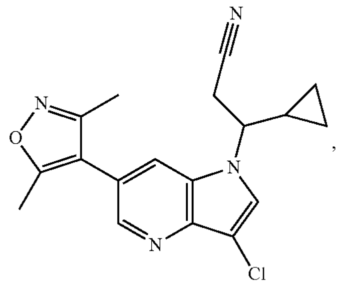
,
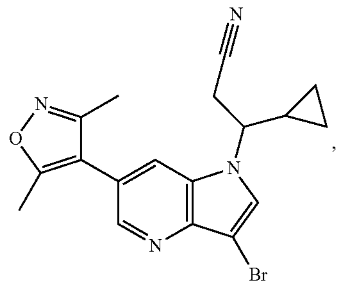
,
-continued
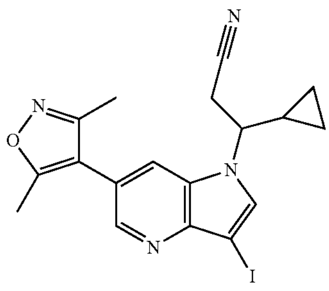
,
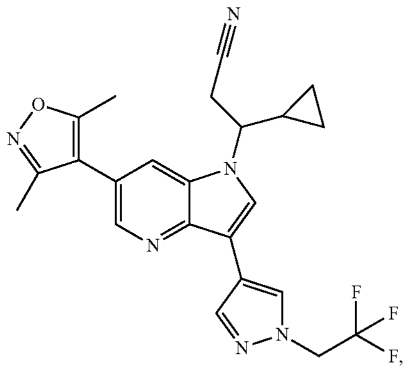
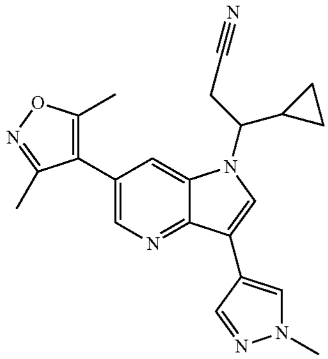
,
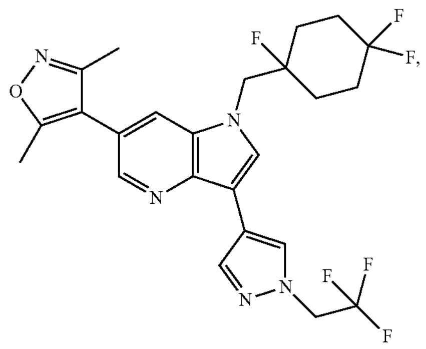
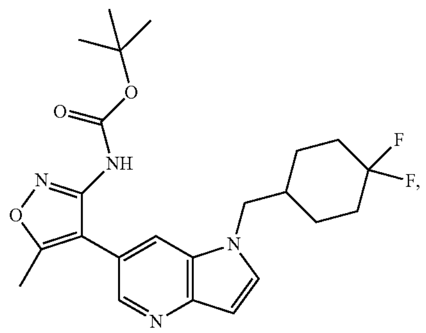

-continued
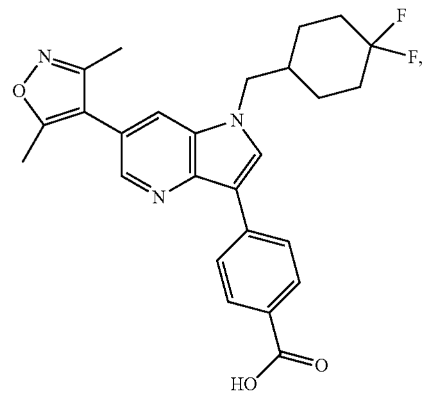
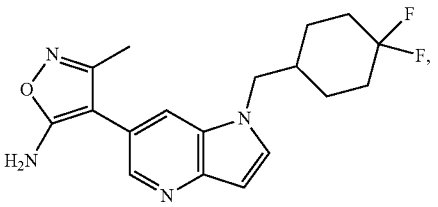
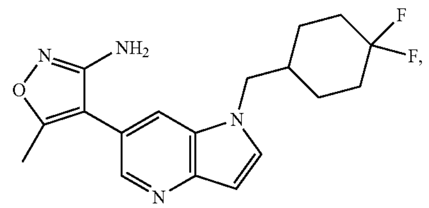
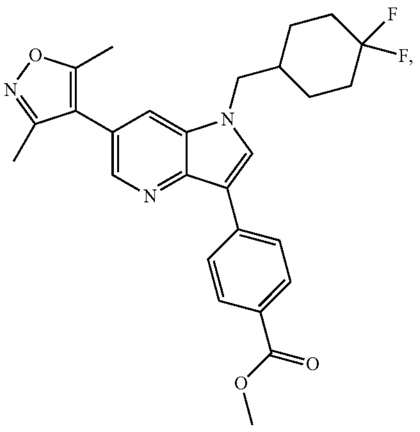
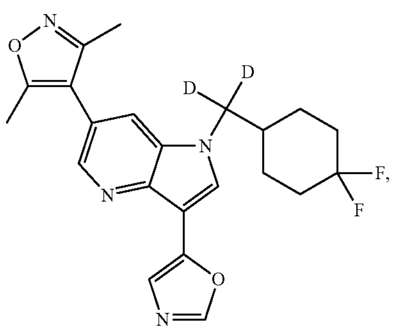
-continued
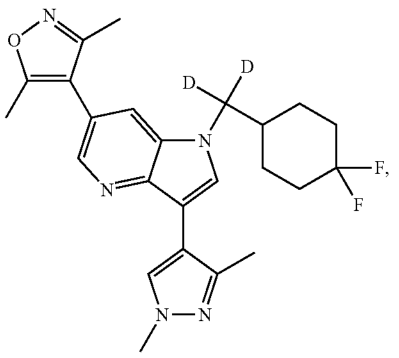
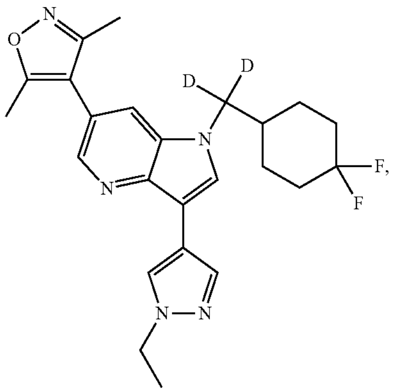
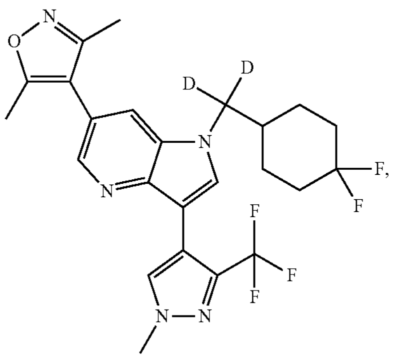
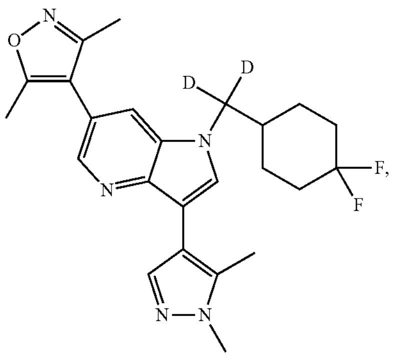

-continued
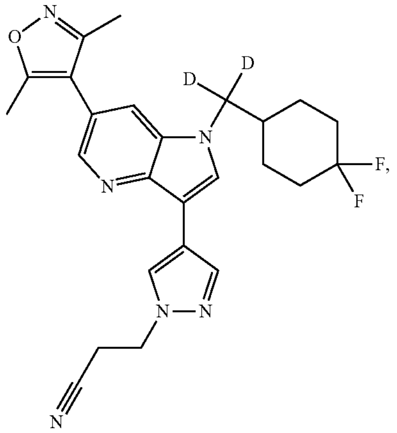
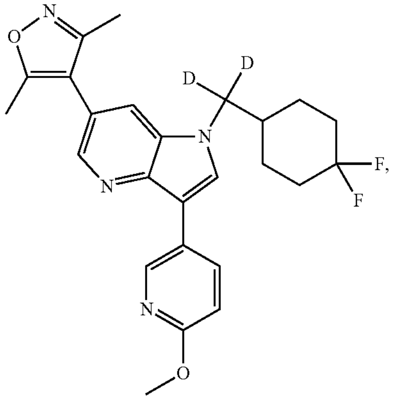
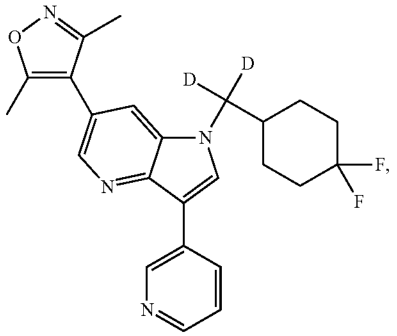
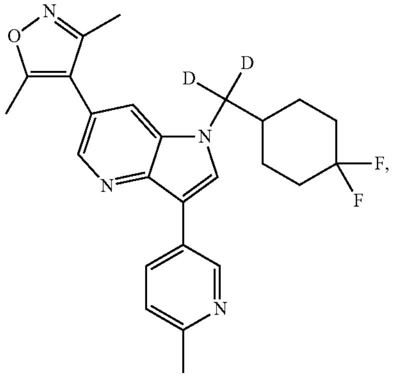
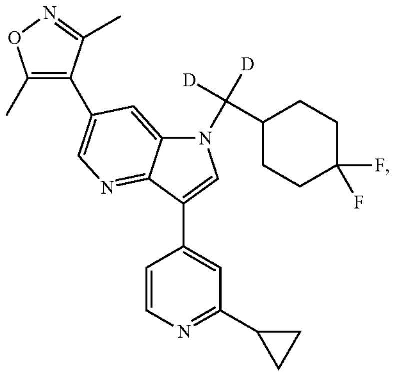
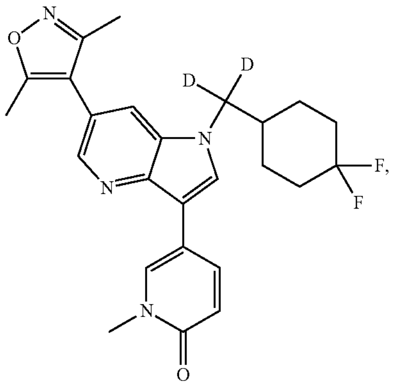
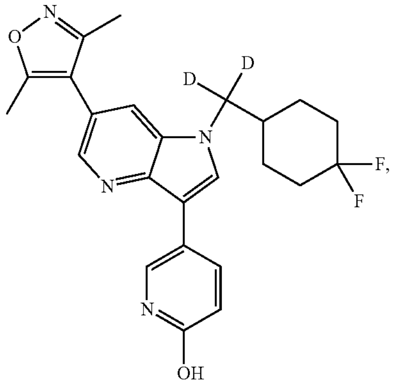
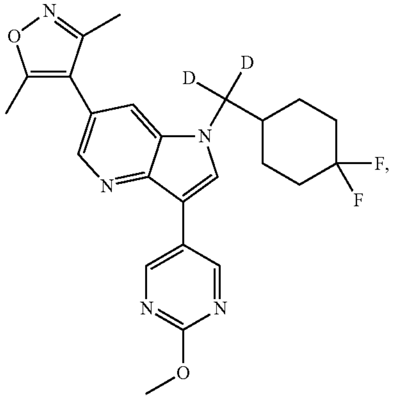
-continued -continued
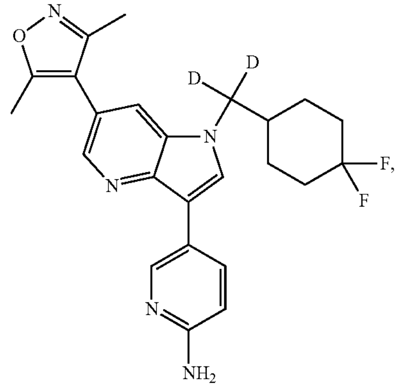
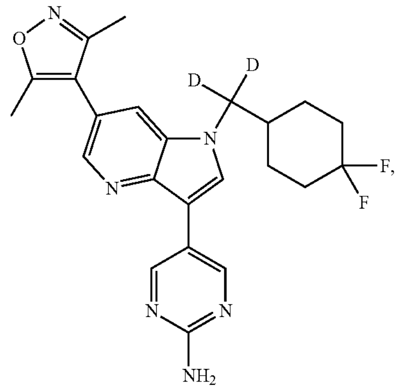
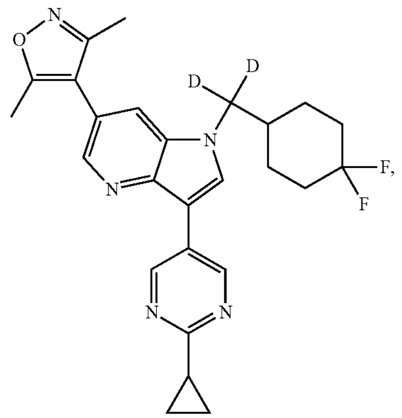
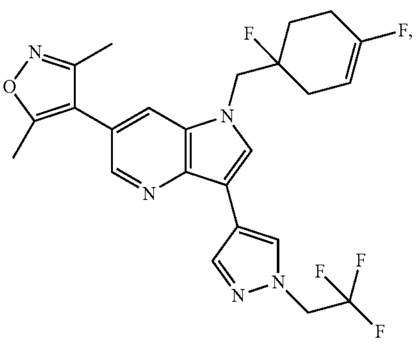
-continued
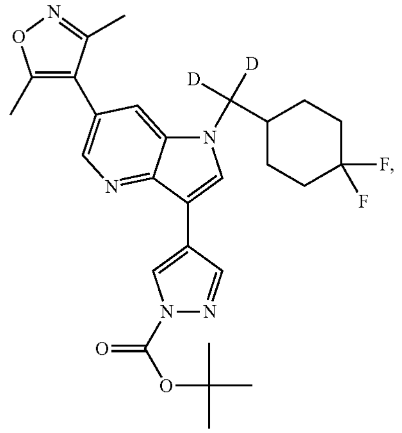
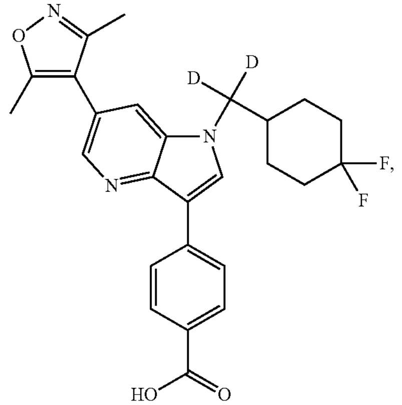
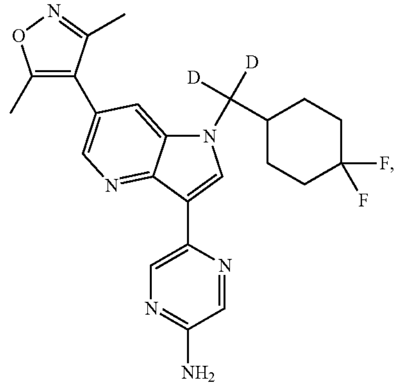
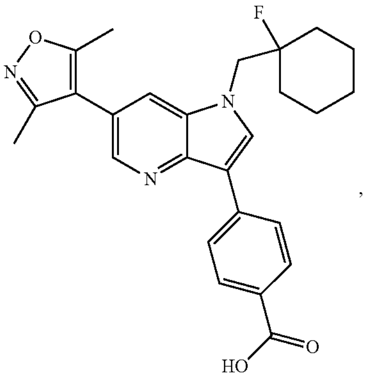
, -continued
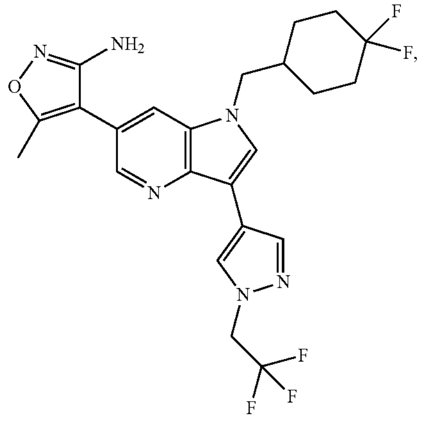
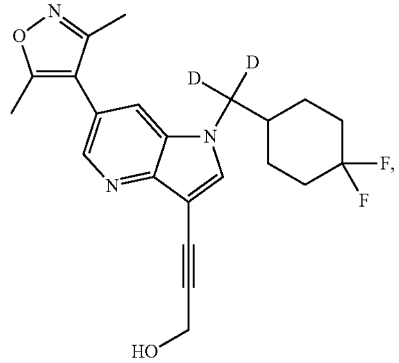
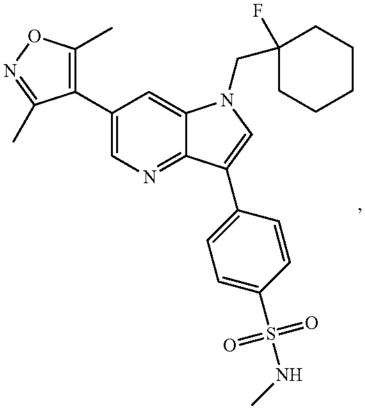
,
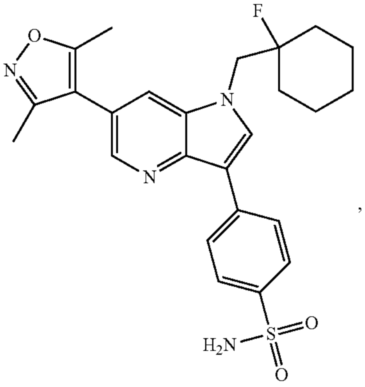
,
-continued
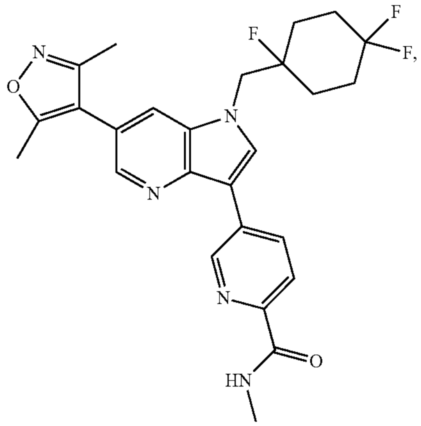
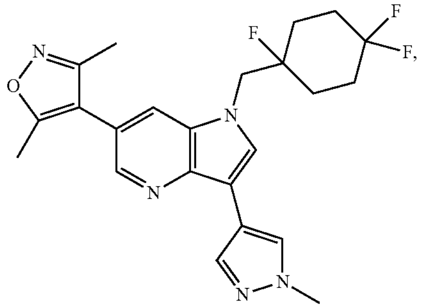
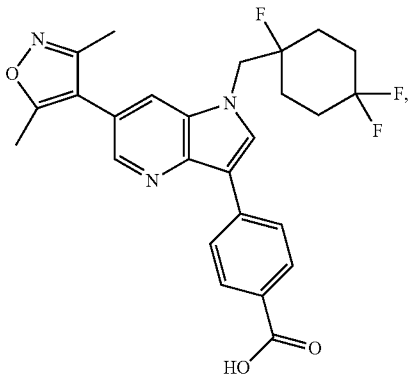
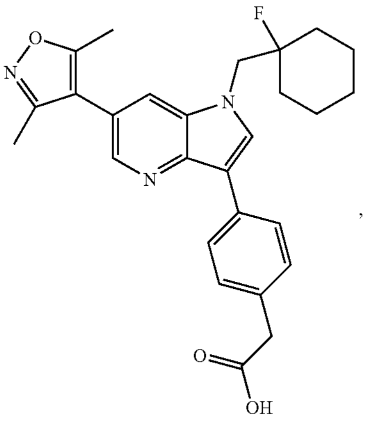
, -continued
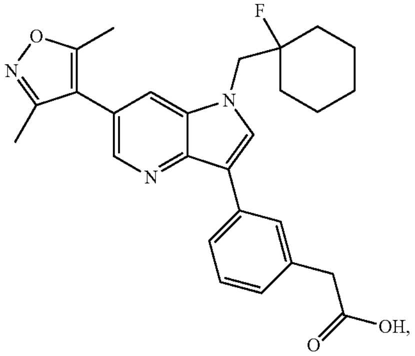
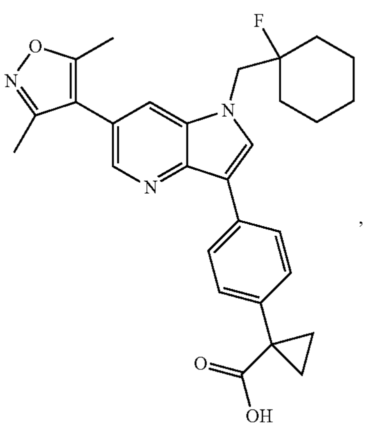
,
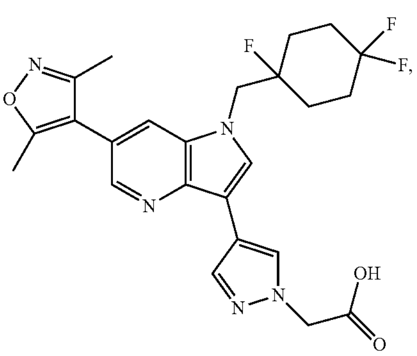
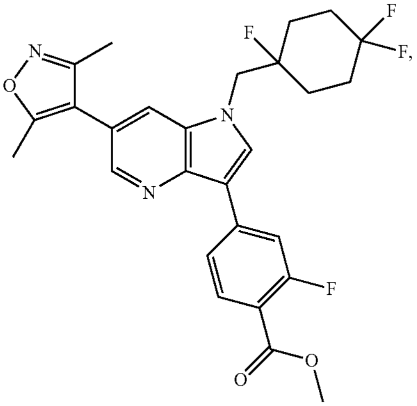
-continued
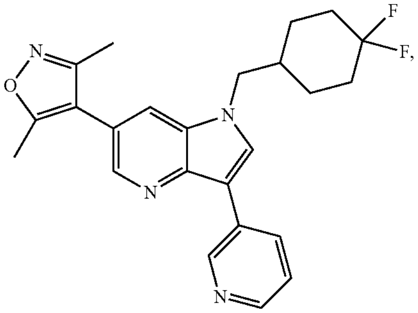
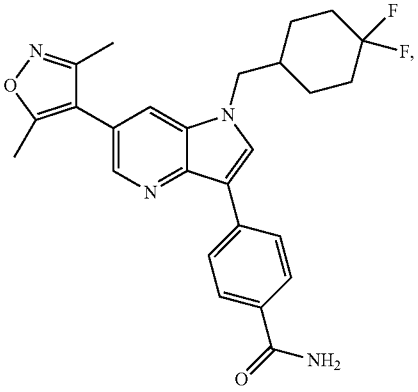
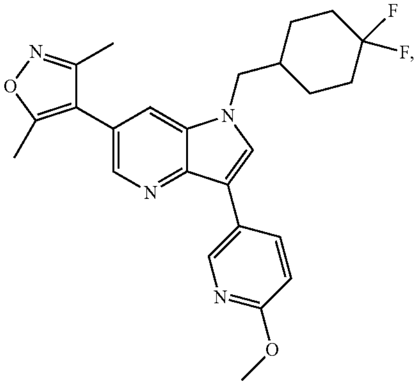
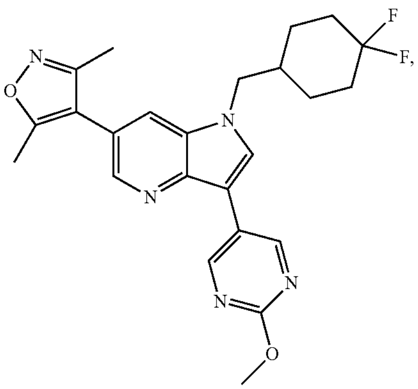

-continued
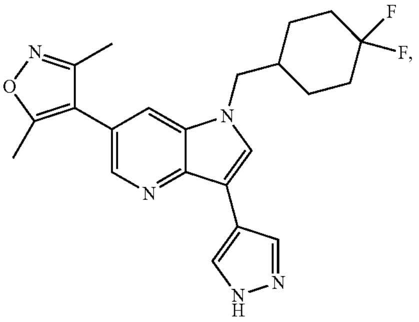
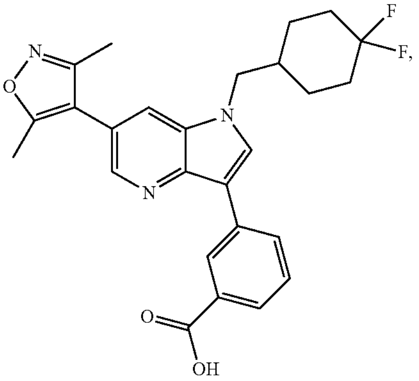
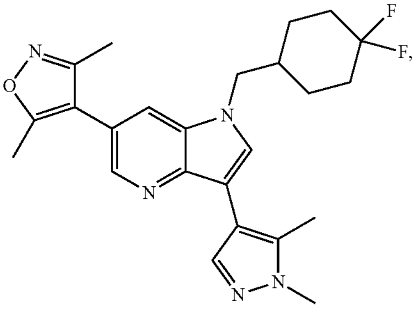
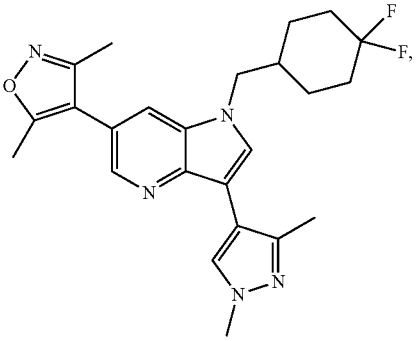
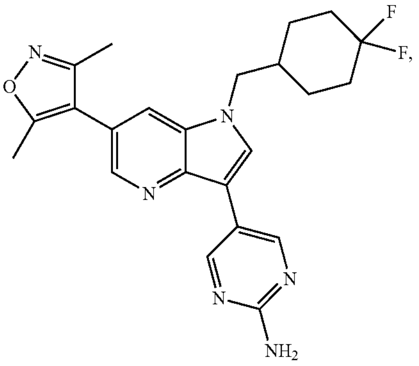
-continued
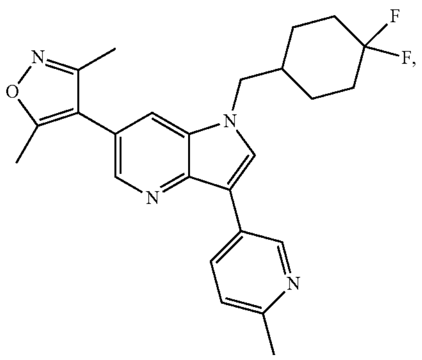
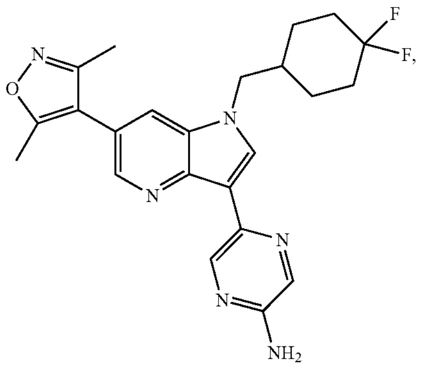
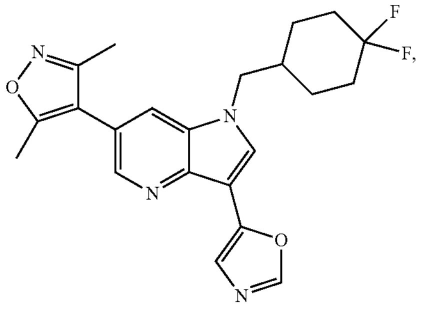
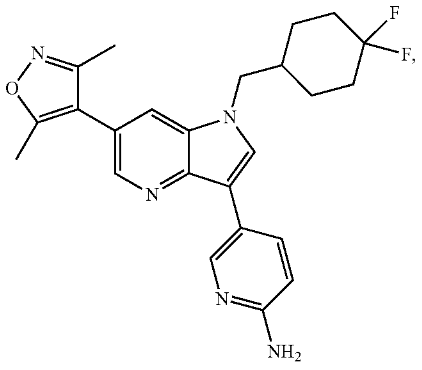

-continued
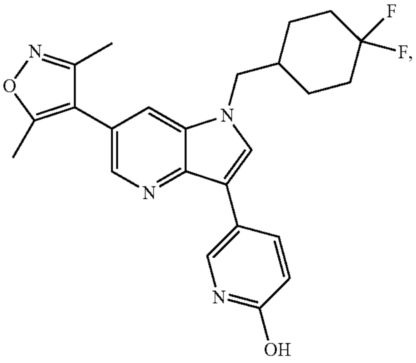
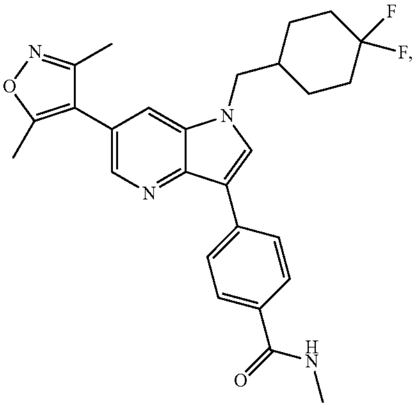
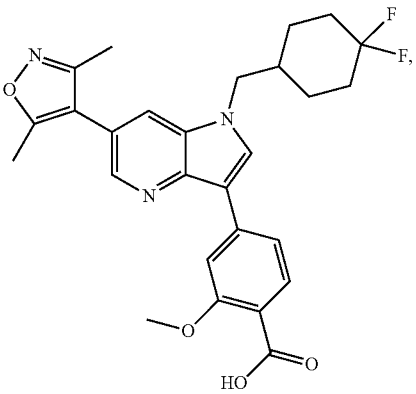
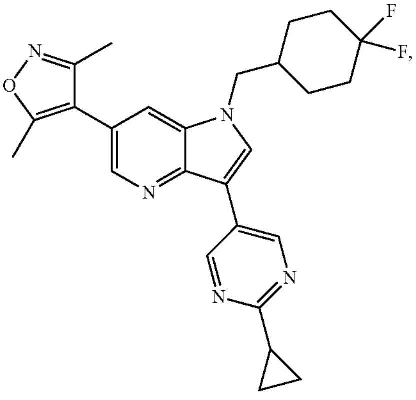
-continued
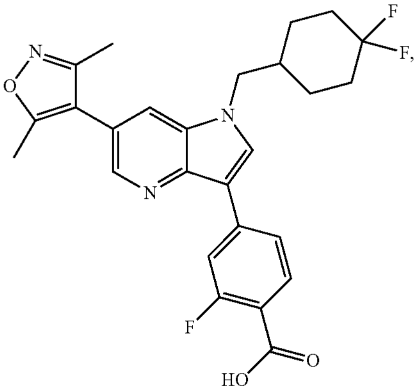
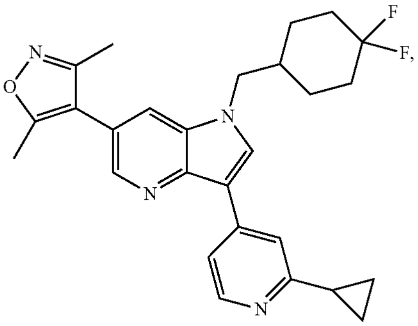
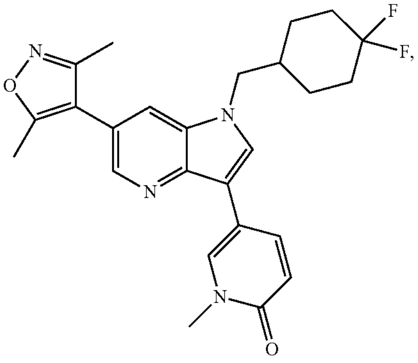
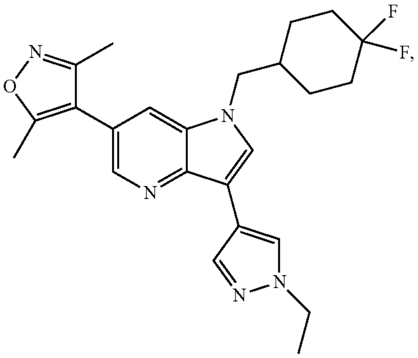

-continued
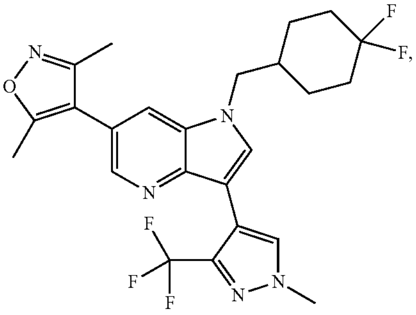
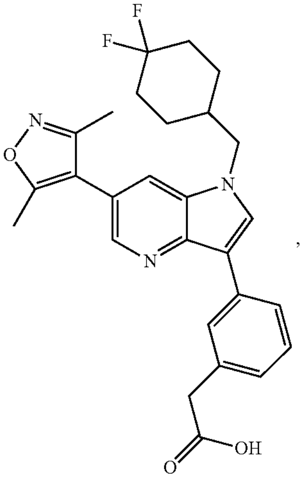
,
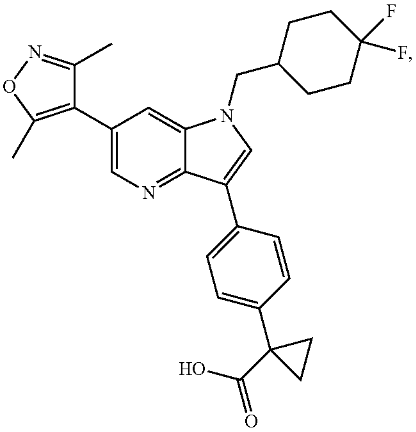
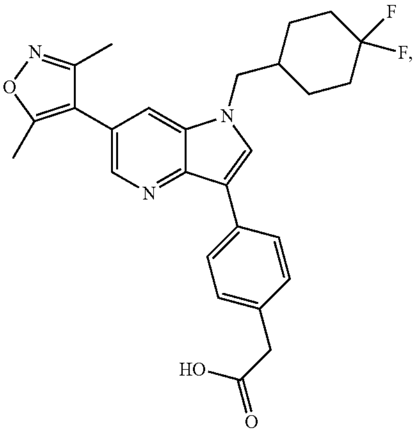
-continued
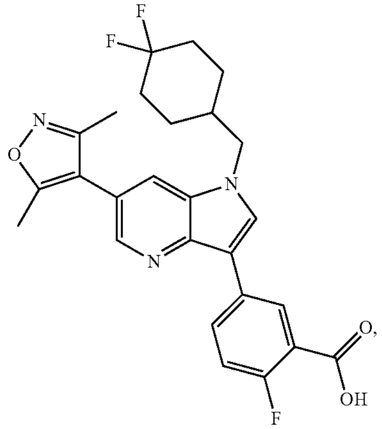
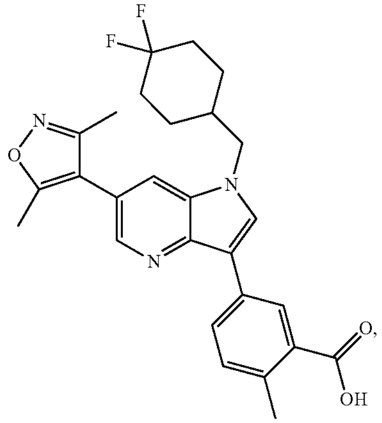
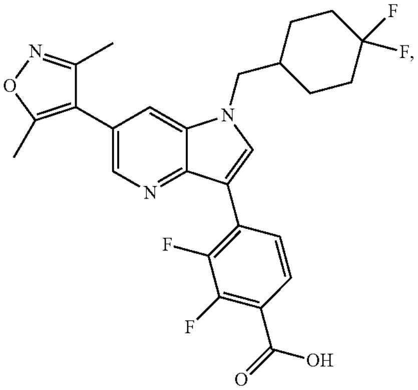
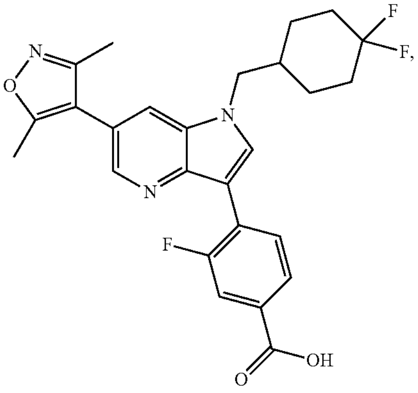

-continued
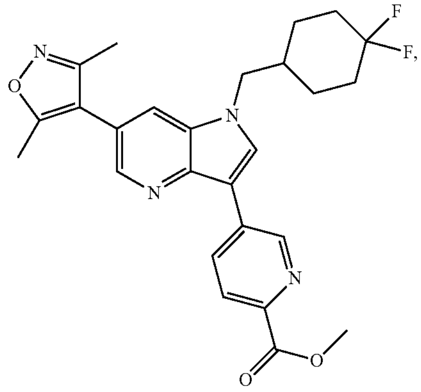
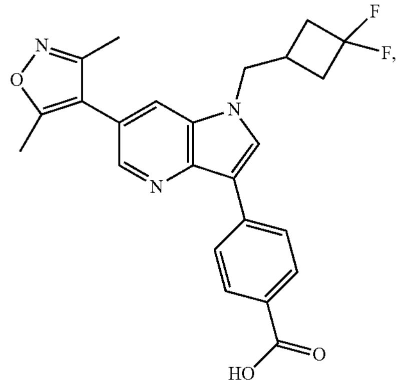
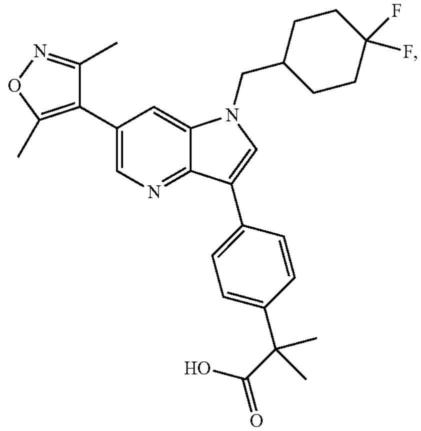
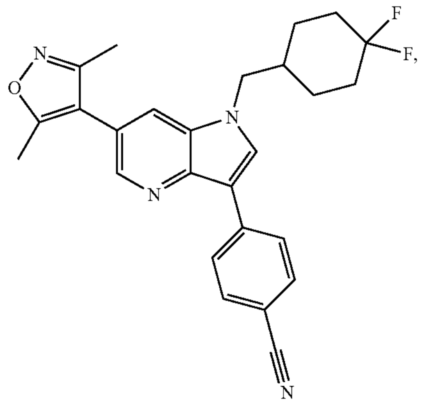
-continued
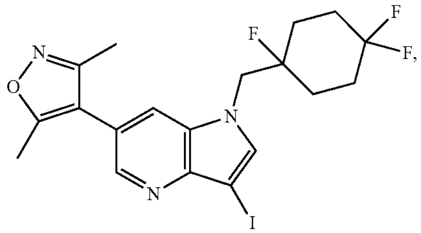
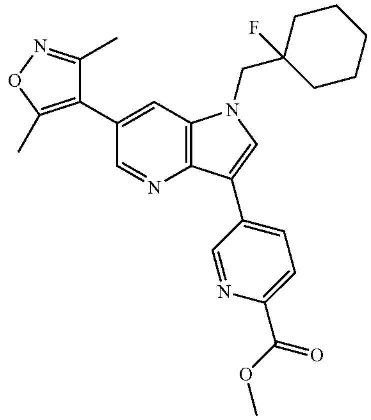
,
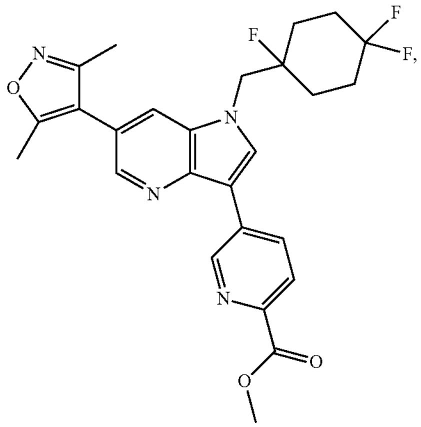
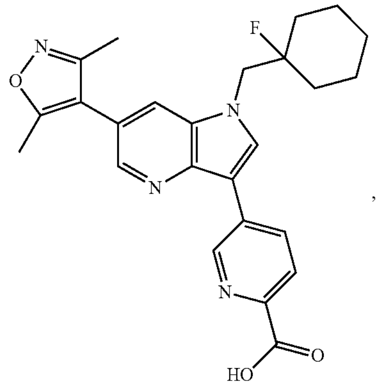
, -continued
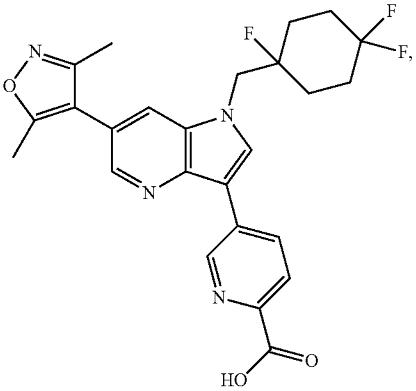
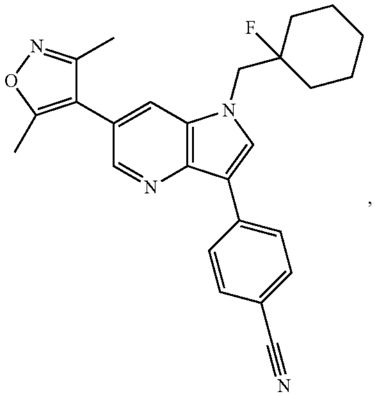
,
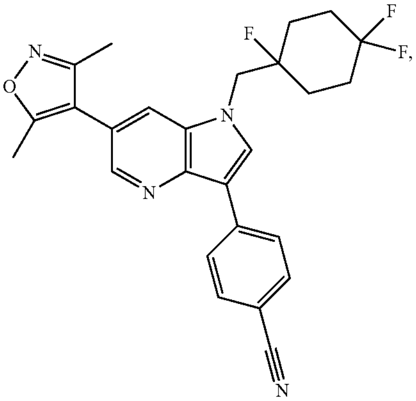
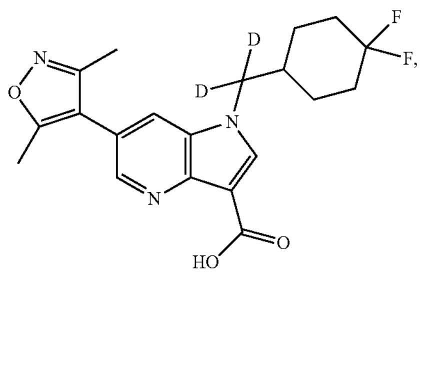
-continued
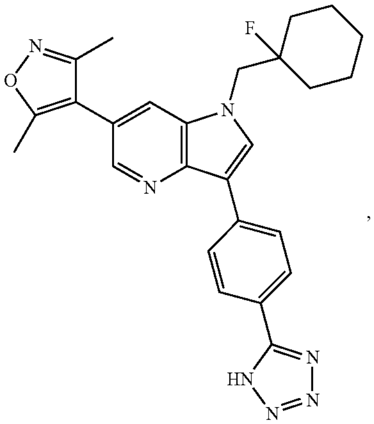
,
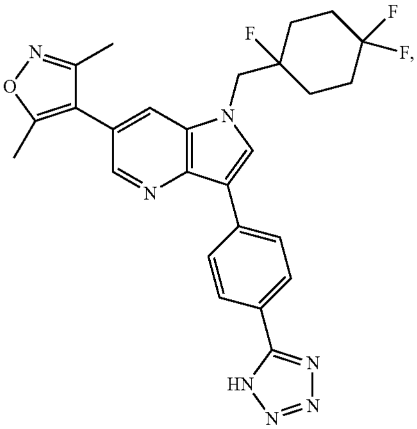
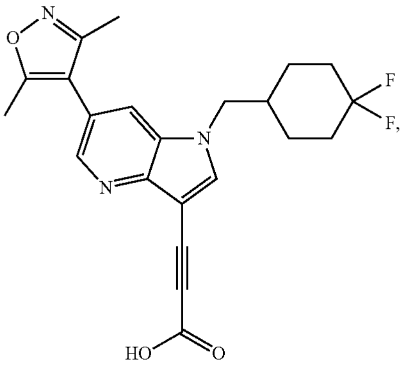
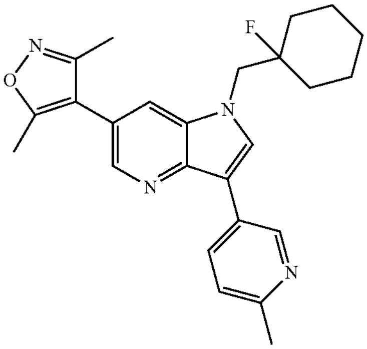
, -continued
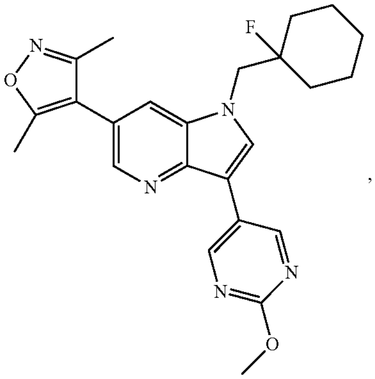
,
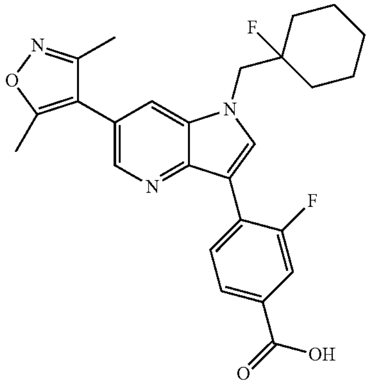
,
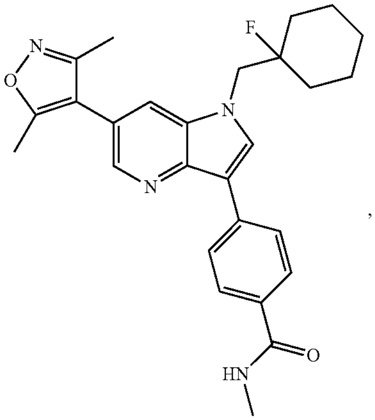
,
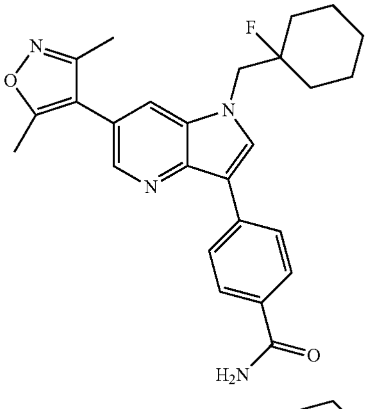
,
-continued
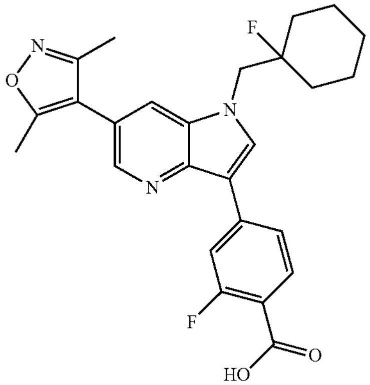
,
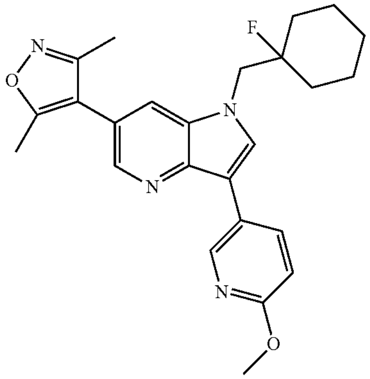
,
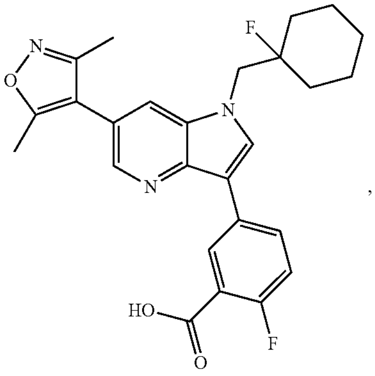
,
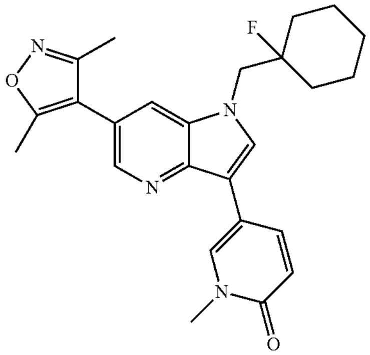
, -continued
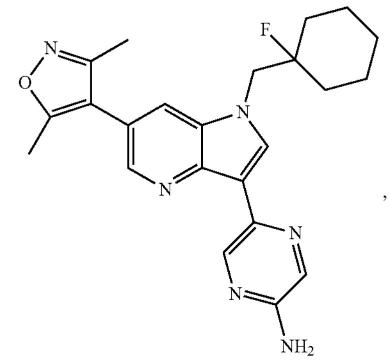
,
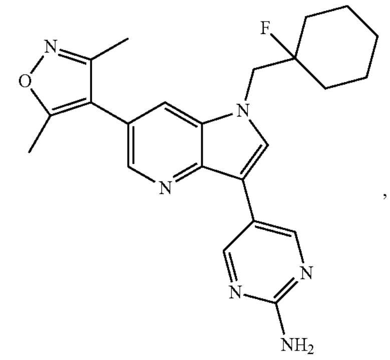
,
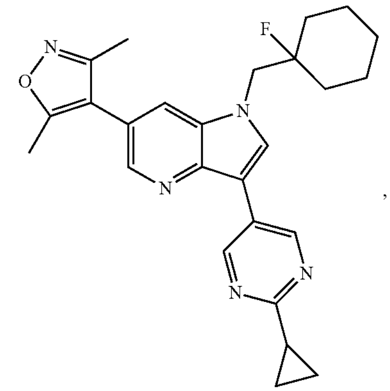
,
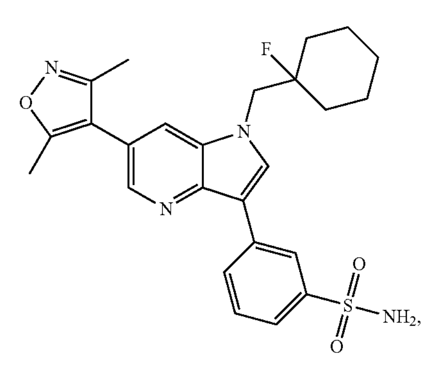
-continued
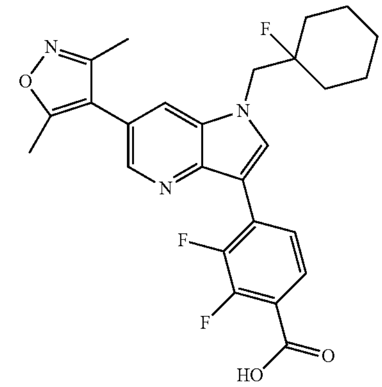
,
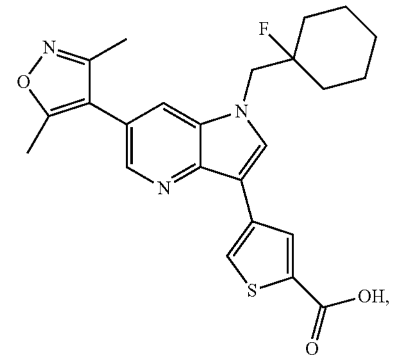
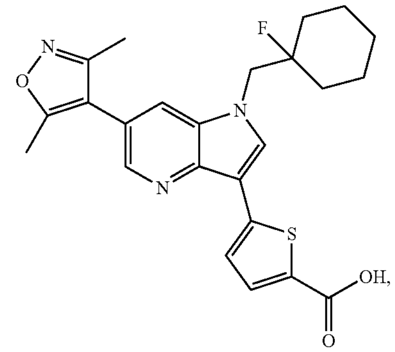
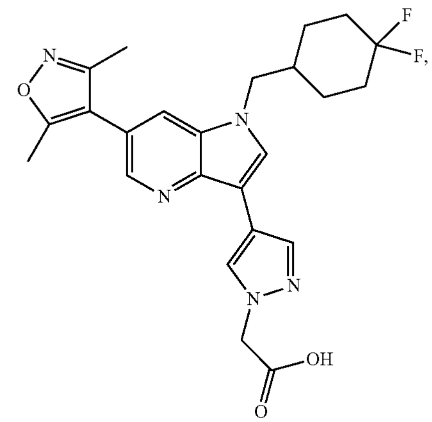

-continued
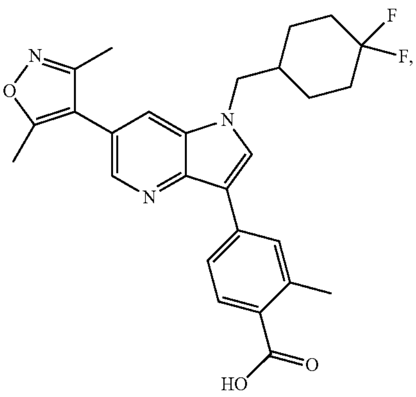
,
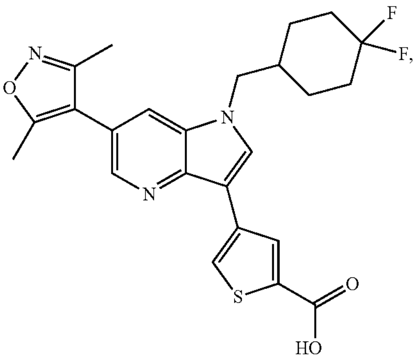
,
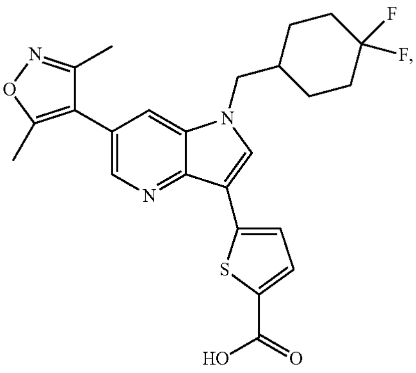
,
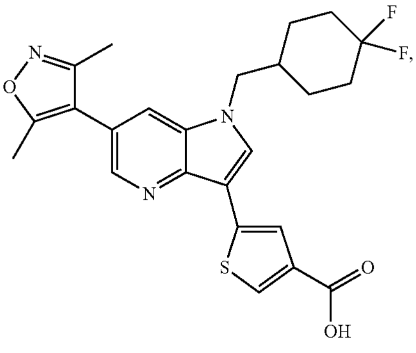
,
-continued
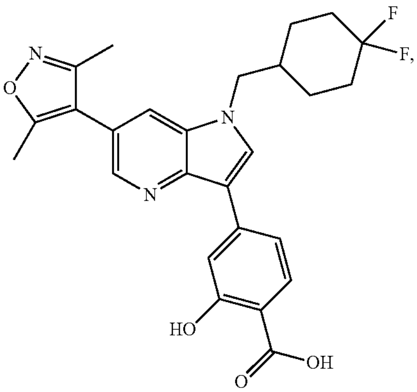
,
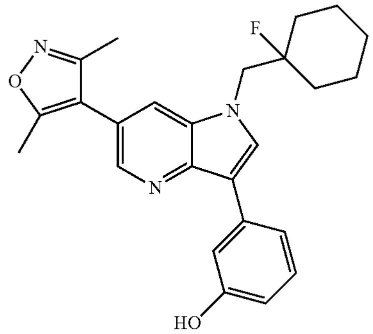
,
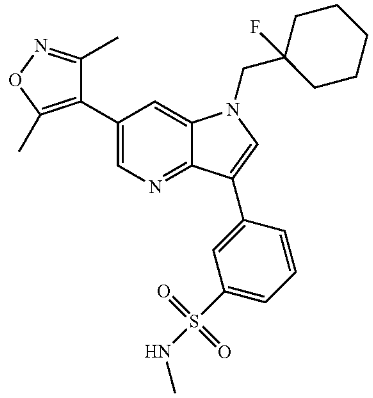
,
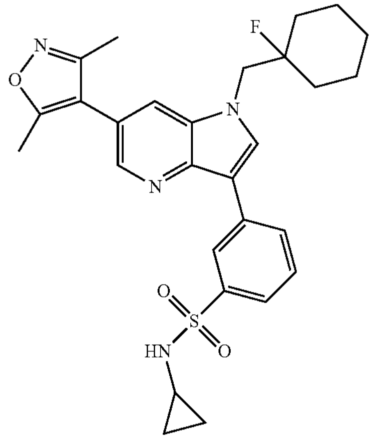
, -continued
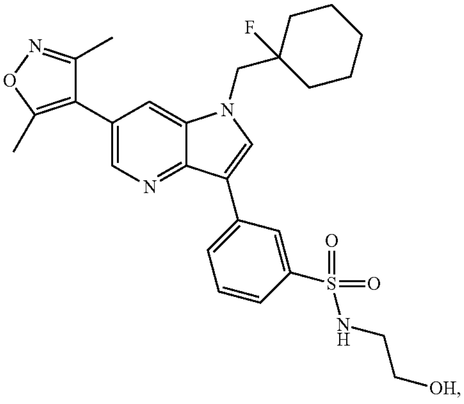
,
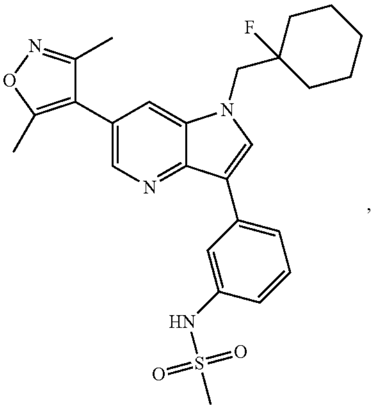
,
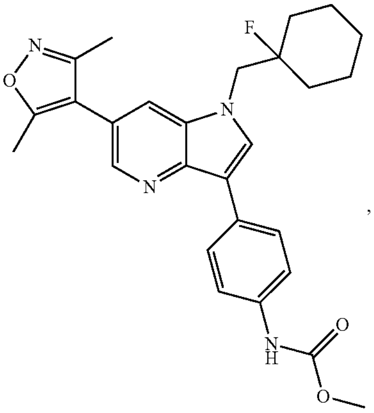
,
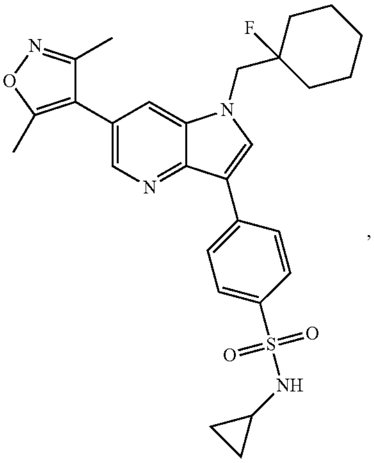
,
-continued
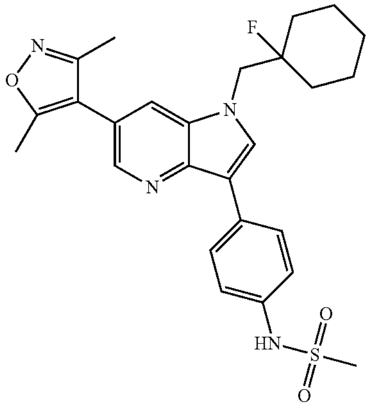
,
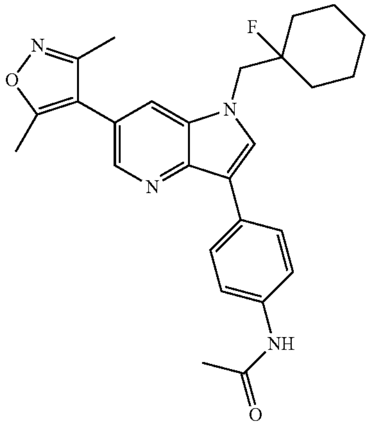
,
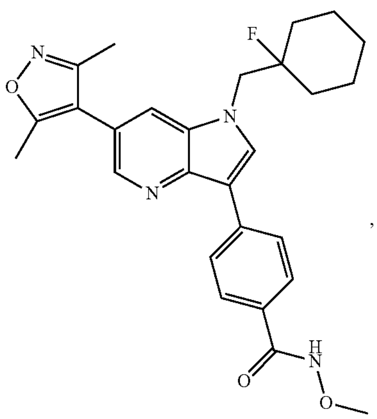
,
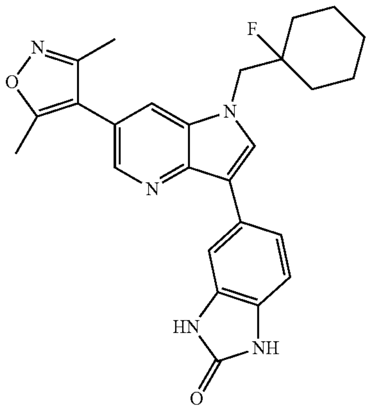
, -continued
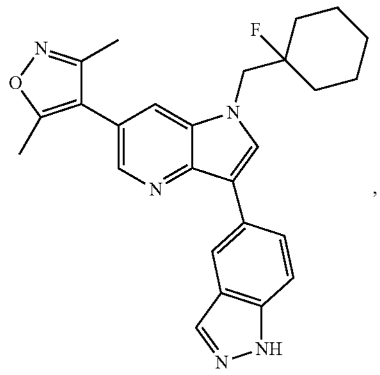
,
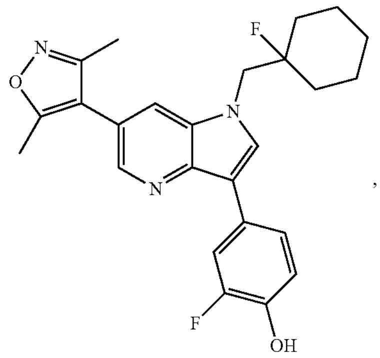
,
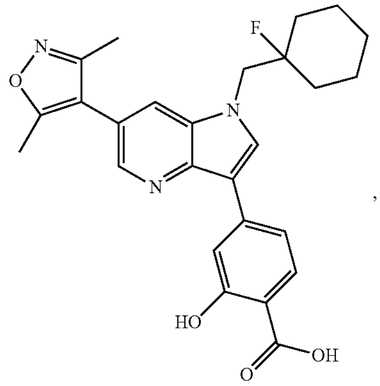
,
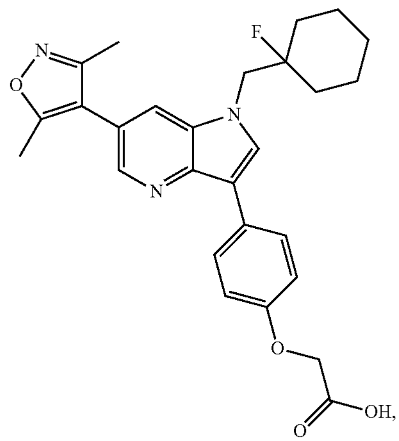
-continued
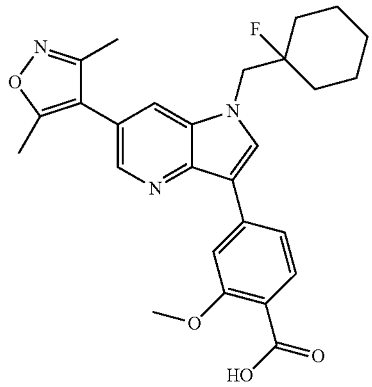
,
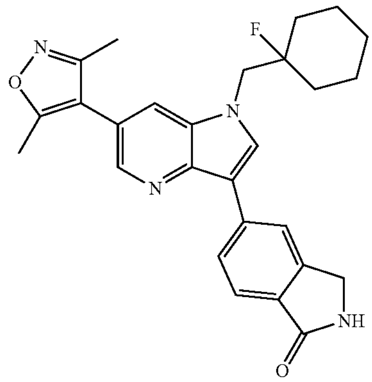
,
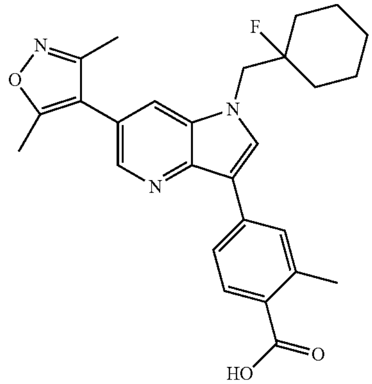
,
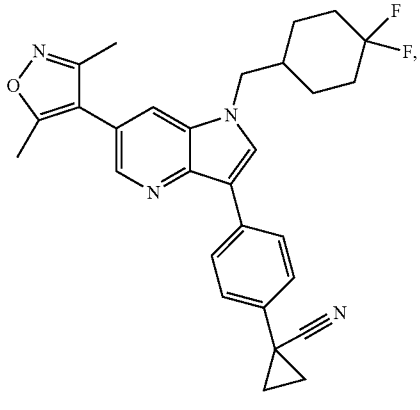

-continued
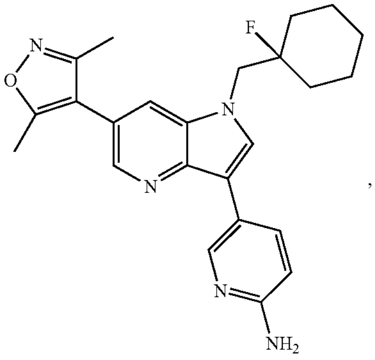
,
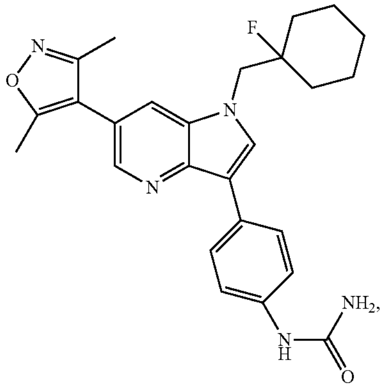
,
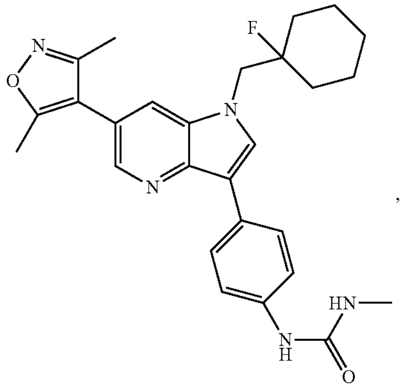
,
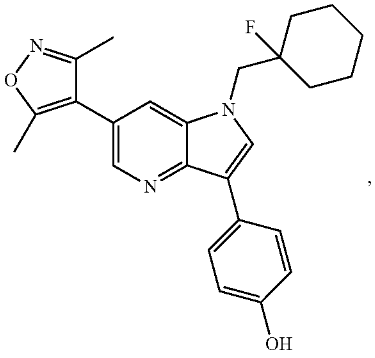
,
-continued
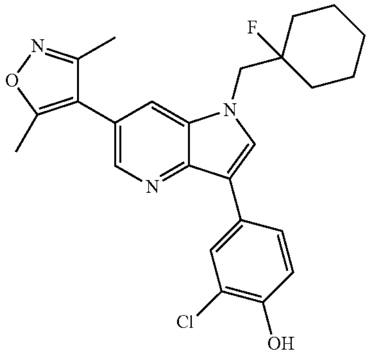
,
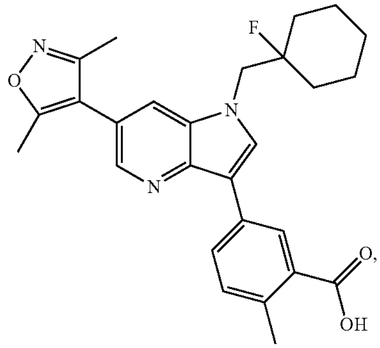
,
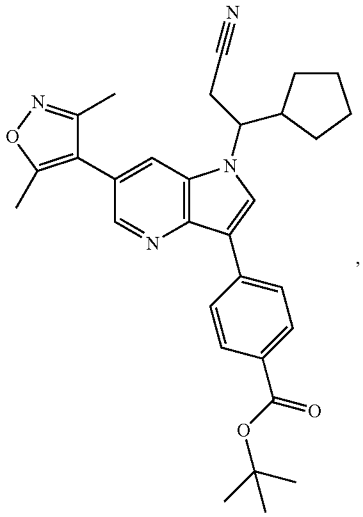
,
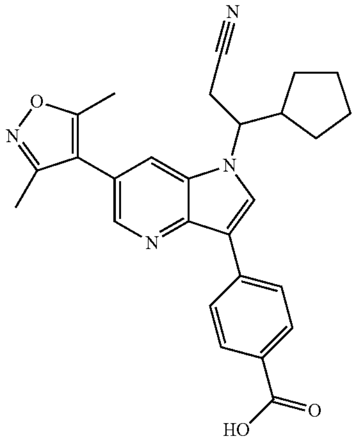
, -continued
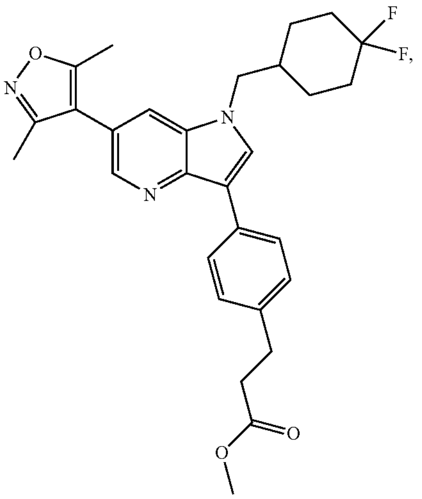
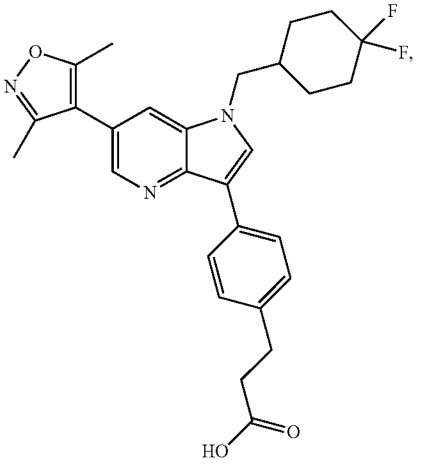
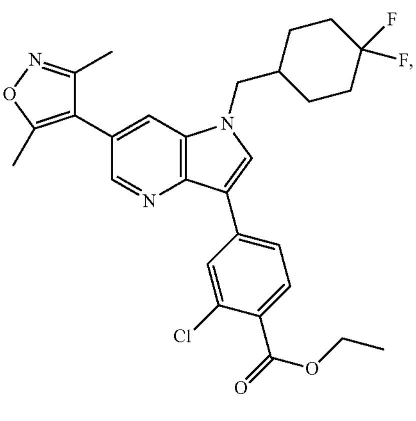
-continued
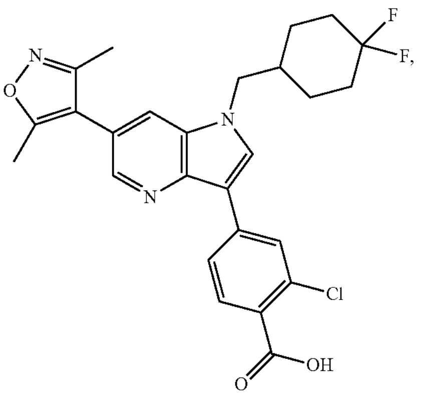
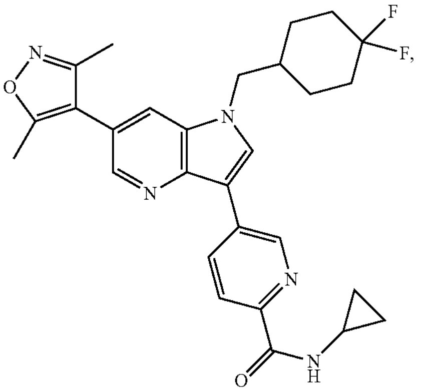
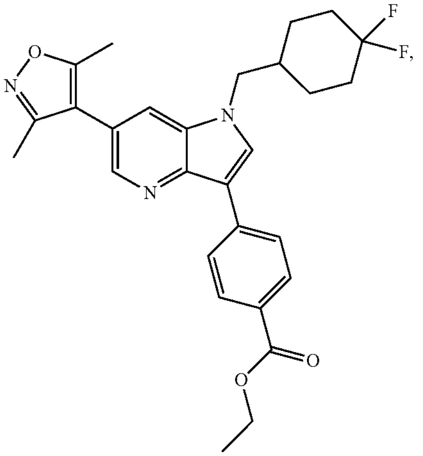
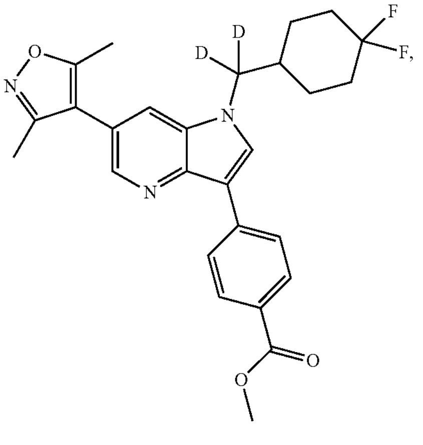

-continued
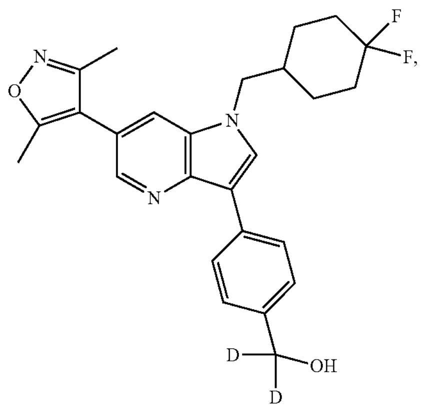
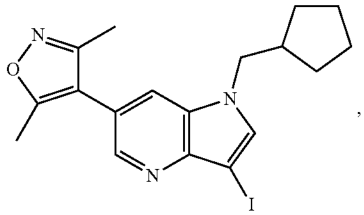
,
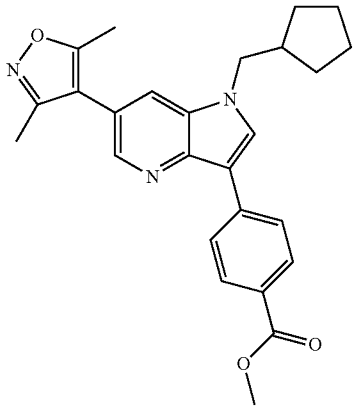
,
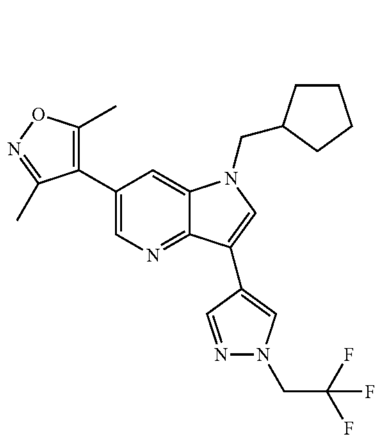
-continued
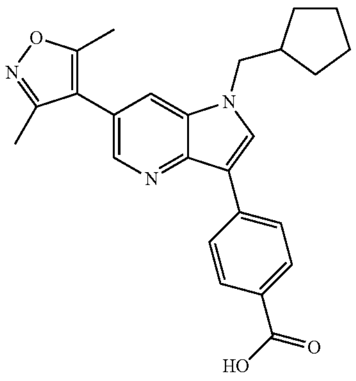
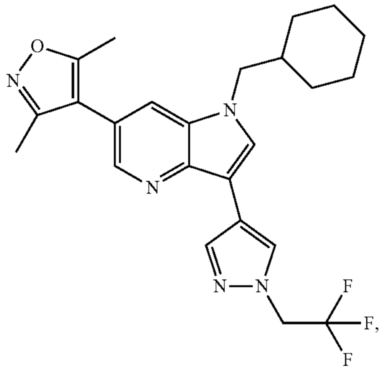
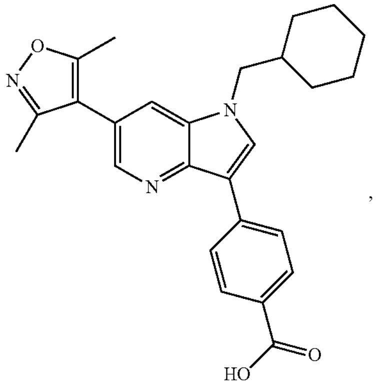
,
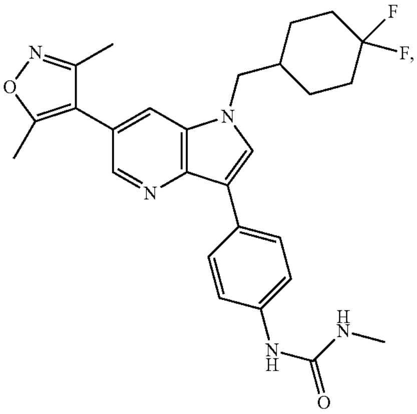

-continued
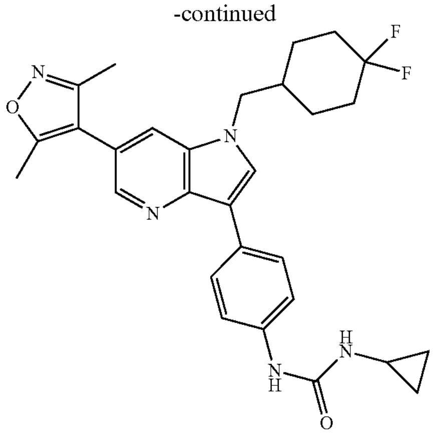
,
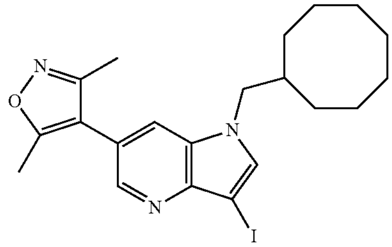
,
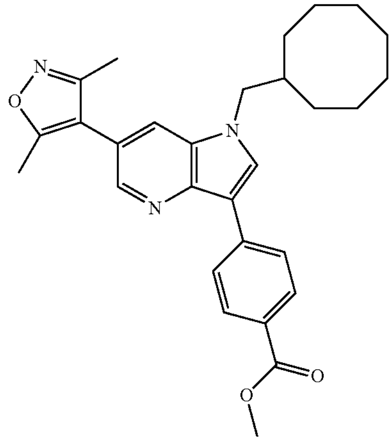
,
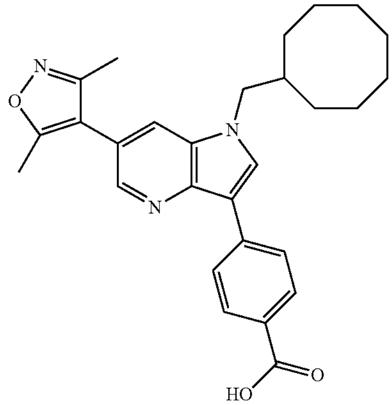
,
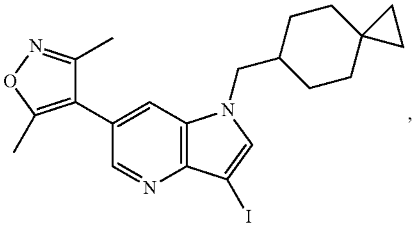
,
-continued
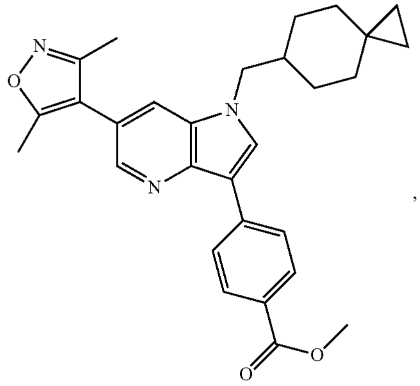
,
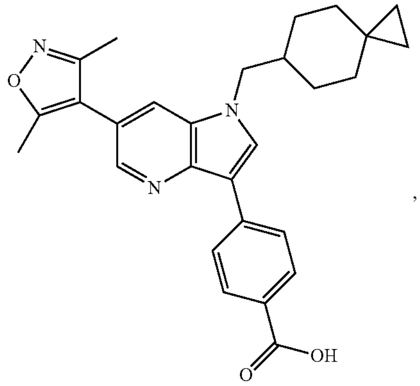
,
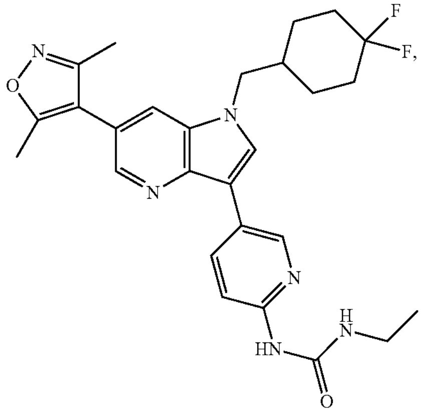
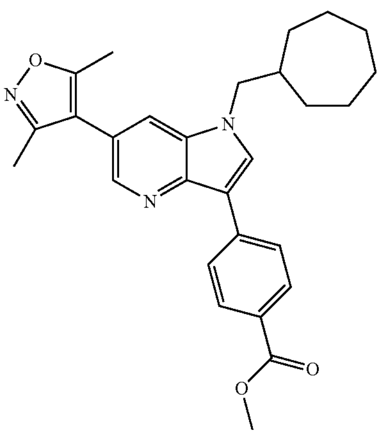
, -continued
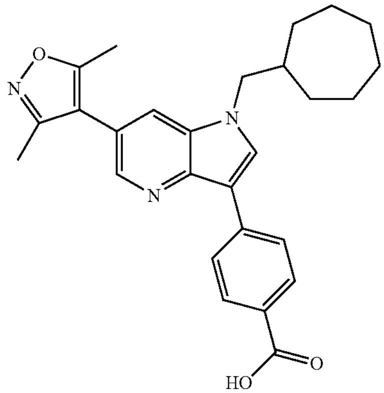
,
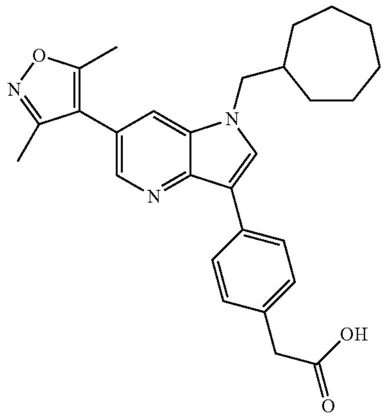
,
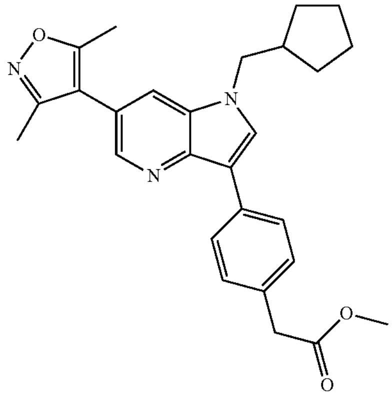
,
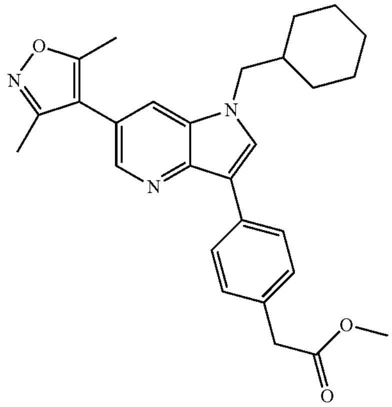
,
-continued
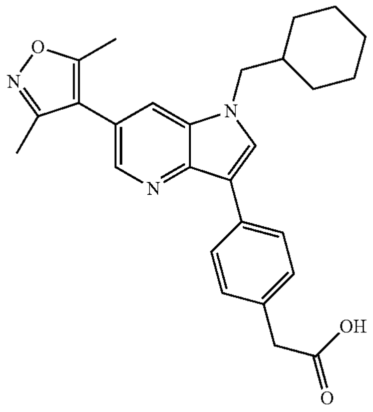
,
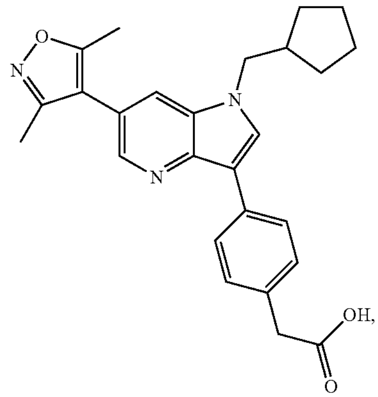
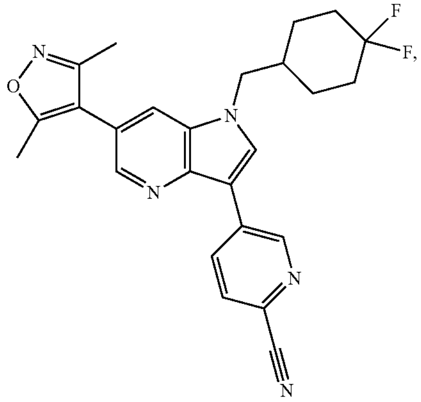
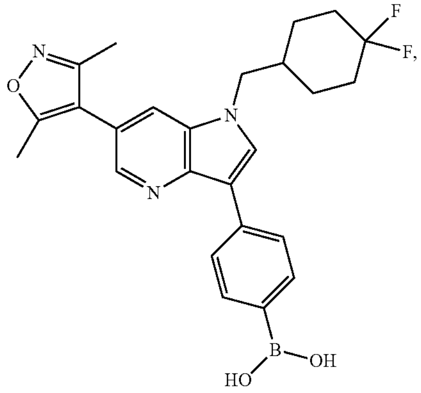

-continued
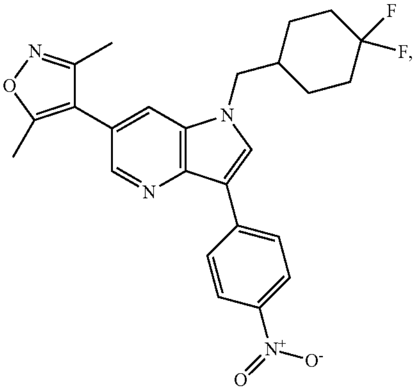
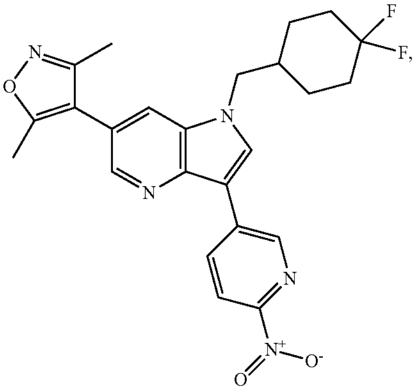
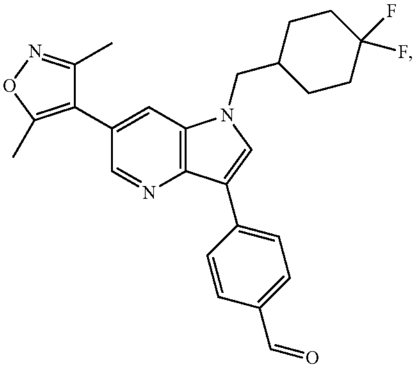
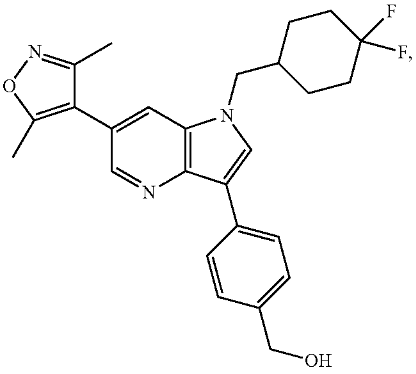
-continued
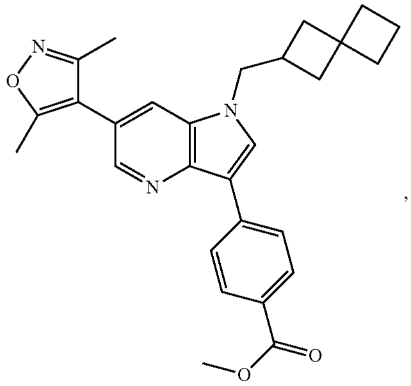
,
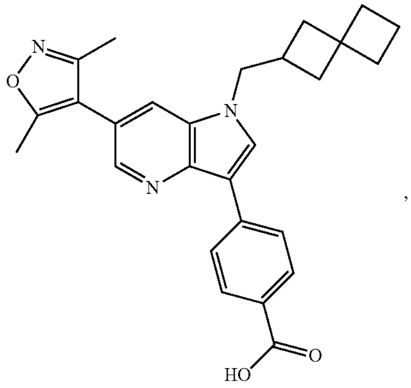
,
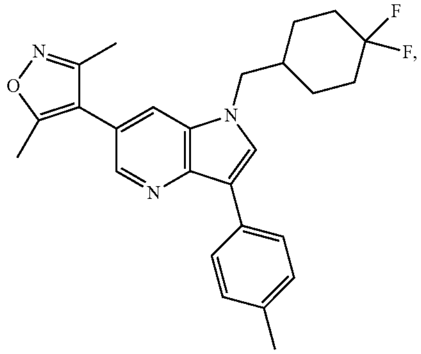
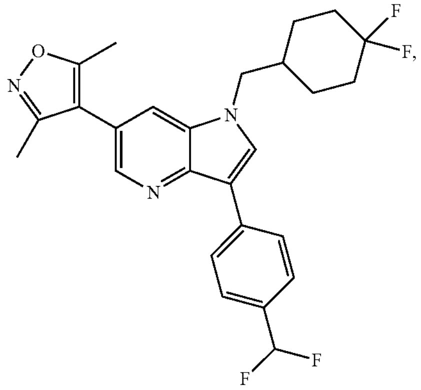

-continued
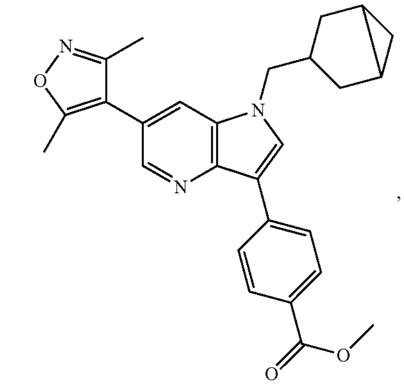
,
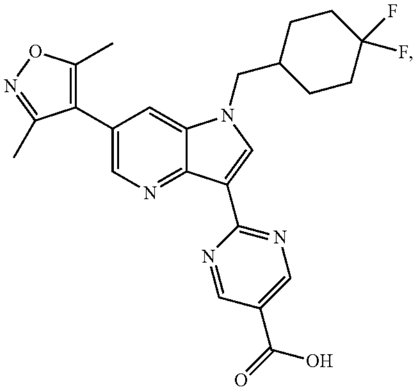
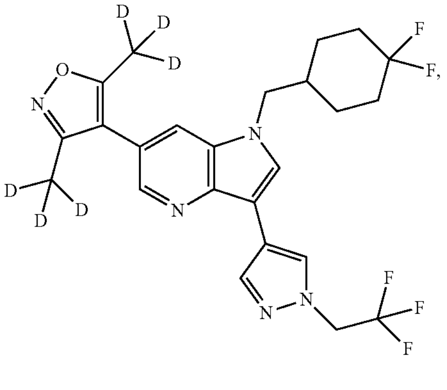
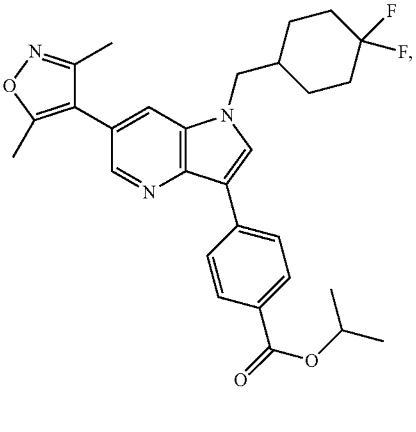
-continued
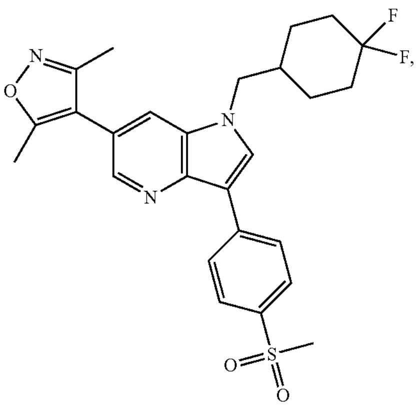
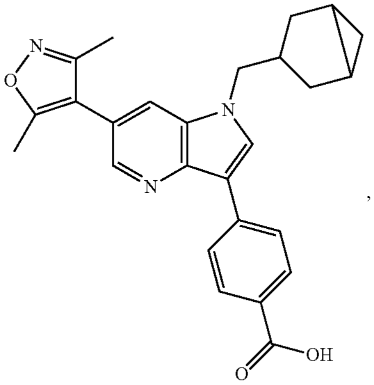
,
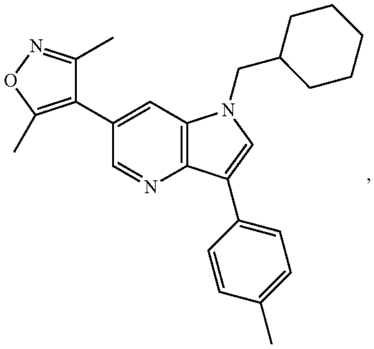
,
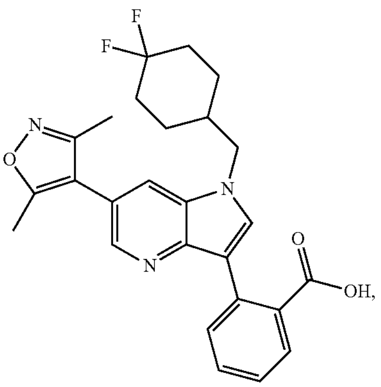

-continued
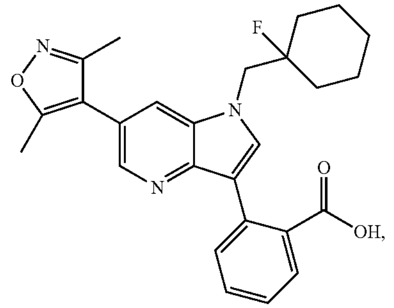
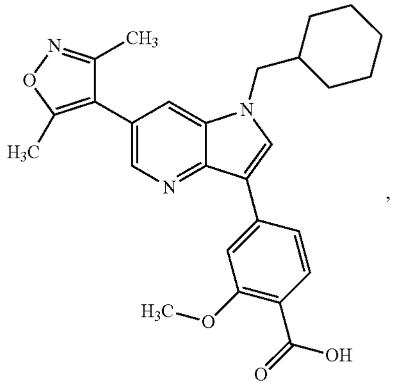
,
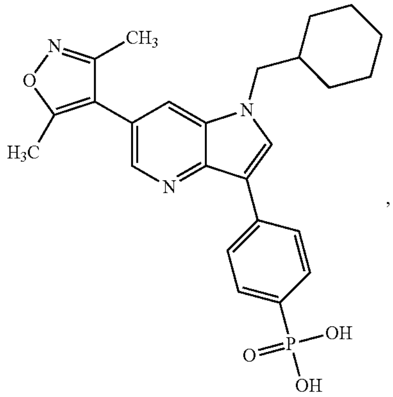
,
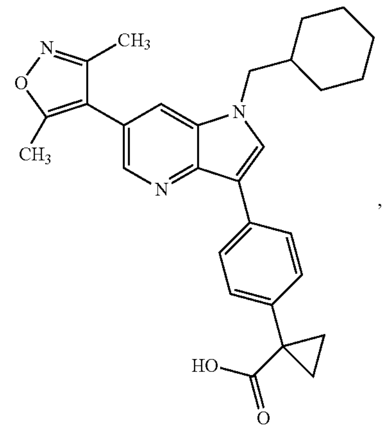
,
-continued
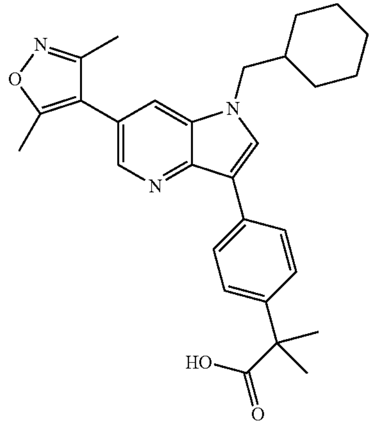
,
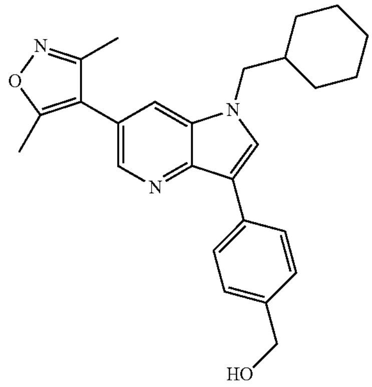
,
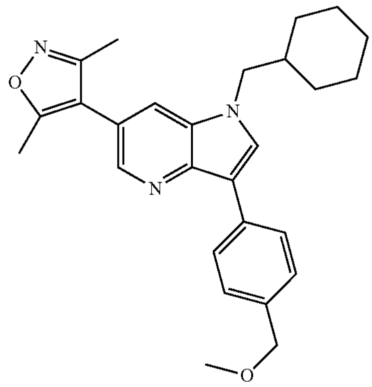
,
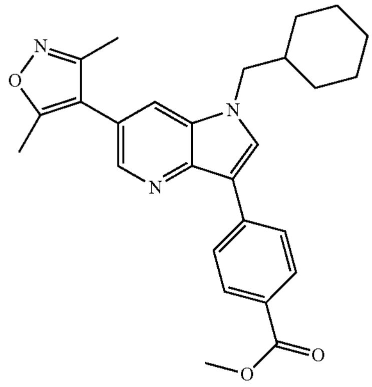
,

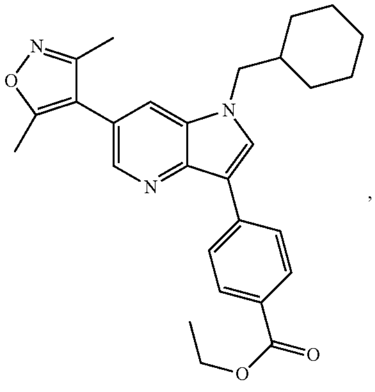
,
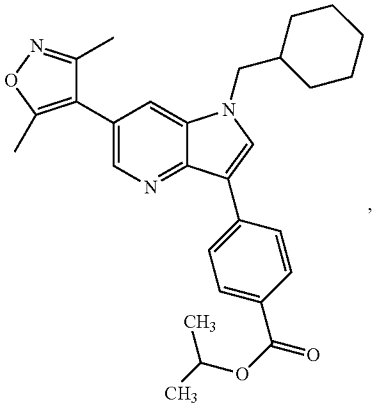
,
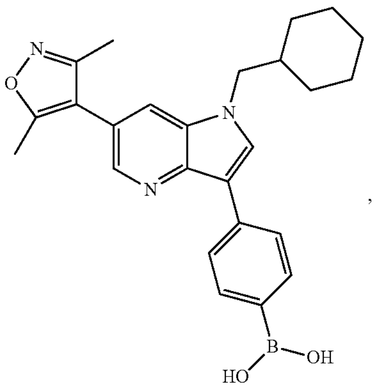
,
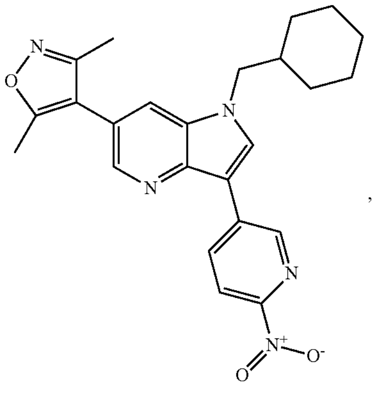
,
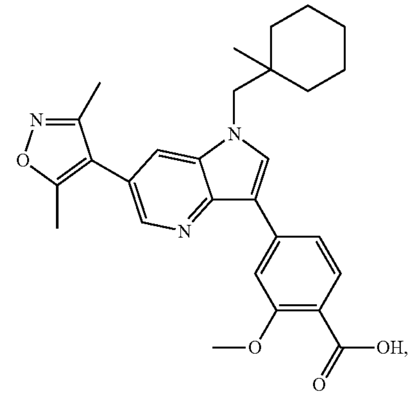
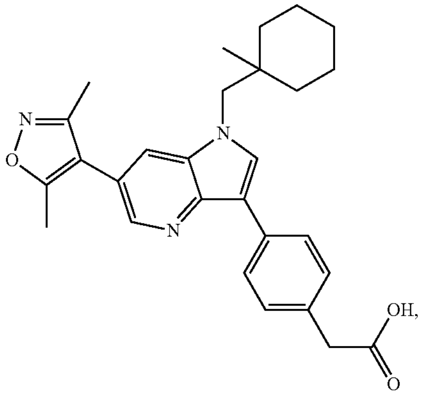
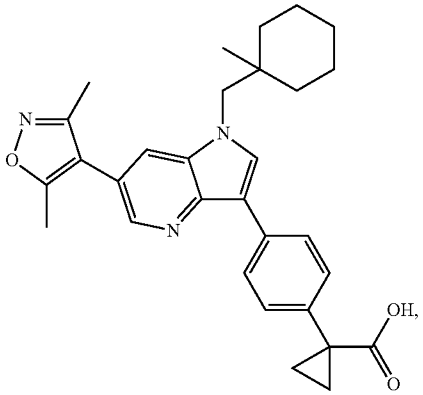
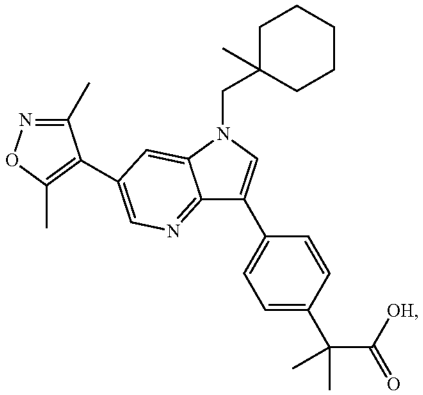

-continued
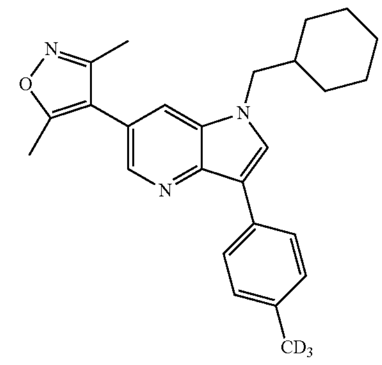
,
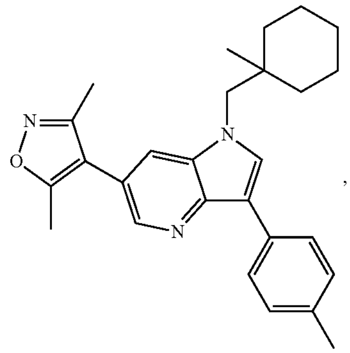
,
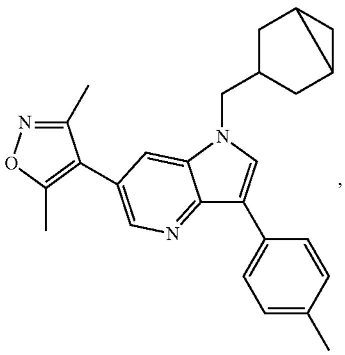
,
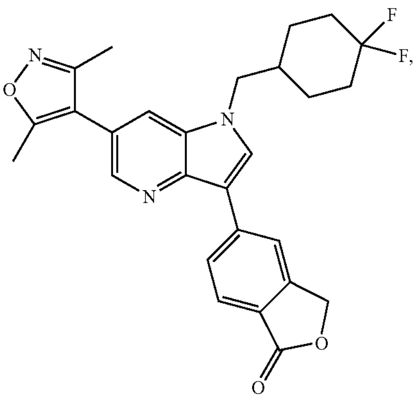
-continued
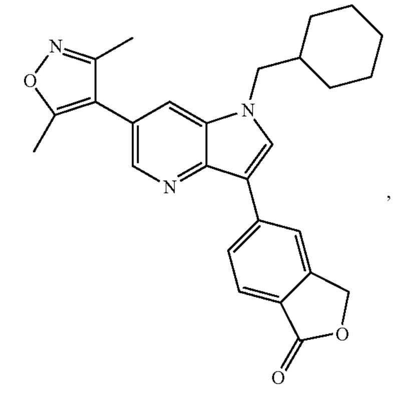
,
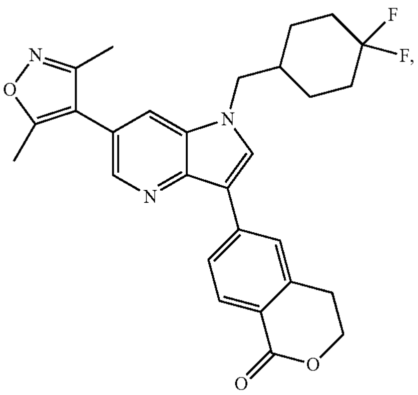
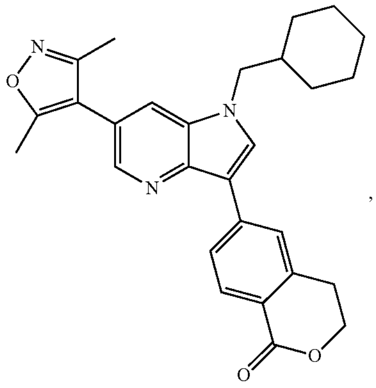
,
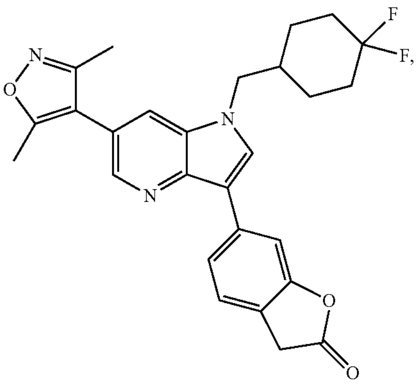

-continued
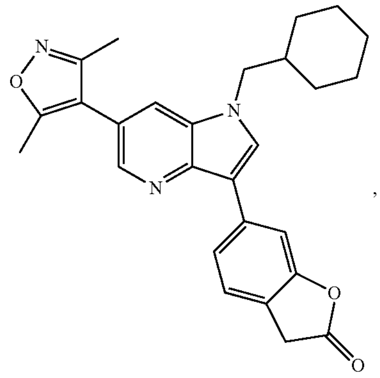
,
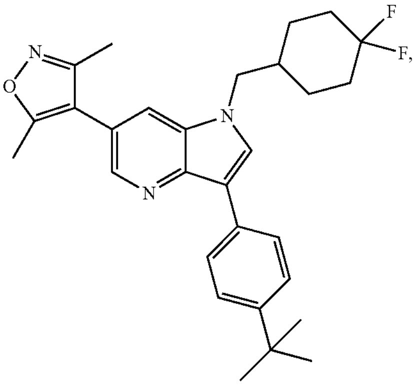
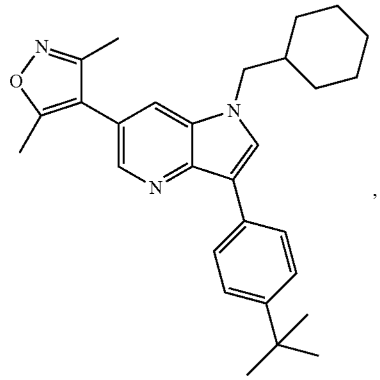
,
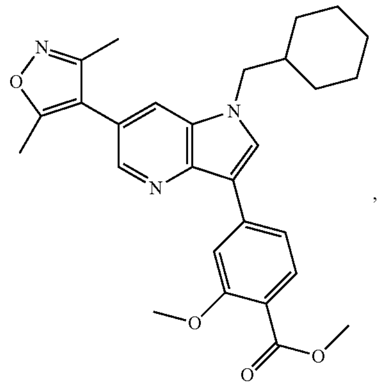
,
-continued
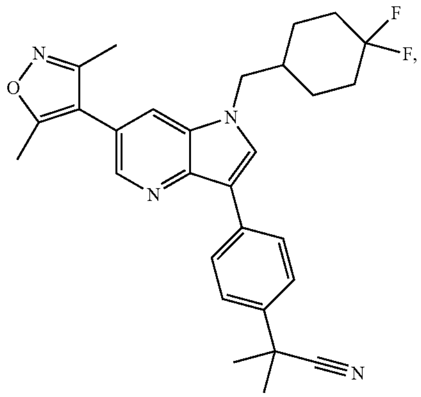
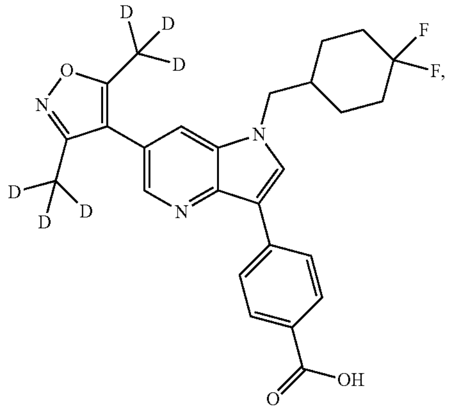
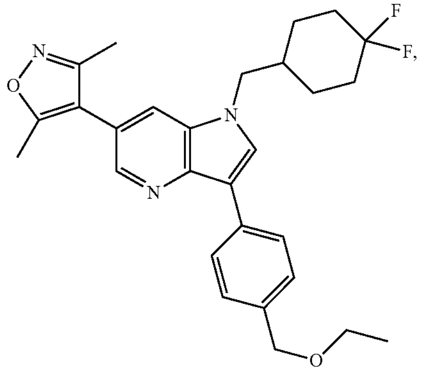
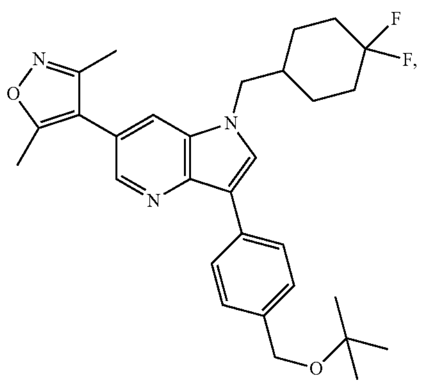

-continued
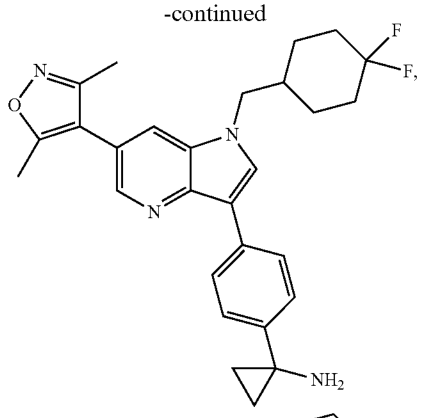
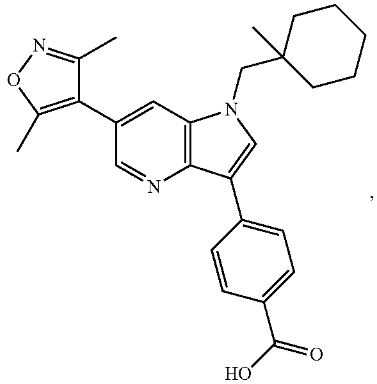
, and
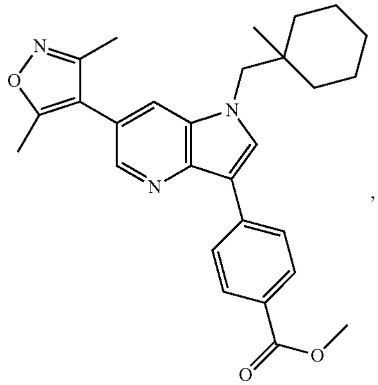 [SMILES: COC(=O)c1ccc(-c2cn(CC3(C)CCCCC3)c3cc(-c4c(C)noc4C)cnc23)cc1]
,
or a pharmaceutically acceptable salt, a solvate, a tautomer, a stereoisomer or a deuterated analog thereof.
11. A compound selected from:
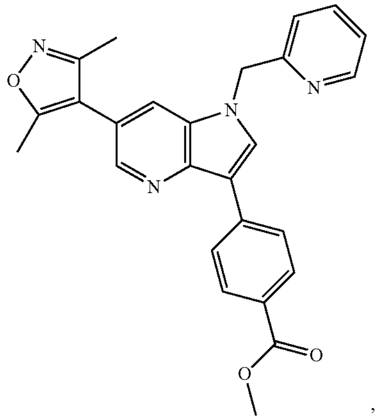
,
-continued
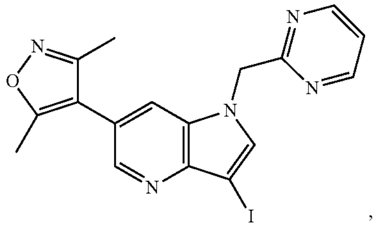
,
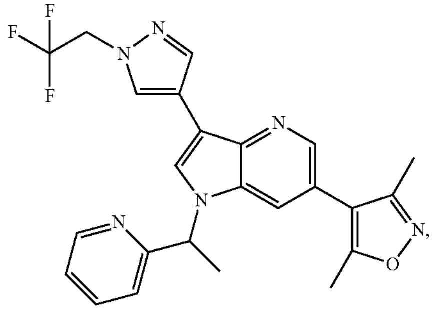
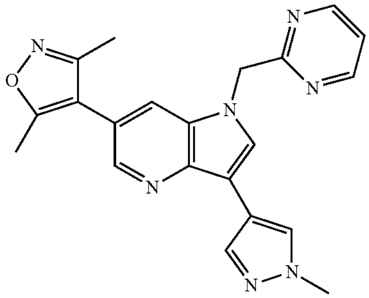
,
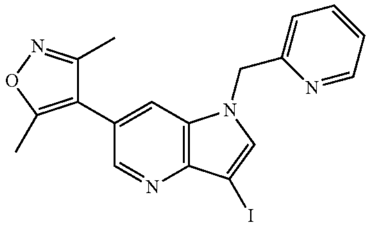
,
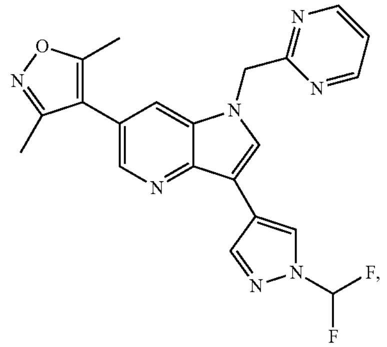
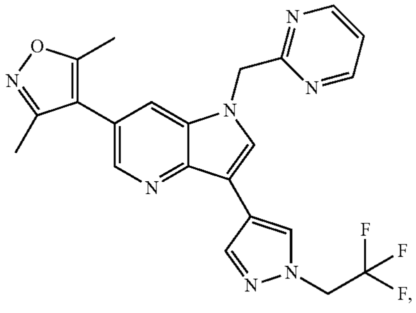

-continued
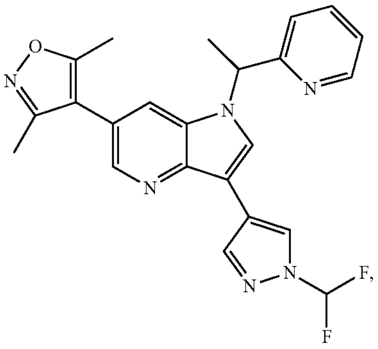
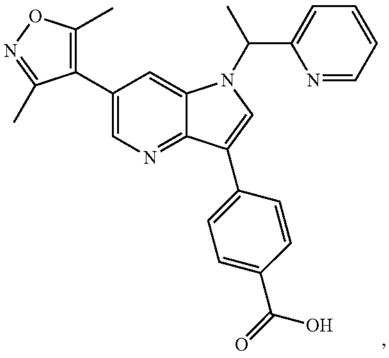
,
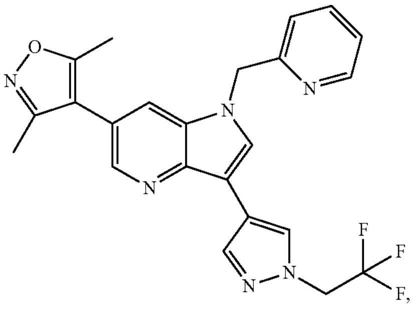
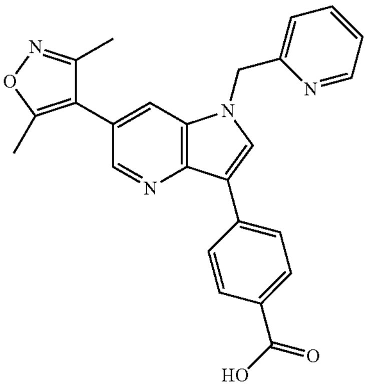
,
-continued
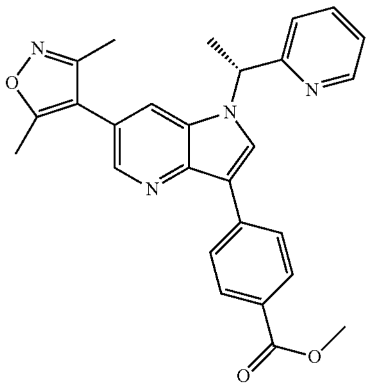
,
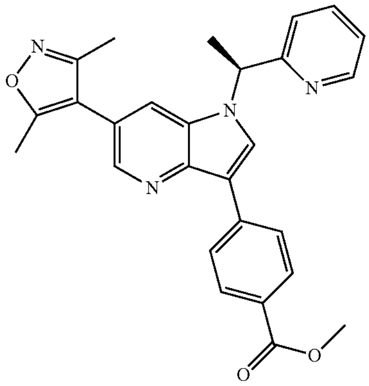
,
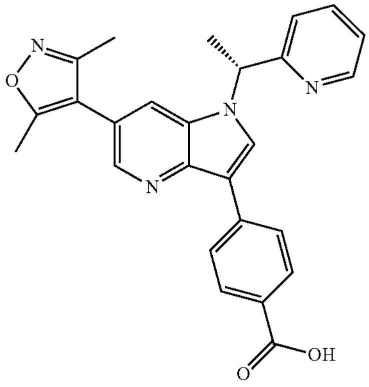
,
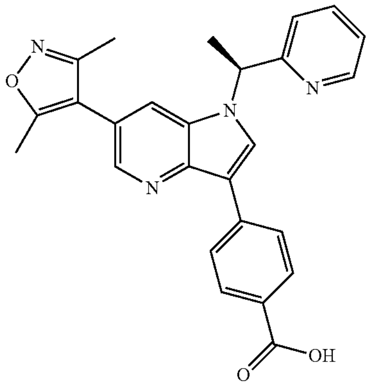
, -continued
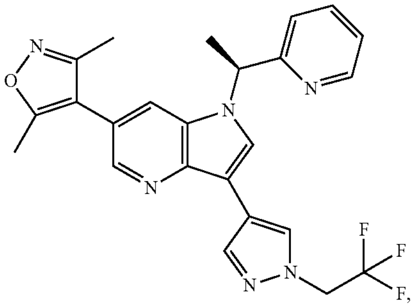
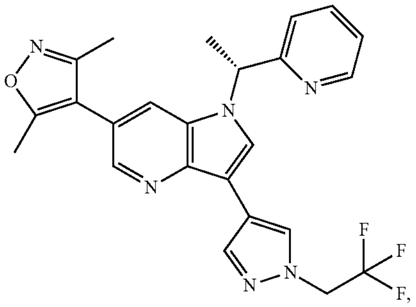
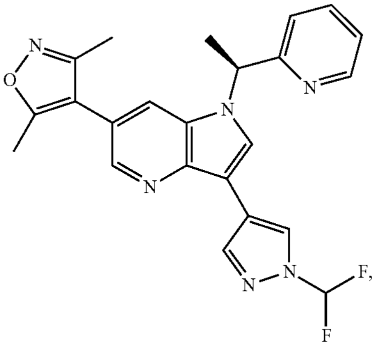
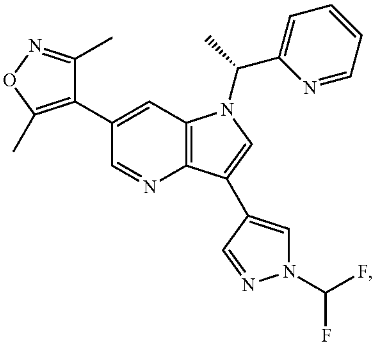
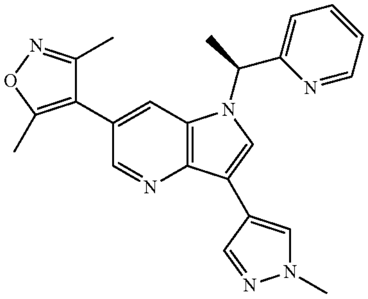
,
-continued
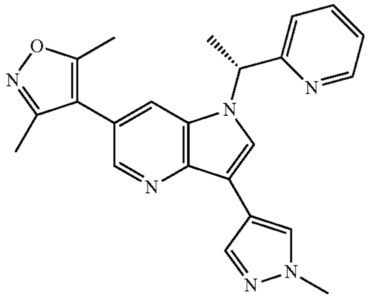
,
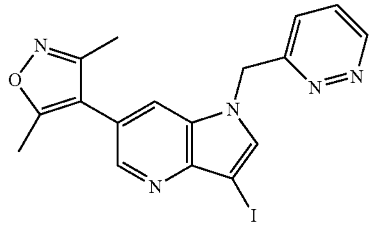
,
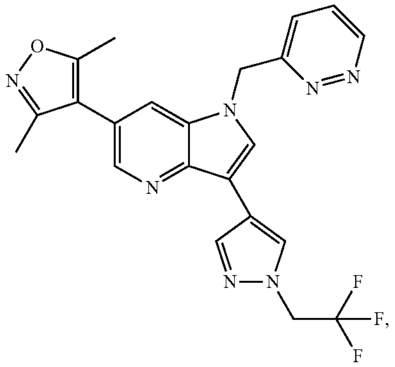
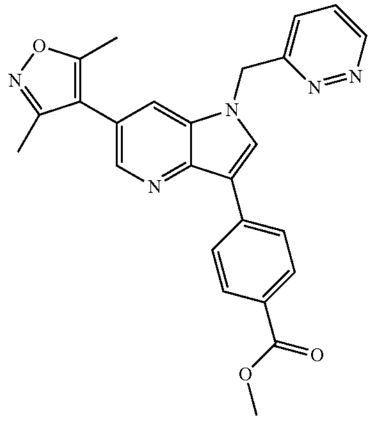
,
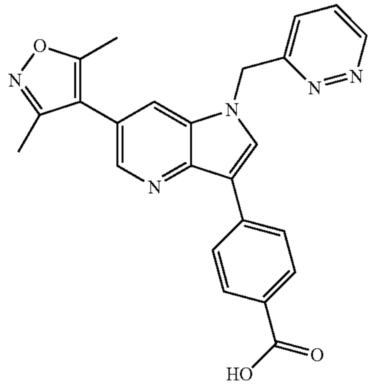
, -continued
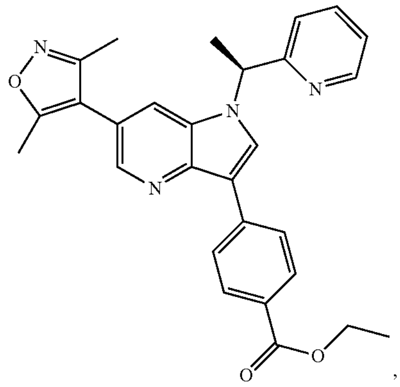
,
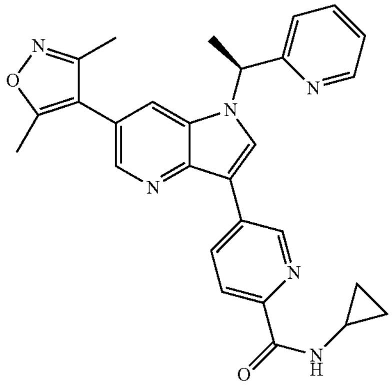
,
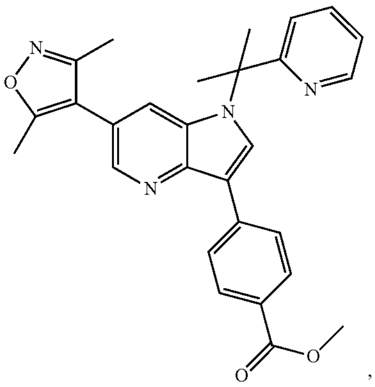
,
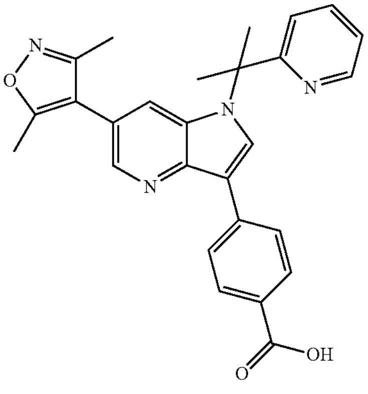
,
-continued
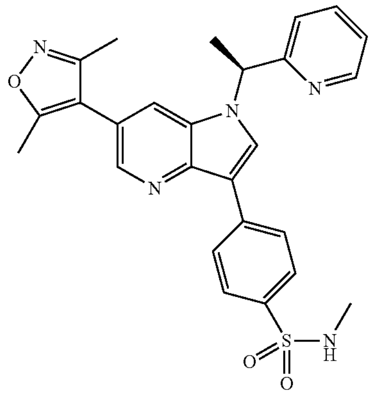
,
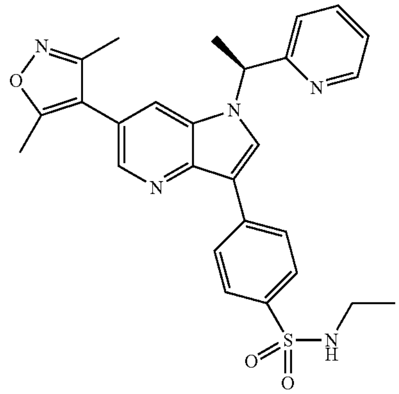
,
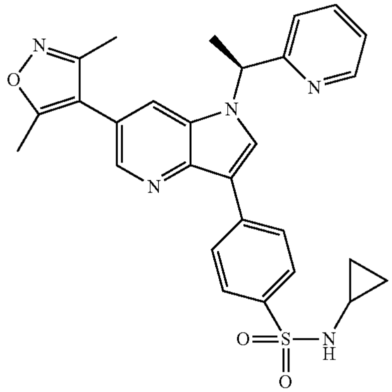
,
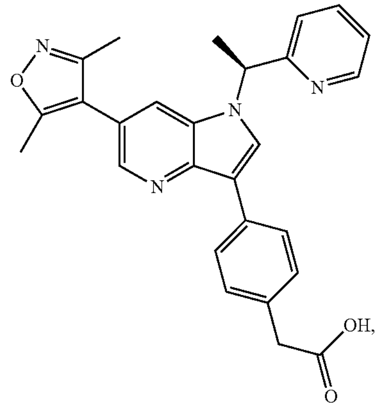

-continued
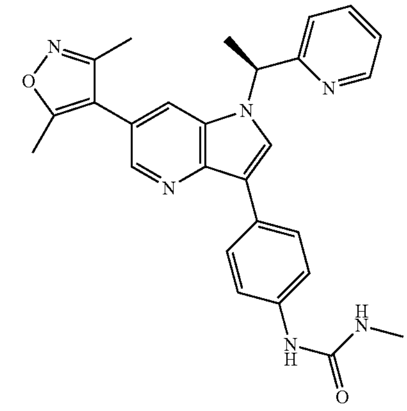
,
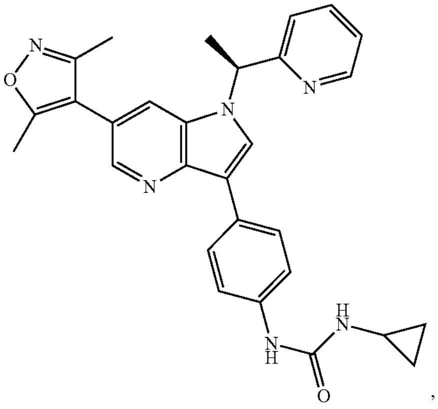
,
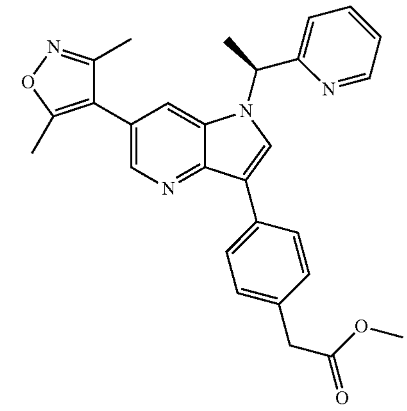
,
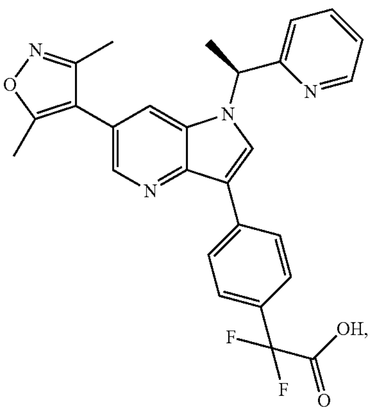
-continued
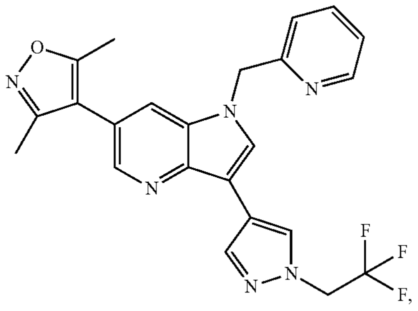
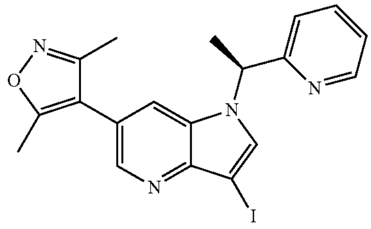
,
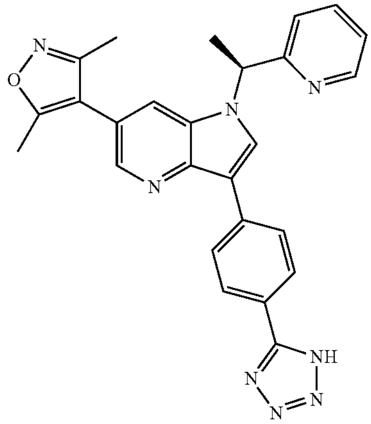
,
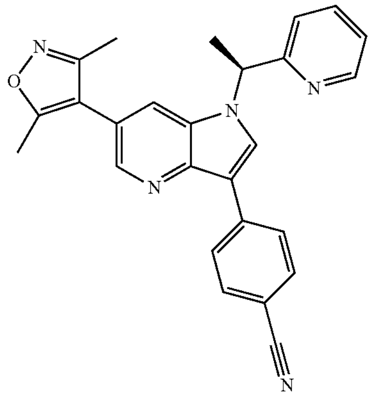
, -continued
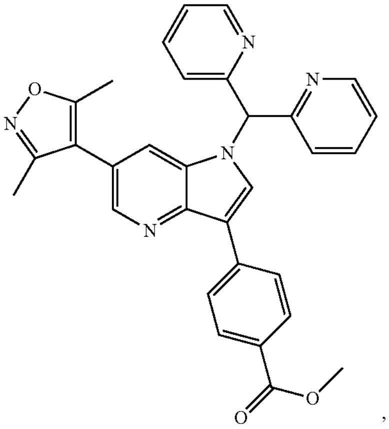
,
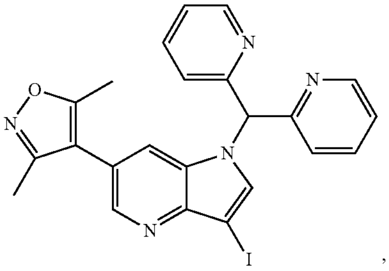
,
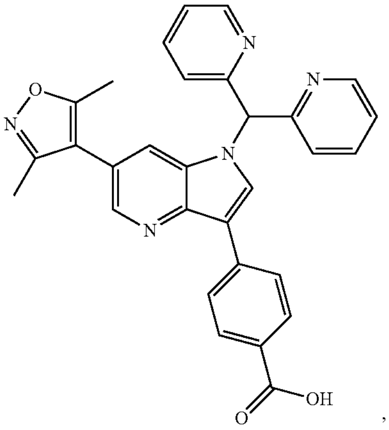
,
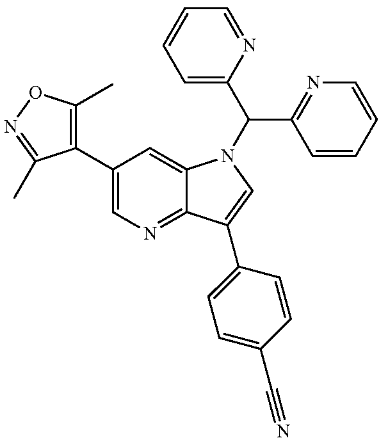
,
-continued
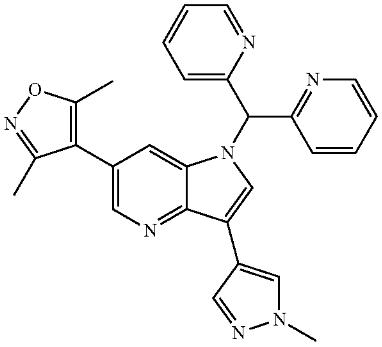
,
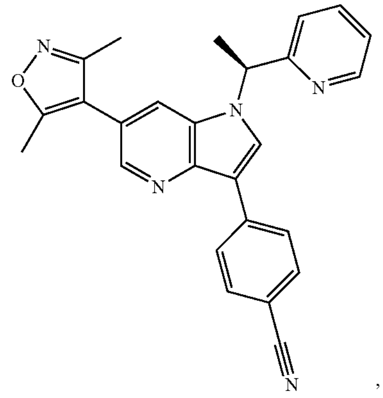
,
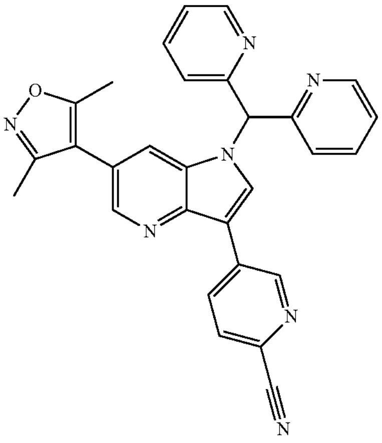
,
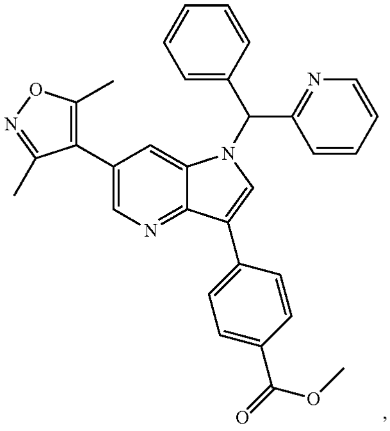
, -continued
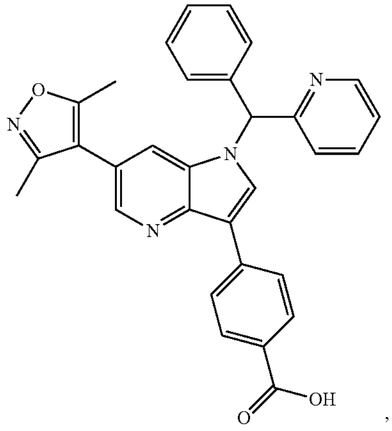
,
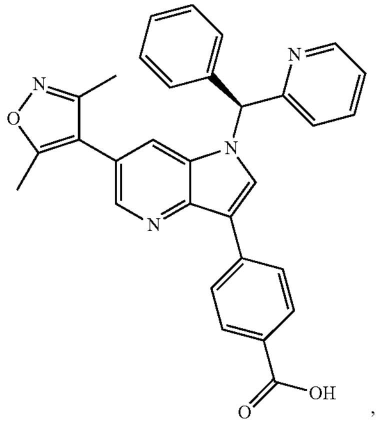
,
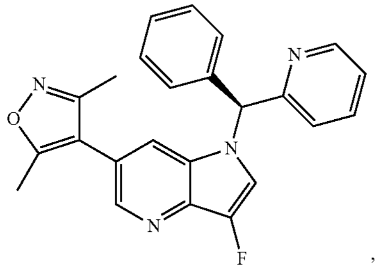
,
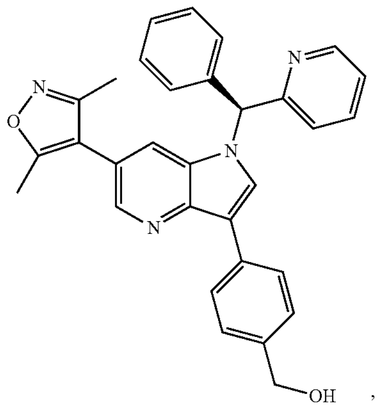
,
-continued
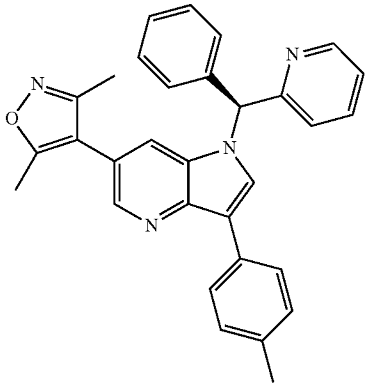
,
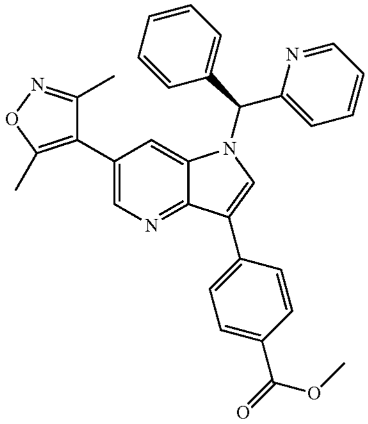
,
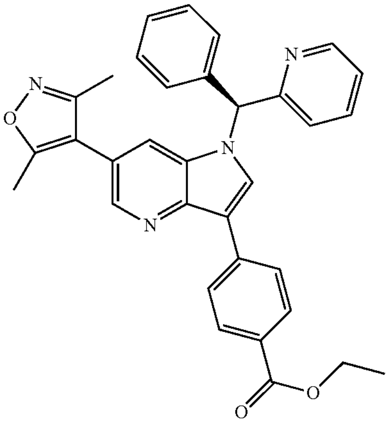
,
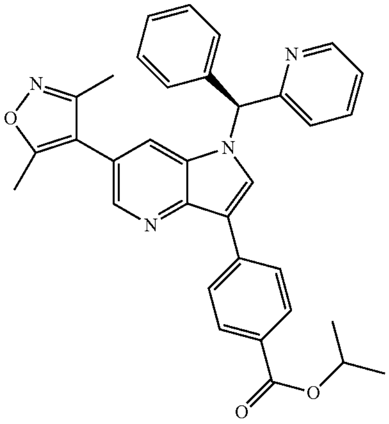
, -continued
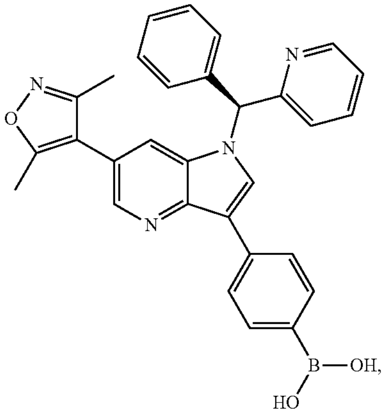
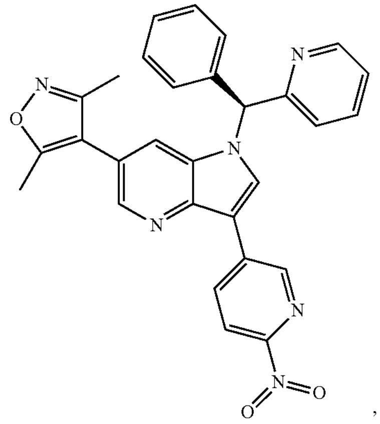
,
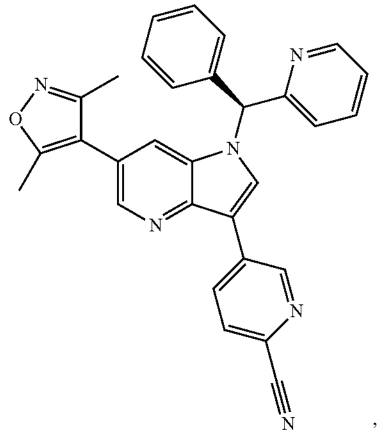
,
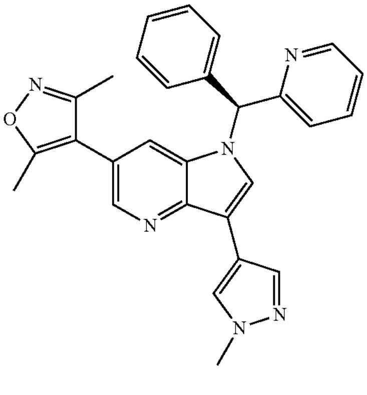
,
-continued
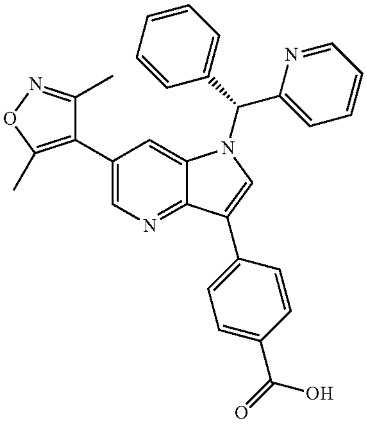
,
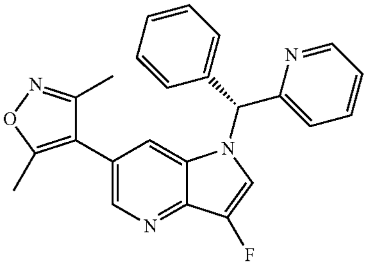
,
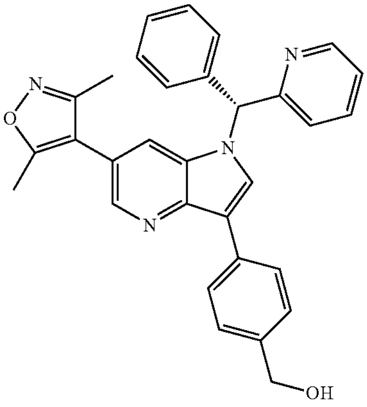
,
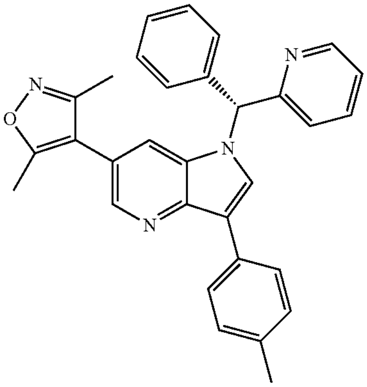
, -continued
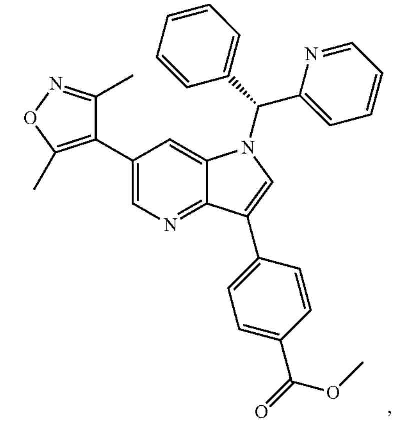
,
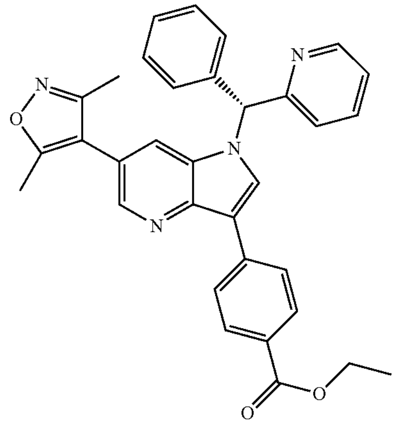
,
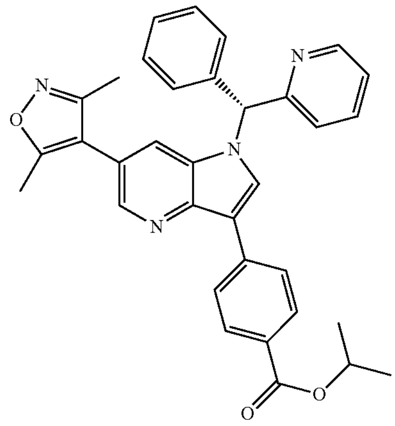
,
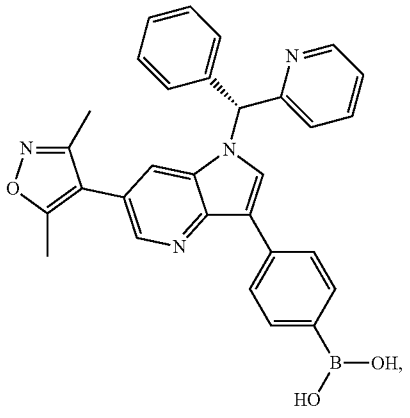
-continued
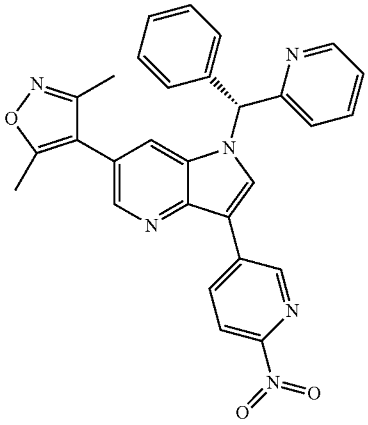
,
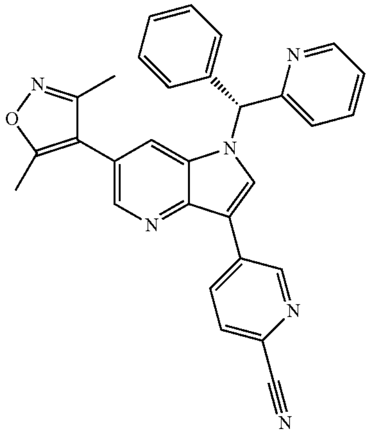
,
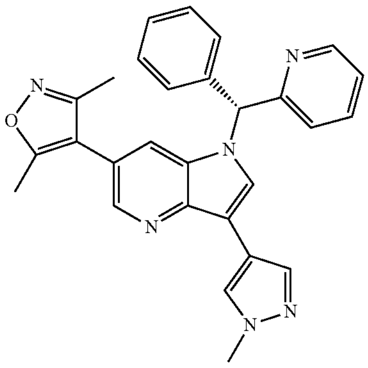
,
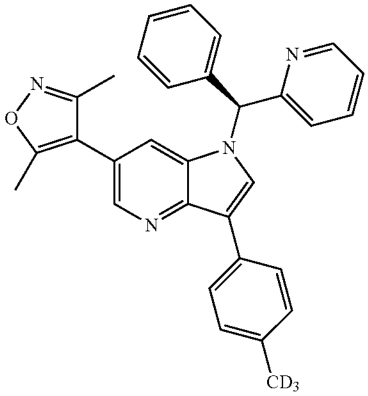
, -continued
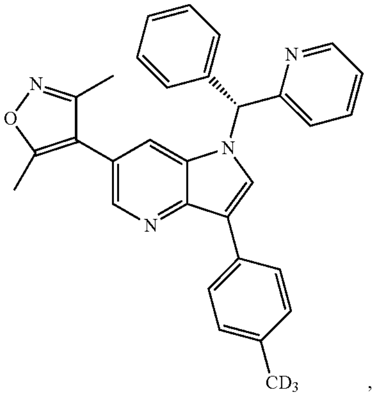
,
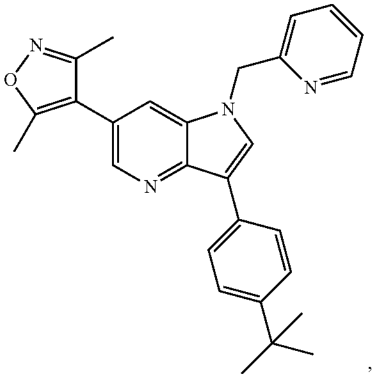
,
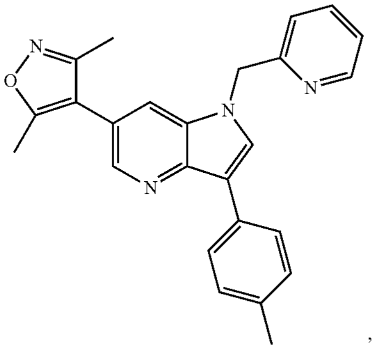
,
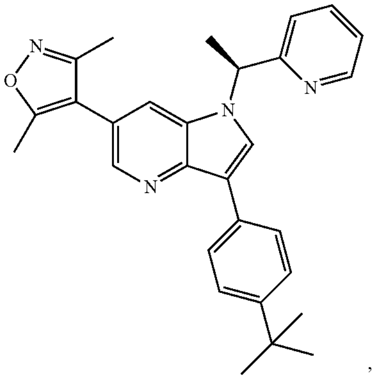
,
-continued
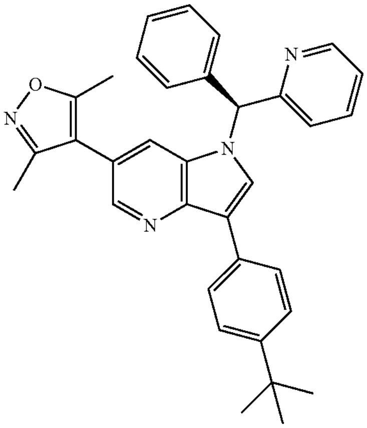
,
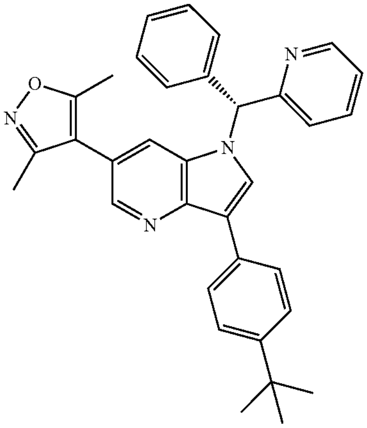
,
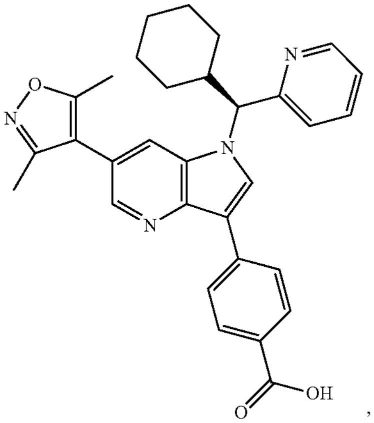 [SMILES: Cc1noc(C)c1-c1cnc2c(-c3ccc(C(=O)O)cc3)cn([C@H](c3ccccn3)C3CCCCC3)c2c1]
,
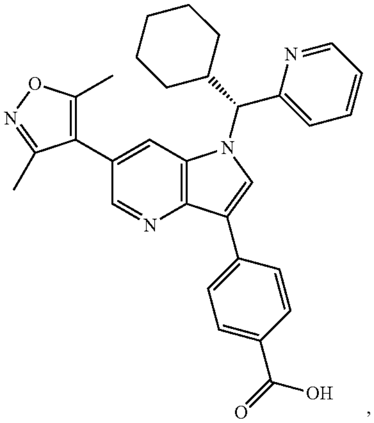
, -continued
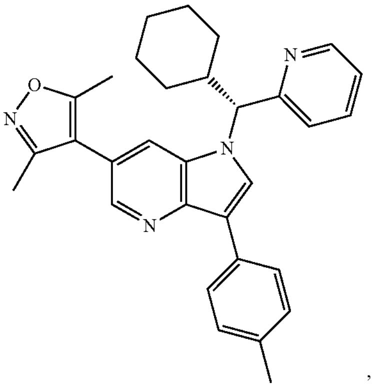
,
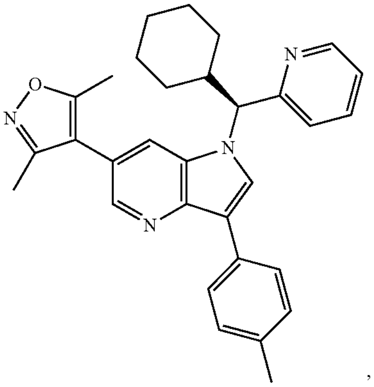
,
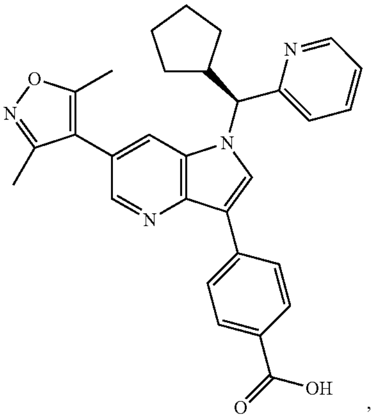
,
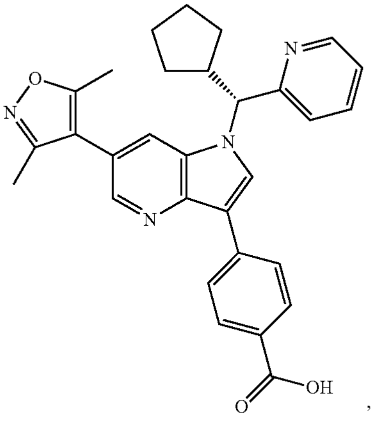
,
-continued
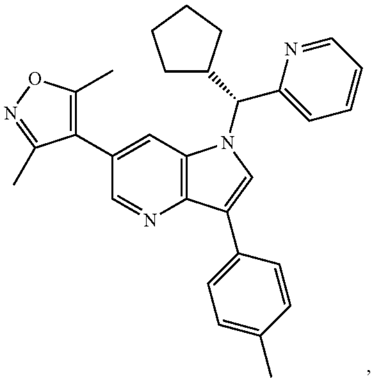
,
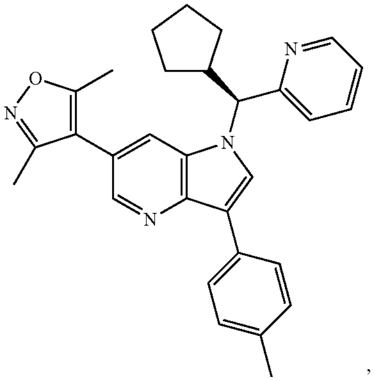
,
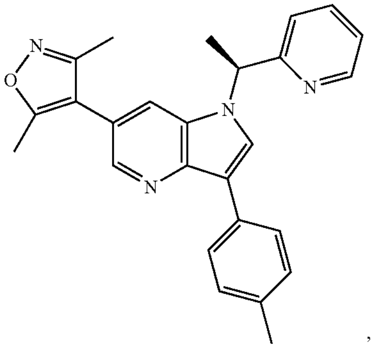
,
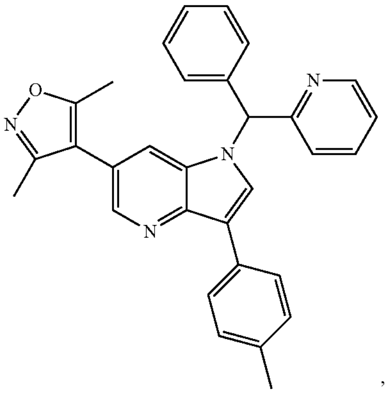
, -continued
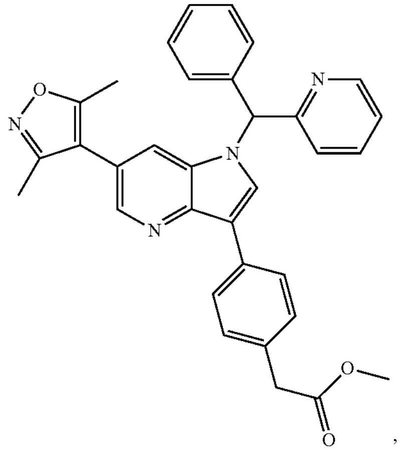
,
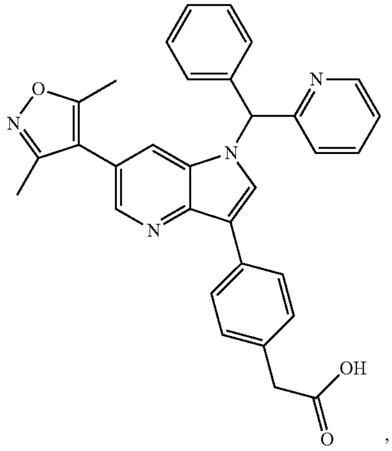
,
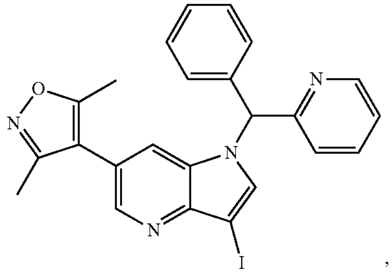
,
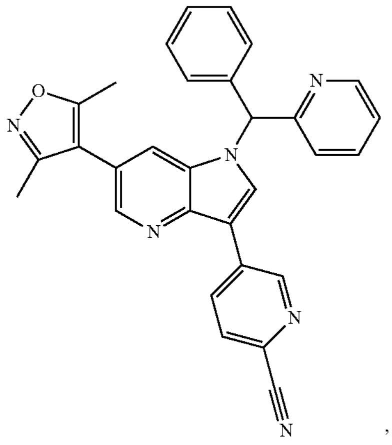
,
-continued
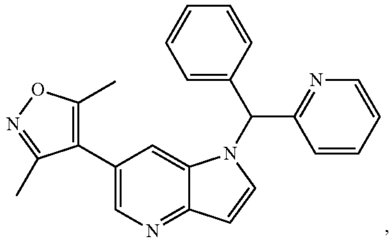
,
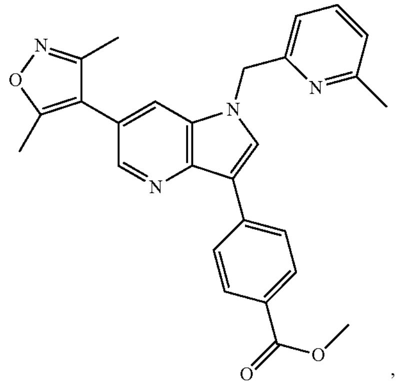
,
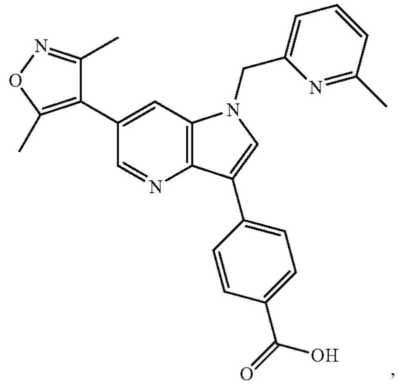
,
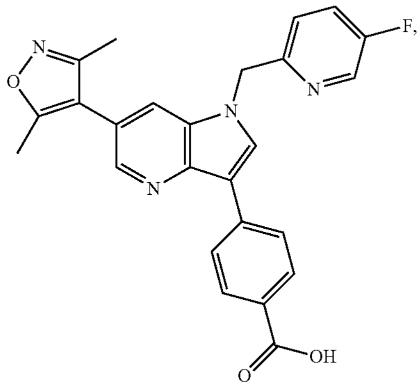
, -continued
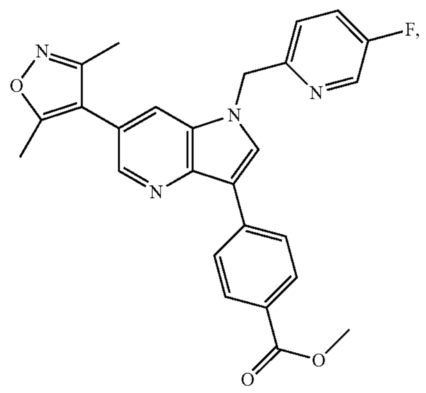
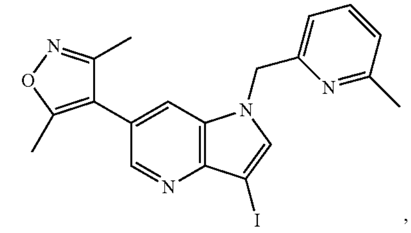
,
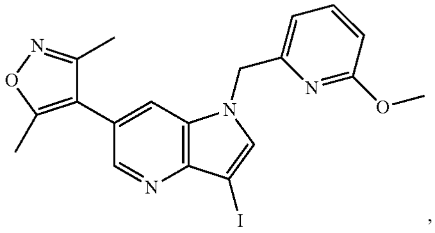
,
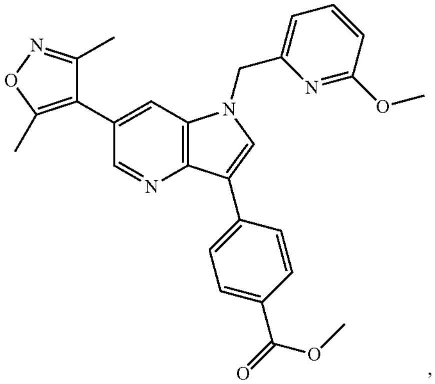
,
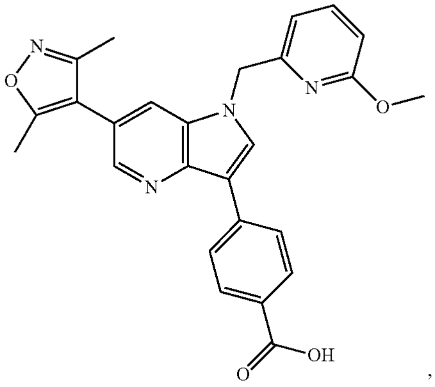
,
-continued
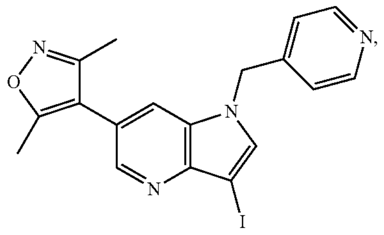
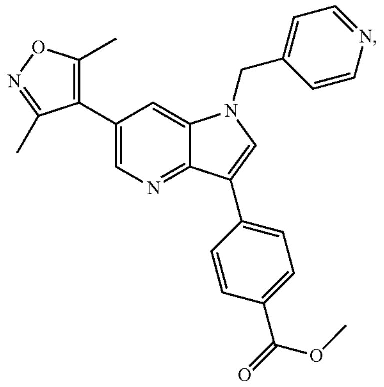
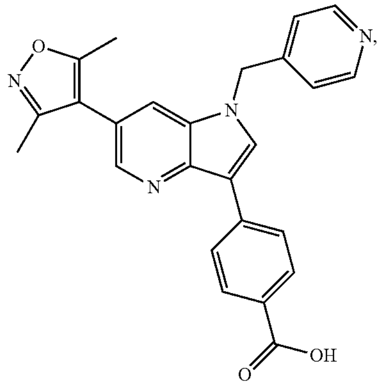
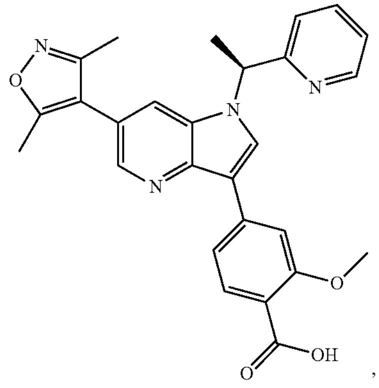
, -continued
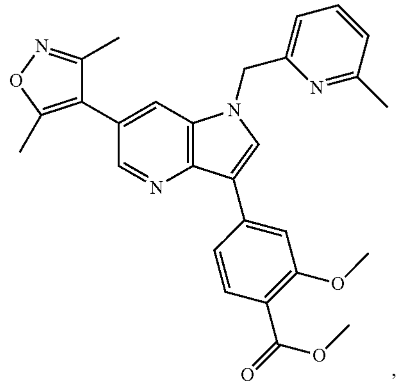
,
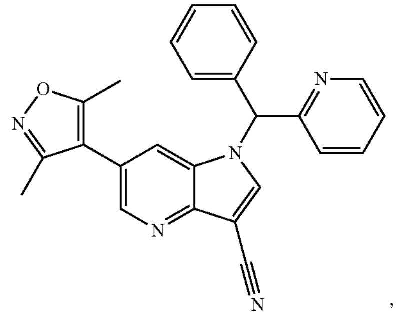
,
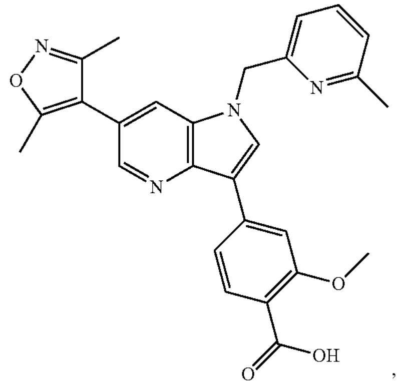
,
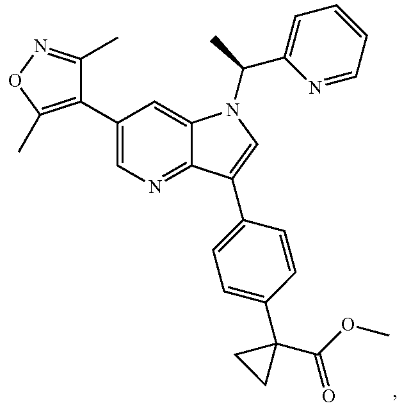
,
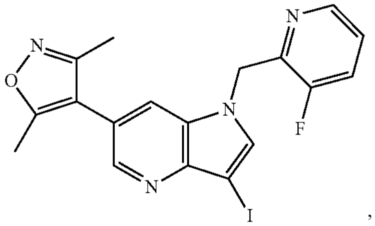
,
-continued
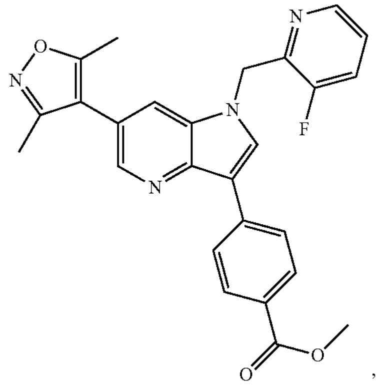
,
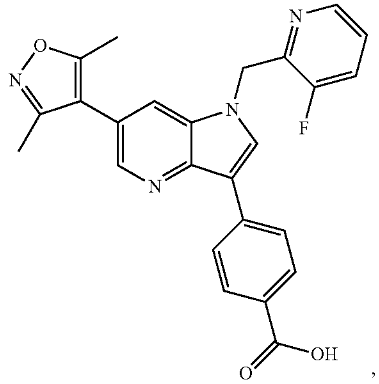
,
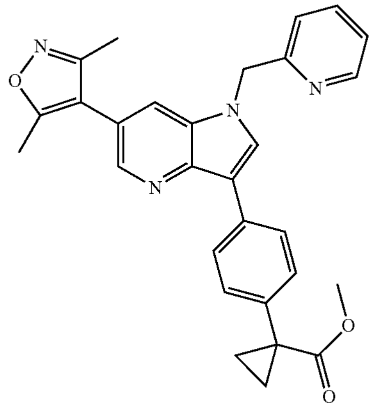
,
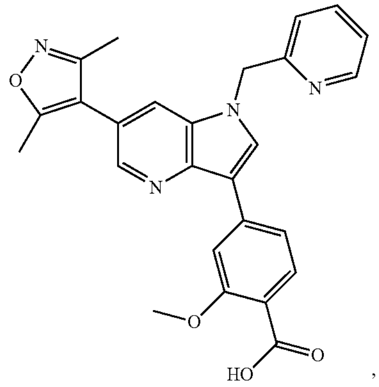
, -continued
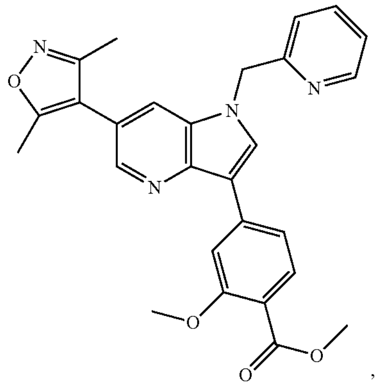
,
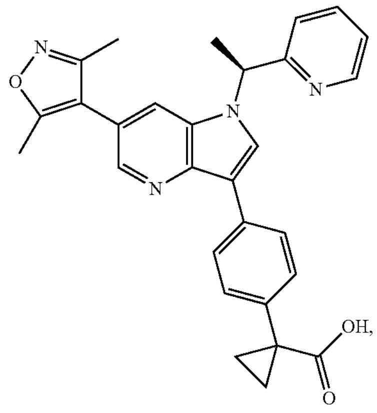
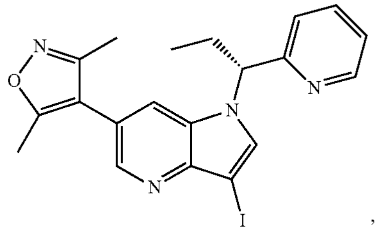
,
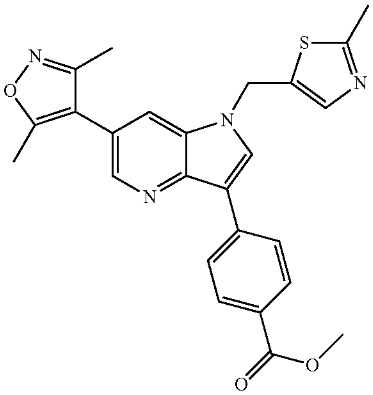
,
-continued
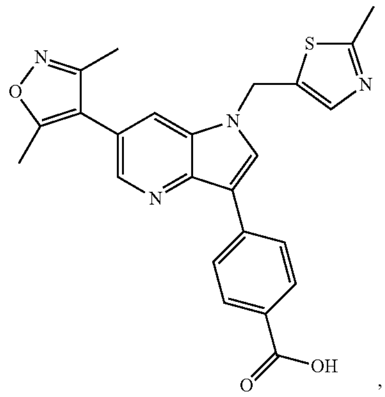
,
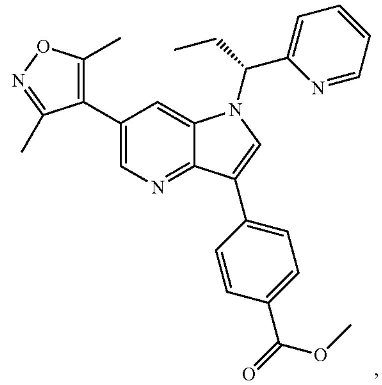
,
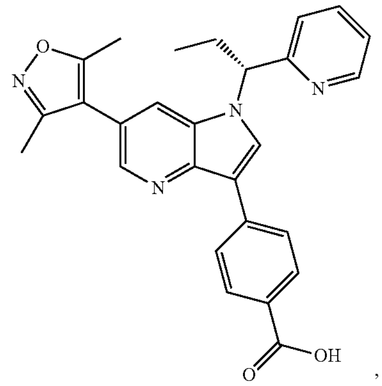
,
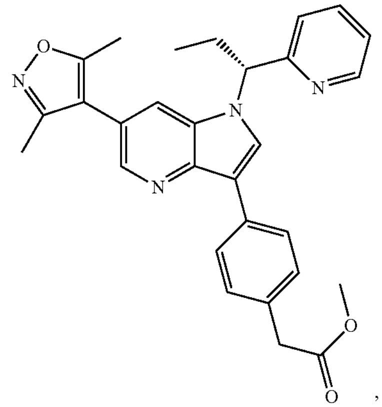
, -continued
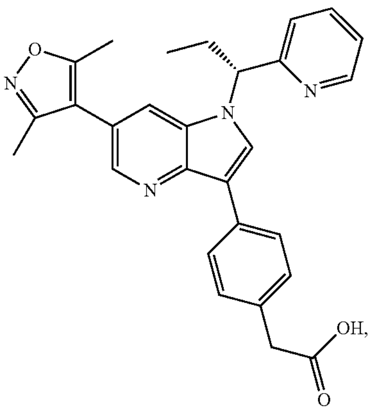
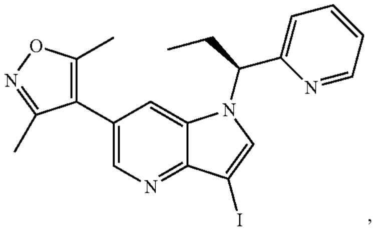
,
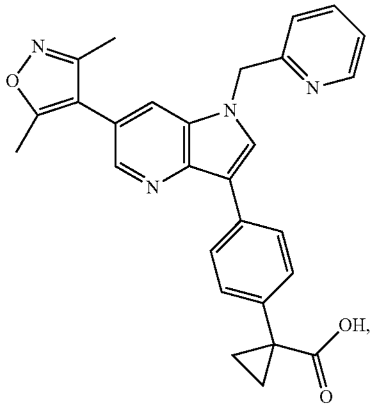
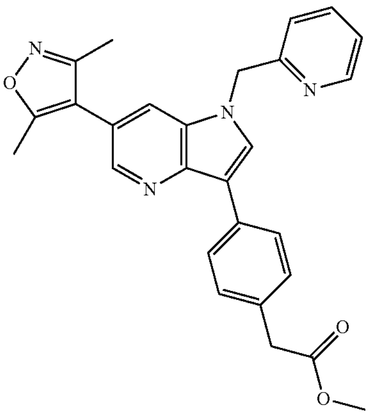
,
-continued
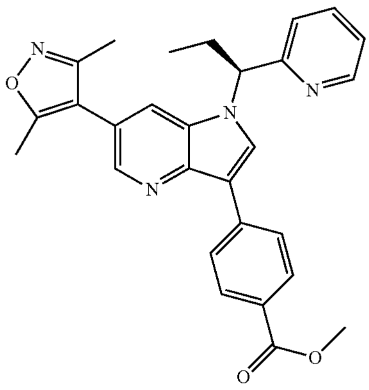
,
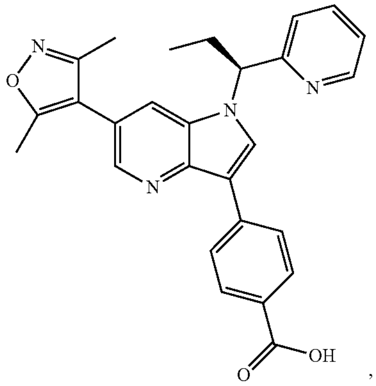
,
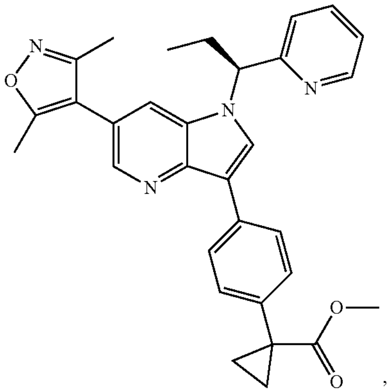 [SMILES: CC[C@@H](c1ccccn1)n1cc(-c2ccc(C3(C(=O)OC)CC3)cc2)c2ncc(-c3c(C)noc3C)cc21]
,
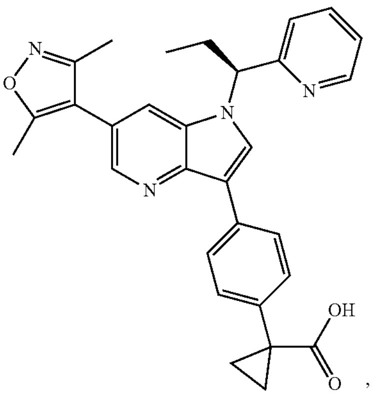
, -continued
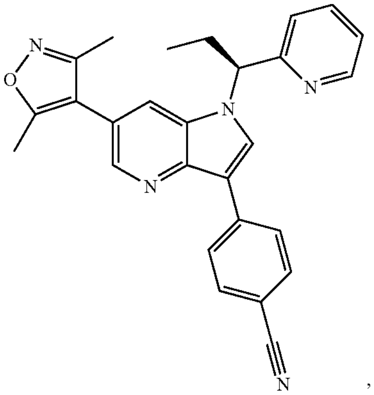
,
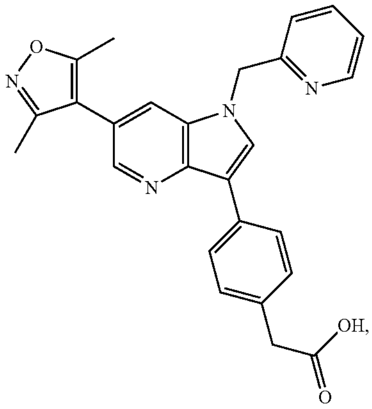
,
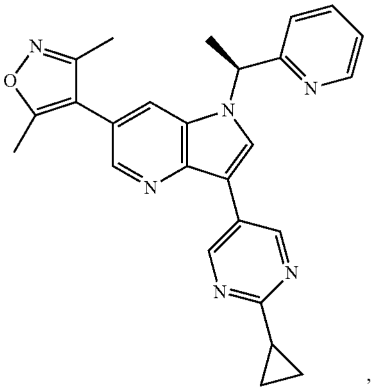
,
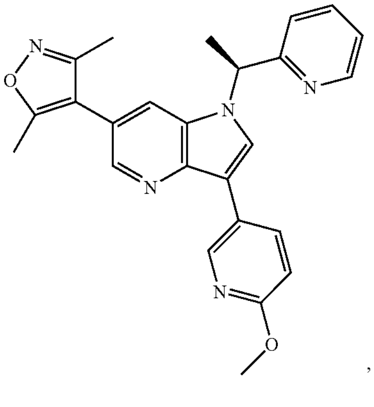
,
-continued
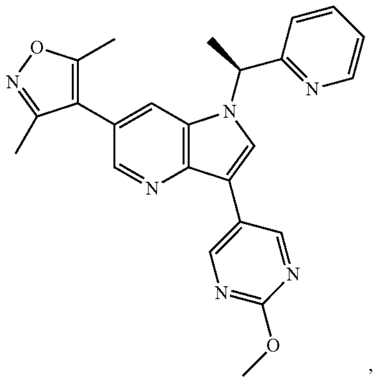
,
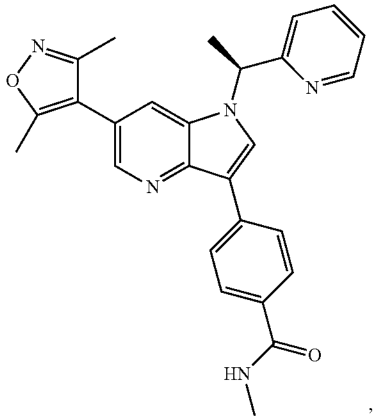
,
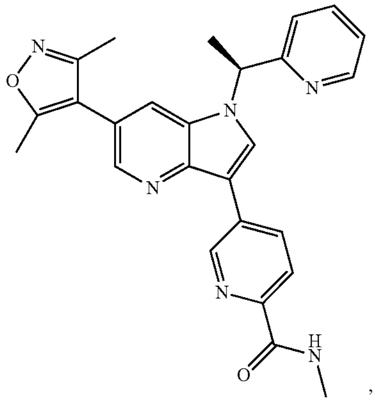
,
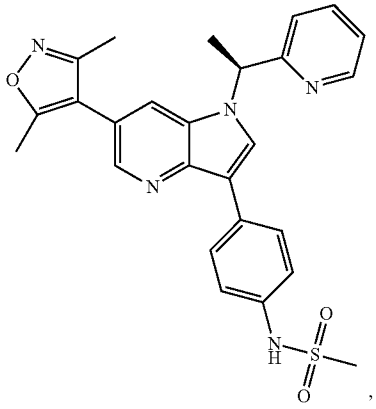
, -continued
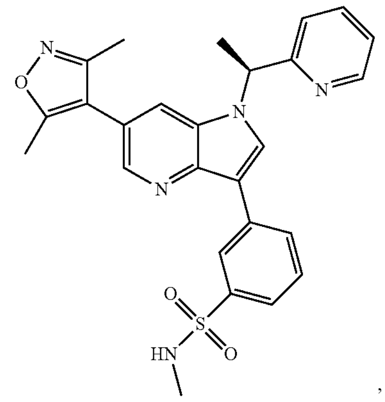
,
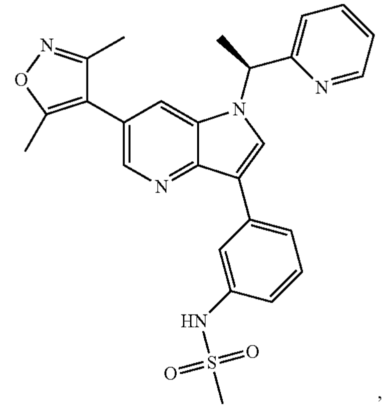
,
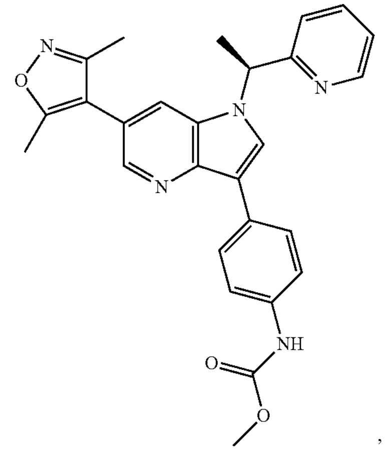
,
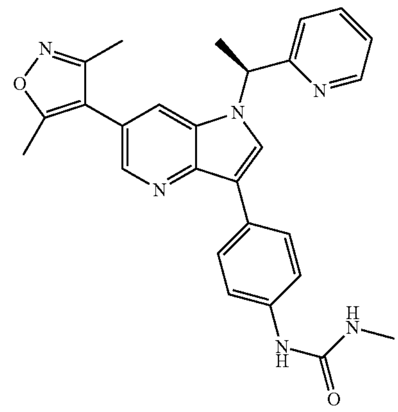
,
-continued
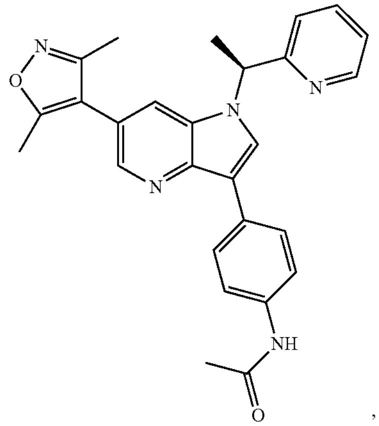
,
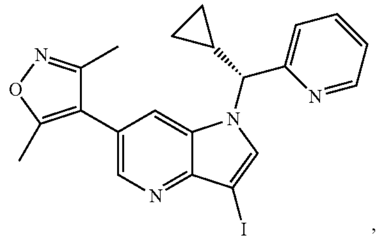
,
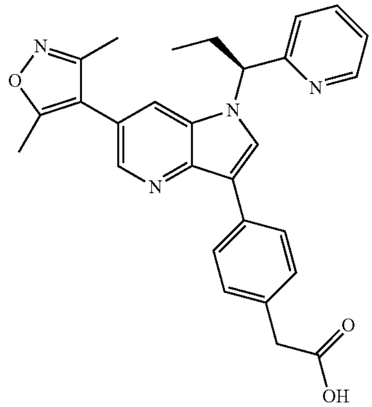
,
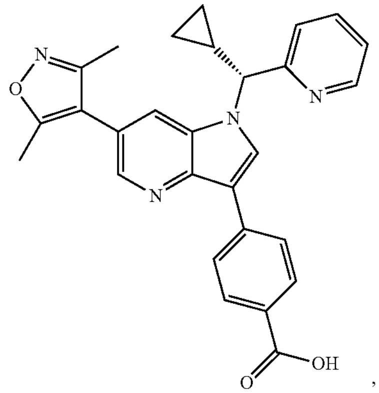
,
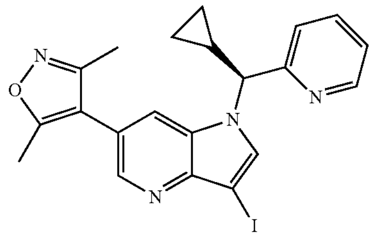
, -continued
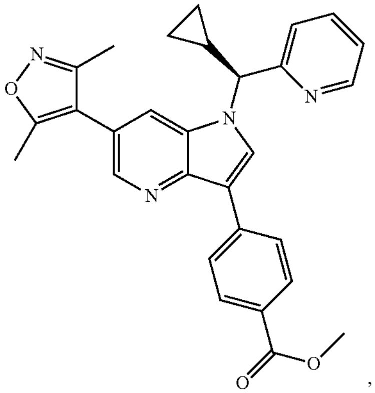
,
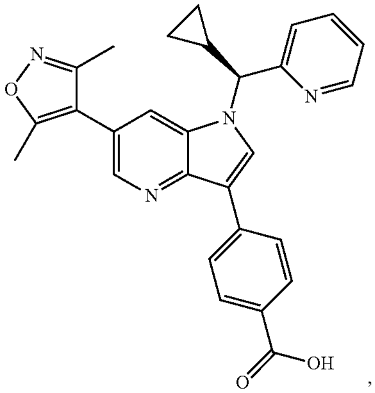
,
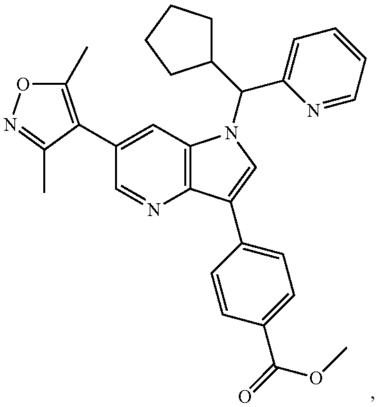
,
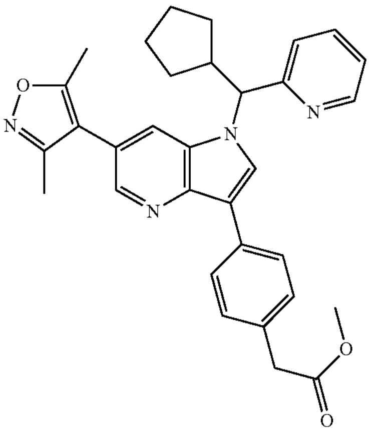
,
-continued
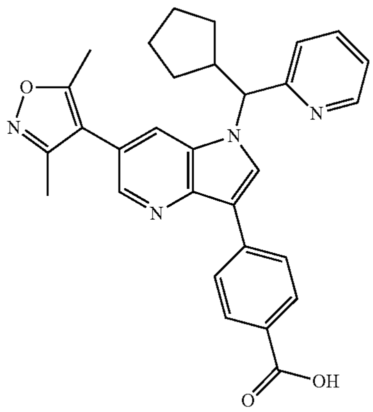
,
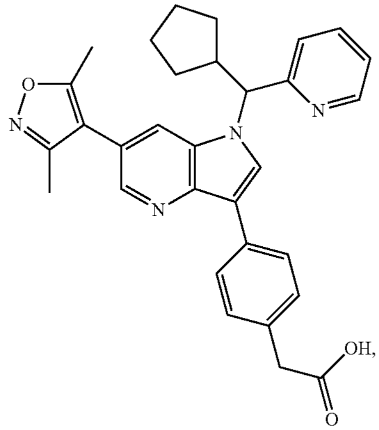
,
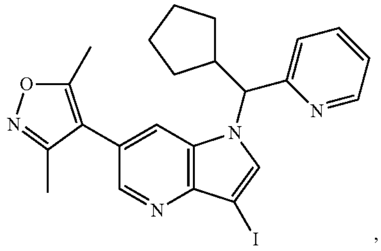
,
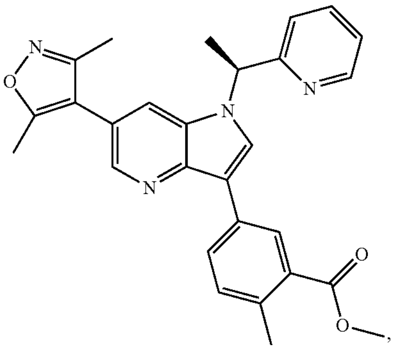
, -continued
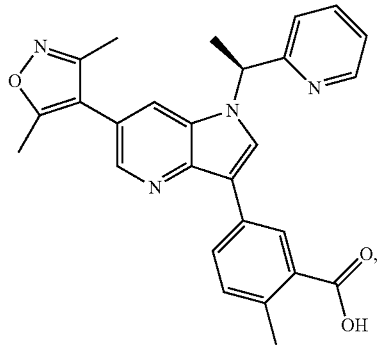
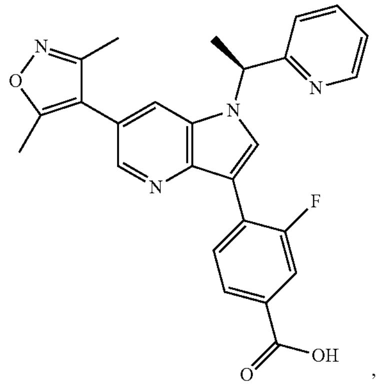
,
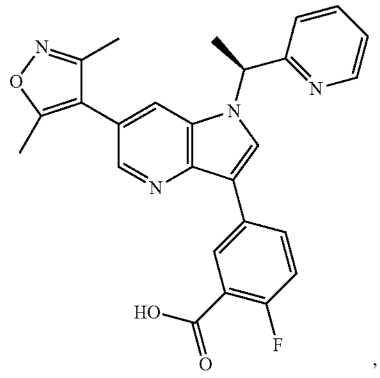
,
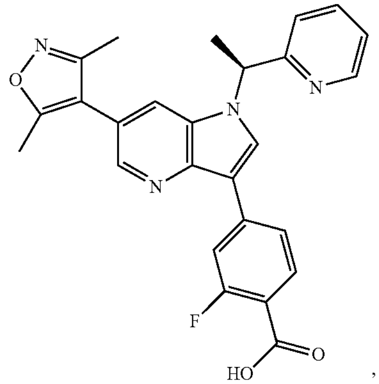
,
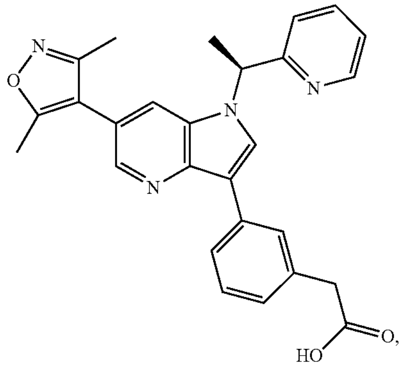
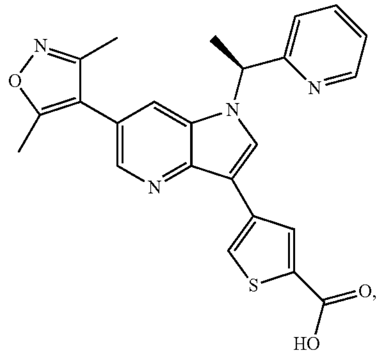
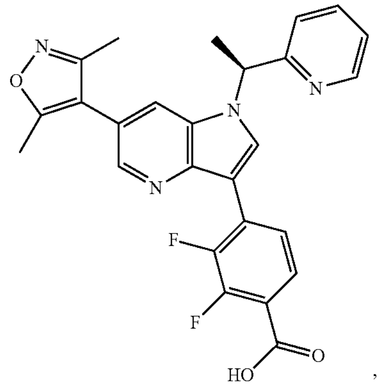
,
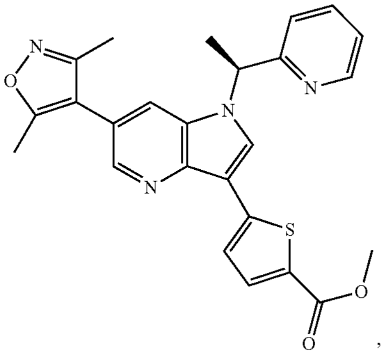
, -continued
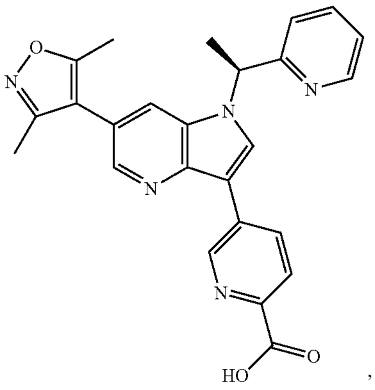
,
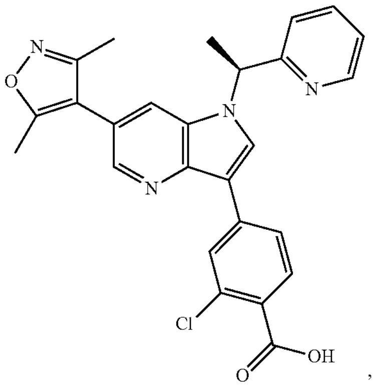
,
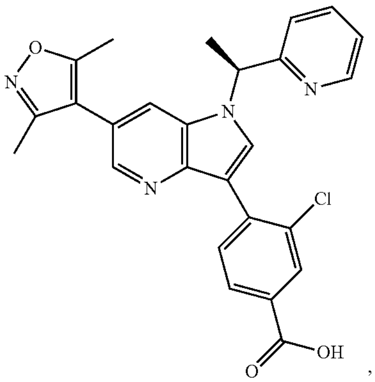
,
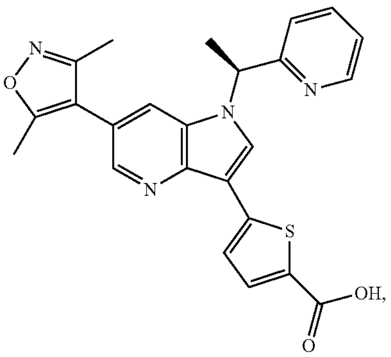
-continued
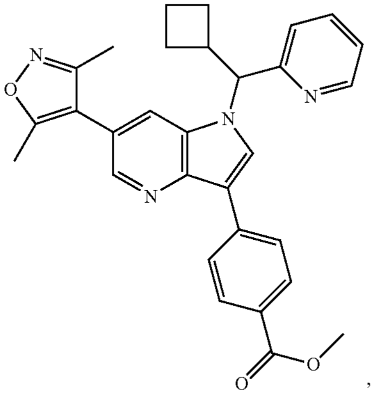
,
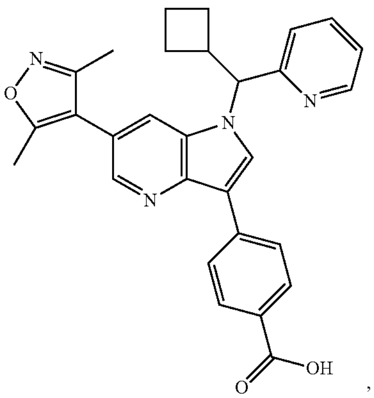
,
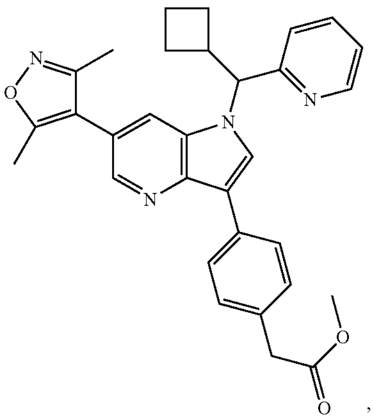
,
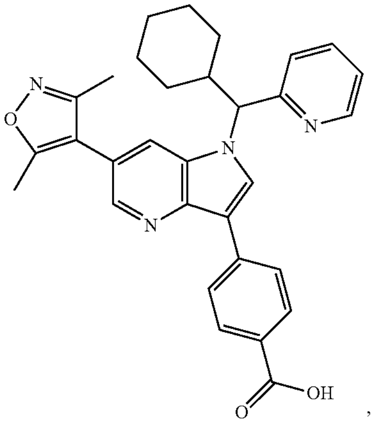
, -continued
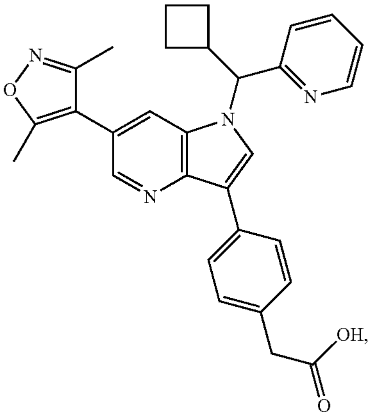
,
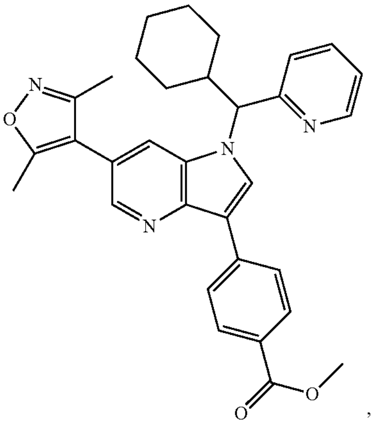
,
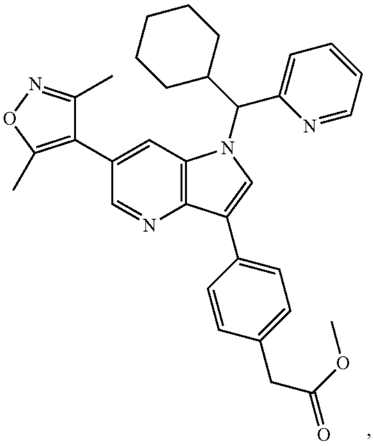
,
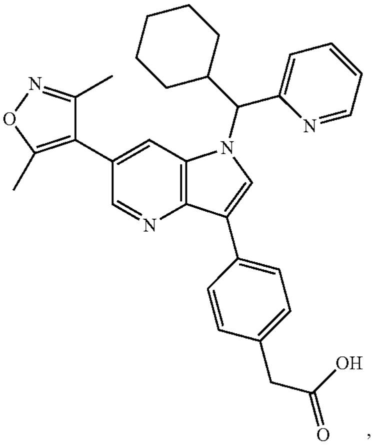
,
-continued
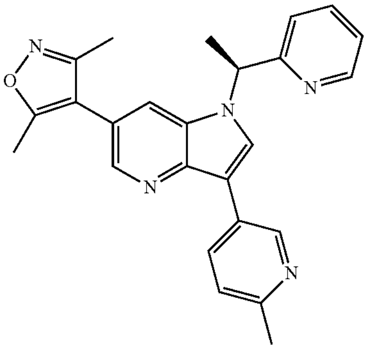
,
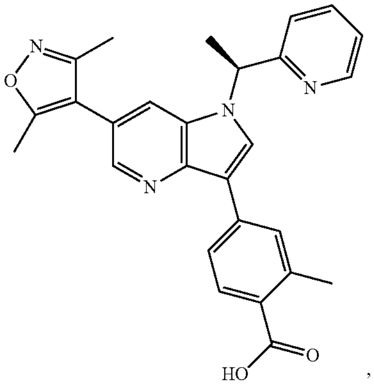
,
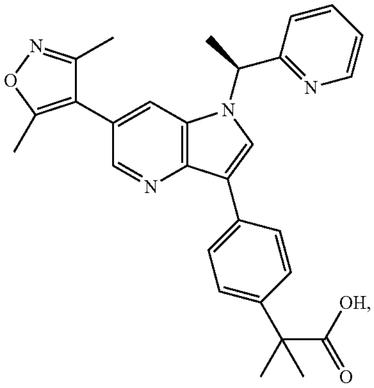
,
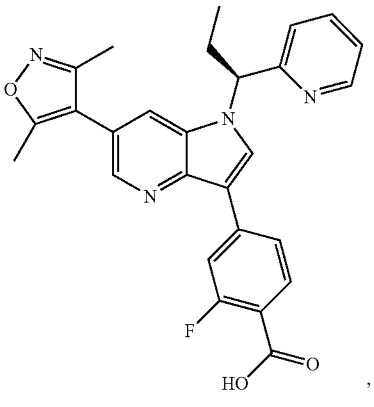
, -continued
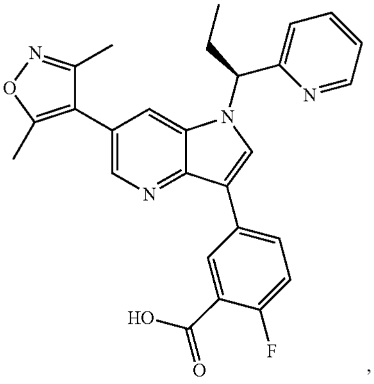
,
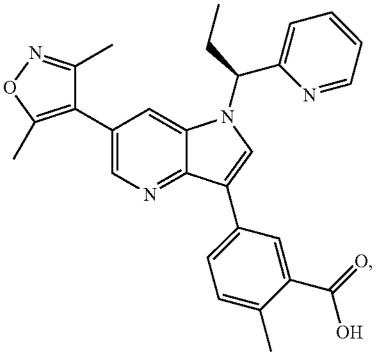
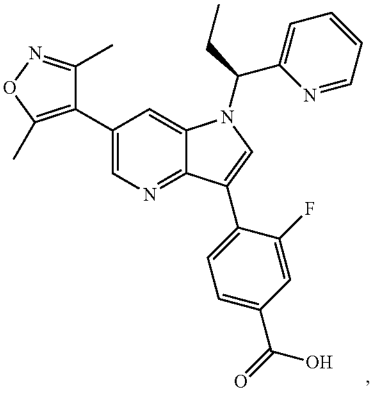
,
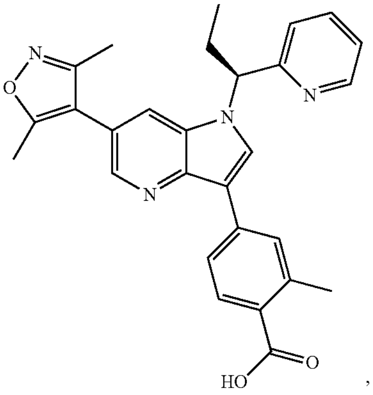
,
-continued
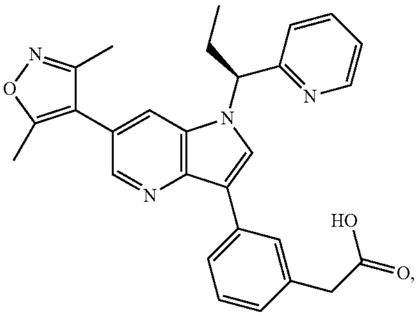
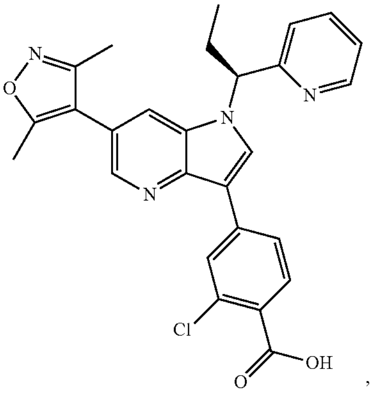
,
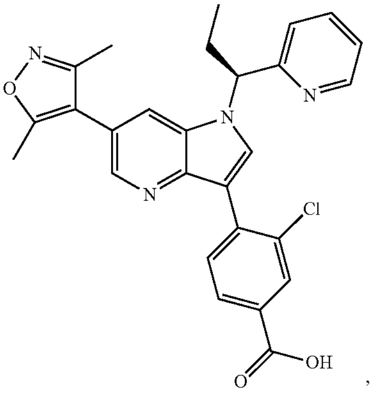
,
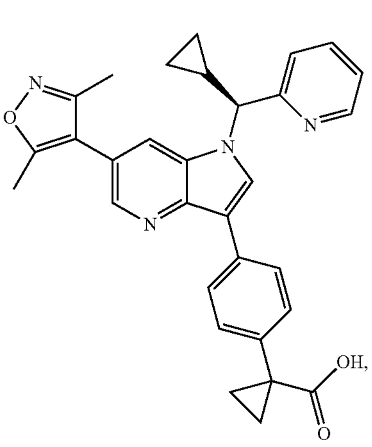

-continued
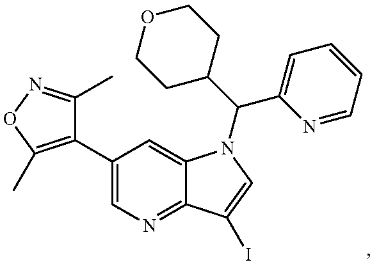
,
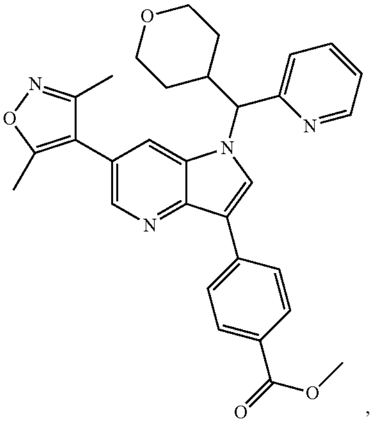
,
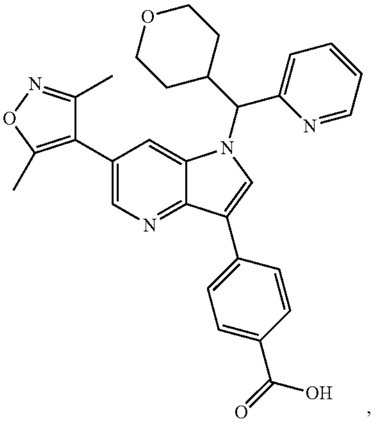
,
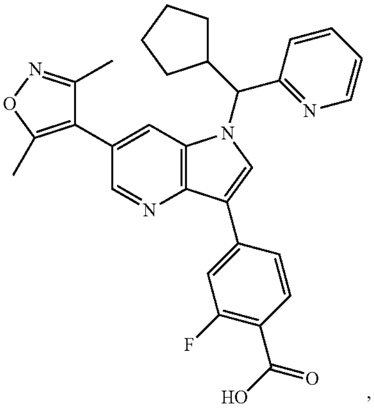
,
-continued
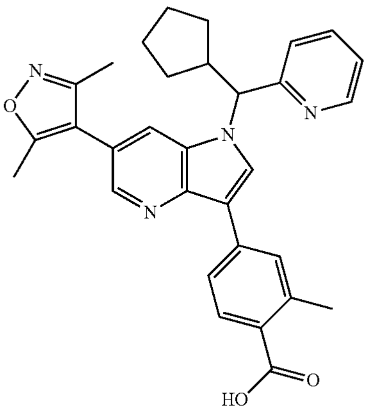
,
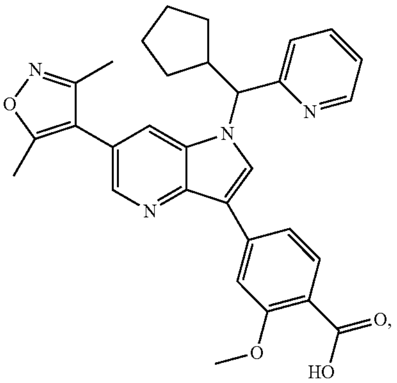
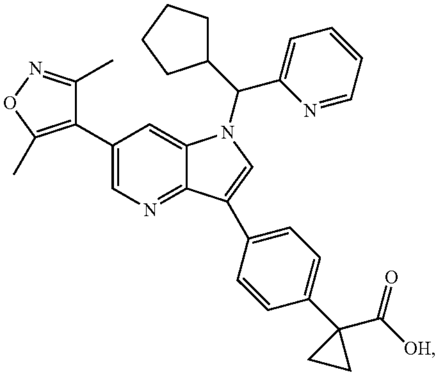
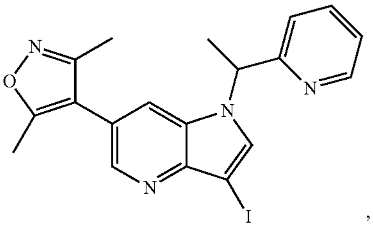
, and -continued
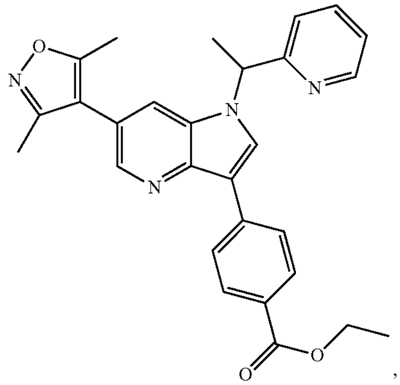 [SMILES: CCOC(=O)c1ccc(-c2cn(C(C)c3ccccn3)c3cc(-c4c(C)noc4C)cnc23)cc1]
,
or a pharmaceutically acceptable salt, a solvate, a tautomer, a stereoisomer or a deuterated analog thereof.
12. A compound selected from:
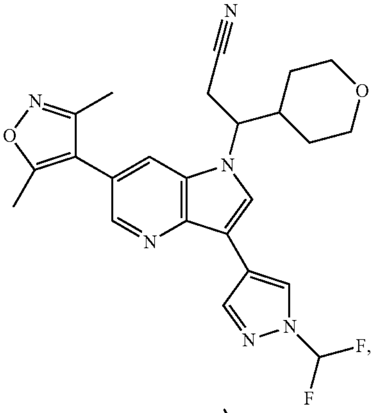
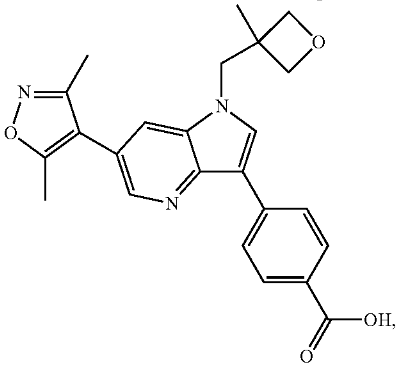
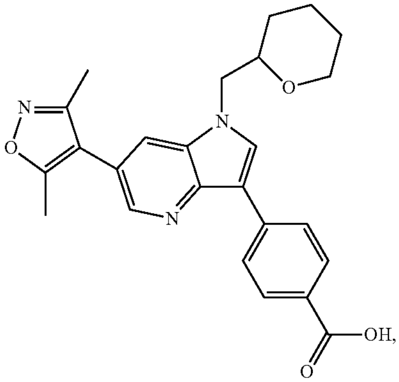
-continued
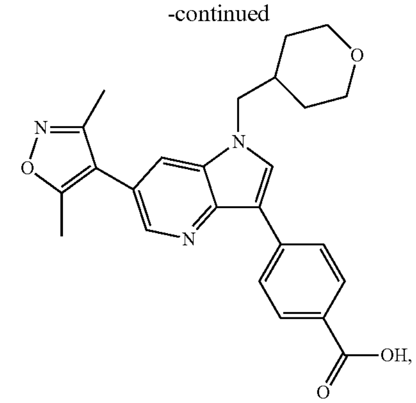
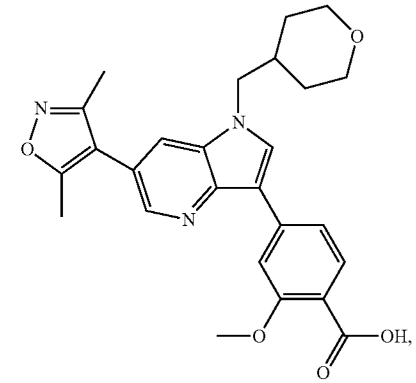
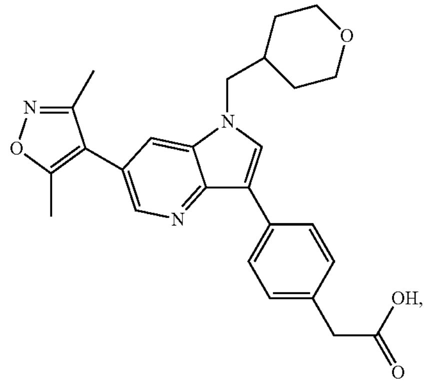
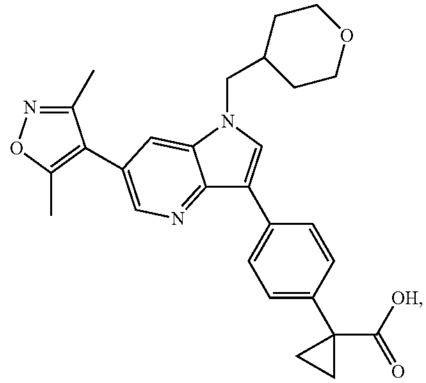

-continued
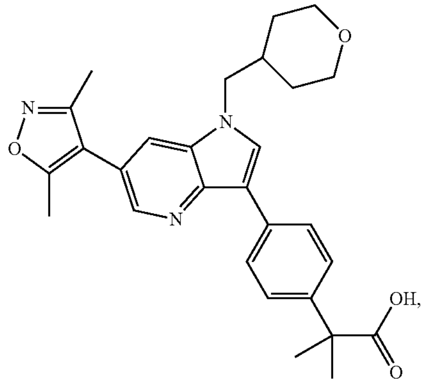
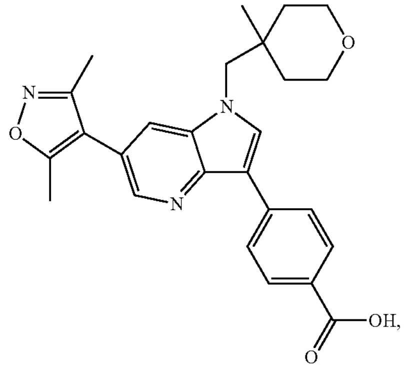
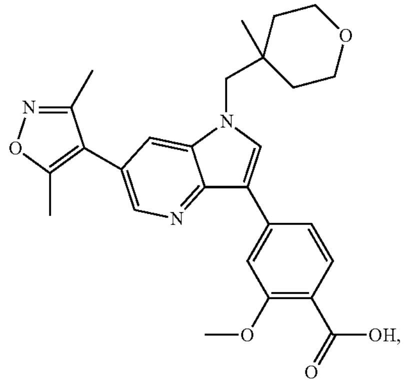
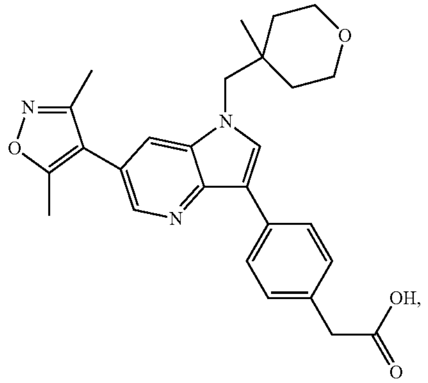
-continued
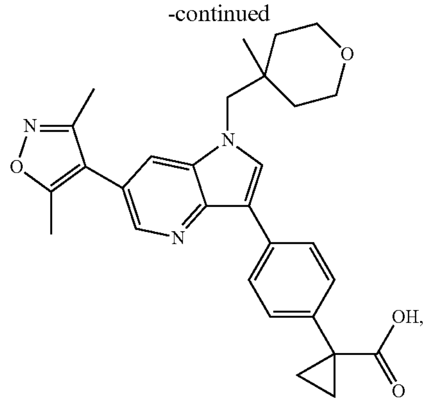
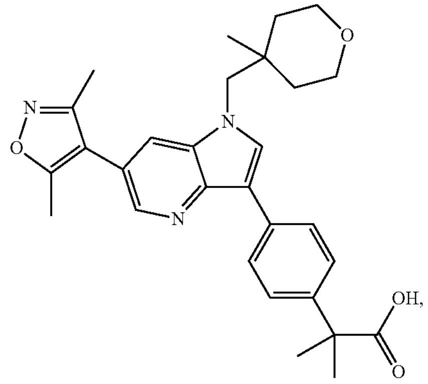
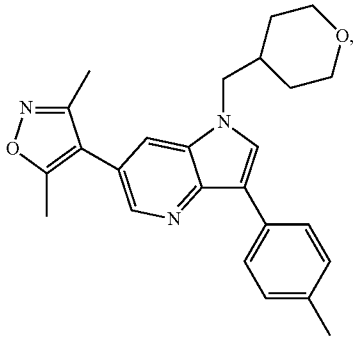
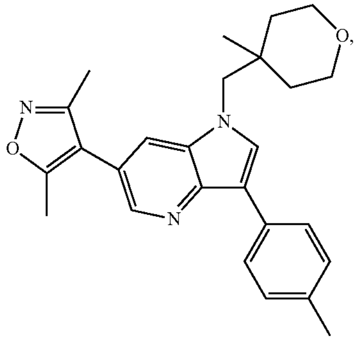

-continued
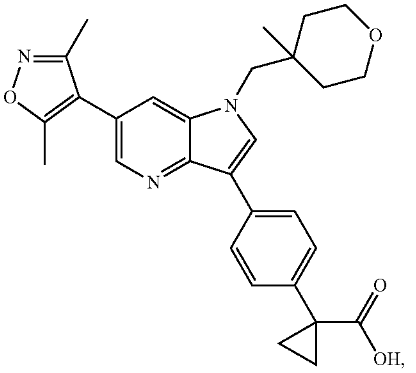
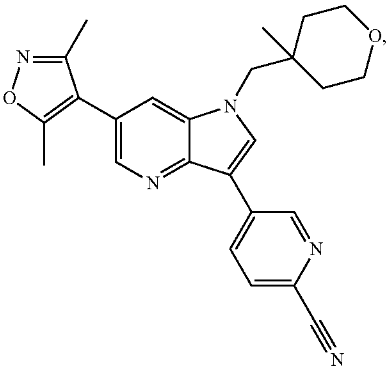
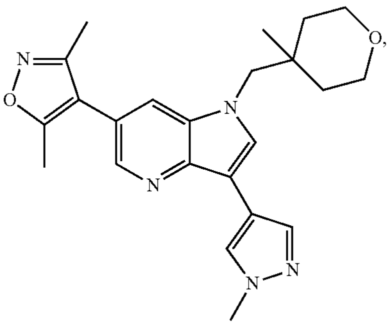
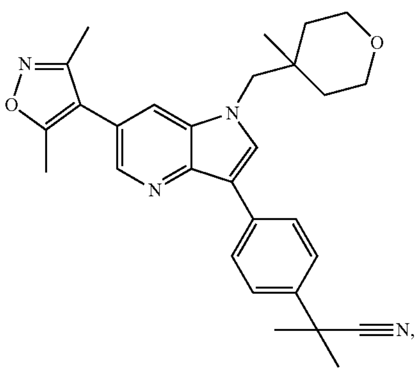
-continued
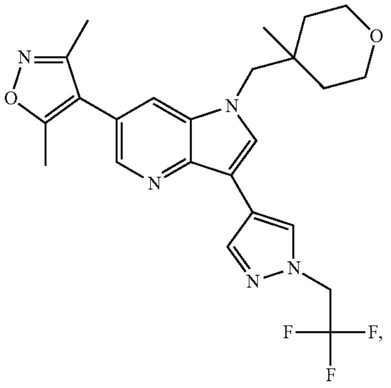
and
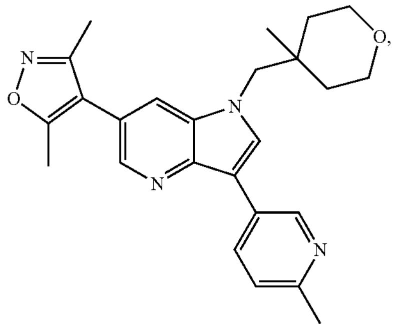 [SMILES: Cc1ccc(-c2cn(CC3(C)CCOCC3)c3cc(-c4c(C)noc4C)cnc23)cn1]
or a pharmaceutically acceptable salt, a solvate, a tautomer, a stereoisomer or a deuterated analog thereof.
13. A pharmaceutical composition comprising a compound of claim 11 and a pharmaceutical acceptable excipient or carrier.
14. A compound of formula:
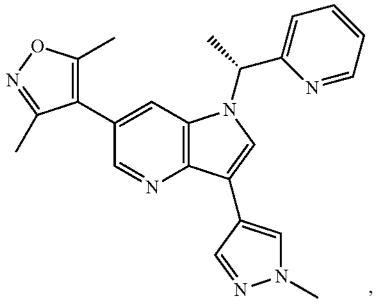 [SMILES: Cc1noc(C)c1-c1cnc2c(-c3cnn(C)c3)cn([C@H](C)c3ccccn3)c2c1]
or a pharmaceutically acceptable salt thereof.

15. A compound of formula:

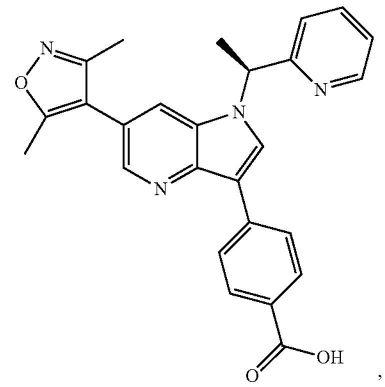 [SMILES: Cc1noc(C)c1-c1cnc2c(-c3ccc(C(=O)O)cc3)cn([C@@H](C)c3ccccn3)c2c1]

, or a pharmaceutically acceptable salt thereof.

16. A compound of formula:

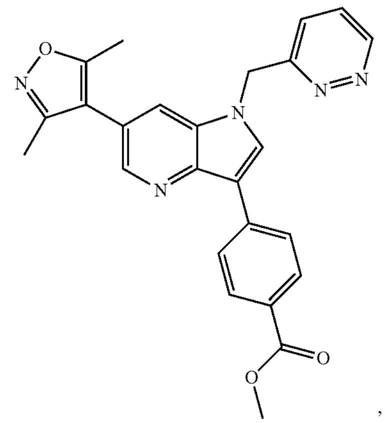 [SMILES: COC(=O)c1ccc(-c2cn(Cc3cccnn3)c3cc(-c4c(C)noc4C)cnc23)cc1]

, or a pharmaceutically acceptable salt thereof.

17. A compound of formula:

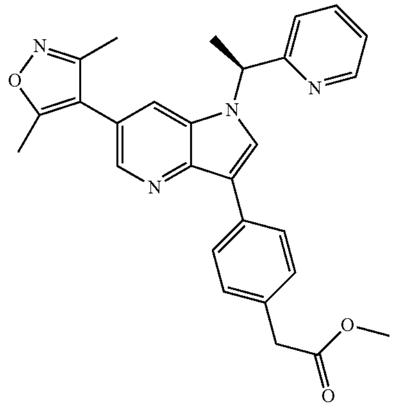

, or a pharmaceutically acceptable salt thereof.

18. A compound of formula:

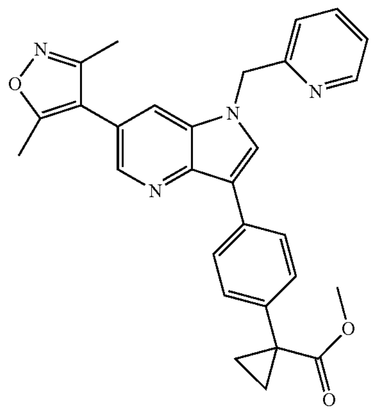

, or a pharmaceutically acceptable salt thereof.

19. A compound of formula:

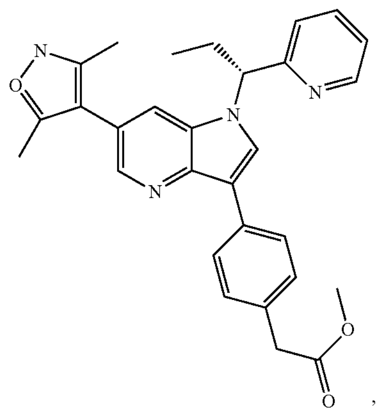

, or a pharmaceutically acceptable salt thereof.

20. A compound of formula:

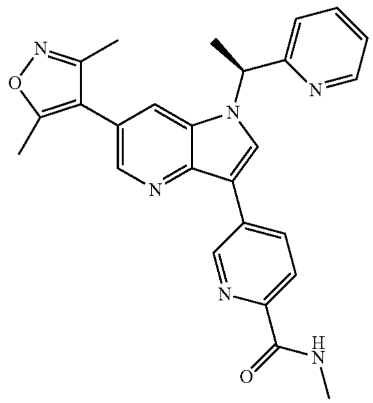

, or a pharmaceutically acceptable salt thereof.

21. A compound of formula:
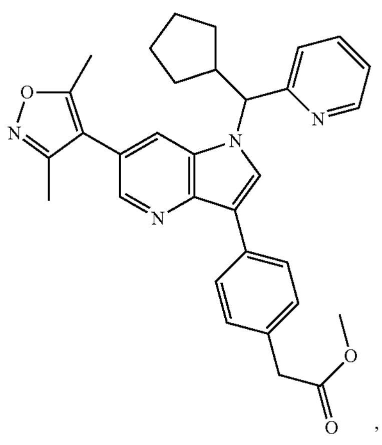 [SMILES: COC(=O)Cc1ccc(-c2cn(C(c3ccccn3)C3CCCC3)c3cc(-c4c(C)noc4C)cnc23)cc1]
,
or a pharmaceutically acceptable salt thereof.
* * * * *